United States Patent
Labelle et al.

(10) Patent No.: US 10,710,975 B2
(45) Date of Patent: Jul. 14, 2020

(54) OXOPIPERAZINE DERIVATIVES

(71) Applicant: Inthera Bioscience AG, Wadenswil (CH)

(72) Inventors: Marc Labelle, Bedford, NH (US); Ulrich Kessler, Zurich (CH); Valentino Cattori, Wadenswil (CH); Cyril Cook, Winnipeg (CA); Ramkrishna Reddy Vakiti, Winnipeg (CA); Kevin R. D. Johnson, Winnipeg (CA); Matinder Kaur, Winnipeg (CA); Jean-d'Amour K. Twibanire, Winnipeg (CA); Farman Ullah, Winnipeg (CA)

(73) Assignee: Inthera Bioscience AG, Wadenswil (CH)

(*) Notice: Subject to any disclaimer, the term of this patent is extended or adjusted under 35 U.S.C. 154(b) by 0 days.

(21) Appl. No.: 16/222,479

(22) Filed: Dec. 17, 2018

(65) Prior Publication Data

US 2019/0185449 A1 Jun. 20, 2019

Related U.S. Application Data

(60) Provisional application No. 62/599,336, filed on Dec. 15, 2017.

(30) Foreign Application Priority Data

Feb. 8, 2018 (CH) .................................. 0152/18

(51) Int. Cl.
| | | |
|---|---|---|
| C07D 401/06 | (2006.01) | |
| C07D 497/10 | (2006.01) | |
| C07D 491/20 | (2006.01) | |
| C07D 471/10 | (2006.01) | |
| C07D 495/04 | (2006.01) | |
| C07D 495/10 | (2006.01) | |
| C07D 491/107 | (2006.01) | |
| C07D 401/14 | (2006.01) | |
| C07D 471/04 | (2006.01) | |
| C07D 491/113 | (2006.01) | |
| A61K 45/06 | (2006.01) | |
| A61P 35/00 | (2006.01) | |
| A61P 35/02 | (2006.01) | |

(52) U.S. Cl.
CPC ............ *C07D 401/06* (2013.01); *A61P 35/00* (2018.01); *A61P 35/02* (2018.01); *C07D 401/14* (2013.01); *C07D 471/04* (2013.01); *C07D 471/10* (2013.01); *C07D 491/107* (2013.01); *C07D 491/113* (2013.01); *C07D 491/20* (2013.01); *C07D 495/04* (2013.01); *C07D 495/10* (2013.01); *C07D 497/10* (2013.01); *A61K 45/06* (2013.01)

(58) Field of Classification Search
CPC .......... A61K 45/06; A61P 35/00; A61P 35/02; C07D 401/06; C07D 401/14; C07D 471/04; C07D 471/10; C07D 491/107; C07D 491/113; C07D 491/20; C07D 495/04; C07D 495/10; C07D 497/10
See application file for complete search history.

(56) References Cited

U.S. PATENT DOCUMENTS 5,885,995 A 3/1999 Dinsmore

FOREIGN PATENT DOCUMENTS

| WO | WO 03/017939 A2 | 3/2003 |
| WO | WO 03/033487 A1 | 4/2003 |
| WO | WO 2004/066951 A2 | 8/2004 |

(Continued)

OTHER PUBLICATIONS

Ali, I. et al., "Lysine Acetylation Goes Global: From Epigenetics to Metabolism and Therapeutics," Chem. Rev., 118:1216-1252 (2018).

(Continued)

*Primary Examiner* — Erich A Leeser
(74) *Attorney, Agent, or Firm* — Cooley LLP; Heidei A. Erlacher; Timothy R. McFadden

(57) ABSTRACT

The present invention relates to novel compounds of formula (I) or formula (Ia)

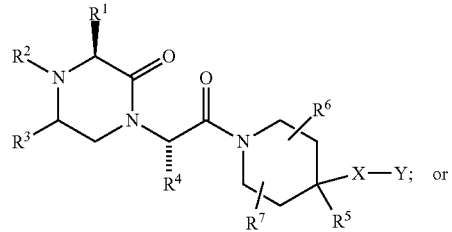

(I)

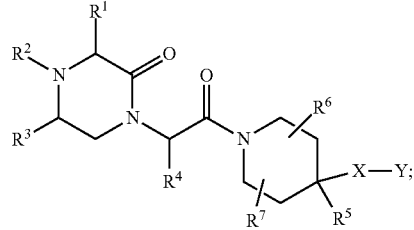

(Ia)

pharmaceutically-acceptable salts, hydrates, solvates, or stereoisomers thereof, and pharmaceutical compositions of these compounds which are useful for preventive and therapeutic use in human and veterinary medicine.

18 Claims, 14 Drawing Sheets

Specification includes a Sequence Listing.

(56) References Cited

FOREIGN PATENT DOCUMENTS

| WO | WO 2012/021144 A1 | 2/2012 | | |
|---|---|---|---|---|
| WO | WO 2013/110134 A1 | 8/2013 | | |
| WO | WO 2013/123511 A1 | 8/2013 | | |
| WO | WO 2014/113794 A2 | 7/2014 | | |
| WO | WO 2015/160914 A1 | 10/2015 | | |
| WO | WO 2015/179547 | * | 11/2015 | ........... A61K 31/496 |
| WO | WO 2015/179547 A2 | 11/2015 | | |

OTHER PUBLICATIONS

Attar, N. & Kurdistani, S. K., "Exploitation of EP300 and CREBBP Lysine Acetyltransferases by Cancer," Cold Spring Harb Perspect Med 2017;7:a026534, 15 pages.
Avantaggiati, M. L. et al., "Recruitment of p300/CBP in p53-Dependent Signal Pathways," Cell, 89:1175-1184 (1997).
Bedford, D. C. et al., "Target gene context influences the transcriptional requirement for the KAT3 family of CBP and p300 histone acetyltransferases," Epigenetics, 5(1):9-15 (2010).
Benson, D. A. et al., "GenBank," Nucleic Acids Research, 41:(D36-D42) (2013).
Berge, S. M. et al., "Pharmaceutical Salts," Journal of Pharmaceutical Sciences, 66(1):1-19 (1977).
Bernat, A. et al., "Interaction between the HPV E7 oncoprotein and the transcriptional coactivator p300," Oncogene, 22:7871-7881 (2003).
Blobel, G. A., "CREB-binding protein and p300: molecular integrators of hematopoietic transcription," Blood, 95(3):745-755 (2000).
Breen, M. E. & Mapp, A. K., "Modulating the masters: chemical tools to dissect CBP and p300 function," Current Opinion in Chemical Biology, 45:195-203 (2018).
Bundgaard, H., "(C) Means to enhance penetration: (1) Prodrugs as a means to improve the delivery of peptide drugs," Advanced Drug Delivery Reviews, 8(1):1-38 (1992).
Bundgaard, H., "Design and Application of Prodrugs," *Textbook of Drug Design and Development*, Ch. 5:113-191, Krogsgaard-Larsen et al. (Eds.) (1991).
Burslem, G. M. et al., "Hypoxia inducible factor (HIF) as a model for studying inhibition of protein-protein interactions," Chem. Sci., 8:4188-4202 (2017).
Cahn, R. S., "An Introduction to the Sequence Rule. A system for the specification of absolute configuration," Journal of Chemical Education, 41(3):116-125 (1964).
Cahn, R.S. & Ingold, C.K., "Specification of configuration about quadricovalent asymmetric atoms," Journal of the Chemical Society, 0:612-622 (1951).
Cahn, R. S. et al., "The Specification of Asymmetric Configuration in Organic Chemistry," Experientia, 12(3):81-94 (1956).
Cahn, R. S. & Ingold, C., "Spezifikation der molekularen Chiralitat," Angew. Chem., 78(8):413-447 (1966), with English language machine translation.
Cahn, R. S. et al. "Errata to 'Specification of Molecular Chirality' published in Angew. Chem. Internat. Edit. vol. 5: 385," Angew. Chem. Internat. Edit. vol. 5 (5): 511 (1966).
Culig, Z., "Androgen Receptor Coactivators in Regulation of Growth and Differentiation in Prostate Cancer," J. Cell Physiol., 231:270-274 (2016).
Dancy, B. M. & Cole, P. A., "Protein Lysine Acetylation by p300/CBP," Chem. Rev., 115:2419-2452 (2015).
Dang, D. T. et al., "Hypoxia-Inducible Factor-1 Target Genes as Indicators of Tumor Vessel Response to Vascular Endothelial Growth Factor Inhibition," Cancer Res., 68(6):1872-1880 (2008).
Di Martile, M. et al., "The multifaceted role of lysine acetylation in cancer: prognostic biomarker and therapeutic target," Oncotarget, 7(34):55789-55810 (2016).
Dutta, R. et al., "CBP/p300 acetyltransferase activity in hematologic malignancies," Molecular Genetics and Metabolism, 119:37-43 (2016).
Eisenhauer, E. A. et al., "New response evaluation criteria in solid tumours: Revised RECIST guideline (version 1.1)," European Journal of Cancer, 45:228-247 (2009).
Fera, D. & Marmorstein, R., "Different Regions of the HPV-E7 and Ad-E1A Viral Oncoproteins Bind Competitively but through Distinct Mechanisms to the CH1 Transactivation Domain of p300," Biochemistry, 51:9524-9534 (2012).
Fleisher, D. et al., "Improved oral drug delivery: solubility limitations overcome by the use of prodrugs," Advanced Drug Delivery Reviews, 19:115-130 (1996).
GenBank Accession No. NP001420.2, histone acetyltransferase p300 isoform 1 [*homo sapiens*], Feb. 26, 2019, 13 pages.
Goodman, R. H. & Smolik, S., "CBP/p300 in cell growth, transformation, and development," Genes & Development, 14:1553-1577 (2000).
Hottiger, M. O. et al., "Modulation of cytokine-induced HIV gene expression by competitive binding of transcription factors to the coactivator p300," The EMBO Journal, 17(11):3124-3134 (1998).
Kamei, Y. et al., "A CBP Integrator Complex Mediates Transcriptional Activation and AP-1 Inhibition by Nuclear Receptors," Cell, 85:403-414 (1996).
Kushal, S. et al., "Protein domain mimetics as in vivo modulators of hypoxia-inducible factor signaling," PNAS, 110(39):15602-15607 (2013).
Lao, B. B. et al., "In vivo modulation of hypoxia-inducible signaling by topographical helix mimetics," PNAS, 111(21):7531-7536 (2014).
Lao, B. B. et al., "Rational Design of Topographical Helix Mimics as Potent Inhibitors of Protein-Protein Interactions," J. Am. Chem. Soc., 136:7877-7888 (2014).
Lee, C. -W. et al., "Functional interplay between p53 and E2F through co-activator p300," Oncogene, 16:2695-2710 (1998).
Li, Y. et al., "Selective killing of cancer cells by β-lapachone: Direct checkpoint activation as a strategy against cancer," PNAS, 100(5):2674-2678 (2003).
Massoud, G. N. & Li, W., "HIF-1α pathway: role regulation and intervention for cancer therapy," Acta Pharm Sin B., 5(5):378-389 (2015).
Nakajima, T. et al., "The Signal-Dependent Coactivator CBP is a Nuclear Target for $pp90_{RSK}$," Cell, 86:465-474 (1996).
Nielsen, N. M. & Bundgaard, H., "Glycolamide Esters as Biolabile Prodrugs of Carboxylic Acid Agents: Synthesis, Stability, Bioconversion, and Physicochemical Properties," Journal of Pharmaceutical Sciences, 77(4):285-298 (1988).
Patel, D. et al., "The E6 protein of human papillomavirus type 16 binds to and inhibits co-activation by CBP and p300," The EMBO Journal, 18(18):5061-5072 (1999).
Pearson, W. R. & Lipman, D. J., "Improved tools for biological sequence comparison," Proc. Natl. Acad. Sci. USA, 85:2444-2448 (1988).
Robinson, R. P. et al., "Discovery of the Hemifumarate and (α-L-Alanyloxy)methyl Ether as Prodrugs of an Antirheumatic Oxindole: Prodrugs for the Enolic OH Group," J. Med. Chem., 39:10-18 (1996).
Saulnier, M. G. et al., "An Efficient Method for the Synthesis of Guanidino Prodrugs," Bioorganic & Medicinal Chemistry Letters, 4(16):1985-1990 (1994).
Tornesello, M. L. et al., "Human Oncoviruses and p53 Tumor Suppressor Pathway Deregulation at the Origin of Human Cancers," Cancers, 10, 213 (2018); doi:10.3390/cancers10070213, 14 pages.
Tošovská, P. & Arora, P.S., "Oligooxopiperazines as Nonpeptidic α-Helix Mimetics," Organic Letters, 12(7):1588-1591 (2010).
Wright, P. E. & Dyson, H. J., "Intrinsically disordered proteins in cellular signalling and regulation," Nat Rev Mol Cell Biol., 16(1):18-29 (2015).
Xie, X. et al., "Targeting HPV16 E6-p300 interaction reactivates p53 and inhibits the tumorigenicity of HPV-positive head and neck squamous cell carcinoma," Oncogene, 33(8):1037-1046 (2014).
Yuan, W. L. & Giordano, A., "Acetyltransferase machinery conserved in p300/CBP-family proteins," Oncogene, 21:2253-2260 (2002).

* cited by examiner

PROLIFERATION CURVES FOR LYMPHOMA CELL LINES a) KARPAS-299 b) KARPAS-422 c) RAMOS d) DAUDI e) RAJI f) GRANTA-519

SEQUENCE LISTING

<160> NUMBER OF SEQ ID NOS: 2

<210> SEQ ID NO 1
<211> LENGTH: 2414
<212> TYPE: PRT
<213> ORGANISM: homo sapiens

<400> SEQUENCE: 1

Met Ala Glu Asn Val Val Glu Pro Gly Pro Pro Ser Ala Lys Arg Pro

-continued

```
1               5                   10                  15
Lys Leu Ser Ser Pro Ala Leu Ser Ala Ser Asp Gly Thr Asp
            20                  25                  30

Phe Gly Ser Leu Phe Asp Leu Glu His Asp Leu Pro Asp Glu Leu Ile
                35                  40                  45

Asn Ser Thr Glu Leu Gly Leu Thr Asn Gly Gly Asp Ile Asn Gln Leu
 50                  55                  60

Gln Thr Ser Leu Gly Met Val Gln Asp Ala Ala Ser Lys His Lys Gln
 65                  70                  75                  80

Leu Ser Glu Leu Leu Arg Ser Gly Ser Pro Asn Leu Asn Met Gly
                85                  90                  95

Val Gly Gly Pro Gly Gln Val Met Ala Ser Gln Ala Gln Gln Ser Ser
                100                 105                 110

Pro Gly Leu Gly Leu Ile Asn Ser Met Val Lys Ser Pro Met Thr Gln
                115                 120                 125

Ala Gly Leu Thr Ser Pro Asn Met Gly Met Gly Thr Ser Gly Pro Asn
130                 135                 140

Gln Gly Pro Thr Gln Ser Thr Gly Met Met Asn Ser Pro Val Asn Gln
145                 150                 155                 160

Pro Ala Met Gly Met Asn Thr Gly Met Asn Ala Gly Met Asn Pro Gly
                165                 170                 175

Met Leu Ala Ala Gly Asn Gly Gln Gly Ile Met Pro Asn Gln Val Met
                180                 185                 190

Asn Gly Ser Ile Gly Ala Gly Arg Gly Arg Gln Asn Met Gln Tyr Pro
                195                 200                 205

Asn Pro Gly Met Gly Ser Ala Gly Asn Leu Leu Thr Glu Pro Leu Gln
                210                 215                 220

Gln Gly Ser Pro Gln Met Gly Gly Gln Thr Gly Leu Arg Gly Pro Gln
225                 230                 235                 240

Pro Leu Lys Met Gly Met Met Asn Asn Pro Asn Pro Tyr Gly Ser Pro
                245                 250                 255

Tyr Thr Gln Asn Pro Gly Gln Gln Ile Gly Ala Ser Gly Leu Gly Leu
                260                 265                 270

Gln Ile Gln Thr Lys Thr Val Leu Ser Asn Asn Leu Ser Pro Phe Ala
                275                 280                 285

Met Asp Lys Lys Ala Val Pro Gly Gly Met Pro Asn Met Gly Gln
                290                 295                 300

Gln Pro Ala Pro Gln Val Gln Gln Pro Gly Leu Val Thr Pro Val Ala
305                 310                 315                 320

Gln Gly Met Gly Ser Gly Ala His Thr Ala Asp Pro Glu Lys Arg Lys
                325                 330                 335

Leu Ile Gln Gln Gln Leu Val Leu Leu Leu His Ala His Lys Cys Gln
                340                 345                 350

Arg Arg Glu Gln Ala Asn Gly Glu Val Arg Gln Cys Asn Leu Pro His
                355                 360                 365

Cys Arg Thr Met Lys Asn Val Leu Asn His Met Thr His Cys Gln Ser
                370                 375                 380

Gly Lys Ser Cys Gln Val Ala His Cys Ala Ser Ser Arg Gln Ile Ile
385                 390                 395                 400

Ser His Trp Lys Asn Cys Thr Arg His Asp Cys Pro Val Cys Leu Pro
                405                 410                 415

Leu Lys Asn Ala Gly Asp Lys Arg Asn Gln Gln Pro Ile Leu Thr Gly
                420                 425                 430
```

```
Ala Pro Val Gly Leu Gly Asn Pro Ser Ser Leu Gly Val Gly Gln Gln
        435                 440                 445

Ser Ala Pro Asn Leu Ser Thr Val Ser Gln Ile Asp Pro Ser Ser Ile
450                 455                 460

Glu Arg Ala Tyr Ala Ala Leu Gly Leu Pro Tyr Gln Val Asn Gln Met
465                 470                 475                 480

Pro Thr Gln Pro Gln Val Gln Ala Lys Asn Gln Gln Asn Gln Gln Pro
                485                 490                 495

Gly Gln Ser Pro Gln Gly Met Arg Pro Met Ser Asn Met Ser Ala Ser
                500                 505                 510

Pro Met Gly Val Asn Gly Gly Val Gly Val Gln Thr Pro Ser Leu Leu
        515                 520                 525

Ser Asp Ser Met Leu His Ser Ala Ile Asn Ser Gln Asn Pro Met Met
530                 535                 540

Ser Glu Asn Ala Ser Val Pro Ser Leu Gly Pro Met Pro Thr Ala Ala
545                 550                 555                 560

Gln Pro Ser Thr Thr Gly Ile Arg Lys Gln Trp His Glu Asp Ile Thr
                565                 570                 575

Gln Asp Leu Arg Asn His Leu Val His Lys Leu Val Gln Ala Ile Phe
                580                 585                 590

Pro Thr Pro Asp Pro Ala Ala Leu Lys Asp Arg Arg Met Glu Asn Leu
        595                 600                 605

Val Ala Tyr Ala Arg Lys Val Glu Gly Asp Met Tyr Glu Ser Ala Asn
        610                 615                 620

Asn Arg Ala Glu Tyr Tyr His Leu Leu Ala Glu Lys Ile Tyr Lys Ile
625                 630                 635                 640

Gln Lys Glu Leu Glu Glu Lys Arg Arg Thr Arg Leu Gln Lys Gln Asn
                645                 650                 655

Met Leu Pro Asn Ala Ala Gly Met Val Pro Val Ser Met Asn Pro Gly
                660                 665                 670

Pro Asn Met Gly Gln Pro Gln Pro Gly Met Thr Ser Asn Gly Pro Leu
        675                 680                 685

Pro Asp Pro Ser Met Ile Arg Gly Ser Val Pro Asn Gln Met Met Pro
        690                 695                 700

Arg Ile Thr Pro Gln Ser Gly Leu Asn Gln Phe Gly Gln Met Ser Met
705                 710                 715                 720

Ala Gln Pro Pro Ile Val Pro Arg Gln Thr Pro Pro Leu Gln His His
                725                 730                 735

Gly Gln Leu Ala Gln Pro Gly Ala Leu Asn Pro Pro Met Gly Tyr Gly
        740                 745                 750

Pro Arg Met Gln Gln Pro Ser Asn Gln Gly Gln Phe Leu Pro Gln Thr
        755                 760                 765

Gln Phe Pro Ser Gln Gly Met Asn Val Thr Asn Ile Pro Leu Ala Pro
        770                 775                 780

Ser Ser Gly Gln Ala Pro Val Ser Gln Ala Gln Met Ser Ser Ser Ser
785                 790                 795                 800

Cys Pro Val Asn Ser Pro Ile Met Pro Pro Gly Ser Gln Gly Ser His
                805                 810                 815

Ile His Cys Pro Gln Leu Pro Gln Pro Ala Leu His Gln Asn Ser Pro
                820                 825                 830

Ser Pro Val Pro Ser Arg Thr Pro Thr Pro His Thr Pro Pro Ser
        835                 840                 845
```

```
Ile Gly Ala Gln Gln Pro Pro Ala Thr Thr Ile Pro Ala Pro Val Pro
850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
            885                 890                 895

Val Gln Pro Ser Leu Pro Ala Ala Pro Ser Ala Asp Gln Pro Gln Gln
                900                 905                 910

Gln Pro Arg Ser Gln Gln Ser Thr Ala Ala Ser Val Pro Thr Pro Thr
            915                 920                 925

Ala Pro Leu Leu Pro Pro Gln Pro Ala Thr Pro Leu Ser Gln Pro Ala
930                 935                 940

Val Ser Ile Glu Gly Gln Val Ser Asn Pro Pro Ser Thr Ser Ser Thr
945                 950                 955                 960

Glu Val Asn Ser Gln Ala Ile Ala Glu Lys Gln Pro Ser Gln Glu Val
                965                 970                 975

Lys Met Glu Ala Lys Met Glu Val Asp Gln Pro Glu Pro Ala Asp Thr
            980                 985                 990

Gln Pro Glu Asp Ile Ser Glu Ser Lys Val Glu Asp Cys Lys Met Glu
            995                 1000                1005

Ser Thr Glu Thr Glu Glu Arg Ser Thr Glu Leu Lys Thr Glu Ile
    1010                1015                1020

Lys Glu Glu Asp Gln Pro Ser Thr Ser Ala Thr Gln Ser Ser
    1025                1030                1035

Pro Ala Pro Gly Gln Ser Lys Lys Lys Ile Phe Lys Pro Glu Glu
    1040                1045                1050

Leu Arg Gln Ala Leu Met Pro Thr Leu Glu Ala Leu Tyr Arg Gln
    1055                1060                1065

Asp Pro Glu Ser Leu Pro Phe Arg Gln Pro Val Asp Pro Gln Leu
    1070                1075                1080

Leu Gly Ile Pro Asp Tyr Phe Asp Ile Val Lys Ser Pro Met Asp
    1085                1090                1095

Leu Ser Thr Ile Lys Arg Lys Leu Asp Thr Gly Gln Tyr Gln Glu
    1100                1105                1110

Pro Trp Gln Tyr Val Asp Asp Ile Trp Leu Met Phe Asn Asn Ala
    1115                1120                1125

Trp Leu Tyr Asn Arg Lys Thr Ser Arg Val Tyr Lys Tyr Cys Ser
    1130                1135                1140

Lys Leu Ser Glu Val Phe Glu Gln Glu Ile Asp Pro Val Met Gln
    1145                1150                1155

Ser Leu Gly Tyr Cys Cys Gly Arg Lys Leu Glu Phe Ser Pro Gln
    1160                1165                1170

Thr Leu Cys Cys Tyr Gly Lys Gln Leu Cys Thr Ile Pro Arg Asp
    1175                1180                1185

Ala Thr Tyr Tyr Ser Tyr Gln Asn Arg Tyr His Phe Cys Glu Lys
    1190                1195                1200

Cys Phe Asn Glu Ile Gln Gly Glu Ser Val Ser Leu Gly Asp Asp
    1205                1210                1215

Pro Ser Gln Pro Gln Thr Thr Ile Asn Lys Glu Gln Phe Ser Lys
    1220                1225                1230

Arg Lys Asn Asp Thr Leu Asp Pro Glu Leu Phe Val Glu Cys Thr
    1235                1240                1245

Glu Cys Gly Arg Lys Met His Gln Ile Cys Val Leu His His Glu
```

-continued

```
            1250                1255                1260
Ile Ile Trp Pro Ala Gly Phe Val Cys Asp Gly Cys Leu Lys Lys
        1265                1270                1275
Ser Ala Arg Thr Arg Lys Glu Asn Lys Phe Ser Ala Lys Arg Leu
        1280                1285                1290
Pro Ser Thr Arg Leu Gly Thr Phe Leu Glu Asn Arg Val Asn Asp
        1295                1300                1305
Phe Leu Arg Arg Gln Asn His Pro Glu Ser Gly Glu Val Thr Val
        1310                1315                1320
Arg Val Val His Ala Ser Asp Lys Thr Val Glu Val Lys Pro Gly
        1325                1330                1335
Met Lys Ala Arg Phe Val Asp Ser Gly Glu Met Ala Glu Ser Phe
        1340                1345                1350
Pro Tyr Arg Thr Lys Ala Leu Phe Ala Phe Glu Glu Ile Asp Gly
        1355                1360                1365
Val Asp Leu Cys Phe Phe Gly Met His Val Gln Glu Tyr Gly Ser
        1370                1375                1380
Asp Cys Pro Pro Pro Asn Gln Arg Arg Val Tyr Ile Ser Tyr Leu
        1385                1390                1395
Asp Ser Val His Phe Phe Arg Pro Lys Cys Leu Arg Thr Ala Val
        1400                1405                1410
Tyr His Glu Ile Leu Ile Gly Tyr Leu Glu Tyr Val Lys Lys Leu
        1415                1420                1425
Gly Tyr Thr Thr Gly His Ile Trp Ala Cys Pro Pro Ser Glu Gly
        1430                1435                1440
Asp Asp Tyr Ile Phe His Cys His Pro Pro Asp Gln Lys Ile Pro
        1445                1450                1455
Lys Pro Lys Arg Leu Gln Glu Trp Tyr Lys Lys Met Leu Asp Lys
        1460                1465                1470
Ala Val Ser Glu Arg Ile Val His Asp Tyr Lys Asp Ile Phe Lys
        1475                1480                1485
Gln Ala Thr Glu Asp Arg Leu Thr Ser Ala Lys Glu Leu Pro Tyr
        1490                1495                1500
Phe Glu Gly Asp Phe Trp Pro Asn Val Leu Glu Glu Ser Ile Lys
        1505                1510                1515
Glu Leu Glu Gln Glu Glu Glu Glu Arg Lys Arg Glu Glu Asn Thr
        1520                1525                1530
Ser Asn Glu Ser Thr Asp Val Thr Lys Gly Asp Ser Lys Asn Ala
        1535                1540                1545
Lys Lys Lys Asn Asn Lys Lys Thr Ser Lys Asn Lys Ser Ser Leu
        1550                1555                1560
Ser Arg Gly Asn Lys Lys Pro Gly Met Pro Asn Val Ser Asn
        1565                1570                1575
Asp Leu Ser Gln Lys Leu Tyr Ala Thr Met Glu Lys His Lys Glu
        1580                1585                1590
Val Phe Phe Val Ile Arg Leu Ile Ala Gly Pro Ala Ala Asn Ser
        1595                1600                1605
Leu Pro Pro Ile Val Asp Pro Asp Pro Leu Ile Pro Cys Asp Leu
        1610                1615                1620
Met Asp Gly Arg Asp Ala Phe Leu Thr Leu Ala Arg Asp Lys His
        1625                1630                1635
Leu Glu Phe Ser Ser Leu Arg Arg Ala Gln Trp Ser Thr Met Cys
        1640                1645                1650
```

```
Met Leu Val Glu Leu His Thr Gln Ser Gln Asp Arg Phe Val Tyr
    1655                1660                1665

Thr Cys Asn Glu Cys Lys His His Val Glu Thr Arg Trp His Cys
    1670                1675                1680

Thr Val Cys Glu Asp Tyr Asp Leu Cys Ile Thr Cys Tyr Asn Thr
    1685                1690                1695

Lys Asn His Asp His Lys Met Glu Lys Leu Gly Leu Gly Leu Asp
    1700                1705                1710

Asp Glu Ser Asn Asn Gln Gln Ala Ala Ala Thr Gln Ser Pro Gly
    1715                1720                1725

Asp Ser Arg Arg Leu Ser Ile Gln Arg Cys Ile Gln Ser Leu Val
    1730                1735                1740

His Ala Cys Gln Cys Arg Asn Ala Asn Cys Ser Leu Pro Ser Cys
    1745                1750                1755

Gln Lys Met Lys Arg Val Val Gln His Thr Lys Gly Cys Lys Arg
    1760                1765                1770

Lys Thr Asn Gly Gly Cys Pro Ile Cys Lys Gln Leu Ile Ala Leu
    1775                1780                1785

Cys Cys Tyr His Ala Lys His Cys Gln Glu Asn Lys Cys Pro Val
    1790                1795                1800

Pro Phe Cys Leu Asn Ile Lys Gln Lys Leu Arg Gln Gln Gln Leu
    1805                1810                1815

Gln His Arg Leu Gln Gln Ala Gln Met Leu Arg Arg Arg Met Ala
    1820                1825                1830

Ser Met Gln Arg Thr Gly Val Val Gly Gln Gln Gln Gly Leu Pro
    1835                1840                1845

Ser Pro Thr Pro Ala Thr Pro Thr Thr Pro Thr Gly Gln Gln Pro
    1850                1855                1860

Thr Thr Pro Gln Thr Pro Gln Pro Thr Ser Gln Pro Gln Pro Thr
    1865                1870                1875

Pro Pro Asn Ser Met Pro Pro Tyr Leu Pro Arg Thr Gln Ala Ala
    1880                1885                1890

Gly Pro Val Ser Gln Gly Lys Ala Ala Gly Gln Val Thr Pro Pro
    1895                1900                1905

Thr Pro Pro Gln Thr Ala Gln Pro Pro Leu Pro Gly Pro Pro Pro
    1910                1915                1920

Ala Ala Val Glu Met Ala Met Gln Ile Gln Arg Ala Ala Glu Thr
    1925                1930                1935

Gln Arg Gln Met Ala His Val Gln Ile Phe Gln Arg Pro Ile Gln
    1940                1945                1950

His Gln Met Pro Pro Met Thr Pro Met Ala Pro Met Gly Met Asn
    1955                1960                1965

Pro Pro Pro Met Thr Arg Gly Pro Ser Gly His Leu Glu Pro Gly
    1970                1975                1980

Met Gly Pro Thr Gly Met Gln Gln Gln Pro Pro Trp Ser Gln Gly
    1985                1990                1995

Gly Leu Pro Gln Pro Gln Gln Leu Gln Ser Gly Met Pro Arg Pro
    2000                2005                2010

Ala Met Met Ser Val Ala Gln His Gly Gln Pro Leu Asn Met Ala
    2015                2020                2025

Pro Gln Pro Gly Leu Gly Gln Val Gly Ile Ser Pro Leu Lys Pro
    2030                2035                2040
```

```
Gly Thr Val Ser Gln Gln Ala Leu Gln Asn Leu Leu Arg Thr Leu
    2045                2050                2055

Arg Ser Pro Ser Ser Pro Leu Gln Gln Gln Gln Val Leu Ser Ile
2060                2065                2070

Leu His Ala Asn Pro Gln Leu Leu Ala Ala Phe Ile Lys Gln Arg
    2075                2080                2085

Ala Ala Lys Tyr Ala Asn Ser Asn Pro Gln Pro Ile Pro Gly Gln
2090                2095                2100

Pro Gly Met Pro Gln Gly Gln Pro Gly Leu Gln Pro Pro Thr Met
    2105                2110                2115

Pro Gly Gln Gln Gly Val His Ser Asn Pro Ala Met Gln Asn Met
    2120                2125                2130

Asn Pro Met Gln Ala Gly Val Gln Arg Ala Gly Leu Pro Gln Gln
    2135                2140                2145

Gln Pro Gln Gln Gln Leu Gln Pro Pro Met Gly Gly Met Ser Pro
    2150                2155                2160

Gln Ala Gln Gln Met Asn Met Asn His Asn Thr Met Pro Ser Gln
    2165                2170                2175

Phe Arg Asp Ile Leu Arg Arg Gln Gln Met Met Gln Gln Gln Gln
    2180                2185                2190

Gln Gln Gly Ala Gly Pro Gly Ile Gly Pro Gly Met Ala Asn His
    2195                2200                2205

Asn Gln Phe Gln Gln Pro Gln Gly Val Gly Tyr Pro Pro Gln Gln
    2210                2215                2220

Gln Gln Arg Met Gln His His Met Gln Gln Met Gln Gln Gly Asn
    2225                2230                2235

Met Gly Gln Ile Gly Gln Leu Pro Gln Ala Leu Gly Ala Glu Ala
    2240                2245                2250

Gly Ala Ser Leu Gln Ala Tyr Gln Gln Arg Leu Leu Gln Gln Gln
    2255                2260                2265

Met Gly Ser Pro Val Gln Pro Asn Pro Met Ser Pro Gln Gln His
    2270                2275                2280

Met Leu Pro Asn Gln Ala Gln Ser Pro His Leu Gln Gly Gln Gln
    2285                2290                2295

Ile Pro Asn Ser Leu Ser Asn Gln Val Arg Ser Pro Gln Pro Val
    2300                2305                2310

Pro Ser Pro Arg Pro Gln Ser Gln Pro Pro His Ser Ser Pro Ser
    2315                2320                2325

Pro Arg Met Gln Pro Gln Pro Ser Pro His His Val Ser Pro Gln
    2330                2335                2340

Thr Ser Ser Pro His Pro Gly Leu Val Ala Ala Gln Ala Asn Pro
    2345                2350                2355

Met Glu Gln Gly His Phe Ala Ser Pro Asp Gln Asn Ser Met Leu
    2360                2365                2370

Ser Gln Leu Ala Ser Asn Pro Gly Met Ala Asn Leu His Gly Ala
    2375                2380                2385

Ser Ala Thr Asp Leu Gly Leu Ser Thr Asp Asn Ser Asp Leu Asn
    2390                2395                2400

Ser Asn Leu Ser Gln Ser Thr Leu Asp Ile His
    2405                2410
```

<210> SEQ ID NO 2
<211> LENGTH: 8779
<212> TYPE: DNA

<213> ORGANISM: homo sapiens

<400> SEQUENCE: 2

```
gagaaggagg aggacagcgc cgaggaggaa gaggttgatg gcggcggcgg agctccgaga        60
gacctcggct gggcagggc cggccgtggc gggccgggga ctgcgcctct agagccgcga       120
gttctcggga attcgccgca gcggacgcgc tcggcgaatt tgtgctcttg tgccctcctc       180
cgggcttggg cccaggcccg gcccctcgca cttgccctta ccttttctat cgagtccgca       240
tccctctcca gccactgcga cccggcgaag agaaaaagga acttccccca ccccctcggg       300
tgccgtcgga gcccccagc ccaccctgg gtgcggcgcg gggacccgg gccgaagaag         360
agatttcctg aggattctgg ttttcctcgc ttgtatctcc gaaagaatta aaaatggccg       420
agaatgtggt ggaaccgggg ccgccttcag ccaagcggcc taaactctca tctccggccc       480
tctcggcgtc cgccagcgat ggcacagatt ttggctctct atttgacttg gagcacgact       540
taccagatga attaatcaac tctacagaat tgggactaac caatggtggt gatattaatc       600
agcttcagac aagtcttggc atggtacaag atgcagcttc taaacataaa cagctgtcag       660
aattgctgcg atctggtagt tcccctaacc tcaatatggg agttggtggc ccaggtcaag       720
tcatggccag ccaggcccaa cagagcagtc ctggattagg tttgataaat agcatggtca       780
aaagcccaat gacacaggca ggcttgactt ctcccaacat ggggatgggc actagtggac       840
caaatcaggg tcctacgcag tcaacaggta tgatgaacag tccagtaaat cagcctgcca       900
tgggaatgaa cacagggatg aatgcgggca tgaatcctgg aatgttggct gcaggcaatg       960
gacaagggat aatgcctaat caagtcatga acggttcaat tggagcaggc cgagggcgac      1020
agaatatgca gtacccaaac ccaggcatgg gaagtgctgg caacttactg actgagcctc      1080
ttcagcaggg ctctccccag atgggaggac aaacaggatt gagaggcccc cagcctctta      1140
agatgggaat gatgaacaac cccaatcctt atggttcacc atatactcag aatcctggac      1200
agcagattgg agccagtggc cttggtctcc agattcagac aaaaactgta ctatcaaata      1260
acttatctcc atttgctatg gacaaaaagg cagttcctgg tggaggaatg cccaacatgg      1320
gtcaacagcc agccccgcag gtccagcagc caggcctggt gactccagtt gcccaaggga      1380
tgggttctgg agcacataca gctgatccag agaagcgcaa gctcatccag cagcagcttg      1440
ttcttcctttt gcatgctcac aagtgccagc gcgggaaca ggccaatggg gaagtgaggc      1500
agtgcaacct tcccccactgt cgcacaatga agaatgtcct aaaccacatg acacactgcc      1560
agtcaggcaa gtcttgccaa gtggcacact gtgcatcttc tcgacaaatc atttcacact      1620
ggaagaattg tacaagacat gattgtcctg tgtgtctccc cctcaaaaat gctggtgata      1680
agagaaatca acagccaatt ttgactggag caccgttgg acttggaaat cctagctctc      1740
tagggggtggg tcaacagtct gcccccaacc taagcactgt tagtcagatt gatcccagct      1800
ccatagaaag agcctatgca gctcttggac taccctatca agtaaatcag atgccgacac      1860
aaccccaggt gcaagcaaag aaccagcaga atcagcagcc tggcagtct ccccaaggca      1920
tgcggcccat gagcaacatg agtgctagtc ctatgggagt aaatggaggt gtaggagttc      1980
aaacgccgag tcttctttct gactcaatgt tgcattcagc cataaattct caaaacccaa      2040
tgatgagtga aaatgccagt gtgccctccc tgggtcctat gccaacagca gctcaaccat      2100
ccactactgg aattcggaaa cagtggcacg aagatattac tcaggatctt cgaaatcatc      2160
ttgttcacaa actcgtccaa gccatatttc ctacgccgga tctgctgct ttaaaagaca      2220
gacggatgga aaacctagtt gcatatgctc ggaaagttga aggggacatg tatgaatctg      2280
```

```
caaacaatcg agcggaatac taccaccttc tagctgagaa aatctataag atccagaaag    2340
aactagaaga aaaacgaagg accagactac agaagcagaa catgctacca aatgctgcag    2400
gcatggttcc agtttccatg aatccagggc ctaacatggg acagccgcaa ccaggaatga    2460
cttctaatgg ccctctacct gacccaagta tgatccgtgg cagtgtgcca aaccagatga    2520
tgcctcgaat aactccacaa tctggtttga atcaatttgg ccagatgagc atggcccagc    2580
cccctattgt accccggcaa accccctcctc ttcagcacca tggacagttg gctcaacctg    2640
gagctctcaa cccgcctatg ggctatgggc ctcgtatgca acagccttcc aaccagggcc    2700
agttccttcc tcagactcag ttcccatcac agggaatgaa tgtaacaaat atcccttttgg   2760
ctccgtccag cggtcaagct ccagtgtctc aagcacaaat gtctagttct tcctgcccgg    2820
tgaactctcc tataatgcct ccagggtctc aggggagcca cattcactgt ccccagcttc    2880
ctcaaccagc tcttcatcag aattcaccct cgcctgtacc tagtcgtacc cccacccctc    2940
accatactcc cccaagcata ggggctcagc agccaccagc aacaacaatt ccagcccctg    3000
ttcctacacc tcctgccatg ccacctgggc cacagtccca ggctctacat cccctccaa    3060
ggcagacacc tacaccacca acaacacaac ttccccaaca agtgcagcct tcacttcctg    3120
ctgcaccttc tgctgaccag ccccagcagc agcctcgctc acagcagagc acagcagcgt    3180
ctgttcctac cccaacagca ccgctgcttc tccgcagcc tgcaactcca ctttcccagc    3240
cagctgtaag cattgaagga caggtatcaa atcctccatc tactagtagc acagaagtga    3300
attctcaggc cattgctgag aagcagcctt cccaggaagt gaagatggag gccaaaatgg    3360
aagtggatca accagaacca gcagatactc agccggagga tatttcagag tctaaagtgg    3420
aagactgtaa aatggaatct accgaaacag aagagagaag cactgagtta aaaactgaaa    3480
taaaagagga ggaagaccag ccaagtactt cagctaccca gtcatctccg gctccaggac    3540
agtcaaagaa aaagatttttc aaaccagaag aactacgaca ggcactgatg ccaactttgg    3600
aggcactttta ccgtcaggat ccagaatccc ttcccttttcg tcaacctgtg accctcagc    3660
ttttaggaat ccctgattac tttgatattg tgaagagccc catggatctt tctaccatta    3720
agaggaagtt agacactgga cagtatcagg agccctggca gtatgtcgat gatatttggc    3780
ttatgttcaa taatgcctgg ttatataacc ggaaaacatc acgggtatac aaatactgct    3840
ccaagctctc tgaggtcttt gaacaagaaa ttgacccagt gatgcaaagc cttggatact    3900
gttgtggcag aaagttggag ttctctccac agacactgtg ttgctacggc aaacagttgt    3960
gcacaatacc tcgtgatgcc acttattaca gttaccagaa caggtatcat ttctgtgaga    4020
agtgtttcaa tgagatccaa ggggagagcg tttctttggg ggatgaccct tcccagcctc    4080
aaactacaat aaataaagaa caattttcca agagaaaaaa tgacacactg gatcctgaac    4140
tgtttgttga atgtacagag tgcggaagaa agatgcatca gatctgtgtc cttcaccatg    4200
agatcatctg gcctgctgga ttcgtctgtg atggctgttt aaagaaaagt gcacgaacta    4260
ggaaagaaaa taagttttct gctaaaaggt tgccatctac cagacttggc acctttctag    4320
agaatcgtgt gaatgacttt ctgaggcgac agaatcaccc tgagtcagga gaggtcactg    4380
ttagagtagt tcatgcttct gacaaaaccg tggaagtaaa accaggcatg aaagcaaggt    4440
tgtggacag tggagagatg gcagaatcct ttccataccg aaccaaagcc ctctttgcct    4500
ttgaagaaat tgatggtgtt gacctgtgct tctttggcat gcatgttcaa gagtatggct    4560
ctgactgccc tccacccaac cagaggagag tatacatatc ttacctcgat agtgttcatt    4620
```

```
tcttccgtcc taaatgcttg aggactgcag tctatcatga atcctaatt ggatatttag    4680 aatatgtcaa gaaattaggt tacacaacag gcatatttg gcatgtcca ccaagtgagg     4740 gagatgatta tatcttccat tgccatcctc ctgaccagaa gatacccaag cccaagcgac   4800
tgcaggaatg gtacaaaaaa atgcttgaca aggctgtatc agagcgtatt gtccatgact   4860
acaaggatat ttttaaacaa gctactgaag atagattaac aagtgcaaag gaattgcctt   4920
atttcgaggg tgatttctgg cccaatgttc tggaagaaag cattaaggaa ctggaacagg   4980
aggaagaaga gagaaaacga gaggaaaaca ccagcaatga aagcacagat gtgaccaagg   5040
gagacagcaa aaatgctaaa aagaagaata ataagaaaac cagcaaaaat aagagcagcc   5100
tgagtagggg caacaagaag aaacccggga tgcccaatgt atctaacgac ctctcacaga   5160
aactatatgc caccatggag aagcataaag aggtcttctt tgtgatccgc ctcattgctg   5220
gccctgctgc caactccctg cctcccattg ttgatcctga tcctctcatc ccctgcgatc   5280
tgatggatgg tcgggatgcg tttctcacgc tggcaaggga caagcacctg gagttctctt   5340
cactccgaag agcccagtgg tccaccatgt gcatgctggt ggagctgcac acgcagagcc   5400
aggaccgctt tgtctacacc tgcaatgaat gcaagcacca tgtggagaca cgctggcact   5460
gtactgtctg tgaggattat gacttgtgta tcacctgcta taacactaaa aaccatgacc   5520
acaaaatgga gaaactaggc cttggcttag atgatgagag caacaaccag caggctgcag   5580
ccacccagag cccaggcgat tctcgccgcc tgagtatcca gcgctgcatc cagtctctgg   5640
tccatgcttg ccagtgtcgg aatgccaatt gctcactgcc atcctgccag aagatgaagc   5700
gggttgtgca gcataccaag ggttgcaaac ggaaaaccaa tggcgggtgc cccatctgca   5760
agcagctcat tgccctctgc tgctaccatg ccaagcactg ccaggagaac aaatgcccgg   5820
tgccgttctg cctaaacatc aagcagaagc tccggcagca acagctgcag caccgactac   5880
agcaggccca aatgcttcgc aggaggatgg ccagcatgca gcggactggt gtggttgggc   5940
agcaacaggg cctcccttcc cccactcctg ccactccaac gacaccaact ggccaacagc   6000
caaccacccc gcagacgccc cagcccactt ctcagcctca gcctacccct cccaatagca   6060
tgccacccta cttgcccagg actcaagctg ctggccctgt gtcccagggt aaggcagcag   6120
gccaggtgac ccctccaacc cctcctcaga ctgctcagcc accccttcca gggcccccac   6180
ctgcagcagt ggaaatggca atgcagattc agagagcagc ggagacgcag cgccagatgg   6240
cccacgtgca aattttttcaa aggccaatcc aacaccagat gccccgatg actcccatgg   6300 cccccatggg tatgaaccca cctcccatga ccagaggtcc cagtgggcat ttggagccag   6360
ggatgggacc gacagggatg cagcaacagc caccctggag ccaaggagga ttgcctcagc   6420
cccagcaact acagtctggg atgccaaggc cagccatgat gtcagtggcc cagcatggtc   6480
aacctttgaa catggctcca caaccaggat tgggccaggt aggtatcagc ccactcaaac   6540
caggcactgt gtctcaacaa gccttacaaa acctttgcg gactctcagg tctcccagct   6600
ctcccctgca gcagcaacag gtgcttagta tccttcacgc caacccccag ctgttggctg   6660
cattcatcaa gcagcgggct gccaagtatg ccaactctaa tccacaaccc atccctgggc   6720
agcctggcat gccccagggg cagccagggc tacagccacc taccatgcca ggtcagcagg   6780
gggtccactc caatccagcc atgcagaaca tgaatccaat gcaggcgggc gttcagaggg   6840
ctggcctgcc ccagcagcaa ccacagcagc aactccagcc acccatggga gggatgagcc   6900
cccaggctca gcagatgaac atgaaccaca acaccatgcc ttcacaattc cgagacatct   6960
tgagacgaca gcaaatgatg caacagcagc agcaacaggg agcagggcca ggaataggcc   7020
```

```
ctggaatggc caaccataac cagttccagc aacccoaagg agttggctac ccaccacagc    7080
agcagcagcg gatgcagcat cacatgcaac agatgcaaca aggaaatatg ggacagatag    7140
gccagcttcc ccaggccttg ggagcagagg caggtgccag tctacaggcc tatcagcagc    7200
gactccttca gcaacagatg gggtcccctg ttcagcccaa ccccatgagc ccccagcagc    7260
atatgctccc aaatcaggcc cagtcoccac acctacaagg ccagcagatc cctaattctc    7320
tctccaatca agtgcgctct ccccagcctg tccctcttcc acggccacag tcccagcccc    7380
cccactccag tccttcccca aggatgcagc ctcagccttc tccacaccac gtttccccac    7440
agacaagttc cccacatcct ggactggtag ctgcccaggc caaccccatg gaacaagggc    7500
attttgccag cccggaccag aattcaatgc tttctcagct tgctagcaat ccaggcatgg    7560
caaacctcca tggtgcaagc gccacggacc tgggactcag caccgataac tcagacttga    7620
attcaaacct ctcacagagt acactagaca tacactagag acaccttgta gtattttggg    7680
agcaaaaaaa ttattttctc ttaacaagac tttttgtact gaaaacaatt tttttgaatc    7740
tttcgtagcc taaaagacaa ttttccttgg aacacataag aactgtgcag tagccgtttg    7800
tggtttaaag caaacatgca agatgaacct gagggatgat agaatacaaa gaatatattt    7860
ttgttatggc tggttaccac cagcctttct tcccctttgt gtgtgtggtt caagtgtgca    7920
ctgggaggag gctgaggcct gtgaagccaa acaatatgct cctgccttgc acctccaata    7980
ggttttatta ttttttttaa attaatgaac atatgtaata ttaatagtta ttatttactg    8040
gtgcagatgg ttgacatttt tccctatttt cctcacttta tggaagagtt aaaacatttc    8100
taaaccagag gacaaagggg gttaatgtta cttaaaatt acattctata tatatataaa    8160
tatatataaa tatatattaa aataccagtt tttttctct gggtgcaaag atgttcattc    8220
ttttaaaaaa tgtttaaaaa aaaaaaaaaa ctgcctttct tcccctcaag tcaacttttg    8280
tgctccagaa aattttctat tctgtaagtc tgagcgtaaa acttcaagta ttaaaataat    8340
ttgtacatgt agagagaaaa atgacttttt caaaaatata caggggcagc tgccaaattg    8400
atgtattata tattgtggtt tctgtttctt gaaagaattt ttttcgttat ttttacatct    8460
aacaaagtaa aaaaattaaa aagagggtaa gaaacgattc cggtgggatg attttaacat    8520
gcaaaatgtc cctgggggtt tcttctttgc ttgctttctt cctccttacc ctaccccca    8580
ctcacacaca cacacacaca cacacacaca cacacacaca cacactttct ataaaacttg    8640
aaaatagcaa aaaccctcaa ctgttgtaaa tcatgcaatt aaagttgatt acttataaat    8700
atgaactttg gatcactgta tagactgtta aatttgattt cttattacct attgttaaat    8760
aaactgtgtg agacagaca                                                 8779
```

OXOPIPERAZINE DERIVATIVES

CROSS-REFERENCE TO RELATED APPLICATIONS

This application claims priority to, and the benefit of U.S. Application No. 62/599,336, filed Dec. 15, 2017 and Swiss Application No. 00152/18, filed Feb. 8, 2018, the entire contents of each of which are incorporated herein by reference.

INCORPORATION OF THE SEQUENCE LISTING

The contents of the text file named "NTHR-001-001WO_SeqList" which was created on Dec. 12, 2018 and is 32 KB in size are hereby incorporated by reference in their entirety.

FIELD OF THE INVENTION

The present invention relates to novel compounds of formula (I) or formula (Ia):

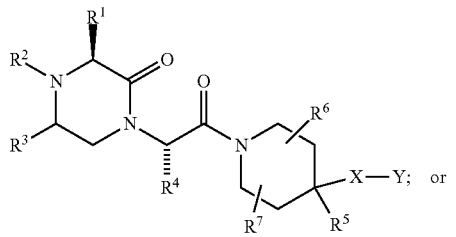

(I)

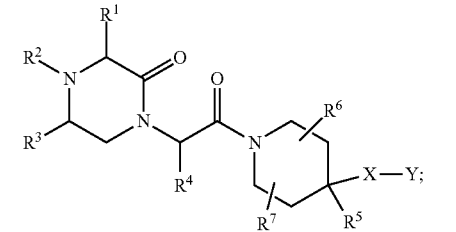

(Ia)

pharmaceutically-acceptable salts, hydrates, solvates, or stereoisomers thereof, and pharmaceutical compositions of these compounds which are useful for preventive and therapeutic use in human and veterinary medicine.

BACKGROUND

Despite the ever increasing number of cancer therapies in general, and combination cancer therapies in particular, cancer is still the third most common cause of death worldwide after cardiovascular diseases and infectious/parasitic diseases; in absolute numbers, this corresponds to 7.6 million deaths (ca. 13% of all deaths) in any given year. The World Health Organization (WHO) estimates deaths due to cancer to increase to 13.1 million by 2030, while the American Cancer Society expects over 1,685,210 new cancer cases diagnosed and 595,690 cancer deaths in the U.S. in 2016. A 2012 survey by McMillan Cancer Support in the U.K. has revealed that the median survival time of cancer patients overall has increased from 1 year to 6 years since the 1970s. However, for many cancers including esophageal-, stomach-, lung-, brain- and pancreatic cancer, median survival has barely improved, remaining less than one year.

These statistics illustrate the fact that cancer remains a critical health condition and that there is an urgent need for new anticancer drugs.

SUMMARY

The present invention relates to novel compounds of formula (Ia). The present invention provides novel compounds according to formula (Ia):

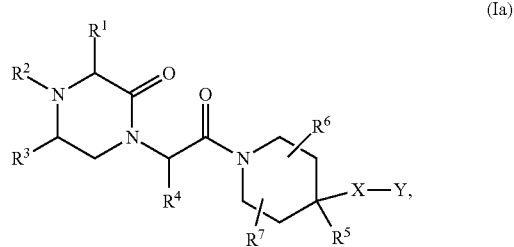

(Ia)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and wherein $R^6$ can form a ring with any part of X; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-9}$ cycloalkanediyl, $C_{4-6}$ cycloalkenediyl, —O—, $C_{1-3}$ alkanediyl-O—, —O—$C_{1-7}$ alkanediyl, —O—$C_{3-9}$ cycloalkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring or a polycyclic system with any part of $R^5$, $R^6$, or Y, wherein the ring optionally contains a carbonyl group;

Y is selected from H, $C(O)NR^{10}R^{12}$, $C(O)OR^{10}$, $R^{11}NC(O)NR^{11}R^{12}$, $OC(O)R^{10}$, $OC(O)NR^{11}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In another aspect, the present invention relates to novel compounds of formula (I). The present invention provides novel compounds according to formula (I):

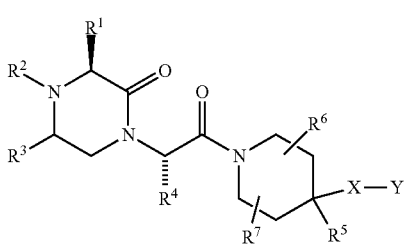

(I)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by $C(O)NR^8R^{11}$; $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from H, $C(O)NR^{10}R^{12}$, $C(O)OR^{10}$, $R^{11}NC(O)NR^{11}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; aryl, or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

The present invention also relates to pharmaceutical compositions useful for preventive and therapeutic use in human and veterinary medicine comprising compounds of the formula (I) and/or formula (Ia) and pharmaceutically-acceptable salts, hydrates, solvates, or stereoisomers thereof. The present invention is useful in methods for preventing and treating cancer.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to hose described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of compounds disclosed herein, the chemical structures will control.

Other features and advantages of the disclosure will be apparent from the following detailed description and claims.

DETAILED DESCRIPTION

Figure 1:
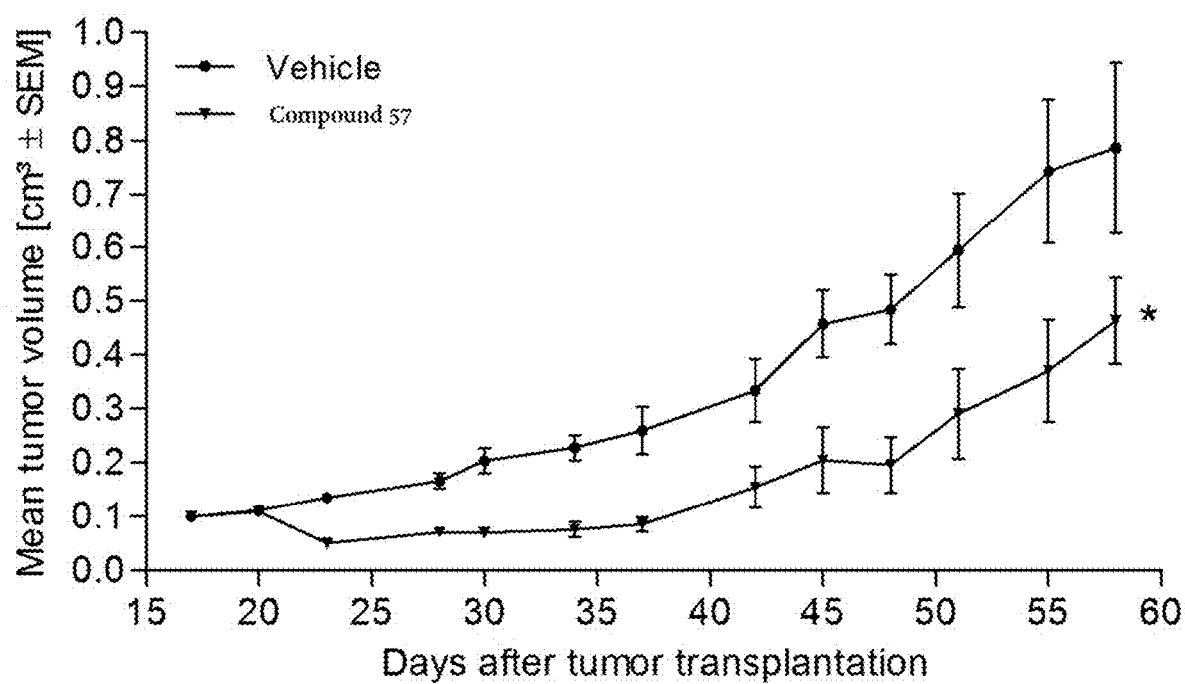
FIG. 1 is a graph showing tumor growth inhibition in a patient-derived xenograft model of head and neck cancer. NMRI nude mice bearing HN11873 subcutaneous tumors were treated p.o. BID with either vehicle (control) or 30 mg/kg test Compound 57.
Figure 2A:
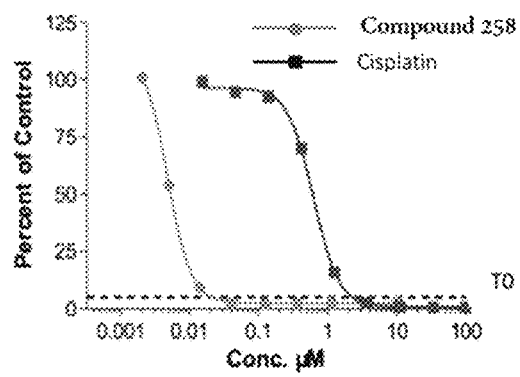
FIG. 2A-2F are graphs depicting characteristic 5-day cell proliferation inhibition curves. The figure shows the inhibition curves for the values reported for lymphoma cell lines and Compound 258 (light gray line) in TABLE 5. Concentrations are given in micromol/lt (μM), $T_0$=day 0 reading (proliferation reference). The cisplatin (quality control) inhibition curve is shown in dark grey.
Figure 2B:
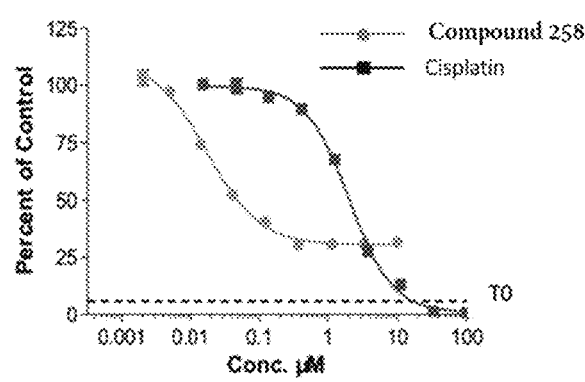
Figure 2C:
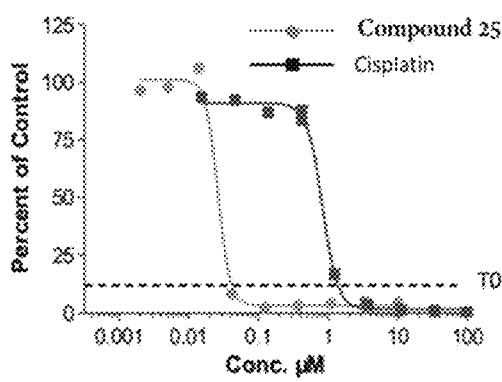
Figure 2D:
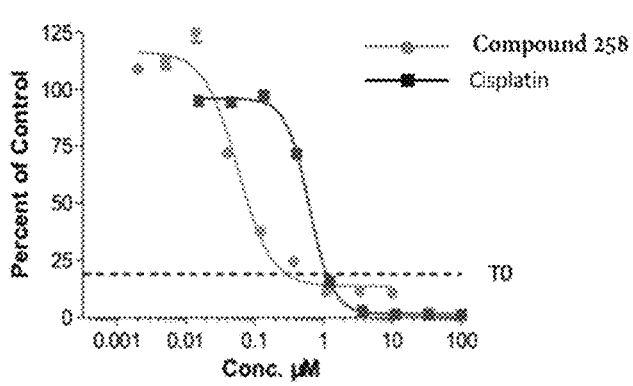
Figure 2E:
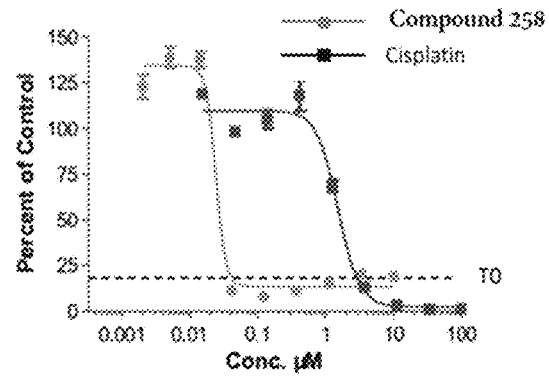
Figure 2F:
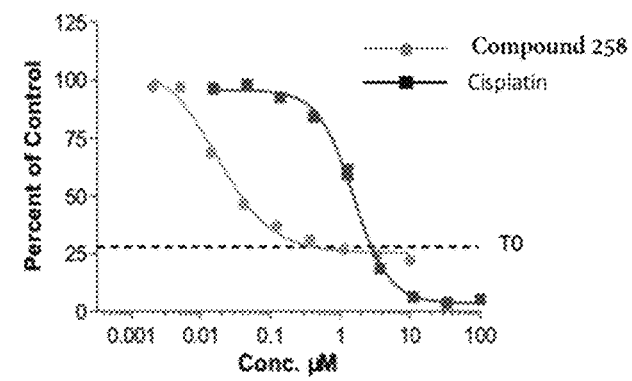

The present invention is directed to a series of compounds having strong activities against a broad variety of tumor types, including, but not limited to, prostate, colon, head-and-neck and cervical cancer as well as hematological malignancies.

The present invention is directed to a series of compounds having a strong activity as p300/CBP inhibitors, including stereoisomers, tautomers, pharmaceutically acceptable salts and prodrugs thereof, and the use of such compounds to treat p300/CBP-related conditions or diseases, such as cancer.

Exemplary conditions which can be treated with the disclosed compounds include cancer. The cancer types which can be treated include, but are not limited to, prostate cancer, renal cancer, pancreatic cancer, liver cancer, breast cancer, gastric cancer, colorectal cancer, cervical cancer, ovarian cancer, head-and-neck cancer, esophageal cancer, leukemia, lymphoma, lung cancer, brain cancer, cancer of the central nervous system and skin cancer.

The invention provides pharmaceutical compositions of the described compounds, comprising the described compounds and pharmaceutically acceptable carriers, diluents or excipients.

The invention provides pharmaceutical compositions of the described compounds, wherein the compounds are administered in combination with one or more anti-cancer treatments or anti-cancer therapeutic agents. In one aspect, the pharmaceutical composition consists of the combination of one of the compounds with an immune checkpoint inhibitor of programmed cell death protein 1 (PD-1).

Definitions

The following are definitions of terms used in present application. The initial definition provided for a group or term herein applies to that group or term throughout the description and the claims, individually or as part of another group, unless otherwise indicated.

The term "alkyl" as used herein refers to a saturated straight or branched chain group of carbon atoms derived from an alkane by the removal of one hydrogen atom. $C_{1-3}$ alkyl includes, but is not limited to, for example methyl, ethyl, n-propyl, i-propyl. $C_{1-4}$ alkyl comprises for example methyl, ethyl, n-propyl, i-propyl, n-butyl, i-butyl, tert-butyl. $C_{1-5}$ alkyl comprises for example methyl, ethyl, n-propyl, i-propyl, n-butyl, i-butyl, tert-butyl, n-pentyl, $C_{1-7}$ alkyl comprises for example methyl, ethyl, n-propyl, i-propyl, n-butyl, i-butyl, tert-butyl, n-pentyl, n-hexyl or n-heptyl. The alkyl groups of this invention can be optionally substituted.

The term "$C_{2-5}$ alkenyl" and "$C_{2-7}$ alkenyl" as used herein refers to straight or branched chain hydrocarbon groups having 2 to 5 carbon atoms and 2 to 7 carbon atoms, respectively and at least one double bond.

The term "$C_{2-5}$ alkynyl" and "$C_{2-7}$ alkynyl" as used herein refers to straight or branched chain hydrocarbon groups having 2 to 5 carbon atoms and 2 to 7 carbon atoms, respectively and at least one triple bond.

The term "$C_{3-7}$ cycloalkyl" and "$C_{3-5}$ cycloalkyl" as used herein refers to a monovalent saturated cyclic or bicyclic hydrocarbon group of 3-7 or 3-5 carbons, respectively derived from a cycloalkane by the removal of a single hydrogen atom. "$C_{3-5}$ cycloalkyl" includes, but is not limited to, cyclopropyl, cyclobutyl, and cyclopentyl. "$C_{3-7}$ cycloalkyl" includes, but is not limited to, cyclopropyl, cyclobutyl, cyclopentyl, cyclohexyl and cycloheptyl. The term "$C_{3-7}$ cycloalkyl" and "$C_{3-5}$ cycloalkyl" as used herein also includes cycloalkyl groups that comprise a $C_{1-3}$-alkyl radical. Examples of such "$C_{3-7}$ cycloalkyl" groups comprise cyclopropylmethyl, 2-cyclopropylethyl, cyclobutylmethyl, 2-cyclobutylethyl, cyclopentylmethyl, 2-cyclopentylethyl. Examples of such "$C_{3-5}$ cycloalkyl" groups comprise cyclopropylmethyl, 2-cyclopropylethyl, cyclobutylmethyl. Cycloalkyl groups of this invention can be optionally substituted. Substitutents can be e.g. halogen, $C_{1-4}$ alkyl or $C_{3-5}$ cycloalkyl.

The term "$C_{4-7}$ cycloalkenyl" as used herein refers to a monovalent cyclic or bicyclic hydrocarbon group of 4-7 carbons having at least one double bond, derived from a cycloalkene by the removal of a single hydrogen atom. The term "$C_{4-7}$ cycloalkenyl" as used herein also includes cycloalkenyl groups that comprise a $C_{1-3}$-alkyl radical.

The term "$C_{1-3}$ alkanediyl", "$C_{1-6}$ alkanediyl" and "$C_{1-7}$ alkanediyl" as used herein refers to a diradical of a saturated straight or branched chain hydrocarbon group, having 1 to 3, 1 to 6 carbon and 1 to 7 carbon atoms, respectively. Examples of alkanediyl groups include methane-diyl, ethane-1,2-diyl, and the like.

The term "$C_{2-6}$ alkenediyl" and "$C_{2-7}$ alkenediyl" as used herein refers to a diradical of a straight or branched chain hydrocarbon groups having 2 to 6 carbon atoms and 2 to 7 carbon atoms, respectively and at least one double bond. Examples of alkenediyl groups include ethene-1,2-diyl and the like.

The term "$C_{2-6}$ alkynediyl" and "$C_{2-7}$ alkynediyl" as used herein refers to a diradical of a straight or branched chain hydrocarbon groups having 2 to 6 carbon atoms and 2 to 7 carbon atoms, respectively and at least one triple bond. Examples of alkynediyl groups include ethene-1,2-diyl and the like.

The term "$C_{3-6}$ cycloalkanediyl" as used herein refers to a diradical saturated cyclic or bicyclic hydrocarbon group of 3-6 carbons.

The term "$C_{3-6}$ cycloalkenediyl" as used herein refers to a diradical cyclic or bicyclic hydrocarbon group of 3-6 carbons having at least one double bond.

The term "heteroalkyl" or "heteroalkanediyl" as used herein refers to an alkyl radical or an alkanediyl radical as defined herein wherein one, two, three or four hydrogen atoms have been replaced with a substituent independently selected from the group consisting of OH, $NH_2$ and halogen. Representative examples include, but are not limited to, 2-hydroxyethyl, 2-hydroxypropyl, 3-hydroxypropyl, 2-hydroxy-1-hydroxymethylethyl, 2-hydroxy-1-methylethyl, 2,3-dihydroxypropyl, 1-hydroxymethylethyl, 3-hydroxybutyl, 2,3-dihydroxybutyl, 1-hydroxy-2-methylpropyl, 3-hydroxy-1-(2-hydroxyethyl)-propyl, 2-hydroxy-1-methylpropyl, 1,1,1-trifluoroethyl, 2,2,3,3-tetrafluoropropyl.

The term "aryl" as used herein refers to a mono- or bicyclic carbocyclic ring system having one or two aromatic rings. The aryl group can also be fused to a cyclohexane, cyclohexene, cyclopentane, or cyclopentene ring or to a cyclohexane, cyclohexene, cyclopentane, or cyclopentene ring comprising a carbonyl group. Thus the aryl group includes e.g. indane or mono-oxo substituted indane rings. The aryl groups of this invention can be optionally substituted as further described below. A preferred aryl group and optionally substituted aryl group, respectively of this invention is a phenyl group or substituted phenyl group. Substitutents can be e.g. halogen, $C_{1-4}$ alkyl or $C_{3-5}$ cycloalkyl.

The term "heteroaryl" as used herein refers to substituted and unsubstituted aromatic 5-, or 6-membered monocyclic groups and 9- or 10-membered bicyclic groups, which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups must include at least one fully aromatic ring but the other fused ring or rings may be aromatic or non-aromatic. The heteroaryl group may be attached at any available nitrogen or carbon atom of any ring. Heteroaryl groups of this invention can be optionally substituted as further described below. Usually, a heteroaryl group and optionally substituted heteroaryl group, respectively of this invention is selected from the group consisting of substituted and/or unsubstituted aromatic 5-, or 6-membered monocyclic groups, which have at least one heteroatom (O, S or N), preferably one heteroatom (O, S or N), more preferably one O or N in the ring, even more preferably two N in the ring. A preferred heteroaryl group and optionally substituted heteroaryl group, respectively of this invention is selected from the group consisting of a pyridinyl group, a substituted pyridinyl group, a imidazole group, a substituted imidazole group, a pyrazole group, a substituted pyrazole group, a triazole group, a substituted triazole group, a benzimidazole group and a substituted benzimidazole group. More preferably a substituted pyridinyl group, a pyridinyl group, a triazole group, a substituted triazole group, a imidazole group, and/or a substituted imidazole group, is used as heteroaryl group in the present invention.

Most preferably a substituted pyridinyl group, a pyridinyl group, an imidazole group, and/or a substituted imidazole group, is used as heteroaryl group in the present invention. Substitutents can be e.g. halogen, $C_{1-4}$ alkyl or $C_{3-5}$ cycloalkyl.

The term "S-aryl" as used herein refers to a radical —SR where R is an aryl as defined herein.

The term "O-aryl" as used herein refers to a radical —OR where R is an aryl as defined herein.

The term "S-heteroaryl" as used herein refers to a radical —SR where R is an heteroaryl as defined herein.

The term "O-heteroaryl" as used herein refers to a radical —OR where R is an heteroaryl as defined herein.

The term "$C_{1-3}$ alkyl-aryl" as used herein refers to a radical of $C_{1-3}$ alkyl as defined herein to which an aryl group as defined herein is bonded at any carbon of the alkyl.

The term "$C_{1-3}$ alkyl-heteroaryl" as used herein refers to a radical of $C_{1-3}$ alkyl as defined herein to which a heteroaryl group as defined herein is bonded at any carbon of the alkyl.

The terms "halo" or "halogen" as used herein refers to F, Cl, Br, or I and is preferably F, Cl, or Br.

Compounds of the Present Disclosure

In some aspects, the present disclosure relates to a compound of Formula (Ia):

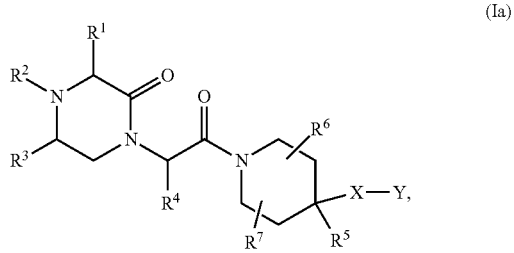

(Ia)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and wherein $R^6$ can form a ring with any part of X; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-9}$ cycloalkanediyl, $C_{4-6}$ cycloalkenediyl, —O—, $C_{1-3}$ alkanediyl-O—, —O—$C_{1-7}$ alkanediyl, —O—$C_{3-9}$ cycloalkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring or a polycyclic system with any part of $R^5$, $R^6$, or Y, wherein the ring optionally contains a carbonyl group;

Y is selected from H, $C(O)NR^{10}R^{12}$, $C(O)OR^{10}$, $R^{10}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring optionally substituted by $R^9$ or $R^{14}$; wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some aspects, the present disclosure relates to a compound of Formula (I):

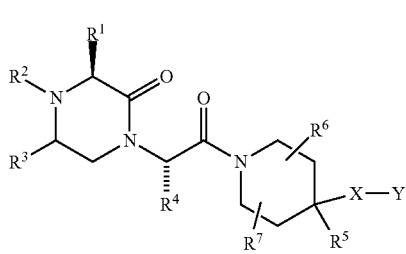

(I)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from H, $C(O)NR^{10}R^{12}$, $C(O)OR^{10}$, $R^{10}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^0SO_2R^0$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

It is understood that, for a compound of Formula (I) or Formula (Ia), $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, X, and Y can each be, where applicable, selected from the groups described herein, and any group described herein for any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, X, and Y can be combined, where applicable, with any group described herein for one or more of the remainder of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, X, and Y.

In some embodiments, $R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl In some embodiments, $R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^1$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^1$ is selected from $C_{2-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^1$ is selected from $C_{3-7}$ alkyl, $C_{3-7}$ cycloalkyl, or $C_{1-3}$ alkyl substituted by aryl or heteroaryl.

In some embodiments, $R^1$ is H.

In some embodiments, $R^1$ is $C_{3-7}$ cycloalkyl.

In some embodiments, $R^1$ is selected from cyclopropyl, cyclobutyl, cyclopentyl, cyclohexyl or cycloheptyl.

In some embodiments, $R^1$ is selected from cyclopropyl or cyclohexyl.

In some embodiments, $R^1$ is cyclopropyl.

In some embodiments, $R^1$ is cyclohexyl.

In some embodiments, $R^1$ is $C_{1-7}$ alkyl.

In some embodiments, $R^1$ is $C_{2-7}$ alkyl.

In some embodiments, $R^1$ is $C_{3-7}$ alkyl.

In some embodiments, $R^1$ is selected from methyl, ethyl, propyl, isopropyl, butyl, sec-butyl, isobutyl, or tert-butyl.

In some embodiments, $R^1$ is selected from ethyl, propyl, isopropyl, butyl, sec-butyl, isobutyl, or tert-butyl.

In some embodiments, $R^1$ is selected from propyl, isopropyl, butyl, sec-butyl, isobutyl, or tert-butyl.

In some embodiments, $R^1$ is isobutyl.

In some embodiments, $R^1$ is $C_{1-3}$ alkyl substituted by cycloalkyl.

In some embodiments, $R^1$ is methyl, ethyl, or propyl substituted by cyclopropyl, cyclobutyl, cyclopentyl, cyclohexyl or cycloheptyl.

In some embodiments, $R^1$ is ethyl or propyl substituted by cyclopropyl or cyclohexyl.

In some embodiments, $R^1$ is $C_{1-3}$ alkyl substituted by aryl or heteroaryl.

In some embodiments, $R^1$ is methyl, ethyl, or propyl substituted by phenyl, imidazole, pyridine, or triazole.

In some embodiments, $R^1$ is ethyl or propyl substituted by phenyl or pyridine.

In some embodiments, $R^1$ is ethyl substituted by phenyl.

In some embodiments, $R^1$ is

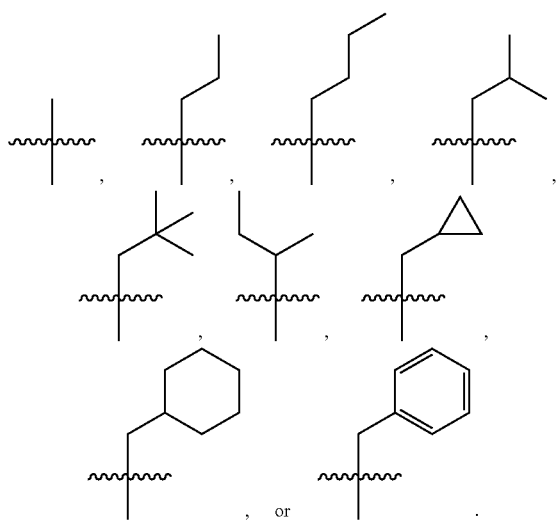

In some embodiments, $R^1$ is

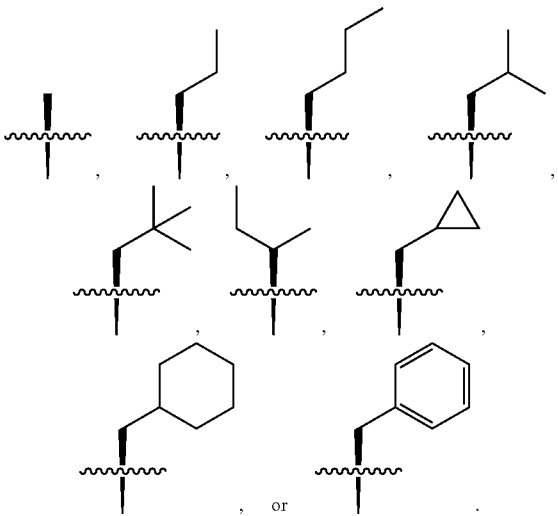

In some embodiments, $R^1$ is

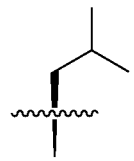

In some embodiments, $R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

In some embodiments, $R^2$ is selected from H, $C(O)R^{14}$, $C(O)NR^5R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

In some embodiments, $R^2$ is selected from H, $C(O)R^{14}$, $C(O)OR^{15}$, $C_{1-7}$ alkyl, $C_{3-7}$ cycloalkyl, $C_{1-3}$ alkanediyl-O—$C_{1-3}$ alkanediyl-O—$C_{1-3}$ alkanediyl, $C_{1-5}$ alkyl-$OR^8$, $C_{1-5}$ alkyl-$NHCOR^{13}$, or $C_{1-3}$ alkyl substituted by aryl, wherein the aryl is optionally substituted by halogen, $C_{1-4}$ alkyl or $C_{3-5}$ cycloalkyl.

In some embodiments, $R^2$ is selected from H, $C(O)R^{14}$, $C_{1-7}$ alkyl, $C_{3-7}$ cycloalkyl, $C_{1-5}$ alkyl-$OR^8$, $C_{1-5}$ alkyl-NH- COR$^{13}$, or C$_{1-3}$ alkyl substituted by aryl, wherein the aryl is optionally substituted by halogen, C$_{1-4}$ alkyl or C$_{3-5}$ cycloalkyl.

In some embodiments, R$^2$ is selected from H, C(O)R$^{14}$, wherein R$^{14}$ is C$_{1-7}$ alkyl; C$_{1-7}$ alkyl, C$_{3-7}$ cycloalkyl, C$_{1-5}$ alkyl-OR; C$_{1-5}$ alkyl-NHCOR$^{13}$, wherein R$^{13}$ is pentylamino-5-oxopentyl-7-thia-2,4-diazabicyclo[3.3.0]octan-3-one; or C$_{1-3}$ alkyl substituted by aryl, wherein the aryl is optionally substituted by halogen, C$_{1-4}$ alkyl or C$_{3-5}$ cycloalkyl.

In some embodiments, R$^2$ is selected from H, C(O)R$^{14}$, wherein R$^{14}$ is C$_{1-7}$ alkyl; C$_{1-7}$ alkyl, C$_{3-7}$ cycloalkyl, C$_{1-5}$ alkyl-OR$^8$, wherein R$^8$ is C$_{1-7}$ alkyl; C$_{1-5}$ alkyl-NHCOR$^{13}$, wherein R$^{13}$ is pentylamino-5-oxopentyl-7-thia-2,4-diazabicyclo[3.3.0]octan-3-one; or C$_{1-3}$ alkyl substituted by aryl, wherein the aryl is optionally substituted by halogen, C$_{1-4}$ alkyl or C$_{3-5}$ cycloalkyl.

In some embodiments, R$^2$ is H.

In some embodiments, R$^2$ is C$_{1-7}$ alkyl.

In some embodiments, R$^2$ is selected from methyl, ethyl, propyl, isopropyl, butyl, sec-butyl, isobutyl, or tert-butyl.

In some embodiments, R$^2$ is selected from methyl, ethyl, or propyl.

In some embodiments, R$^2$ is C(O)R$^{14}$, and R$^{14}$ is methyl, ethyl, propyl, isopropyl, butyl, sec-butyl, isobutyl, or tert-butyl.

In some embodiments, R$^2$ is C(O)NR$^{15}$R$^{15}$, wherein each R$^{15}$ is independently selected from H, C$_{1-7}$ alkyl, C$_{2-7}$ alkenyl, C$_{2-7}$ alkynyl, C$_{3-7}$ cycloalkyl, C$_{4-7}$ cycloalkenyl, OR$^8$, or C$_{1-3}$ alkyl-OR$^8$.

In some embodiments, R$^2$ is C(O)NR$^{15}$R$^{15}$, wherein each R$^{15}$ is independently selected from methyl, ethyl, propyl, isopropyl, butyl, sec-butyl, isobutyl, or tert-butyl.

In some embodiments, R$^2$ is C(O)NR$^{15}$R$^{15}$, wherein each R$^{15}$ is independently selected from methyl or ethyl.

In some embodiments, R$^2$ is C(O)NR$^{15}$R$^{15}$, wherein each R$^{15}$ is methyl.

In some embodiments, R$^2$ is C$_{3-7}$ cycloalkyl.

In some embodiments, R$^2$ is selected from cyclopropyl, cyclobutyl, cyclopentyl, cyclohexyl or cycloheptyl.

In some embodiments, R$^2$ is cyclopropyl.

In some embodiments, R$^2$ is C$_{1-5}$ alkyl-OR$^8$, wherein R$^8$ is C$_{1-7}$ alkyl In some embodiments, R$^2$ is methyl-OR$^8$, ethyl-OR$^8$, propyl-OR$^8$, or butyl-OR$^8$ wherein R$^8$ is methyl, ethyl, propyl, or butyl.

In some embodiments, R$^2$ is ethyl-OR$^8$ wherein R$^8$ is methyl, ethyl, propyl, or butyl.

In some embodiments, R$^2$ is ethyl-OR$^8$ wherein R$^8$ is methyl.

In some embodiments, R$^2$ is C$_{1-3}$ alkyl substituted by cycloalkyl.

In some embodiments, R$^2$ is methyl, ethyl, or propyl substituted by cyclopropyl, cyclobutyl, cyclopentyl, cyclohexyl or cycloheptyl.

In some embodiments, R$^2$ is ethyl or propyl substituted by cyclopropyl or cyclohexyl.

In some embodiments, R$^2$ is ethyl substituted by cyclopropyl.

In some embodiments, R$^2$ is C$_{1-3}$ alkyl substituted by aryl or heteroaryl.

In some embodiments, R$^2$ is methyl, ethyl, or propyl substituted by phenyl, imidazole, pyridine, or triazole.

In some embodiments, R$^2$ is ethyl or propyl substituted by phenyl or pyridine.

In some embodiments, R$^2$ is ethyl substituted by phenyl.

In some embodiments, R$^2$ is C$_{1-3}$ alkyl substituted by aryl or heteroaryl, wherein the aryl or heteroaryl is optionally substituted by halogen, C$_{1-4}$ alkyl or C$_{3-5}$ cycloalkyl.

In some embodiments, R$^2$ is methyl, ethyl, or propyl substituted by phenyl, imidazole, pyridine, or triazole substituted by fluoro, iodo, or bromo.

In some embodiments, R$^2$ is ethyl or propyl substituted by phenyl or pyridine substituted fluoro, iodo, or bromo.

In some embodiments, R$^2$ is ethyl substituted by phenyl substituted fluoro.

In some embodiments, R$^2$ is

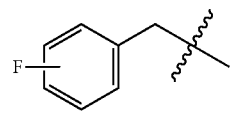

In some embodiments, R$^2$ is C$_{1-5}$ alkyl-NHCOR$^{13}$, wherein R$^{13}$ is pentylamino-5-oxopentyl-7-thia-2,4-diazabicyclo[3.3.0]octan-3-one.

In some embodiments, R$^2$ is methyl-NHCOR$^{13}$, ethyl-NHCOR$^{13}$, propyl-NHCOR$^{13}$, butyl-NHCOR$^{13}$, or pentyl-NHCOR$^{13}$, wherein R$^{13}$ is pentylamino-5-oxopentyl-7-thia-2,4-diazabicyclo[3.3.0]octan-3-one.

In some embodiments, R$^2$ is pentyl-NHCOR$^{13}$, wherein R$^{13}$ is pentylamino-5-oxopentyl-7-thia-2,4-diazabicyclo[3.3.0]octan-3-one.

In some embodiments, R$^2$ is

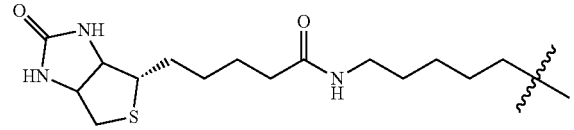

In some embodiments, R$^2$ is C$_{1-3}$ alkyl substituted by aryl, wherein the aryl is optionally substituted by halogen, C$_{1-4}$ alkyl or C$_{3-5}$ cycloalkyl.

In some embodiments, R$^2$ is

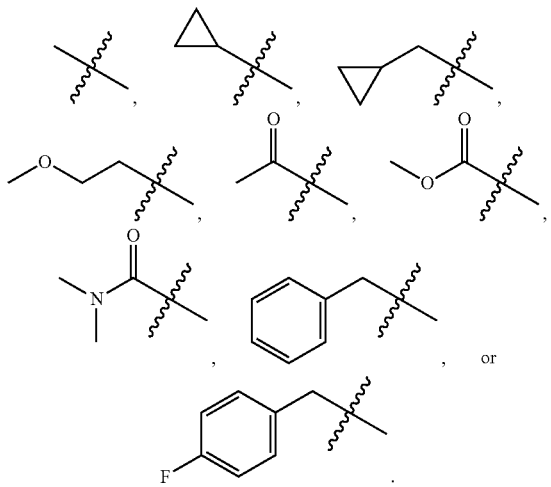

In some embodiments, R$^3$ is selected from H, C$_{1-7}$ alkyl, C$_{2-7}$ alkenyl, C$_{2-7}$ alkynyl, C$_{3-7}$ cycloalkyl, or C$_{4-7}$ cycloalkenyl, all optionally substituted by halogen, OR$^8$, NR$^8$R$^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^3$ is selected from H, $C_{1-7}$ alkyl, $C_{2-7}$ alkenyl, $C_{2-7}$ alkynyl, $C_{3-7}$ cycloalkyl, or $C_{4-7}$ cycloalkenyl.

In some embodiments, $R^3$ is $C_{1-7}$ alkyl.

In some embodiments, $R^3$ is selected from methyl, ethyl, propyl, isopropyl, butyl, sec-butyl, isobutyl, or tert-butyl.

In some embodiments, $R^3$ is $C_{2-7}$ alkenyl.

In some embodiments, $R^3$ is vinyl.

In some embodiments, $R^3$ is $C_{3-7}$ cycloalkyl.

In some embodiments, $R^3$ is selected from cyclopropyl, cyclobutyl, cyclopentyl, cyclohexyl or cycloheptyl.

In some embodiments, $R^3$ is H.

In some embodiments, $R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl In some embodiments, $R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl.

In some embodiments, $R^3$ and $R^7$ are each independently $C_{1-7}$ alkyl.

In some embodiments, $R^3$ and $R^7$ are each independently selected from methyl, ethyl, propyl, isopropyl, butyl, sec-butyl, isobutyl, or tert-butyl.

In some embodiments, $R^3$ and $R^7$ are each independently $C_{2-7}$ alkenyl.

In some embodiments, $R^3$ and $R^7$ are each vinyl.

In some embodiments, $R^3$ and $R^7$ are each independently $C_{3-7}$ cycloalkyl.

In some embodiments, $R^3$ and $R^7$ are each independently selected from cyclopropyl, cyclobutyl, cyclopentyl, cyclohexyl or cycloheptyl.

In some embodiments, $R^3$ and $R^7$ are each H.

In some embodiments, $R^7$ is selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^7$ is selected from H, $C_{1-7}$ alkyl, $C_{2-7}$ alkenyl, $C_{2-7}$ alkynyl, $C_{3-7}$ cycloalkyl, or $C_{4-7}$ cycloalkenyl.

In some embodiments, $R^7$ is $C_{1-7}$ alkyl.

In some embodiments, $R^7$ is selected from methyl, ethyl, propyl, isopropyl, butyl, sec-butyl, isobutyl, or tert-butyl.

In some embodiments, $R^7$ is $C_{2-7}$ alkenyl.

In some embodiments, $R^7$ is vinyl.

In some embodiments, $R^7$ is $C_{3-7}$ cycloalkyl.

In some embodiments, $R^7$ is selected from cyclopropyl, cyclobutyl, cyclopentyl, cyclohexyl or cycloheptyl.

In some embodiments, $R^7$ is H.

In some embodiments, the group $R^7$ is in position −5 of the piperidine ring.

In some embodiments, the group $R^7$ is in position −6 of the piperidine ring.

In some embodiments, the group $R^6$ is in position −2 of the piperidine ring.

In some embodiments, the group $R^6$ is in position −2 of the piperidine ring and/or the group $R^7$ is in position −5 of the piperidine ring.

In some embodiments, the group $R^6$ is in position −2 of the piperidine ring and the group $R^7$ is in position −5 of the piperidine ring.

In some embodiments, $R^4$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl In some embodiments, $R^4$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^4$ is selected from $C_{1-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^4$ is selected from $C_{2-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^4$ is selected from $C_{3-7}$ alkyl, $C_{3-7}$ cycloalkyl, or $C_{1-3}$ alkyl substituted by aryl or heteroaryl.

In some embodiments, $R^4$ is H.

In some embodiments, $R^4$ is $C_{3-7}$ cycloalkyl.

In some embodiments, $R^4$ is selected from cyclopropyl, cyclobutyl, cyclopentyl, cyclohexyl or cycloheptyl.

In some embodiments, $R^4$ is selected from cyclopropyl or cyclohexyl.

In some embodiments, $R^4$ is cyclopropyl.

In some embodiments, $R^4$ is cyclohexyl.

In some embodiments, $R^4$ is $C_{1-7}$ alkyl.

In some embodiments, $R^4$ is $C_{2-7}$ alkyl.

In some embodiments, $R^4$ is $C_{3-7}$ alkyl.

In some embodiments, $R^4$ is selected from methyl, ethyl, propyl, isopropyl, butyl, sec-butyl, isobutyl, or tert-butyl.

In some embodiments, $R^4$ is selected from ethyl, propyl, isopropyl, butyl, sec-butyl, isobutyl, or tert-butyl.

In some embodiments, $R^4$ is selected from propyl, isopropyl, butyl, sec-butyl, isobutyl, or tert-butyl.

In some embodiments, $R^4$ is isobutyl.

In some embodiments, $R^4$ is $C_{1-3}$ alkyl substituted by cycloalkyl.

In some embodiments, $R^4$ is methyl, ethyl, or propyl substituted by cyclopropyl, cyclobutyl, cyclopentyl, cyclohexyl or cycloheptyl.

In some embodiments, $R^4$ is ethyl or propyl substituted by cyclopropyl or cyclohexyl.

In some embodiments, $R^4$ is $C_{1-3}$ alkyl substituted by aryl or heteroaryl.

In some embodiments, $R^4$ is methyl, ethyl, or propyl substituted by phenyl, imidazole, pyridine, or triazole.

In some embodiments, $R^4$ is ethyl or propyl substituted by phenyl or pyridine.

In some embodiments, $R^4$ is ethyl substituted by phenyl.

In some embodiments, $R^4$ is

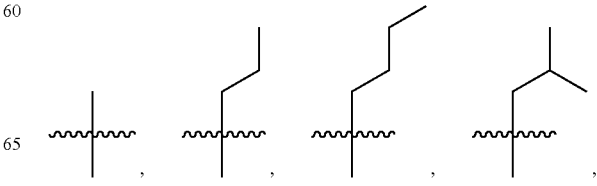

-continued

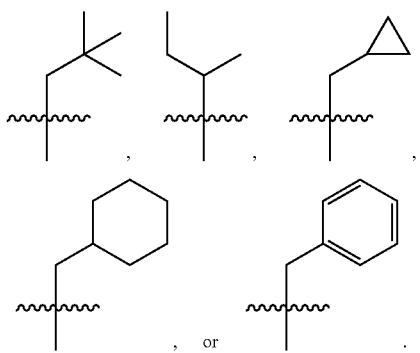

, or  .

In some embodiments, $R^4$ is

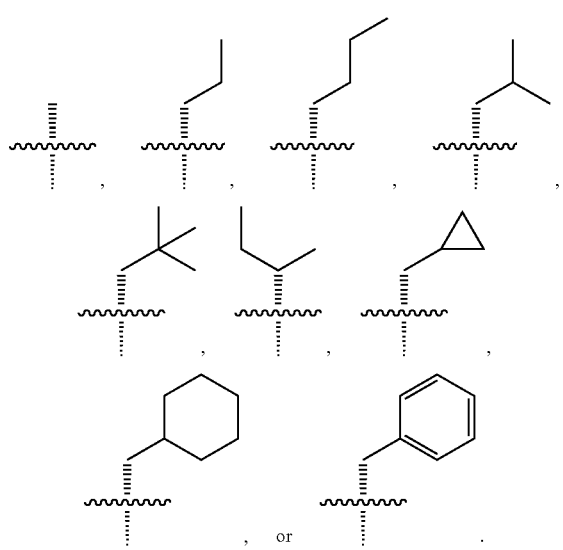

, or  .

In some embodiments, $R^4$ is

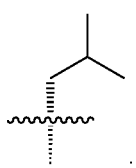

.

In some embodiments, the compound is of any one of Formulae (IIa), (IIb), or (IIc):

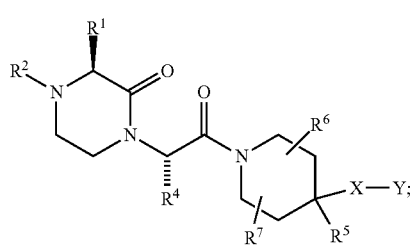

(IIa)

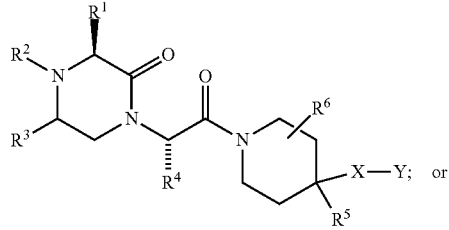

(IIb)

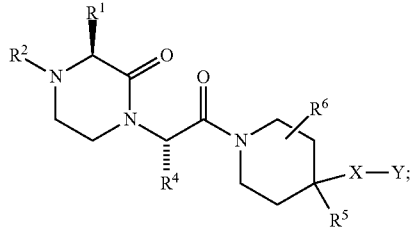

(IIc)

or a pharmaceutically acceptable salt, hydrate, solvate or stereoisomer thereof, wherein $R^1$, $R^2$, $R^3$, $R^4$, $R^5$, $R^6$, $R^7$, X, and Y are as described herein.

In some embodiments, the compound is of Formula (IIa) or a pharmaceutically acceptable salt, hydrate, solvate or stereoisomer thereof, wherein $R^1$, $R^2$, $R^3$, $R^4$, $R^5$, $R^6$, $R^7$, X, and Y are as described herein.

In some embodiments, the compound is of Formula (IIb) or a pharmaceutically acceptable salt, hydrate, solvate or stereoisomer thereof, wherein $R^1$, $R^2$, $R^3$, $R^4$, $R^5$, $R^6$, $R^7$, X, and Y are as described herein.

In some embodiments, the compound is of Formula (IIc) or a pharmaceutically acceptable salt, hydrate, solvate or stereoisomer thereof, wherein $R^1$, $R^2$, $R^3$, $R^4$, $R^5$, $R^6$, $R^7$, X, and Y are as described herein.

In some embodiments, the compound is of any one of Formulae (IIIa), (IIIb), (IIIc), or (IIId):

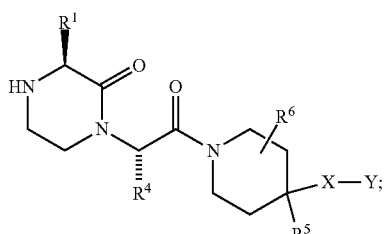

(IIIa)

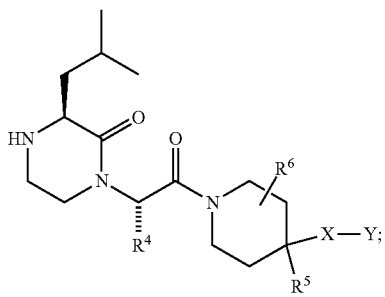

(IIIb)

(IIIc)

(IIId)

or a pharmaceutically acceptable salt, hydrate, solvate or stereoisomer thereof, wherein $R^1$, $R^4$, $R^5$, $R^6$, X, and Y are as described herein.

In some embodiments, the compound is of Formula (IIIa) or a pharmaceutically acceptable salt, hydrate, solvate or stereoisomer thereof, wherein $R^1$, $R^4$, $R^5$, $R^6$, X, and Y are as described herein.

In some embodiments, the compound is of Formula (IIIb) or a pharmaceutically acceptable salt, hydrate, solvate or stereoisomer thereof, wherein $R^1$, $R^4$, $R^5$, $R^6$, X, and Y are as described herein.

In some embodiments, the compound is of Formula (IIIc) or a pharmaceutically acceptable salt, hydrate, solvate or stereoisomer thereof, wherein $R^1$, $R^4$, $R^5$, $R^6$, X, and Y are as described herein.

In some embodiments, the compound is of Formula (IIId) or a pharmaceutically acceptable salt, hydrate, solvate or stereoisomer thereof, wherein $R^1$, $R^4$, $R^5$, $R^6$, X, and Y are as described herein.

In some embodiments, the group $R^6$ is in position −2 of the piperidine ring.

In some embodiments, the group $R^6$ is in position −3 of the piperidine ring.

In some embodiments, the group $R^6$ is in position −2 of the piperidine ring and/or the group $R^7$ is in position −5 of the piperidine ring.

In some embodiments, the group $R^6$ is in position −2 of the piperidine ring and the group $R^7$ is in position −5 of the piperidine ring.

In some embodiments, $R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and wherein $R^6$ can form a ring with any part of X; or is imidazolidinone.

In some embodiments, $R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone.

In some embodiments, $R^6$ is selected from H, $C_{1-7}$ alkyl, $C_{2-7}$ alkenyl, $C_{2-7}$ alkynyl, $C_{3-7}$ cycloalkyl, or $C_{4-7}$ cycloalkenyl; or is imidazolidinone.

In some embodiments, $R^6$ is H, $C_{1-7}$ alkyl, or imidazolidinone.

In some embodiments, $R^6$ is H or $C_{1-7}$ alkyl.

In some embodiments, $R^6$ is H.

In some embodiments, $R^6$ is in position −2 of the piperidine ring and is H.

In some embodiments, $R^6$ is in position −3 of the piperidine ring and is H.

In some embodiments, $R^6$ is imidazolidinone.

In some embodiments, $R^6$ is

In some embodiments, $R^6$ is $C_{1-7}$ alkyl.

In some embodiments, $R^6$ is selected from methyl, ethyl, propyl, isopropyl, butyl, sec-butyl, isobutyl, or tert-butyl.

In some embodiments, $R^6$ is methyl.

In some embodiments, $R^6$ is in position −2 of the piperidine ring and is $C_{1-7}$ alkyl.

In some embodiments, $R^6$ is in position −2 of the piperidine ring and is selected from methyl, ethyl, propyl, isopropyl, butyl, sec-butyl, isobutyl, or tert-butyl.

In some embodiments, $R^6$ is in position −2 of the piperidine ring and is methyl.

In some embodiments, $R^6$ is selected from the group consisting of H,

, , and .

In some embodiments, $R^6$ is in position −2 of the piperidine ring and is selected from the group consisting of H, , , and .

In some embodiments, $R^6$ is

.

In some embodiments, $R^6$ is in position −2 of the piperidine ring and is

In some embodiments, $R^6$ is $C_{1-3}$ alkyl substituted by $C(O)NR^8R^{11}$.

In some embodiments, $R^6$ is $C_{1-3}$ alkyl substituted by $C(O)NR^8R^{11}$, wherein $R^8$ is H.

In some embodiments, $R^6$ is $C_{1-3}$ alkyl substituted by $C(O)NR^8R^{11}$, wherein $R^{11}$ is H.

In some embodiments, $R^6$ is $C_{1-3}$ alkyl substituted by $C(O)NR^8R^{11}$, wherein $R^8$ and $R^{11}$ is H.

In some embodiments, $R^6$ is $C_{1-3}$ alkyl substituted by $C(O)NH_2$.

In some embodiments, $R^6$ is methyl, ethyl, or propyl substituted by $C(O)NH_2$.

In some embodiments, $R^6$ is ethyl substituted by $C(O)NH_2$.

In some embodiments, $R^6$ is propyl substituted by $C(O)NH_2$.

In some embodiments, $R^6$ is selected from the group consisting of

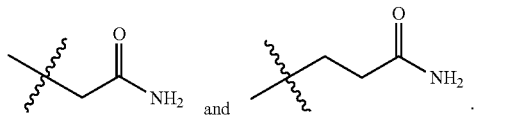 [SMILES: *CC(N)=O ; *CCC(N)=O]

In some embodiments, $R^6$ is in position -3 of the piperidine ring and is selected from the group consisting of

In some embodiments, $R^6$ forms a ring with any part of X.

In some embodiments, $R^6$ is in position -3 of the piperidine ring and forms a ring with any part of X.

In some embodiments, $R^6$ is in position -3 of the piperidine ring and forms a 3-membered, a 4-membered, 5-membered, or 6-membered ring with any part of X.

In some embodiments, $R^6$ is in position -3 of the piperidine ring and forms a 4-membered or 6-membered ring with any part of X.

In some embodiments, $R^6$ is in position -3 of the piperidine ring and forms a 4-membered or ring with any part of X.

In some embodiments, $R^6$ is in position -3 of the piperidine ring and forms a 6-membered ring with any part of X.

In some embodiments, the compound is of any one of Formulae (IVa), (IVb), (IVc) or (IVd):

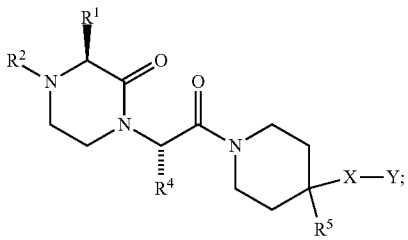
(IVa)

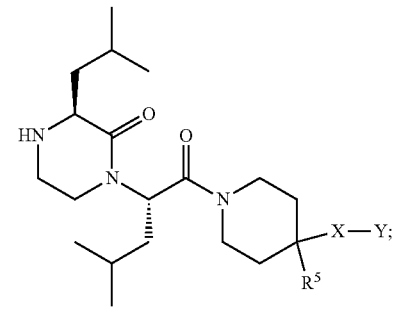
(IVb)

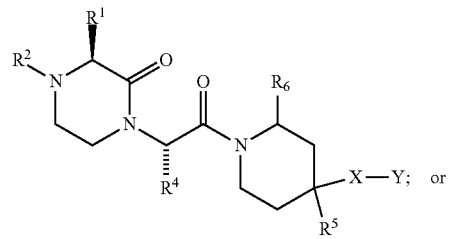
(IVc)

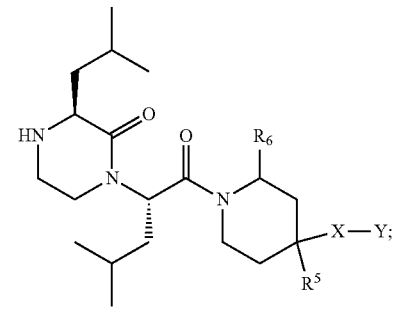
(IVd)

or a pharmaceutically acceptable salt, hydrate, solvate or stereoisomer thereof, wherein $R^1$, $R^2$, $R^4$, $R^5$, $R^6$, X, and Y are as described herein.

In some embodiments, the compound is of Formula (IVa) or a pharmaceutically acceptable salt, hydrate, solvate or stereoisomer thereof, wherein $R^1$, $R^2$, $R^4$, $R^5$, $R^6$, X, and Y are as described herein.

In some embodiments, the compound is of Formula (IVb) or a pharmaceutically acceptable salt, hydrate, solvate or stereoisomer thereof, wherein $R^1$, $R^2$, $R^4$, $R^5$, $R^6$, X, and Y are as described herein.

In some embodiments, the compound is of Formula (IVc) or a pharmaceutically acceptable salt, hydrate, solvate or stereoisomer thereof, wherein $R^1$, $R^2$, $R^4$, $R^5$, $R^6$, X, and Y are as described herein.

In some embodiments, the compound is of Formula (IVd) or a pharmaceutically acceptable salt, hydrate, solvate or stereoisomer thereof, wherein $R^1$, $R^2$, $R^4$, $R^5$, $R^6$, X, and Y are as described herein.

In some embodiments, $R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

In some embodiments, $R^5$ is selected from H, $C_{1-7}$ alkyl, $OR^8$, or $SR^8$; and wherein $C_{1-7}$ alkyl, $OR^8$ or $SR^8$ of $R^5$ can form a ring with any part of X or Y, wherein the ring optionally contains a carbonyl group.

In some embodiments, $R^5$ is selected from H, $C_{1-7}$ alkyl, $OR^8$, or $SR^8$; and wherein $C_{1-7}$ alkyl, $OR^8$ or $SR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group.

In some embodiments, $R^5$ is selected from H, $C_{1-7}$ alkyl, or $OR^8$; and wherein $C_{1-7}$ alkyl or $OR^8$ can form a ring with any part of X or Y, wherein the ring optionally contains a carbonyl group.

In some embodiments, $R^5$ is selected from H, $C_{1-7}$ alkyl, or $OR^8$; and wherein $C_{1-7}$ alkyl or $OR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group.

In some embodiments, $R^5$ is selected from $C_{1-7}$ alkyl, $OR^8$, or $SR^8$; wherein $C_{1-7}$ alkyl, $OR^8$ or $SR^8$ can form a ring with any part of X.

In some embodiments, $R^5$ is $OR^8$, wherein $R^8$ of $OR^8$ is $C_{1-7}$ alkyl, and wherein $OR^8$ can form a ring with any part of X.

In some embodiments, $R^5$ is selected from H and $C_{1-7}$ alkyl; and wherein $C_{1-7}$ alkyl can form a ring with any part of X or Y, wherein the ring optionally contains a carbonyl group.

In some embodiments, $R^5$ is selected from H and $C_{1-7}$ alkyl; and wherein $C_{1-7}$ alkyl of $R^5$ can form a ring with any part of X or, when Y is is $C(O)NR^{10}R^{12}$ or $NR^{10}R^{12}$, $C_{1-7}$ alkyl of $R^5$ can form a ring with any part of Y, wherein the ring optionally contains a carbonyl group.

In some embodiments, $R^5$ is selected from H and $C_{1-7}$ alkyl.

In some embodiments, $R^5$ is selected from H, methyl, and ethyl.

In some embodiments, $R^5$ is H.

In some embodiments, $R^5$ is methyl.

In some embodiments, $R^5$ is ethyl.

In some embodiments, $R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl.

In some embodiments, $R^8$ and $R^{11}$ are each independently selected from H, $C_{1-7}$ alkyl, $C_{2-7}$ alkenyl, and $C_{3-7}$ cycloalkyl.

In some embodiments, $R^8$ is $C_{1-7}$ alkyl and/or $R^{11}$ is selected from H, $C_{1-7}$ alkyl, $C_{2-7}$ alkenyl, and $C_{3-7}$ cycloalkyl.

In some embodiments, $R^8$ is $C_{1-7}$ alkyl and/or $R^{11}$ is $C_{1-7}$ alkyl.

In some embodiments, $R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2.

In some embodiments, $R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$.

In some embodiments, $R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$.

In some embodiments, $R^{10}$ and $R^{12}$ are each independently selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$.

In some embodiments, $R^{10}$ and $R^{12}$ are each independently selected from H, $C_{1-7}$ alkyl, $C_{3-7}$ cycloalkyl, $C_{1-3}$ alkanediyl-O—$C_{1-3}$ alkanediyl-O—$C_{1-3}$ alkanediyl, or $C_{1-3}$ alkyl-aryl, all these groups optionally substituted by halogen.

In some embodiments, Y is $C(O)NR^{10}R^{12}$ or $NR^{10}R^{12}$, and $R^{10}$ and $R^{12}$ can form a ring optionally substituted by $R^9$ or $R^{14}$; wherein the ring contains the N of $NR^{10}R^{12}$ and optionally one further heteroatom selected from O and N, wherein if the one further heteroatom is N, it is optionally substituted by $R^8$.

In some embodiments, $R^{13}$ is $C_{1-5}$ alkyl substituted by a bicyclic ring optionally containing at least one heteroatom and a carbonyl group.

In some embodiments, $R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^{14}$ is selected from $C_{1-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

In some embodiments, $R^{14}$ is selected from $C_{1-7}$ alkyl and $C_{3-7}$ cycloalkyl.

In some embodiments, $R^{14}$ is $C_{1-7}$ alkyl.

In some embodiments, each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, each $R^{15}$ is independently selected from H, $C_{1-7}$ alkyl, and $C_{3-7}$ cycloalkyl.

In some embodiments, each $R^{15}$ is independently selected from H and $C_{1-7}$ alkyl.

In some embodiments, X is selected from a bond, $C_{1-7}$ alkanediyl, $C_{2-7}$ alkenediyl, $C_{2-7}$ alkynediyl, $C_{3-9}$ cycloalkanediyl, $C_{4-6}$ cycloalkenediyl, —O—, $C_{1-3}$ alkanediyl-O—, —O—$C_{1-7}$ alkanediyl, —O—$C_{3-9}$ cycloalkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring or a polycyclic system with any part of $R^5$, $R^6$, or Y, wherein the ring optionally contains a carbonyl group.

In some embodiments, X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group.

In some embodiments, X is selected from a bond, $C_{1-7}$ alkanediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group.

In some embodiments, X is selected from a bond, $C_{1-7}$ alkanediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or, when Y is $C(O)NR^{10}R^{12}$ or $NR^{10}R^{12}$, X can form a ring with any part of Y, wherein the ring optionally contains a carbonyl group.

In some embodiments, X is selected from a bond, —O—$C_{1-7}$ alkanediyl, —S—$C_{1-7}$ alkanediyl and $C_{1-7}$ alkanediyl; and wherein —O—$C_{1-7}$ alkanediyl, S—$C_{1-7}$ alkanediyl or $C_{1-7}$ alkanediyl of X can form a ring with any part of $R^5$ or Y, wherein the ring optionally contains a carbonyl group.

In some embodiments, X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y, wherein the ring optionally contains a carbonyl group.

In some embodiments, X is selected from a bond, —O—$C_{1-7}$ alkanediyl, S—$C_{1-7}$ alkanediyl and $C_{1-7}$ alkanediyl, and wherein —O—$C_{1-7}$ alkanediyl, S—$C_{1-7}$ alkanediyl or $C_{1-7}$ alkanediyl can form a ring with any part of $R^5$, wherein the ring optionally contains a carbonyl group.

In some embodiments, X is selected from a bond and $C_{1-7}$ alkanediyl, wherein $C_{1-7}$ alkanediyl can form a ring with any part of $R^5$ or Y.

In some embodiments, X is selected from a bond and $C_{1-7}$ alkanediyl, wherein $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y.

In some embodiments, X is selected from a bond and $C_{1-7}$ alkanediyl, wherein $C_{1-7}$ alkanediyl can form a ring with any part of Y.

In some embodiments, X is selected from a bond and $C_{1-7}$ alkanediyl, wherein $C_{1-7}$ alkanediyl of X can form a ring with any part of Y when Y is $C(O)NR^{10}R^{12}$ or $NR^{10}R^{12}$.

In some embodiments, the ring which can be formed by $R^5$ and any part of X or Y, the ring which can be formed by X and any part of $R^5$ or Y, and/or the ring which can be formed by Y and any part of X or $R^5$ is a non-aromatic ring, preferably a non-aromatic ring containing between four and six atoms e.g. between four and six carbon and heteroatoms, more preferably a non-aromatic ring containing between three and five carbon and one nitrogen atom or a non-aromatic ring containing between two and four carbon and one or two, preferably two, oxygen or sulfur, preferably oxygen, atoms.

In some embodiments, Y is $C(O)NR^{10}R^{12}$ or $NR^{10}R^{12}$ and $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$, wherein the ring, $R^{10}$ and $R^{12}$ can form is a non-aromatic ring, preferably a non-aromatic ring containing between four and seven atoms e.g. between three and six carbon atoms and the N of $NR^{10}R^{12}$, or between three and five carbon atoms and the N of $NR^{10}R^{12}$ and optionally one further heteroatom selected from O and N, wherein if the one further heteroatom is N, it is optionally substituted by $R^8$.

In some embodiments, $R^2$ is $C(O)NR^{15}R^{15}$ and both $R^{15}$ can form a ring wherein the ring contains the N of $NR^{15}R^{15}$ and optionally one further heteroatom selected from O and N, wherein if the one further heteroatom is N, it is optionally substituted by $R^8$, wherein the ring, both $R^{15}$ can form is a non-aromatic ring, preferably a non-aromatic ring containing between four and seven atoms e.g. between three and six carbon atoms and the N of $NR^{15}R^{15}$, or between three and five carbon atoms and the N of $NR^{15}R^{15}$ and optionally one further heteroatom selected from O and N, wherein if the one further heteroatom is N, it is optionally substituted by $R^8$.

In some embodiments, the integer n of $S(O)_nR^8$ is 1 or 2.

In some embodiments, Y is selected from H, $C(O)NR^{10}R^{12}$, $C(O)OR^{10}$, $R^{10}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from $NR^{10}R^{12}$ and $C_{3-7}$-cycloalkyl optionally containing a heteroatom in the ring selected from O and N wherein if the heteroatom is N it is optionally substituted by $R^8$; and wherein Y can form a ring with any part of X or $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, $R^5$ is selected from H and $C_{1-7}$ alkyl; wherein $C_{1-7}$ alkyl of $R^5$ can form a ring with any part of Y;

X is selected from a bond and $C_{1-7}$ alkanediyl, and wherein $C_{1-7}$ alkanediyl of X can form a ring with any part of Y;

Y is selected from $NR^{10}R^{12}$ and $C_{3-7}$-cycloalkyl optionally containing a hetero atom in the ring wherein the heteroatom is N and is optionally substituted by $R^8$ wherein $R^8$ is $C_{1-7}$ alkyl; wherein Y can form a ring with any part of $C_{1-7}$ alkanediyl of X or with any part of $C_{1-7}$ alkyl of $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$; and $R^{10}$ and $R^{12}$ are each independently selected from H, $C_{1-7}$ alkyl, $C_{3-7}$ cycloalkyl, or $C_{1-3}$ alkyl-aryl, all these groups optionally substituted by halogen.

In some embodiments, $R^5$ is selected from $C_{1-7}$ alkyl, OR, or $SR^8$; wherein $C_{1-7}$ alkyl, $OR^8$ or $SR^8$ of $R^5$ can form a ring with any part of X;

X is selected from —O—$C_{1-7}$ alkanediyl, —S—$C_{1-7}$ alkanediyl, or $C_{1-7}$ alkanediyl, and wherein —O—$C_{1-7}$ alkanediyl, —S—$C_{1-7}$ alkanediyl or $C_{1-7}$ alkanediyl of X can form a ring with any part of $R^5$; and Y is $NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, $R^5$ is $OR^8$, wherein $R^8$ of $OR^8$ is $C_{1-7}$ alkyl, wherein $OR^8$ of $R^5$ can form a ring with any part of X;

X is —O—$C_{1-7}$ alkanediyl and wherein —O—$C_{1-7}$ alkanediyl of X can form a ring with any part of $R^5$; and Y is $NR^{10}R^{12}$ wherein $R^{10}$ and $R^{12}$ can form a ring wherein the ring contains the N of $NR^{10}R^{12}$ and four or five carbon atoms.

In some embodiments, Y is aryl or heteroaryl, wherein the aryl or the heteroaryl is optionally substituted by one or more of $R^8$; or S-heteroaryl, wherein the S-heteroaryl is optionally substituted by one or more $R^4$.

In some embodiments, Y is heteroaryl, wherein the heteroaryl is optionally substituted by one or more of $R^8$; or S-heteroaryl, wherein the S-heteroaryl is optionally substituted by one or more $R^{14}$.

In some embodiments, $R^5$ is selected from H and $C_{1-7}$ alkyl;

X is selected from a bond and $C_{1-7}$ alkanediyl; and

Y is aryl or heteroaryl, wherein the aryl or the heteroaryl is optionally substituted by one or more of $R^8$; or S-heteroaryl wherein the S-heteroaryl is optionally substituted by one or more $R^{14}$.

In some embodiments, $R^5$ is selected from H and $C_{1-7}$ alkyl;

X is selected from a bond and $C_{1-7}$ alkanediyl; and

Y is heteroaryl, wherein the heteroaryl is optionally substituted by one or more of $R^8$; or S-heteroaryl wherein the S-heteroaryl is optionally substituted by one or more $R^{14}$.

In some embodiments, $R^5$ is selected from H and $C_{1-7}$ alkyl;

X is selected from a bond and $C_{1-7}$ alkanediyl; and

Y is aryl or heteroaryl, wherein the aryl or the heteroaryl is optionally substituted by one of $R^8$ wherein $R^8$ is selected from $C_{1-7}$ alkyl, $C_{2-7}$ alkenyl, or $C_{3-7}$ cycloalkyl; or S-heteroaryl wherein the S-heteroaryl is optionally substituted by one of $R^{14}$ wherein $R^{14}$ is selected from $C_{1-7}$ alkyl, $C_{2-7}$ alkenyl, or $C_{3-7}$ cycloalkyl.

In some embodiments, $R^5$ is selected from H and $C_{1-7}$ alkyl;

X is selected from a bond and $C_{1-7}$ alkanediyl; and

Y is heteroaryl, wherein the heteroaryl is optionally substituted by one of $R^8$ wherein $R^8$ is selected from $C_{1-7}$ alkyl, $C_{2-7}$ alkenyl, $C_{3-7}$ cycloalky; or S-heteroaryl wherein the S-heteroaryl is optionally substituted by one of $R^{14}$ wherein $R^{14}$ is selected from $C_{1-7}$ alkyl, $C_{2-7}$ alkenyl, $C_{3-7}$ cycloalkyl.

In some embodiments, the compound is of any one of Formulae (Va), (Vb), (Vc), or (Vd):

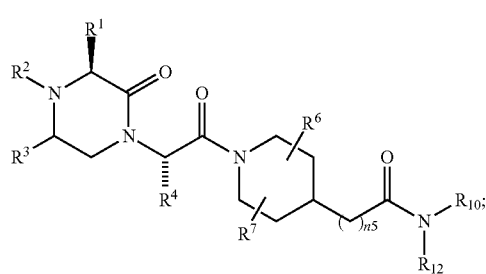

(Va)

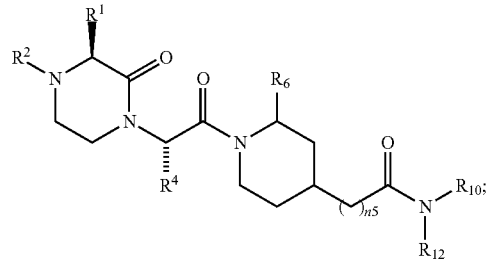

(Vb)

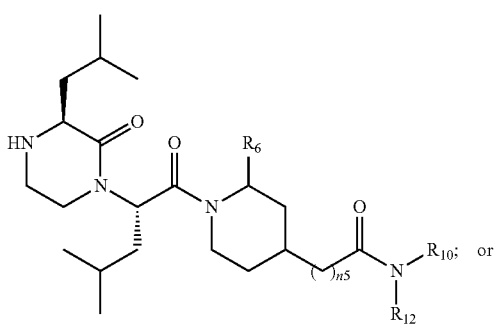

(Vc)

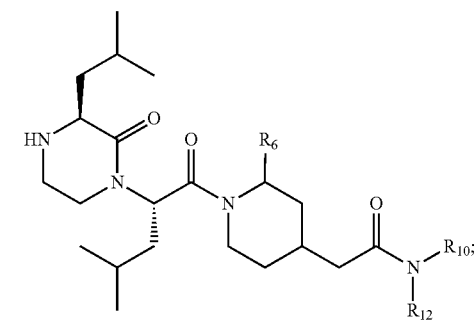

(Vd)

or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (Va) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (Vb) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (Vc) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (Vd) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, $R^5$ is H and X—Y is

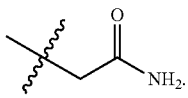 [SMILES: *CC(N)=O]

In some embodiments, the compound is of any one of Formulae (VIa), (VIb), (VIc), or (VId):

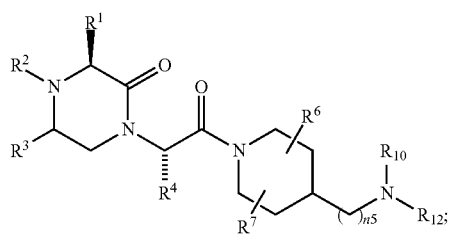
(VIa)

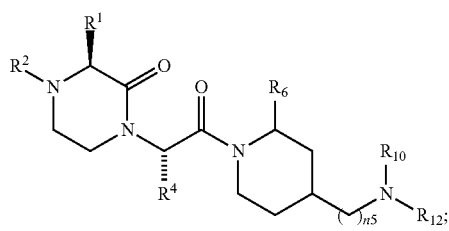
(VIb)

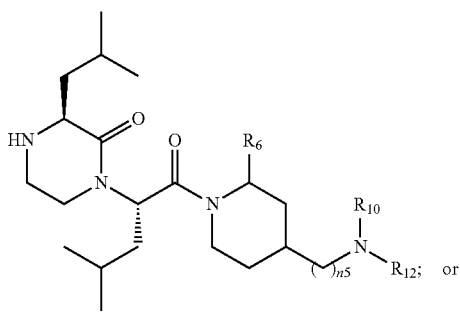
(VIc)

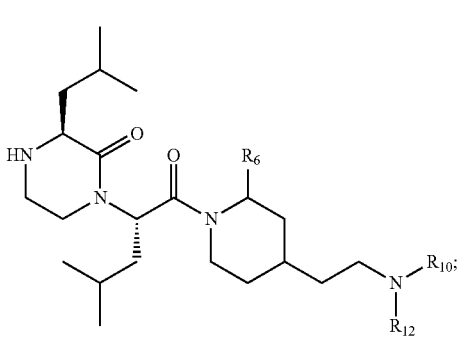
(VId)

or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (VIa) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (VIb) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (VIc) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, the compound is of Formula (VId) or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

In some embodiments, Y is $C(O)NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, $R^5$ is H and X—Y is

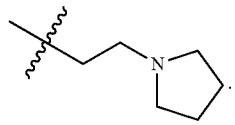 [SMILES: *CCN1CCCC1]

In some embodiments, $R^5$ is selected from H and $C_{1-7}$ alkyl;

X is selected from a bond and $C_{1-7}$ alkanediyl;

Y is $C(O)NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$; and $R^{10}$ and $R^{12}$ are each independently selected from H, $C_{1-7}$ alkyl, $C_{2-7}$ alkenyl, $C_{3-7}$ cycloalkyl, or $C_{1-3}$ alkyl-aryl.

In some embodiments, Y is selected from S-aryl, O-aryl, S-heteroaryl, or O-heteroaryl, wherein the S-aryl, O-aryl, S-heteroaryl, or O-heteroaryl are optionally substituted by one or more $R^9$ or $R^{14}$.

In some embodiments, Y is selected from O-aryl and O-heteroaryl, wherein the O-aryl and O-heteroaryl are optionally substituted by one or more $R^9$ or $R^{14}$.

In some embodiments, Y is selected from S-aryl, O-aryl, S-heteroaryl, or O-heteroaryl, wherein the S-aryl, O-aryl, S-heteroaryl, or O-heteroaryl are optionally substituted by one or more $R^9$; wherein $R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$.

In some embodiments, $R^5$ is selected from H and $C_{1-7}$ alkyl;

X is selected from a bond and $C_{1-7}$ alkanediyl; and

Y is selected from O-aryl and O-heteroaryl, wherein the O-aryl and O-heteroaryl is optionally substituted by one or more $R^9$; wherein $R^9$ is selected from H, $C_{1-5}$ alkyl, halogen, $C_{1-5}$ alkyl-$NR^8R^{11}$, $C_{1-5}$ alkyl-$C(O)NR^8R^{11}$, $C_{1-5}$ alkyl-$C(O)OR^8$, CN, $C(O)R^8$, $C(O)NR^8R^{11}$, $C(O)OR^8$, and $OR^8$.

In some embodiments, Y is $C(O)OR^{10}$.

In some embodiments, $R^5$ is selected from H and $C_{1-7}$ alkyl;

X is selected from a bond and $C_{1-7}$ alkanediyl;

Y is $C(O)OR^{10}$; and $R^{10}$ is selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by $OR^8$.

In some embodiments, Y is H.

In some embodiments, $R^5$ is $C_{1-7}$ alkyl; X is a bond; and Y is H.

In some embodiments, Y is CN.

In some embodiments, $R^5$ is H; X is $C_{1-7}$ alkanediyl; and Y is CN.

In some embodiments, Y is selected from H, C(O)$NR^{10}R^{12}$, C(O)$OR^{10}$, $NR^{10}R^{12}$, CN, $C_{3-7}$-cycloalkyl optionally containing a hetero atom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; aryl, or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is C(O)$NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, C(O)$R^{14}$, C(O)$NR^{15}R^{15}$, C(O)OR, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is C(O)$NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by C(O)$NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from H, C(O)$NR^{10}R^{12}$, C(O)$OR^{10}$, $NR^{10}R^{12}$, CN, $C_{3-7}$-cycloalkyl optionally containing a hetero atom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is C(O)$NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, halogen, $C_{1-5}$ alkyl-$OR^8$, $C_{1-5}$ alkyl-$SR^8$, $C_{1-5}$ alkyl-$NR^8R^{11}$, $C_{1-5}$ alkyl-C(O)$OR^8$, $C_{1-5}$ alkyl-C(O)$NR^8R^{11}$, $C_{1-5}$ alkyl-C(O)$R^{10}$, CN, C(O)$R^8$, C(O)$NR^8R^{11}$, C(O)$OR^8$, $NR^8$C(O)$NR^8R^{11}$, OC(O)$NR^8R^{11}$, $SO_2NR^8R^{11}$, $NR^8SO_2R^8$, $OR^8$, $NR^8R^{11}$, or S(O)$_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, Y is selected from H, C(O)$NR^{10}R^{12}$, C(O)$OR^{10}$, $NR^{10}R^{12}$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein, when Y is C(O)$NR^{10}R^{12}$ or $NR^{10}R^{12}$, Y can form a ring with any part of X or $R^5$, wherein the ring optionally contains a carbonyl group; with the proviso that when Y is C(O)$NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or, when Y is $C(O)NR^{10}R^{12}$ or $NR^{10}R^{12}$, $R^5$ can form a ring with any part of Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or, when Y is $C(O)NR^{10}R^{12}$ or $NR^{10}R^{12}$, X can form a ring with any part of Y, wherein the ring optionally contains a carbonyl group;

Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein, when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-OR; $C_{1-5}$ alkyl-$NHCOR^{13}$ wherein $R^{13}$ is pentylamino-5-oxopentyl-7-thia-2.4-diazabicyclo [3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, or $OR^8$; and wherein $C_{1-7}$ alkyl or $OR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group;

$R^6$ is H, $C_{1-7}$ alkyl, or imidazolidinone;

$R^8$ and $R^{11}$ are each independently selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y, wherein the ring optionally contains a carbonyl group;

Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N it is optionally substituted by $R^8$; O-aryl, S-heteroaryl, O-heteroaryl wherein the O-aryl or the O-heteroaryl are optionally substituted by one or more $R^9$ and wherein the S-heteroaryl is optionally substituted by one or more $R^{14}$; or aryl, heteroaryl wherein the aryl or the heteroaryl is optionally substituted by one or more of $R^8$; and wherein, when Y is $C(O)NR^{10}R^{12}$ or $NR^{10}R^{12}$, Y can form a ring with any part of $C_{1-7}$ alkanediyl of X or any part of $C_{1-7}$ alkyl of $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$;

$R^{10}$ and $R^{12}$ are each independently selected selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$; and $R^{14}$ is $C_{1-7}$ alkyl.

In some embodiments, Y is selected from H, $C(O)NR^{10}R^{12}$, $C(O)OR^{10}$, $NR^{10}R^{12}$, $C_{3-7}$-cycloalkyl optionally containing a hetero atom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from H, $C(O)NR^{10}R^{12}$, $C(O)OR^{10}$, $NR^{10}R^{12}$, $C_{3-7}$-cycloalkyl optionally containing a hetero atom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein, when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, C(O)OR, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from H, $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, halogen, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)NR^8R^{11}$, $C_{1-5}$ alkyl-$C(O)OR^8$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-$OR^8$; $C_{1-5}$ alkyl-$NHCOR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, or $OR^8$; and wherein $C_{1-7}$ alkyl or $OR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group;

$R^6$ is H, $C_{1-7}$ alkyl, or imidazolidinone;

$R^8$ and $R^{11}$ are each independently selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y, wherein the ring optionally contains a carbonyl group;

Y is selected from H, $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; O-aryl, S-heteroaryl, O-heteroaryl wherein the O-aryl or the O-heteroaryl are optionally substituted by one or more $R^9$ and wherein the S-heteroaryl is optionally substituted by one or more $R^{14}$; or aryl, heteroaryl wherein the aryl or the heteroaryl is optionally substituted by one or more of $R^8$; and wherein, when Y is $C(O)NR^{10}R^{12}$ or $NR^{10}R^{12}$, Y can form a ring with any part of $C_{1-7}$ alkanediyl of X or any part of $C_{1-7}$ alkyl of $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, $C_{1-5}$ alkyl, halogen, $C_{1-5}$ alkyl-$NR^8R^{11}$, $C_{1-5}$ alkyl-$C(O)NR^8R^{11}$, $C_{1-5}$ alkyl-$C(O)OR^8$, CN, $C(O)R^8$, $C(O)NR^8R^{11}$, $C(O)OR^8$, and $OR^8$;

$R^{10}$ and $R^{12}$ are each independently selected selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$; and $R^{14}$ is $C_{1-7}$ alkyl.

In some embodiments, Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from $C(O)NR^{10}R^{12}$, $C(O)OR^{10}$, $NR^{10}R^{12}$, $C_{3-7}$-cycloalkyl optionally containing a hetero atom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein, when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-$OR^8$; $C_{1-5}$ alkyl-$NHCOR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, or $OR^8$; and wherein $C_{1-7}$ alkyl or $OR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group;

$R^6$ is H or $C_{1-7}$ alkyl;

$R^8$ and $R^{11}$ are each independently selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y, wherein the ring optionally contains a carbonyl group;

Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; O-aryl, S-heteroaryl, O-heteroaryl wherein the O-aryl or the O-heteroaryl are optionally substituted by one or more $R^9$ and wherein the S-heteroaryl is optionally substituted by one or more $R^{14}$; or aryl, heteroaryl wherein the aryl or the heteroaryl is optionally substituted by one or more of $R^8$; and wherein, when Y is $C(O)NR^{10}R^{12}$ or $NR^{10}R^{12}$, Y can form a ring with any part of $C_{1-7}$ alkanediyl of X or any part of $C_{1-7}$ alkyl of $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$;

$R^{10}$ and $R^{12}$ are each independently selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$; and $R^{14}$ is $C_{1-7}$ alkyl.

In some embodiments, Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein, when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)NR^8R^{11}$, $C_{1-5}$ alkyl-$C(O)OR^8$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

wherein $R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-OR; $C_{1-5}$ alkyl-$NHCOR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, or $OR^8$; and wherein $C_{1-7}$ alkyl or $OR^8$ of $R^5$ can form a ring with any part of X or, when Y is $C(O)NR^{10}R^{12}$ or $NR^{10}R^{12}$, $C_{1-7}$ alkyl of $R^5$ can form a ring with any part of Y, wherein the ring optionally contains a carbonyl group;

$R^6$ is H or $C_{1-7}$ alkyl;

$R^8$ and $R^{11}$ are each independently selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $C(O)NR^{10}R^{12}$ or $NR^{10}R^{12}$, $C_{1-7}$ alkanediyl of X can form a ring with any part of Y, wherein the ring optionally contains a carbonyl group;

Y is selected from $C(O)NR^{10}R^{12}$, $C(O)OR^{10}$, $NR^{10}R^{12}$, $C_{3-7}$-cycloalkyl optionally containing a heteroatom in the ring selected from O and N wherein if the heteroatom is N it is optionally substituted by $R^8$; O-aryl, S-heteroaryl, O-heteroaryl wherein the O-aryl or the O-heteroaryl are optionally substituted by one or more $R^9$ and wherein the S-heteroaryl is optionally substituted by one or more $R^{14}$; or heteroaryl wherein the heteroaryl is optionally substituted by one or more of $R^8$; and wherein, when Y is $C(O)NR^{10}R^{12}$ or $NR^{10}R^{12}$, Y can form a ring with any part of $C_{1-7}$ alkanediyl of X or any part of $C_{1-7}$ alkyl of $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, $C_{1-5}$ alkyl, halogen, $C_{1-5}$ alkyl-$NR^8R^{11}$, $C_{1-5}$ alkyl-$C(O)NR^8R^{11}$, $C_{1-5}$ alkyl-$C(O)OR^8$, CN, $C(O)R^8$, $C(O)NR^8R^{11}$, $C(O)OR^8$, and $OR^8$;

$R^{10}$ and $R^{12}$ are each independently selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$; and $R^{14}$ is $C_{1-7}$ alkyl.

In some embodiments, Y is selected from $C(O)NR^{10}R^{12}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from $C(O)NR^{10}R^{12}$, $NR^{10}R^{12}$, $C_{3\text{-}7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein, when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl;

$R^2$ is selected from H, $C(O)R^{14}$, $C(O)NR^{15}R^{15}$, $C(O)OR^{15}$, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, $C_{1\text{-}5}$ alkyl-$OR^8$, $C_{1\text{-}3}$ alkanediyl-O—$C_{1\text{-}3}$ alkanediyl-O—$C_{1\text{-}3}$ alkanediyl, $C_{1\text{-}5}$ alkyl-$NHCOR^{13}$, or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, all optionally substituted by halogen, $OR^8$, $NR^8R^{11}$; or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl;

$R^4$ is selected from $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl;

$R^5$ is selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, $OR^8$, $C_{1\text{-}3}$ alkyl-$OR^8$, or $SR^8$; and wherein $R^5$ can form a ring with any part of X or Y, wherein the ring optionally contains a carbonyl group;

$R^6$ is selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, all optionally substituted by halogen, $OR^8$, $NR^8R^{11}$; $C_{1\text{-}3}$ alkyl substituted by $C(O)NR^8R^{11}$; or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl; or is imidazolidinone;

$R^8$ and $R^{11}$ are each independently selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl;

X is selected from a bond, $C_{1\text{-}7}$ alkanediyl, $C_{2\text{-}7}$ alkenediyl, $C_{2\text{-}7}$ alkynediyl, $C_{3\text{-}6}$ cycloalkanediyl, $C_{4\text{-}6}$ cycloalkenediyl, —O—, $C_{1\text{-}3}$ alkanediyl-O—, —O—$C_{1\text{-}7}$ alkanediyl, $C_{1\text{-}3}$ alkanediyl-O—$C_{1\text{-}7}$ alkanediyl, $C_{1\text{-}7}$ heteroalkanediyl, or —S—$C_{1\text{-}7}$ alkanediyl; and wherein X can form a ring with any part of $R^5$ or Y, wherein the ring optionally contains a carbonyl group;

Y is selected from $C(O)NR^{10}R^{12}$, $NR^{10}R^{12}$, $C_{3\text{-}7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1\text{-}5}$ alkyl, $C_{2\text{-}5}$ alkenyl, $C_{2\text{-}5}$ alkynyl, $C_{3\text{-}5}$ cycloalkyl, $C_{1\text{-}5}$ alkyl-$OR^8$, $C_{1\text{-}5}$ alkyl-$SR^8$, $C_{1\text{-}5}$ alkyl-$NR^8R^{11}$, $C_{1\text{-}5}$ alkyl-$C(O)OR^8$, $C_{1\text{-}5}$ alkyl-$C(O)NR^8R^{11}$, $C_{1\text{-}5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, $C_{1\text{-}3}$ alkanediyl-O—$C_{1\text{-}3}$ alkanediyl-O—$C_{1\text{-}3}$ alkanediyl, $C_{1\text{-}3}$ alkyl-aryl, or $C_{1\text{-}3}$ alkyl-heteroaryl, all these groups optionally substituted by halogen, $OR^8$, or $NR^8R^{11}$;

$R^{13}$ is $C_{1\text{-}5}$ alkyl substituted by a bicyclic ring optionally containing at least one heteroatom and a carbonyl group;

$R^{14}$ is selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, or $C_{1\text{-}3}$ alkyl substituted by aryl or heteroaryl, wherein the aryl or the heteroaryl is optionally substituted by halogen, $C_{1\text{-}4}$ alkyl or $C_{3\text{-}5}$ cycloalkyl; and each $R^{15}$ is independently selected from H, $C_{1\text{-}7}$ alkyl, $C_{2\text{-}7}$ alkenyl, $C_{2\text{-}7}$ alkynyl, $C_{3\text{-}7}$ cycloalkyl, $C_{4\text{-}7}$ cycloalkenyl, $OR^8$, $C_{1\text{-}3}$ alkyl-$OR^8$.

In some embodiments, the compound is a compound of Formula (I) or Formula (Ia), wherein:

$R^1$ is selected from $C_{3\text{-}7}$ alkyl, $C_{3\text{-}7}$ cycloalkyl, $C_{1\text{-}3}$ alkyl substituted by aryl or heteroaryl;

$R^2$ is selected from H, $C(O)R^{14}$, $C_{1\text{-}7}$ alkyl, $C_{3\text{-}7}$ cycloalkyl, $C_{1\text{-}5}$ alkyl-OR; $C_{1\text{-}5}$ alkyl-$NHCOR^{13}$ wherein $R^{13}$ is pentylamino-5-oxopentyl-7-thia-2,4-diazabicyclo[3.3.0]octan-3-one; or $C_{1\text{-}3}$ alkyl substituted by aryl, wherein the aryl is optionally substituted by halogen, $C_{1\text{-}4}$ alkyl or $C_{3\text{-}5}$ cycloalkyl;

$R^3$ and $R^7$ are H;

$R^4$ is selected from $C_{3\text{-}7}$ alkyl, $C_{3\text{-}7}$ cycloalkyl, or $C_{1\text{-}3}$ alkyl substituted by aryl or heteroaryl;

$R^5$ is selected from H, $C_{1\text{-}7}$ alkyl, or $OR^8$; and wherein $C_{1\text{-}7}$ alkyl or $OR^8$ of $R^5$ can form a ring with any part of X or, when Y is $C(O)NR^{10}R^{12}$ or $NR^{10}R^{12}$, $C_{1\text{-}7}$ alkyl of $R^5$ can form a ring with any part of Y, wherein the ring optionally contains a carbonyl group;

$R^6$ is H or $C_{1\text{-}7}$ alkyl;

$R^8$ and $R^{11}$ are each independently selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is C(O)NR$^{10}$R$^{12}$ or NR$^{10}$R$^{12}$, $C_{1-7}$ alkanediyl of X can form a ring with any part of Y, wherein the ring optionally contains a carbonyl group;

Y is selected from C(O)NR$^{10}$R$^{12}$, NR$^{10}$R$^{12}$, $C_{3-7}$-cycloalkyl optionally containing a heteroatom in the ring selected from O and N wherein if the heteroatom is N it is optionally substituted by $R^8$; O-aryl, S-heteroaryl, O-heteroaryl wherein the O-aryl or the O-heteroaryl are optionally substituted by one or more $R^9$ and wherein the S-heteroaryl is optionally substituted by one or more $R^{14}$; or heteroaryl wherein the heteroaryl is optionally substituted by one or more of $R^8$; and wherein, when Y is C(O)NR$^{10}$R$^{12}$ or NR$^{10}$R$^{12}$, Y can form a ring with any part of $C_{1-7}$ alkanediyl of X or any part of $C_{1-7}$ alkyl of $R^5$, wherein the ring optionally contains a carbonyl group; with the proviso that when Y is C(O)NR$^{10}$R$^{12}$ or NR$^{10}$R$^{12}$, $R^{10}$ and $R^{12}$ can form a ring wherein the ring contains the N of NR$^{10}$R$^{12}$ and optionally one further heteroatom selected from O and N, wherein if the one further heteroatom is N, it is optionally substituted by $R^8$;

$R^9$ is selected from H, $C_{1-5}$ alkyl, halogen, $C_{1-5}$ alkyl-NR$^8$R$^{11}$, $C_{1-5}$ alkyl-C(O)NR$^8$R$^{11}$, $C_{1-5}$ alkyl-C(O)OR$^8$, CN, C(O)R$^8$, C(O)NR$^8$R$^{11}$, C(O)OR$^8$, and OR$^8$;

$R^{10}$ and $R^{12}$ are each independently selected from H, $C_{1-7}$ alkyl, $C_{3-7}$ cycloalkyl, $C_{1-3}$ alkyl-aryl, all these groups optionally substituted by halogen; and $R^{14}$ is $C_{1-7}$ alkyl.

In some embodiments, Y is selected from NR$^{10}$R$^{12}$, $C_{3-7}$-cycloalkyl optionally containing a heteroatom in the ring selected from O and N wherein if the heteroatom is N it is optionally substituted by $R^8$; S-heteroaryl, wherein the S-heteroaryl is optionally substituted by one or more $R^{14}$; aryl, or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is NR$^{10}$R$^{12}$, $R^{10}$ and $R^{12}$ can form a ring wherein the ring contains the N of NR$^{10}$R$^{12}$ and optionally one further heteroatom selected from O and N, wherein if the one further heteroatom is N, it is optionally substituted by $R^8$.

In some embodiments, Y is selected from NR$^{10}$R$^{12}$, $C_{3-7}$-cycloalkyl optionally containing a heteroatom in the ring selected from O and N wherein if the heteroatom is N it is optionally substituted by $R^8$; S-heteroaryl, wherein the S-heteroaryl is optionally substituted by one or more $R^{14}$; aryl, or heteroaryl wherein the aryl or heteroaryl is optionally substituted by one or more of $R^8$; and wherein, when Y is NR$^{10}$R$^{12}$, Y can form a ring with any part of X or $R^5$, wherein the ring optionally contains a carbonyl group; with the proviso that when Y is NR$^{10}$R$^{12}$, $R^{10}$ and $R^{12}$ can form a ring wherein the ring contains the N of NR$^{10}$R$^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, C(O)R$^{14}$, C(O)NR$^{15}$R$^{15}$, C(O)OR, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-OR$^8$, $C_{1-3}$ alkanediyl-O—$C_{1-3}$ alkanediyl-O—$C_{1-3}$ alkanediyl, $C_{1-5}$ alkyl-NHCOR$^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is C(O)NR$^{15}$R$^{15}$, both $R^{15}$ can form a ring wherein the ring contains the N of NR$^{15}$R$^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, OR$^8$, NR$^8$R$^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, OR$^8$, $C_{1-3}$ alkyl-OR$^8$, or SR$^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, OR$^8$, NR$^8$R$^{11}$; $C_{1-3}$ alkyl substituted by C(O)NR$^8$R$^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from NR$^{10}$R$^{12}$, $C_{3-7}$-cycloalkyl optionally containing a heteroatom in the ring selected from O and N wherein if the heteroatom is N it is optionally substituted by $R^8$; S-heteroaryl, wherein the S-heteroaryl is optionally substituted by one or $R^{14}$; aryl, or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is NR$^{10}$R$^{12}$, $R^{10}$ and $R^{12}$ can form a ring wherein the ring contains the N of NR$^{10}$R$^{12}$ and optionally one further heteroatom selected from O and N, wherein if the one further heteroatom is N, it is optionally substituted by $R^8$;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, OR$^8$, or NR$^8$R$^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-$OR^8$; $C_{1-5}$ alkyl-$NHCOR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, or $OR^8$; and wherein $C_{1-7}$ alkyl or $OR^8$ of $R^5$ can form a ring with any part of X or, when Y is $NR^{10}R^{12}$, $C_{1-7}$ alkyl of $R^5$ can form a ring with any part of Y;

$R^6$ is H;

$R^8$ is selected from H, $C_{1-7}$ alkyl, $C_{2-7}$ alkenyl, and $C_{3-7}$ cycloalkyl;

X is selected from a bond, —O—$C_{1-7}$ alkanediyl and $C_{1-7}$ alkanediyl; and wherein —O—$C_{1-7}$ alkanediyl or $C_{1-7}$ alkanediyl of X can form a ring with any part of $R^5$ or, when Y is $NR^{10}R^{12}$, $C_{1-7}$ alkanediyl of X can form a ring with any part of Y;

Y is selected from $NR^{10}R^{12}$, $C_{3-7}$-cycloalkyl optionally containing a heteroatom in the ring selected from O and N wherein if the heteroatom is N it is optionally substituted by $R^8$, wherein $R^8$ is $C_{1-7}$ alkyl; S-heteroaryl wherein the S-heteroaryl is optionally substituted by one or more $R^{14}$; aryl, or heteroaryl wherein the aryl or the heteroaryl is optionally substituted by one or more of $R^8$; and wherein, when Y is $NR^{10}R^{12}$, Y can form a ring with any part of $C_{1-7}$ alkanediyl of X or any part of $C_{1-7}$ alkyl of $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^{10}$ and $R^{12}$ are each independently selected from H, $C_{1-7}$ alkyl, $C_{3-7}$ cycloalkyl, or $C_{1-3}$ alkyl-aryl, all these groups optionally substituted by halogen; and $R^{14}$ is $C_{1-7}$ alkyl.

In some embodiments, the aryl, the heteroaryl or the S-heteroaryl group of any of the compounds of the present disclosure are preferably selected from the group consisting of phenyl, imidazole, pyridine and triazole, more preferably selected from the group consisting of phenyl, imidazole and pyridine.

In some embodiments, Y is selected from $NR^{10}R^{12}$, $C_{3-7}$-cycloalkyl optionally containing a heteroatom in the ring selected from O and N wherein if the heteroatom is N it is optionally substituted by $R^8$; S-heteroaryl, wherein the S-heteroaryl is optionally substituted by one or more $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, Y is selected from $NR^{10}R^{12}$, $C_{3-7}$-cycloalkyl optionally containing a heteroatom in the ring selected from O and N wherein if the heteroatom is N it is optionally substituted by $R^8$; S-heteroaryl, wherein the S-heteroaryl is optionally substituted by one or $R^{14}$; or heteroaryl wherein the heteroaryl is optionally substituted by one or more of $R^8$; and wherein, when Y is $NR^{10}R^{12}$, Y can form a ring with any part of X or $R^5$, wherein the ring optionally contains a carbonyl group; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from $NR^{10}R^{12}$, $C_{3-7}$-cycloalkyl optionally containing a heteroatom in the ring selected from O and N wherein if the heteroatom is N it is optionally substituted by R$^8$; S-heteroaryl, wherein the S-heteroaryl is optionally substituted by one or R$^{14}$; or heteroaryl wherein the heteroaryl is optionally substituted by one or more of R$^8$; and wherein Y can form a ring with any part of X or R$^5$, wherein the ring optionally contains a carbonyl group; with the proviso that when Y is NR$^{10}$R$^{12}$, R$^{10}$ and R$^{12}$ can form a ring wherein the ring contains the N of NR$^{10}$R$^{12}$ and optionally one further heteroatom selected from O and N, wherein if the one further heteroatom is N, it is optionally substituted by R$^8$;

R$^{10}$ and R$^{12}$ are each independently selected from H, C$_{1-7}$ alkyl, C$_{2-7}$ alkenyl, C$_{2-7}$ alkynyl, C$_{3-7}$ cycloalkyl, C$_{4-7}$ cycloalkenyl, C$_{1-3}$ alkanediyl-O—C$_{1-3}$ alkanediyl-O—C$_{1-3}$ alkanediyl, C$_{1-3}$ alkyl-aryl, or C$_{1-3}$ alkyl-heteroaryl, all these groups optionally substituted by halogen, OR$^8$, or NR$^8$R$^{11}$;

R$^{13}$ is C$_{1-5}$ alkyl substituted by a bicyclic ring optionally containing at least one heteroatom and a carbonyl group;

R$^{14}$ is selected from H, C$_{1-7}$ alkyl, C$_{2-7}$ alkenyl, C$_{2-7}$ alkynyl, C$_{3-7}$ cycloalkyl, C$_{4-7}$ cycloalkenyl, or C$_{1-3}$ alkyl substituted by aryl or heteroaryl, wherein the aryl or the heteroaryl is optionally substituted by halogen, C$_{1-4}$ alkyl or C$_{3-5}$ cycloalkyl; and each R$^{15}$ is independently selected from H, C$_{1-7}$ alkyl, C$_{2-7}$ alkenyl, C$_{2-7}$ alkynyl, C$_{3-7}$ cycloalkyl, C$_{4-7}$ cycloalkenyl, OR$^8$, or C$_{1-3}$ alkyl-OR$^8$.

In some embodiments, the compound is a compound of Formula (I) or Formula (Ia), wherein:

R$^1$ is selected from C$_{3-7}$ alkyl, C$_{3-7}$ cycloalkyl, or C$_{1-3}$ alkyl substituted by aryl or heteroaryl;

R$^2$ is selected from H, C(O)R$^{14}$, C$_{1-7}$ alkyl, C$_{3-7}$ cycloalkyl, C$_{1-5}$ alkyl-OR$^8$; C$_{1-5}$ alkyl-NHCOR$^{13}$ wherein R$^{13}$ is pentylamino-5-oxopentyl-7-thia-2,4-diazabicyclo[3.3.0]octan-3-one; or C$_{1-3}$ alkyl substituted by aryl, wherein the aryl is optionally substituted by halogen, C$_{1-4}$ alkyl or C$_{3-5}$ cycloalkyl;

R$^3$ and R$^7$ are H;

R$^4$ is selected from C$_{3-7}$ alkyl, C$_{3-7}$ cycloalkyl, or C$_{1-3}$ alkyl substituted by aryl or heteroaryl;

R$^5$ is selected from H, C$_{1-7}$ alkyl, or OR$^8$; and wherein C$_{1-7}$ alkyl or OR$^8$ of R$^5$ can form a ring with any part of X or, when Y is NR$^{10}$R$^{12}$, C$_{1-7}$ alkyl of R$^5$ can form a ring with any part of Y;

R$^6$ is H;

R$^8$ is selected from H, C$_{1-7}$ alkyl, C$_{2-7}$ alkenyl, and C$_{3-7}$ cycloalkyl;

X is selected from a bond, —O—C$_{1-7}$ alkanediyl and C$_{1-7}$ alkanediyl; and wherein —O—C$_{1-7}$ alkanediyl or C$_{1-7}$ alkanediyl of X can form a ring with any part of R$^5$ or, when Y is NR$^{10}$R$^{12}$, C$_{1-7}$ alkanediyl of X can form a ring with any part of Y;

Y is selected from NR$^{10}$R$^{12}$, C$_{3-7}$-cycloalkyl optionally containing a heteroatom in the ring selected from O and N wherein if the heteroatom is N it is optionally substituted by R$^8$, wherein R$^8$ is C$_{1-7}$ alkyl; S-heteroaryl wherein the S-heteroaryl is optionally substituted by one or more R$^{14}$; or heteroaryl wherein the heteroaryl is optionally substituted by one or more of R$^8$; and wherein, when Y is NR$^{10}$R$^{12}$, Y can form a ring with any part of C$_{1-7}$ alkanediyl of X or any part of C$_{1-7}$ alkyl of R$^5$; with the proviso that when Y is NR$^{10}$R$^{12}$, R$^{10}$ and R$^{12}$ can form a ring wherein the ring contains the N of NR$^{10}$R$^{12}$ and optionally one further heteroatom selected from O and N, wherein if the one further heteroatom is N, it is optionally substituted by R$^8$; and R$^{14}$ is C$_{1-7}$ alkyl.

In some embodiments, the aryl, the heteroaryl or the S-heteroaryl group of the compounds of the present disclosure are preferably selected from the group consisting of phenyl, imidazole, pyridine and triazole, more preferably selected from the group consisting of phenyl, imidazole and pyridine.

In some embodiments, Y is selected from NR$^{10}$R$^{12}$ and C$_{3-7}$-cycloalkyl optionally containing a heteroatom in the ring selected from O and N wherein if the heteroatom is N it is optionally substituted by R$^8$; and wherein Y can form a ring with any part of X or R$^5$; with the proviso that when Y is NR$^{10}$R$^{12}$, R$^{10}$ and R$^{12}$ can form a ring wherein the ring contains the N of NR$^{10}$R$^{12}$ and optionally one further heteroatom selected from O and N, wherein if the one further heteroatom is N, it is optionally substituted by R$^8$.

In some embodiments, Y is selected from NR$^{10}$R$^{12}$ and C$_{3-7}$-cycloalkyl optionally containing a heteroatom in the ring selected from O and N wherein if the heteroatom is N it is optionally substituted by R$^8$; and wherein, when Y is NR$^{10}$R$^{12}$, Y can form a ring with any part of X or R$^5$; with the proviso that when Y is NR$^{10}$R$^{12}$, R$^{10}$ and R$^{12}$ can form a ring wherein the ring contains the N of NR$^{10}$R$^{12}$ and optionally one further heteroatom selected from O and N, wherein if the one further heteroatom is N, it is optionally substituted by R$^8$.

In some embodiments, the compound is a compound of Formula (I) or Formula (Ia), wherein:

R$^1$ is selected from H, C$_{1-7}$ alkyl, C$_{2-7}$ alkenyl, C$_{2-7}$ alkynyl, C$_{3-7}$ cycloalkyl, C$_{4-7}$ cycloalkenyl, or C$_{1-3}$ alkyl substituted by aryl or heteroaryl, wherein the aryl or the heteroaryl is optionally substituted by halogen, C$_{1-4}$ alkyl or C$_{3-5}$ cycloalkyl;

R$^2$ is selected from H, C(O)R$^{14}$, C(O)NR$^{15}$R$^{15}$, C(O)OR, C$_{1-7}$ alkyl, C$_{2-7}$ alkenyl, C$_{2-7}$ alkynyl, C$_{3-7}$ cycloalkyl, C$_{4-7}$ cycloalkenyl, C$_{1-5}$ alkyl-OR$^8$, C$_{1-3}$ alkanediyl-O—C$_{1-3}$ alkanediyl-O—C$_{1-3}$ alkanediyl, C$_{1-5}$ alkyl-NHCOR$^{13}$, or C$_{1-3}$ alkyl substituted by aryl or heteroaryl, wherein the aryl or the heteroaryl is optionally substituted by halogen, C$_{1-4}$ alkyl or C$_{3-5}$ cycloalkyl; with the proviso that when R$^2$ is C(O)NR$^{15}$R$^{15}$, both R$^{15}$ can form a ring wherein the ring contains the N of NR$^{15}$R$^{15}$ and optionally one further heteroatom selected from O and N, wherein if the one further heteroatom is N, it is optionally substituted by R$^8$;

R$^3$ and R$^7$ are each independently selected from H, C$_{1-7}$ alkyl, C$_{2-7}$ alkenyl, C$_{2-7}$ alkynyl, C$_{3-7}$ cycloalkyl, C$_{4-7}$ cycloalkenyl, all optionally substituted by halogen, OR$^8$, NR$^8$R$^{11}$; or C$_{1-3}$ alkyl substituted by aryl or heteroaryl, wherein the aryl or the heteroaryl is optionally substituted by halogen, C$_{1-4}$ alkyl or C$_{3-5}$ cycloalkyl;

R$^4$ is selected from C$_{1-7}$ alkyl, C$_{2-7}$ alkenyl, C$_{2-7}$ alkynyl, C$_{3-7}$ cycloalkyl, C$_{4-7}$ cycloalkenyl, or C$_{1-3}$ alkyl substituted by aryl or heteroaryl, wherein the aryl or the heteroaryl is optionally substituted by halogen, C$_{1-4}$ alkyl or C$_{3-5}$ cycloalkyl;

R$^5$ is selected from H, C$_{1-7}$ alkyl, C$_{2-7}$ alkenyl, C$_{2-7}$ alkynyl, C$_{3-7}$ cycloalkyl, C$_{4-7}$ cycloalkenyl, OR$^8$, C$_{1-3}$ alkyl-OR$^8$, or SR$^8$; and wherein R$^5$ can form a ring with any part of X or Y, wherein the ring optionally contains a carbonyl group;

R$^6$ is selected from H, C$_{1-7}$ alkyl, C$_{2-7}$ alkenyl, C$_{2-7}$ alkynyl, C$_{3-7}$ cycloalkyl, C$_{4-7}$ cycloalkenyl, all optionally substituted by halogen, OR$^8$, NR$^8$R$^{11}$; C$_{1-3}$ alkyl substituted by C(O)NR$^8$R$^{11}$; or C$_{1-3}$ alkyl substituted by aryl or heteroaryl, wherein the aryl or the heteroaryl is optionally substituted by halogen, C$_{1-4}$ alkyl or C$_{3-5}$ cycloalkyl; or is imidazolidinone;

R$^8$ and R$^{11}$ are each independently selected from H, C$_{1-7}$ alkyl, C$_{2-7}$ alkenyl, C$_{2-7}$ alkynyl, C$_{3-7}$ cycloalkyl, or C$_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from $NR^{10}R^{12}$ and $C_{3-7}$-cycloalkyl optionally containing a heteroatom in the ring selected from O and N wherein if the heteroatom is N it is optionally substituted by $R^8$; and wherein Y can form a ring with any part of X or $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, $C_{1-3}$ alkyl substituted by aryl or heteroaryl;

$R^2$ is selected from H, $C(O)R^4$, wherein $R^{14}$ is $C_{1-7}$ alkyl; $C_{1-7}$ alkyl, $C_{3-7}$ cycloalkyl, $C_{1-5}$ alkyl-$OR^8$; $C_{1-5}$ alkyl-NH-$COR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H and $C_{1-7}$ alkyl; and wherein $C_{1-7}$ alkyl of $R^5$ can form a ring with any part of Y;

$R^6$ is H;

$R^8$ is selected from H, $C_{1-7}$ alkyl, $C_{2-7}$ alkenyl, and $C_{3-7}$ cycloalkyl;

X is selected from a bond and $C_{1-7}$ alkanediyl, and wherein $C_{1-7}$ alkanediyl of X can form a ring with any part of Y;

Y is selected from $NR^{10}R^{12}$ or $C_{3-7}$-cycloalkyl optionally containing a heteroatom in the ring selected from O and N wherein if the heteroatom is N it is optionally substituted by $R^8$, wherein $R^8$ is $C_{1-7}$ alkyl; and wherein, when Y is $NR^{10}R^{12}$, Y can form a ring with any part of $C_{1-7}$ alkanediyl of X or any part of $C_{1-7}$ alkyl of $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$; and $R^{10}$ and $R^{12}$ are each independently selected from H, $C_{1-7}$ alkyl, $C_{3-7}$ cycloalkyl, $C_{1-3}$ alkyl-aryl, all these groups optionally substituted by halogen.

In some embodiments, the aryl or the heteroaryl group of the compounds of the present disclosure are preferably selected from the group consisting of phenyl, imidazole, pyridine and triazole, more preferably selected from the group consisting of phenyl, imidazole and pyridine.

In some embodiments, the compound is of any one of Formulae (VIIa), (VIIb), (VIIc), (VIId), (VIIe), or (VIIf):

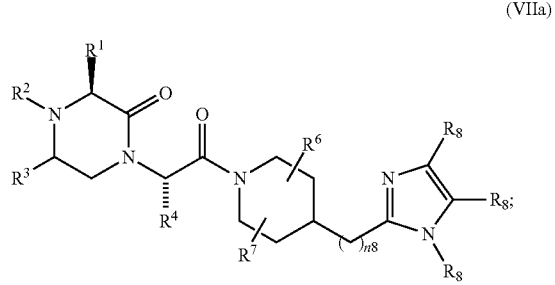

(VIIa)

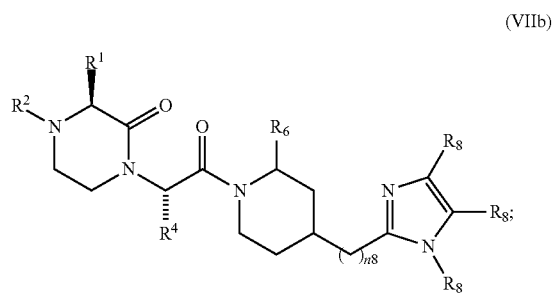

(VIIb)

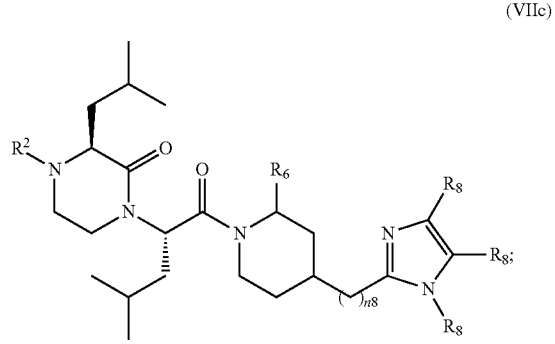

(VIIc)

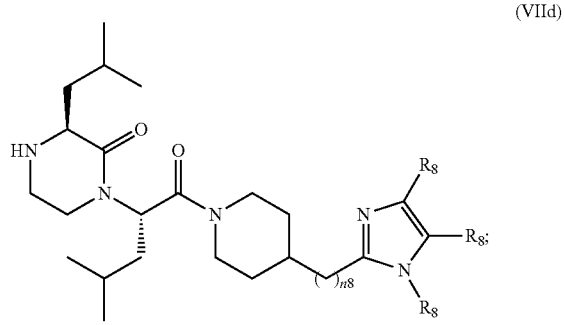

(VIId)

-continued (VIIe)

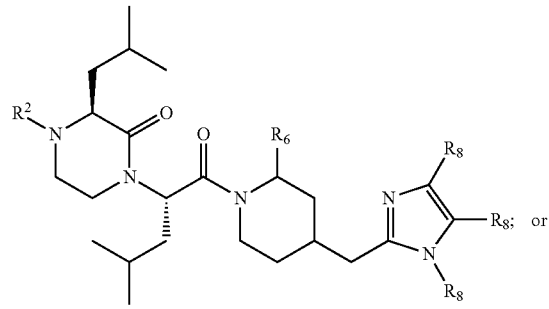

(VIIf)

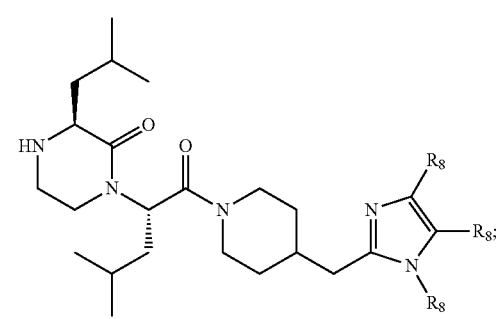

or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIIa) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIIb) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIIc) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIId) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIIe) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, the compound is of Formula (VIIf) or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

In some embodiments, $R^5$ is H and X—Y is

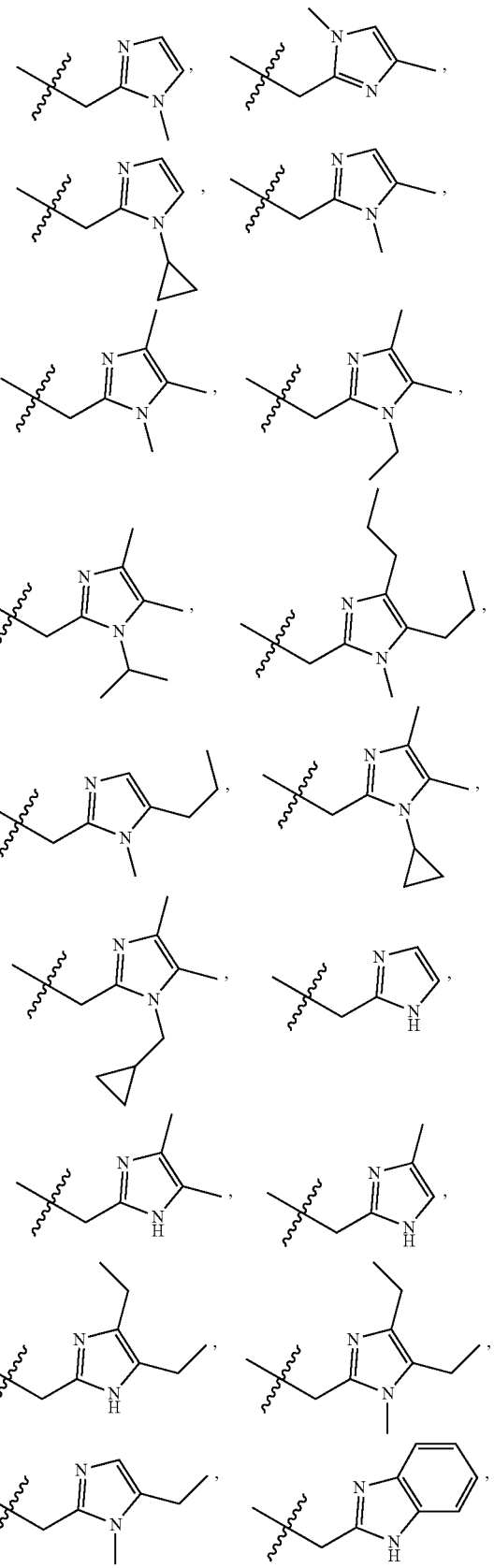

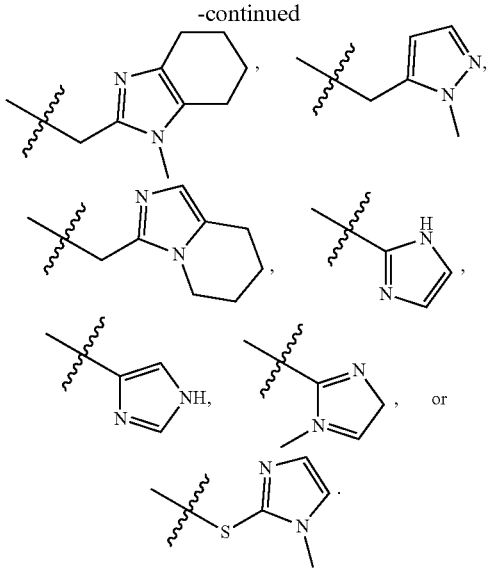

In some embodiments, Y is aryl or heteroaryl, wherein the aryl or the heteroaryl is optionally substituted by one or more of $R^8$; or S-heteroaryl, wherein the S-heteroaryl is optionally substituted by one or more $R^{14}$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-NHCOR$^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl;

Y is aryl or heteroaryl, wherein the aryl or the heteroaryl is optionally substituted by one or more of $R^8$; or S-heteroaryl, wherein the S-heteroaryl is optionally substituted by one or more $R^{14}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-OR; $C_{1-5}$ alkyl-NHCOR$^{13}$ wherein $R^{13}$ is pentylamino-5-oxopentyl-7-thia-2,4-diazabicyclo [3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H and $C_{1-7}$ alkyl;

$R^6$ is H;

$R^8$ is selected from H, $C_{1-7}$ alkyl, $C_{2-7}$ alkenyl, and $C_{3-7}$ cycloalkyl;

X is selected from a bond and $C_{1-7}$ alkanediyl;

Y is aryl or heteroaryl, wherein the aryl or the heteroaryl is optionally substituted by one or more of $R^8$; or S-heteroaryl, wherein the S-heteroaryl is optionally substituted by one or more $R^{14}$; and $R^{14}$ is $C_{1-7}$ alkyl.

In some embodiments, the aryl, the heteroaryl or the S-heteroaryl group of any of the compounds of the present disclosure are preferably selected from the group consisting of phenyl, imidazole, pyridine and triazole, more preferably selected from the group consisting of phenyl, imidazole and pyridine.

In some embodiments, Y is heteroaryl, wherein the heteroaryl is optionally substituted by one or more of $R^8$; or S-heteroaryl, wherein the S-heteroaryl is optionally substituted by one or more $R^{14}$.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-NHCOR$^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl;

Y is heteroaryl, wherein the heteroaryl is optionally substituted by one or more of $R^8$; or S-heteroaryl, wherein the S-heteroaryl is optionally substituted by one or more $R^{14}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-$OR^8$; $C_{1-5}$ alkyl-$NHCOR^{13}$ wherein $R^{13}$ is pentylamino-5-oxopentyl-7-thia-2.4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H and $C_{1-7}$ alkyl;

$R^6$ is H;

$R^8$ is selected from H, $C_{1-7}$ alkyl, $C_{2-7}$ alkenyl, and $C_{3-7}$ cycloalkyl;

X is selected from a bond and $C_{1-7}$ alkanediyl;

Y is heteroaryl, wherein the heteroaryl is optionally substituted by one or more of $R^8$; or S-heteroaryl, wherein the S-heteroaryl is optionally substituted by one or more $R^{14}$; and $R^{14}$ is $C_{1-7}$ alkyl.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-OR; $C_{1-5}$ alkyl-$NHCOR^{13}$ wherein $R^{13}$ is pentylamino-5-oxopentyl-7-thia-2.4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, or $C_{1-3}$ alkyl substituted by aryl or heteroaryl;

$R^5$ is selected from H, $C_{1-7}$ alkyl, $OR^8$, and O—$C_{1-7}$ alkyl;

$R^6$ is H;

$R^8$ is selected from H, $C_{1-7}$ alkyl, $C_{2-7}$ alkenyl, and $C_{3-7}$ cycloalkyl;

X is selected from a bond, $C_{1-7}$ alkanediyl, —O—, and —O—$C_{1-7}$ alkanediyl;

Y is heteroaryl, wherein the heteroaryl is optionally substituted by one or more of $R^8$; or S-heteroaryl, wherein the S-heteroaryl is optionally substituted by one or more $R^{14}$; and $R^{14}$ is $C_{1-7}$ alkyl.

In some embodiments, the aryl, the heteroaryl or the S-heteroaryl group of any of the compounds of the present disclosure are preferably selected from the group consisting of phenyl, imidazole, pyridine and triazole, more preferably selected from the group consisting of phenyl, imidazole and pyridine.

In some embodiments, $R^5$, X and Y form a spirane or spiro compound at the −4 position of the piperidine ring.

In some embodiments, $R^5$, X and Y form a spirane or spiro compound at the −4 position of the piperidine ring and $R^5$, X and Y form -continued
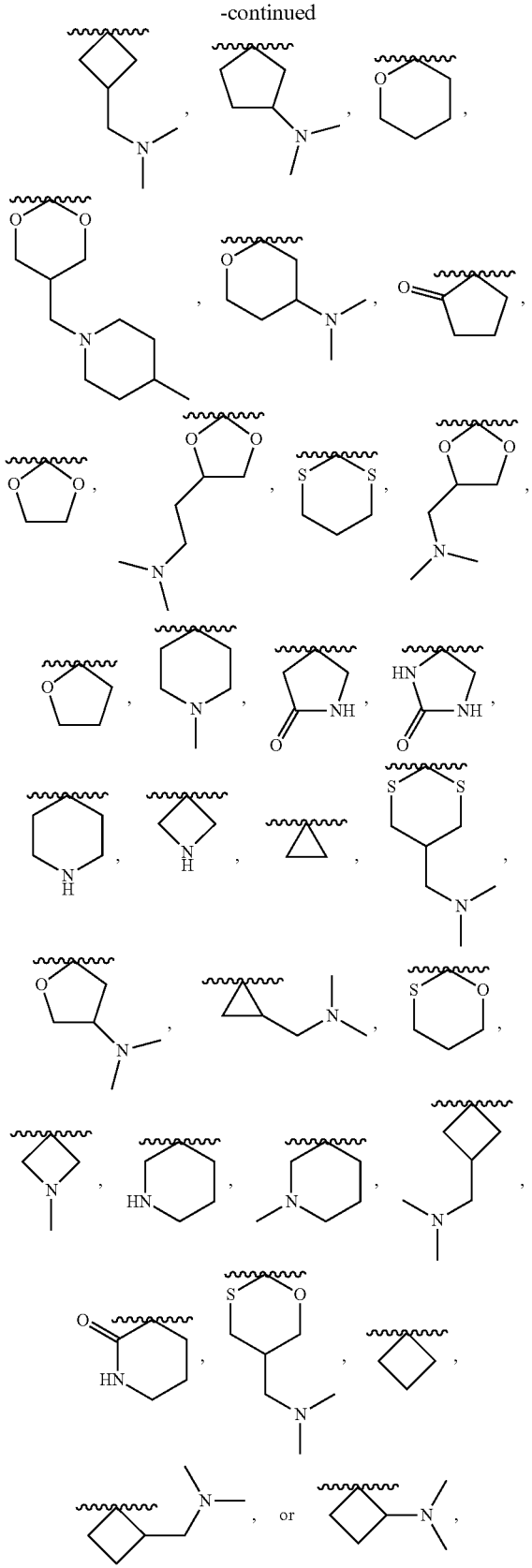
wherein ⁓ indicates the –4 position of the piperidine ring, the common atom of the spirane
In some embodiments, the compound is of any one of Formulae (VIIIa), (VIIIb), (VIIIc), (VIIId), (VIIIe), (VIIIf), (VIIIg), (VIIIh), (VIIIi), (VIIIj), (VIIIk), (VIIIl):
(VIIIa)
(VIIIb)
(VIIIc)
(VIIId)
(VIIIe)
(VIIIf)

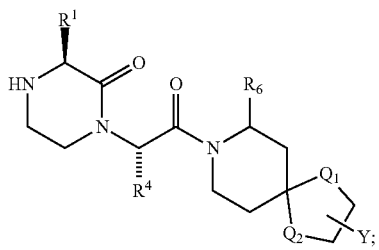 (VIIIg)

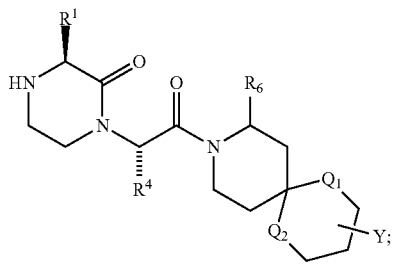 (VIIIh)

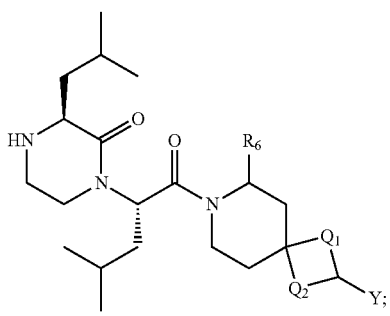 (VIIIi)

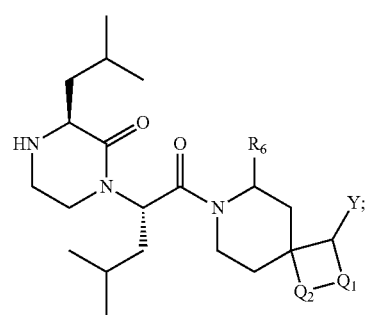 (VIIIj)

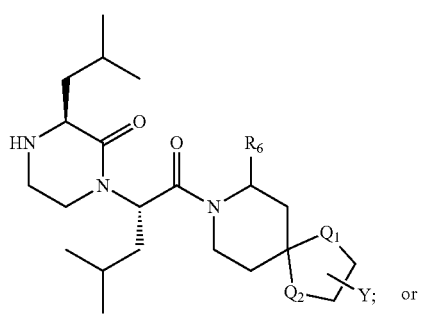 (VIIIk)

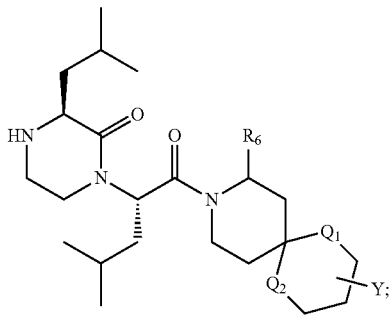 (VIIIl)

or a pharmaceutically acceptable salt, hydrate, solvate, or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIa) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIb) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIc) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIId) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIe) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIf) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIg) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIh) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIi) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIj) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIk) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of Formula (VIIIl) or a pharmaceutically acceptable salt, hydrate, solvate or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

In some embodiments, the compound is of any one of Formulae (VIIIa1), (VIIIb1), (VIIIc1), (VIIId1), (VIIIe1), (VIIIf1), (VIIIg1), (VIIIh1), (VIIIi1), (VIIIj1), (VIIIk1), (VIIIl1):

(VIIIa1)
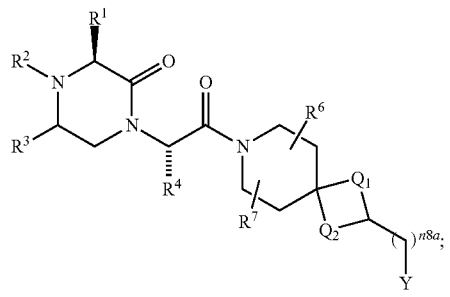

(VIIIb1)
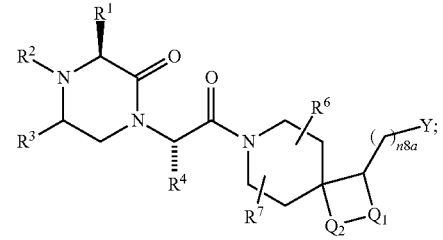

(VIIIc1)
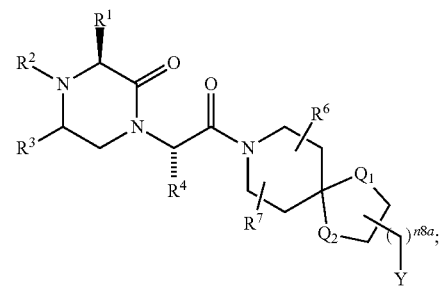

(VIIId1)
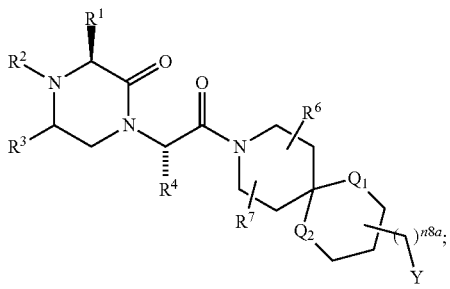

-continued (VIIIe1)
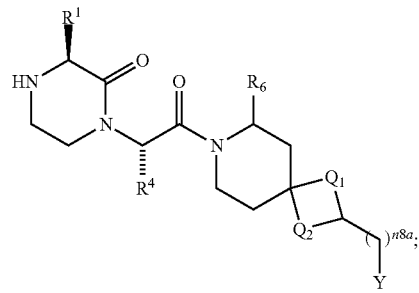

(VIIIf1)
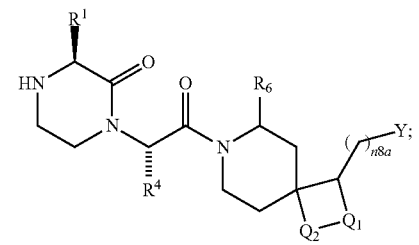

(VIIIg1)
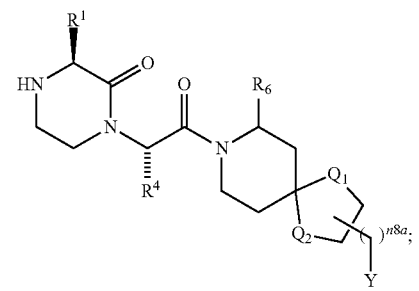

(VIIIh1)
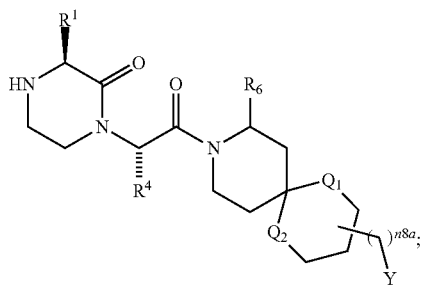

(VIIIi1)
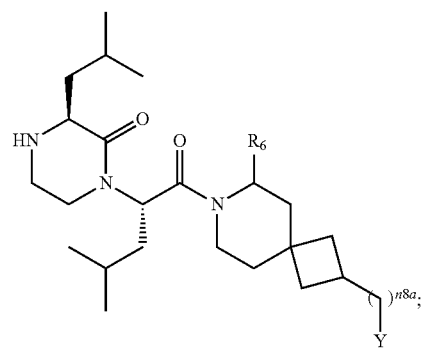

-continued

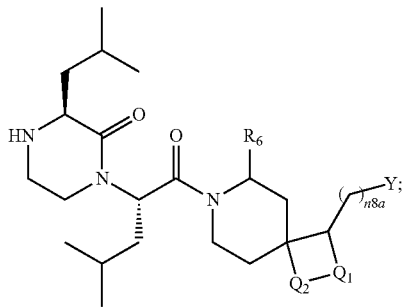
(VIIIj1)

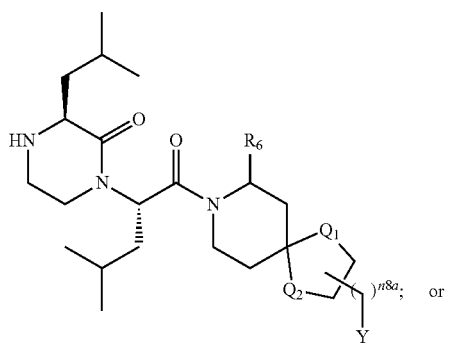
(VIIIk1)

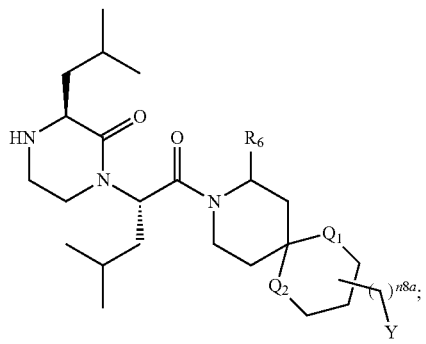
(VIIIl1)

or a pharmaceutically acceptable salt, hydrate, solvate, or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIa1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIb1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIc1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIId1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIe1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIf1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIg1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIh1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIi1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIj1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIk1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, the compound is of Formula (VIIIl1) or a pharmaceutically acceptable salt, hydrate, solvate or stereoisomer thereof, wherein $Q_1$ and $Q_2$ are each independently O, S, $NR^8$, or $CR^8$, n8a is 0, 1, 2, 3, 4, 5, 6, or 7, preferably 1, 2, or 3, and $R^1$, $R^2$, $R^3$, $R^4$, $R^6$, $R^7$, $R^8$, and Y are as described herein.

In some embodiments, Y is $NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

In some embodiments, the compound is of any one of Formulae (IXa), (IXb), (IXc), or (IXd):

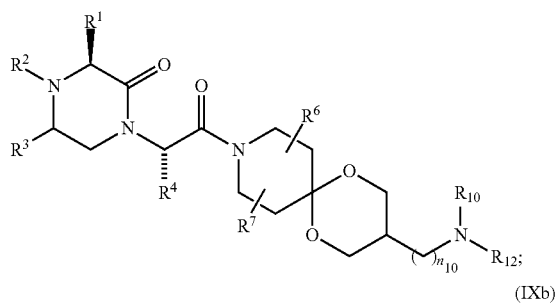

(IXa)

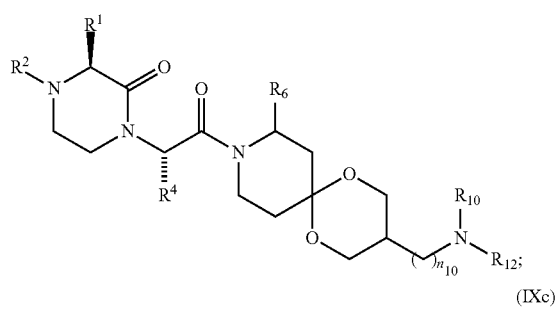

(IXb)

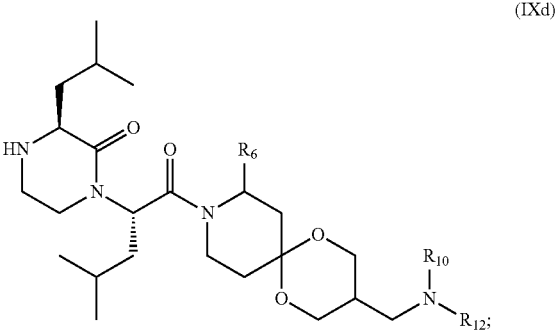

(IXc)

or a pharmaceutically acceptable salt, hydrate, solvate, or stereoisomer thereof, wherein n10 is 0, 1, 2, 3, 4, 5, 6, or 7, preferably 1, 2, or 3, and $R^1, R^2, R^3, R^4, R^6, R^7, R^{10}, R^{12}$ and Y are as described herein.

In some embodiments, the compound is of Formula (IXa) or a pharmaceutically acceptable salt, hydrate, solvate, or stereoisomer thereof, wherein n10 is 0, 1, 2, 3, 4, 5, 6, or 7, preferably 1, 2, or 3, and $R^1, R^2, R^3, R^4, R^6, R^7, R^{10}, R^{12}$ and Y are as described herein.

In some embodiments, the compound is of Formula (IXb) or a pharmaceutically acceptable salt, hydrate, solvate, or stereoisomer thereof, wherein n10 is 0, 1, 2, 3, 4, 5, 6, or 7, preferably 1, 2, or 3, and $R^1, R^2, R^3, R^4, R^6, R^7, R^{10}, R^{12}$ and Y are as described herein.

In some embodiments, the compound is of Formula (IXc) or a pharmaceutically acceptable salt, hydrate, solvate, or stereoisomer thereof, wherein n10 is 0, 1, 2, 3, 4, 5, 6, or 7, preferably 1, 2, or 3, and $R^1, R^2, R^3, R^4, R^6, R^7, R^{10}, R^{12}$ and Y are as described herein.

In some embodiments, the compound is of Formula (IXd) or a pharmaceutically acceptable salt, hydrate, solvate, or stereoisomer thereof, wherein n10 is 0, 1, 2, 3, 4, 5, 6, or 7, preferably 1, 2, or 3, and $R^1, R^2, R^3, R^4, R^6, R^7, R^{10}, R^{12}$ and Y are as described herein.

In some embodiments, the compound is of any one of Formulae (IXa1), (IXb1), (IXc1), or (IXd1):


(IXa1)


(IXb1)

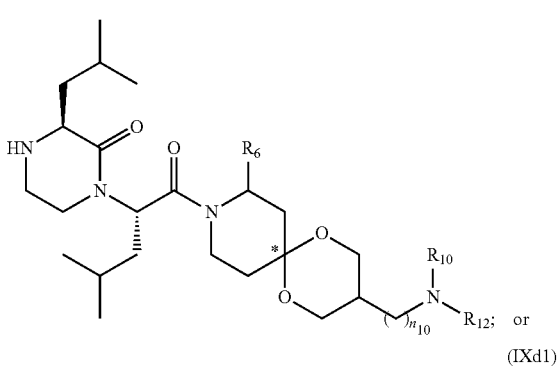

(IXc1)

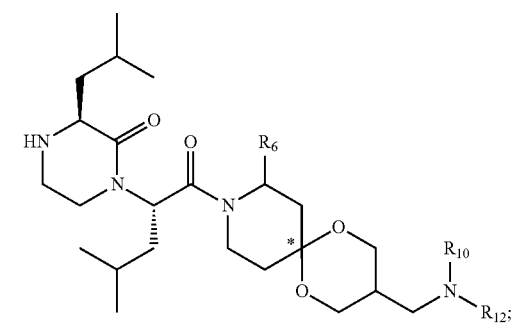

(IXd1)

or a pharmaceutically acceptable salt, hydrate, solvate, or stereoisomer thereof, wherein n10 is 0, 1, 2, 3, 4, 5, 6, or 7, preferably 1, 2, or 3, $R^1$, $R^2$, $R^3$, $R^4$, $R^6$, $R^7$, $R^{10}$, $R^{12}$ and Y are as described herein, and * indicates the Z-isomer of the spiro compound.

In some embodiments, the compound is of Formula (IXa1) or a pharmaceutically acceptable salt, hydrate, solvate, or stereoisomer thereof, wherein n10 is 0, 1, 2, 3, 4, 5, 6, or 7, preferably 1, 2, or 3, $R^1$, $R^2$, $R^3$, $R^4$, $R^6$, $R^7$, $R^{10}$, $R^{12}$ and Y are as described herein, and * indicates the Z-isomer of the spiro compound.

In some embodiments, the compound is of Formula (IXb1) or a pharmaceutically acceptable salt, hydrate, solvate, or stereoisomer thereof, wherein n10 is 0, 1, 2, 3, 4, 5, 6, or 7, preferably 1, 2, or 3, $R^1$, $R^2$, $R^3$, $R^4$, $R^6$, $R^7$, $R^{10}$, $R^{12}$ and Y are as described herein, and * indicates the Z-isomer of the spiro compound.

In some embodiments, the compound is of Formula (IXc1) or a pharmaceutically acceptable salt, hydrate, solvate, or stereoisomer thereof, wherein n10 is 0, 1, 2, 3, 4, 5, 6, or 7, preferably 1, 2, or 3, $R^1$, $R^2$, $R^3$, $R^4$, $R^6$, $R^7$, $R^{10}$, $R^{12}$ and Y are as described herein, and * indicates the Z-isomer of the spiro compound.

In some embodiments, the compound is of Formula (IXd1) or a pharmaceutically acceptable salt, hydrate, solvate, or stereoisomer thereof, wherein n10 is 0, 1, 2, 3, 4, 5, 6, or 7, preferably 1, 2, or 3, $R^1$, $R^2$, $R^3$, $R^4$, $R^6$, $R^7$, $R^{10}$, $R^{12}$ and Y are as described herein, and * indicates the Z-isomer of the spiro compound.

In some embodiments, the compound is a compound of Formula (I) or Formula (Ia), wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, C(O)OR, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from $C_{1-7}$ alkyl, $OR^8$, or $SR^8$; wherein $C_{1-7}$ alkyl, $OR^8$ or $SR^8$ of $R^5$ can form a ring with any part of X;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from —O—$C_{1-7}$ alkanediyl, —S—$C_{1-7}$ alkanediyl, or $C_{1-7}$ alkanediyl, and wherein —O—$C_{1-7}$ alkanediyl, —S—$C_{1-7}$ alkanediyl or $C_{1-7}$ alkanediyl of X can form a ring with any part of $R^5$;

Y is $NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

In some embodiments, the compound is a compound of Formula (I) or Formula (Ia), wherein:

$R^1$ is selected from $C_{3-7}$ alkyl, $C_{3-7}$ cycloalkyl, or $C_{1-3}$ alkyl substituted by aryl or heteroaryl;

$R^2$ is selected from H, $C(O)R^{14}$, $C_{1-7}$ alkyl, $C_{3-7}$ cycloalkyl, $C_{1-5}$ alkyl-$OR^8$; $C_{1-5}$ alkyl-$NHCOR^{13}$ wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl;

$R^3$ and $R^7$ are H;

$R^4$ is selected from $C_{3-7}$ alkyl, $C_{3-7}$ cycloalkyl, $C_{1-3}$ alkyl substituted by aryl or heteroaryl;

$R^5$ is $OR^8$, and $OR^8$ of $R^5$ can form a ring with any part of X;

$R^6$ is H;

$R^8$ and $R^{11}$ are $C_{1-7}$ alkyl;

X is —O—$C_{1-7}$ alkanediyl and wherein —O—$C_{1-7}$ alkanediyl of X can form a ring with any part of $R^5$; and Y is $NR^{10}R^{12}$, wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

Some preferred embodiments of the present application relate to the compounds having one of the following structures or being one of the following compounds, pharmaceutically-acceptable salts, hydrates, solvates, or stereoisomers thereof:

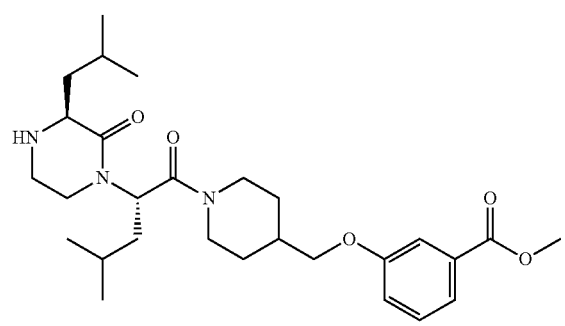

75
-continued
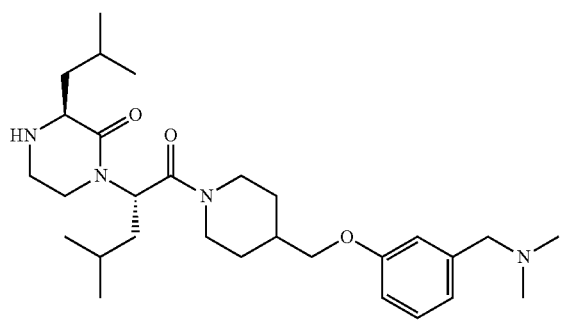
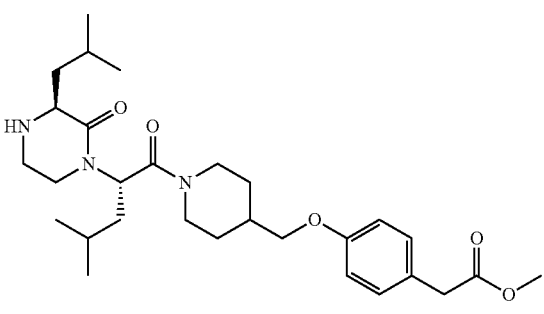
76
-continued
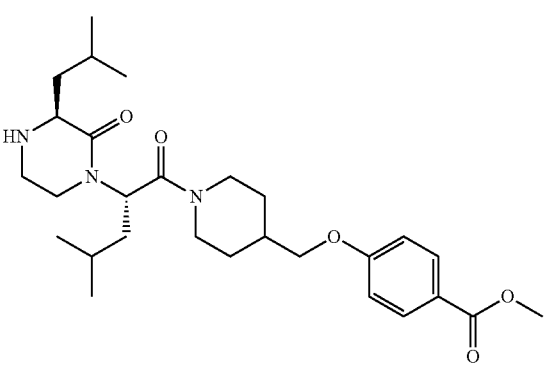
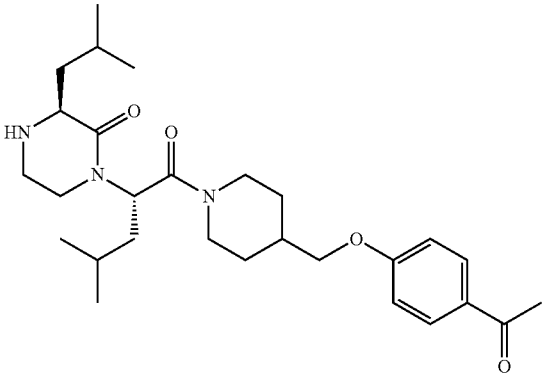
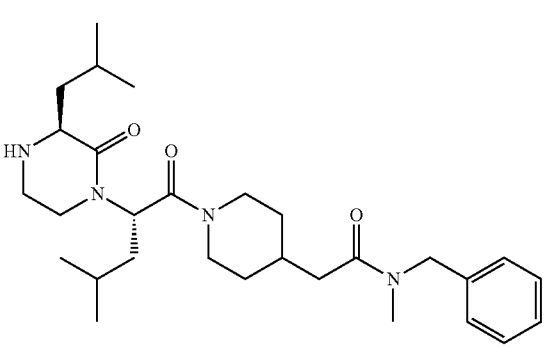

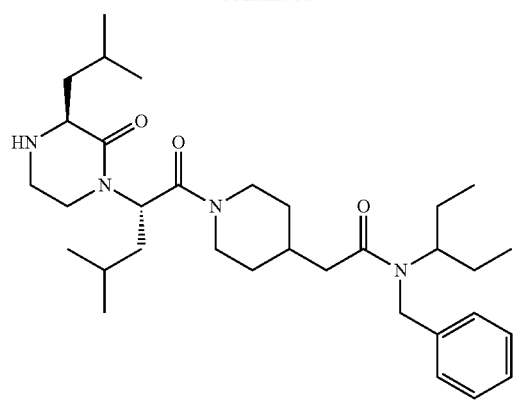
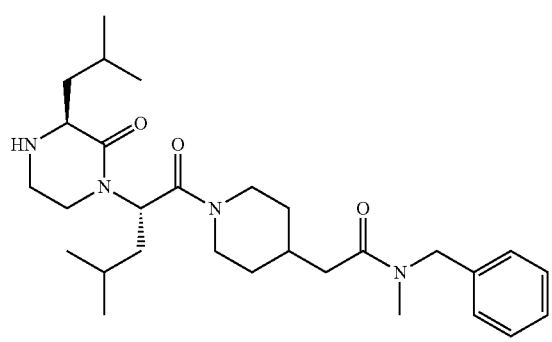
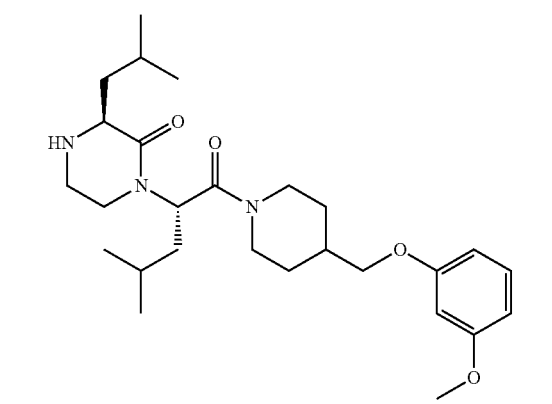
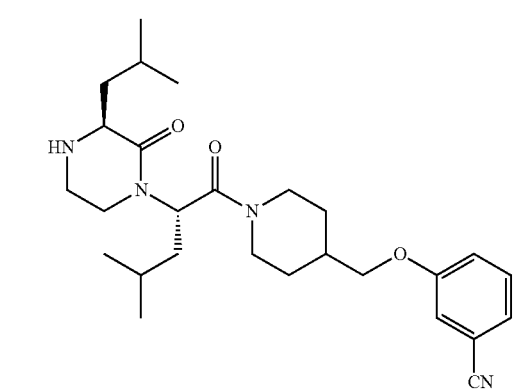
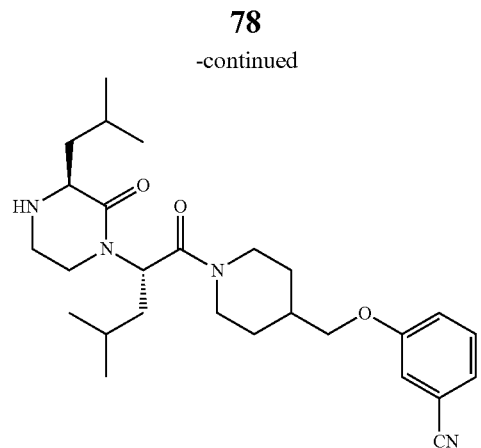
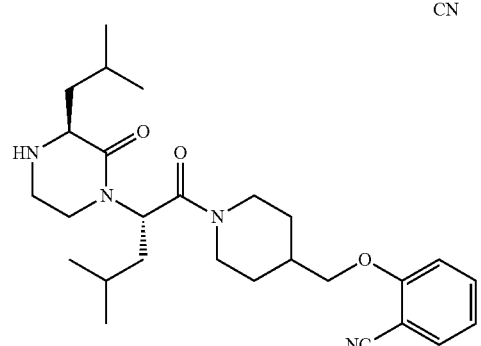
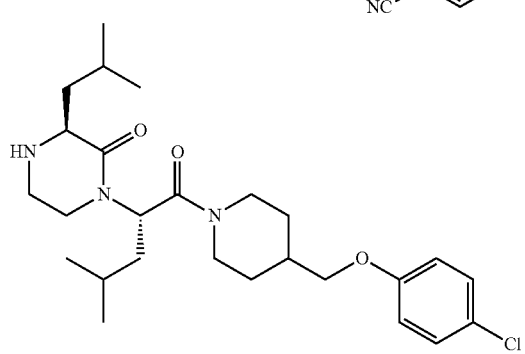
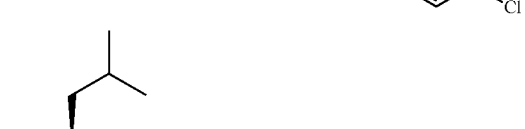
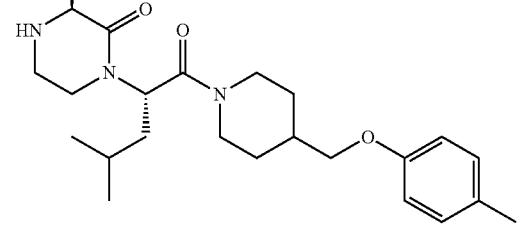
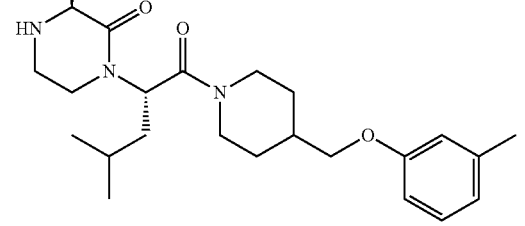

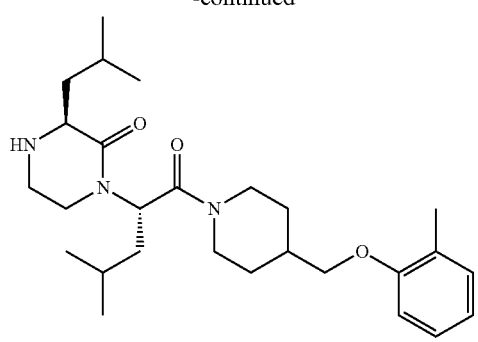
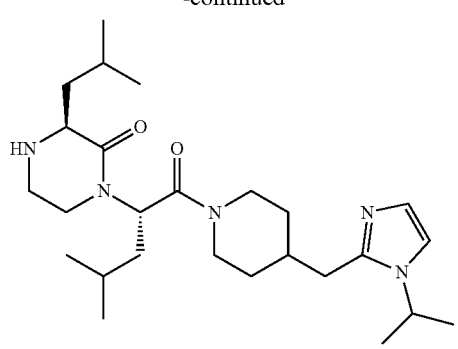
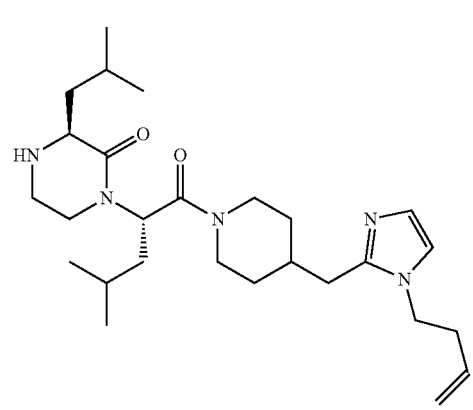
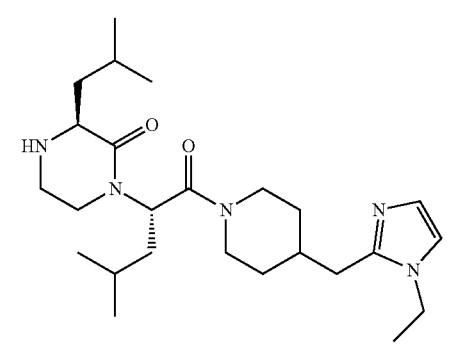
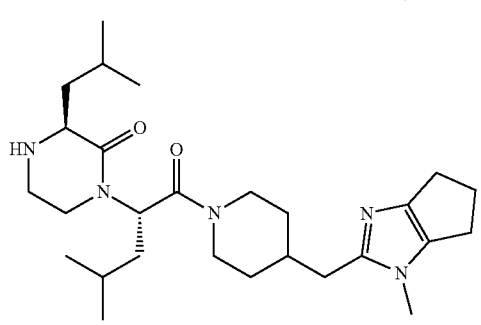
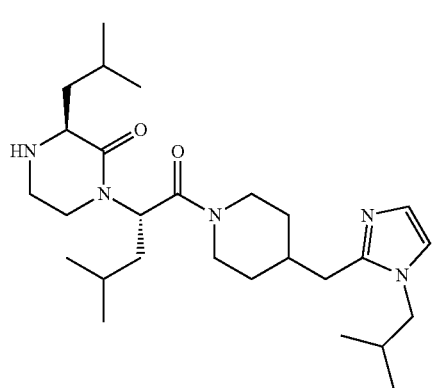
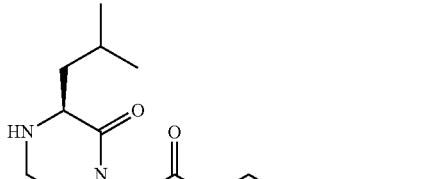
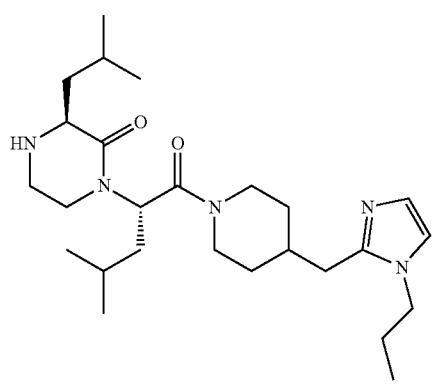
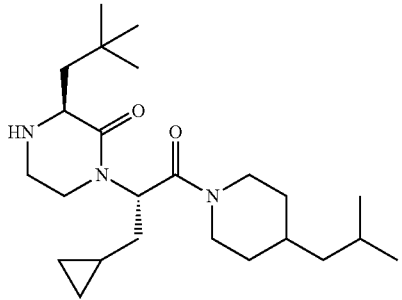

81
-continued
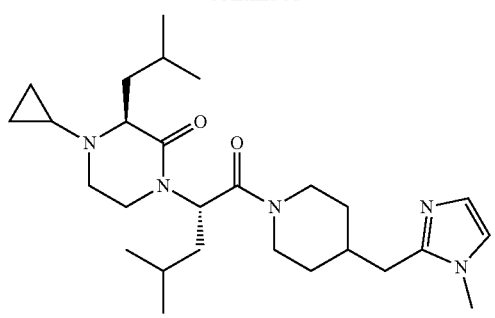
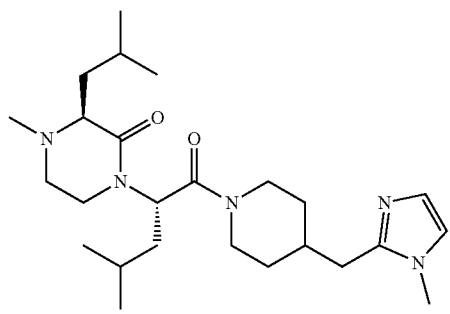
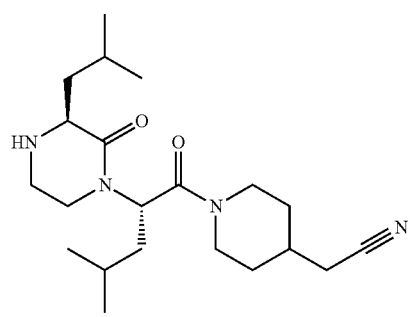
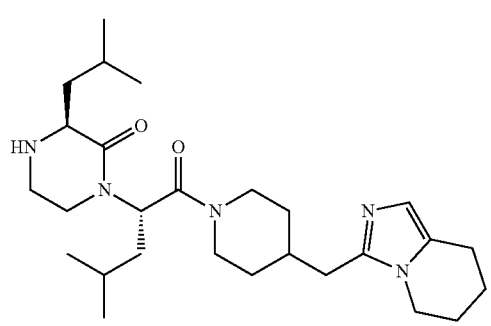
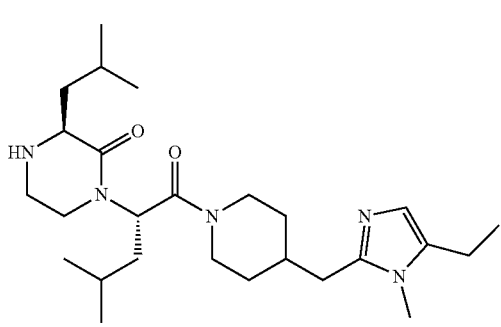
82
-continued
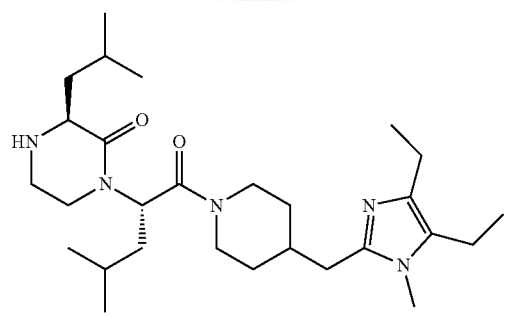
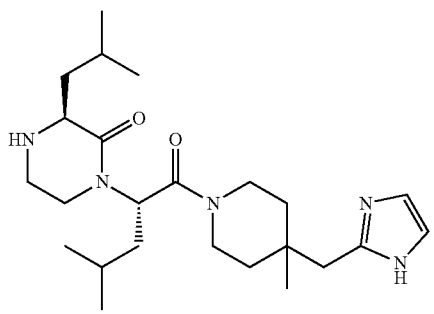
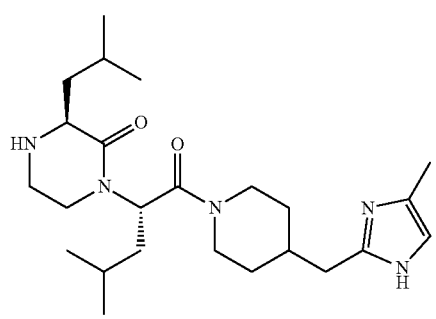
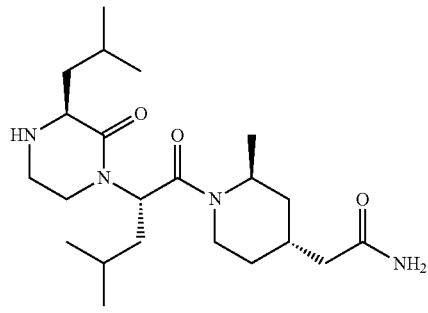
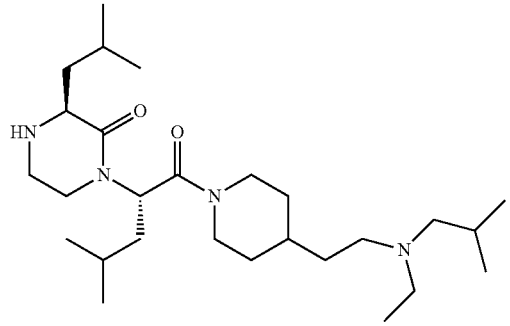

83
-continued
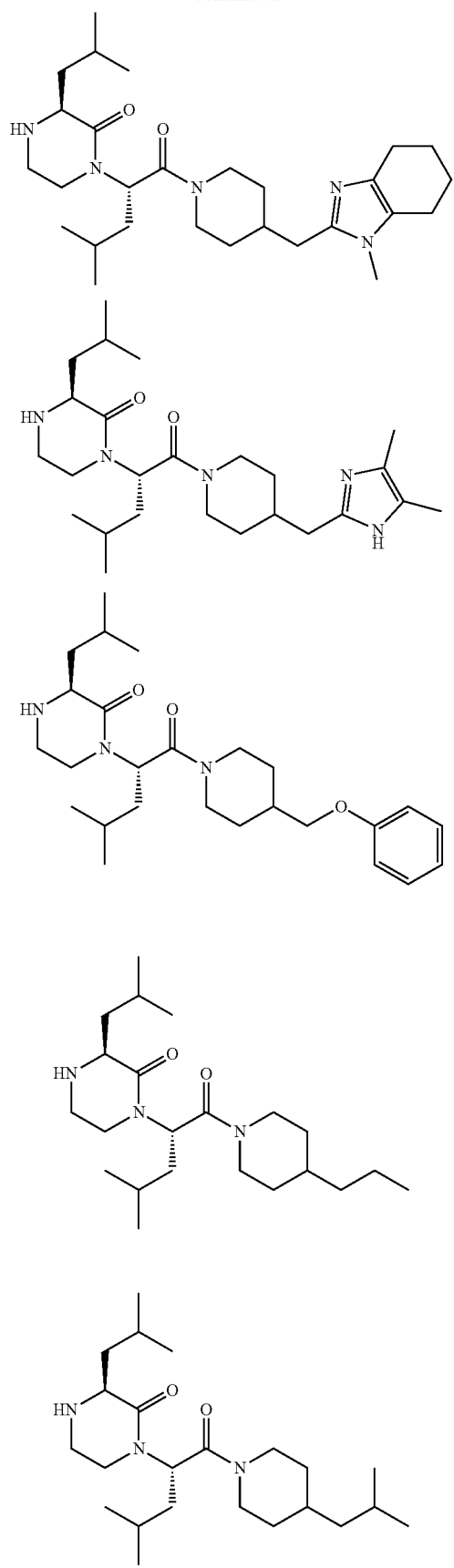
84
-continued
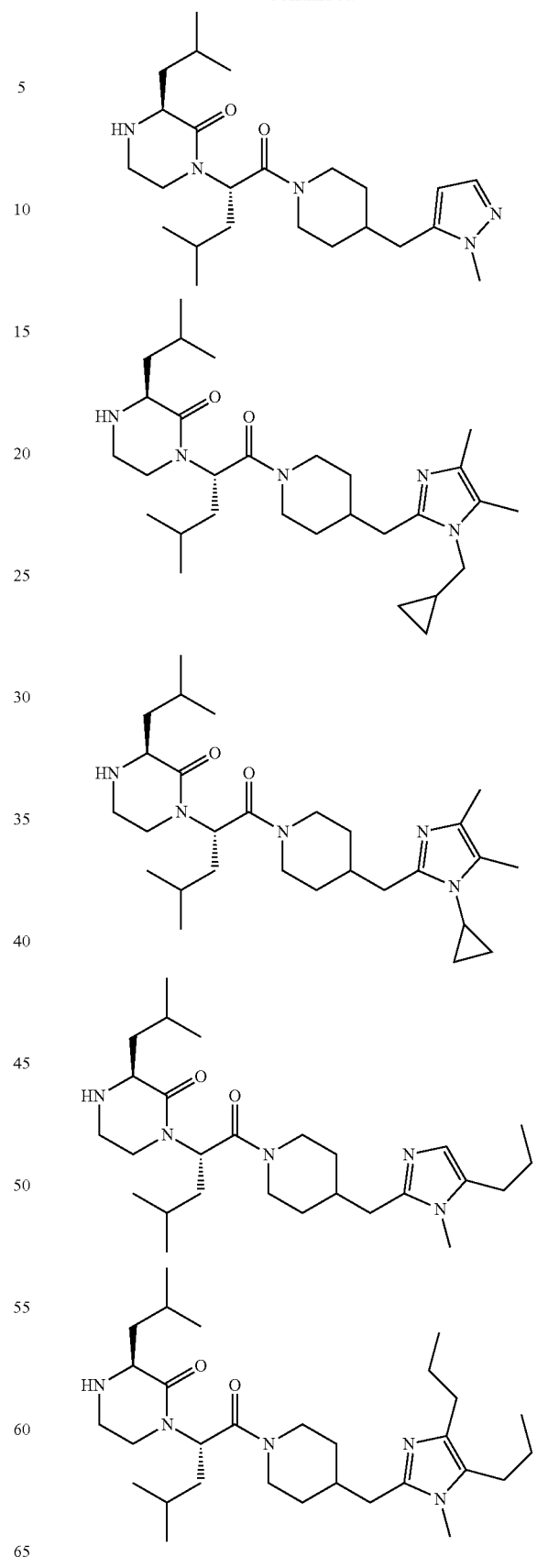

85
-continued
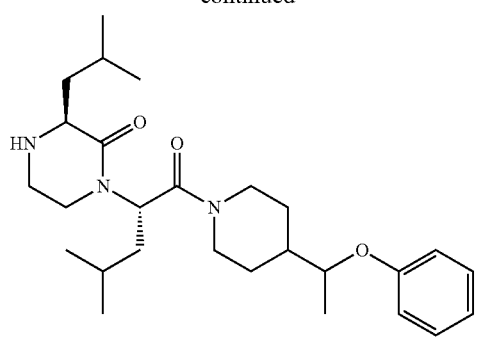
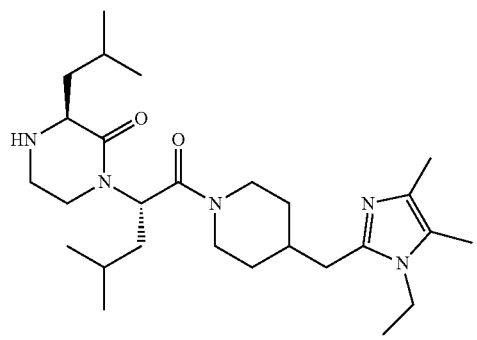
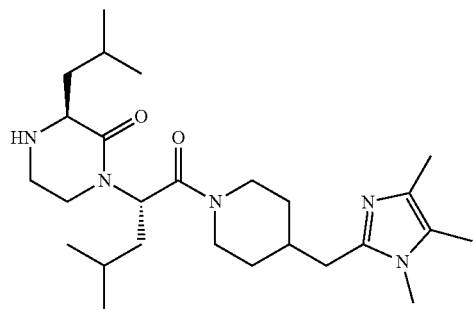
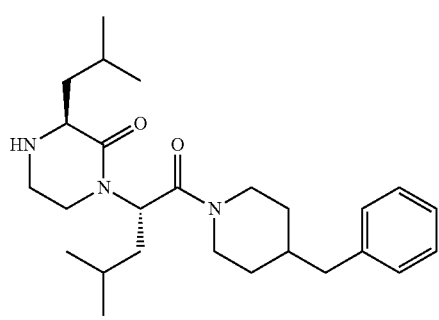
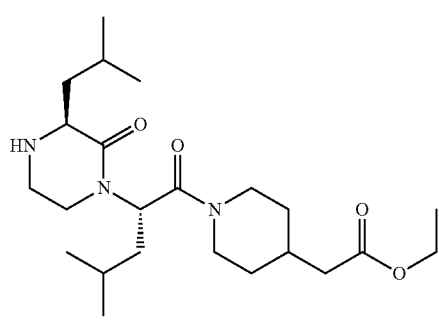
86
-continued
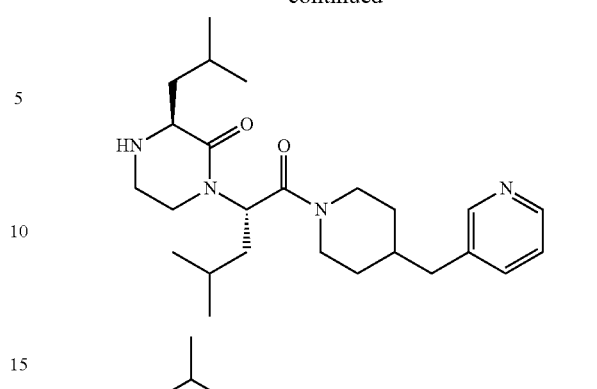
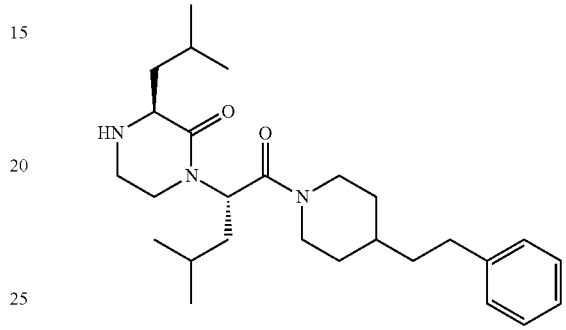
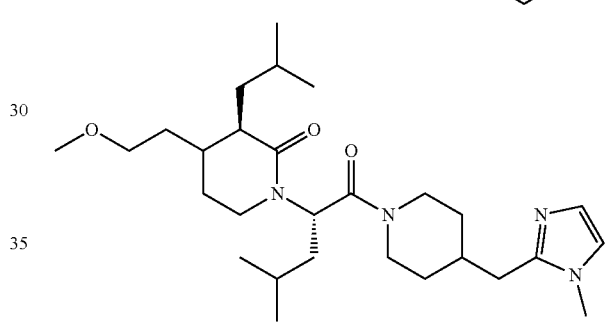
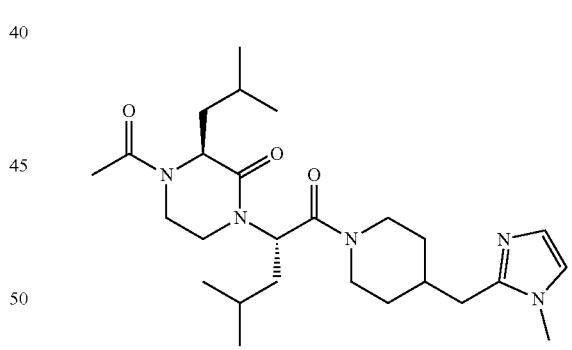
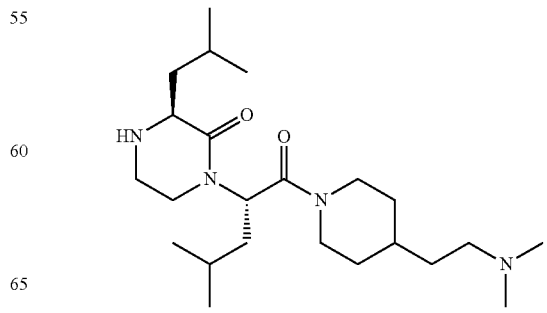

87
-continued
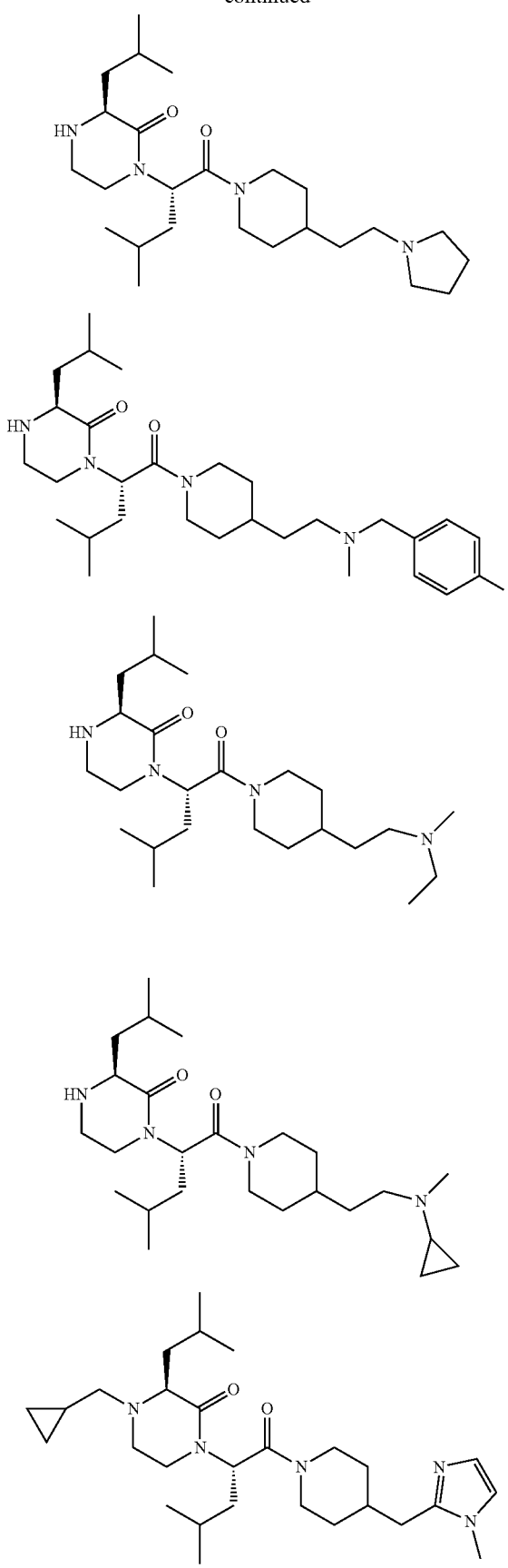
88
-continued
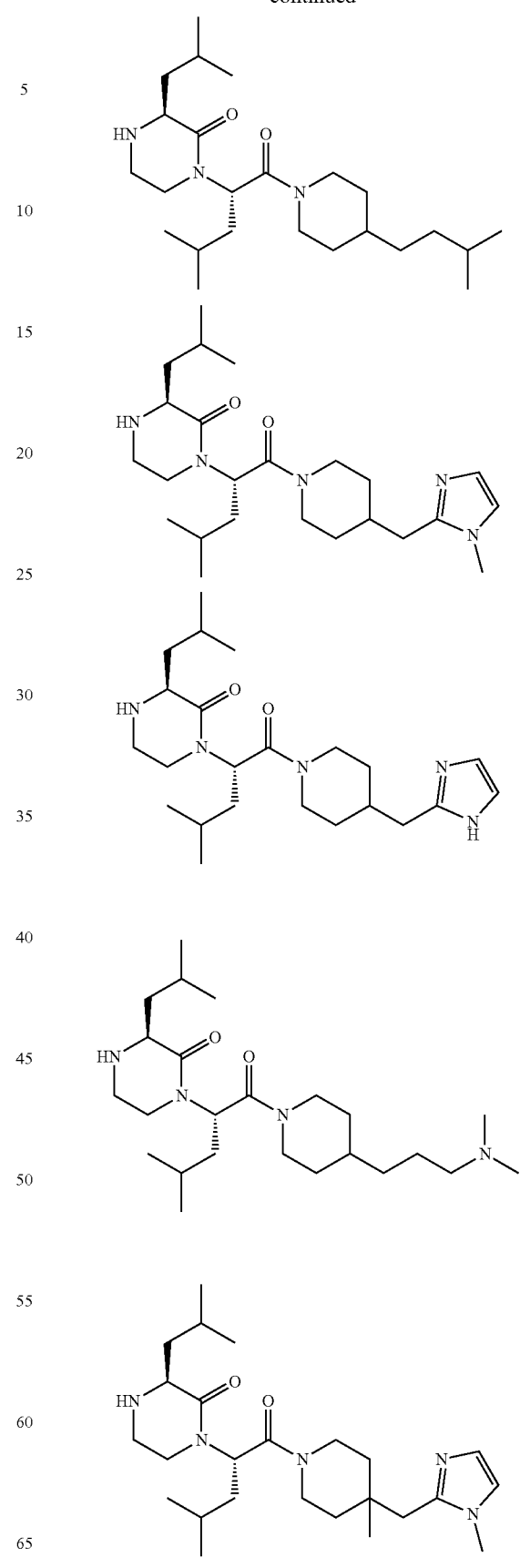

89
-continued
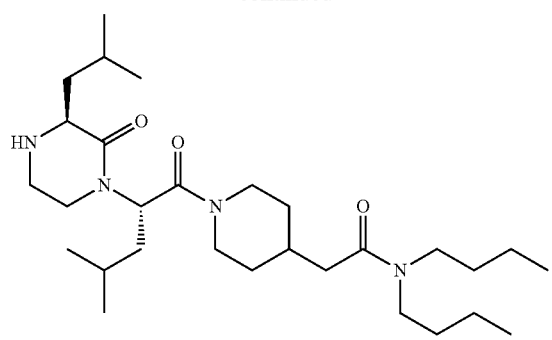
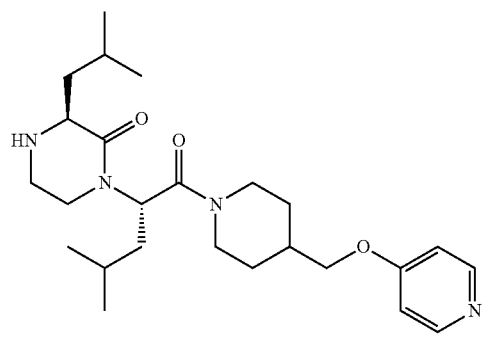
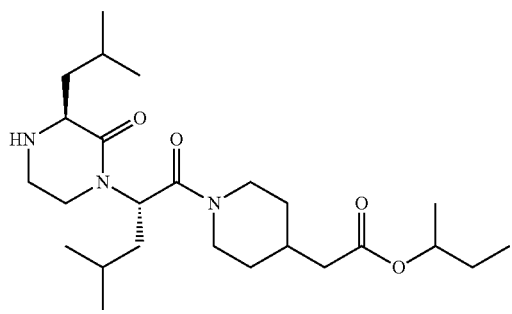
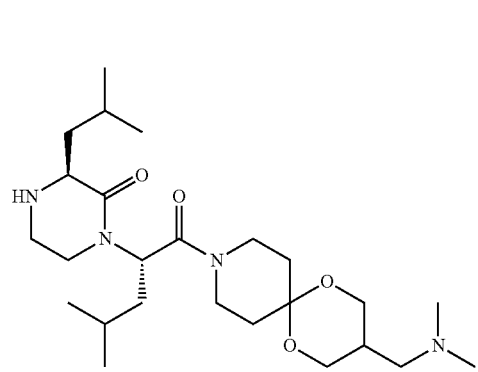
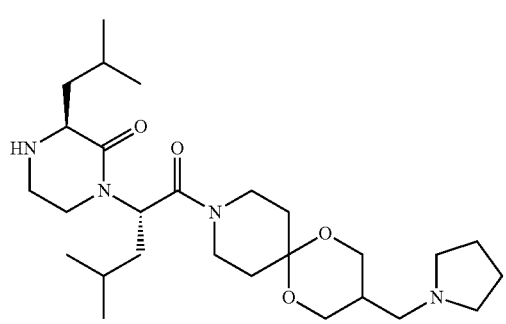
and
90
-continued
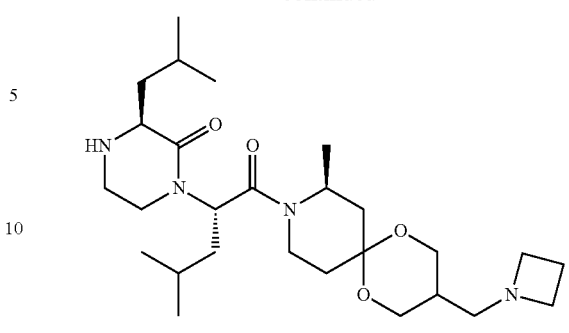
Some preferred embodiments of the present application relate to the compounds having one of the following structures or being one of the following compounds, pharmaceutically-acceptable salts, hydrates, solvates, or stereoisomers thereof:
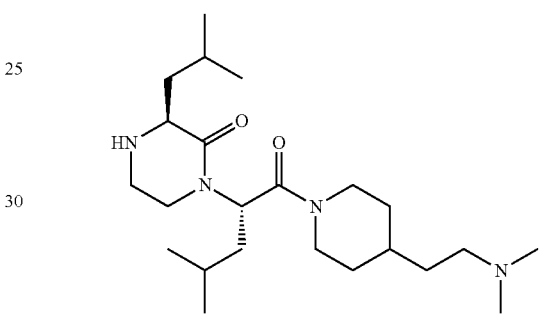
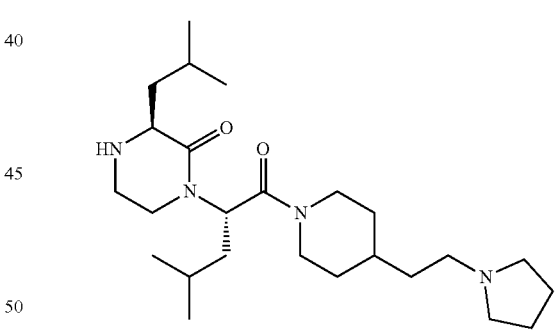
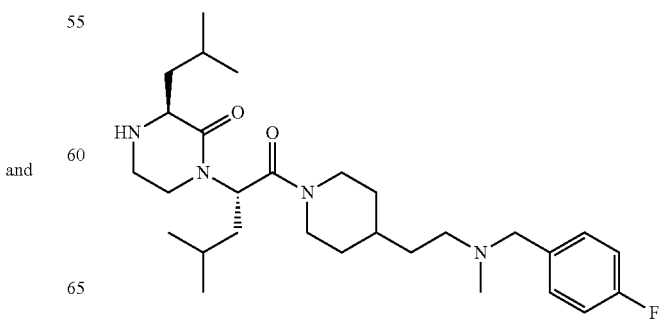

91
-continued
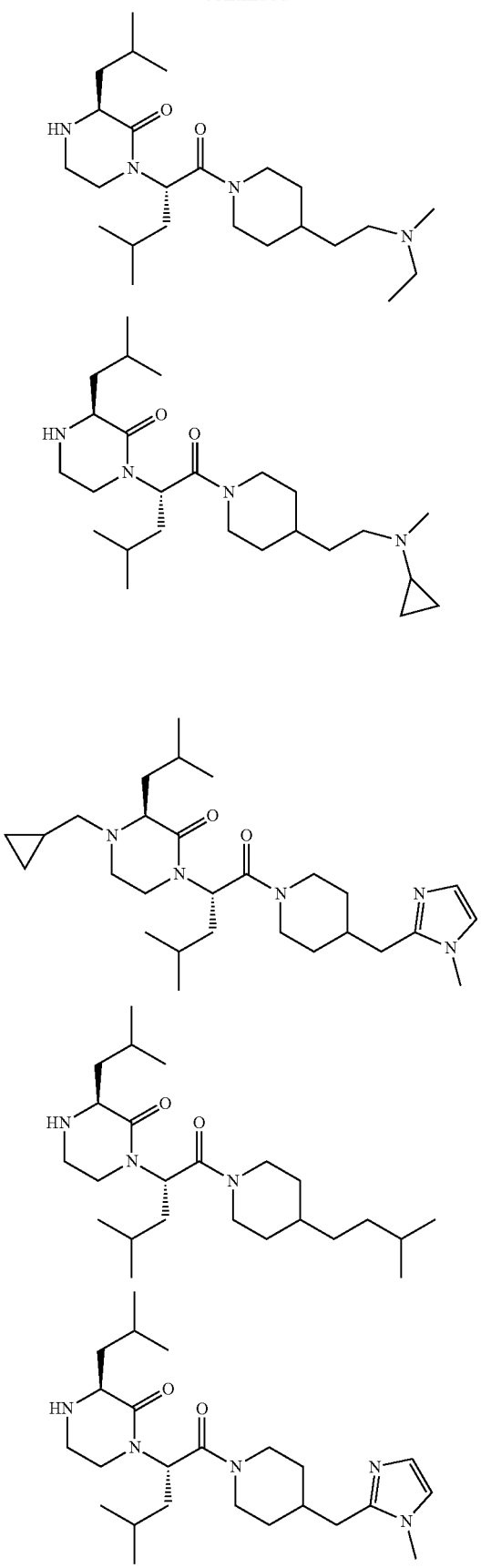
92
-continued
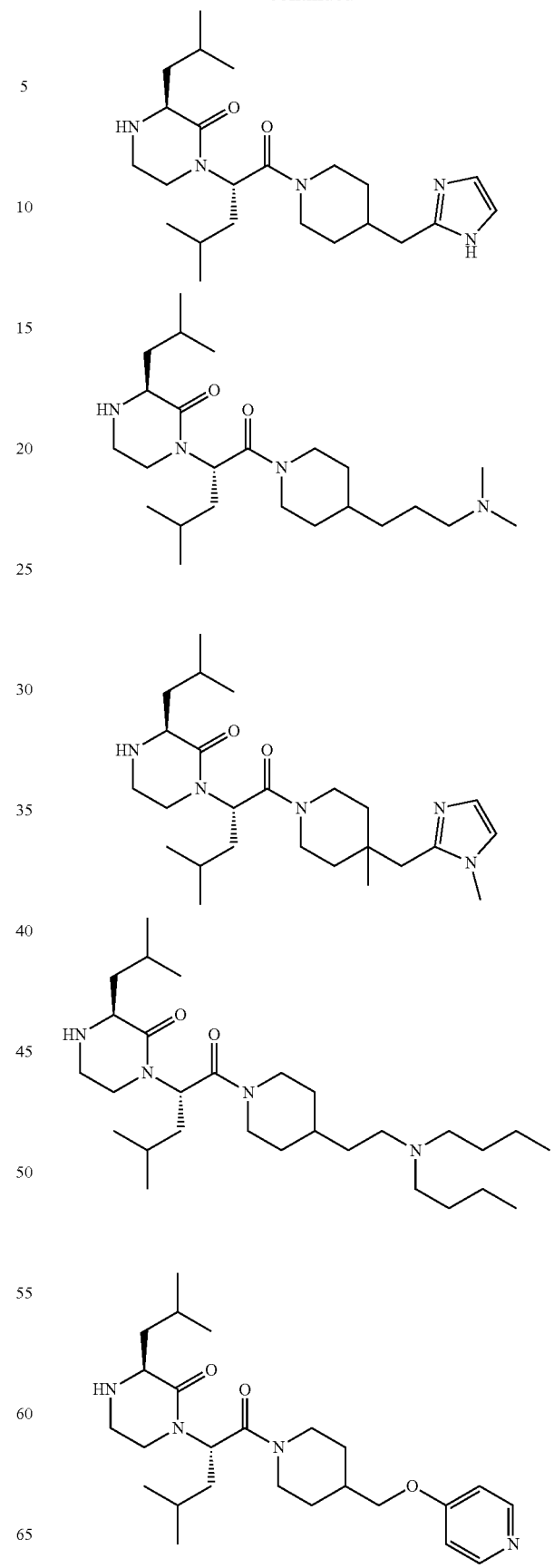

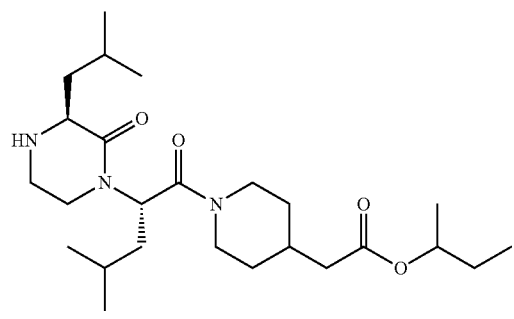
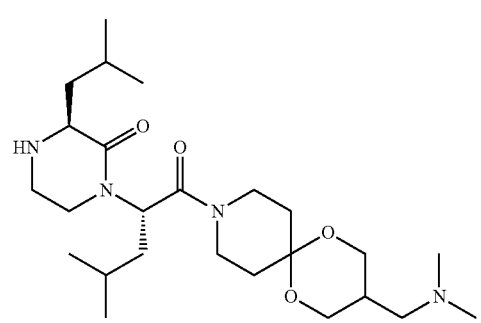
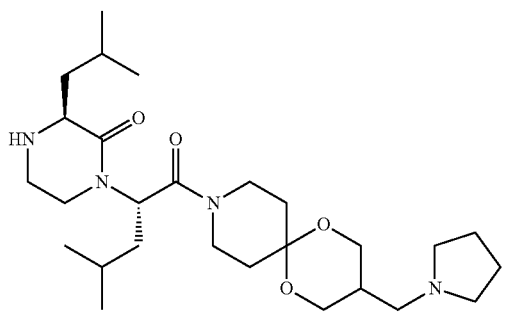
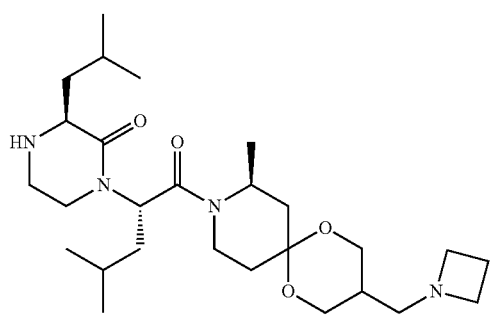 [SMILES: CC(C)C[C@@H]1NCCN([C@@H](CC(C)C)C(=O)N2CCC3(C[C@@H]2C)OCC(CN2CCC2)CO3)C1=O]
and
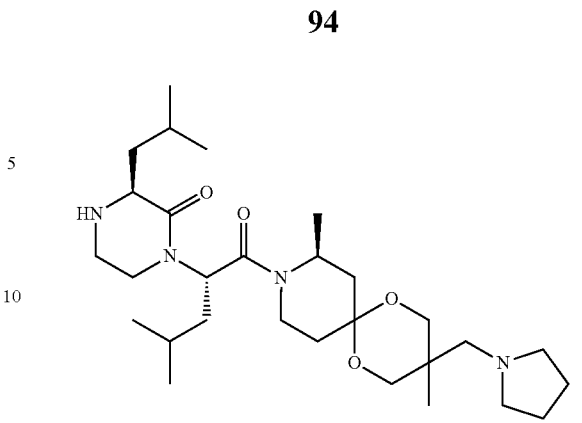
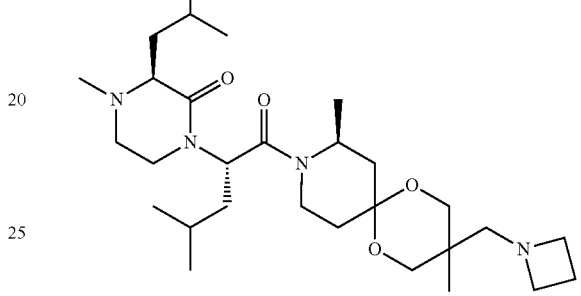
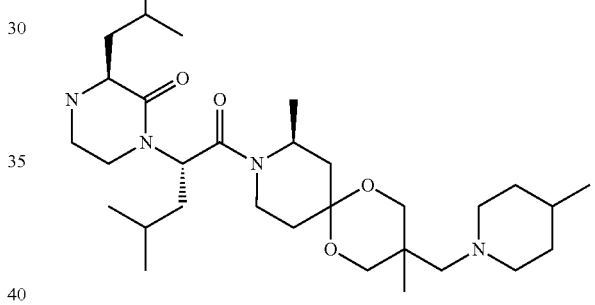
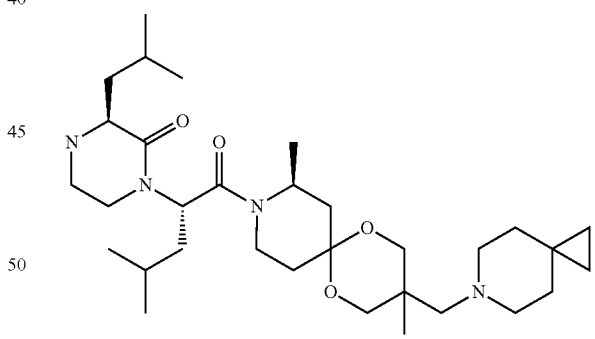
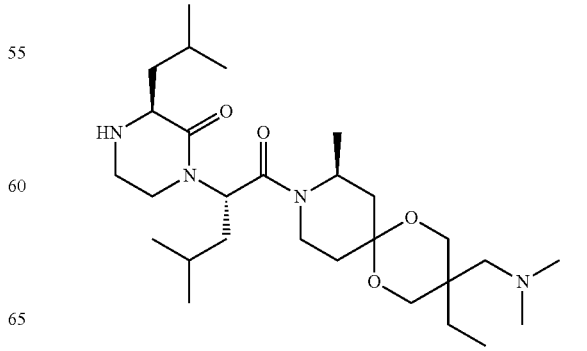
Some embodiments of the present application relate to the compounds having one of the following structures or being one of the following compounds, pharmaceutically-acceptable salts, hydrates, solvates, or stereoisomers thereof:

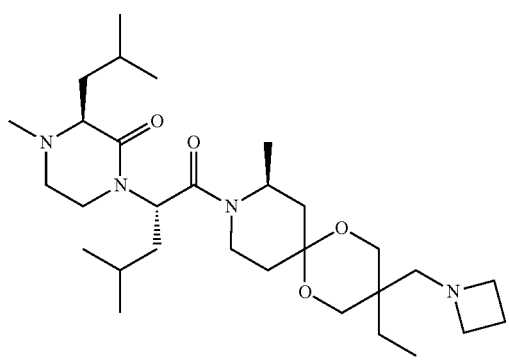
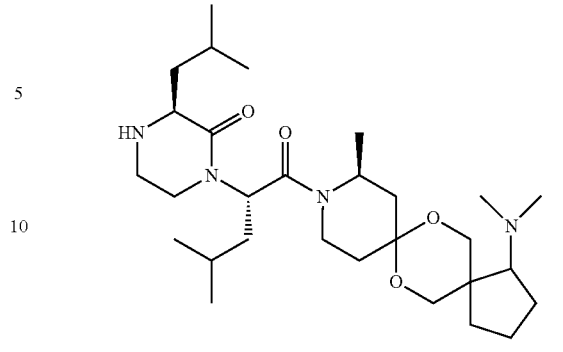
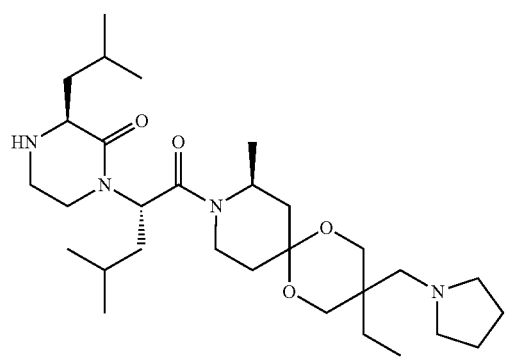
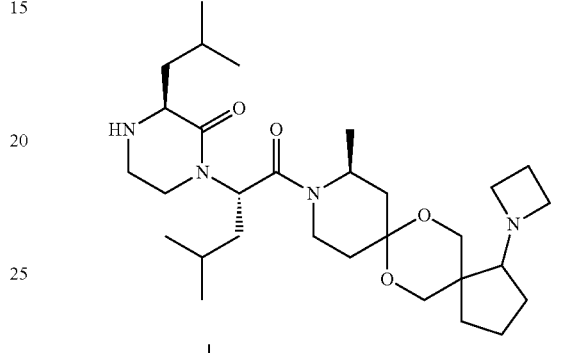
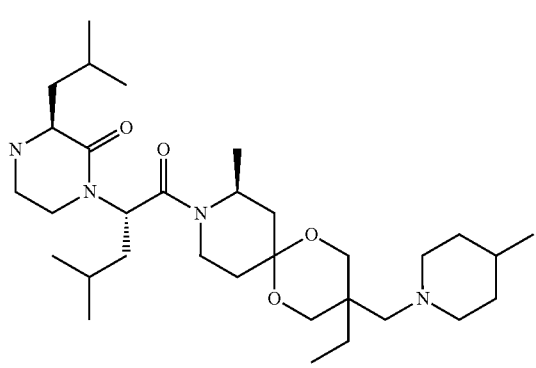
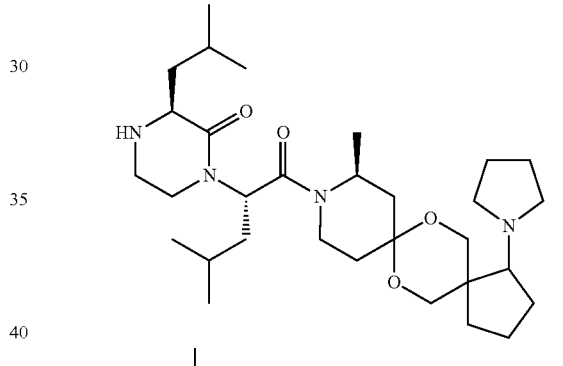
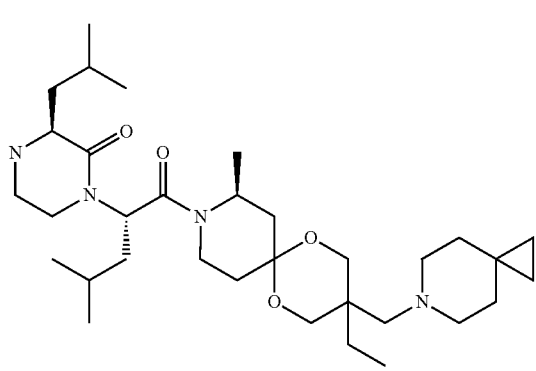
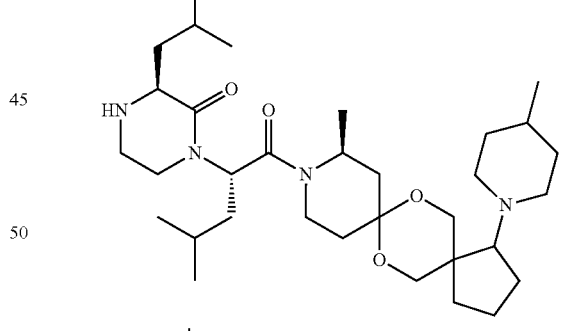

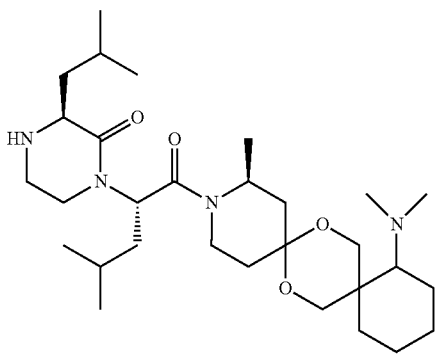

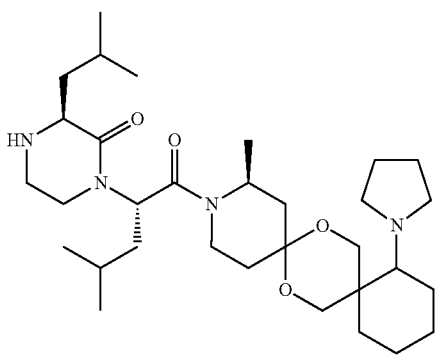

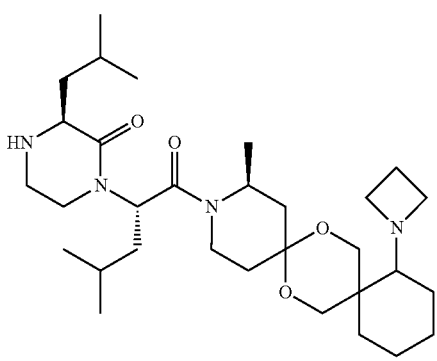

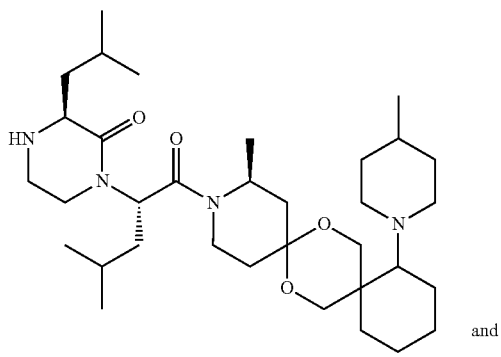

and

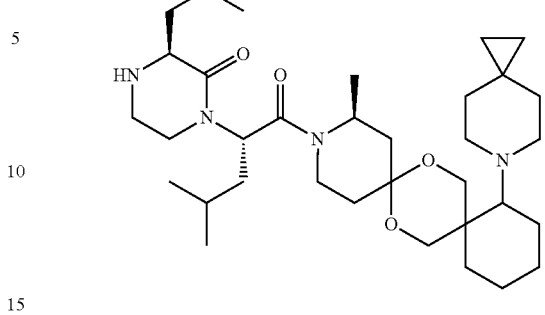

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences*, 66: 1-19 (1977). The salts can be prepared in situ during the final isolation and purification of the compounds of the application, or separately by reacting the free base or acid function with a suitable acid or base.

Examples of pharmaceutically acceptable salts include, but are not limited to, nontoxic acid addition salts: salts formed with inorganic acids such as hydrochloric acid, hydrobromic acid, phosphoric acid, sulfuric acid and perchloric acid, or with organic acids such as acetic acid, maleic acid, tartaric acid, citric acid, succinic acid or malonic acid. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein, refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present application. "Prodrug", as used herein, means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of compounds of the application. For example, compounds of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

The application also provides for a pharmaceutical composition comprising a therapeutically effective amount of a compound of the application, or an enantiomer, diastereomer, stereoisomer, or pharmaceutically acceptable salt thereof, and a pharmaceutically acceptable carrier.

In another aspect, the application provides a method of synthesizing a compound disclosed herein.

The synthesis of the compounds of the application can be found herein and in the Examples below.

Other embodiments are a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of the compounds of the application can be prepared using salts of the starting materials or intermediates.

The free acid or free base forms of the compounds of the application can be prepared from the corresponding base addition salt or acid addition salt from, respectively. For example, a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. The salts may be prepared in situ during the final isolation and purification of the compounds of the invention or separately by reacting a free base function with a suitable acid.

Representative acid addition salts include, but are not limited to trifluoroacetic acid (TFA), formate, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Prodrugs of the compounds of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of the compounds of the application can be made by means known to those of ordinary skill in the art. A detailed description of techniques applicable to the creation of protecting groups and their removal include, but are not limited to, those illustrated in T. W. Greene, "Protecting Groups in Organic Chemistry", 3rd edition, John Wiley and Sons, Inc., 1999.

Compounds of the present application can be conveniently prepared or formed during the process of the application, as solvates (e.g., hydrates). Hydrates of compounds of the present application can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

When any variable (e.g., $R^{14}$) occurs more than one time in any constituent or formula for a compound, its definition at each occurrence is independent of its definition at every other occurrence. Thus, for example, if a group is shown to be substituted with one or more $R^{14}$ moieties, then $R^{14}$ at each occurrence is selected independently from the definition of $R^{14}$. Also, combinations of substituents and/or variables are permissible, but only if such combinations result in stable compounds within a designated atom's normal valency.

In addition, some of the compounds of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)-for amino acids. When the compounds described herein contain olefinic double bonds or other centers of geometric asymmetry or even E or Z isomerism across several bonds and/or rings, and unless specified otherwise, it is intended that the compounds include both E and Z geometric isomers. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds and/or other rigid structures such as a ring or polycyclic system. These configurations are differentiated in their names by the prefixes cis and trans, or Z and E, which indicate that the groups are on the same or opposite side of the double bond and/or other rigid structures such as a ring or a polycyclic system in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. The compounds of this application may also be represented in multiple tautomeric forms, in such instances, the application expressly includes all tautomeric forms of the compounds described herein (e.g., alkylation of a ring system may result in alkylation at multiple sites, the application expressly includes all such reaction products).

In the present application, the structural formula of the compound represents a certain isomer for convenience in some cases, but the present application includes all isomers, such as geometrical isomers, optical isomers based on an asymmetrical carbon, stereoisomers, tautomers, and the like. In the present specification, the structural formula of the compound represents a certain isomer for convenience in some cases, but the present application includes all isomers, such as geometrical isomers, optical isomers based on an asymmetrical carbon, stereoisomers, tautomers, and the like.

Compounds of the present invention can exist as stereoisomers wherein asymmetric or chiral centers are present. These compounds are designated by the symbols "R" or "S", depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic or heterocyclic ring.

Compounds of the present invention can also exist as racemates which is given the descriptor "rac". The term racemate, as used herein, means an equimolar mixture of a pair of enantiomers. A racemate is usually formed when synthesis results in the generation of a stereocenter. As used herein, the term racemic mixture means racemate. Compounds of the present invention can also exist as diastereomeric meso forms which is given the descriptor "rel". The term diastereomeric meso form as used herein means achiral forms with a pseudostereogenic C-atom, which is given the descriptor "r" or "s", respectively.

Additionally, the compounds of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

It should be appreciated that solvates and hydrates of the compound according to formula (I) or formula (Ia) are also within the scope of the present application. Methods of solvation are generally known in the art.

A further embodiment of the present invention may also include compounds which are identical to the compounds of formula (I) or formula (Ia) except that one or more atoms are replaced by an atom having an atomic mass number or mass different from the atomic mass number or mass usually found in nature, e.g. compounds enriched in $^2H$ (D), $^3H$, $^{13}C$, $^{127}I$, etc. These isotopic analogs and their pharmaceutical salts and formulations are considered useful agents in therapy and/or diagnosis, for example, but not limited to, where a fine-tuning of in vivo half-life time could lead to an optimized dosage regimen.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the application are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Methods of Synthesizing the Compounds

The compounds of the invention may be prepared by the exemplary processes described in the following reaction schemes or by the processes described in the examples below. Exemplary reagents and procedures for these reactions appear hereinafter. Starting materials can be purchased or readily prepared by one of ordinary skill in the art.

Compounds of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5th edition, John Wiley & Sons: New York, 2001; and Greene, T. W., Wuts, P. G. M., *Protective Groups in Organic Synthesis*, 3rd edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present application. The processes generally provide the desired final compound at or near the end of the overall process, although it may be desirable in certain instances to further convert the compound to a pharmaceutically acceptable salt, ester or prodrug thereof. Suitable synthetic routes are depicted in the schemes below.

Those skilled in the art will recognize if a stereocenter exists in the compounds disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds of the present application can be prepared in a number of ways well known to those skilled in the art of organic synthesis. By way of example, compounds of the present application can be synthesized using the methods described below, together with synthetic methods known in the art of synthetic organic chemistry, or variations thereon as appreciated by those skilled in the art. Preferred methods include but are not limited to those methods described below.

Compounds of the present application can be synthesized by following the steps outlined in General Scheme 1 (Method A), General Scheme 2 (Method B1 and Method B2) and General Scheme 3 (Method C) which comprise different sequences of assembling intermediates. Starting materials are either commercially available or made by known procedures in the reported literature or as illustrated.

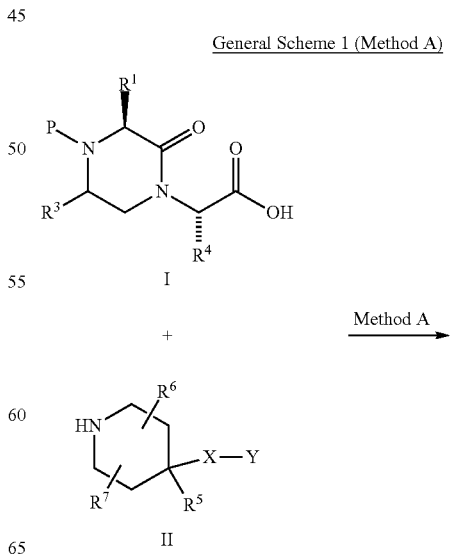

General Scheme 1 (Method A)

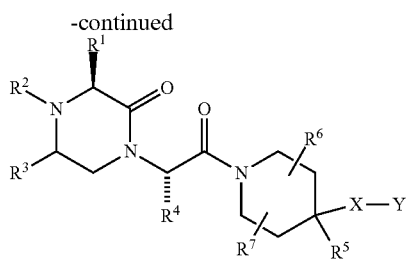

Method A: Using I where P is a suitable protecting group such as tBoc or nosyl, I and II are coupled using a dehydrating agent such as DCC or HATU in a suitable solvent such as DMF or NMP. The compounds where $R^2$ is H are obtained by deprotection under standard conditions. The compounds where is $R^2$ is $C(O)R^{14}$, $C(O)NR^{15}R^{15}$ or $C(O)OR^{15}$ are obtained by acylation of the secondary amine. The compounds where is $R^2$ not the above are obtained by reductive amination of the secondary amine with the appropriate aldehyde or ketone.

General Scheme 2 (Method B1 and B2)

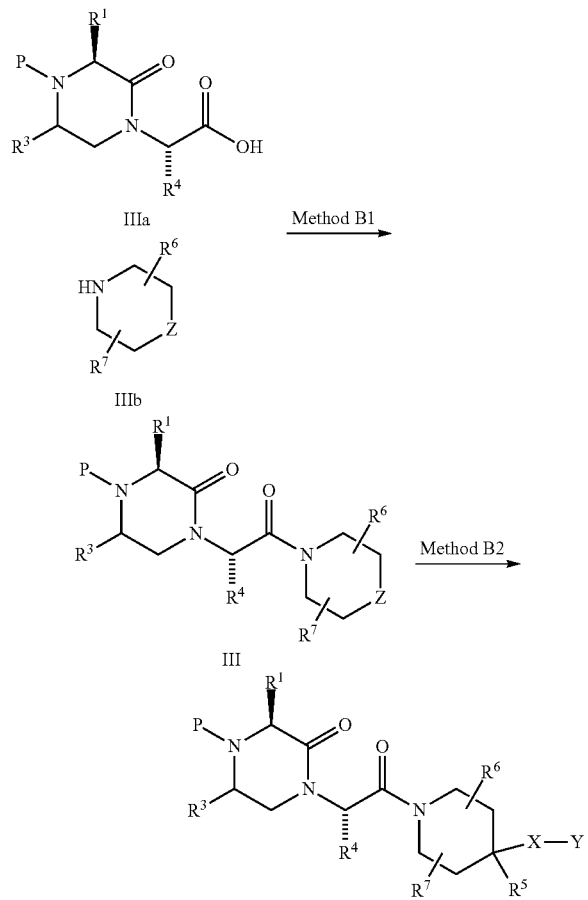

Method B1: Using the appropriate precursor IIIa and IIIb, III is prepared by amide coupling using a dehydrating agent such as DCC or HATU in a suitable solvent such as DMF or NMP.

Method B2: Z can be elaborated into the desired functional group using reaction sequences described in Table X. In cases where compound of the invention has $R^2$=H, the starting material of Method B will have P as a protecting group, such as t-Boc or Nosyl. The compounds of the invention are then obtained by deprotection under standard conditions. The compounds where is $R^2$ is $C(O)R^{14}$, $C(O)NR^{15}R^{15}$ or $C(O)OR^{15}$ are obtained by acylation of the secondary amine at this point. The compounds where is $R^2$ is not the above are obtained by reductive amination of the secondary amine with the appropriate aldehyde or ketone.

General Scheme 3 (Method C)

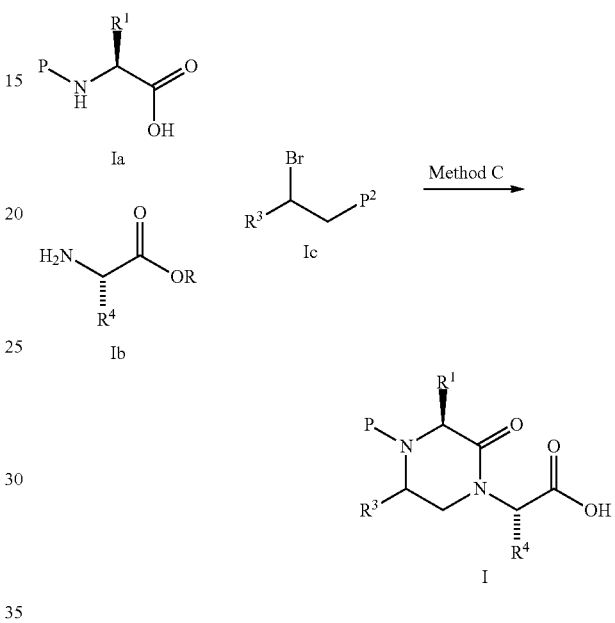

Method C: I may be prepared following the sequence described in Method C. Using the appropriate Ia bearing a protecting group P and Ib bearing a short alkyl group R, the coupling is performed by using a dehydrating agent such as DCC or HATU in a suitable solvent such as DMF or NMP. The resulting dipeptide ester is reacted with Ic. When P2 is Br, Ic is reacted in a suitable solvent such as DMF or DMSO in the presence of a base such as potassium carbonate or cesium carbonate to yield a short-chain ester derivative of I. When P2 is a protected alcohol such as OTHP or OTBDMS, the short chain ester of I is obtained by first reacting Ic with the dipeptide ester in a suitable solvent such as DMF or DMSO in the presence of a base such as potassium carbonate or cesium carbonate, followed by alcohol deprotection, followed by alcohol activation and coupling using methods like the Mitsunobu reaction or the formation of a mesylate and base-catalyzed cyclization. I is finally obtained by hydrolysis using a base such as sodium hydroxide or potassium carbonate, in a suitable solvent such as water or a water-THF mixture.

Pharmaceutical Compositions

In a further aspect the present invention provides a pharmaceutical composition comprising a compound of formula (I) or formula (Ia) according to the invention and a pharmaceutically acceptable diluent, excipient or carrier.

In one embodiment the pharmaceutical composition further comprises another pharmaceutical active agent.

In one embodiment, the invention provides a pharmaceutical composition comprising a compound of formula (I) or formula (Ia) according to the invention and a pharmaceutically acceptable diluent, excipient or carrier, wherein said compound of formula (I) or formula (Ia) is present in a therapeutically effective amount.

The expression "effective amount" or "therapeutically effective amount" as used herein refers to an amount capable of invoking one or more of the following effects in a subject receiving the combination of the present invention: (i) inhibition or arrest of tumor growth, including, reducing the rate of tumor growth or causing complete growth arrest; (ii) reduction in the number of tumor cells; (iii) reduction in tumor size; (iv) reduction in tumor number; (v) inhibition of metastasis (i.e., reduction, slowing down or complete stopping) of tumor cell infiltration into peripheral organs; (vi) enhancement of antitumor immune response, which may, but does not have to, result in the regression or elimination of the tumor; (vii) relief, to some extent, of one or more symptoms associated with cancer; (viii) increase in progression-free survival (PFS) and/or; overall survival (OS) of the subject receiving the combination.

The compounds of the present invention may, in accordance with the invention, be administered in single or divided doses by oral, parenteral, inhalatory, rectal or topical administration including cutaneous, ophthalmic, mucosal scalp, sublingual, buccal and intranasal routes of administration; further, the compounds provided by the invention may be formulated to be used for the treatment of leukocyte populations in vivo, ex vivo and in vitro.

When the compounds of the present invention are to be administered e.g. by the oral route, they may be administered as medicaments in the form of pharmaceutical compositions which contain them in association with a pharmaceutically acceptable diluent, excipient or carrier material. Thus the present invention also provides a pharmaceutical composition comprising the compounds according to the invention as described supra and one or more pharmaceutically acceptable diluent, excipient or carrier. The pharmaceutical compositions can be prepared in a conventional manner and finished dosage forms can be solid dosage forms, for example, tablets, dragees, capsules, and the like, or liquid dosage forms, for example solutions, suspensions, emulsions and the like. Pharmaceutically acceptable diluent, excipient or carrier include sterile aqueous solutions or dispersions and sterile powders for the extemporaneous preparation of sterile injectable solutions or dispersion. The use of such media and agents for pharmaceutically active substances is known in the art.

In one embodiment, the invention provides a pharmaceutical composition comprising a compound of formula (I) or formula (Ia) according to the invention and at least one pharmaceutically acceptable diluent, excipient or carrier, wherein the composition is a tablet or a capsule, preferably a tablet.

The amount of the compounds of the invention to be administered will vary depending upon factors such as the particular compound, disease condition and its severity, according to the particular circumstances surrounding the case, including, e.g., the specific compound being administered, the route of administration, the condition being treated, the target area being treated, and the subject or host being treated In another aspect, the application provides a pharmaceutical composition comprising a therapeutically effective amount of a compound of the present application or an enantiomer, diastereomer, or stereoisomer thereof, or pharmaceutically acceptable salt, hydrate, solvate, or prodrug thereof, and a pharmaceutically acceptable carrier.

Compounds of the application can be administered as pharmaceutical compositions by any conventional route, in particular enterally, e.g., orally, e.g., in the form of tablets or capsules, or parenterally, e.g., in the form of injectable solutions or suspensions, or topically, e.g., in the form of lotions, gels, ointments or creams, or in a nasal or suppository form. Pharmaceutical compositions comprising a compound of the present application in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxy propylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, com, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds and compositions of the application can be administered in therapeutically effective amounts in a combinational therapy with one or more therapeutic agents (pharmaceutical combinations) or modalities, e.g., an anti-proliferative, anti-cancer, immunomodulatory or anti-inflammatory agent. Where the compounds of the application are administered in conjunction with other therapies, dosages of the co-administered compounds will of course vary depending on the type of co-drug employed, on the specific drug employed, on the condition being treated and so forth. Compounds and compositions of the application can be administered in therapeutically effective amounts in a combinational therapy with one or more therapeutic agents (pharmaceutical combinations) or modalities, e.g., anti-proliferative, anti-cancer, immunomodulatory or anti-inflammatory agent, and/or non-drug therapies, etc. For example, synergistic effects can occur with anti-proliferative, anti-cancer, immunomodulatory or anti-inflammatory substances. Where the compounds of the application are administered in conjunction with other therapies, dosages of the co-administered compounds will of course vary depending on the type of co-drug employed, on the specific drug employed, on the condition being treated and so forth.

Combination therapy includes the administration of the subject compounds in further combination with one or more other biologically active ingredients. For instance, the compounds of the application can be used in combination with other pharmaceutically active compounds, preferably compounds that are able to enhance the effect of the compounds of the application. The compounds of the application can be administered simultaneously (as a single preparation or separate preparation), in temporal proximity, or sequentially to the other drug therapy or treatment modality. In general, a combination therapy envisions administration of two or more drugs during a single cycle or course of therapy.

In another aspect of the application, the compounds may be administered in combination with one or more separate pharmaceutical agents, e.g., a chemotherapeutic agent, an immunotherapeutic agent, or an adjunctive therapeutic agent.

Methods of Treatment

The compounds according to the invention as described supra have preventive and therapeutic utility in human and veterinary diseases.

Thus, in a further aspect the present invention provides the use of the compounds as described herein and the use of the pharmaceutical composition described herein for preventive and/or therapeutic purposes.

In one embodiment of the present invention, the compounds according to the invention as described herein or the pharmaceutical composition as described herein may be used as a medicament, preferably for use in human medicine and/or veterinarian medicine. Accordingly the present invention provides the compounds according to the invention as described herein or a pharmaceutical composition as described herein, for use as a medicament.

In another embodiment, the compounds according to the invention as described herein or the pharmaceutical composition as described herein may be used in a method for preventing or treating cancer in a subject.

Also provided is the use of the compounds according to the invention as described herein or the pharmaceutical composition as described herein for the manufacture of a medicament for the prevention or treatment of cancer in a subject.

Also provided is the use of the compounds according to the invention as described herein or the pharmaceutical composition as described herein for the prevention or treatment of cancer in a subject.

Also provided is a method for the prevention or treatment of cancer in a subject, comprising administering to said subject a therapeutically effective amount of the compounds according to the invention as described herein or the pharmaceutical composition as described herein.

The terms "treatment"/"treating" as used herein includes: (1) delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

Preventive treatments comprise prophylactic treatments. In preventive applications, the pharmaceutical combination of the invention is administered to a subject suspected of having, or at risk for developing cancer. In therapeutic applications, the pharmaceutical combination is administered to a subject such as a patient already suffering from cancer, in an amount sufficient to cure or at least partially arrest the symptoms of the disease. Amounts effective for this use will depend on the severity and course of the disease, previous therapy, the subject's health status and response to the drugs, and the judgment of the treating physician.

In the case wherein the subject's condition does not improve, the pharmaceutical combination of the invention may be administered chronically, which is, for an extended period of time, including throughout the duration of the subject's life in order to ameliorate or otherwise control or limit the symptoms of the subject's disease or condition.

In the case wherein the subject's status does improve, the pharmaceutical combination may be administered continuously; alternatively, the dose of drugs being administered may be temporarily reduced or temporarily suspended for a certain length of time (i.e., a "drug holiday"). Once improvement of the patient's condition has occurred, a maintenance dose of the pharmaceutical combination of the invention is administered if necessary. Subsequently, the dosage or the frequency of administration, or both, is optionally reduced, as a function of the symptoms, to a level at which the improved disease is retained.

When provided preventively, the compound(s) are provided in advance of established disease. The preventive administration of a compound of the present invention serves to prevent or attenuate the evolution of disease. The therapeutic administration of a compound of the present invention serves to attenuate established disease. Thus, in accordance with the invention, a compound of the present invention can be administered either prior to the onset of disease or during the course of disease.

In one embodiment of the invention, there is provided the compounds according to the invention as described supra or the pharmaceutical composition as described supra, for use in a method for the prevention or treatment of cancer in a subject. Preferably the cancer is selected from the group consisting of head cancer and neck cancer.

P300

Dysregulation of the cellular transcription machinery is a fundamental feature of cancer. E1A binding protein (p300) and CREB binding protein (CBP) are two closely related paralog transcriptional co-activators involved in the expression of oncogenic drivers in cancer cells (Attar and Kurdistani in Cold Spring Harbor Perspectives in Medicine 7:a026534 (2017)).

P300/CBP interact through their conserved domains with hundreds of proteins; can act synergistically or antagonistically; and modulate downstream biological processes in a highly context-dependent manner to promote either apoptosis or cell proliferation (Bedford and co-workers in Epigenetics 5(1): 9 (2010); Goodman and Smolik in Genes & Development 14(13):1553 (2000); Dancy and Cole in Chemical Reviews 115(6):2419 (2015)). These domains include the nuclear receptor interaction domain (RID), the cysteine/histidine regions CH1 (TAZ1) and CH3 (TAZ2), the CREB and MYB interaction domain (KIX), Bromodomain, the plant homeodomain (PHD), the histone acetyltransferase and/or lysine acetyltransferase domain (KAT/HAT), the ZZ type zinc finger domain (ZZ), and the interferon response binding domain (IBiD (NCBD)).

The following examples (from Dancy and Cole in Chemical Reviews 115(6):2419 (2015)) demonstrate the context-dependency of gene expression regulation by p300/CBP. For instance, Hottiger and co-workers (in EMBO Journal 17, 3124 (1998)) showed that HIV gene expression could be upregulated by tumor-necrosis factor alpha through binding of the RelA subunit of NFκB to p300/CBP-CH1 but was repressed through interferon-alpha-mediated binding of STAT2 to the same motif. In other studies, p300/CBP mediated both induction and repression of antioxidant response genes, via AP-1 binding to the C-terminal region, respectively by p53-binding to CH1/CH3 and glucocorticoid receptor-binding to the NRID domain (Avantaggiati and co-workers in Cell 89:1175 (1997); Kamei and co-workers in Cell 85:403 (1996)). P53 binding to p300/CBP/CH3 and consequent induction of p53-dependent genes results in cell cycle arrest (e.g., as a consequence of genotoxic insults), but apoptosis is induced when overexpressed E2F-1 (a central protein in cell cycle regulation that can act through p53 as well) is bound to p300/CBP/CH3 (Goodman and Smolik in Genes & Development 14:1553 (2000); Lee and co-workers in Oncogene 16:2695 (1998)). Cyclic-AMP response is both induced and repressed by p300/CBP via CREB binding to the KIX domain, respectively S6 kinase pp90RSK binding to the CH3 domain (Nakajima and co-workers in Cell 86:465 (1996)).

Modulation of cancer-relevant pathways by p300/CBP include hormone-dependent androgen receptor signaling in prostate cancer (Culig in Journal of Cell Physiology 231(2): 270 (2016)); the HIF-1 alpha/VEGF pathway in hypoxia-dependent tumor growth (Masoud and Li in Acta Pharmacologica Sinica B 5(5):378 (2015)); and the interaction with tumor suppressor p53 and HPV-E6 oncoprotein in HPV-positive carcinomas (Tornesello and co-workers in Cancers (Basel) 10(7)pii:E213 (2018)).

P300 and CBP also play an important role in hematopoiesis and control processes whose disruption can lead to the development of leukemias and lymphomas (Blobel in Blood 95(3):745 (2000); Dutta and co-workers in Molecular Genetics and Metabolism 119(1-2):37 (2016)).

Taken together, these studies highlight how indispensable p300/CBP is to many cellular signaling pathways and how p300 and CBP utilize their protein-protein interactions to determine how the cell responds to environmental stimuli. This makes CBP/p300 an ideal target for the development of novel cancer therapies (Di Martile and co-workers in Oncotarget 7(34):55789 (2016); Ali and co-workers in Chemical Reviews 118(3):1216 (2018)).

Exploitation of CBP/p300 protein-protein interactions for drug discovery has nonetheless proven difficult because of the inherent highly disordered nature of the protein structure (Wright and Dyson in Nature Reviews in Molecular and Cell Biology 16(1): 18-29 (2015)). Yet specific inhibitors have been developed against highly conserved, more ordered domains such as the HAT/KAT catalytic site, KIX and bromodomain (Breen and Mapp in Current Opinion in Chemical Biology 45:195-203 (2018); Dancy and Cole in Chemical Reviews 115(6):2419-2452 (2015)).

Without being bound by any particular theory, an extremely well-conserved p300/CBP domain that can be a suitable drug target is the transcriptional adaptor and zinc finger 1 CH1/TAZ1 domain, as highlighted by several publications showing e.g. that the interaction between p300/CBP-CH1/TAZ1 and HIF1-alpha as well as the interaction between HPV-E6/E7 and p300/CBP-CH1/TAZ1 in HPV-positive Cervical and Head-and-Neck cancer can potentially be exploited for the development of anticancer therapies (Wuchano Yuan and Giordano in Oncogene 21:2253-2260 (2002); Breen and Mapp in Current Opinion in Chemical Biology 45:195-203 (2018); Lao and co-workers in PNAS 111(21):7531 (2014); Kushal and co-workers in PNAS 110(39):15602 (2013); Masoud and Li in Acta Pharmacologica Sinica B 5(5):378 (2015); Burslem and co-workers in Chemical Science 8(6):4188 (2017); Fera and co-workers in Biochemistry 51 (47):9524 (2012); Xie and co-workers in Oncogene 33(8):1037 (2014); Patel and co-workers in The EMBO Journal 18(18):5061 (1999); Bernat and co-workers in Oncogene 22(39):7871 (2003)).

In summary, reprogramming the transcriptional profile of cancer cells by modulation of p300/CBP activity—for example by targeting the CH1/TAZ1 domain—represents a novel and broadly applicable approach for the treatment of cancer.

Without being bound by any particular theory, compounds of the disclosure can inhibit or modify the activity of p300 by inhibiting or modifying the activity of any p300 domain. For example, compounds of the disclosure can inhibit or modify the activity of the CH1/TAZ1, CH2/TAZ2, RID, KIX, KAT/HAT, PHD, Bromodomain, ZZ or IBiD domains. Compounds of the disclosure can inhibit or modify the interaction of p300 with any one of its protein interaction partners, or combination of protein interaction partners, through the CH1/TAZ1, CH2/TAZ2, RID, KIX, IBiD or any other p300 protein-protein interaction domain. A non-limiting list of p300 interaction partners whose interaction with p300 can be affected by compounds of the disclosure includes transcription coactivator BCL3 (BCL3), beta-catenin, breast cancer 1, early onset (BRCA1), caudal type homeobox 2 (CDX2), CCAAT enhancer binding protein beta (CEBPB) and CCAAT enhancer binding protein epsilon (CEBPE), Cbp/p300 interacting transactivator with Glu/Asp rich carboxy-terminal domain 1 (CITED1), Cbp/p300 interacting transactivator with Glu/Asp rich carboxy-terminal domain 2 (CITED2), DEAD-box helicase 5 (DDX5), deltex E3 ubiquitin ligase 1 (DTX1), EP300 interacting inhibitor of differentiation 1 (EID1), ELK1, ETS transcription factor (ELK1), estrogen receptor 1 (ESR1), flap structure-specific endonuclease 1 (FEN1), G protein pathway suppressor 2 (GPS2), hypoxia inducible factor 1 subunit alpha (HIF1A), HNF1 homeobox A (HNF1A), heterogeneous nuclear ribonucleoprotein U (HNRPU), inhibitor of growth family member 4 (ING4), inhibitor of growth family member 5 (ING5), interferon regulatory factor 2 (IRF2), lymphoid enhancer binding factor 1 (LEF 1), MAF bZIP transcription factor (MAF), mastermind like transcriptional coactivator 1 (MAML1), myocyte enhancer factor 2C (MEF2C), myocyte enhancer factor 2D (MEF2D), MYB proto-oncogene like 2 (MYBL2), MDM2 proto-oncogene (Mdm2), myogenic differentiation 1 (MyoD), myocyte enhancer factor 2A (MEF2A), nuclear receptor coactivator 6 (NCOA6), nuclear factor of activated T cells 2 (NFATC2), neuronal PAS domain protein 2 (NPAS2), tumor protein p53 (P53), paired box 6 (PAX6), proliferating cell nuclear antigen (PCNA), prospero homeobox 1 (PROX1), prothymosin alpha (PTMA), peroxisome proliferator activated receptor alpha (PPARA), peroxisome proliferator activated receptor gamma (PPARG), RAR related orphan receptor A (RORA), RELA proto-oncogene, NF-kB subunit (RELA), SMAD family member 1 (SMAD1), SMAD family member 2 (SMAD2), MAD family member 7 (SMAD7), Smad nuclear interacting protein 1 (SNIP1), SS18, nBAF chromatin remodeling complex subunit (SS18), signal transducer and activator of transcription 3 (STAT3), signal transducer and activator of transcription 6 (STAT6), TAL bHLH transcription factor 1, erythroid differentiation factor (TAL1), transcription factor 3 (TCF3), transcription factor AP-2 alpha (TFAP2A), trimethylguanosine synthase 1 (TGS1), transcriptional regulating factor 1 (TRERF1), tumor susceptibility 101 (TSG101), twist family bHLH transcription factor 1 (TWIST1), YY1 transcription factor (YY1) and early growth response 1 (Zif-268).

Without wishing to be bound by any particular theory, inhibiting or modifying the ability of p300 to interact with protein-protein interaction partners can inhibit or modify the ability of p300 or protein complexes comprising p300 to bind to DNA. For example, a compound of the disclosure can prevent p300 or a protein complex comprising p300 from binding to a target promoter, thereby preventing transcription of a target gene. A compound of the disclosure can prevent p300 or protein complexes comprising p300 from binding to a subset of all p300 target promoters, thereby altering the transcriptional profile of a cell, for example a cancer cell. Alternatively, or in addition, a compound of the disclosure can inhibit or modify the ability of p300 or a p300 protein complex to recruit one or more additional transcription factors, for example, transcription co-activators, to a promoter. Without limiting the possible pathways affected, a compound of the disclosure can alter the expression of genes involved in cell cycle progression, Wnt, Notch and Hedgehog signaling, DNA damage response, apoptosis, antioxidant response, Cyclic-AMP response, hormone-dependent androgen receptor signaling, hypoxia-dependent tumor growth, hematopoiesis or a combination thereof, thereby reducing the proliferation of or otherwise reducing the viability of cancer cells. For example, compounds of the disclosure can inhibit p300 interaction with CBP-HPVE6-p53, thereby rescuing p53 protein expression and acetylation and restoring the DNA damage response pathway in cervical cancer cells. Alternatively, or in addition, compounds of the disclosure can inhibit the formation of the p300/CBP-HIF1alpha protein complex, and reducing the transcription of growth factors and pro-proliferation genes such as vascular endothelial growth factor A (VEGF) in cancer cells. Alternatively, or in addition, compounds of the disclosure can disrupt p300-CH1/TAZ1 androgen receptor (AR) in castration resistant prostate cancers inhibiting the expression of AR target genes.

Without wishing to be bound by any particular theory, compounds of the disclosure can inhibit the activity of p300 in its regulation of oncogenic transcription factors that contribute to cancer progression.

Without wishing to be bound by any particular theory, compounds of the disclosure can act by inhibiting or modifying the acetyltransferase activity of the KAT/HAT domain.

An exemplary human p300 protein sequence can be found in NCBI NP_001420.2, the contents of which are hereby incorporated by reference in their entirety. An exemplary human p300 protein comprises a sequence of:

```
                                                          (SEQ ID NO: 1)
   1    maenvvepgp   psakrpklss   palsasasdg   tdfgslfdle   hdlpdelins   telgltnggd 61    inqlqtslgm   vqdaaskhkq   lsellrsgss   pnlnmgvggp   gqvmasqaqq   sspglglins 121    mvkspmtqag   ltspnmgmgt   sgpnqgptqs   tgmmnspvnq   pamgmntgmn   agmnpgmlaa 181    gngqgimpnq   vmngsigagr   grqnmqypnp   gmgsagnllt   eplqqgspqm   ggqtglrgpq 241    plkmgmmnnp   npygspytqn   pgqqigasgl   glqiqtktvl   snnlspfamd   kkavpgggmp 301    nmgqqpapqv   qqpglvtpva   qgmgsgahta   dpekrkliqq   qlvlllhahk   cqrreqange 361    vrqcnlphcr   tmknvlnhmt   hcqsgkscqv   ahcassrqii   shwknctrhd   cpvclplkna 421    gdkrnqqpil   tgapvglgnp   sslgvgqqsa   pnlstvsqid   pssierayaa   lglpyqvnqm 481    ptqpqvqakn   qqnqqpgqsp   qgmrpmsnms   aspmgvnggv   gvqtpsllsd   smlhsainsq 541    npmmsenasv   pslgpmptaa   qpsttgirkq   wheditqdlr   nhlvhklvqa   ifptpdpaal 601    kdrrmenlva   yarkvegdmy   esannraeyy   hllaekiyki   qkeleekrrt   rlqkqnmlpn 661    aagmvpvsmn   pgpnmgqpqp   gmtsngplpd   psmirgsvpn   qmmpritpqs   glnqfgqmsm 721    aqppivprqt   pplqhhgqla   qpgalnppmg   ygprmqqpsn   qgqflpqtqf   psqgmnvtni 781    plapssgqap   vsqaqmssss   cpvnspimpp   gsqgshihcp   qlpgpalhqn   spspvpsrtp 841    tphhtppsig   aqqppattip   apvptppamp   pgpqsqalhp   pprqtptppt   tqlpqqvqps 901    lpaapsadqp   qqqprsqqst   aasvptptap   llppqpatpl   sqpavsiegq   vsnppstsst 961    evnsqaiaek   qpsqevkmea   kmevdqpepa   dtqpedises   kvedckmest   eteerstelk 1021    teikeeedqp   stsatqsspa   pgqskkkifk   peelrqalmp   tlealyrqdp   eslpfrqpvd 1081    pqllgipdyf   divkspmdls   tikrkldtgq   yqepwqyvdd   iwlmfnnawl   ynrktsrvyk 1141    ycsklsevfe   qeidpvmqsl   gyccgrklef   spqtlccygk   qlctiprdat   yysyqnryhf 1201    cekcfneiqg   esyslgddps   qpqttinkeq   fskrkndtld   pelfvectec   grkmhqicvl
```

```
1261  hheiiwpagf vcdgclkksa rtrkenkfsa krlpstrlgt flenrvndfl rrqnhpesge 1321  vtvrvvhasd ktvevkpgmk arfvdsgema esfpyrtkal fafeeidgvd loffgmhvqe 1381  ygsdcpppnq rrvyisylds vhffrpkclr tavyheilig yleyvkklgy ttghiwacpp 1441  segddyifhc hppdqkipkp krlqewykkm ldkavseriv hdykdifkqa tedrltsake 1501  lpyfegdfwp nvleesikel eqeeeerkre entsnestdv tkgdsknakk knnkktsknk 1561  sslsrgnkkk pgmpnvsndl sqklyatmek hkevffvirl iagpaanslp pivdpdplip 1621  cdlmdgrdaf ltlardkhle fsslrraqws tmcmlvelht qsqdrfvytc neckhhvetr 1681  whctvcedyd lcitcyntkn hdhkmeklgl glddesnnqq aaatqspgds rrlsiqrciq 1741  slvhacqcrn ancslpscqk mkrvvqhtkg ckrktnggcp ickqlialcc yhakhcqenk 1801  cpvpfclnik qklrqqqlqh rlqqaqmlrr rmasmqrtgv vgqqqglpsp tpatpttptg 1861  qqpttpqtpq ptsqpqptpp nsmppylprt qaagpvsqgk aagqvtpptp pqtaqpplpg 1921  pppaavemam qiqraaetqr qmahvqifqr piqhqmppmt pmapmgmnpp pmtrgpsghl 1981  epgmgptgmq qqppwsqggl pqpqqlqsgm prpammsvaq hgqplnmapq pglgqvgisp 2041  lkpgtvsqqa lqnllrtlrs pssplqqqqv lsilhanpql laafikqraa kyansnpqpi 2101  pgqpgmpqgq pglqpptmpg qqgvhsnpam gnmnpmqagv qraglpqqqp qqqlqppmgg 2161  mspqaqqmnm nhntmpsqfr dilrrqqmmq qqqqqgagpg igpgmanhnq fqqpqgvgyp 2221  pqqqqrmqhh mqqmqqgnmg qigqlpqalg aeagaslqay qqrllqqqmg spvqpnpmsp 2281  qqhmlpnqaq sphlqgqqip nslsnqvrsp qpvpsprpqs qpphsspspr mqpqpsphhv 2341  spqtssphpg lvaaqanpme qghfaspdqn smlsqlasnp gmanlhgasa tdlglstdns 2401  dlnsnlsqst ldih.
```

In some embodiments, a p300 protein comprises a protein having at least 85% identity to SEQ ID NO: 1, at least 90% identity to SEQ ID NO: 1, at least 95% identity to SEQ ID NO: 1, 50 at least 96% identity to SEQ ID NO: 1, at least 97% identity to SEQ ID NO: 1, at least 98% identity to SEQ ID NO: 1, at least 99% identity to SEQ ID NO: 1 or at least 99.8% identity to SEQ ID NO: 1. In some embodiments, a p300 protein is identical to a protein of SEQ ID NO: 1.

The CH1/TAZ domain corresponds approximately to amino acids 347-414 of SEQ ID NO: 1. The KIX domain corresponds approximately to amino acids 566-646 of SEQ ID NO: 1. The bromodomain corresponds approximately to amino acids 1051-1158 of SEQ ID NO: 1. The PHD domain corresponds approximately to amino acids 1243-1277 of SEQ ID NO: 1. The HAT/KAT domain corresponds approximately to amino acids 1306-1612 of SEQ ID NO: 1. The ZZ domain corresponds approximately to amino acids 1668-1708 of SEQ ID NO: 1. The TAZ2 domain corresponds approximately to amino acids 1729-1807 of SEQ ID NO: 1.

As used herein in the context of polypeptides, nucleic acids, and chemical compounds, the term "corresponding to", designates the position/identity of a structural element, e.g., of an amino acid residue, a nucleotide residue, or a chemical moiety, in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190th amino acid in a particular amino acid chain but rather corresponds to the residue found at position 190 in the reference polypeptide; those of ordinary skill in the art readily appreciate how to identify "corresponding" amino acids (see. e.g., Benson et al. Nucl. Acids Res. (1 Jan. 2013) 41 (Dl): D36-D42; Pearson et al. PNAS Vol. 85, pp. 2444-2448, April 1988). Those skilled in the art will be aware of various sequence alignment strategies, including software programs such as, for example, BLAST, CS-BLAST, CUSASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that can be utilized, for example, to identify "corresponding" residues in polypeptides and/or nucleic acids in accordance with the present disclosure.

As used herein the term "domain" refers to a section or portion of a polypeptide. In some embodiments, a "domain" is associated with a particular structural and/or functional feature of the polypeptide so that, when the domain is physically separated from the rest of its parent polypeptide, it substantially or entirely retains the particular structural and/or functional feature. In some embodiments, a domain may include a portion of a polypeptide that, when separated from that (parent) polypeptide and linked with a different (recipient) polypeptide, substantially retains and/or imparts on the recipient polypeptide one or more structural and/or functional features that characterized it in the parent polypeptide. In some embodiments, a domain is a section of a polypeptide. In some such embodiments, a domain is characterized by a particular structural element (e.g., a particular amino acid sequence or sequence motif, oc-helix character, b-sheet character, coiled-coil character, random coil character), and/or by a particular functional feature (e.g., binding activity, enzymatic activity, folding activity, signaling activity). One of ordinary skill will appreciate that domain boundaries are typically determined experimentally or via sequence alignment, and may be approximate. In some embodiments, domain boundaries may vary by at least 1, at least 2, at least 3, at least 4, at least 5, at least 6, at least 10, at least 15 or at least 20 amino acids without affecting the in vivo function of the domain.

An exemplary nucleic acid sequence encoding a p300 protein comprises a sequence of:

```
                                                          (SEQ ID NO: 2)
   1  gagaaggagg aggacagcgc cgaggaggaa gaggttgatg gcggcggcgg agctccgaga
  61  gacctcggct gggcaggggc cggccgtggc gggccgggga ctgcgcctct agagccgcga
 121  gttctcggga attcgccgca gcggacgcgc tcggcgaatt tgtgctcttg tgccctcctc
 181  cgggcttggg cccaggcccg gcccctcgca cttgcccta cctttctat cgagtccgca
 241  tccctctcca gccactgcga cccggcgaag agaaaaagga acttcccca ccccctcggg
 301  tgccgtcgga gcccccagc ccaccctgg gtgcggcgcg gggacccgg gccgaagaag
 361  agatttcctg aggattctgg ttttcctcgc ttgtatctcc gaaagaatta aaaatggccg
 421  agaatgtggt ggaaccgggg ccgccttcag ccaagcggcc taaactctca tctccggccc
 481  tctcggcgtc cgccagcgat ggcacagatt ttggctctct atttgacttg gagcacgact
 541  taccagatga attaatcaac tctacagaat tgggactaac caatggtggt gatattaatc
 601  agcttcagac aagtcttggc atggtacaag atgcagcttc taaacataaa cagctgtcag
 661  aattgctgcg atctggtagt tcccctaacc tcaatatggg agttggtggc ccaggtcaag
 721  tcatggccag ccaggccaa cagagcagtc ctggattagg tttgataaat agcatggtca
 781  aaagcccaat gacacaggca ggcttgactt ctcccaacat ggggatgggc actagtggac
 841  caaatcaggg tcctacgcag tcaacaggta tgatgaacag tccagtaaat cagcctgcca
 901  tgggaatgaa cacagggatg aatgcgggca tgaatcctgg aatgttggct gcaggcaatg
 961  gacaagggat aatgcctaat caagtcatga acggttcaat tggagcaggc cgagggcgac
1021  agaatatgca gtacccaaac ccaggcatgg gaagtgctgg caacttactg actgagcctc
1081  ttcagcaggg ctctccccag atgggaggac aaacaggatt gagaggcccc cagcctctta
1141  agatgggaat gatgaacaac cccaatcctt atggttcacc atatactcag aatcctggac
1201  agcagattgg agccagtggc cttggtctcc agattcagac aaaaactgta ctatcaaata
1261  acttatctcc atttgctatg gacaaaaagg cagttcctgg tggaggaatg cccaacatgg
1321  gtcaacagcc agcccgcag gtccagcagc caggcctggt gactccagtt gcccaaggga
1381  tgggttctgg agcacataca gctgatccag agaagcgcaa gctcatccag cagcagcttg
1441  ttctcctttt gcatgctcac aagtgccagc gcgggaaca ggccaatggg gaagtgaggc
1501  agtgcaacct tcccactgt cgcacaatga agaatgtcct aaaccacatg acacactgcc
1561  agtcaggcaa gtcttgccaa gtggcacact gtgcatcttc tcgacaaatc atttcacact
1621  ggaagaattg tacaagacat gattgtcctg tgtgtctccc cctcaaaaat gctggtgata
1681  agagaaatca acagccaatt ttgactggag caccgttgg acttggaaat cctagctctc
1741  tagggggtggg tcaacagtct gcccccaacc taagcactgt tagtcagatt gatcccagct
1801  ccatagaaag agcctatgca gctcttggac taccctatca gtaaatcag atgccgacac
1861  aaccccaggt gcaagcaaag aaccagcaga atcagcagcc tggcagtct ccccaaggca
1921  tgcggcccat gagcaacatg agtgctagtc ctatgggagt aaatggaggt gtaggagttc
1981  aaacgcgag tcttctttct gactcaatgt tgcattcagc cataaattct caaaacccaa
2041  tgatgagtga aaatgccagt gtgccctccc tgggtcctat gccaacagca gctcaaccat
```

-continued

```
2101  ccactactgg aattcggaaa cagtggcacg aagatattac tcaggatctt cgaaatcatc
2161  ttgttcacaa actcgtccaa gccatatttc ctacgccgga tcctgctgct ttaaaagaca
2221  gacggatgga aaacctagtt gcatatgctc ggaaagttga aggggacatg tatgaatctg
2281  caaacaatcg agcggaatac taccaccttc tagctgagaa aatctataag atccagaaag
2341  aactagaaga aaaacgaagg accagactac agaagcagaa catgctacca aatgctgcag
2401  gcatggttcc agtttccatg aatccagggc ctaacatggg acagccgcaa ccaggaatga
2461  cttctaatgg ccctctacct gacccaagta tgatccgtgg cagtgtgcca aaccagatga
2521  tgcctcgaat aactccacaa tctggtttga atcaatttgg ccagatgagc atggcccagc
2581  cccctattgt accccggcaa acccctcctc ttcagcacca tggacagttg gctcaacctg
2641  gagctctcaa cccgcctatg ggctatgggc ctcgtatgca acagccttcc aaccagggcc
2701  agttccttcc tcagactcag ttcccatcac agggaatgaa tgtaacaaat atccctttgg
2761  ctccgtccag cggtcaagct ccagtgtctc aagcacaaat gtctagttct tcctgcccgg
2821  tgaactctcc tataatgcct ccagggtctc aggggagcca cattcactgt ccccagcttc
2881  ctcaaccagc tcttcatcag aattcaccct cgcctgtacc tagtcgtacc cccacccctc
2941  accatactcc cccaagcata ggggctcagc agccaccagc aacaacaatt ccagcccctg
3001  ttcctacacc tcctgccatg ccacctgggc cacagtccca ggctctacat cccctccaa
3061  ggcagacacc tacaccacca acaacacaac ttccccaaca agtgcagcct tcacttcctg
3121  ctgcaccttc tgctgaccag cccagcagc agcctcgctc acagcagagc acagcagcgt
3181  ctgttcctac cccaacagca ccgctgcttc ctccgcagcc tgcaactcca ctttcccagc
3241  cagctgtaag cattgaagga caggtatcaa atcctccatc tactagtagc acagaagtga
3301  attctcaggc cattgctgag aagcagcctt cccaggaagt gaagatggag gccaaaatgg
3361  aagtggatca accagaacca gcagatactc agccggagga tatttcagag tctaaagtgg
3421  aagactgtaa aatggaatct accgaaacag aagagagaag cactgagtta aaaactgaaa
3481  taaaagagga ggaagaccag ccaagtactt cagctaccca gtcatctccg gctccaggac
3541  agtcaaagaa aaagattttc aaaccagaag aactacgaca ggcactgatg ccaactttgg
3601  aggcacttta ccgtcaggat ccagaatccc ttccctttcg tcaacctgtg gaccctcagc
3661  ttttaggaat ccctgattac tttgatattg tgaagagccc catggatctt tctaccatta
3721  agaggaagtt agacactgga cagtatcagg agccctggca gtatgtcgat gatatttggc
3781  ttatgttcaa taatgcctgg ttatataacc ggaaaacatc acgggtatac aaatactgct
3841  ccaagctctc tgaggtcttt gaacaagaaa ttgacccagt gatgcaaagc cttggatact
3901  gttgtggcag aaagttggag ttctctccac agacactgtg ttgctacggc aaacagttgt
3961  gcacaatacc tcgtgatgcc acttattaca gttaccagaa caggtatcat ttctgtgaga
4021  agtgtttcaa tgagatccaa ggggagagcg tttctttggg ggatgaccct tcccagcctc
4081  aaactacaat aaataaagaa caattttcca agagaaaaaa tgacacactg gatcctgaac
4141  tgtttgttga atgtacagag tgcggaagaa agatgcatca gatctgtgtc cttcaccatg
4201  agatcatctg gcctgctgga ttcgtctgtg atggctgttt aaagaaaagt gcacgaacta
4261  ggaaagaaaa taagtttttct gctaaaaggt tgccatctac cagacttggc acctttctag
4321  agaatcgtgt gaatgacttt ctgaggcgac agaatcaccc tgagtcagga gaggtcactg
4381  ttagagtagt tcatgcttct gacaaaaccg tggaagtaaa accaggcatg aaagcaaggt
4441  ttgtggacag tggagagatg gcagaatcct ttccataccg aaccaaagcc ctctttgcct
4501  ttgaagaaat tgatggtgtt gacctgtgct tctttggcat gcatgttcaa gagtatggct
```

-continued

```
4561  ctgactgccc tccacccaac cagaggagag tatacatatc ttacctcgat agtgttcatt
4621  tcttccgtcc taaatgcttg aggactgcag tctatcatga aatcctaatt ggatatttag
4681  aatatgtcaa gaaattaggt tacacaacag ggcatatttg ggcatgtcca ccaagtgagg
4741  gagatgatta tatcttccat tgccatcctc ctgaccagaa gataccaag cccaagcgac
4801  tgcaggaatg gtacaaaaaa atgcttgaca aggctgtatc agagcgtatt gtccatgact
4861  acaaggatat ttttaaacaa gctactgaag atagattaac aagtgcaaag gaattgcctt
4921  atttcgaggg tgatttctgg cccaatgttc tggaagaaag cattaaggaa ctggaacagg
4981  aggaagaaga gagaaaacga gaggaaaaca ccagcaatga aagcacagat gtgaccaagg
5041  gagacagcaa aaatgctaaa aagaagaata ataagaaaac cagcaaaaat aagagcagcc
5101  tgagtagggg caacaagaag aaacccggga tgcccaatgt atctaacgac ctctcacaga
5161  aactatatgc caccatggag aagcataaag aggtcttctt tgtgatccgc ctcattgctg
5221  gccctgctgc caactccctg cctcccattg ttgatcctga tcctctcatc ccctgcgatc
5281  tgatggatgg tcgggatgcg tttctcacgc tggcaaggga caagcacctg gagttctctt
5341  cactccgaag agcccagtgg tccaccatgt gcatgctggt ggagctgcac acgcagagcc
5401  aggaccgctt tgtctacacc tgcaatgaat gcaagcacca tgtggagaca cgctggcact
5461  gtactgtctg tgaggattat gacttgtgta tcacctgcta taacactaaa aaccatgacc
5521  acaaaatgga gaaactaggc cttggcttag atgatgagag caacaaccag caggctgcag
5581  ccacccagag cccaggcgat tctcgccgcc tgagtatcca gcgctgcatc cagtctctgg
5641  tccatgcttg ccagtgtcgg aatgccaatt gctcactgcc atcctgccag aagatgaagc
5701  gggttgtgca gcataccaag ggttgcaaac ggaaaaccaa tggcgggtgc cccatctgca
5761  agcagctcat tgccctctgc tgctaccatg ccaagcactg ccaggagaac aaatgcccgg
5821  tgccgttctg cctaaacatc aagcagaagc tccggcagca acagctgcag caccgactac
5881  agcaggccca aatgcttcgc aggaggatgg ccagcatgca gcggactggt gtggttgggc
5941  agcaacaggg cctcccttcc cccactcctg ccactccaac gacaccaact ggccaacagc
6001  caaccacccc gcagacgccc cagcccactt ctcagcctca gcctaccccct cccaatagca
6061  tgccacccta cttgcccagg actcaagctg ctggccctgt gtcccagggt aaggcagcag
6121  gccaggtgac ccctccaacc cctcctcaga ctgctcagcc acccccttcca gggcccccac
6181  ctgcagcagt ggaaatggca atgcagattc agagagcagc ggagacgcag cgccagatgg
6241  cccacgtgca aattttcaa aggccaatcc aacaccagat gcccccgatg actcccatgg
6301  cccccatggg tatgaaccca cctcccatga ccagaggtcc cagtgggcat ttggagccag
6361  ggatgggacc gacaggatg cagcaacagc cacccctggag ccaaggagga ttgcctcagc
6421  cccagcaact acagtctggg atgccaaggc cagccatgat gtcagtggcc cagcatggtc
6481  aacctttgaa catggctcca caaccaggat tgggccaggt aggtatcagc ccactcaaac
6541  caggcactgt gtctcaacaa gccttacaaa acctttttgcg gactctcagg tctcccagct
6601  ctcccctgca gcagcaacag gtgcttagta tccttcacgc caacccccag ctgttggctg
6661  cattcatcaa gcagcgggct gccaagtatg ccaactctaa tccacaaccc atccctgggc
6721  agcctggcat gcccagggc cagccagggc tacagccacc taccatgcca ggtcagcagg
6781  gggtccactc caatccagcc atgcagaaca tgaatccaat gcaggcgggc gttcagaggg
6841  ctggcctgcc ccagcagcaa ccacagcagc aactccagcc acccatggga gggatgagcc
6901  cccaggctca gcagatgaac atgaaccaca acaccatgcc ttcacaattc cgagacatct
```

```
6961  tgagacgaca gcaaatgatg caacagcagc agcaacaggg agcagggcca ggaataggcc
7021  ctggaatggc caaccataac cagttccagc aaccccaagg agttggctac ccaccacagc
7081  agcagcagcg gatgcagcat cacatgcaac agatgcaaca aggaaatatg ggacagatag
7141  gccagcttcc ccaggccttg ggagcagagg caggtgccag tctacaggcc tatcagcagc
7201  gactccttca gcaacagatg gggtcccctg ttcagcccaa ccccatgagc cccagcagc
7261  atatgctccc aaatcaggcc cagtccccac acctacaagg ccagcagatc cctaattctc
7321  tctccaatca agtgcgctct ccccagcctg tcccttctcc acggccacag tcccagcccc
7381  cccactccag tccttcccca aggatgcagc ctcagccttc tccacaccac gtttccccac
7441  agacaagttc cccacatcct ggactggtag ctgcccaggc caacccatg gaacaagggc
7501  attttgccag cccggaccag aattcaatgc tttctcagct tgctagcaat ccaggcatgg
7561  caaacctcca tggtgcaagc gccacggacc tgggactcag caccgataac tcagacttga
7621  attcaaacct ctcacagagt acactagaca tacactagag acaccttgta gtattttggg
7681  agcaaaaaaa ttattttctc ttaacaagac tttttgtact gaaaacaatt tttttgaatc
7741  tttcgtagcc taaaagacaa ttttccttgg aacacataag aactgtgcag tagccgtttg
7801  tggtttaaag caaacatgca agatgaacct gagggatgat agaatacaaa gaatatattt
7861  ttgttatggc tggttaccac cagcctttct tccccttgt gtgtgtggtt caagtgtgca
7921  ctgggaggag gctgaggcct gtgaagccaa acaatatgct cctgccttgc acctccaata
7981  ggttttatta ttttttttaa attaatgaac atatgtaata ttaatagtta ttatttactg
8041  gtgcagatgg ttgacatttt tccctatttt cctcacttta tggaagagtt aaaacatttc
8101  taaaccagag gacaaaaggg gttaatgtta ctttaaaatt acattctata tatatataaa
8161  tatatataaa tatatattaa aataccagtt ttttttctct gggtgcaaag atgttcattc
8221  ttttaaaaaa tgtttaaaaa aaaaaaaaaa ctgcctttct tccctcaag tcaacttttg
8281  tgctccagaa aattttctat tctgtaagtc tgagcgtaaa acttcaagta ttaaaataat
8341  ttgtacatgt agagagaaaa atgacttttt caaaaatata caggggcagc tgccaaattg
8401  atgtattata tattgtggtt tctgtttctt gaaagaattt ttttcgttat ttttacatct
8461  aacaaagtaa aaaaattaaa aagagggtaa gaaacgattc cggtgggatg attttaacat
8521  gcaaaatgtc cctgggggtt tcttcttgc ttgctttctt cctccttacc ctaccccca
8581  ctcacacaca cacacacaca cacacacaca cacacacaca cacactttct ataaaacttg
8641  aaaatagcaa aaaccctcaa ctgttgtaaa tcatgcaatt aaagttgatt acttataaat
8701  atgaactttg gatcactgta tagactgtta aatttgattt cttattacct attgttaaat
8761  aaactgtgtg agacagaca
```

In some embodiments, a nucleic acid sequence encoding a p300 protein comprises a nucleic acid sequence encoding a protein having at least 85% identity to SEQ ID NO:1, at least 90% identity to SEQ ID NO: 1, at least 95% identity to SEQ ID NO: 1, at least 96% identity to SEQ ID NO: 1, at least 97% identity to SEQ ID NO: 1, at least 98% identity to SEQ ID NO: 1, at least 99% identity to SEQ ID NO: 1 or at least 99.8% identity to SEQ ID NO: 1. In some embodiments, nucleic acid sequence encoding a p300 protein comprises a nucleic acid sequence encoding a protein identical to SEQ ID NO: 1. In some embodiments, a nucleic acid sequence encoding a p300 protein comprises a nucleic acid sequence e having at least 85% identity to SEQ ID NO: 2, at least 90% identity to SEQ ID NO: 2, at least 95% identity to SEQ ID NO: 2, at least 96% identity to SEQ ID NO: 2, at least 97% identity to SEQ ID NO: 2, at least 98% identity to SEQ ID NO: 2, at least 99% identity to SEQ ID NO: 2 or at least 99.8% identity to SEQ ID NO: 2. In some embodiments, a nucleic acid sequence encoding a p300 protein comprises a nucleic acid sequence identical to SEQ ID NO: 2 or a portion or subsequence thereof.

As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

As used herein, the term "nucleic acid" refers to a polymer of at least three nucleotides. In some embodiments, a nucleic acid comprises DNA. In some embodiments comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis).

Methods of Treating Cancer

Cancer is a disease caused by the uncontrolled division of cells in the body. Abnormally dividing cancer cells can form a primary tumor, which can then invade nearby tissues, and spread throughout the body through the blood and lymphatic systems (metastatic cancers). Cancer can arise from many organs and cell types in the body, including but not limited to, cells of the lymphatic system, bone marrow, blood, brain and nervous system tissue, breast, cervix, ovary, colorectal cells, stomach and gastric cells, head and neck, kidney, liver, lung, oesophagus, pancreas, prostate and skin.

As used herein, the term "tumor" refers to an abnormal growth of cells or tissue. In some embodiments, a tumor may comprise cells that are precancerous (e.g., benign), malignant, pre-metastatic, metastatic, and/or non-metastatic. In some embodiments, a tumor is associated with, or is a manifestation of, a cancer.

In some embodiments, a tumor may be a disperse tumor or a liquid tumor. Liquid tumors can affect bone marrow, blood cells and the lymphatic system. Exemplary liquid tumors include leukemias and lymphomas. Types of lymphomas include, but are not limited to, Hodgkin lymphomas, non-Hodgkin lymphomas, B cell lymphomas, T-cell lymphomas, Burkitt's lymphomas, mantle cell lymphomas, small lymphocytic lymphomas, histiocytic lymphomas and primary mediastinal B cell lymphomas. Types of leukemias include, but are not limited to, acute myeloid leukemia, T cell leukemias, acute lymphoblastic leukemias and chronic myelogenous leukemias.

In some embodiments, a tumor may be a solid tumor. Exemplary solid tumors include, but are not limited to Carcinomas, Sarcomas, Myelomas, germ cell tumors, carcinoid tumors, neuroendocrine tumors and tumors of mixed type (a tumor which comprises multiple types of cancer cells). Carcinomas arise from epithelial tissues, either internal or external, such as cells of the gastrointestinal tract. Exemplary carcinomas include adenocarcinoma, which develops in an organ or gland, and squamous cell carcinoma, which originates in the squamous epithelium. Sarcomas are cancers that originate in supportive or connective tissues such as bones, tendons, cartilage, muscle and fat. Exemplary sarcomas include osteosarcoma, chondrosarcoma, leiomyosarcoma, rhabdomyosarcoma, mesothelial sarcoma, fibrosarcoma, angiosarcoma, liposarcoma, glioma or astrocytoma, myxosarcoma and mesenchymous or mixed mesodermal tumors.

Tumors can arise from most organs and tissue in the body, including, but not limited to, brain and nervous tissue, breast, cervix, ovary, uterus, colorectal, stomach and gastric tissue, kidney, liver, lung oesophagus, pancreas, prostate, skin, bone, head and neck, and lung. Exemplary brain and nervous system cancers include neurogliomas and glioblastomas. Exemplary breast cancers include human breast carcinomas, breast adenocarcinomas and invasive ductal carcinomas. Exemplary cervical cancers include epidermoid carcinomas, cervical carcinomas and HPV positive cervical cancers. Exemplary ovarian cancers include ovarian carcinomas. Exemplary colorectal cancers include colorectal carcinomas and colon colorectal adenocarcinomas. Exemplary stomach and gastric cancers include gastric adenocarcinomas, stomach adenocarcinomas and gastric carcinomas. Exemplary kidney cancers include renal cell adenocarcinomas and kidney clear cell carcinomas. Exemplary liver cancers include hepatocellular carcinomas and hepatomas. Exemplary lung cancers include small cell lung cancers, non-small cell lung cancers, lung carcinomas, lung adenocarcinomas, squamous cell carcinomas and large cell carcinomas. Exemplary esophageal cancers include esophageal squamous cell carcinoma. Exemplary pancreatic cancers include pancreatic carcinoma and pancreatic ductal adenocarcinoma. Exemplary prostate cancers include prostate carcinomas, prostate adenocarcinomas and castrate resistant prostate cancers. Exemplary skin cancers include melanomas, squamous cell carcinomas and basal cell carcinomas. Exemplary head and neck cancers include squamous cell carcinomas.

As used herein, the term "subject" refers to an organism, for example, a mammal (e.g., a human, a non-human mammal, a non-human primate, a primate, a laboratory animal, a mouse, a rat, a hamster, a gerbil, a cat, a dog). In some embodiments a human subject is an adult, adolescent, or pediatric subject (a child). In some embodiments, a subject is suffering from a disease, disorder or condition, e.g., a disease, disorder or condition that can be treated as provided herein, e.g., a cancer or a tumor listed herein. In some embodiments, a subject displays one or more symptoms of a disease, disorder or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

A cancer that is to be treated can be staged according to the American Joint Committee on Cancer (AJCC) TNM classification system, where the tumor (T) has been assigned a stage of TX, T1, T1mic, T1a, Tib, Tic, T2, T3, T4, T4a, T4b, T4c, or T4d; and where the regional lymph nodes (N) have been assigned a stage of NX, NO, N1, N2, N2a, N2b, N3, N3a, N3b, or N3c; and where distant metastasis (M) can be assigned a stage of MX, MO, or Ml. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pNO, PNO (I−), PNO (I+), PNO (mol−), PNO (mol+), PN1, PN1(mi), PN1a, PN1b, PN1c, pN2, pN2a, pN2b, pN3, pN3a, pN3b, or pN3c.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, polymorph, solvate, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate one or more symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, polymorph, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, polymorph, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer can result in a reduction in the rate of cellular proliferation.

Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating cancer can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of non dividing cells in a tissue sample. The proportion of proliferating cells can be equivalent to the mitotic index.

Treating cancer can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., Proc Natl Acad Sci USA. 100(5): 2674-8, 2003. In an aspect, cell death occurs by apoptosis.

As used herein, the term "selectively" means tending to occur at a higher frequency in one population than in another population. The compared populations can be cell populations. Preferably, a compound of the present invention, or a pharmaceutically acceptable salt, polymorph or solvate thereof, acts selectively on a cancer or precancerous cell but not on a normal cell. Preferably, a compound of the present invention, or a pharmaceutically acceptable salt, polymorph or solvate thereof, acts selectively to modulate one molecular target (e.g., p300) but does not significantly modulate another molecular target (e.g., a non-target protein). The invention also provides a method for selectively inhibiting the activity of a protein such as p300. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, polymorph or solvate thereof, can modulate the activity of a molecular target (e.g., p300). Modulating refers to stimulating or inhibiting an activity of a molecular target. Preferably, a compound of the present invention, or a pharmaceutically acceptable salt, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

Preferably, a compound of the present invention, or a pharmaceutically acceptable salt, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, polymorph or solvate thereof, to a cell or a subject in need thereof can result in modulation (i.e., stimulation or inhibition) of an activity of a protein of interest.

Administering a compound of the present invention, or a pharmaceutically acceptable salt, polymorph or solvate thereof, to a cell or a subject in need thereof results in modulation (i.e., stimulation or inhibition) of an activity of an intracellular target (e.g., substrate).

Preferably, an effective amount of a compound of the present invention, or a pharmaceutically acceptable salt, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, polymorph or solvate thereof, can induce or activate cell death selectively in cancer cells. Administering to a subject in need thereof a compound of the present invention, or a pharmaceutically acceptable salt, polymorph or solvate thereof, can induce or activate cell death selectively in cancer cells. Contacting a cell with a compound of the present invention, or a pharmaceutically acceptable salt, polymorph or solvate thereof, can induce cell death selectively in one or more cells affected by a cell proliferative disorder. Preferably, administering to a subject in need thereof a compound of the present invention, or a pharmaceutically acceptable salt, polymorph or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al, Current Protocols in Molecular Biology, John Wiley and Sons, Inc. (2005); Sambrook et al, Molecular Cloning, A Laboratory Manual (3rd edition), Cold Spring Harbor Press, Cold Spring Harbor, N.Y. (2000); Coligan et al, Current Protocols in Immunology, John Wiley & Sons, N.Y.; Enna et al, Current Protocols in Pharmacology, John Wiley & Sons, N.Y.; Fingl et al, The Pharmacological Basis of Therapeutics (1975), Remington's Pharmaceutical Sciences, Mack Publishing Co., Easton, Pa., $18^{th}$ edition (1990). These texts can, of course, also be referred to in making or using an aspect of the invention.

Dosing Regimen

An exemplary treatment regime entails administration once daily, twice daily, three times daily, every second day, twice per week, once per week. The composition of the invention is usually administered on multiple occasions. Intervals between single dosages can be, for example, less than a day, daily, every second day, twice per week, or weekly. The composition of the invention may be given as a continuous uninterrupted treatment. In an exemplary treatment regimen the compound of formula (I) or formula (Ia) according to the invention can be administered from 0.1-1500 mg per day.

As used herein, the term "therapeutically effective amount" refers to an amount that produces a desired effect (e.g., a desired biological, clinical, or pharmacological effect) in a subject or population to which it is administered. In some embodiments, the term refers to an amount statistically likely to achieve the desired effect when administered to a subject in accordance with a particular dosing regimen (e.g., a therapeutic dosing regimen). In some embodiments, the term refers to an amount sufficient to produce the effect in at least a significant percentage (e.g., at least about 25%, about 30%, about 40%, about 50%, about 60%, about 70%, about 80%, about 90%, about 95%, or more) of a population that is suffering from and/or susceptible to a disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be an amount that provides a particular desired response in a significant number of subjects when administered to patients in need of such treatment, e.g., in at least about 25%, about 30%, about 40%, about 50%, about 60%, about 70%, about 80%, about 90%, about 95%, or more patients within a treated patient population. In some embodiments, reference to a therapeutically effective amount may be a reference to an amount sufficient to induce a desired effect as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

In some embodiments, a compound or pharmaceutical composition for use in accordance with the present disclosure is formulated, dosed, and/or administered in a therapeutically effective amount using pharmaceutical compositions and dosing regimens that are consistent with good medical practice and appropriate for the relevant agent(s) and subject(s). In principle, compounds and pharmaceutical compositions can be administered by any appropriate method known in the art, including, without limitation, oral, mucosal, by-inhalation, topical, buccal, nasal, rectal, or parenteral (e.g. intravenous, infusion, intratumoral, intranodal, subcutaneous, intraperitoneal, intramuscular, intradermal, transdermal, or other kinds of administration involving physical breaching of a tissue of a subject and administration of the therapeutic composition through the breach in the tissue). In some embodiments, the compound or pharmaceutical composition is administered directly to the tumor (e.g., by intratumoral injection).

In some embodiments, a dosing regimen for a particular active agent may involve intermittent or continuous (e.g., by perfusion or other slow release system) administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto) the site of delivery of the agent, the nature of the agent (e.g. an antibody or other polypeptide-based compound), the mode and/or route of administration of the agent, the presence or absence of combination therapy, and other factors known to medical practitioners. For example, in the treatment of cancer, relevant features of the indication being treated may include, for example, one or more of cancer type, stage, location.

In some embodiments, one or more features of a particular pharmaceutical composition and/or of a utilized dosing regimen may be modified over time (e.g., increasing or decreasing the amount of active agent in any individual dose, increasing or decreasing time intervals between doses), for example in order to optimize a desired therapeutic effect or response (e.g., inhibition or modulation of a p300 gene or gene product).

In general, type, amount, and frequency of dosing of compounds or pharmaceutical compositions in accordance with the present invention are governed by safety and efficacy requirements that apply when one or more relevant agent(s) is/are administered to a mammal, preferably a human. In general, such features of dosing are selected to provide a particular, and typically detectable, therapeutic response as compared to what is observed absent therapy.

In some embodiments, a "therapeutically effective amount" or "therapeutically effective dose" is an amount of a compound or pharmaceutical composition of the disclosure, or a combination of two or more compounds or pharmaceutical compositions of the disclosure, or a combination of a compound or pharmaceutical composition of the disclosure with one or more additional therapeutic agent(s), which inhibits, totally or partially, the progression of the condition or alleviates, at least partially, one or more symptoms of the condition. In some embodiments, a therapeutically effective amount can be an amount which is prophylactically effective. In some embodiments, an amount which is therapeutically effective may depend upon a patient's size and/or gender, the condition to be treated, severity of the condition and/or the result sought. In some embodiments, a therapeutically effective amount refers to that amount that results in amelioration of at least one symptom in a patient. In some embodiments, for a given patient, a therapeutically effective amount may be determined by methods known to those of skill in the art.

In some embodiments, toxicity and/or therapeutic efficacy of a compound or pharmaceutical composition of the disclosure can be determined by standard pharmaceutical procedures in cell cultures or experimental animals, e.g., for determining the maximum tolerated dose (MTD) and the $ED_{50}$ (effective dose for 50% maximal response). Typically, the dose ratio between toxic and therapeutic effects is the therapeutic index; in some embodiments, this ratio can be expressed as the ratio between MTD and $ED_{50}$. Data obtained from such cell culture assays and animal studies can be used in formulating a range of dosage for use in humans.

In some embodiments, dosage may be guided by monitoring the effect of a compound or pharmaceutical composition of the disclosure on one or more pharmacodynamic markers of p300 function in diseased or surrogate tissue. For example, cell culture or animal experiments can be used to determine the relationship between doses required for changes in pharmacodynamic markers such as p300 downstream target genes or p53 acetylation and doses required for therapeutic efficacy can be determined in cell culture or animal experiments or early stage clinical trials. In some embodiments, dosage of a compound or pharmaceutical composition of the disclosure lies preferably within a range of circulating concentrations that include the $ED_{50}$ with little or no toxicity. In some embodiments, dosage may vary within such a range, for example depending upon the dosage form employed and/or the route of administration utilized. The exact formulation, route of administration and dosage can be chosen by the individual physician in view of the patient's condition. In the treatment of crises or severe conditions, administration of a dosage approaching the MTD may be required to obtain a rapid response.

In some embodiments, dosage amount and/or interval may be adjusted individually, for example to provide plasma levels of an active moiety which are sufficient to maintain, for example a desired effect, or a minimal effective concentration (MEC) for a period of time required to achieve therapeutic efficacy. In some embodiments, MEC for a particular compound or pharmaceutical composition of the disclosure can be estimated, for example, from in vitro data and/or animal experiments. Dosages necessary to achieve the MEC will depend on individual characteristics and route of administration. In some embodiments, high pressure liquid chromatography (HPLC) assays or bioassays can be used to determine plasma concentrations.

In some embodiments, dosage intervals can be determined using the MEC value. In certain embodiments, a compound or pharmaceutical composition of the disclosure should be administered using a regimen which maintains plasma levels above the MEC for 10-90% of the time, preferably between 30-90% and most preferably between 50-90% until the desired amelioration of a symptom is achieved. In other embodiments, different MEC plasma levels will be maintained for differing amounts of time. In cases of local administration or selective uptake, the effective local concentration of the drug may not be related to plasma concentration.

One of skill in the art can select from a variety of administration regimens and will understand that an effective amount of a particular a compound or pharmaceutical composition of the disclosure may be dependent on the subject being treated, on the subject's weight, the severity of the affliction, the manner of administration and/or the judgment of the prescribing physician.

Combination Therapy

In some embodiments, compounds or pharmaceutical compositions of the disclosure can be administered to a subject in need thereof as a cancer monotherapy. Alternatively, or in addition, compounds or pharmaceutical compositions of the disclosure can be administered to a subject in need thereof in combination with at least one additional cancer therapy.

In some embodiments, the at least one additional cancer therapy comprises a standard of care for the cancer of the subject. As used herein, "standard of care" refers to a treatment of a particular cancer that is accepted by persons of skill in the art as the generally accepted treatment for that indication, and whose practice is common amongst medical professionals. For example, standard of care for primary tumors that can be surgically resected without undue risk to the subject comprises surgical removal of the tumor. The person of ordinary skill in the art will readily understand what is a "standard of care" for a particular cancer indication.

In some embodiments, the at least one additional cancer therapy comprises surgical resection of the cancer, radiation therapy, or a combination thereof.

In some embodiments, compounds or pharmaceutical compositions of the disclosure can be used in combination with another therapeutic agent to treat cancer in the subject in a combinational therapy. In some embodiments, the combinational therapy is in addition to a standard of care therapies, surgical resection and/or radiation therapy.

In some embodiments, compounds or pharmaceutical compositions of the disclosure can optionally contain, and/or be administered in combination with, one or more additional therapeutic agents, such as a cancer therapeutic agent, e.g., a chemotherapeutic agent or a biological agent.

An additional agent can be, for example, a therapeutic agent that is e.g., an anti-cancer agent, or an agent that ameliorates a symptom associated with the disease or condition being treated. The additional agent also can be an agent that imparts a beneficial attribute to the therapeutic composition (e.g., an agent that affects the viscosity of the composition). For example, in some embodiments, compounds or pharmaceutical compositions of the disclosure are administered to a subject who has received, is receiving, and/or will receive therapy with another therapeutic agent or modality (e.g., with a chemotherapeutic agent, surgery, radiation, or a combination thereof).

Some embodiments of combination therapy modalities provided by the present disclosure provide, for example, administration of compounds or pharmaceutical compositions of the disclosure and additional cancer therapeutic agent(s) in a single pharmaceutical formulation.

Some embodiments provide administration of compounds or pharmaceutical compositions of the disclosure and administration of additional cancer therapeutic agent(s) in separate pharmaceutical formulations. In some embodiments, the compounds or pharmaceutical compositions of the disclosure and the additional cancer therapeutic agent are administered simultaneously. Simultaneous administration can be by the same modality (e.g., both by oral administration), or by different modalities (e.g., one oral, one injected). In some embodiments, the compounds or pharmaceutical compositions of the disclosure and the additional cancer therapeutic agent are administered in temporal proximity. For example, the compounds or pharmaceutical compositions of the disclosure and the additional cancer therapeutic agent are administered within 1 minute, 2 minutes, 5 minutes, 10 minutes, 15 minutes, 30 minutes, 1 hour, 2 hours, 3 hours, 4 hours, 5 hours, 6 hours, 12 hours or 24 hours of each other. In some embodiments, the compounds or pharmaceutical compositions of the disclosure and the additional cancer therapeutic agent are administered in sequence. For example, the compounds or pharmaceutical compositions of the disclosure and the additional cancer therapeutic agent can be administered in an alternating sequence.

In some embodiments, the at least one additional cancer therapeutic agent comprises a chemotherapeutic agent.

Examples of chemotherapeutic agents that can be used in combination with compound or pharmaceutical composition described herein include platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteasome inhibitors (e.g., bortezomib), epipodophyllotoxins (e.g., etoposide and teniposide), DNA synthesis inhibitors (e.g., hydroxyurea), vinca alkaloids (e.g., vincristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., enzalutamide, tamoxifen, raloxifene, leuprolide, bicalutamide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

In some embodiments, the additional agent affects (e.g., inhibits) histone modifications, such as histone acetylation or histone methylation. In certain embodiments, an additional anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, LPAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®); biologies (such as Alpha Interferon, *Bacillus* Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Velcade® and Zevalin™); small molecules (such as Tykerb®); corticosteroids (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

Examples of biological agents that can be used in combination with the compositions and methods described herein include monoclonal antibodies (e.g., rituximab, cetuximab, obinutuzumab, ofatumumab, ibritumomab, brentuximab, bevacizumab, panitumumab, pembrolizumab, tositumomab, trastuzumab, alemtuzumab, gemtuzumab ozogamicin, bevacizumab, catumaxomab, denosumab, obinutuzumab, ofatumumab, ramucirumab, pertuzumab, ipilimumab, nivolumab, nimotuzumab, lambrolizumab, pidilizumab, siltuximab, tremelimumab, or others known in the art), enzymes (e.g., L-asparaginase), cytokines (e.g., interferons and interleukins), growth factors (e.g., colony stimulating factors and erythropoietin) or inhibitors thereof, cancer vaccines, gene therapy vectors, or any combination thereof. In some embodiments, the growth factor inhibitor comprises an inhibitor of vascular endothelial growth factor A (VEGFA). In some embodiments, the inhibitor of VEGFA comprises Avastin® (bevacizumab).

In some embodiments, biological agents comprise adoptive cell therapies. For example, chimeric antigen receptor T cell (CAR-T) therapies. In some embodiments, the adoptive cell therapy is autologous. In some embodiments, the adoptive cell therapy is allogeneic.

In some embodiments, the at least one additional cancer therapeutic agent comprises an immune checkpoint inhibitor. Immune checkpoint inhibitors target immune checkpoints, which regulate the immune system, and under certain circumstances, can prevent the immune system from targeting tumors. In some embodiments, the immune checkpoint comprises a PD-1/PD-L1 immune checkpoint. In some embodiments, the immune checkpoint comprises a CLTA-4 immune checkpoint. In some embodiments, the immune checkpoint inhibitor is an antibody or a small molecule. Exemplary PD-1 inhibitors include, but are not limited, nivolumab and pembrolizumab. Exemplary PD-L1 inhibitors include, but are not limited to, atezolizumab, avelumab and durvalumab. Exemplary CLTA-4 inhibitors include, but are not limited to, ipilimumab.

The additional agents that can be used in combination with compositions and methods of the disclosure as set forth above are for illustrative purposes and not intended to be limiting. The combinations embraced by this disclosure, include, without limitation, one or more compounds or pharmaceutical compositions as provided herein and at least one additional agent selected from the categories or lists above or otherwise provided herein. The compounds and pharmaceutical compositions of the disclosure can also be used in combination with one or with more than one additional agent, e.g., with two, three, four, five, or six, or more, additional agents.

In some embodiments, treatment methods described herein are performed on subjects for which other treatments of the medical condition have failed or have had less success in treatment through other means, e.g., in subjects having a cancer refractory to standard-of-care treatment. Additionally, the treatment methods described herein can be performed in conjunction with one or more additional treatments of the medical condition, e.g., in addition to or in combination with standard-of-care treatment. For instance, the method can comprise administering a cancer regimen, e.g., nonmyeloablative chemotherapy, surgery, hormone therapy, and/or radiation, prior to, substantially simultaneously with, in temporal proximity to, in sequence with or after the administration of a compound or pharmaceutical composition described herein.

Additional Methods

The invention encompasses methods comprising providing at least one compound, measuring the activity of the compound and determining if the activity of the compound is above or below a predetermined level.

Methods of measuring the activity of a compound will be readily apparent to one of ordinary skill in the art. Exemplary methods include measuring growth-inhibitory concentration (GI50) in vitro in a cell proliferation assay or a colony survival assay. Cell proliferation can be measured using any technique known in the art. For example, cell proliferation can be measured by measuring colony formation using stains such as Crystal Violet/DBPS and measuring 600 nm absorbance. Alternatively, or in addition, cells can be treated with a dye that permeabilizes the cells and reacts with certain enzymes to provide a measure of metabolic activity (for example, MTT or WST-1). Proliferation can be measured using fluorescence dyes such as CyQUANT (ThermoFisher Scientific). Alternatively, or in addition, cell proliferation can be measured by examining one or more proliferation markers, such as BrdU incorporation or proliferating cell nuclear antigen (PCNA) expression.

Alternatively, or in addition, the method of measuring activity of a compound of the disclosure comprises measuring an effect of the compound on tumor growth in an animal. Exemplary animal cancer models include, but are not limited to, patient derived xenograft (PDX) cancer models, transgenic models and gene knock out or gene knock in models that modify one or more tumor suppressor or oncogenes and syngeneic models. In a PDX model, cancer cells derived from a patient or cell line isolated or derived from a cancer of interest are transplanted into an immune deficient animal. In some embodiments, the immune deficient animal is a severely compromised immune deficient (SCID) mouse, a NOD-SCID mouse, or a recombination-activity gene 2 (Rag2) knockout mouse, which prevents transplant rejection. In a syngeneic model, e.g. a syngeneic mouse model, tumor tissues from the same genetic background as the given immuno-competent mouse strain are transplanted into the mouse to induce tumor formation. Optionally, cancer cells can be transformed with one or more markers to facilitate analysis, for example, a Luciferase gene to mark PDX acute myeloid leukemia cells transplanted into an immune deficient mouse via bone marrow engraftment. In some embodiments, the animal model is an animal that has been genetically modified to contain mutations that lead to cancer, for example by knocking out one or more genes which suppress cancer formation, or introducing (knocking in) one or more mutations that cause cancer, optionally in a tissue specific manner using tissue specific drivers and recombination cassettes such as Cre-LOX. For example, mice that are engineered to be p53+/− can be used to study cancers as these animals spontaneously give rise to tumors in clones of cells that have lost the wild type p53 allele.

Alternatively, or in addition, the method of measuring activity comprises measuring a change in RNA expression of certain genes in tumor-derived cell cultures, blood, diseased tissues or diseased organs of treated individuals. The gene or genes can be, for example, genes that are regulated by p300. p300 regulation of target genes can be either direct (e.g. transcriptional regulation, through p300 activity at the cognate gene promoter), or indirect (e.g., through p300 regulation of upstream transcription factors involved in regulation of a target gene). Exemplary p300 target genes include, but are not limited to, androgen response genes such as kallikrein related peptidase 3/prostate-specific antigen (KLK3/PSA), transmembrane serine protease 2 (TMPRSS2) and solute carrier family 45 member 3 (SLC45A3), VEGF and P53.

Alternatively, or in addition, the method of measuring activity comprises measuring the change in RNA expression of p300 target genes in vitro in cell culture assays. Methods of measuring RNA expression of p300 target genes will be readily apparent to one of ordinary skill in the art. For example, levels of RNA expression can be measured using high throughput sequencing methods, microarrays, reverse transcription polymerase chain reaction (RT-PCR), quantitative RT-PCR (RT-qPCR) and droplet digital PCR (ddPCR) as well as any other method known in the art. In some embodiments, the method of measuring activity comprises measuring the change in RNA expression of Androgen Receptor—responsive genes in vitro in cell culture assays (for example, KLK3, TMPRSS2 and/or SLC45A3). In some embodiments, the method of measuring activity comprises measuring the amount of Tumor-specific Protein 53 ($p5^3$) in vitro in cell culture assays.

In some embodiments, the method of measuring activity comprises measuring the amount of acetylated p53 lysine 382 (p53K382Ac) in vitro in cell culture assays. The amount of acetylated p53 lysine 382 can be measured, for example, by using a p53K382Ac specific antibody and Western Blot.

In some embodiments, the method of measuring activity comprises measuring the amount of Prostate-Specific Antigen protein in serum of treated individuals. The amount of PSA can be measured, for example, with a PSA specific antibody and by Western Blot or ELISA.

In some embodiments, the method of measuring activity comprises measuring the amount of Vascular Endothelial Growth Factor (VEGF) protein in serum, diseased tissues or diseased organs of treated individuals. The amount of VEGF protein can be measured, for example, with a VEGF specific antibody and by Western Blot or ELISA. Alternatively, or in addition, the method of measuring activity comprises measuring the amount of VEGF RNA in serum, diseased tissues or diseased organs of treated individuals.

Kits and Article of Manufacture

The disclosure provides kits comprising the compounds and pharmaceutical compositions of the disclosure and instructions for use in treating a cancer in a subject in need thereof.

In some embodiments, the kits further comprise at least one additional cancer therapeutic agent. Any additional cancer therapeutic described herein is envisaged as being within the scope of a kit of the disclosure. In some embodiments, the compounds or pharmaceutical compositions of the disclosure and the at least one additional cancer therapeutic are different compositions. In some embodiments, the compounds or pharmaceutical compositions of the disclosure and the at least one additional cancer therapeutic formulated in the same composition.

In some embodiments, the at least one additional cancer therapeutic agent comprises a chemotherapeutic agent. Exemplary chemotherapeutic agents include, but are not limited to a platinum compound, an alkylating agent, an antitumor antibiotic, a taxane, an antimetabolite, a nucleoside analog, a topoisomerase inhibitor, a hypomethylating agent, a proteasome inhibitor, an epipodophyllotoxin, a DNA synthesis inhibitor, a vinca alkaloid, a tyrosine kinase inhibitor, a nitrosourea, hexamethylmelamine, mitotane, an angiogenesis inhibitor, a steroid, a hormonal agent, an aromatase inhibitor, arsenic trioxide, tretinoin, a nonselective cyclooxygenase inhibitor, a selective cyclooxygenase-2 (COX-2) inhibitors, or a combination thereof.

In some embodiments, the additional cancer therapeutic agent comprises a biological agent. Exemplary biological agents include, but are not limited to, an antibody therapy, an adoptive cell therapy, an enzyme, a cytokine, a growth factor or inhibitor thereof, a gene therapy a cancer vaccine or a combination thereof.

In some embodiments, the additional cancer therapeutic agent comprises an immune checkpoint inhibitor. The immune checkpoint inhibitor can be a small molecule, or an antibody. Exemplary antibodies include, but are not limited to, nivolumab, pembrolizumab, atezolizumab, avelumab, durvalumab or ipilimumab.

Kits comprising the compounds and pharmaceutical compositions of the disclosure are for the use in treating a cancer in a subject. Exemplary cancers include liquid tumors such as leukemias and lymphomas, and solid tumors such as carcinomas, sarcomas, myelomas, germ cell tumors, carcinoid tumors, neuroendocrine tumors or tumors of mixed type. Exemplary cancers include, but are not limited to prostate cancer, colon cancer, head-and-neck cancer, cervical cancer, brain or nervous system cancer, ovarian cancer, stomach or gastric cancer, kidney cancer, liver cancer, oesophageal cancer, pancreatic cancer, skin cancer and lung cancer.

Articles of manufacture include, but are not limited to labels, instructional pamphlets, vials and syringes.

Enumerated Embodiments

The invention may be defined by reference to the following enumerated, illustrative embodiments:
1. A compound of formula (Ia)

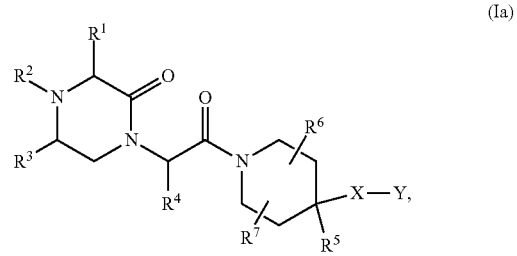

(Ia)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl, all optionally substituted by halogen, $OR^8$, $NR^8R^{11}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by cycloalkyl, aryl or heteroaryl, wherein the cycloalkyl, aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloakenyl, all optionally substituted by halogen, $OR^8$, $NR^8R^{11}$; $C_{1-3}$ alkyl substituted by $C(O)NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and wherein $R^6$ can form a ring with any part of X; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-9}$ cycloalkanediyl, $C_{4-6}$ cycloalkenediyl, —O—, $C_{1-3}$ alkanediyl-O—, —O—$C_{1-7}$ alkanediyl, —O—$C_{3-9}$ cycloalkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring or a polycyclic system with any part of $R^5$, $R^6$, or Y, wherein the ring optionally contains a carbonyl group;

Y is selected from H, $C(O)NR^{10}R^{12}$, $C(O)OR^{10}$, $R^{11}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

2. A compound of formula (I)

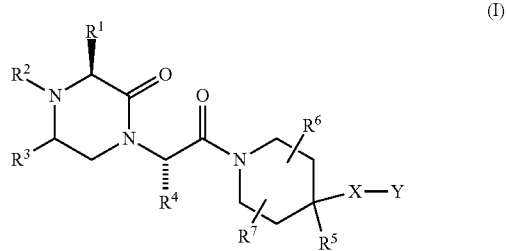

(I)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, it is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, or $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, all optionally substituted by halogen, $OR^8$, $NR^8R^{11}$; or $C_{1-3}$ alkyl substituted by $C(O)NR^8R^{11}$; $C_{1-3}$ alkyl substituted by aryl or heteroaryl, wherein the aryl or the heteroaryl is optionally substituted by halogen, $C_{1-4}$ alkyl or $C_{3-5}$ cycloalkyl; or is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group;

Y is selected from H, $C(O)NR^{10}R^{12}$, $C(O)OR^{10}$, $R^{11}NC(O)NR^{11}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; aryl, or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, or $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, or $C_{1-3}$ alkyl-$OR^8$.

3. The compound according to any one of the previous embodiments, wherein $R^1$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

4. The compound according to any one of the previous embodiments, wherein $R^1$ is selected from $C_{2-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

5. The compound according to any one of the previous embodiments, wherein $R^1$ is selected from $C_{3-7}$ alkyl, $C_{3-7}$ cycloalkyl, or $C_{1-3}$ alkyl substituted by aryl or heteroaryl.

6. The compound according to any one of the previous embodiments, wherein $R^2$ is selected from H, $C(O)R^{14}$, $C(O)OR^{15}$, $C_{1-7}$ alkyl, $C_{3-7}$ cycloalkyl, $C_{1-3}$ alkanediyl-O—$C_{1-3}$ alkanediyl-O—$C_{1-3}$ alkanediyl, $C_{1-5}$ alkyl-$OR^8$, $C_{1-5}$ alkyl-$NHCOR^{13}$, or $C_{1-3}$ alkyl substituted by aryl, wherein the aryl is optionally substituted by halogen, $C_{1-4}$ alkyl or $C_{3-5}$ cycloalkyl.

7. The compound according to any one of the previous embodiments, wherein $R^2$ is selected from H, $C(O)R^{14}$, wherein $R^{14}$ is $C_{1-7}$ alkyl; $C_{1-7}$ alkyl, $C_{3-7}$ cycloalkyl, $C_{1-5}$ alkyl-$OR^8$, $C_{1-5}$ alkyl-$NHCOR^{13}$, wherein $R^{13}$ is pentylamino-5-oxopentyl-7-thia-2,4-diazabicyclo[3.3.0]octan-3-one; or $C_{1-3}$ alkyl substituted by aryl, wherein the aryl is optionally substituted by halogen, $C_{1-4}$ alkyl or $C_{3-5}$ cycloalkyl.

8. The compound according to any one of the previous embodiments, wherein $R^3$ and $R^7$ are each independently selected from H, $C_{1-7}$ alkyl, $C_{2-7}$ alkenyl, $C_{2-7}$ alkynyl, $C_{3-7}$ cycloalkyl, or $C_{4-7}$ cycloalkenyl.

9. The compound according to any one of the previous embodiments, wherein $R^3$ and $R^7$ are H.

10. The compound according to any one of the previous embodiments, wherein $R^4$ is selected from $C_{1-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

11. The compound according to any one of the previous embodiments, wherein $R^4$ is selected from $C_{2-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

12. The compound according to any one of the previous embodiments, wherein $R^4$ is selected from $C_{3-7}$ alkyl, $C_{3-7}$ cycloalkyl, or $C_{1-3}$ alkyl substituted by aryl or heteroaryl.

13. The compound according to any one of the previous embodiments, wherein the compound is of any one of Formulae (IIa), (IIb), or (IIc):

(IIa)

(IIb)

(IIc)

or a pharmaceutically acceptable salt, hydrate, solvate or stereoisomer thereof, wherein $R^1$, $R^2$, $R^3$, $R^4$, $R^5$, $R^6$, $R^7$, X, and Y are as described herein.

14. The compound according to any one of the previous embodiments, wherein the compound is of any one of Formulae (IIIa), (IIIb), (IIIc), or (IIId):

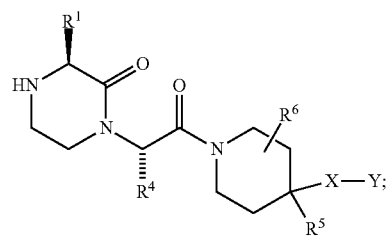
(IIIa)

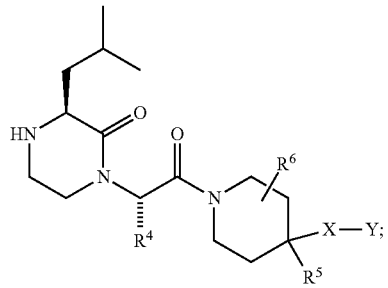
(IIIb)

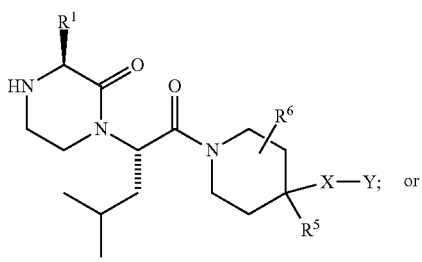
(IIIc)

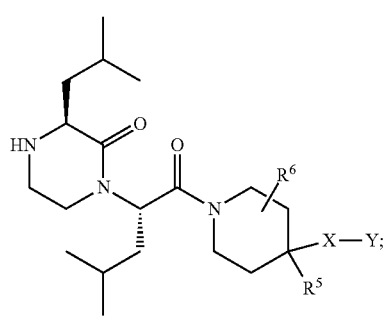
(IIId)

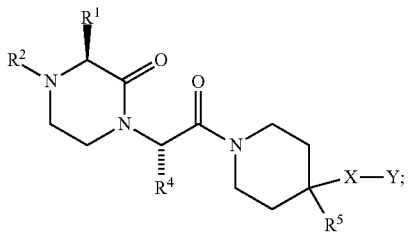
(IVa)

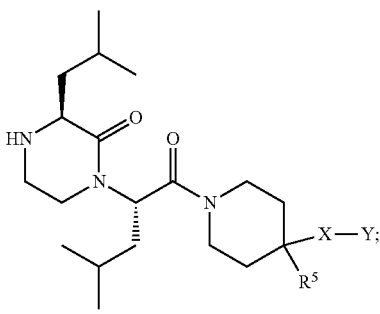
(IVb)

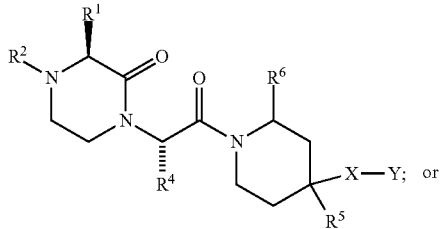
(IVc)

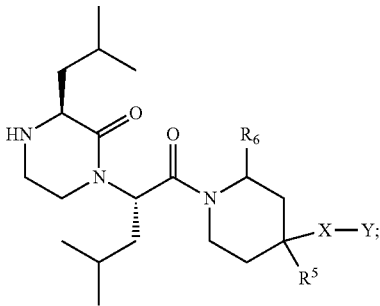
(IVd)

or a pharmaceutically acceptable salt, hydrate, solvate or stereoisomer thereof, wherein $R^1$, $R^4$, $R^5$, $R^6$, X, and Y are as described herein.

15. The compound according to any one of the previous embodiments, wherein $R^5$ is selected from H, $C_{1-7}$ alkyl, $OR^8$, or $SR^8$; and wherein $C_{1-7}$ alkyl, $OR^8$ or $SR^8$ of $R^5$ can form a ring with any part of X or Y, wherein the ring optionally contains a carbonyl group.

16. The compound according to any one of the previous embodiments, wherein $R^6$ is selected from H, $C_{1-7}$ alkyl, $C_{2-7}$ alkenyl, $C_{2-7}$ alkynyl, $C_{3-7}$ cycloalkyl, or $C_{4-7}$ cycloalkenyl; or is imidazolidinone.

17. The compound according to any one of the previous embodiments, wherein $R^6$ is H, $C_{1-7}$ alkyl, or imidazolidinone.

18. The compound according to any one of the previous embodiments, wherein the compound is of any one of Formulae (IVa), (IVb), (IVc) or (IVd):

or a pharmaceutically acceptable salt, hydrate, solvate or stereoisomer thereof, wherein $R^1$, $R^2$, $R^4$, $R^5$, $R^6$, X, and Y are as described herein.

19. The compound according to any one of the previous embodiments, wherein $R^8$ and $R^{11}$ are each independently selected from H, $C_{1-7}$ alkyl, $C_{2-7}$ alkenyl, or $C_{3-7}$ cycloalkyl.

20. The compound according to any one of the previous embodiments, wherein $R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, or $OR^8$.

21. The compound according to any one of the previous embodiments, wherein $R^{10}$ and $R^{12}$ are each independently selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by halogen or $OR^8$.

22. The compound according to any one of the previous embodiments, wherein $R^{14}$ is selected from $C_{1-7}$ alkyl, $C_{3-7}$ cycloalkyl, or $C_{1-3}$ alkyl substituted by aryl or heteroaryl, wherein the aryl or the heteroaryl is optionally substituted by halogen, $C_{1-4}$ alkyl or $C_{3-5}$ cycloalkyl.

23. The compound according to any one of the previous embodiments, wherein $R^{14}$ is selected from $C_{1-7}$ alkyl or $C_{3-7}$ cycloalkyl.

24. The compound according to any one of the previous embodiments, wherein $R^{14}$ is $C_{1-7}$ alkyl.

25. The compound according to any one of the previous embodiments, wherein each $R^{15}$ is independently selected from H, $C_{1-7}$ alkyl, or $C_{3-7}$ cycloalkyl.

26. The compound according to any one of the previous embodiments, wherein each $R^{15}$ is independently selected from H, $C_{1-7}$ alkyl.

27. The compound according to any one of the previous embodiments, wherein X is selected from a bond, $C_{1-7}$ alkanediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, or —S—$C_{1-7}$ alkanediyl; and wherein X can form a ring with any part of $R^5$ or Y, wherein the ring optionally contains a carbonyl group.

28. The compound according to any one of the previous embodiments, wherein X is selected from a bond and $C_{1-7}$ alkanediyl, and wherein $C_{1-7}$ alkanediyl of X can form a ring with any part of Y.

29. The compound according to any one of the previous embodiments, wherein X is selected from a bond, —O—$C_{1-7}$ alkanediyl, —S—$C_{1-7}$ alkanediyl and $C_{1-7}$ alkanediyl, and wherein —O—$C_{1-7}$ alkanediyl, —S—$C_{1-7}$ alkanediyl or $C_{1-7}$ alkanediyl of X can form a ring with any part of $R^5$, wherein the ring optionally contains a carbonyl group.

30. The compound according to any one of the previous embodiments, wherein Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein when Y is $C(O)NR^1R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

31. The compound according to any one of the previous embodiments, wherein Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or aryl, heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

32. The compound according to any one of the previous embodiments, wherein Y is selected from $C(O)NR^{10}R^{12}$, $NR^{10}R^{12}$, $C_{3-7}$-cycloalkyl optionally containing a heteroatom in the ring selected from O and N wherein if the heteroatom is N it is optionally substituted by $R^8$; S-aryl, O-aryl, S-heteroaryl, O-heteroaryl wherein the S-aryl, O-aryl, S-heteroaryl, O-heteroaryl are optionally substituted by one or more $R^9$ or $R^{14}$; or heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

33. The compound according to any one of the previous embodiments, wherein the compound is of any one of Formulae (Va), (Vb), (Vc), or (Vd):

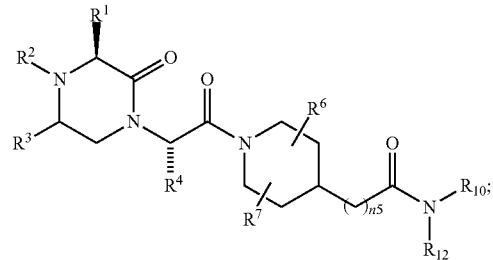

(Va)

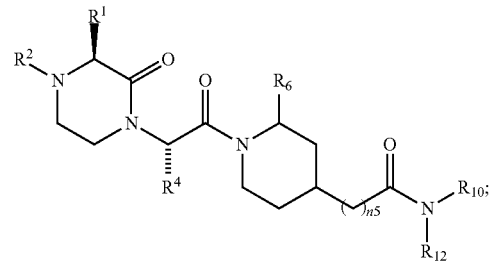

(Vb)

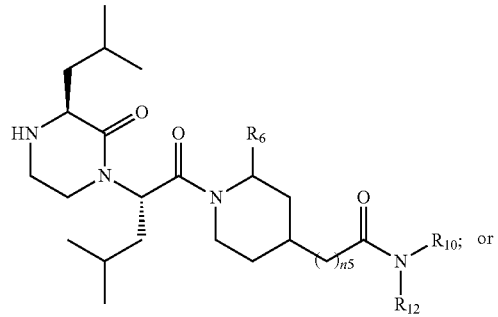

(Vc)

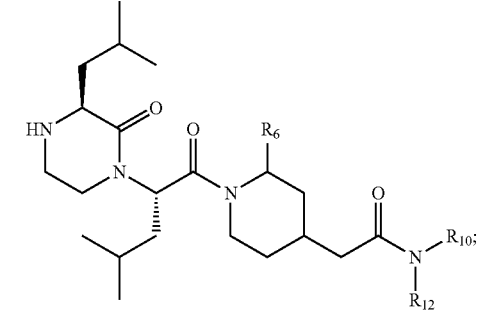

(Vd)

or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

34. The compound according to any one of the previous embodiments, wherein the compound is of any one of Formulae (VIa), (VIb), (VIc), or (VId):

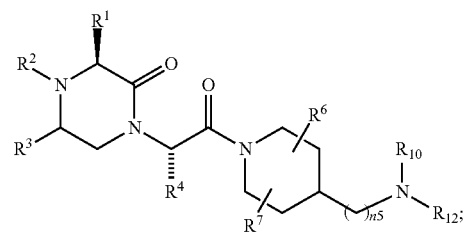
(VIa)

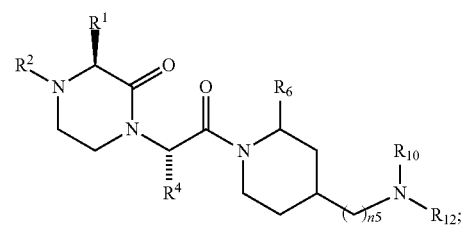
(VIb)

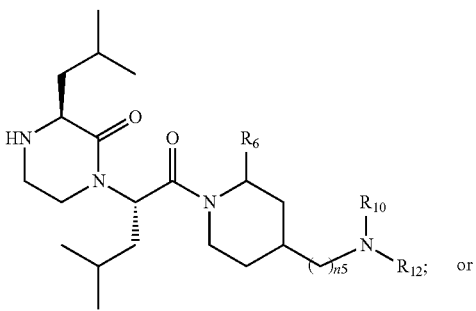
(VIc)

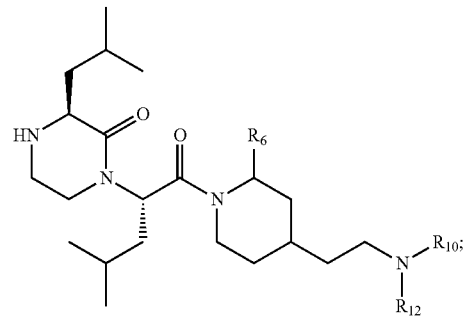
(VId)

or a pharmaceutically acceptable salt, hydrate, solvate or stereoisomer thereof, wherein n5 is 0, 1, 2, 3, 4, 5, 6, or 7, preferably 1, 2, or 3, and $R^1$, $R^2$, $R^3$, $R^4$, $R^6$, $R^7$, $R^{10}$ and $R^{12}$ are as described herein.

35. The compound according to any one of the previous embodiments, wherein Y is selected from $NR^{10}R^{12}$ and $C_{3-7}$-cycloalkyl optionally containing a heteroatom in the ring selected from O and N wherein if the heteroatom is N it is optionally substituted by $R^8$; and wherein Y can form a ring with any part of X or $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

36. The compound according to any one of the previous embodiments, wherein $R^5$ is selected from H and $C_{1-7}$ alkyl; wherein $C_{1-7}$ alkyl of $R^5$ can form a ring with any part of Y; wherein X is selected from a bond and $C_{1-7}$ alkanediyl, and wherein $C_{1-7}$ alkanediyl of X can form a ring with any part of Y;

wherein Y is selected from $NR^{10}R^{12}$ and $C_{3-7}$-cycloalkyl optionally containing a heteroatom in the ring wherein the heteroatom is N and is optionally substituted by $R^8$ wherein $R^8$ is $C_{1-7}$ alkyl;

wherein Y can form a ring with any part of $C_{1-7}$ alkanediyl of X or with any part of $C_{1-7}$ alkyl of $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$; and wherein $R^{10}$ and $R^{12}$ are each independently selected from H, $C_{1-7}$ alkyl, $C_{3-7}$ cycloalkyl, $C_{1-3}$ alkyl-aryl, all these groups optionally substituted by halogen.

37. The compound according to any one of the previous embodiments, wherein $R^5$ is selected from $C_{1-7}$ alkyl, $OR^8$, or $SR^8$; wherein $C_{1-7}$ alkyl, $OR^8$ or $SR^8$ of $R^5$ can form a ring with any part of X;

wherein X is selected from $-O-C_{1-7}$ alkanediyl, $-S-C_{1-7}$ alkanediyl, or $C_{1-7}$ alkanediyl, and wherein $-O-C_{1-7}$ alkanediyl, $-S-C_{1-7}$ alkanediyl or $C_{1-7}$ alkanediyl of X can form a ring with any part of $R^5$; and wherein Y is $NR^{10}R^{12}$ wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

38. The compound according to any one of the previous embodiments, wherein $R^5$ is $OR^8$, wherein $R^8$ of $OR^8$ is $C_{1-7}$ alkyl, and wherein $OR^8$ of $R^5$ can form a ring with any part of X;

wherein X is $-O-C_{1-7}$ alkanediyl and wherein $-O-C_{1-7}$ alkanediyl of X can form a ring with any part of $R^5$; and wherein Y is $NR^{10}R^{12}$ wherein $R^{10}$ and $R^{12}$ can form a ring wherein the ring contains the N of $NR^{10}R^{12}$ and four or five carbon atoms.

39. The compound according to any one of the previous embodiments, wherein the compound is of any one of Formulae (VIIa), (VIIb), (VIIc), (VIId), (VIIe), or (VIIf):

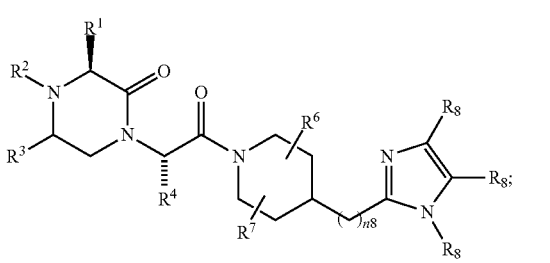
(VIIa)

-continued (VIIb)
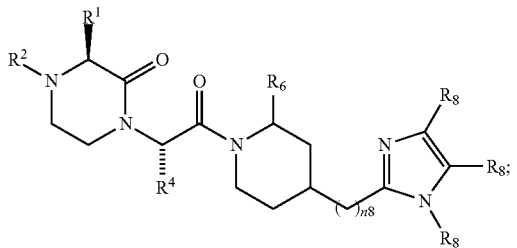

(VIIc)
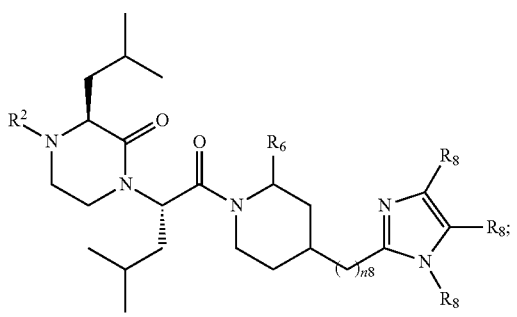

(VIId)
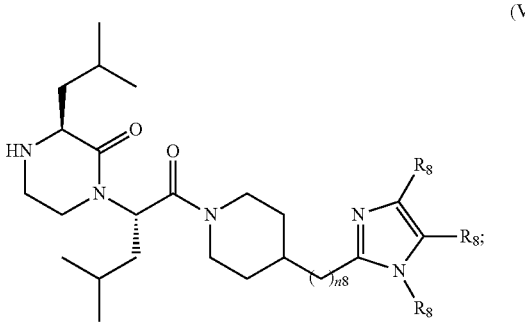

(VIIe)
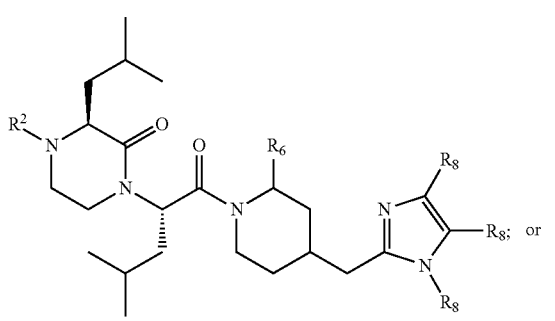

(VIIf)
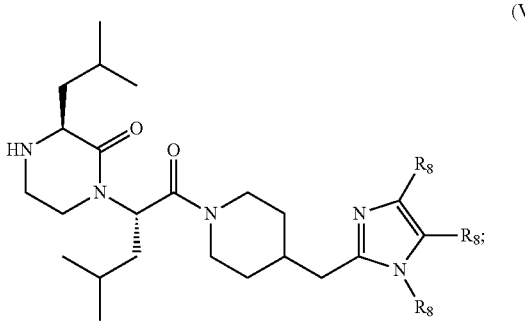

or a pharmaceutically acceptable salt, hydrate, solvate or stereoisomer thereof, wherein n8 is 0, 1, 2, 3, 4, 5, 6, or 7, preferably 1, 2, or 3, and $R^1$, $R^2$, $R^3$, $R^4$, $R^6$, $R^7$, and $R^8$ are as described herein.

40. The compound according to any one of the previous embodiments,
wherein Y is aryl or heteroaryl, wherein the aryl or heteroaryl is optionally substituted by one or more of $R^8$; or S-heteroaryl, wherein the S-heteroaryl is optionally substituted by one or more $R^{14}$ 41. The compound according to any one of the previous embodiments,
wherein $R^5$ is selected from H and $C_{1-7}$ alkyl;
wherein X is selected from a bond and $C_{1-7}$ alkanediyl;
wherein Y is heteroaryl, wherein the heteroaryl is optionally substituted by one or more of $R^8$; or S-heteroaryl, wherein the S-heteroaryl is optionally substituted by one or more $R^{14}$.

42. The compound according to any one of the previous embodiments,
wherein Y is $C(O)NR^{10}R^{12}$; and wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$.

43. The compound according to any one of the previous embodiments, wherein $R^5$ is selected from H and $C_{1-7}$ alkyl;
wherein X is selected from a bond and $C_{1-7}$ alkanediyl;
wherein Y is $C(O)NR^{10}R^{12}$; and wherein $R^{10}$ and $R^{12}$ can form a ring wherein the ring contains the N of $NR^{10}R^{12}$ and optionally one further heteroatom selected from O and N, wherein if the one further heteroatom is N, it is optionally substituted by $R^8$; and wherein $R^{10}$ and $R^{12}$ are each independently selected from H, $C_{1-7}$ alkyl, $C_{2-7}$ alkenyl, $C_{3-7}$ cycloalkyl, $C_{1-3}$ alkyl-aryl.

44. The compound according to any one of the previous embodiments, wherein Y is selected from S-aryl, O-aryl, S-heteroaryl, O-heteroaryl, wherein the S-aryl, O-aryl, S-heteroaryl, O-heteroaryl are optionally substituted by one or more $R^9$ or $R^{14}$ 45. The compound according to any one of the previous embodiments,
wherein $R^5$ is selected from H and $C_{1-7}$ alkyl;
wherein X is selected from a bond and $C_{1-7}$ alkanediyl,
wherein Y is selected from O-aryl and O-heteroaryl, wherein the O-aryl or O-heteroaryl is optionally substituted by one or more $R^9$;
wherein $R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$.

46. The compound according to any one of the previous embodiments, wherein Y is $C(O)OR^{10}$.

47. The compound according to any one of the previous embodiments, wherein
wherein $R^5$ is selected from H and $C_{1-7}$ alkyl;
wherein X is selected from a bond and $C_{1-7}$ alkanediyl;
wherein Y is $C(O)OR^{10}$; and
wherein $R^{10}$ is selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, or $C_{1-3}$ alkyl-heteroaryl, all these groups optionally substituted by $OR^8$.

48. The compound according to any one of the previous embodiments, wherein Y is H.

49. The compound according to any one of the previous embodiments, wherein wherein $R^5$ is $C_{1-7}$ alkyl;

wherein X is a bond; and wherein Y is H.

50. The compound according to any one of the previous embodiments, wherein Y is CN.

51. The compound according to any one of the previous embodiments, wherein $R^5$ is H;

X is $C_{1-7}$ alkanediyl; and

Y is CN.

52. The compound according to any one of the previous embodiments, wherein the compound is of any one of Formulae (VIIIa), (VIIIb), (VIIIc), (VIIId), (VIIIe), (VIIIf), (VIIIg), (VIIIh), (VIIIi), (VIIIj), (VIIIk), (VIIIl):

(VIIIa)
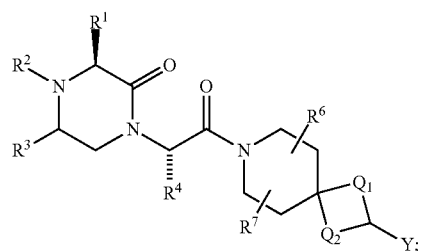

(VIIIb)
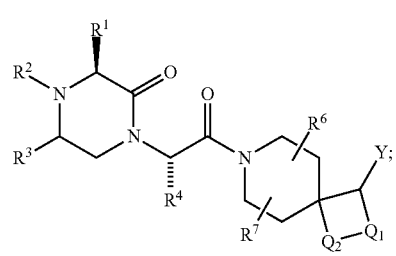

(VIIIc)
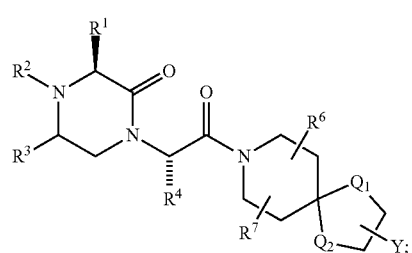

(VIIId)
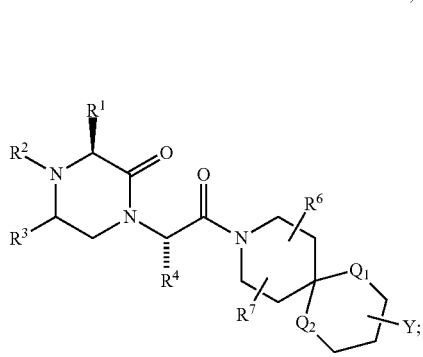

-continued (VIIIe)
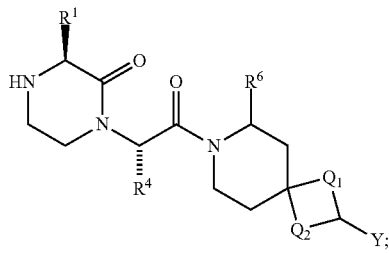

(VIIIf)
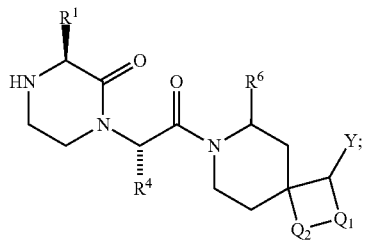

(VIIIg)
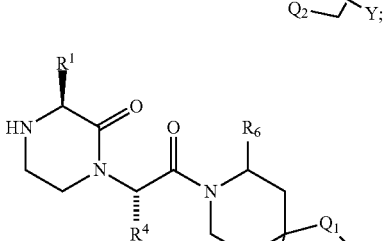

(VIIIh)
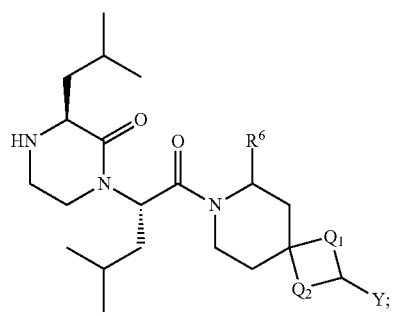

(VIIIi)
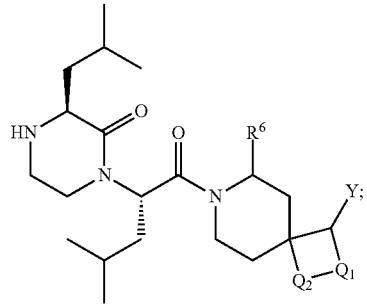

(VIIIj)

(VIIIk)

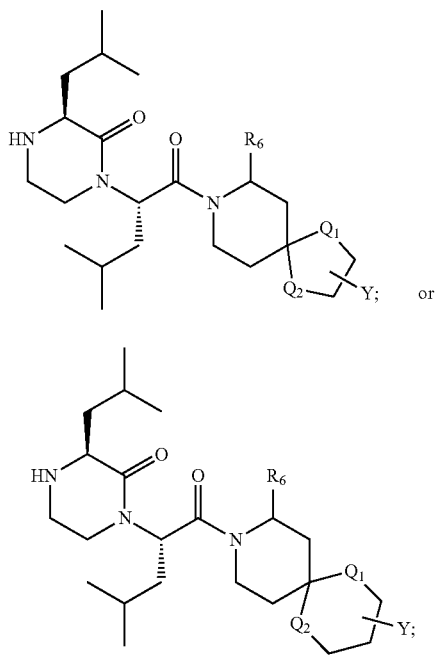

or (VIIIl)

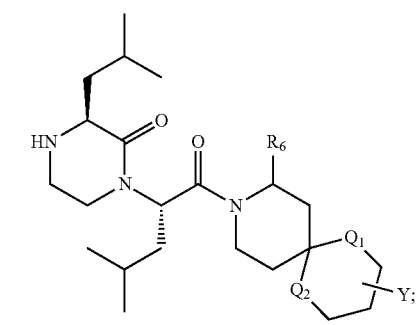

or a pharmaceutically acceptable salt, hydrate, solvate, or stereoisomer thereof, wherein $Q_1$ and $Q_2$ are each independently O, S, $NR^8$, or $CR^8$, and $R^1$, $R^2$, $R^3$, $R^4$, $R^6$, $R^7$, $R^8$, and Y are as described herein.

53. The compound according to any one of the previous embodiments, wherein the compound is of any one of Formulae (IXa), (IXb), (IXc), or (IXd):

(IXa)

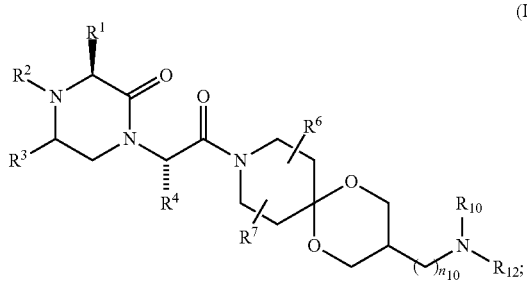

(IXb)

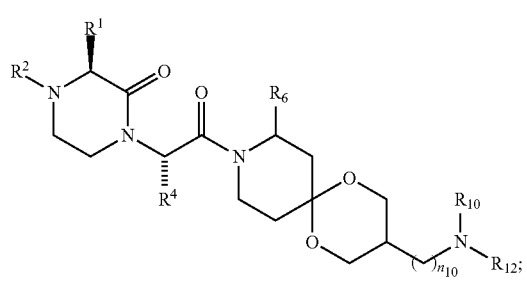

(IXc)

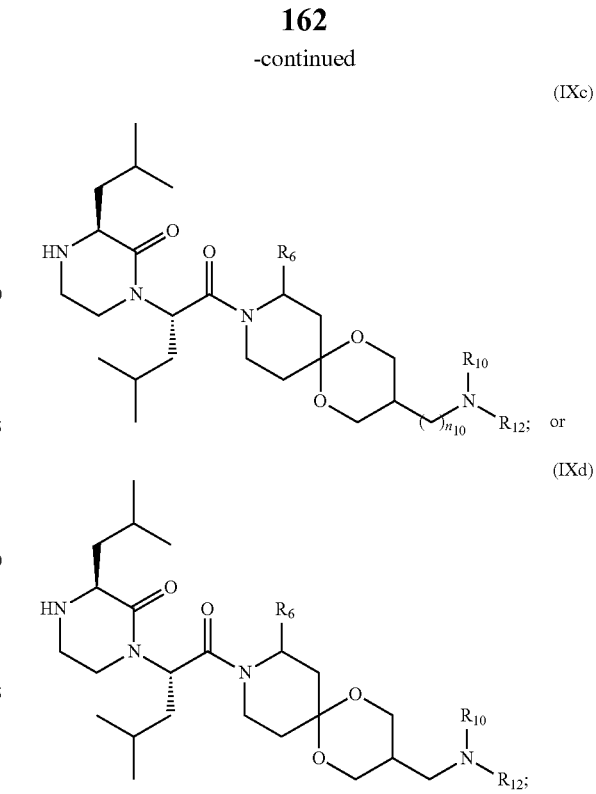

or (IXd)

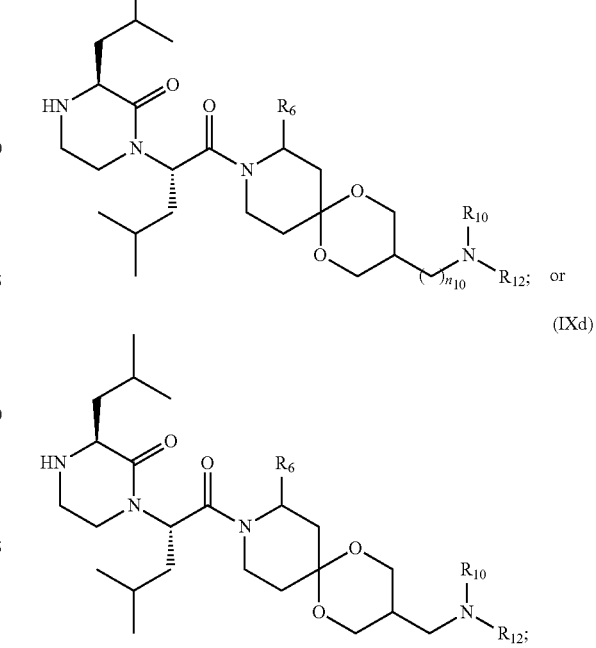

or a pharmaceutically acceptable salt, hydrate, solvate, or stereoisomer thereof, wherein n10 is 0, 1, 2, 3, 4, 5, 6, or 7, preferably 1, 2, or 3, and $R^1$, $R^2$, $R^3$, $R^4$, $R^6$, $R^7$, $R^{10}$, $R^{12}$ and Y are as described herein.

54. A compound selected from the group consisting of:

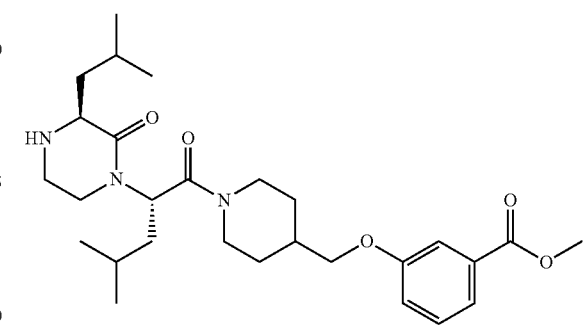

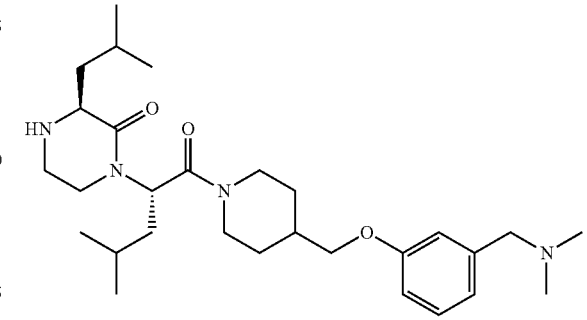

163
-continued
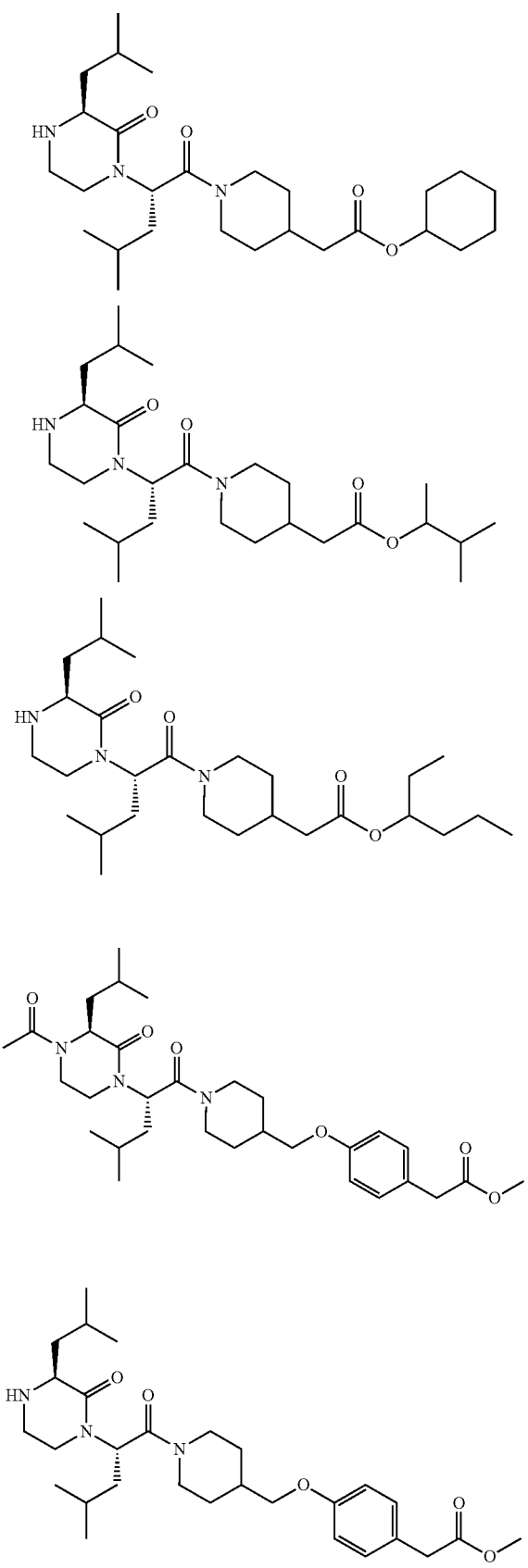
164
-continued
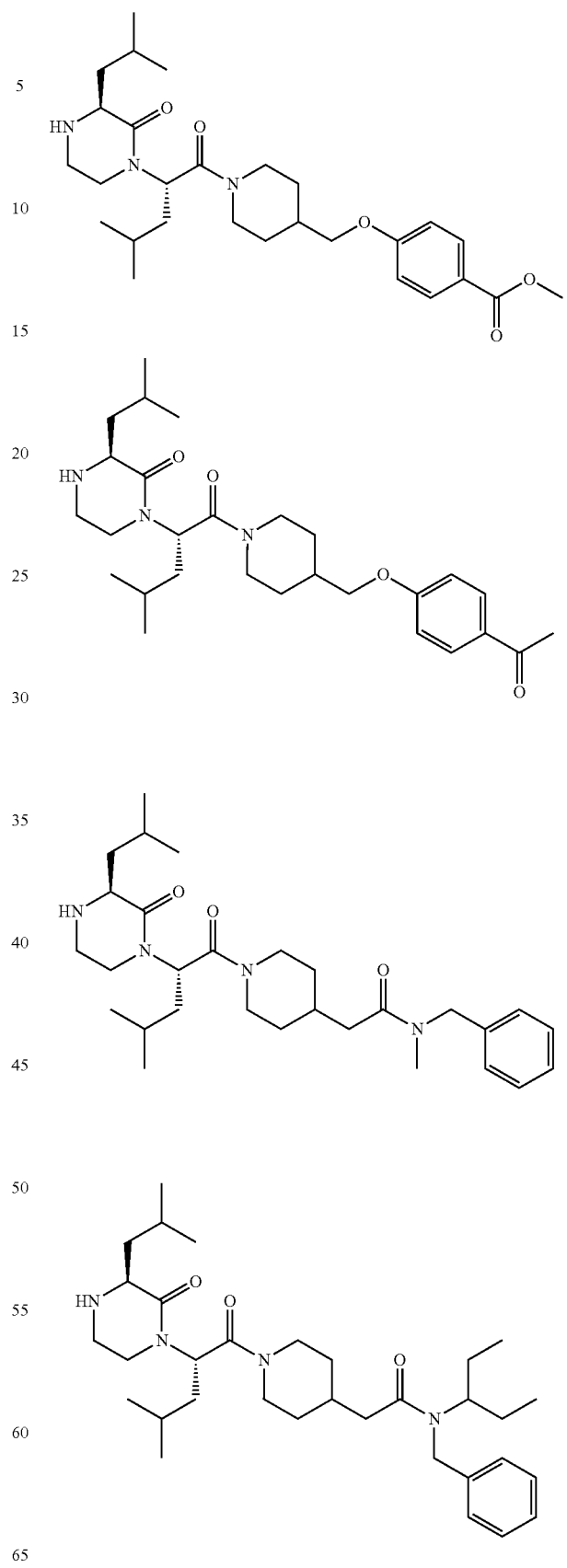

165
-continued
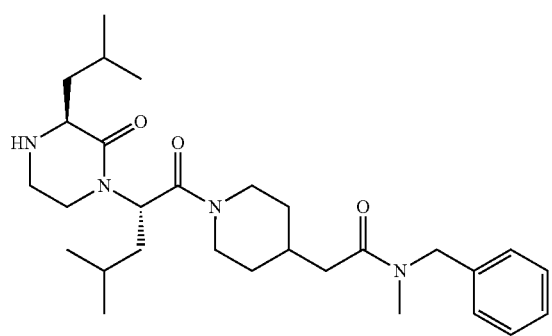
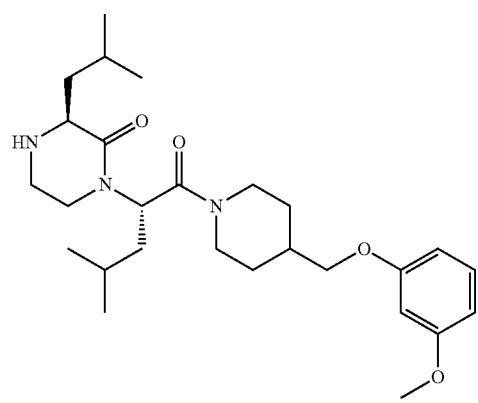
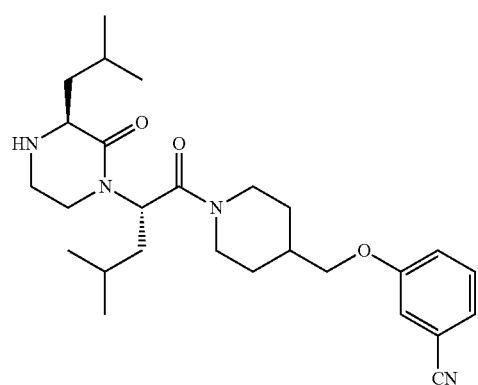
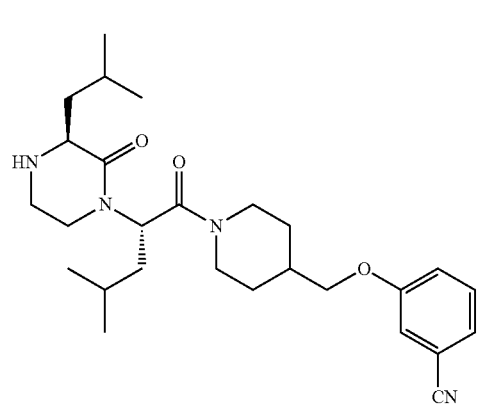
166
-continued
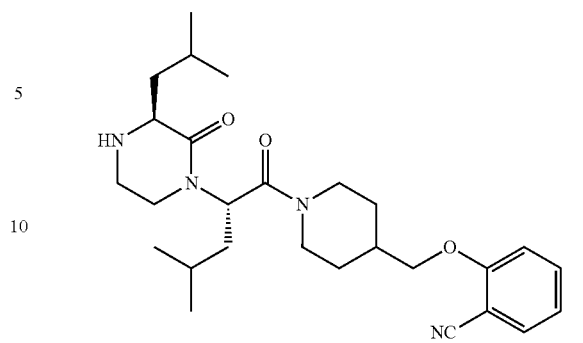
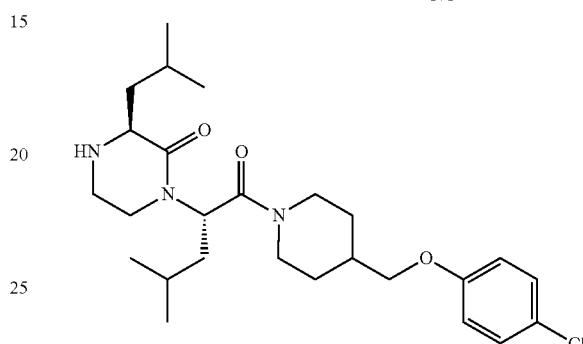
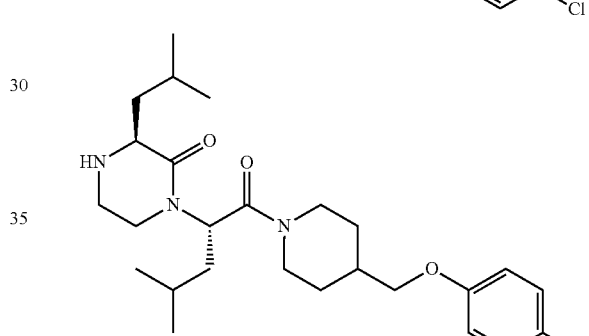
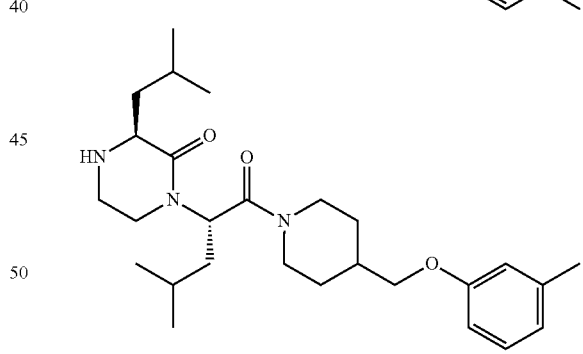
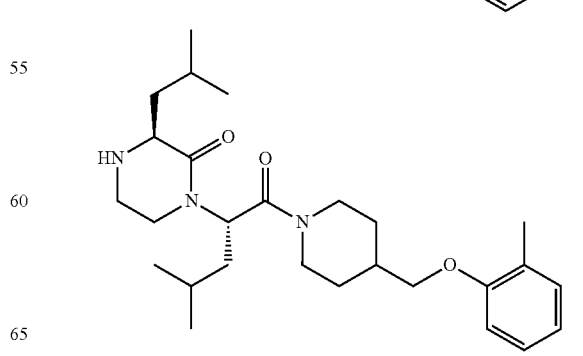

167
-continued
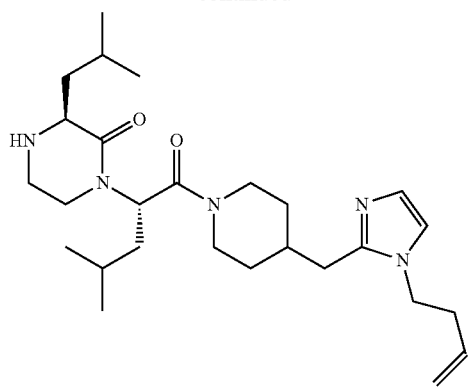
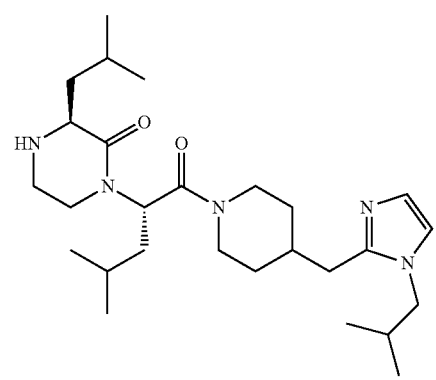
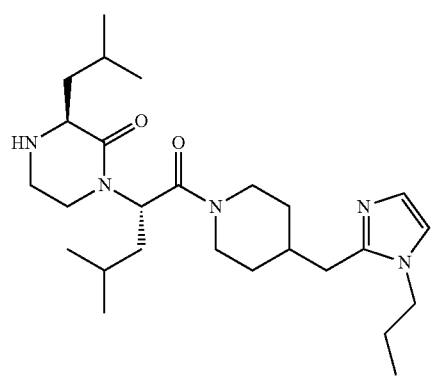
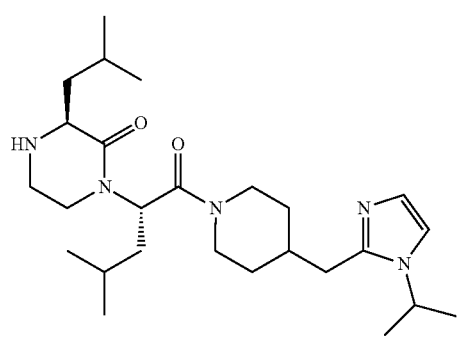
168
-continued
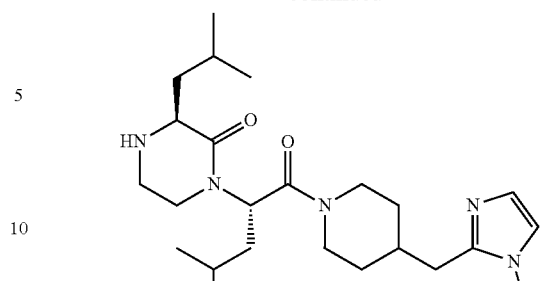
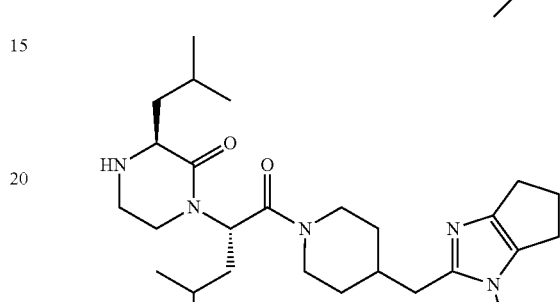
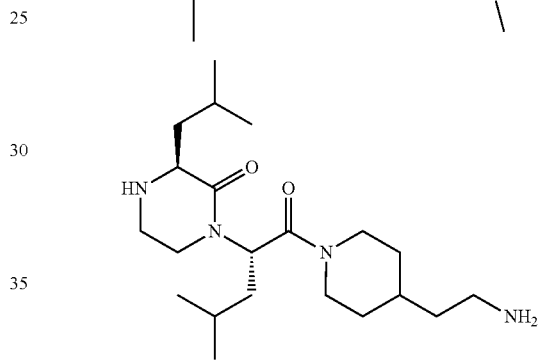
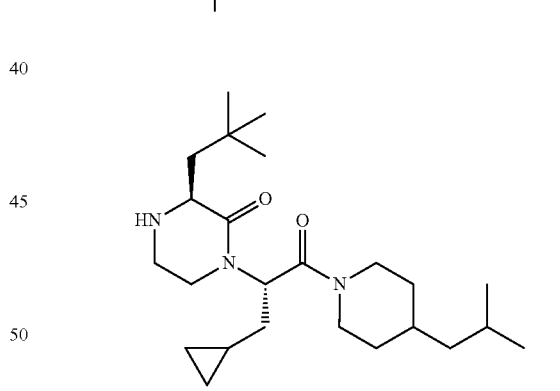
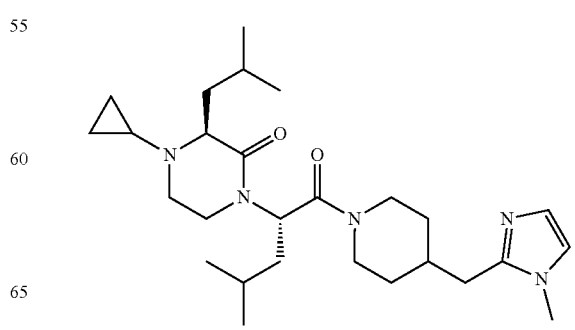

169
-continued
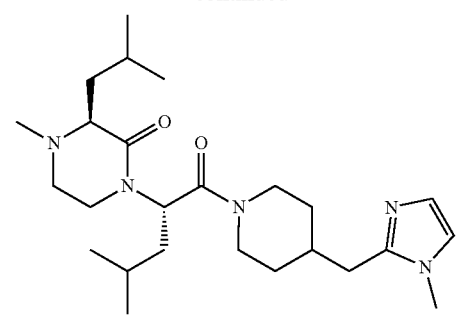
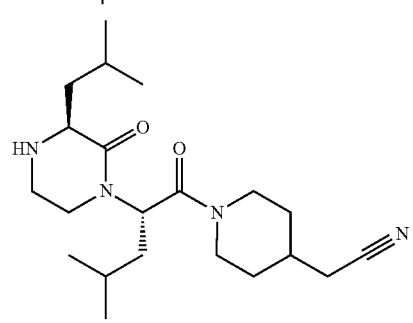
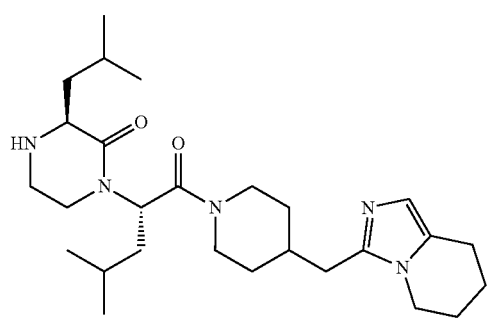
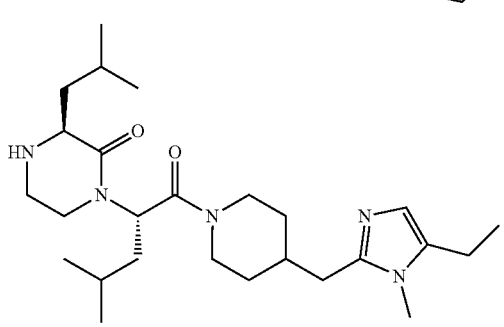
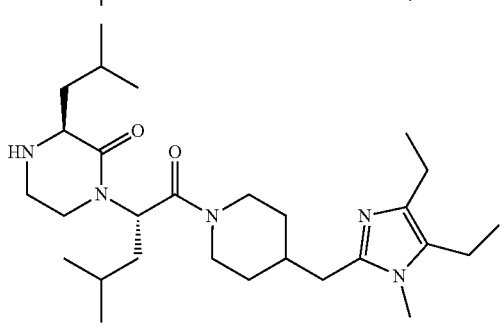
170
-continued
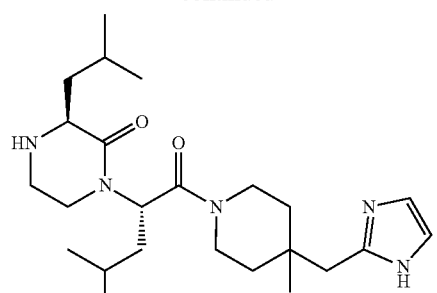
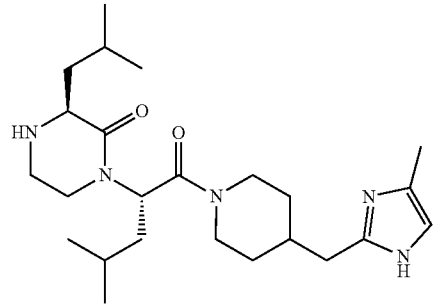
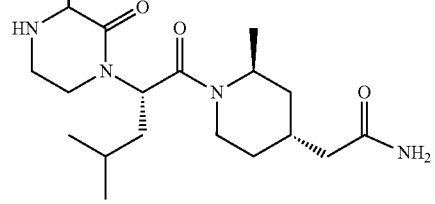
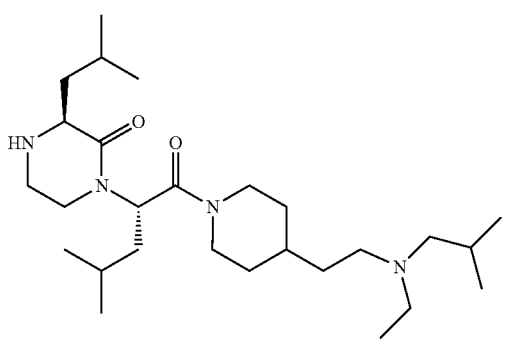
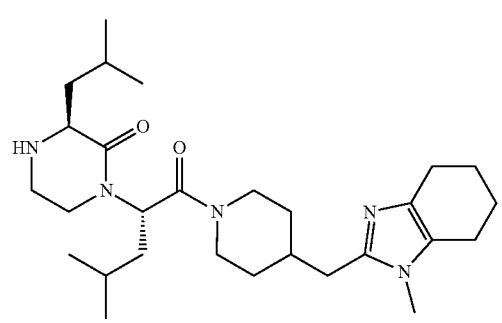

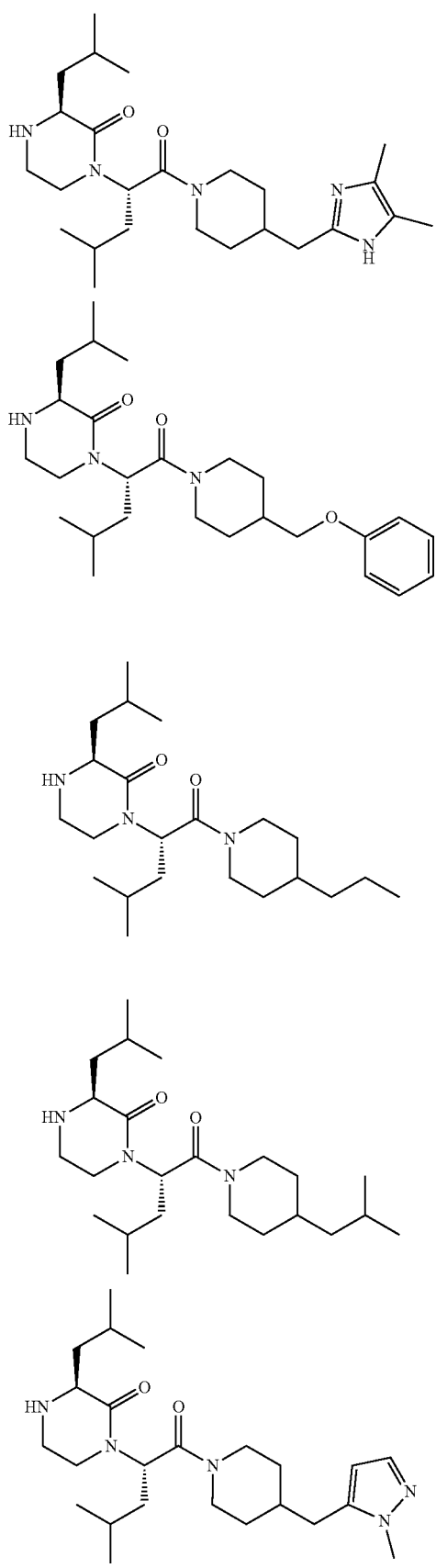
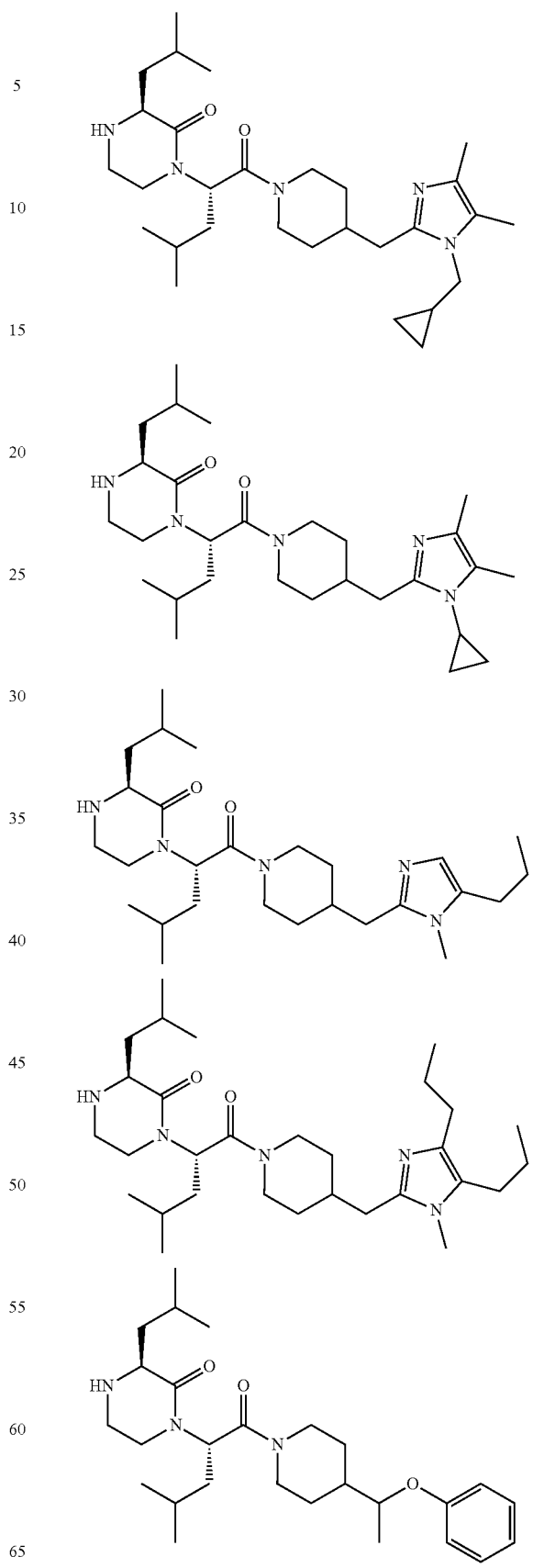

173
-continued
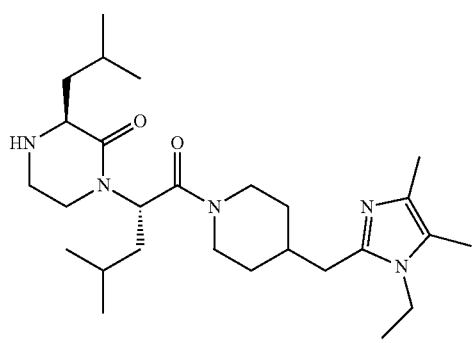
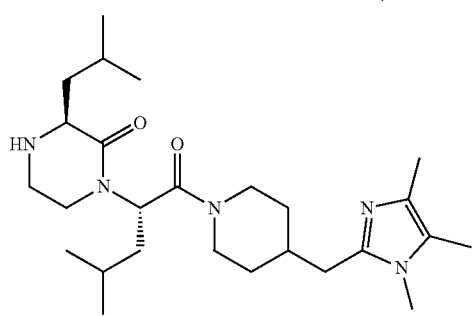
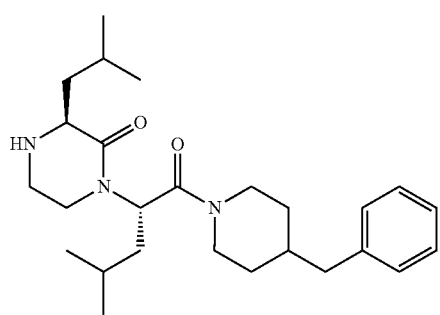
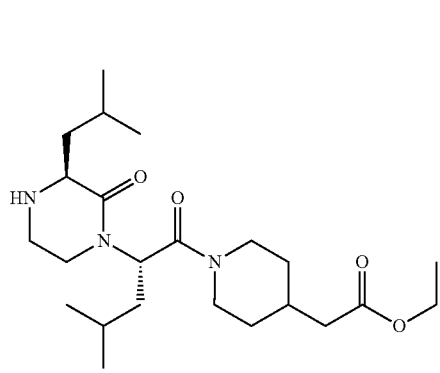
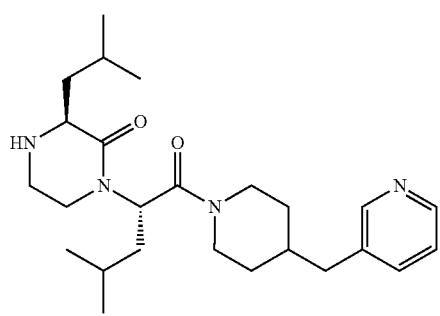
174
-continued
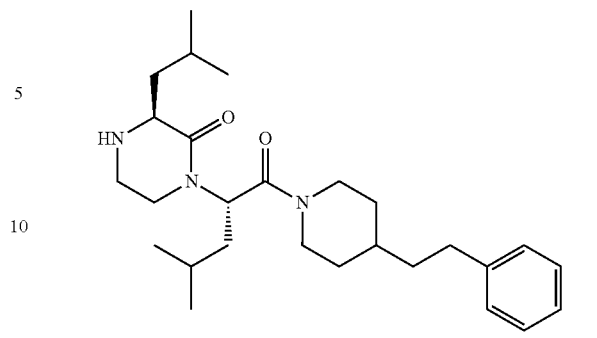
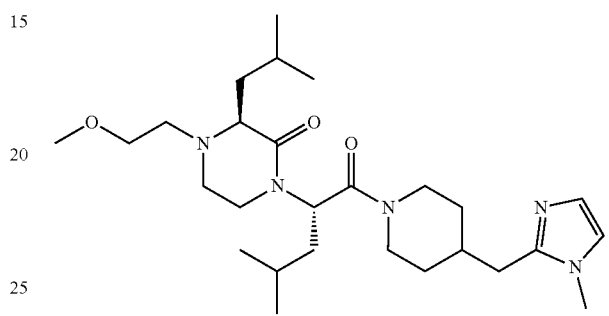
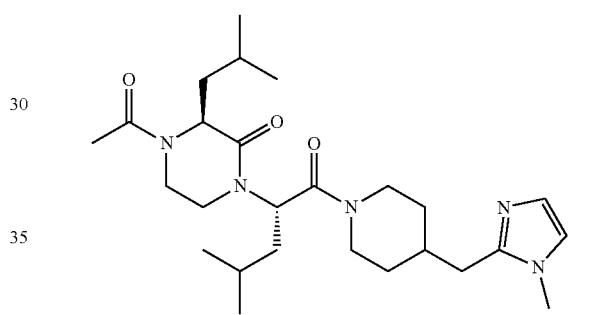
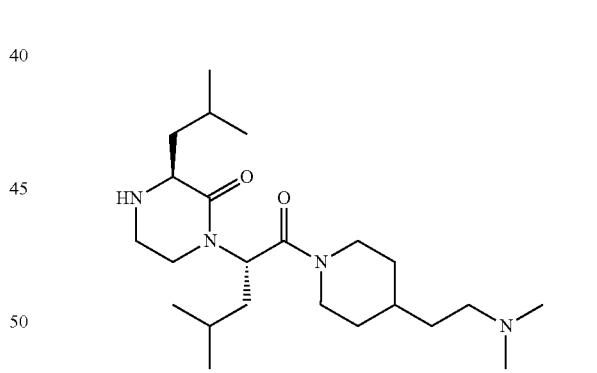
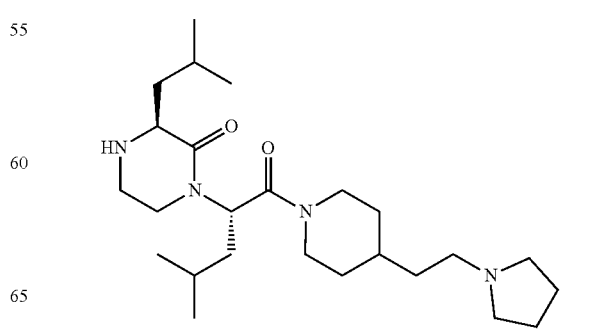

175
-continued
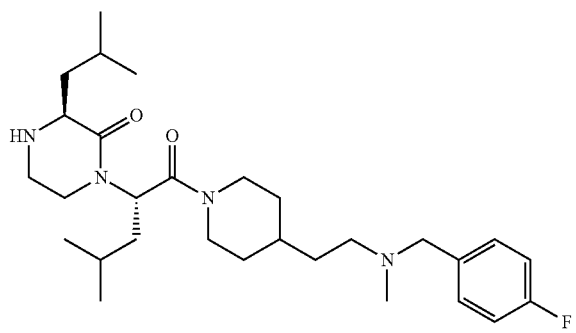
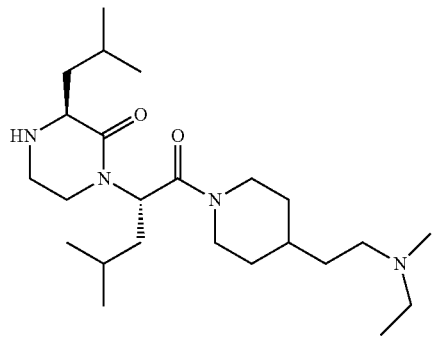
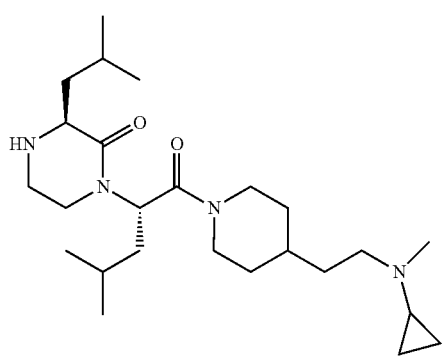
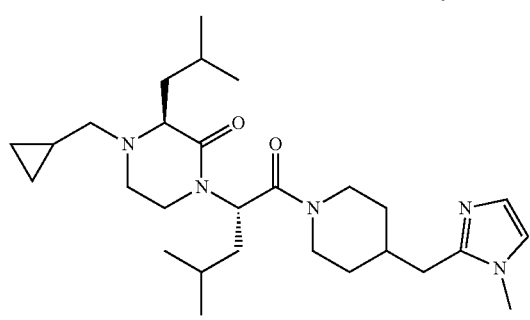
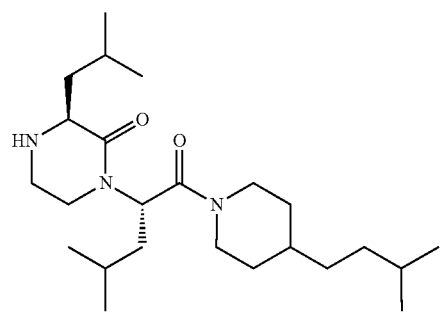
176
-continued
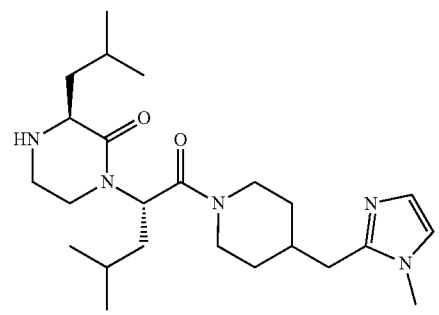
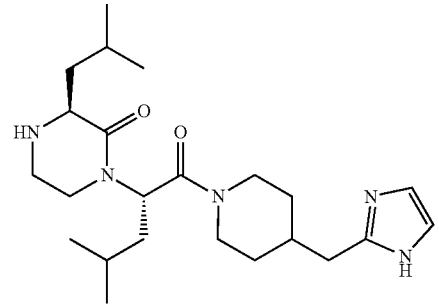
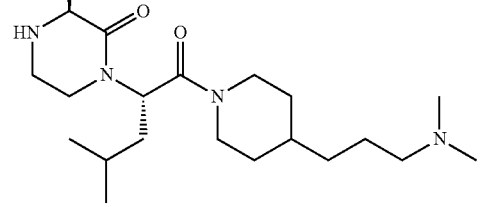
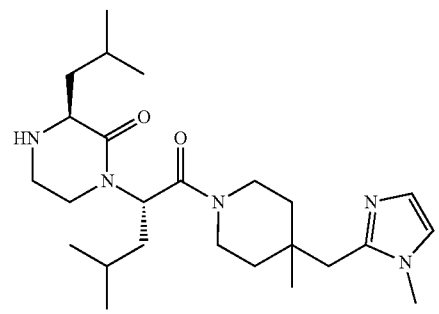
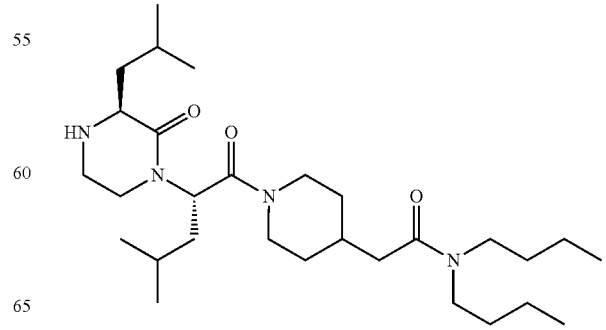

-continued
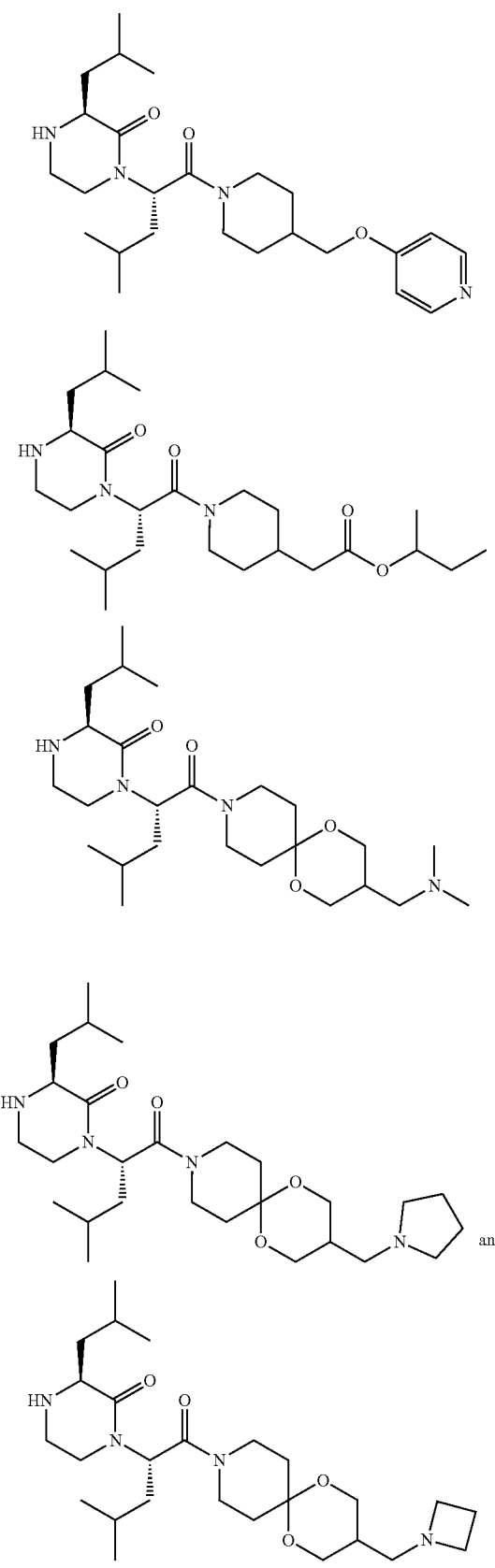
55. A compound selected from the group consisting of:
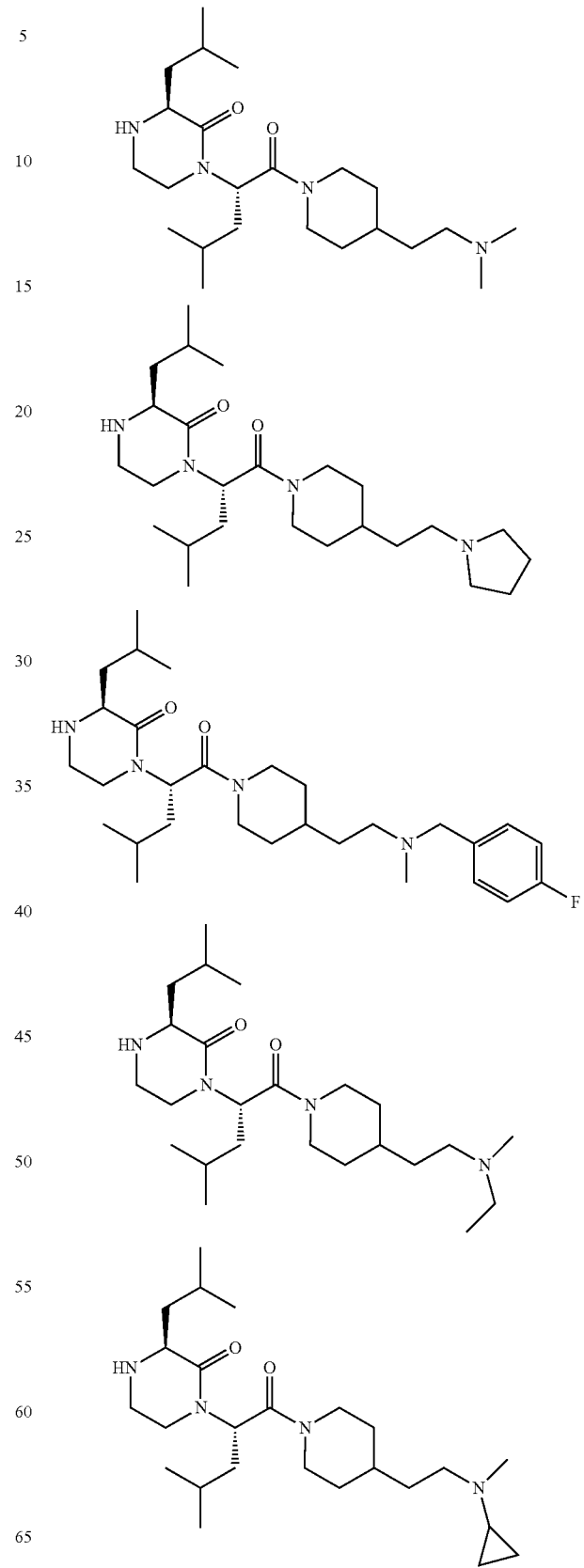

179
-continued
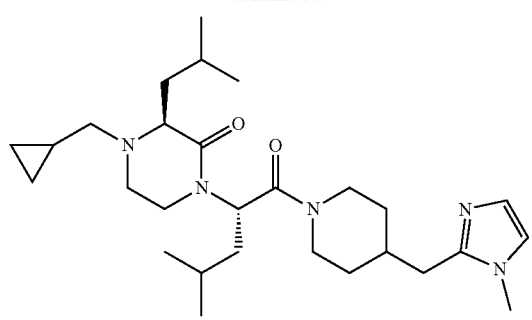
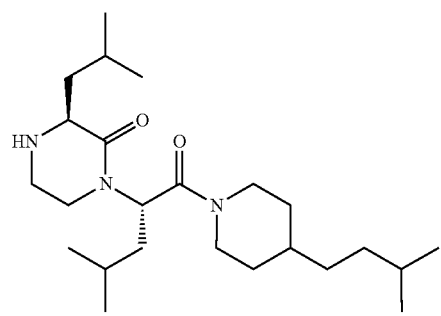
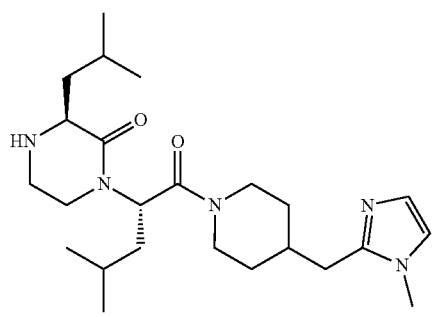
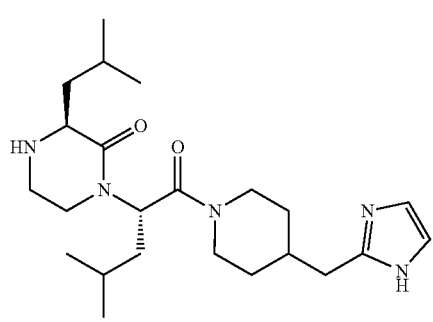
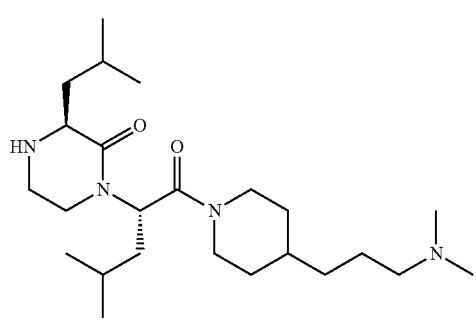
180
-continued
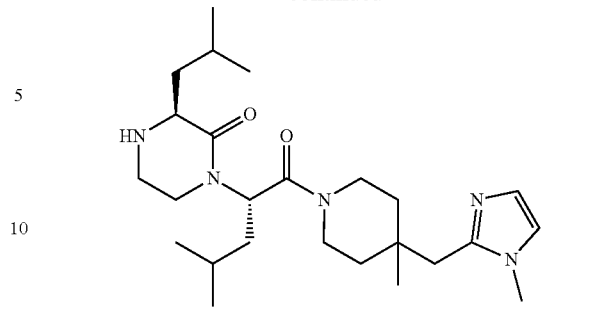
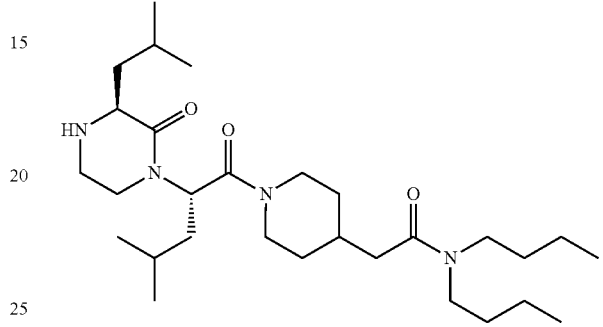
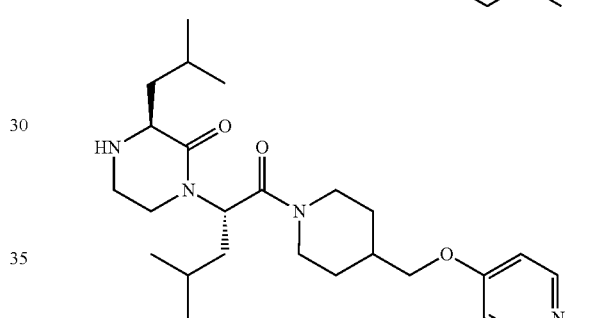
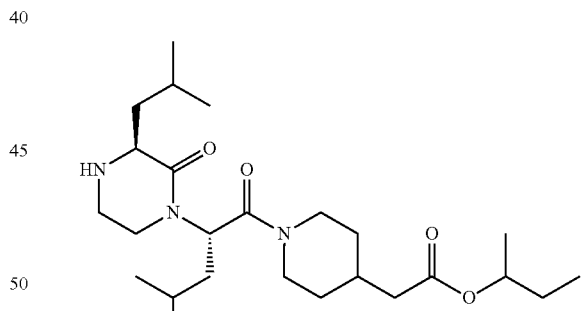
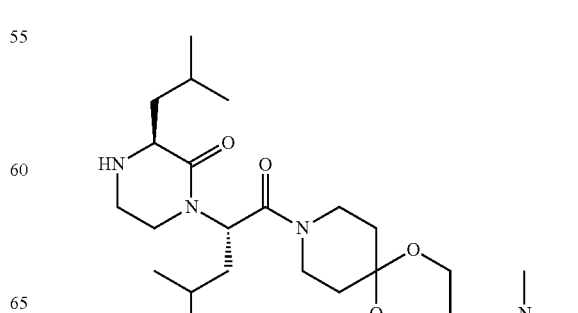

-continued

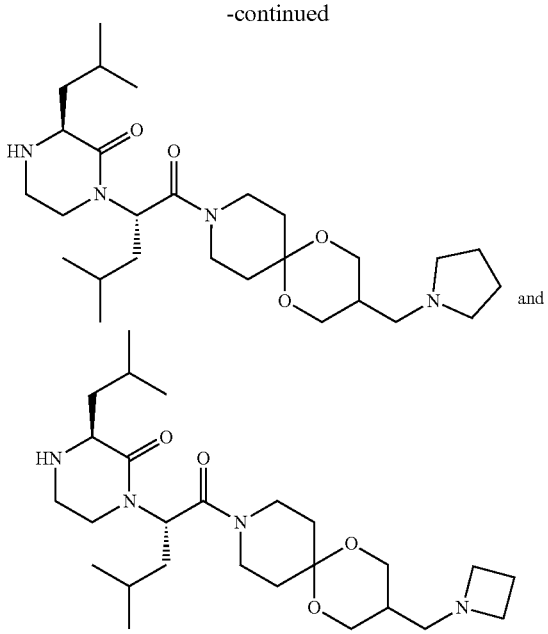

and

56. The compound according to any one of the previous embodiments, wherein the compound is selected from a compound of any one of Table 2 or Table 3.

57. A pharmaceutical composition comprising a compound according to any one of the previous embodiments and a pharmaceutically acceptable diluent, excipient or carrier.

58. The pharmaceutical composition according to embodiment 57, further comprising an additional pharmaceutically active agent.

59. The pharmaceutical composition according to embodiment 58, wherein the additional pharmaceutically active agent comprises an additional cancer therapy.

60. The compound according to any one of embodiments 1-56 or the pharmaceutical composition according to embodiment 57 or 58 for use as a medicament.

61. The compound according to any one of embodiments 1-56 or the or the pharmaceutical composition according to embodiment 57 or 58 for use in a method for preventing or treating cancer in a subject in need thereof.

62. The compound according to any one of embodiments 1-56 or the pharmaceutical composition according to embodiment 57 or 58 for the use in the manufacture of a medicament for the treatment of cancer in a subject in need thereof.

63. A method of treating cancer in a subject in need thereof, comprising administering to the subject a therapeutically effective amount of a composition comprising the compound of any one of embodiments 1-56 or the pharmaceutical composition of embodiment 57 or 58.

64. The method or composition for use according to any one of embodiments 61-63, wherein the cancer comprises a solid tumor or a liquid tumor.

65. The method or composition for use according to embodiment 64, wherein the solid tumor is a primary tumor or a metastatic tumor.

66. The method or composition for use according to embodiment 64, wherein the solid tumor is a carcinoma, a sarcoma, a myeloma, a germ cell tumor, a carcinoid tumor, a neuroendocrine tumor or a tumor of mixed type.

67. The method or composition for use according to embodiment 64, wherein the cancer comprises a lymphoma, a leukemia, a brain cancer, a nervous system cancer, a breast cancer, a cervical cancer, an ovarian cancer, a colorectal cancer, a stomach cancer, a gastric cancer, a kidney cancer, a liver cancer, a lung cancer, an oesophageal cancer, a pancreatic cancer, a prostate cancer, a colon cancer, a skin cancer or a head-and-neck cancer.

68. The method or composition for use according to embodiment 64, wherein the liquid tumor is a leukemia or a lymphoma.

69. The method of composition for use according to any one of embodiments 61-66, wherein the cancer is Stage I, Stage IIA, Stage IIB, Stage IIIA, Stage IIIB, Stage IIIC, or Stage IV cancer.

70. The method or composition for use according to any one of embodiments 61-69, wherein the subject is a mouse, a rat, a rabbit, a non-human primate or a human.

71. The method or composition for use according to embodiment 70, wherein the human is a child, an adolescent or an adult.

72. The method of composition for use according to any one of embodiments 61-71, wherein the compound or pharmaceutical composition is suitable for oral administration.

73. The method of composition for use according to any one of embodiments 61-71, wherein the compound or pharmaceutical composition is suitable for parenteral administration.

74. The method or composition for use according to embodiment 73, wherein the parenteral administration comprises subcutaneous administration, intravenous injection, intravenous infusion, intraperitoneal injection, intramuscular injection or intratumoral injection.

75. The method or composition for use according to any one of embodiments 61-74, wherein the method or use of the composition further comprises at least one additional cancer therapy.

76. The method or composition for use according to embodiment 75, wherein the at least one additional cancer therapy comprises a standard of care for the cancer.

77. The method or composition for use according to embodiment 75 or 76, wherein the at least one additional cancer therapy comprises surgical resection of the cancer, radiation therapy, or a combination thereof.

78. The method or composition for use according to embodiment 75, wherein the at least one additional cancer therapy comprises administration of at least one additional cancer therapeutic agent.

79. The method or composition for use according to embodiment 78, wherein the administration comprises simultaneous administration of the compound or pharmaceutical composition and the at least one additional cancer therapeutic agent.

80. The method or composition for use according to embodiment 79, wherein the compound or pharmaceutical composition and the at least one additional cancer therapeutic agent are in the same composition.

81. The method or composition for use according to embodiment 78, wherein the administration comprises administration in temporal proximity of the compound or pharmaceutical composition and the at least one additional cancer therapeutic agent.

82. The method or composition for use according to embodiment 78, wherein the administration comprises sequential administration of the compound or pharmaceutical composition and the at least one additional cancer therapeutic agent.

83. The method or composition for use according to any one of embodiments 78-82, wherein the at least one additional cancer therapeutic agent comprises a chemotherapeutic agent.

84. The method or composition for use according to embodiment 83, wherein the chemotherapeutic agent comprises a platinum compound, an alkylating agent, an antitumor antibiotic, a taxane, an antimetabolite, a nucleoside analog, a topoisomerase inhibitor, a hypomethylating agent, a proteasome inhibitor, an epipodophyllotoxin, a DNA synthesis inhibitor, a vinca alkaloid, a tyrosine kinase inhibitor, a nitrosourea, hexamethylmelamine, mitotane, an angiogenesis inhibitor, a steroid, a hormonal agent, an aromatase inhibitor, arsenic trioxide, tretinoin, a nonselective cyclooxygenase inhibitor, a selective cyclooxygenase-2 (COX-2) inhibitors, or a combination thereof.

85. The method or composition for use according to any one of embodiments 78-82, wherein the at least one additional cancer therapeutic agent comprises a biological agent.

86. The method or composition for use according to embodiment 85, wherein the biological agent comprises an antibody therapy, an adoptive cell therapy, an enzyme, a cytokine, a growth factor, an inhibitor of a growth factor, a gene therapy a cancer vaccine or a combination thereof.

87. The method or composition for use according to embodiment 86, wherein the antibody therapy comprises ituximab, cetuximab, obinutuzumab, ofatumumab, ibritumomab, brentuximab, bevacizumab, panitumumab, pembrolizumab, tositumomab, trastuzumab, alemtuzumab, gemtuzumab ozogamicin, bevacizumab, catumaxomab, denosumab, obinutuzumab, ofatumumab, ramucirumab, pertuzumab, ipilimumab, nivolumab, nimotuzumab, lambrolizumab, pidilizumab, siltuximab, tremelimumab.

88. The method or composition for use according to embodiment 86, wherein the adoptive cell therapy comprises a chimeric antigen receptor T cell (CAR-T) therapy.

89. The method or composition for use according to embodiment 88, wherein the adoptive cell therapy is autologous or allogeneic.

90. The method or composition for use according to any one of embodiments 78-82, wherein the at least one additional cancer therapeutic agent comprises an immune checkpoint inhibitor.

91. The method or composition for use according to embodiment 90, wherein the immune checkpoint inhibitor comprises nivolumab, pembrolizumab, atezolizumab, avelumab, durvalumab or ipilimumab.

92. The method or composition for use according to embodiment 86, wherein the antibody therapy comprises a VEGFA antibody.

93. The method or composition for use according to embodiment 92, wherein the VEGFA antibody comprises bevacizumab (Avastin®).

94. The method or composition for use according to any one of embodiments 61-93, wherein the method or use of the composition alleviates a sign or a symptom of the cancer.

95. The method or composition for use according to embodiment 94, wherein alleviating a sign or a symptom of the cancer comprises a reduction in tumor volume, a reduction in tumor size, a reduction in tumor number, a decrease in the rate of growth of a tumor or a combination thereof.

96. A kit, comprising the compound according to any one of embodiments 1-56 or the pharmaceutical composition according to embodiment 57 or 58 and instructions for use in treating cancer in a subject in need thereof.

97. The kit according to embodiment 96, further comprising at least one additional cancer therapeutic agent.

98. The kit according to embodiment 97, wherein the at least one additional cancer therapeutic agent comprises a chemotherapeutic agent.

99. The kit according to embodiment 98, wherein the chemotherapeutic agent comprises a platinum compound, an alkylating agent, an antitumor antibiotic, a taxane, an antimetabolite, a nucleoside analog, a topoisomerase inhibitor, a hypomethylating agent, a proteasome inhibitor, an epipodophyllotoxin, a DNA synthesis inhibitor, a vinca alkaloid, a tyrosine kinase inhibitor, a nitrosourea, hexamethylmelamine, mitotane, an angiogenesis inhibitor, a steroid, a hormonal agent, an aromatase inhibitor, arsenic trioxide, tretinoin, a nonselective cyclooxygenase inhibitor, a selective cyclooxygenase-2 (COX-2) inhibitors, or a combination thereof.

100. The kit of embodiment according to embodiment 97, wherein the at least one additional cancer therapeutic agent comprises a biological agent.

101. The kit according to embodiment 100, wherein biological agent comprises an antibody therapy, an adoptive cell therapy, an enzyme, a cytokine, a growth factor, an inhibitor of a growth factor, a gene therapy a cancer vaccine or a combination thereof.

102. The kit according to embodiment 97, wherein the at least one additional cancer therapeutic agent comprises an immune checkpoint inhibitor.

103. The kit according to embodiment 102, wherein the immune checkpoint inhibitor comprises nivolumab, pembrolizumab, atezolizumab, avelumab, durvalumab or ipilimumab.

EXAMPLES

Abbreviations used in the following examples and elsewhere herein are:

DCC: dicyclohexylcarbodiimide

DCM: dichloromethane

DMF: dimethylformamide

DMP: Dess-Martin periodinane; 1,1,1-Triacetoxy-1,1-dihydro-1,2-benziodoxol-3(1H)-one DMSO: dimethylsulfoxide HATU: 1-[bis(dimethylamino)methylene]-1H-1,2,3-triazolo[4,5-b]pyridinium 3-oxide hexafluorophosphate MS–: mass spectrum NMP: N-methyl-2-pyrrolidone NMR: nuclear magnetic resonance Nosyl: 2-nitrosulfonyl TBDMS–: t-butyldimethylsilyl tBOC or BOC: t-butyloxycarbonyl TFA: trifluoroacetic acid THF: tetrahydrofuran THP: 2-tetrahydropyranyl The compounds have been prepared in accordance to the following schemes/methods. However, other methods are known for the synthesis.

Scheme 1 (Method A)

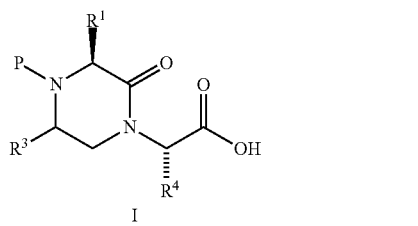

I

+

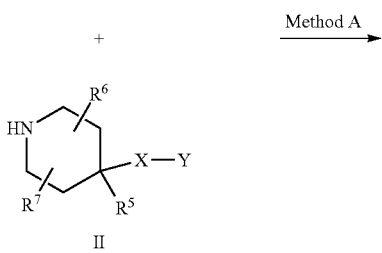

II

Method A →

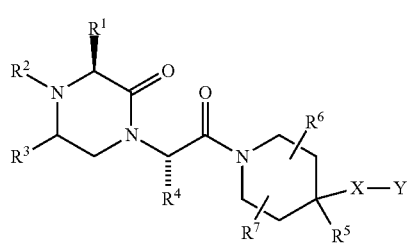

III

Scheme 2 (Method B1 and Method B2)

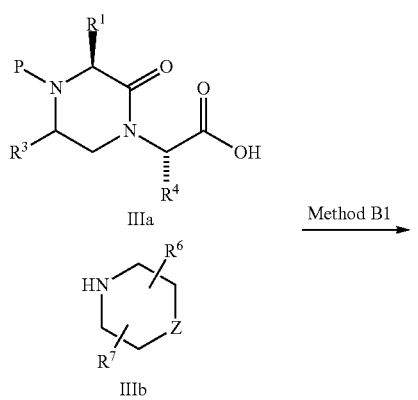

IIIa

Method B1 →

IIIb

Method B2 →

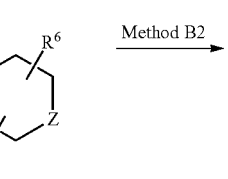

III

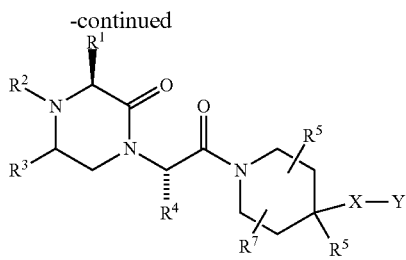

Scheme 3 (Method C)

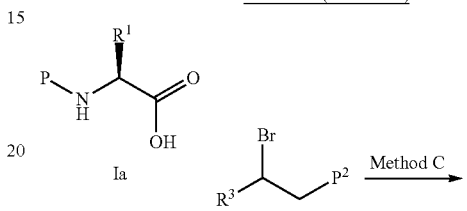

Ia

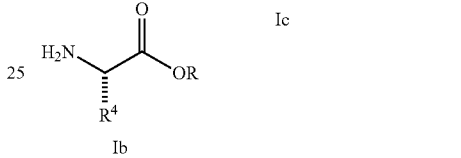

Ic

Method C →

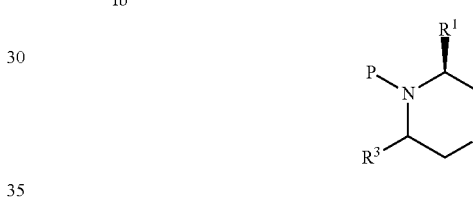

Ib

I

Synthesis of I, (S)-2-[(S)-3-isobutyl-4-(o-nitrophenylsulfonyl)-2-oxo-1-piperazinyl]-4-methylvaleric Acid According to Synthetic Method C (Scheme 3)

Synthesis of Ia
(S)-4-methyl-2-(o-nitrophenylsulfonylamino)valeric Acid

To a solution of L-leucine (1 eq.) and N,N-diisopropylethylamine (3.2 eq.) in a water/THF solvent mixture cooled at 0° C. is added o-(chlorosulfonyl)nitrobenzene (1.3 eq.). The solution is allowed to warm up to room temperature and stirred overnight. The residue is acidified, extracted and concentrated to yield the title compound as an orange solid.
$^1$H NMR (300 MHz, CD$_3$OD), δ (ppm): 8.16-8.03 (m, 1H), 7.90-7.73 (m, 3H), 4.07 (dd, 1H), 1.88-1.72 (m, 1H), 1.66-1.51 (m, 2H), 0.94 (d, 3H), 0.88 (d, 3H)
MS$^-$: 315 (M–H)

Synthesis of methyl (S)-2-[(S)-4-methyl-2-(o-nitrophenylsulfonylamino)valerylamino]-4-methylvalerate To a solution of Ia ((S)-4-methyl-2-(o-nitrophenylsulfonylamino)valeric acid) (1 eq.), Ib (methyl (S)-2-amino-4-methylvalerate hydrochloride) (1.1 eq.) and N,N-diisopropylethylamine (3 eq.) in DMF is added HATU reagent (1.1 eq.). The solution is stirred at room temperature overnight.

After aqueous work-up, the organic residue is concentrated and re-crystallized to yield the title compound as a colourless solid.

$^1$H NMR (300 MHz, CDCl$_3$), δ (ppm): 8.14-8.09 (m, 1H), 7.94-7.88 (m, 1H), 7.78-7.70 (m, 2H), 6.48 (d, 1H), 6.15 (d, 1H), 4.45-4.35 (m, 1H), 4.06-3.97 (m, 1H), 3.68 (s, 3H), 1.80-1.37 (m, 8H), 0.90-0.85 (m, 6H), 0.82-0.78 (m, 6H)

MS$^-$: 442 (M−H)

Synthesis of methyl (S)-2-[(S)-3-isobutyl-4-(o-nitrophenylsulfonyl)-2-oxo-1-piperazinyl]-4-methylvalerate To a solution of methyl (S)-2-[(S)-4-methyl-2-(o-nitrophenyl sulfonylamino)valerylamino]-4-methylvalerate (1 eq.) and Ic (1,2-dibromoethane) (4 eq.) in DMF is added potassium carbonate (4 eq.). The mixture is stirred at 65° C. overnight. After aqueous work-up, the organic residue is purified by flash chromatography to yield the title compound as an orange solid.

$^1$H NMR (300 MHz, CDCl$_3$), δ (ppm): 8.06-8.02 (m, 1H), 7.78-7.66 (m, 3H), 5.09 (dd, 1H), 4.53 (dd, 1H), 4.07-3.98 (m, 1H), 3.65-3.55 (m, 1H), 3.58 (s, 3H), 3.45-3.36 (m, 1H), 3.18-3.10 (m, 1H), 1.77-1.61 (m, 5H), 1.41-1.24 (m, 1H), 0.96-0.85 (m, 12H)

MS$^+$: 470 (M+H)

Synthesis of I, (S)-2-[(S)-3-isobutyl-4-(o-nitrophenylsulfonyl)-2-oxo-1-piperazinyl]-4-methylvaleric Acid To a solution of methyl (S)-2-[(S)-3-isobutyl-4-(o-nitrophenylsulfonyl)-2-oxo-1-piperazinyl]-4-methylvalerate (1 eq.) in methanol is added a solution of lithium hydroxide (1.5 eq.) in water. The mixture is stirred at room temperature for 2 h then concentrated. The residue is acidified, extracted and concentrated to a gum that is re-crystallized to yield the title compound as a colourless solid.

$^1$H NMR (300 MHz, CDCl$_3$), δ (ppm): 8.85-7.85 (br s, 1H), 8.06-8.01 (m, 1H), 7.78-7.63 (m, 3H), 5.09 (dd, 1H), 4.59 (m, 1H), 4.14-4.05 (m, 1H), 3.65-3.54 (m, 1H), 3.45-3.33 (m, 1H), 3.17-3.09 (m, 1H), 1.78-1.61 (m, 5H), 1.45-1.30 (m, 1H), 0.97-0.87 (m, 12H)

MS$^-$: 454 (M−H)

Synthesis of (S)-1-[(S)-1-({4-[(1-cyclopropyl-1H-imidazol-2-yl)methyl]-1-piperidyl}carbonyl)-3-methylbutyl]-3-isobutyl-2-piperazinone Following Synthetic Method A (Scheme 1)

Synthesis of II

Synthesis of tert-butyl 4-(2-hydroxyethyl)-1-piperidinecarboxylate

To a solution of 2-(4-piperidyl)ethanol (1 eq.) in a mixture THF/water is added di-tert-butyl dicarbonate (1.3 eq.) and sodium bicarbonate (2 eq.). The mixture is stirred at room temperature overnight. After aqueous work-up, the residue is purified by flash chromatography to yield the title compound as a light yellow oil.

$^1$H NMR (300 MHz, CDCl$_3$), δ (ppm): 4.08 (br d, 2H), 3.71 (t, 2H), 2.70 (br t, 2H), 1.73-1.47 (m, 6H), 1.46 (s, 9H), 1.21-1.04 (m, 2H)

Synthesis of tert-butyl 4-(formylmethyl)-1-piperidinecarboxylate

To a solution of tert-butyl 4-(2-hydroxyethyl)-1-piperidinecarboxylate (1 eq.) in DCM is added DMP (2 eq.). The mixture is stirred at room temperature overnight. After aqueous work-up, the residue is purified by flash chromatography to yield the title compound as a yellow oil.

$^1$H NMR (300 MHz, CDCl$_3$), δ (ppm): 9.78 (br s, 1H), 4.08 (br d, 2H), 2.74 (br t, 2H), 2.39 (d, 2H), 2.12-1.89 (m, 1H), 1.79-1.64 (m, 2H), 1.45 (s, 9H), 1.26-1.10 (m, 2H)

Synthesis of tert-butyl 4-[(1-cyclopropyl-1H-imidazol-2-yl)methyl]-1-piperidinecarboxylate To a solution of tert-butyl 4-(formylmethyl)-1-piperidinecarboxylate (1 eq.) and glyoxal (1.2 eq.) in methanol is added cyclopropylamine (2 eq.) and ammonium acetate (1 eq.). The mixture is stirred at room temperature overnight then concentrated. The residue is purified by flash chromatography to yield the title compound as a yellow oil.

$^1$H NMR (300 MHz, CDCl$_3$), δ (ppm): 6.89 (s, 1H), 6.75 (s, 1H), 4.12-3.93 (m, 2H), 3.16-3.07 (m, 1H), 2.77-2.58 (m, 4H), 1.72-1.57 (m, 2H), 1.40 (s, 9H), 1.22-0.86 (m, 7H)

Synthesis of II, 1-cyclopropyl-2-[(4-piperidyl)methyl]-1H-imidazole

To a cooled solution of tert-butyl 4-[(1-cyclopropyl-1H-imidazol-2-yl)methyl]-1-piperidinecarboxylate in DCM is added TFA. The solution is stirred at room temperature for 1 h then concentrated and the residue is neutralized with sodium hydroxide to yield the title compound as a yellow gum.

$^1$H NMR (300 MHz, CD$_3$OD), δ (ppm): 7.06 (s, 1H), 6.91 (s, 1H), 3.27-3.20 (m, 2H), 2.95-2.79 (m, 4H), 2.20-2.05 (m, 1H), 1.86-1.73 (m, 2H), 1.56-1.25 (m, 3H), 1.08-0.99 (m, 2H), 0.94-0.86 (m, 2H)

Synthesis of (S)-1-[(S)-1-({4-[(1-cyclopropyl-1H-imidazol-2-yl)methyl]-1-piperidyl}carbonyl)-3-methylbutyl]-3-isobutyl-4-(o-nitrophenylsulfonyl)-2-piperazinone To a cooled solution of I (vide supra) (1 eq.) and II (1-cyclopropyl-2-[(4-piperidyl)methyl]-1H-imidazole) (1 eq.) in DMF is added HATU reagent (2 eq.). The solution is stirred at room temperature overnight. After an aqueous work-up, the organic residue is purified by flash chromatography to yield the title compound as a yellow oil.

$^1$H NMR (300 MHz, CDCl$_3$), δ (ppm): 8.12-8.04 (m, 1H), 7.84-7.64 (m, 3H), 7.07-6.90 (m, 2H), 5.62 (t, 0.55H), 5.48 (t, 0.45H), 4.54-4.33 (m, 2H), 4.24-4.14 (m, 0.5H), 4.03-3.84 (m, 1.5H), 3.57-3.43 (m, 1H), 3.40-3.00 (m, 4H), 2.86-2.78 (m, 1.5H), 2.71-2.33 (m, 1.5H), 2.27-2.04 (m, 1H), 1.79-1.30 (m, 9H), 1.21-1.10 (m, 2H), 1.05-0.95 (m, 2H), 0.95-0.83 (m, 12H), 0.83-0.76 (m, 2H)

MS$^+$: 643 (M+H)

Synthesis of (S)-1-[(S)-1-({4-[(1-cyclopropyl-1H-imidazol-2-yl)methyl]-1-piperidyl}carbonyl)-3-methylbutyl]-3-isobutyl-2-piperazinone A mixture of (S)-1-[(S)-1-({4-[(1-cyclopropyl-1H-imidazol-2-yl)methyl]-1-piperidyl}carbonyl)-3-methylbutyl]-3-isobutyl-4-(o-nitrophenylsulfonyl)-2-piperazinone (1 eq.), 2-mercaptoethanol (2 eq.) and cesium carbonate (3 eq.) in DMF is stirred at room temperature for 2 h. After filtration, concentration and flash chromatography purification, the title compound is obtained as a colourless oil.

$^1$H NMR (300 MHz, CD$_3$OD), δ (ppm): 6.98 (s, 1H), 6.82 (s, 1H), 5.63-5.52 (m, 1H), 4.58-4.42 (m, 1H), 4.19-3.99 (m, 1H), 3.48-3.40 (m, 1H), 3.38-3.27 (m, 2H), 3.19-3.03 (m, 2H), 2.98-2.85 (m, 1H), 2.80 (d, 2H), 2.77-2.61 (m, 1H), 2.27-2.09 (m, 1H), 1.90-1.43 (m, 8H), 1.30-1.06 (m, 4H), 1.04-0.86 (m, 15H)

MS$^+$: 458 (M+H), 480 (M+Na)

Synthesis of (S)-1-[(S)-3-methyl-1-({4-[2-(4-methyl-1-piperazinyl)-2-oxoethyl]-1-piperidyl}carbonyl)butyl]-3-isobutyl-2-piperazinone Following Synthetic Method B (Scheme 2)

Synthesis of III (methyl (1-{(S)-2-[(S)-3-isobutyl-4-(o-nitrophenylsulfonyl)-2-oxo-1-piperazinyl]-4-methylvaleryl}-4-piperidyl)acetate) by Method B1

HATU reagent (1.5 eq.) is added to a cooled solution of IIIa ((S)-2-[(S)-3-isobutyl-4-(o-nitrophenylsulfonyl)-2-oxo-1-piperazinyl]-4-methylvaleric acid, vide supra) (1 eq.) and IIIb (methyl (4-piperidyl)acetate) (2 eq.) in DMF. The solution is stirred at room temperature overnight. After an aqueous work-up, the organic residue is purified by flash chromatography to yield the title compound as a light yellow solid.

$^1$H NMR (300 MHz, CDCl$_3$), δ (ppm): 8.13-8.05 (m, 1H), 7.81-7.67 (m, 3H), 5.65-5.57 (m, 0.5H), 5.54-5.46 (m, 0.5H), 4.52-4.39 (m, 2H), 4.21-4.12 (m, 0.5H), 4.00-3.86 (m, 1.5H), 3.69 (s, 3H), 3.57-3.32 (m, 1.5H), 3.30-3.16 (m, 1.5H), 3.01 (t, 0.5H), 2.77 (t, 0.5H), 2.62-2.40 (m, 1H), 2.32-2.18 (m, 2H), 2.08-1.91 (m, 1H), 1.82-1.32 (m, 8H), 1.22-0.97 (m, 2H), 0.97-0.78 (m, 12H)

Synthesis of (1-{(S)-2-[(S)-3-isobutyl-4-(o-nitrophenylsulfonyl)-2-oxo-1-piperazinyl]-4-methylvaleryl}-4-piperidyl)acetic Acid (Part of Method B2)

Sodium hydroxide (1.5 eq.) is added to a solution of methyl (1-{(S)-2-[(S)-3-isobutyl-4-(o-nitrophenyl sulfonyl)-2-oxo-1-piperazinyl]-4-methylvaleryl}-4-piperidyl)acetate (1 eq.) in a mixture methanol/water. The solution is stirred at room temperature overnight then acidified and extracted to yield the titled compound as a light yellow solid.

$^1$H NMR (300 MHz, CDCl$_3$), δ (ppm): 8.14-8.07 (m, 1H), 7.81-7.67 (m, 3H), 5.67-5.60 (m, 0.5H), 5.56-5.48 (m, 0.5H), 4.55-4.40 (m, 2H), 4.24-4.14 (m, 0.5H), 4.00-3.88 (m, 1.5H), 3.58-3.34 (m, 1.5H), 3.31-3.16 (m, 1.5H), 3.07-2.96 (m, 0.5H), 2.81-2.69 (m, 0.5H), 2.62-2.41 (m, 1H), 2.36-2.22 (m, 2H), 2.09-1.91 (m, 1H), 1.86-1.32 (m, 8H), 1.25-0.99 (m, 2H), 0.97-0.77 (m, 12H)

MS$^-$: 579 (M−H)

Synthesis of (S)-1-[(S)-3-methyl-1-({4-[2-(4-methyl-1-piperazinyl)-2-oxoethyl]-1-piperidyl}carbonyl)butyl]-3-isobutyl-4-(o-nitrophenylsulfonyl)-2-piperazinone (Part of Method B2)

Oxalyl chloride (2 eq.) is added to a cooled solution of (1-{(S)-2-[(S)-3-isobutyl-4-(o-nitrophenylsulfonyl)-2-oxo-1-piperazinyl]-4-methylvaleryl}-4-piperidyl)acetic acid (1 eq.) and catalytic DMF in DCM. The solution is stirred at room temperature for 3 hours then 1-methylpiperazine (5 eq.) is added at 0° C. and the solution is stirred at room temperature overnight. Concentration and flash chromatography purification yield to the title compound as a light yellow gum.

$^1$H NMR (300 MHz, CDCl$_3$), δ (ppm): 8.10-8.04 (m, 1H), 7.82-7.67 (m, 3H), 5.67-5.60 (m, 0.6H), 5.53-5.46 (m, 0.4H), 4.55-4.39 (m, 2H), 4.20-4.11 (m, 0.6H), 3.97-3.85 (m, 1.4H), 3.70-3.60 (m, 2H), 3.56-3.32 (m, 3.6H), 3.28-3.15 (m, 1.4H), 3.02 (t, 0.6H), 2.74-2.62 (m, 0.4H), 2.62-2.43 (m, 1H), 2.43-2.34 (m, 4H), 2.34-1.96 (m, 6H), 1.87-1.33 (m, 8H), 1.25-0.97 (m, 2H), 0.96-0.80 (m, 12H)

Synthesis of (S)-1-[(S)-3-methyl-1-({4-[2-(4-methyl-1-piperazinyl)-2-oxoethyl]-1-piperidyl}carbonyl)butyl]-3-isobutyl-2-piperazinone (part of Method B2)

A mixture of (S)-1-[(S)-3-methyl-1-({4-[2-(4-methyl-1-piperazinyl)-2-oxoethyl]-1-piperidyl}carbonyl)butyl]-3-isobutyl-4-(o-nitrophenylsulfonyl)-2-piperazinone (1 eq.), polymer-supported benzyl mercaptan (2.5-5 eq.) and cesium carbonate (3 eq.) in DMF is shaken at room temperature overnight. After filtration, concentration, and flash chromatography purification if necessary, the title compound is obtained as a light yellow gum.

$^1$H NMR (300 MHz, CD$_3$OD), δ (ppm): 5.62-5.52 (m, 1H), 4.56-4.42 (m, 1H), 4.18-4.01 (m, 1H), 3.67-3.56 (m, 4H), 3.47-3.41 (m, 1H), 3.39-3.29 (m, 2H), 3.19-3.04 (m, 2H), 3.00-2.87 (m, 1H), 2.79-2.63 (m, 1H), 2.50-2.40 (m, 4H), 2.40-2.35 (m, 2H), 2.33 (s, 3H), 2.14-2.00 (m, 1H), 1.90-1.46 (m, 8H), 1.27-1.04 (m, 2H), 1.02-0.92 (m, 12H)

MS$^+$: 478 (M+H), 500 (M+Na).

Examples 1-319

The following compounds have been synthesized according to the methods outlined supra and the compounds have been characterized by their nmr signals. Synthesesis of precursor I was according to Method C. Starting material for precursor I used was as indicated in Table 1. Synthesesis of precursor II and III was as indicated in Tables 2 and 3 below.

TABLE 1

Starting material for precursor I

| Ex./Cmpd. # | Precursor Ia | Precursor Ib | Precursor Ic |
|---|---|---|---|
| 1-7, 9-32, 36-47, 52-60, 63-87, 95-103, 111, 124, 125, 135-138, 141-229 | N-(2-nosyl)-L-leucine | L-leucine methyl ester hydrochloride | 1,2-dibromoethane |
| 8, 33, 34, 109 | (S)-3-cyclopropyl-2-(o-nitrophenylsulfonylamino)propionic acid | Methyl (S)-2-amino-3-cyclopropylpropionate hydrochloride | 1,2-dibromoethane |
| 35, 115, 133, 134 | N-(2-nosyl)-L-α-neopentylglycine | Methyl (S)-2-amino-3-cyclopropylpropionate hydrochloride | 1,2-dibromoethane |

TABLE 1-continued

| | Starting material for precursor I | | |
|---|---|---|---|
| Ex./Cmpd. # | Precursor Ia | Precursor Ib | Precursor Ic |
| 48, 51, 88 | N-(2-nosyl)-L-leucine | L-phenylalanine methyl ester hydrochloride | 1,2-dibromoethane |
| 49, 50, 90 | N-(2-nosyl)-L-leucine | L-valine methyl ester hydrochloride | 1,2-dibromoethane |
| 61, 62, 91 | (S)-3-cyclopropyl-2-(o-nitrophenylsulfonylamino)propionic acid | L-leucine methyl ester hydrochloride | 1,2-dibromoethane |
| 89 | N-(2-nosyl)-L-phenylalanine | L-leucine methyl ester hydrochloride | 1,2-dibromoethane |
| 92 | (S)-3-cyclopropyl-2-(o-nitrophenylsulfonylamino)propionic acid | Methyl (S)-2-aminovalerate hydrochloride | 1,2-dibromoethane |
| 93 | (S)-3-cyclopropyl-2-(o-nitrophenylsulfonylamino)propionic acid | Methyl (S)-2-aminohexanoate hydrochloride | 1,2-dibromoethane |
| 94 | (S)-3-cyclopropyl-2-(o-nitrophenylsulfonylamino)propionic acid | Methyl (S)-2-amino-4,4-dimethylvalerate hydrochloride | 1,2-dibromoethane |
| 104 | N-(2-nosyl)-L-leucine | Methyl (S)-2-aminohexanoate hydrochloride | 1,2-dibromoethane |
| 105 | N-(2-nosyl)-L-leucine | Methyl (S)-2-amino-3-cyclopropylpropionate hydrochloride | 1,2-dibromoethane |
| 106 | N-(2-nosyl)-L-norleucine | Methyl (S)-2-amino-3-cyclopropylpropionate hydrochloride | 1,2-dibromoethane |
| 107 | N-(2-nosyl)-L-norleucine | Methyl (S)-2-aminohexanoate hydrochloride | 1,2-dibromoethane |
| 108 | N-(2-nosyl)-L-norleucine | Methyl (S)-2-aminovalerate hydrochloride | 1,2-dibromoethane |
| 110 | N-(2-nosyl)-L-norleucine | L-leucine methyl ester hydrochloride | 1,2-dibromoethane |
| 112 | N-(2-nosyl)-L-α-neopentylglycine | Methyl (S)-2-aminovalerate hydrochloride | 1,2-dibromoethane |
| 113 | N-(2-nosyl)-L-α-neopentylglycine | Methyl (S)-2-aminohexanoate hydrochloride | 1,2-dibromoethane |
| 114 | N-(2-nosyl)-L-α-neopentylglycine | L-leucine methyl ester hydrochloride | 1,2-dibromoethane |
| 116 | N-(2-nosyl)-L-leucine | Methyl (S)-2-amino-4,4-dimethylvalerate hydrochloride | 1,2-dibromoethane |
| 117 | N-(2-nosyl)-L-norvaline | Methyl (S)-2-amino-4,4-dimethylvalerate hydrochloride | 1,2-dibromoethane |
| 118 | N-(2-nosyl)-L-α-neopentylglycine | Methyl (S)-2-amino-4,4-dimethylvalerate hydrochloride | 1,2-dibromoethane |
| 119, 139 | N-(2-nosyl)-L-leucine | L-alanine methyl ester hydrochloride | 1,2-dibromoethane |
| 120 | N-(2-nosyl)-L-leucine | Methyl (S)-2-amino-3-cyclohexylpropionate hydrochloride | 1,2-dibromoethane |
| 121, 140 | N-(2-nosyl)-L-alanine | L-leucine methyl ester hydrochloride | 1,2-dibromoethane |
| 122 | (S)-3-cyclohexyl-2-(o-nitrophenylsulfonylamino) propionic acid | L-leucine methyl ester hydrochloride | 1,2-dibromoethane |
| 123 | N-(2-nosyl)-L-norleucine | Methyl (S)-2-amino-4,4-dimethylvalerate hydrochloride | 1,2-dibromoethane |
| 126 | N-(2-nosyl)-L-leucine | L-isoleucine methyl ester hydrochloride | 1,2-dibromoethane |
| 127 | N-(2-nosyl)-L-isoleucine | L-leucine methyl ester hydrochloride | 1,2-dibromoethane |
| 128 | N-(2-nosyl)-L-norvaline | L-leucine methyl ester hydrochloride | 1,2-dibromoethane |
| 129 | N-(2-nosyl)-L-norvaline | Methyl (S)-2-aminohexanoate hydrochloride | 1,2-dibromoethane |
| 130 | N-(2-nosyl)-L-norvaline | Methyl (S)-2-aminovalerate | 1,2-dibromoethane |

TABLE 1-continued

| | Starting material for precursor I | | |
|---|---|---|---|
| Ex./Cmpd. # | Precursor Ia | Precursor Ib | Precursor Ic |
| 131 | N-(2-nosyl)-L-leucine | Methyl (S)-2-aminovalerate hydrochloride | 1,2-dibromoethane |
| 132 | N-(2-nosyl)-L-norvaline | Methyl (S)-2-amino-3-cyclopropylpropionate hydrochloride | 1,2-dibromoethane |

All starting materials for precursor I have been obtained from Sigma-Aldrich, except (S)-2-Amino-3-cyclohexylpropionic acid, (S)-2-Amino-3-cyclopropylpropionic acid, Methyl (S)-2-aminovalerate hydrochloride, Methyl (S)-2-aminohexanoate hydrochloride and Methyl (S)-2-amino-3-cyclohexylpropionate hydrochloride, (all Combi-Blocks), Methyl (S)-2-amino-4,4-dimethylvalerate hydrochloride (Enamine BB), and Methyl (S)-2-amino-3-cyclopropylpropionate hydrochloride (Activate Scientific).

TABLE 2

Compounds made through Method A

| Structure | Ex. Cmpd # | name | Precursor II synthesis | Characteristic ¹H NMR signals (300 MHz) | Activity |
|---|---|---|---|---|---|
| 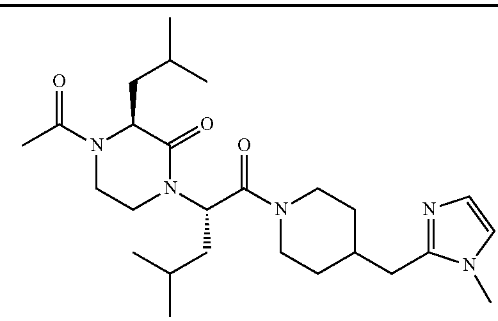 | 1 | (S)-1-[(S)-3-Methyl-1-({4-[(1-methyl-1H-imidazol-2-yl)methyl]-1-piperidyl}carbonyl)butyl]-4-acetyl-3-isobutyl-2-piperazinone | 1-methyl-2-[(4-piperidyl)methyl]-1H-imidazole (Enamine BB) | CD₃OD: δ 6.98, (s, 1H), 3.64 (br s, 3H), 2.17 (m, 3H), 0.98 (m, 12H) | +++ |
| 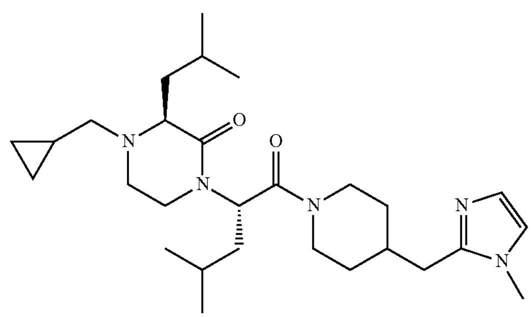 [SMILES: CC(C)C[C@H]1C(=O)N([C@@H](CC(C)C)C(=O)N2CCC(Cc3nccn3C)CC2)CCN1CC1CC1] | 2 | (S)-1-[(S)-3-Methyl-1-({4-[(1-methyl-1H-imidazol-2-yl)methyl]-1-piperidyl}carbonyl)butyl]-4-(cyclopropylmethyl)-3-isobutyl-2-piperazinone | 1-methyl-2-[(4-piperidyl)methyl]-1H-imidazole (Enamine BB) | CD₃OD: δ 6.97 (s, 1H), 3.64 (br s, 3H), 0.95 (m, 14H), 0.15 (m, 2H) | +++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 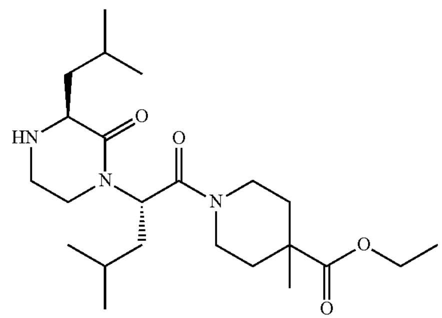 [SMILES: CCOC(=O)C1(C)CCN(C(=O)[C@H](CC(C)C)N2CCN[C@@H](CC(C)C)C2=O)CC1] | 3 | Ethyl 1-{(S)-2-[(S)-3-isobutyl-2-oxo-1-piperazinyl]-4-methylvaleryl}-4-methyl-4-piperidine-carboxylate | Ethyl 4-methyl-4-piperidine-carboxylate (Combi-Blocks) | CD$_3$OD: δ 5.47 (m, 1H), 2.11-1.93 (br m, 2H), 1.22-1.12 (m, 6H), 0.88 (m, 12H) | ++ |
| 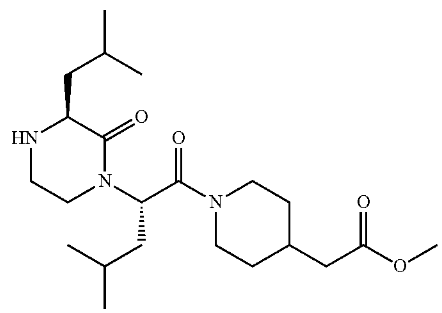 [SMILES: COC(=O)CC1CCN(C(=O)[C@H](CC(C)C)N2CCN[C@@H](CC(C)C)C2=O)CC1] | 4 | Methyl (1-{(S)-2-[(S)-3-isobutyl-2-oxo-1-piperazinyl]-4-methylvaleryl}-4-piperidyl)acetate | Methyl (4-piperidyl)acetate (Combi-Blocks) | CD$_3$OD: δ 5.55 (m, 1H), 4.47 (t, 1H), 3.66 (s, 3H), 2.30 (d, 2H), 0.95 (m, 12H) | ++ |
| 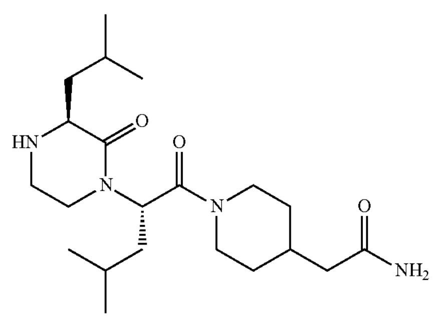 [SMILES: CC(C)C[C@@H]1NCCN([C@@H](CC(C)C)C(=O)N2CCC(CC(N)=O)CC2)C1=O] | 5 | (1-{(S)-2-[(S)-3-Isobutyl-2-oxo-1-piperazinyl]-4-methylvaleryl}-4-piperidyl)acetamide | (4-Piperidyl)acetamide (Enamine BB) | CD$_3$OD: δ 5.56 (m, 1H), 4.47 (t, 1H), 2.15 (m, 2H), 2.03 (m, 1H), 0.95 (m, 12H) | +* |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 6 | 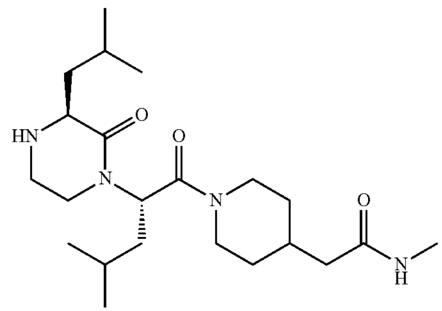 [SMILES: CNC(=O)CC1CCN(C(=O)[C@H](CC(C)C)N2CCN[C@@H](CC(C)C)C2=O)CC1] | (S)-1-[(S)-3-Methyl-1-({4-[2-(methylamino)-oxoethyl]-1-piperidyl}carbonyl)butyl]-3-isobutyl-2-piperazinone | 1-(Methylamino)-2-(4-piperidyl)-1-ethanone (Enamine BB) | CD$_3$OD: δ 5.55 (m, 1H), 4.46 (t, 1H), 2.71 (s, 3H), 1.24-1.03 (br m, 3H), 0.95 (m, 12H) | +* |
| 7 | 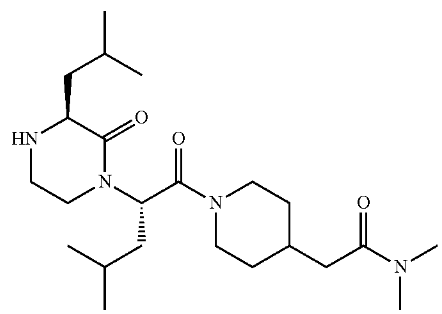 [SMILES: CC(C)C[C@@H]1NCCN([C@@H](CC(C)C)C(=O)N2CCC(CC(=O)N(C)C)CC2)C1=O] | (S)-1-(S)-1-({4-[2-(Dimethylamino)ethyl]-1-piperidyl}carbonyl)-3-methylbutyl]-3-isobutyl-2-piperazinone | tert-Butyl 4-(2-hydroxyethyl)-1-piperidine-carboxylate; DMP oxidation to aldehyde, reductive amination with dimethylamine, BOC removal | CD$_3$OD: δ 5.55 (m, 1H), 4.46 (t, 1H), 2.43 (t, 2H), 2.29 (s, 6H), 0.95 (m, 12H) | ++++ |
| 8 | 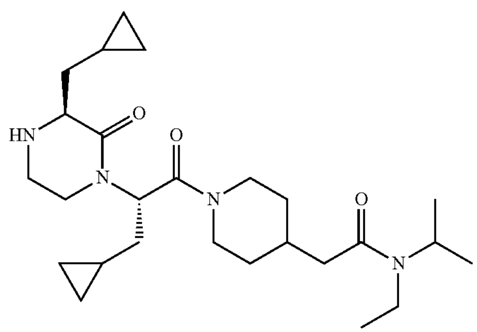 [SMILES: CCN(C(=O)CC1CCN(C(=O)[C@H](CC2CC2)N2CCN[C@@H](CC3CC3)C2=O)CC1)C(C)C] | (S)-1-[(S)-2-(4-{2-[N-Ethyl(isopropyl)amino]-2-oxoethyl}-1-piperidyl)-1-(cyclopropylmethyl)-2-oxoethyl]-3-(cyclopropylmethyl)-2-piperazinone | (1-tert-Butoxycarbonyl-4-piperidyl)acetic acid: amide coupling with N-Ethyl(isopropyl)amine, BOC removal | CD$_3$OD: δ 5.55 (m, 1H), 1.27-1.08 (br m, 12H), 0.47 (m, 4H), 0.13 (m, 4H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 9 | [structure] | (S)-1-[(S)-3-Methyl-1-({4-[(1-methyl-1H-imidazol-2-yl)methyl]-1-piperidyl}carbonyl)butyl]-3-isobutyl-4-(2-methoxyethyl)-2-piperazinone | 1-methyl-2-[(4-piperidyl)methyl]-1H-imidazole (Enamine BB) | CD₃OD: δ 6.98 (s, 1H), 6.86 (s, 1H), 5.55 (m, 1H), 3.64, (s, 3H), 3.32 (m, 3H), 0.95 (m, 14H) | +++ |
| 10 | [structure] | (S)-1-{(S)-3-Methyl-1-[(4-phenethyl-1-piperidyl)carbonyl]butyl}-3-isobutyl-2-piperazinone | 4-phenethyl-piperidine (Enamine BB) | CD₃OD: δ 7.29-7.11 (br m, 5H), 5.57 (m, 1H), 1.81 (m, 4H), 1.57 (m, 7H), 0.96 (m, 13H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 11 | 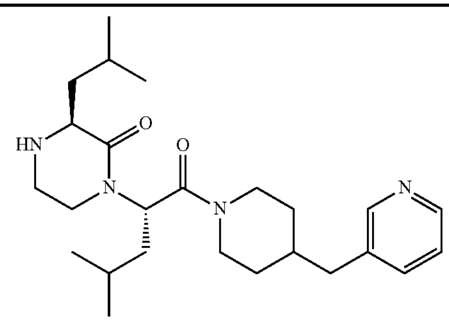 | (S)-1-[(S)-3-Methyl-1-({4-[(3-pyridyl)methyl]-1-piperidyl}carbonyl)butyl]-3-isobutyl-2-piperazinone | 3-(piperidin-4-ylmethyl)pyridine (Enamine BB) | CD$_3$OD: δ 8.39 (m, 2H), 7.41 (m, 1H), 7.18 (m, 1H), 5.53 (m, 1H), 4.51 (t, 1H), 0.89 (m, 14H) | +++ |
| 12 | 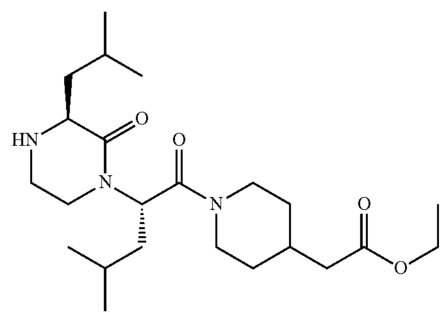 [SMILES: CCOC(=O)CC1CCN(C(=O)[C@H](CC(C)C)N2CCN[C@@H](CC(C)C)C2=O)CC1] | Ethyl (1-{(S)-2-[(S)-3-isobutyl-2-oxo-1-piperazinyl]-4-methylvaleryl}-4-piperidyl)acetate | Ethyl (4-piperidyl)acetate (Combi-Blocks) | CD$_3$OD: δ 5.64 (m, 1H), 4.56 (t, 1H), 4.21 (q, 2H), 2.37 (m, 2H), 1.33 (t, 3H), 1.04 (m, 12H) | +++ |
| 13 | 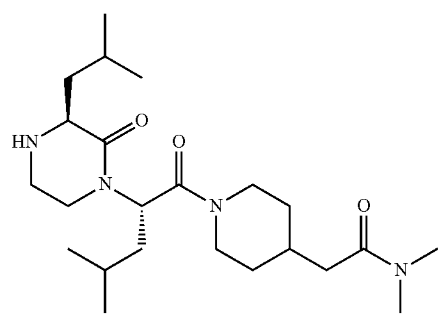 [SMILES: CC(C)C[C@@H]1NCCN([C@@H](CC(C)C)C(=O)N2CCC(CC(=O)N(C)C)CC2)C1=O] | (S)-1-[(S)-1-({4-[2-(Dimethylamino)-2-oxoethyl]-1-piperidyl}carbonyl)-3-methylbutyl]-3-isobutyl-2-piperazinone | 1-(Dimethylamino)-2-(4-piperidyl)-1-ethanone (Enamine BB) | CD$_3$OD: δ 5.61 (m, 1H), 4.53 (t, 1H), 3.12 (s, 3H), 2.99 (s, 3H), 2.40 (m, 3H), 1.01 (m, 12H) | +* |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 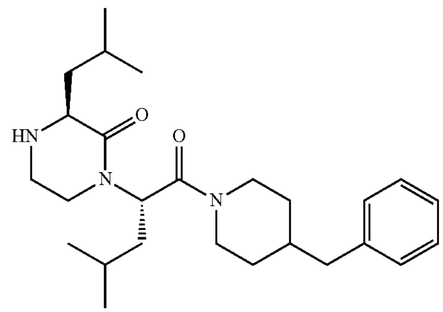 [SMILES: CC(C)C[C@@H]1NCCN([C@@H](CC(C)C)C(=O)N2CCC(Cc3ccccc3)CC2)C1=O] | 14 | (S)-1-{(S)-1-[(4-Benzyl-1-piperidyl)carbonyl]-3-methylbutyl}-3-isobutyl-2-piperazinone | 4-Benzyl-piperidine | CD$_3$OD: δ 7.18 (m, 5H), 5.57 (m, 1H), 4.52 (t, 1H), 1.67 (m, 10H), 0.93 (m, 12H). | +++ |
| 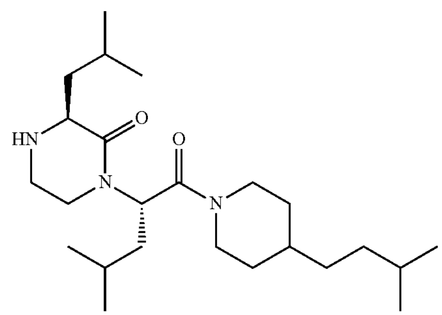 | 15 | (S)-1-{(S)-1-[(4-Isopentyl-1-piperidyl)carbonyl]-3-methylbutyl}-3-isobutyl-2-piperazinone | 4-Isopentyl-piperidine (Enamine BB) | CD$_3$OD: δ 5.54 (m, 1H), 4.48 (t, 1H), 1.58 (m, 12H), 1.14 (m, 4H), 0.93 (m, 12H), 0.81 (m, 6H). | +++ |
| 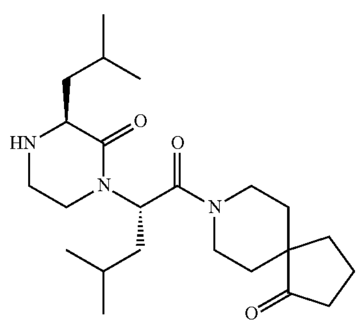 [SMILES: CC(C)C[C@@H]1NCCN([C@@H](CC(C)C)C(=O)N2CCC3(CCCC3=O)CC2)C1=O] | 16 | (S)-1-[(S)-1-{(8-Azaspiro[4.5]decan-8-oyl)carbonyl]-3-methylbutyl}-3-isobutyl-2-piperazinone | 8-azaspiro[4.5]decan-1-one (Enamine BB) | CDCl$_3$: δ 5.56 (q, 1H), 4.45 (t, 1H), 2.35 (m 2H), 0.95, (m, 12H). | ++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 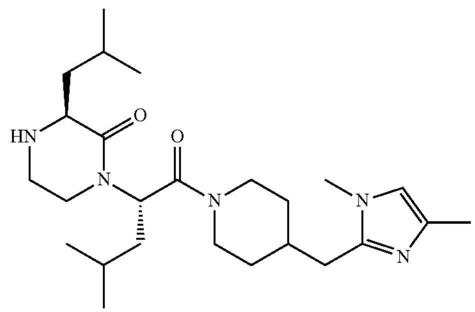 [SMILES: Cc1cn(C)c(CC2CCN(C(=O)[C@H](CC(C)C)N3CCN[C@@H](CC(C)C)C3=O)CC2)n1] | 17 | (S)-1-[(S)-3-Methyl-1-({4-[(1-methyl-1H-imidazol-2-yl)methyl]-1-piperidyl}carbonyl)butyl]-3-isobutyl-2-piperazinone | 2-(4-piperidyl)ethanol; tBOC protection, oxidation to aldehyde, N-methyl imidazole construction (Amide formation, oxidation, cyclization), tBOC removal | CD$_3$OD: δ 6.65 (s, 1H), 5.56 (q, 1H), 4.57 (t, 1H), 3.51 (s, 3H), 2.15 (s, 3H), 0.95 (m, 12H). | ++ |
| 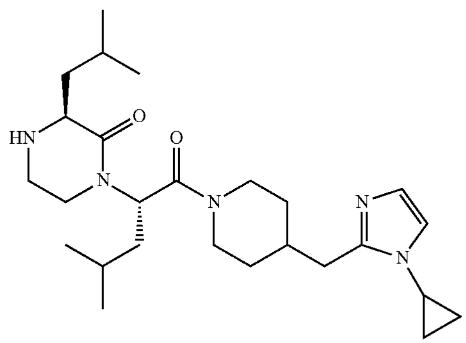 [SMILES: CC(C)C[C@@H]1NCCN([C@@H](CC(C)C)C(=O)N2CCC(Cc3nccn3C3CC3)CC2)C1=O] | 18 | (S)-1-Cyclopropyl-1-({4-[(1H-imidazol-2-yl)methyl]-1-piperidyl}carbonyl)-3-methylbutyl]-3-isobutyl-2-piperazinone | 2-(4-piperidyl)ethanol; tBOC protection, oxidation to aldehyde, N-cyclopropylamine imidazole construction (with ammonia, cyclopropylamine and glyoxal), tBOC removal | CD$_3$OD: δ, 6.95 (s, 1H), 6.82 (s, 1H), 5.50 (q, 1H), 4.45 (t, 1H), 0.95, (m, 16H). | ++ |
| 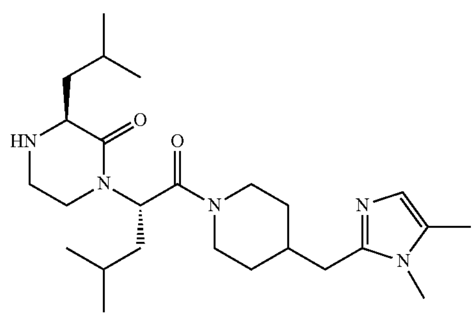 [SMILES: Cc1cnc(CC2CCN(C(=O)[C@H](CC(C)C)N3CCN[C@@H](CC(C)C)C3=O)CC2)n1C] | 19 | (S)-1-[(S)-3-Methyl-1-({4-[(1-methyl-5-methyl-1H-imidazol-2-yl)methyl]-1-piperidyl}carbonyl)butyl]-3-isobutyl-2-piperazinone | 2-(4-piperidyl)ethanol; tBOC protection, oxidation to aldehyde, N-methyl imidazole construction (Amide formation, oxidation, cydization, tBOC removal | CD$_3$OD: δ, 6.75 (s, 1H), 5.55 (q, 1H), 4.45 (t, 1H), 3.55 (s, 3H), 2.50 (s, 3H), 0.96, (m, 12H). | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 20 | 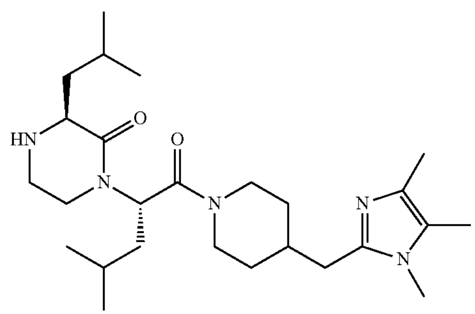 [SMILES: Cc1nc(CC2CCN(C(=O)[C@H](CC(C)C)N3CCN[C@@H](CC(C)C)C3=O)CC2)n(C)c1C] | (S)-1-[(S)-3-Methyl-1-({4-[(1-methyl-4,5-dimethyl-1H-imidazol-2-yl)methyl]-1-piperidyl}carbonyl)butyl]-3-isobutyl-2-piperazinone | 2-(4-piperidyl)ethanol; tBOC protection, DMP oxidation to aldehyde, imidazole formation with biacetyl, NH₄OAc and methylamine, BOC removal. | ¹H NMR (CD₃OD) δ 0.89 (m, 12H), 1.22 (m, 1H), 1.67 (m, 8H), 2.67 (m, 3H), 3.01 (m, 4H), 3.42 (m, 2H), 3.54 (s, 3H), 5.55 (m, 1H). | +++ |
| 21 | 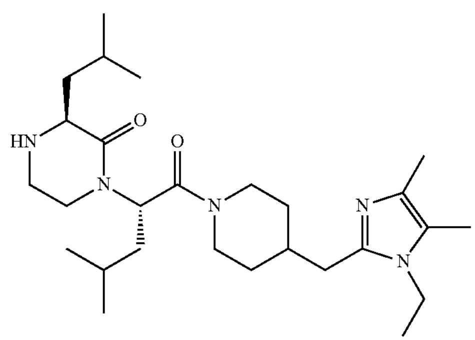 [SMILES: CCn1c(CC2CCN(C(=O)[C@H](CC(C)C)N3CCN[C@@H](CC(C)C)C3=O)CC2)nc(C)c1C] | (S)-1-[(S)-1-({4-[(1-Ethyl-4,5-dimethyl-1H-imidazol-2-yl)methyl]-1-piperidyl}carbonyl)-3-methylbutyl]-3-isobutyl-2-piperazinone | 2-(4-piperidyl)ethanol; tBOC protection, DMP oxidation to aldehyde, imidazole formation with biacetyl, NH₄OAc and ethylamine, BOC removal. | ¹H NMR (CD₃OD) δ 0.96 (m, 12H), 1.17 (m, 2H), 1.28 (m, 3H), 1.54 (m, 3H), 1.74 (m, 6H), 2.04 (m, 1H), 2.67 (m, 3H), 3.96 (m, 2H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 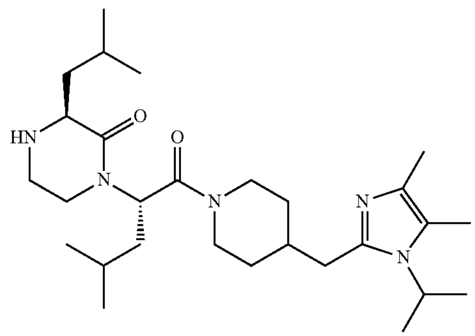 [SMILES: Cc1nc(CC2CCN(C(=O)[C@H](CC(C)C)N3CCN[C@@H](CC(C)C)C3=O)CC2)n(C(C)C)c1C] | 22 | (S)-1-[(S)-1-({4-[(1-Isopropyl-4,5-dimethyl-1H-imidazol-2-yl)methyl]-1-piperidyl}carbonyl)-3-methylbutyl]-2-piperazinone | 2-(4-piperidyl)ethanol; tBOC protection, DMP oxidation to aldehyde, imidazole formation with biacetyl, NH₄OAc and isopropylamine, BOC removal. | ¹H NMR (CD₃OD) δ 0.96 (m, 12H), 1.22 (m, 2H), 1.56 (m, 9H), 2.66 (m, 1H), 2.85 (m, 2H), 5.56 (m, 1H) | ++ |
| 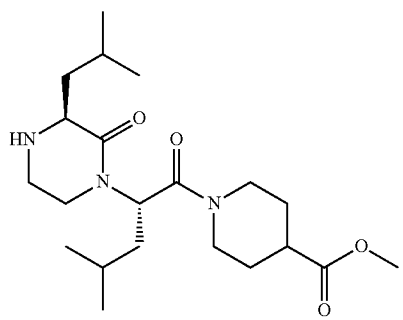 [SMILES: COC(=O)C1CCN(C(=O)[C@H](CC(C)C)N2CCN[C@@H](CC(C)C)C2=O)CC1] | 23 | Methyl 1-{(S)-2-[(S)-3-isobutyl-2-oxo-1-piperazinyl]-4-methylvaleryl}-4-piperidine-carboxylate | Methyl 4-piperidine-carboxylate | CD₃OD: δ 5.49 (m, 1H), 3.61 (m, 3H), 1.93-1.81 (br m, 2H), 0.88 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 24 | 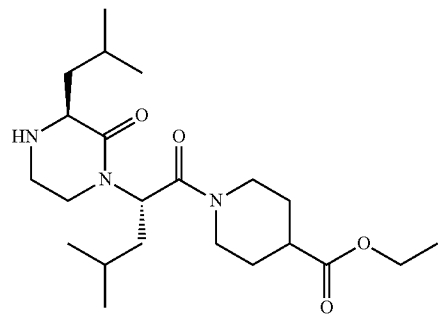 [SMILES: CCOC(=O)C1CCN(C(=O)[C@H](CC(C)C)N2CCN[C@@H](CC(C)C)C2=O)CC1] | Ethyl 1-[(S)-2-[(S)-3-isobutyl-2-oxo-1-piperazinyl]-4-methylvaleryl]-4-piperidine-carboxylate | Ethyl 4-piperidine-carboxylate | CD$_3$OD: δ 5.52 (m, 1H), 1.96-1.84 (br m, 2H), 1.21 (t, 3H), 0.91 (m, 12H) | +* |
| 25 | 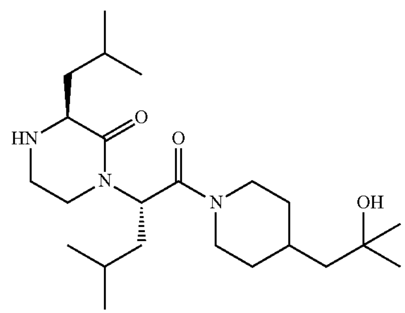 [SMILES: CC(C)C[C@@H]1NCCN([C@@H](CC(C)C)C(=O)N2CCC(CC(C)(C)O)CC2)C1=O] | (S)-1-[(S)-1-{[4-(2-Hydroxy-2-methylpropyl)-1-piperidyl]carbonyl}-3-methylbutyl]-3-isobutyl-2-piperazinone | Methyl (4-piperidyl)acetate; benzyl protection, di-methylation, benzyl removal | CD$_3$OD: δ 5.57 (m, 1H), 4.43 (m, 1H), 1.23 (s, 6H), 0.97 (m, 12H) | ++ |
| 26 | 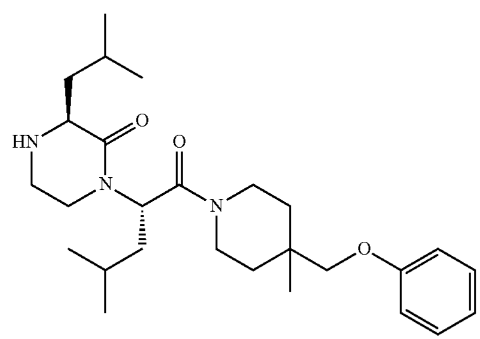 [SMILES: CC(C)C[C@@H]1NCCN([C@@H](CC(C)C)C(=O)N2CCC(C)(COc3ccccc3)CC2)C1=O] | (S)-1-[(S)-3-Methyl-1-{[4-methyl-4-(phenoxymethyl)-1-piperidyl]carbonyl}butyl]-3-isobutyl-2-piperazinone | tert-Butyl 4-(hydroxymethyl)-4-methyl-1-piperidine-carboxylate (Combi-Blocks); activation of alcohol, substitution with phenol, tBOC removal | CD$_3$OD: δ 7.26 (t, 2H), 5.60 (m, 1H), 1.17 (m, 3H), 0.97 (m, 12H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 27 | 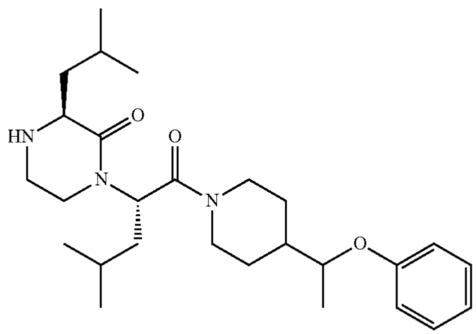 [SMILES: CC(C)C[C@@H]1NCCN([C@@H](CC(C)C)C(=O)N2CCC(C(C)Oc3ccccc3)CC2)C1=O] | (S)-1-[(S)-3-Methyl-1-{[4-(1-phenoxyethyl)-1-piperidyl]carbonyl}butyl]-3-isobutyl-2-piperazinone | tert-Butyl 4-(1-hydroxyethyl)-1-piperidine-carboxylate (AstaTech); activation of alcohol, substitution with phenol, tBOC removal | CD$_3$OD: δ 7.26 (t, 2H), 5.59 (m, 1H), 1.26 (d, 3H), 0.96 (m, 12H) | +++ |
| 28 | 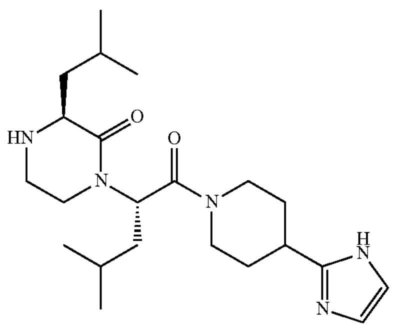 [SMILES: CC(C)C[C@@H]1NCCN([C@@H](CC(C)C)C(=O)N2CCC(c3ncc[nH]3)CC2)C1=O] | (S)-1-[(S)-1-{[4-(1H-Imidazol-2-yl)-1-piperidyl]carbonyl}-3-methylbutyl]-3-isobutyl-2-piperazinone | 2-(4-Piperidyl)-1H-imidazole (Enamine BB) | CD$_3$OD: δ 6.95 (s, 2H), 5.59 (m, 1H), 4.54 (m, 1H), 2.01 (d, 2H), 0.95 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 29 | 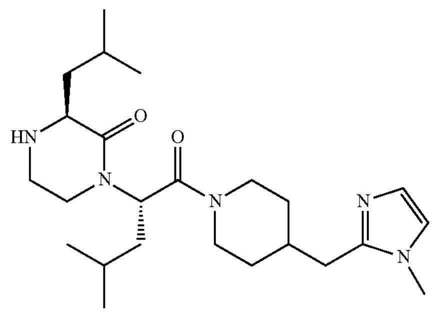 | (S)-1-[(S)-3-Methyl-1-({4-[(1-methyl-1H-imidazol-2-yl)methyl]-1-piperidyl}carbonyl)butyl]-3-isobutyl-2-piperazinone | 1-methyl-2-[(4-piperidyl)methyl]-1H-imidazole (Enamine BB) | CD$_3$OD: δ 6.98 (s, 1H), 6.86 (m, 1H), 5.55 (m, 1H), 4.47 (t, 1H), 4.07 (m, 1H), 3.64 (s, 3H), 3.42 (m, 1H), 3.33 (m, 1H), 3.19-2.98 (br m, 2H), 2.91 (m, 1H), 2.77-2.57 (br m, 3H), 2.04 (m, 1H), 1.92-1.02 (br m, 11H), 0.95 (m, 12H) | +++ |
| 30 | 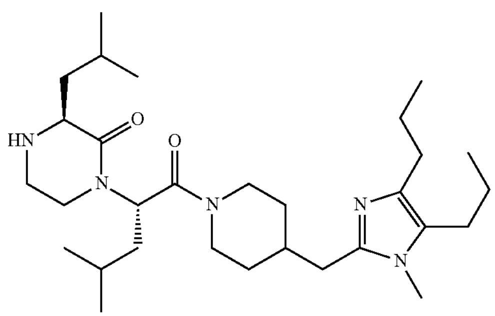 [SMILES: CCCc1nc(CC2CCN(C(=O)[C@H](CC(C)C)N3CCN[C@@H](CC(C)C)C3=O)CC2)n(C)c1CCC] | (S)-1-[(S)-3-Methyl-1-({4-[(1-methyl-4,5-dipropyl-1H-imidazol-2-yl)methyl]-1-piperidyl}carbonyl)butyl]-3-isobutyl-2-piperazinone | p-toluene-sulfonylmethyl isocyanide; alkylation with 1-iodopropane in the presence of NaOH and NBu$_4$I, Van Leusen imidazole formation using butyraldehyde and methylamine, deprotonation with nBuLi followed by addition to tert-butyl 4-formyl-1-piperidine-carboxylate, mesylation of alcohol with methanesulfonyl chloride, catalytic hydrogenation using Pd/C and H$_2$ at 40 psi, BOC removal | CD$_3$OD: δ 5.55 (m, 1H), 4.49 (t, 1H), 3.58 (s, 3H), 2.57 (t, 2H), 2.50 (t, 2H), 2.03 (m, 1H), 0.95 (m, 18H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 31 | 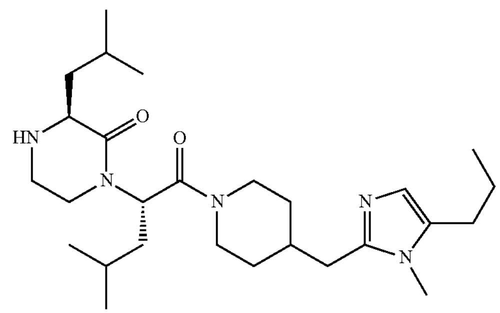 [SMILES: CCCc1cnc(CC2CCN(C(=O)[C@H](CC(C)C)N3CCN[C@@H](CC(C)C)C3=O)CC2)n1C] | (S)-1-[(S)-3-Methyl-1-({4-[(1-methyl-5-propyl-1H-imidazol-2-yl)methyl]-1-piperidyl}carbonyl)butyl]-3-isobutyl-2-piperazinone | p-toluenesulfonyl methyl isocyanide; Van Leusen imidazole formation using butyraldehyde and methylamine, deprotonation with nBuLi followed by addition to tert-butyl 4-formyl-1-piperidine-carboxylate, mesylation of alcohol with methanesulfonyl chloride, elimination of mesylate at 110° C., catalytic hydrogenation using Pd/C and H$_2$ at 40 psi, BOC removal | CD$_3$OD: δ 6.66 (s, 1H), 5.55 (m, 1H), 4.47 (t, 1H), 3.52 (s, 3H), 2.54 (t, 2H), 2.02 (m, 1H), 0.97 (m, 15H) | +++ |
| 32 | 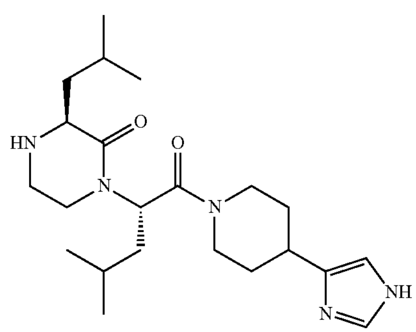 [SMILES: CC(C)C[C@@H]1NCCN([C@@H](CC(C)C)C(=O)N2CCC(c3c[nH]cn3)CC2)C1=O] | (S)-1-[(S)-1-{[4-(1H-Imidazol-4-yl)-1-piperidyl]carbonyl}-3-methylbutyl]-3-isobutyl-2-piperazinone | 4-(4-Piperidyl)-1H-imidazole (Enamine BB) | CD$_3$OD: δ 7.68 (s, 1H), 6.87 (s, 1H), 5.59 (m, 1H), 4.54 (m, 1H), 2.03 (d, 2H), 0.95 (m, 12H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 33 | 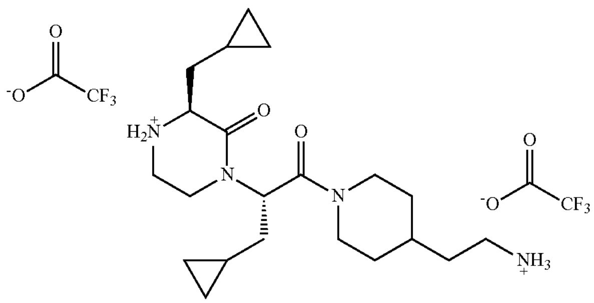 | (S)-1-{(S)-2-[4-(2-Aminoethyl)-1-piperidyl]-1-(cyclopropylmethyl)-2-oxoethyl}-3-(cyclopropylmethyl)-2-piperazinone (2TFA) | 4-[2-(tert-Butoxycarbonyl-aminoethyl]piperidine (Combi-Blocks) | CD$_3$OD: δ 5.54 (m, 1H), 2.99 (m, 2H), 0.76–0.43 (br m, 5H), 0.31–0.096 (br m, 4H) | ++ |
| 34 | 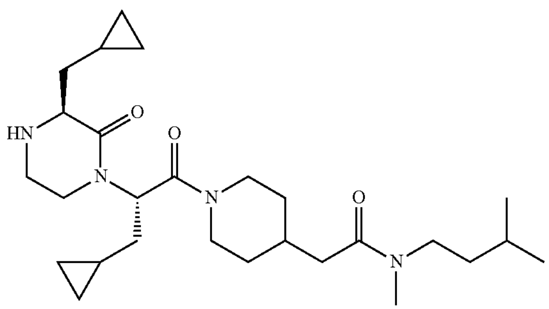 [SMILES: CC(C)CCN(C)C(=O)CC1CCN(C(=O)[C@H](CC2CC2)N2CCN[C@@H](CC3CC3)C2=O)CC1] | (S)-1-{(S)-2-(4-{2-[N-Methyl(isopentyl)amino]-2-oxoethyl}-1-piperidyl)-1-(cyclopropylmethyl)-2-oxoethyl]-3-(cyclopropylmethyl)-2-piperazinone | (1-tert-Butoxycarbonyl-4-piperidyl)acetic acid: amide coupling with N-Methyl(isopentyl)amine, BOC removal | CD$_3$OD: δ 5.57 (m, 1H), 4.50 (t, 1H), 4.09 (m, 1H), 0.96 (m, 6H), 0.47 (m, 4H), 0.14 (m, 4H) | +* |
| 35 | 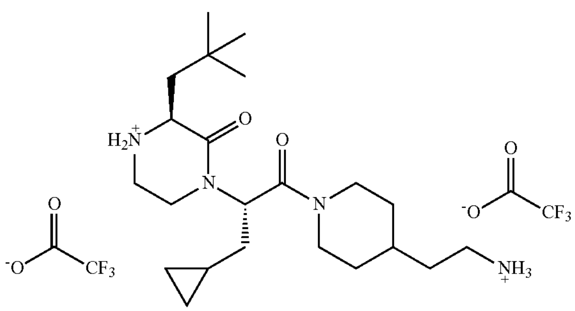 | (S)-1-{(S)-2-[4-(2-Aminoethyl)-1-piperidyl]-1-(cyclopropylmethyl)-2-oxoethyl]-3-neopentyl-2-piperazinone (2TFA) | 4-[2-(tert-Butoxycarbonylamino)ethyl]piperidine (Combi-Blocks) | CD$_3$OD: δ 5.52 (m, 1H), 4.49 (d, 1H), 1.03 (s, 9H), 0.69 (m, 1H), 0.50 (m, 2H), 0.16 (m, 2H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 36 | 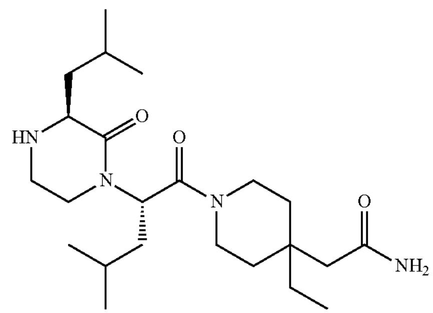 [SMILES: CCC1(CC(N)=O)CCN(C(=O)[C@H](CC(C)C)N2CCN[C@@H](CC(C)C)C2=O)CC1] | (1-{(S)-2-[(S)-3-Isobutyl-2-oxo-1-piperazinyl]-4-methylvaleryl}-4-ethyl-4-piperidyl)acetamide | 1-Boc-4-piperidone, Meldrum's acid condensation, Grignard reaction, amide formation, tBOC removal | CDCl3: δ, 5.70 (m, 1H), 5.50 (t, 1H), 2.18 (2s, 2H), 0.95, (m, 15H). | ++ |
| 37 | 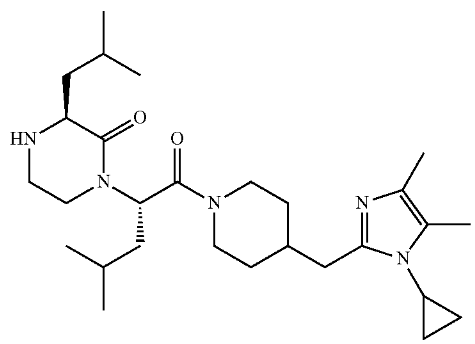 [SMILES: Cc1nc(CC2CCN(C(=O)[C@H](CC(C)C)N3CCN[C@@H](CC(C)C)C3=O)CC2)n(C2CC2)c1C] | (S)-1-[(S)-1-({4-[(1-Cyclopropyl-4,5-dimethyl-1H-imidazol-2-yl)methyl]-1-piperidyl}-carbonyl)-3-methylbutyl]-3-isobutyl-2-piperazinone | 2-(4-piperidyl)ethanol; tBOC protection, DMP oxidation to aldehyde, imidazole formation with biacetyl, NH4OAc and cyclopropylamine, BOC removal. | ¹H NMR (CD3OD) δ 0.96 (m, 12H), 1.17 (m, 6H), 1.65 (m, 8H), 2.71 (m, 3H), 5.56 (m, 1H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 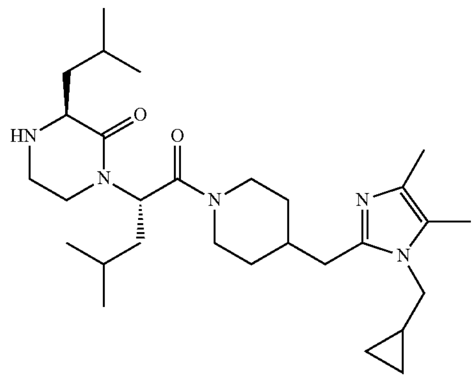 [SMILES: Cc1nc(CC2CCN(C(=O)[C@H](CC(C)C)N3CCN[C@@H](CC(C)C)C3=O)CC2)n(CC2CC2)c1C] | 38 | (S)-1-[(S)-1-[(4-{[1-(Cyclopropylmethyl)-4,5-dimethyl-1H-imidazol-2-yl]methyl}-1-piperidyl)carbonyl]-3-methylbutyl]-2-piperazinone | 2-(4-piperidyl)ethanol; tBOC protection, DMP oxidation to aldehyde, imidazole formation with biacetyl, NH₄OAc and cyclopropyl-methanamine, BOC removal. | ¹H NMR (CD₃OD) δ 0.38 (m, 2H), 0.61 (m, 2H), 0.95 (m, 12H), 2.61 (m, 3H), 3.82 (m, 2H), 5.56 (m, 1H) | +++ |
| 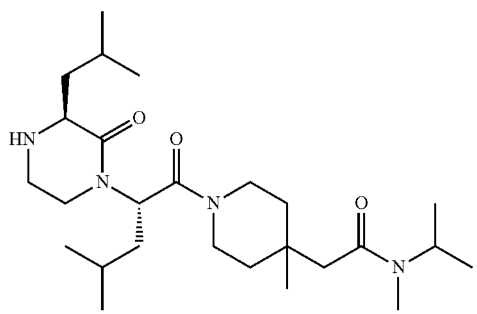 [SMILES: CC(C)C[C@@H]1NCCN([C@@H](CC(C)C)C(=O)N2CCC(C)(CC(=O)N(C)C(C)C)CC2)C1=O] | 39 | (S)-1-[(S)-1-[(4-{2-[N-Methyl(isopentyl)amino]-2-oxoethyl}-4-methyl-1-piperidyl)carbonyl]-3-methylbutyl]-2-piperazinone | (4-Methyl-1-tert-butoxycarbonyl-4-piperidyl)acetic acid (AstaTech) and N,3-dimethylbutan-1-amine; amide formation, BOC removal. | 1H NMR (CD₃OD) δ 0.96 (m 18H), 1.15 (m, 3H), 1.62 (m, 14H), 3.56 (m, 7H), 5.56 (m, 1H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 40 | 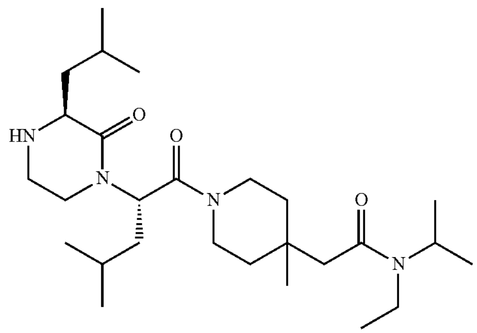 [SMILES: CCN(C(=O)CC1(C)CCN(C(=O)[C@H](CC(C)C)N2CCN[C@@H](CC(C)C)C2=O)CC1)C(C)C] | (S)-1-[(S)-1-[(4-{2-[N-Ethyl(isopropyl)amino]-2-oxoethyl}-4-methyl-1-piperidyl)carbonyl]-3-methylbutyl]-2-piperazinone | (4-Methyl-1-tert-butoxycarbonyl-4-piperidyl)acetic acid (AstaTech) and N-Ethyl(isopropyl)amine; amide formation, BOC removal. | ¹H NMR (CD₃OD) δ 0.96 (m, 12H), 1.19 (m, 12H), 1.63 (m, 10H), 2.40 (m, 2H), 5.58 (m, 1H) | +* |
| 41 | 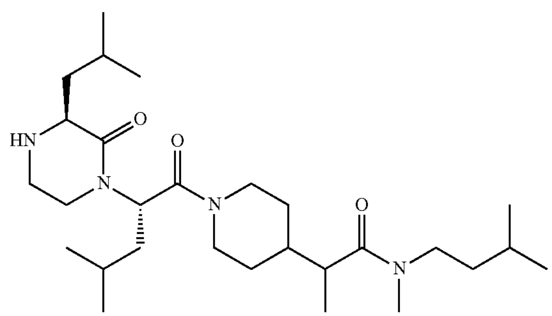 [SMILES: CC(C)CCN(C)C(=O)C(C)C1CCN(C(=O)[C@H](CC(C)C)N2CCN[C@@H](CC(C)C)C2=O)CC1] | (S)-1-[(S)-1-[(4-{2-[N-Methyl(isopentyl)amino]-1-methyl-2-oxoethyl}-1-piperidyl)carbonyl]-3-methylbutyl]-2-piperazinone | 2-(1-tert-Butoxycarbonyl-4-piperidyl)propionic acid (AstaTech) and N,3-dimethylbutan-1-amine; amide formation, BOC removal. | ¹H NMR (CD₃OD) δ 0.96 (m, 18H), 1.10 (m, 6H), 2.62 (m, 2H), 4.52 (m, 1H), 5.56 (m, 1H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 42 | 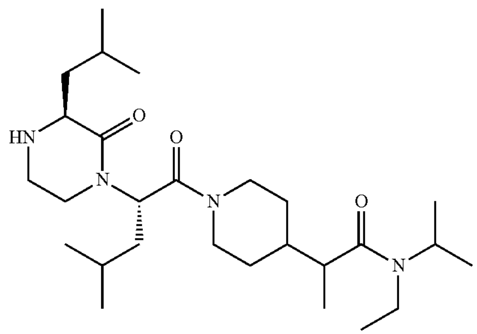 [SMILES: CCN(C(=O)C(C)C1CCN(C(=O)[C@H](CC(C)C)N2CCN[C@@H](CC(C)C)C2=O)CC1)C(C)C] | (S)-1-[(S)-1-(4-{2-[N-Ethyl(isopropyl)amino]-1-methyl-2-oxoethyl}-1-piperidyl)carbonyl]-3-methylbutyl]-3-isobutyl-2-piperazinone | 2-(1-tert-Butoxycarbonyl-4-piperidyl)propionic acid (AstaTech)and N-Ethyl(isopropyl)amine; amide formation, BOC removal. | ¹H NMR (CD$_3$OD) δ 0.96 (m, 14H), 1.17 (m, 16H), 1.68 (m, 10H), 5.56 (m, 1H) | +* |
| 43 | 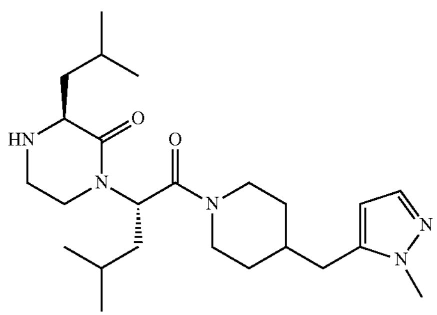 [SMILES: CC(C)C[C@@H]1NCCN([C@@H](CC(C)C)C(=O)N2CCC(Cc3ccnn3C)CC2)C1=O] | (S)-1-[(S)-3-Methyl-1-({4-[(2-methyl-2H-pyrazol-3-yl)methyl]-1-piperidyl}carbonyl)butyl]-3-isobutyl-2-piperazinone | 1-Methyl-5-[(4-piperidyl)methyl]-1H-pyrazole (Enamine) | CD$_3$OD: δ 7.35 (s, 1H), 6.09 (s, 1H), 5.55 (m, 1H), 4.48 (t, 1H), 3.78 (s, 3H), 2.88 (m, 1H), 0.95 (m, 12H) | +++ |
| 44 | 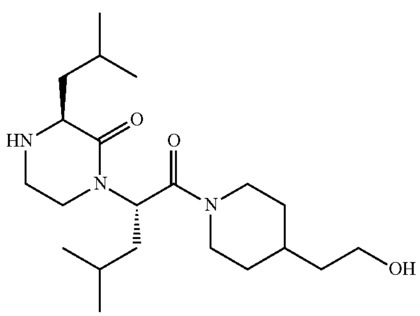 [SMILES: CC(C)C[C@@H]1NCCN([C@@H](CC(C)C)C(=O)N2CCC(CCO)CC2)C1=O] | (S)-1-[(S)-1-{[4-(2-Hydroxyethyl)-1-piperidyl]carbonyl}-3-methylbutyl]-3-isobutyl-2-piperazinone | 2-(4-Piperidyl)ethanol | CD$_3$OD: δ 5.56 (m, 1H), 4.47 (t, 1H), 3.62 (t, 3H), 2.67 (q, 1H), 0.95 (m, 12H) | ++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 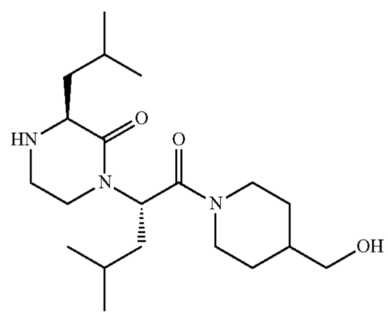 [SMILES: CC(C)C[C@@H]1NCCN([C@@H](CC(C)C)C(=O)N2CCC(CO)CC2)C1=O] | 45 | (S)-1-[(S)-1-{[4-(Hydroxymethyl)-1-piperidyl]carbonyl}-1-3-methylbutyl]-3-isobutyl-2-piperazinone | (4-Piperidyl) methanol | CD$_3$OD: δ 5.57 (m, 1H), 4.51 (t, 1H), 2.67 (q, 1H), 1.13 (m, 2H), 0.95 (m, 12H) | +* |
| 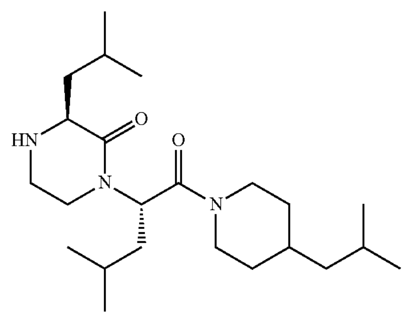 [SMILES: CC(C)CC1CCN(C(=O)[C@H](CC(C)C)N2CCN[C@@H](CC(C)C)C2=O)CC1] | 46 | (S)-1-[(S)-1-[(4-Isobutyl-1-piperidyl)carbonyl]-3-methylbutyl]-3-isobutyl-2-piperazinone | 4-Isobutylpiperidine (Enamine BB) | CD$_3$OD: δ 5.56 (m, 1H), 4.46 (t, 1H), 2.66 (q, 1H), 1.87-1.38 (br m, 10H), 1.20-1.02 (br m, 3H), 1.02-0.72 (br m, 19H) | +++ |
| 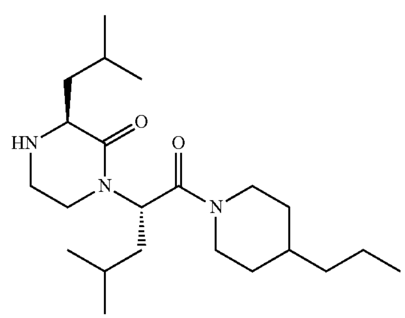 [SMILES: CCCC1CCN(C(=O)[C@H](CC(C)C)N2CCN[C@@H](CC(C)C)C2=O)CC1] | 47 | (S)-1-[(S)-3-Methyl-1-[(4-propyl-1-piperidyl)carbonyl]butyl]-3-isobutyl-2-piperazinone | 4-Propylpiperidine | CD$_3$OD: δ 5.56 (m, 1H), 4.46 (t, 1H), 2.64 (q, 1H), 1.92-1.44 (br m, 9H), 1.44-1.19 (br m, 4H), 1.19-0.81 (br m, 17H) | +++ |

TABLE 2-continued

Compounds made through Method A

| Ex. Cmpd # | Structure | name | Precursor II synthesis | Characteristic 1H NMR signals (300 MHz) | Activity |
|---|---|---|---|---|---|
| 48 | 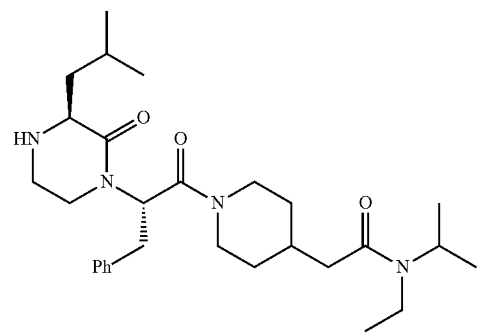 [SMILES: CCN(C(=O)CC1CCN(C(=O)[C@H](Cc2ccccc2)N2CCN[C@@H](CC(C)C)C2=O)CC1)C(C)C] | (S)-1-[(S)-2-(4-{2-[N-Ethyl(isopropyl)amino]-2-oxoethyl}-1-piperidyl)-1-benzyl-2-oxoethyl]-3-isobutyl-2-piperazinone | (1-tert-Butoxycarbonyl-4-piperidyl)acetic acid; amide coupling with N-Ethyl(isopropyl)amine, BOC removal | CD$_3$OD: δ 7.27 (m, 5H), 5.76 (m, 1H), 4.52 (m, 2H), 4.09 (m, 2H), 1.25-1.07 (br m, 12H), 0.96-0.80 (m, 8H) | ++ |
| 49 | 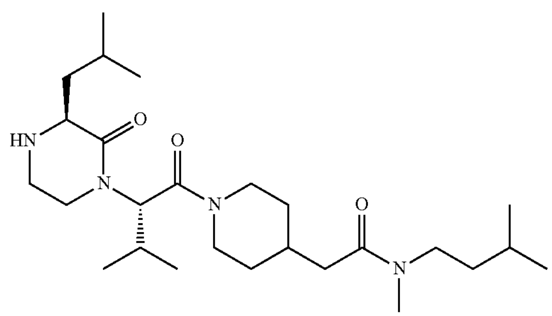 [SMILES: CC(C)CCN(C)C(=O)CC1CCN(C(=O)[C@H](C(C)C)N2CCN[C@@H](CC(C)C)C2=O)CC1] | (S)-1-[(S)-1-[(4-{2-[N-Methyl(isopentyl)amino]-2-oxoethyl}-1-piperidyl)carbonyl]-2-methylpropyl]-3-isobutyl-2-piperazinone | (1-tert-Butoxycarbonyl-4-piperidyl)acetic acid; amide coupling with N-Methyl(isopentyl)amine, BOC removal | CD$_3$OD: δ 5.13 (m, 1H), 4.52 (t, 1H), 4.25 (m, 1H), 1.01-0.84 (br m, 19H) | +* |

TABLE 2-continued

Compounds made through Method A

| Ex. Cmpd # | name | Precursor II synthesis | Characteristic ¹H NMR signals (300 MHz) | Activity |
|---|---|---|---|---|
| 50 | (S)-1-[(S)-1-[4-{2-[N-Ethyl(isopropyl)amino]-2-oxoethyl}-1-piperidyl)carbonyl]-2-methylpropyl]-3-isobutyl-2-piperazinone | (1-tert-Butoxycarbonyl-4-piperidyl)acetic acid; amide coupling with N-Ethyl(isopropyl)amine, BOC removal | CD$_3$OD: δ 5.13 (m, 1H), 4.55 (m, 2H), 4.22 (m, 2H), 1.26-1.07 (br m, 12H), 1.03-0.81 (br m, 14H) | +* |
| 51 | (2-(1-((S)-2-((S)-3-isobutyl-2-oxopiperazin-1-yl)-3-phenylpropanoyl)piperidin-4-yl)-N-isopentyl-N-methylacetamide | (1-tert-Butoxycarbonyl-4-piperidyl)acetic acid; amide coupling with N-Methyl(isopentyl)amine, BOC removal | CD$_3$OD: δ 7.25 (m, 5H), 5.77 (m, 1H), 4.47 (t, 1H), 4.01 (t, 1H), 1.01-0.81 (m, 14H) | ++ |
| 52 | (6S)-6-(5-{[(S)-1-({4-[2-(Dimethylamino)ethyl]-1-piperidyl}-carbonyl)-3-methylbutyl]-2-isobutyl-3-oxo-1-piperazinyl}pentylamino)-5-oxopentyl}-7-thia-2,4-diazabicyclo[3.3.0]octan-3-one | N,N-Dimethyl[2-(4-piperidyl)ethyl]amine (Enamine BB) | CD$_3$OD: δ 5.55 (m, 1H), 4.49 (m, 2H), 3.19 (m, 6H), 2.28 (s, 6H), 1.91-1.27 (br m, 25H), 1.0-0.87 (br m, 13H) | ++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 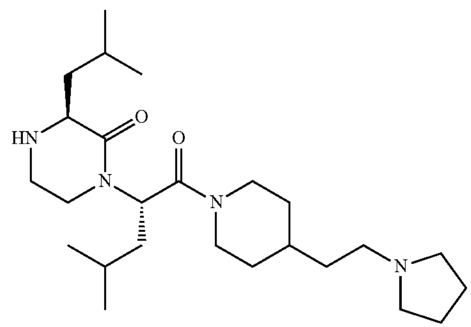 [SMILES: CC(C)C[C@@H]1NCCN([C@@H](CC(C)C)C(=O)N2CCC(CCN3CCCC3)CC2)C1=O] | 53 | (S)-1-[(S)-3-Methyl-1-({4-[2-(1-pyrrolidinyl)ethyl]-1-piperidyl}carbonyl)butyl]-3-isobutyl-2-piperazinone | tert-Butyl 4-(2-hydroxyethyl)-1-piperidine-carboxylate, oxidation to aldehyde, reductive amination with pyrrolidine, BOC deprotection | CD$_3$OD: δ 5.56 (m, 1H), 4.48 (t, 1H), 2.69 (m, 6H), 1.71 (m, 16H), 0.96 (m, 12H) | ++++ |
| 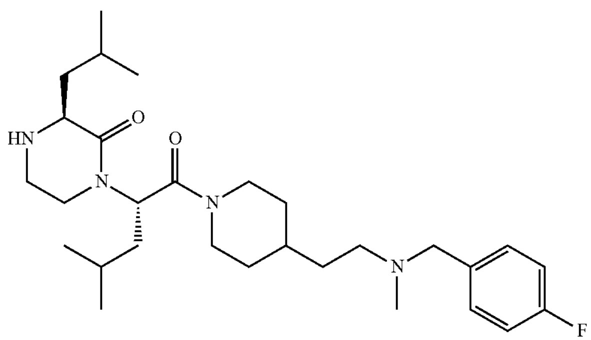 [SMILES: CC(C)C[C@@H]1NCCN([C@@H](CC(C)C)C(=O)N2CCC(CCN(C)Cc3ccc(F)cc3)CC2)C1=O] | 54 | (S)-1-(S)-1-{[4-(2-{N-Methyl[(p-fluorophenyl)methyl]amino}ethyl)-1-piperidyl]carbonyl}-3-methylbutyl]-3-isobutyl-2-piperazinone | tert-Butyl 4-(2-hydroxyethyl)-1-piperidine-carboxylate, oxidation to aldehyde, reductive amination with N-Methyl[(p-fluorophenyl)methyl]amine, BOC removal | CD$_3$OD: δ 7.35 (m, 2H), 7.07 (m, 2H), 5.58 (m, 1H), 4.46 (t, 1H), 3.53 (s, 2H), 2.23 (s, 3H), 0.97 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 55 | 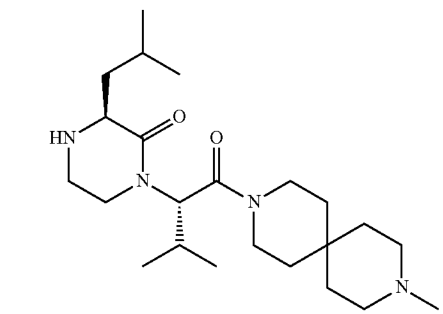 [SMILES: CC(C)C[C@@H]1NCCN([C@H](C(=O)N2CCC3(CCN(C)CC3)CC2)C(C)C)C1=O] | (S)-1-[(S)-3-Methyl-1-{(9-methyl-3,9-diaza-3-spiro[5.5]undecyl}carbonyl]butyl]-3-isobutyl-2-piperazinone | 3-Methyl-3,9-diazaspiro[5.5]undecane (Enamine BB) | CD$_3$OD: δ 5.56 (m, 1H), 2.50 (m, 4H), 2.33 (s, 3H), 1.62 (m, 14H), 0.95 (m, 12H) | +++ |
| 56 | 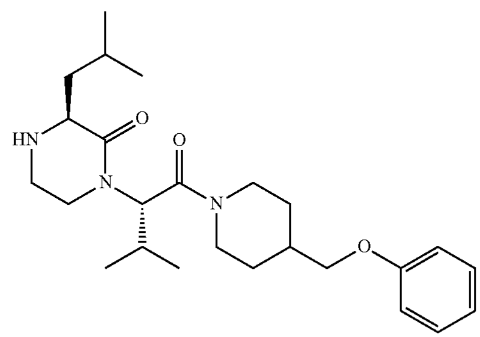 [SMILES: CC(C)C[C@@H]1NCCN([C@H](C(=O)N2CCC(COc3ccccc3)CC2)C(C)C)C1=O] | (S)-1-[(S)-3-Methyl-1-{[4-(phenoxymethyl)-1-piperidyl]carbonyl}butyl]-3-isobutyl-2-piperazinone | 4-(Phenoxymethyl)piperidine (Enamine BB) | CD$_3$OD: δ 7.28 (t, 2H), 6.93 (m, 3H), 5.62 (m, 1H), 4.57 (t, 1H), 3.87 (d, 2H), 0.99 (m, 12H) | +++ |
| 57 | 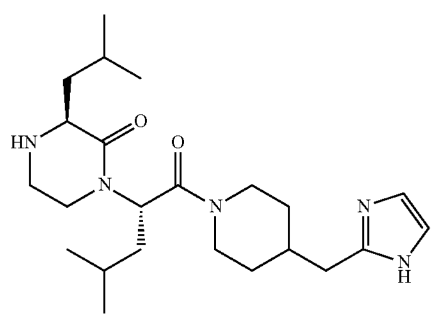 [SMILES: CC(C)C[C@@H]1NCCN([C@@H](CC(C)C)C(=O)N2CCC(Cc3ncc[nH]3)CC2)C1=O] | (S)-1-[(S)-1-({4-[(1H-Imidazol-2-yl)methyl]-1-piperidyl}carbonyl)-3-methylbutyl]-3-isobutyl-2-piperazinone | 2-[(4-Piperidyl)methyl]-1H-imidazole (Enamine BB) | CD$_3$OD: δ 6.86 (s, 2H), 5.45 (m, 1H), 4.37 (t, 1H), 2.57 (d, 2H), 0.85 (m, 12H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 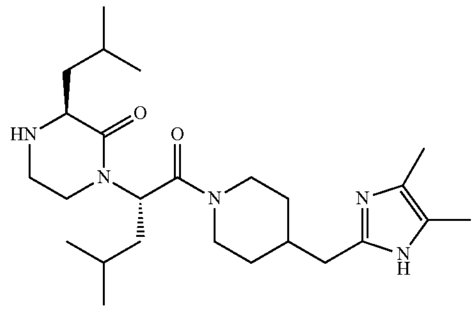 [SMILES: Cc1nc(CC2CCN(C(=O)[C@H](CC(C)C)N3CCN[C@@H](CC(C)C)C3=O)CC2)[nH]c1C] | 58 | (S)-1-[(S)-1-({4-[(4,5-Dimethyl-1H-imidazol-2-yl)methyl]-1-piperidyl}carbonyl)-3-methylbutyl]-3-isobutyl-2-piperazinone | tert-Butyl 4-(2-hydroxyethyl)-1-piperidine-carboxylate, oxidation to aldehyde, imidazole formation using ammonium acetate and 2,3-butanedione, BOC deprotection | CD$_3$OD: δ 5.37 (m, 1H), 4.29 (t, 1H), 2.36 (d, 2H), 1.90 (s, 6H), 0.77 (m, 12H) | +++ |
| 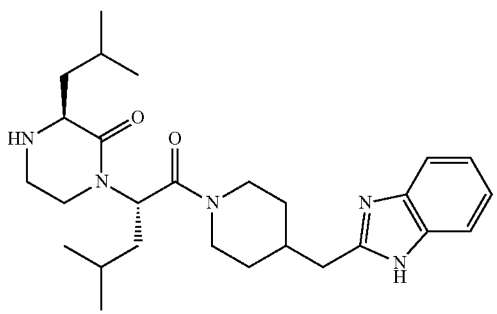 [SMILES: CC(C)C[C@@H]1NCCN([C@@H](CC(C)C)C(=O)N2CCC(Cc3nc4ccccc4[nH]3)CC2)C1=O] | 59 | (S)-1-[(S)-1-({4-[(1,3-Benzimidazol-2-yl)methyl]-1-piperidyl}carbonyl)-3-methylbutyl]-3-isobutyl-2-piperazinone | 2-[(4-Piperidyl)methyl]-1,3-benzimidazole (Enamine BB) | CD$_3$OD: δ 7.45 (dd, 2H), 7.14 (dd, 2H), 5.49 (m, 1H), 4.43 (t, 1H), 2.79 (d, 2H), 0.89 (m, 12H) | ++ |
| 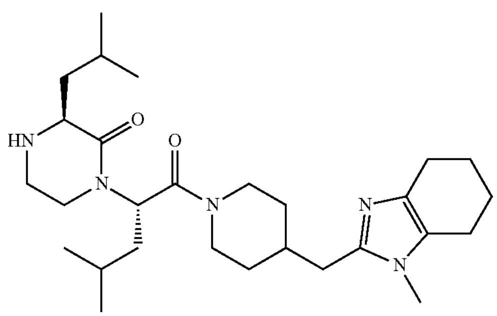 [SMILES: CC(C)C[C@@H]1NCCN([C@@H](CC(C)C)C(=O)N2CCC(Cc3nc4c(n3C)CCCC4)CC2)C1=O] | 60 | (S)-1-[(S)-3-Methyl-1-({4-[(1-methyl-1,3-diaza-4,5,6,7-tetrahydro-1H-inden-2-yl)methyl]-1-piperidyl}carbonyl)butyl]-3-isobutyl-2-piperazinone | tert-Butyl 4-(2-hydroxyethyl)-1-piperidine-carboxylate, oxidation to aldehyde, imidazole formation using ammonium acetate, methylamine and 1,2-cyclohexanedione, BOC deprotection | CD$_3$OD: δ 5.54 (m, 1H), 4.46 (t, 1H), 3.43 (s, 3H), 2.47 (d, 2H), 0.94 (m, 12H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 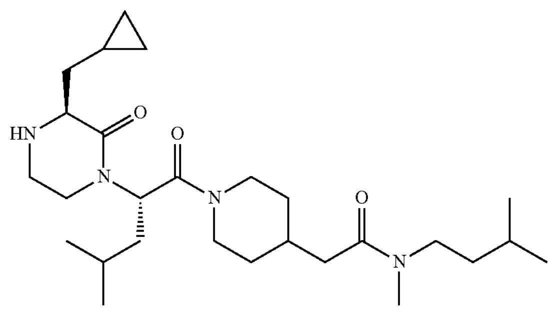 [SMILES: CC(C)CCN(C)C(=O)CC1CCN(C(=O)[C@H](CC(C)C)N2CCN[C@@H](CC3CC3)C2=O)CC1] | 61 | (S)-1-[(S)-1-[(4-{2-[N-Methyl(isopentyl)amino]-2-oxoethyl}-1-piperidyl)carbonyl]-3-methylbutyl]-3-(cyclopropylmethyl)-2-piperazinone | (1-tert-Butoxycarbonyl-4-piperidyl)acetic acid and N,3-dimethylbutan-1-amine; amide formation, BOC removal. | ¹H NMR (CD₃OD) δ 0.16 (m, 2H), 0.49 (m, 2H), 0.96 (m, 12H), 1.15 (m, 2H), 1.60 (m, 11H), 2.33 (m, 2H), 4.08 (m, 1H), 5.56 (m, 1H) | ++ |
| 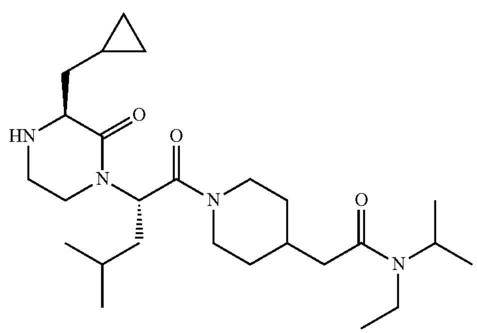 [SMILES: CCN(C(=O)CC1CCN(C(=O)[C@H](CC(C)C)N2CCN[C@@H](CC3CC3)C2=O)CC1)C(C)C] | 62 | (S)-1-[(S)-1-[(4-{2-[N-Ethyl(isopropyl)amino]-2-oxoethyl}-1-piperidyl)carbonyl]-3-methylbutyl]-3-(cyclopropylmethyl)-2-piperazinone | (1-tert-Butoxycarbonyl-4-piperidyl)acetic acid and 2-(isopropylamino)ethan-1-ylium; amide formation, BOC removal. | ¹H NMR (CD₃OD) δ 0.15 (m, 2H), 0.47 (m, 2H), 0.96 (m, 6H), 1.18 (m, 10H), 1.66 (m, 7H), 2.34 (m, 2H), 5.57 (m, 1H) | ++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 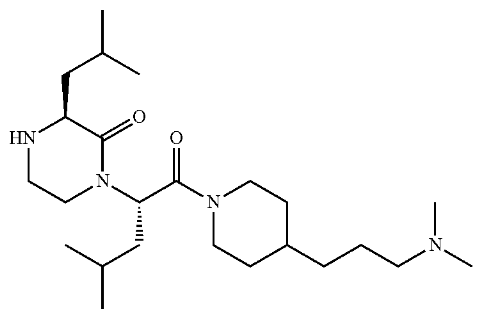 [SMILES: CC(C)C[C@@H]1NCCN([C@@H](CC(C)C)C(=O)N2CCC(CCCN(C)C)CC2)C1=O] | 63 | (S)-1-[(S)-1-({4-[3-(Dimethylamino)propyl]-1-piperidyl}carbonyl)-3-methylbutyl]-3-isobutyl-2-piperazinone | N,N-dimethyl-3-(piperidin-4-yl)propan-1-amine (Enamine BB) | $^1$H NMR (CD$_3$OD) δ 0.99 (m, 14H), 1.29 (m, 2H), 1.67 (m, 11H), 2.42 (S, 6H), 2.52 (m, 2H), 4.47 (m, 1H), 5.57 (m, 1H) | +++ |
| 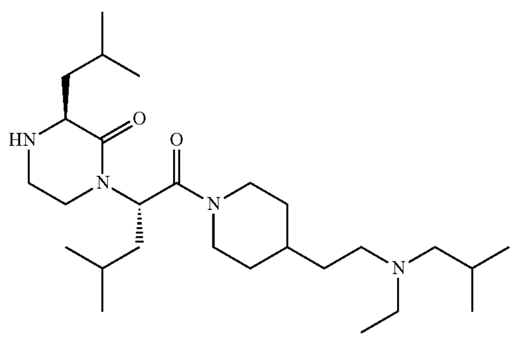 [SMILES: CCN(CCC1CCN(C(=O)[C@H](CC(C)C)N2CCN[C@@H](CC(C)C)C2=O)CC1)CC(C)C] | 64 | (S)-1-[(S)-1-[(4-{2-[N-Ethyl(isobutyl)amino]ethyl}-1-piperidyl)carbonyl]-3-methylbutyl]-3-isobutyl-2-piperazinone | N-ethyl-2-methyl-N-(2-(piperidin-4-yl)ethyl)propan-1-amine (Enamine BB) | $^1$H NMR (CD$_3$OD) δ 1.00 (m, 24H), 1.61 (m, 14H), 2.25 (m, 2H), 2.57 (m, 5H), 4.08 (m, 1H), 5.56 (m, 1H) | +++ |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 65 | 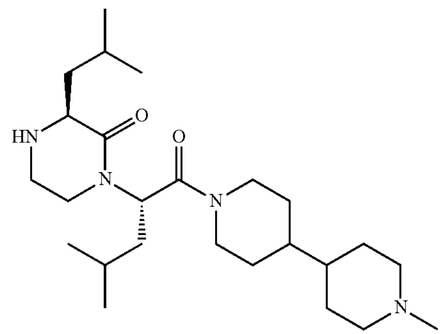 [SMILES: CC(C)C[C@@H]1NCCN([C@@H](CC(C)C)C(=O)N2CCC(C3CCN(C)CC3)CC2)C1=O] | (S)-1-{(S)-3-Methyl-1-[(1'-methyl-4,4'-bipiperidyl-1-yl)carbonyl]butyl}-3-isobutyl-2-piperazinone | 1-methyl-4,4'-bipiperidine dihydrochloride (Matrix Scientific) | $^1$H NMR (CD$_3$OD) δ 0.97 (m, 12H), 1.14 (m, 4H), 1.56 (m, 14H), 2.39 (s, 3H), 5.56 (m, 1H) | +++ |
| 66 | 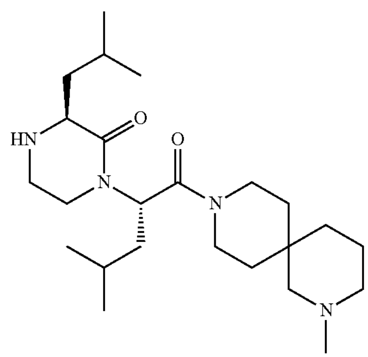 [SMILES: CC(C)C[C@@H]1NCCN([C@@H](CC(C)C)C(=O)N2CCC3(CCCN(C)C3)CC2)C1=O] | (S)-1-[(S)-3-Methyl-1-{(2-methyl-2,9-diaza-9-spiro[5.5]undecyl)carbonyl}butyl]-3-isobutyl-2-piperazinone | 2-methyl-2,9-diazaspiro[5.5]undecane dihydrochloride (Enamine BB) | $^1$H NMR (CD$_3$OD) δ 0.97 (m, 12H), 1.56 (m, 12H), 3.12 (m, 1H), 5.56 (m, 1H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 67 | 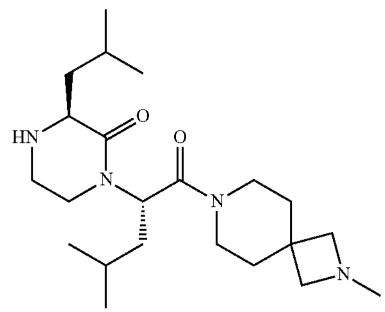 [SMILES: CC(C)C[C@@H]1NCCN([C@@H](CC(C)C)C(=O)N2CCC3(CC2)CN(C)C3)C1=O] | (S)-1-[(S)-3-Methyl-1-{[2-methyl-2,7-diaza-7-spiro[3.5]nonyl]carbonyl}butyl]-3-isobutyl-2-piperazinone | 2-methyl-2,7-diazaspiro[3.5]nonane dihydrochloride (AstaTech) | ¹H NMR (CD₃OD) δ 0.96 (m, 12H), 1.68, (m, 10H), 2.68 (s, 3H), 3.64 (m, 6H), 5.54 (m, 1H) | ++ |
| 68 | 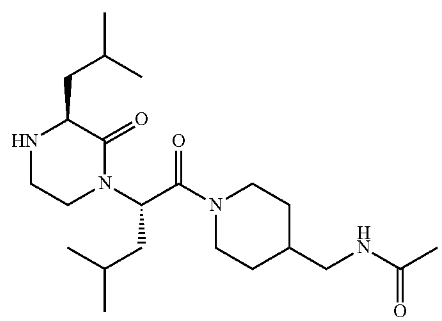 [SMILES: CC(=O)NCC1CCN(C(=O)[C@H](CC(C)C)N2CCN[C@@H](CC(C)C)C2=O)CC1] | (S)-1-[(S)-1-{[4-(Acetylaminomethyl)-1-piperidyl]carbonyl}-3-methylbutyl]-3-isobutyl-2-piperazinone | 1-{[(4-Piperidyl)methyl]amino}-1-ethanone (Enamine BB) | CD₃OD: δ 5.56 (m, 1H), 4.48 (t, 1H), 2.66 (q, 1H), 1.94 (s, 3H), 1.26–0.80 (br m, 15H) | +* |
| 69 | 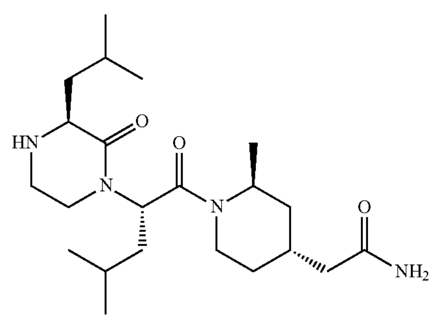 [SMILES: CC(C)C[C@@H]1NCCN([C@@H](CC(C)C)C(=O)N2CC[C@@H](CC(N)=O)C[C@@H]2C)C1=O] | [(2S,4R)-1-{(S)-2-[(S)-3-Isobutyl-2-oxo-1-piperazinyl]-4-methylvaleryl}-2-methyl-4-piperidyl]acetamide | tert-Butyl (S)-2-methyl-4-oxo-1-piperidine-carboxylate (AstaTech); Wittig reaction with methyl (triphenyl-phosphoranylidene) acetate, catalytic hydrogenation using Pd/C and H₂, conversion of ester to amide using NH₄OH, | CD₃OD: δ 5.60–4.43 (br m, 1H), 2.10 (m, 2H), 1.92–1.42 (br m, 8H), 1.42–1.05 (br m, 5H), 0.95 (m, 12H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 70 | 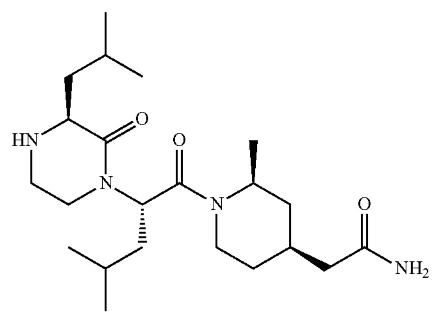 [SMILES: CC(C)C[C@@H]1NCCN([C@@H](CC(C)C)C(=O)N2CC[C@H](CC(N)=O)C[C@@H]2C)C1=O] | [(2S,4S)-1-{(S)-2-[(S)-3-Isobutyl-2-oxo-1-piperazinyl]-4-methylvaleryl}-2-methyl-4-piperidyl]acetamide | tert-Butyl (S)-2-methyl-4-oxo-1-piperidine-carboxylate (AstaTech); Wittig reaction with methyl (triphenyl-phosphoranylidene) acetate, catalytic hydrogenation using Pd/C and H₂, conversion of ester to amide using NH₄OH, BOC removal, diastereomeric resolution by column chromatography | CD₃OD: δ 5.49 (t, 1H), 2.09-1.69 (br m, 5H), 1.69-1.42 (br m, 4H), 1.42-1.09 (br m, 6H), 0.95 (m, 12H) | ++ |
| 71 | 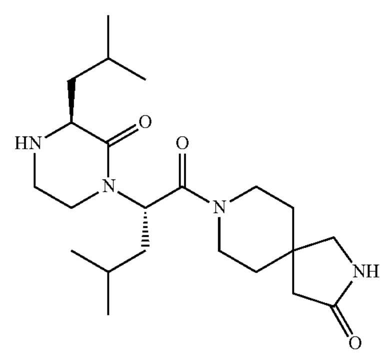 [SMILES: CC(C)C[C@@H]1NCCN([C@@H](CC(C)C)C(=O)N2CCC3(CC2)CNC(=O)C3)C1=O] | (S)-1-[(S)-3-Methyl-1-{(3-oxo-2,8-diaza-spiro[4.5]decyl)carbonyl}butyl]-3-isobutyl-2-piperazinone | 2,8-Diaza-spiro[4.5]decanone (Combi-Blocks) | CD₃OD: δ 5.59 (t, 1H), 2.30 (d, 2H), 1.82 (m, 2H), 1.74-1.40 (br m, 8H), 0.97 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 72 | 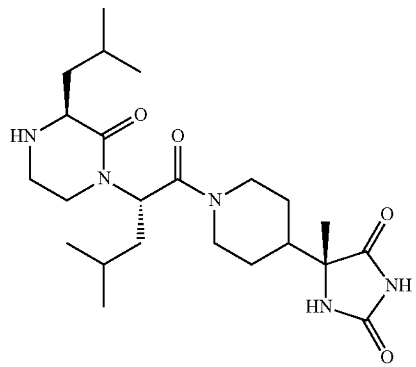 [SMILES: CC(C)C[C@@H]1NCCN([C@@H](CC(C)C)C(=O)N2CCC([C@@]3(C)NC(=O)NC3=O)CC2)C1=O] | (R)-5-(1-{(S)-2-[(S)-3-Isobutyl-2-oxo-1-piperazinyl]-4-methylvaleryl]-4-piperidyl)-5-methyl-2,4-imidazolidinedione | 5-Methyl-5-(4-piperidyl)-2,4-imidazolidinedione (Enamine BB); diastereomeric resolution by column chromatography | CD$_3$OD: δ 5.56 (m, 1H), 4.57 (t, 1H), 2.60 (m, 1H), 1.39 (s, 3H), 0.95 (m, 12H) | +* |
| 73 | 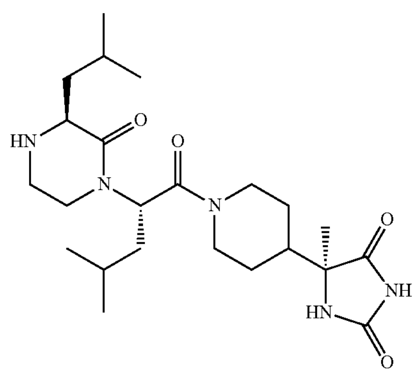 [SMILES: CC(C)C[C@@H]1NCCN([C@@H](CC(C)C)C(=O)N2CCC([C@]3(C)NC(=O)NC3=O)CC2)C1=O] | (S)-5-(1-{(S)-2-[(S)-3-Isobutyl-2-oxo-1-piperazinyl]-4-methylvaleryl]-4-piperidyl)-5-methyl-2,4-imidazolidinedione | 5-Methyl-5-(4-piperidyl)-2,4-imidazolidinedione (Enamine BB); diastereomeric resolution by column chromatography | CD$_3$OD: δ 5.67-5.47 (br m, 1H), 4.58 (t, 1H), 2.61 (m, 1H), 1.38 (s, 3H), 0.95 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 74 | 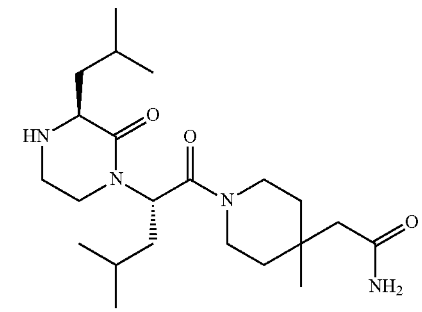 [SMILES: CC(C)C[C@@H]1NCCN([C@@H](CC(C)C)C(=O)N2CCC(C)(CC(N)=O)CC2)C1=O] | (1-{(S)-2-[(S)-3-Isobutyl-2-oxo-1-piperazinyl]-4-methylvaleryl}-4-methyl-4-piperidyl)acetamide | (4-Methyl-1-tert-butoxycarbonyl-4-piperidyl)acetic acid (AstaTech); amide coupling with NH₄OH, BOC removal | CD₃OD: δ 5.56 (m, 1H), 2.19 (d, 2H), 1.14 (m, 3H), 0.95 (m, 12H) | ++ |
| 75 | 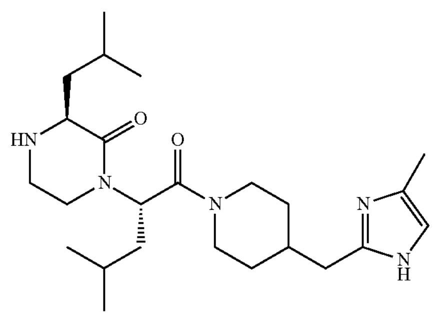 [SMILES: Cc1c[nH]c(CC2CCN(C(=O)[C@H](CC(C)C)N3CCN[C@@H](CC(C)C)C3=O)CC2)n1] | (S)-1-[(S)-3-Methyl-1-({4-[(4-methyl-1H-imidazol-2-yl)methyl]-1-piperidyl}carbonyl)butyl]-3-isobutyl-2-piperazinone | tert-Butyl 4-(2-hydroxyethyl)-1-piperidine-carboxylate, oxidation to aldehyde, imidazole formation using ammonium acetate and pyruvaldehyde, BOC deprotection | CD₃OD: δ 6.59 (s, 1H), 5.52 (m, 1H), 4.45 (t, 1H), 2.57 (d, 2H), 0.93 (m, 12H) | +++ |
| 76 | 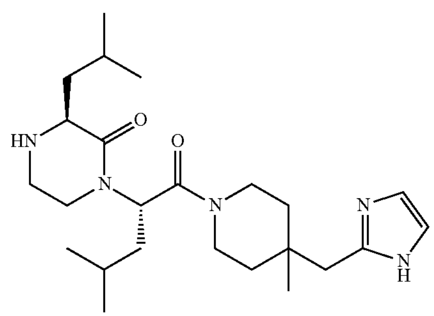 [SMILES: CC(C)C[C@@H]1NCCN([C@@H](CC(C)C)C(=O)N2CCC(C)(Cc3ncc[nH]3)CC2)C1=O] | (S)-1-[(S)-1-({4-[(1H-Imidazol-2-yl)methyl]-4-methyl-1-piperidyl}carbonyl)-4-methylbutyl]-3-methylbutyl]-3-isobutyl-2-piperazinone | tert-Butyl 4-(2-hydroxyethyl)-4-methyl-1-piperidine-carboxylate (Combi-Blocks), oxidation to aldehyde, imidazole formation using ammonium acetate and glyoxal, BOC deprotection | CD₃OD: δ 6.89 (s, 2H), 5.44 (m, 1H), 4.45 (t, 1H), 1.46 (m, 10H), 0.94 (s, 3H), 0.84 (m, 12H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 77 | 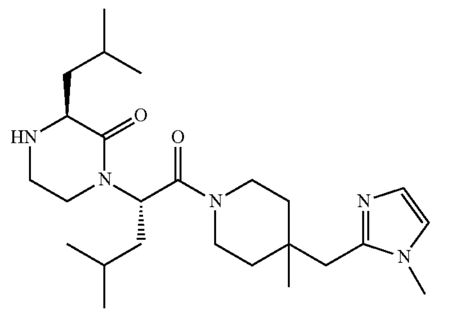 [SMILES: CC(C)C[C@@H]1NCCN([C@@H](CC(C)C)C(=O)N2CCC(C)(Cc3nccn3C)CC2)C1=O] | (S)-1-[(S)-3-Methyl-1-({4-methyl-4-[(1-methyl-1H-imidazol-2-yl)methyl]-1-piperidyl}carbonyl)butyl]-3-isobutyl-2-piperazinone | tert-Butyl 4-(2-hydroxyethyl)-4-methyl-1-piperidine-carboxylate (Combi-Blocks), oxidation to aldehyde, imidazole formation using ammonium acetate, methylamine and glyoxal), BOC deprotection | CDCl₃: δ 7.01 (s, 1H), 6.90 (s, 1H), 5.56 (m, 1H), 3.66 (s, 3H), 1.09 (s, 3H), 0.96 (m, 12H) | +++ |
| 78 | 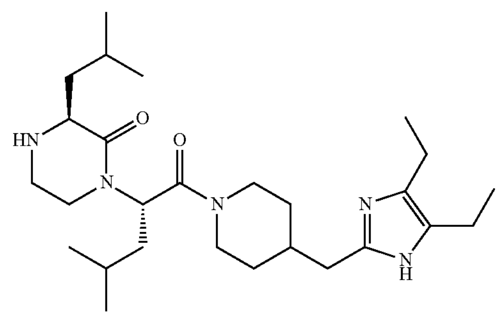 [SMILES: CCc1nc(CC2CCN(C(=O)[C@H](CC(C)C)N3CCN[C@@H](CC(C)C)C3=O)CC2)[nH]c1CC] | (S)-1-[(S)-1-({4-[(4,5-Diethyl-1H-imidazol-2-yl)methyl]-1-piperidyl}carbonyl)-3-methylbutyl]-3-isobutyl-2-piperazinone | tert-Butyl 4-(2-hydroxyethyl)-1-piperidine-carboxylate, oxidation to aldehyde, imidazole formation using ammonium acetate, and 3,4-hexanedione, BOC deprotection | CD₃OD: δ 5.53 (m, 1H), 2.66 (q, 4H), 1.25 (t, 6H), 1.01 (m, 12H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 79 | 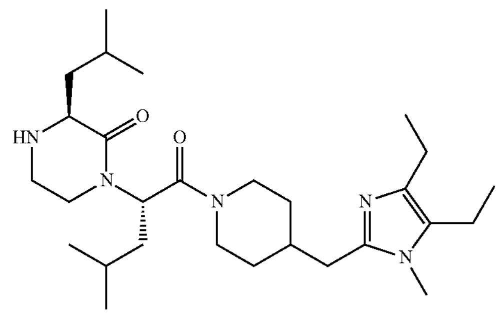 [SMILES: CCc1nc(CC2CCN(C(=O)[C@H](CC(C)C)N3CCN[C@@H](CC(C)C)C3=O)CC2)n(C)c1CC] | (S)-1-[(S)-1-({4-[(4,5-Diethyl-1H-imidazol-2-yl)methyl]-1-piperidyl}carbonyl)-3-methylbutyl]-2-piperazinone | tert-Butyl 4-(2-hydroxyethyl)-1-piperidine-carboxylate, oxidation to aldehyde, imidazole formation using ammonium acetate, methylamine and 3,4-hexanedione, BOC deprotection | CD$_3$OD: δ 5.54 (m, 1H), 3.73 (s, 3H), 2.69 (m, 4H), 1.22 (m, 6H), 0.99 (m, 12H) | +++ |
| 80 | 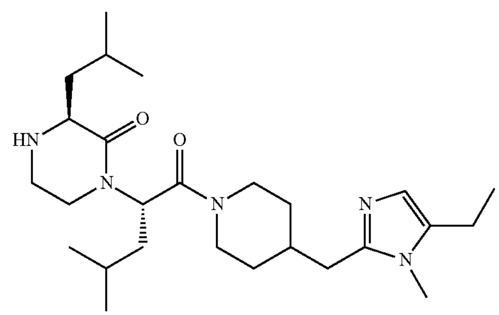 [SMILES: CCc1cnc(CC2CCN(C(=O)[C@H](CC(C)C)N3CCN[C@@H](CC(C)C)C3=O)CC2)n1C] | (S)-1-[(S)-1-({4-[(5-Ethyl-1-methyl-1H-imidazol-2-yl)methyl]-1-piperidyl}carbonyl)-3-methylbutyl]-2-piperazinone | p-toluenesulfonyl methyl isocyanide; Van Leusen imidazole formation using propionaldehyde and methylamine, deprotonation with nBuLi followed by addition to tert-butyl 4-formyl-1-piperidine-carboxylate, mesylation of alcohol, elimination of mesylate by heat, hydrogenation, BOC deprotection | CD$_3$OD: δ 6.62 (s, 1H), 5.55 (m, 1H), 4.48 (t, 1H), 3.51 (s, 3H), 2.57 (q, 2H), 1.25 (t, 3H), 0.95 (m, 12H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 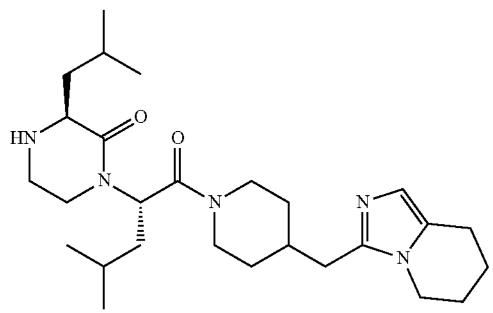 [SMILES: CC(C)C[C@@H]1NCCN([C@@H](CC(C)C)C(=O)N2CCC(Cc3ncc4n3CCCC4)CC2)C1=O] | 81 | (S)-1-[(S)-1-({4-[(2,3a-Diaza-4,5,6,7-tetrahydroinden-3-yl)methyl]-1-piperidyl}carbonyl)-3-methylbutyl]-3-isobutyl-2-piperazinone | 2,3a-Diaza-4,5,6,7-tetrahydroindene (Enamine BB), deprotonation with nBuLi followed by addition to tert-butyl 4-formyl-1-piperidine-carboxylate, mesylation of alcohol, elimination of mesylate by heat, hydrogenation, BOC deprotection | CD₃OD: δ 6.64 (s, 1H), 5.56 (m, 1H), 4.48 (t, 1H), 3.92 (t, 2H), 2.76 (t, 2H), 2.64 (d, 2H), 0.96 (m, 12H) | +++ |
| 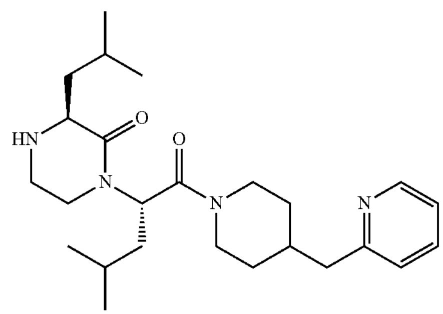 [SMILES: CC(C)C[C@@H]1NCCN([C@@H](CC(C)C)C(=O)N2CCC(Cc3ccccn3)CC2)C1=O] | 82 | (S)-1-[(S)-3-Methyl-1-({4-[(2-pyridyl)methyl]-1-piperidyl}carbonyl)butyl]-3-isobutyl-2-piperazinone | 2-[(4-Piperidyl)methyl]pyridine (Enamine BB) | CD₃OD: δ 8.47 (s, 1H), 7.78 (t, 1H), 7.30 (m, 2H), 5.57 (m, 1H), 4.48 (t, 1H), 2.76 (d, 2H), 0.97 (m, 12H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 83 | 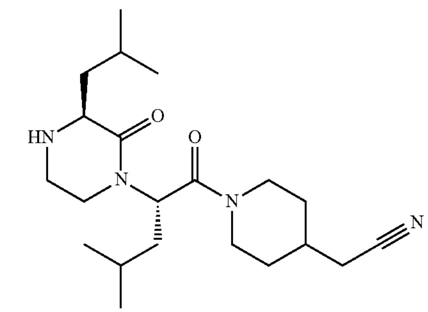 [SMILES: CC(C)C[C@@H]1NCCN([C@@H](CC(C)C)C(=O)N2CCC(CC#N)CC2)C1=O] | (1-{(S)-2-[(S)-3-Isobutyl-2-oxo-1-piperazinyl]-4-methylvaleryl}-4-piperidyl)acetonitrile | (4-Piperidyl)acetonitrile (Enamine BB) | CD$_3$OD: δ 5.63 (m, 1H), 4.59 (t, 1H), 2.55 (d, 2H), 1.01 (m, 12H) | +++ |
| 84 | 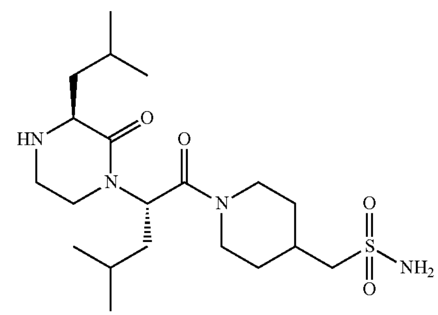 [SMILES: CC(C)C[C@@H]1NCCN([C@@H](CC(C)C)C(=O)N2CCC(CS(N)(=O)=O)CC2)C1=O] | (1-{(S)-2-[(S)-3-Isobutyl-2-oxo-1-piperazinyl]-4-methylvaleryl}-4-piperidyl)methanesulfonamide | (4-Piperidyl)methanesulfonamide (AstaTech) | CD$_3$OD: δ 5.66 (m, 1H), 4.55 (m, 1H), 2.09 (d, 2H), 1.04 (m, 12H) | +* |
| 85 | 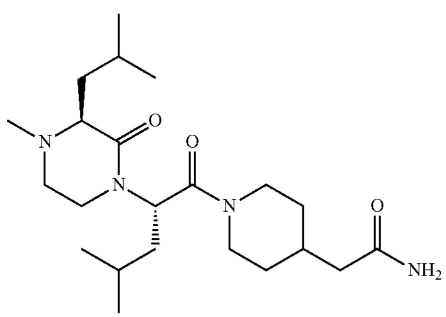 [SMILES: CC(C)C[C@H]1C(=O)N([C@@H](CC(C)C)C(=O)N2CCC(CC(N)=O)CC2)CCN1C] | (1-{(1S)-2-[(S)-3-Isobutyl-4-methyl-2-oxo-1-piperazinyl]-4-methylvaleryl}-4-piperidyl)acetamide | (4-Piperidyl)acetamide (Enamine BB) | CDCl$_3$: δ 5.53 (m, 1H), 4.17 (d, 1H), 3.10-2.87 (br m, 2H), 2.33 (m, 3H), 1.00-0.76 (br m, 12H) | ++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 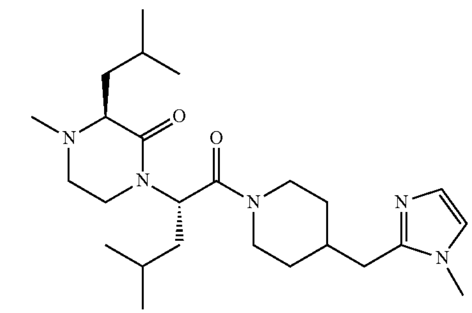 [SMILES: CC(C)C[C@H]1C(=O)N([C@@H](CC(C)C)C(=O)N2CCC(Cc3nccn3C)CC2)CCN1C] | 86 | (S)-1-[(S)-3-Methyl-1-({4-[(1-methyl-1H-imidazol-2-yl)methyl]-1-piperidyl}carbonyl)butyl]-3-isobutyl-4-methyl-2-piperazinone | 1-methyl-2-[(4-piperidyl)methyl]-1H-imidazole (Enamine BB) | CD$_3$OD: δ 6.97 (s, 1H), 6.85 (s, 1H), 5.52 (m, 1H), 4.47 (t, 1H), 3.64 (s, 3H), 2.36 (m, 3H), 1.03-0.81 (br m, 12H) | +++ |
| 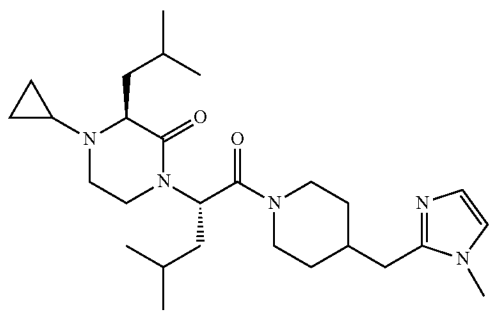 [SMILES: CC(C)C[C@@H](C(=O)N1CCC(Cc2nccn2C)CC1)N1CCN(C2CC2)[C@@H](CC(C)C)C1=O] | 87 | (S)-1-[(S)-3-Methyl-1-({4-[(1-methyl-1H-imidazol-2-yl)methyl]-1-piperidyl}carbonyl)butyl]-4-cyclopropyl-3-isobutyl-2-piperazinone | 1-methyl-2-[(4-piperidyl)methyl]-1H-imidazole (Enamine BB) | CD$_3$OD: δ 6.96 (s, 1H), 6.84 (s, 1H), 5.58 (m, 1H), 4.47 (m, 1H), 3.63 (s, 3H), 0.93 (m, 12H), 0.66-0.33 (br m, 4H) | +++ |
| 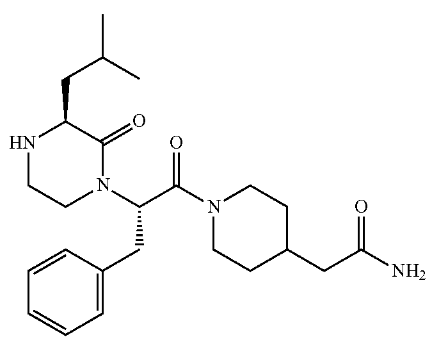 [SMILES: CC(C)C[C@@H]1NCCN([C@@H](Cc2ccccc2)C(=O)N2CCC(CC(N)=O)CC2)C1=O] | 88 | (1-{(S)-2-[(S)-3-Isobutyl-2-oxo-1-piperazinyl]-3-phenylpropionyl}-4-piperidyl)acetamide | (4-Piperidyl)acetamide (Enamine BB) | CD$_3$OD: δ 7.35-7.15 (br m, 5H), 5.86-5.67 (br m, 1H), 4.46 (t, 1H), 2.63 (t, 1H), 0.93-0.81 (br m, 6H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 89 | 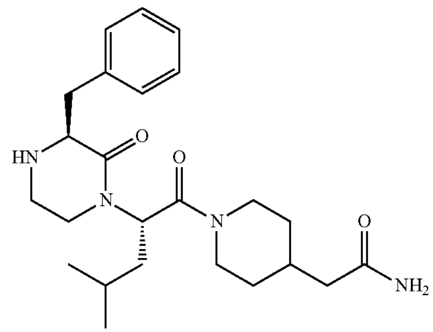 [SMILES: CC(C)C[C@@H](C(=O)N1CCC(CC(N)=O)CC1)N1CCN[C@@H](Cc2ccccc2)C1=O] | (1-{(S)-2-[(S)-3-Benzyl-2-oxo-1-piperazinyl]-4-methylvaleryl}-4-piperidyl)acetamide | (4-Piperidyl)acetamide (Enamine BB) | CD$_3$OD: δ 7.39-7.16 (br m, 5H), 5.58 (m, 1H), 4.46 (t, 1H), 2.68 (q, 1H), 0.94 (m, 6H) | +* |
| 90 | 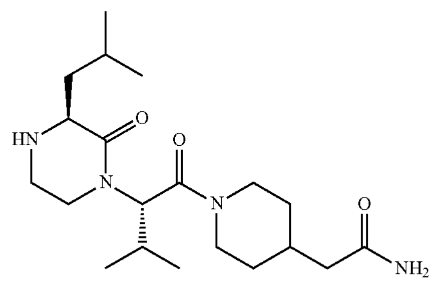 [SMILES: CC(C)C[C@@H]1NCCN([C@H](C(=O)N2CCC(CC(N)=O)CC2)C(C)C)C1=O] | (1-{(S)-2-[(S)-3-Isobutyl-2-oxo-1-piperazinyl]-3-methylbutyryl}-4-piperidyl)acetamide | (4-Piperidyl)acetamide (Enamine BB) | CD$_3$OD: δ 5.12 (m, 1H), 4.52 (t, 1H), 2.69 (q, 1H), 2.33 (m, 1H), 1.00-0.78 (br m, 12H) | ND |
| 91 | 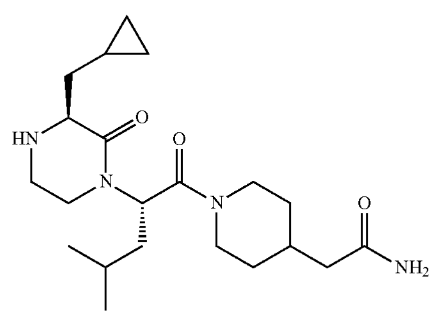 [SMILES: CC(C)C[C@@H](C(=O)N1CCC(CC(N)=O)CC1)N1CCN[C@@H](CC2CC2)C1=O] | (1-{(S)-2-[(S)-3-(Cyclopropylmethyl)-2-oxo-1-piperazinyl]-4-methylvaleryl}-4-piperidyl)acetamide | (4-Piperidyl)acetamide (Enamine BB) | CD$_3$OD: δ 5.57 (m, 1H), 4.47 (t, 1H), 2.69 (q, 1H), 0.96 (m, 6H), 0.85 (m, 1H), 0.58-0.41 (br m, 2H), 0.26-0.06 (br m, 2H) | +* |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 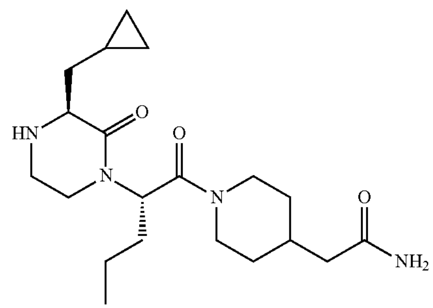 [SMILES: CCC[C@@H](C(=O)N1CCC(CC(N)=O)CC1)N1CCN[C@@H](CC2CC2)C1=O] | 92 | (1-{(S)-2-[(S)-3-(Cyclopropylmethyl)-2-oxo-1-piperazinyl]valeryl}-4-piperidyl)acetamide | (4-Piperidyl) acetamide (Enamine BB) | CD$_3$OD: δ 5.46 (m, 1H), 4.48 (t, 1H), 2.69 (q, 1H), 1.43-1.01 (br m, 5H), 0.95 (m, 3H), 0.85 (m, 1H), 0.59-0.39 (br m, 2H), 0.26-0.06 (br m, 2H) | +* |
| 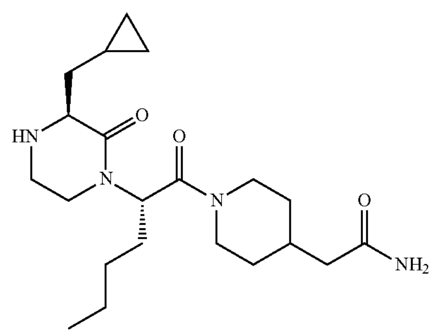 [SMILES: CCCC[C@@H](C(=O)N1CCC(CC(N)=O)CC1)N1CCN[C@@H](CC2CC2)C1=O] | 93 | (1-{(S)-2-[(S)-3-(Cyclopropylmethyl)-2-oxo-1-piperazinyl]hexanoyl}-4-piperidyl)acetamide | (4-Piperidyl) acetamide (Enamine BB) | CD$_3$OD: δ 5.45 (m, 1H), 4.48 (t, 1H), 2.69 (q, 1H), 1.53-1.00 (br m, 7H), 1.00-0.75 (br m, 4H), 0.59-0.39 (br m, 2H), 0.25-0.04 (br m, 2H) | +* |
| 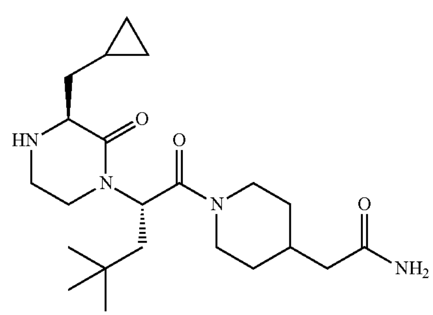 [SMILES: CC(C)(C)C[C@@H](C(=O)N1CCC(CC(N)=O)CC1)N1CCN[C@@H](CC2CC2)C1=O] | 94 | (1-{(S)-2-[(S)-3-(Cyclopropylmethyl)-2-oxo-1-piperazinyl]-4,4-dimethylvaleryl}-4-piperidyl)acetamide | (4-Piperidyl) acetamide (Enamine BB) | CD$_3$OD: δ 5.65 (m, 1H), 4.47 (t, 1H), 2.69 (q, 1H), 0.99-0.75 (br m, 10H), 1.00-0.75 (br m, 4H), 0.57-0.40 (br m, 2H), 0.24-0.06 (br m, 2H) | ND |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 95 | 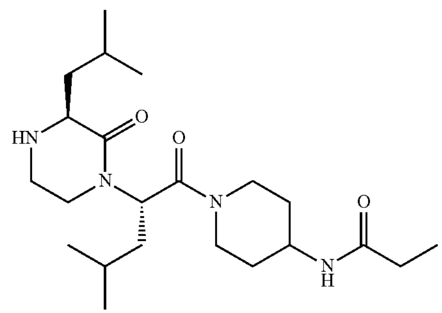 [SMILES: CCC(=O)NC1CCN(C(=O)[C@H](CC(C)C)N2CCN[C@@H](CC(C)C)C2=O)CC1] | (S)-1-{(S)-3-Methyl-1-[(4-propionylamino-1-piperidyl)carbonyl]butyl}-3-isobutyl-2-piperazinone | 1-(4-Piperidylamino)-1-propanone (Enamine BB) | CD$_3$OD: δ 5.61 (m, 1H), 2.23 (q, 2H), 1.16 (t, 3H), 1.01 (m, 12H) | +* |
| 96 | 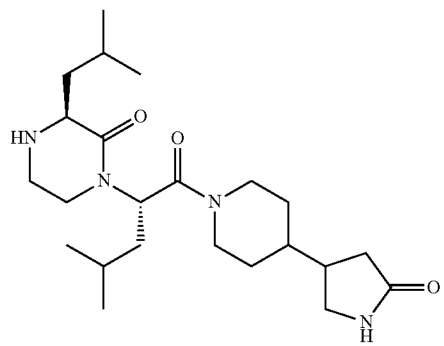 [SMILES: CC(C)C[C@@H]1NCCN([C@@H](CC(C)C)C(=O)N2CCC(C3CNC(=O)C3)CC2)C1=O] | (S)-1-[(S)-3-Methyl-1-{[4-(5-oxo-3-pyrrolidinyl)-1-piperidyl]carbonyl}butyl]-3-isobutyl-2-piperazinone | 4-(4-Piperidyl)-2-pyrrolidinone (Enamine BB) | CD$_3$OD: δ 5.59 (m, 1H), 4.54 (t, 1H), 2.37 (m, 2H), 1.70 (m, 9H), 1.04 (m, 12H) | ++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 97 | 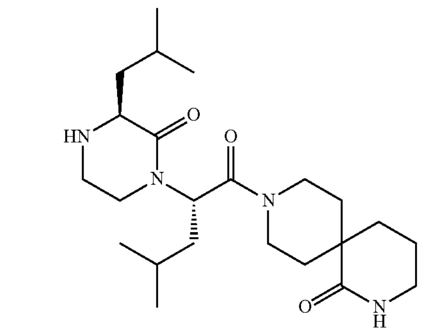 [SMILES: CC(C)C[C@@H]1NCCN([C@@H](CC(C)C)C(=O)N2CCC3(CCCNC3=O)CC2)C1=O] | (S)-1-[(S)-1-{(2,9-Diazaspiro[5.5]undecan-9-oyl)carbonyl}-3-methylbutyl]-3-isobutyl-2-piperazinone | 2,9-Diaza-1-spiro[5.5]undecanone (Combi-Blocks) | CD$_3$OD: δ 5.67 (m, 1H), 3.18 (m, 2H), 1.82 (m, 16H), 1.03 (m, 12H) | ++ |
| 98 | 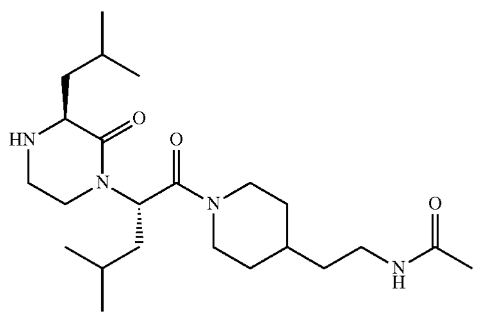 [SMILES: CC(=O)NCCC1CCN(C(=O)[C@H](CC(C)C)N2CCN[C@@H](CC(C)C)C2=O)CC1] | (S)-1-[(S)-1-{[4-(2-Acetylaminoethyl)-1-piperidyl]carbonyl}-3-methylbutyl]-3-isobutyl-2-piperazinone | 1-[2-(4-Piperidyl)ethyl]amino]-1-ethanone (Matrix Scientific) | CD$_3$OD: δ 5.64 (m, 1H), 4.55 (t, 1H), 2.01 (s, 3H), 1.04 (m, 12H) | +* |

TABLE 2-continued

Compounds made through Method A

| Ex. Cmpd # | name | Precursor II synthesis | Characteristic ¹H NMR signals (300 MHz) | Activity |
|---|---|---|---|---|
| 99 | 8-[(S)-2-[(S)-3-Isobutyl-2-oxo-1-piperazinyl]-4-methylvaleryl]-1,3,8-triaza-2-spiro[4.5]decanone | 1,3,8-Triaza-2-spiro[4.5]decanone (AstaTech) | CD$_3$OD: δ 5.58 (m, 1H), 2.71 (d, 2H), 1.68 (m, 10H), 0.94 (m, 12H) | +* |
| 100 | (S)-1-[(S)-3-Methyl-1-({4-[(1-methyl-1H-imidazol-2-yl)methyl]-1-piperidyl}carbonyl)butyl]-4-[(p-fluorophenyl)methyl]-3-isobutyl-2-piperazinone | 1-methyl-2-[(4-piperidyl)methyl]-1H-imidazole (Enamine BB) | CD$_3$OD: δ 7.34 (m, 2H), 7.05 (m, 2H), 5.55 (m, 1H), 4.48 (t, 1H), 3.62 (s, 3H), 0.93 (m, 12H) | ++++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 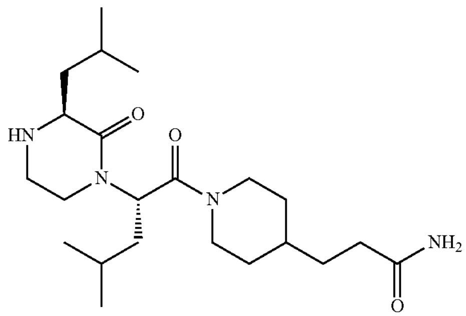 | 101 | 3-(1-{(S)-2-[(S)-3-Isobutyl-2-oxo-1-piperazinyl]-4-methylvaleryl]-4-piperidyl)propionamide | 3-(4-Piperidyl)propionamide (Enamine BB) | CD$_3$OD: δ 5.63 (m, 1H), 4.53 (t, 1H), 4.14 (m, 1H), 2.31 (m, 2H), 1.75 (m, 11H), 1.01 (m, 12H) | ++ |
| 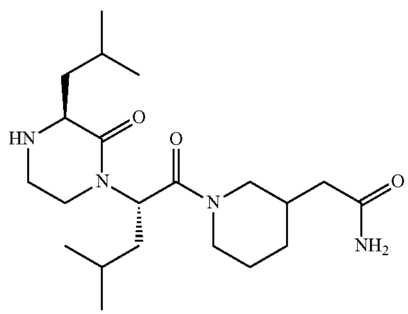 [SMILES: CC(C)C[C@@H]1NCCN([C@@H](CC(C)C)C(=O)N2CCCC(CC(N)=O)C2)C1=O] | 102 | (1-{(S)-2-[(S)-3-Isobutyl-2-oxo-1-piperazinyl]-4-methylvaleryl}-3-piperidyl)acetamide | (3-Piperidyl)acetamide (Enamine BB) | CD$_3$OD: δ 5.61 (m, 1H), 2.20 (m, 2H), 1.70 (m, 11H), 0.99 (m, 12H) | +* |
| 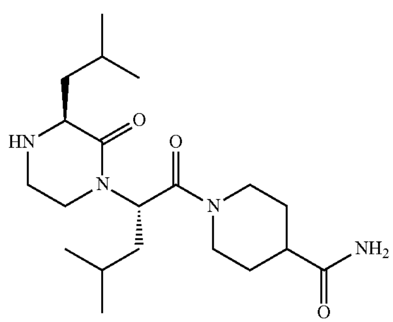 [SMILES: CC(C)C[C@@H]1NCCN([C@@H](CC(C)C)C(=O)N2CCC(C(N)=O)CC2)C1=O] | 103 | 1-{(S)-2-[(S)-3-Isobutyl-2-oxo-1-piperazinyl]-4-methylvaleryl}-4-piperidine-carboxamide | 4-Piperidine-carboxamide | CD$_3$OD: δ 5.64 (m, 1H), 2.59 (m, 1H), 2.10 (m, 1H), 1.74 (m, 10H), 1.01 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 104 | (structure) | (1-{(S)-2-[(S)-3-Isobutyl-2-oxo-1-piperazinyl]hexanoyl}-4-piperidyl)acetamide | (4-Piperidyl)acetamide (Enamine BB) | CD₃OD: δ 5.43 (m, 1H), 4.47 (t, 1H), 2.69 (q, 1H), 1.01-0.82 (br m, 9H) | +* |
| 105 | (structure) | (1-{(S)-2-[(S)-3-Isobutyl-2-oxo-1-piperazinyl]-3-cyclopropyl-propionyl}-4-piperidyl)acetamide | (4-Piperidyl)acetamide (Enamine BB) | CD₃OD: δ 5.55 (m, 1H), 4.48 (t, 1H), 2.69 (q, 1H), 0.95 (m, 6H), 0.66 (m, 1H), 0.53-0.35 (br m, 2H), 0.22-0.04 (br m, 2H) | +* |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 106 | 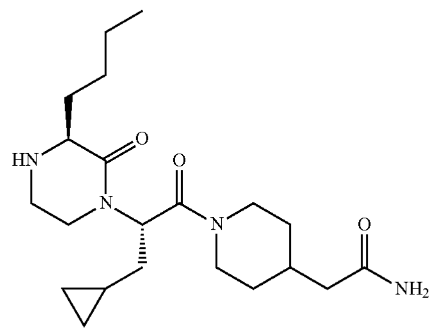 [SMILES: CCCC[C@@H]1NCCN([C@@H](CC2CC2)C(=O)N2CCC(CC(N)=O)CC2)C1=O] | (1-{(S)-2-[(S)-3-Butyl-2-oxo-1-piperazinyl]-3-cyclopropyl-propionyl}-4-piperidyl)acetamide | (4-Piperidyl)acetamide (Enamine BB) | CD$_3$OD: δ 5.56 (m, 1H), 4.48 (t, 1H), 2.69 (q, 1H), 1.50-1.01 (br m, 6H), 0.93 (m, 3H), 0.66 (m, 1H), 0.56-0.36 (br m, 2H), 0.22-0.02 (br m, 2H) | ND |
| 107 | 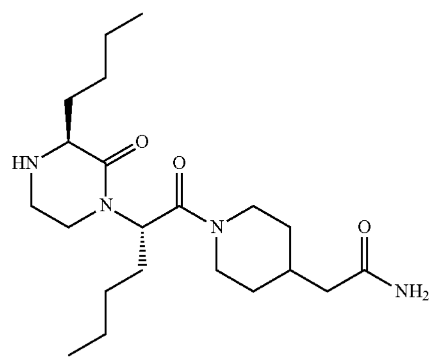 [SMILES: CCCC[C@@H]1NCCN([C@@H](CCCC)C(=O)N2CCC(CC(N)=O)CC2)C1=O] | (1-{(S)-2-[(S)-3-Butyl-2-oxo-1-piperazinyl]hexanoyl}-4-piperidyl)acetamide | (4-Piperidyl)acetamide (Enamine BB) | CD$_3$OD: δ 5.45 (m, 1H), 4.47 (t, 1H), 2.69 (q, 1H), 1.53-1.01 (br m, 10H), 0.93 (m, 6H) | +* |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 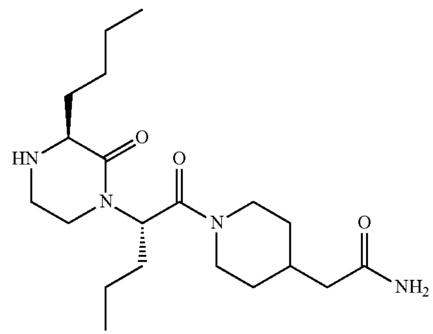 [SMILES: CCCC[C@@H]1NCCN([C@@H](CCC)C(=O)N2CCC(CC(N)=O)CC2)C1=O] | 108 | (1-{(S)-2-[(S)-3-Butyl-2-oxo-1-piperazinyl]valeryl}-4-piperidyl)acetamide | (4-Piperidyl)acetamide (Enamine BB) | CD$_3$OD: δ 5.46 (m, 1H), 4.47 (t, 1H), 2.69 (q, 1H), 1.61-1.01 (br m, 8H), 0.95 (m, 6H) | +* |
| 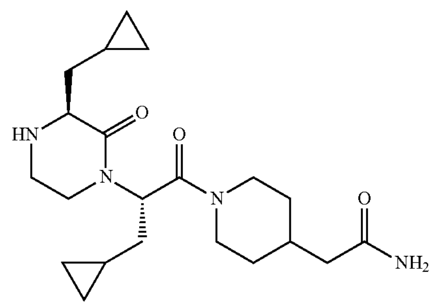 [SMILES: NC(=O)CC1CCN(C(=O)[C@H](CC2CC2)N2CCN[C@@H](CC3CC3)C2=O)CC1] | 109 | (1-{(S)-2-[(S)-3-(Cyclopropylmethyl)-2-oxo-1-piperazinyl]-3-cyclopropyl-propionyl}-4-piperidyl)acetamide | (4-Piperidyl)acetamide (Enamine BB) | CD$_3$OD: δ 5.56 (m, 1H), 4.49 (t, 1H), 2.69 (q, 1H), 0.85 (m, 1H), 0.66 (m, 1H), 0.57-0.34 (br m, 4H), 0.23-0.01 (br m, 4H) | +* |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 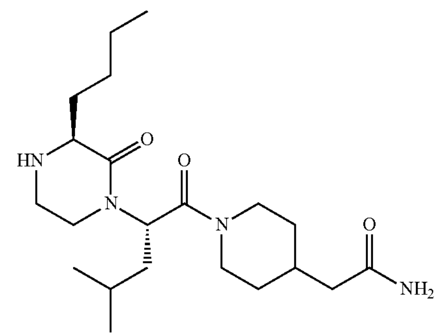 [SMILES: CCCC[C@@H]1NCCN([C@@H](CC(C)C)C(=O)N2CCC(CC(N)=O)CC2)C1=O] | 110 | (1-{(S)-2-[(S)-3-Butyl-2-oxo-1-piperazinyl]-4-methylvaleryl}-4-piperidyl)acetamide | (4-Piperidyl)acetamide (Enamine BB) | CD$_3$OD: δ 5.57 (m, 1H), 4.47 (t, 1H), 2.68 (q, 1H), 1.25–1.05 (br m, 2H), 0.95 (m, 9H) | +* |
| 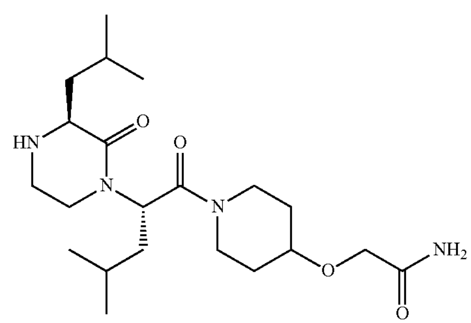 [SMILES: CC(C)C[C@@H]1NCCN([C@@H](CC(C)C)C(=O)N2CCC(OCC(N)=O)CC2)C1=O] | 111 | (1-{(S)-2-[(S)-3-Isobutyl-2-oxo-1-piperazinyl]-4-methylvaleryl}-4-piperidyloxy)acetamide | (4-Piperidyl-oxy)acetamide (AstaTech) | CD$_3$OD: δ 5.65 (m, 1H), 4.07 (s, 2H), 3.51 (m, 1H), 1.77 (m, 10H), 1.03 (m, 12H) | +* |
| 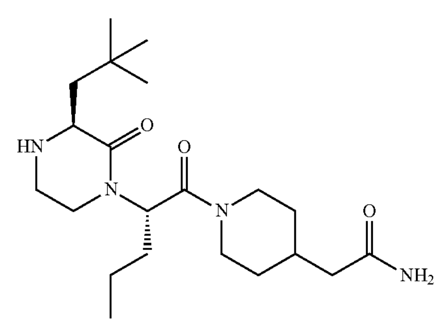 [SMILES: CCC[C@@H](C(=O)N1CCC(CC(N)=O)CC1)N1CCN[C@@H](CC(C)(C)C)C1=O] | 112 | (1-{(S)-2-[(S)-3-Neopentyl-2-oxo-1-piperazinyl]valeryl}-4-piperidyl)acetamide | (4-Piperidyl)acetamide (Enamine BB) | CD$_3$OD: δ 5.49 (m, 1H), 4.51 (t, 1H), 2.19 (d, 2H), 2.06 (m, 2H), 1.03 (m, 12H) | +* |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 113 | 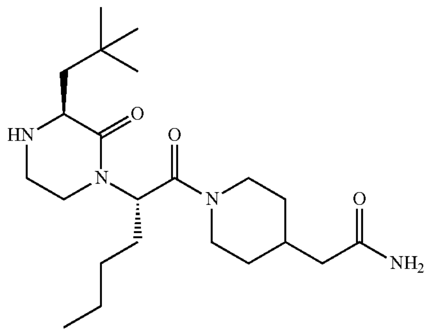 [SMILES: CCCC[C@@H](C(=O)N1CCC(CC(N)=O)CC1)N1CCN[C@@H](CC(C)(C)C)C1=O] | (1-{(S)-2-[(S)-3-Neopentyl-2-oxo-1-piperazinyl]hexanoyl}-4-piperidyl)acetamide | (4-Piperidyl)acetamide (Enamine BB) | CD$_3$OD: δ 5.46 (m, 1H), 4.51 (t, 1H), 2.19 (d, 2H), 2.06 (m, 2H), 1.78 (m, 4H), 1.02 (s, 9H), 0.95 (t, 3H) | +* |
| 114 | 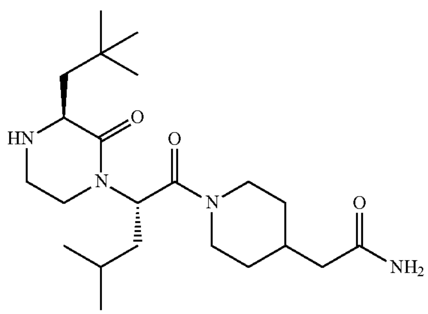 [SMILES: CC(C)C[C@@H](C(=O)N1CCC(CC(N)=O)CC1)N1CCN[C@@H](CC(C)(C)C)C1=O] | (1-{(S)-2-[(S)-3-Neopentyl-2-oxo-1-piperazinyl]-4-methylvaleryl}-4-piperidyl)acetamide | (4-Piperidyl)acetamide (Enamine BB) | CD$_3$OD: δ 5.60 (m, 1H), 4.51 (t, 1H), 2.19 (d, 2H), 2.06 (m, 2H), 1.03 (s, 9H), 0.99 (m, 6H) | ND |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 115 | 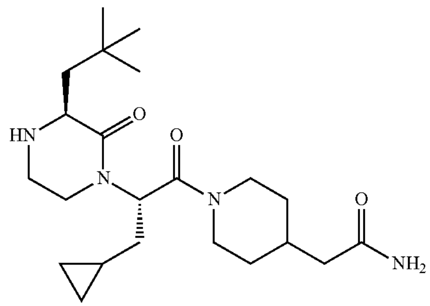 [SMILES: CC(C)(C)C[C@@H]1NCCN([C@@H](CC2CC2)C(=O)N2CCC(CC(N)=O)CC2)C1=O] | (1-{(S)-2-[(S)-3-Neopentyl-2-oxo-1-piperazinyl]-3-cyclopropylpropionyl}-4-piperidyl)acetamide | (4-Piperidyl)acetamide (Enamine BB) | CD$_3$OD: δ 5.58 (m, 1H), 4.52 (t, 1H), 2.20 (d, 2H), 1.03 (s, 9H), 0.69 (m, 1H), 0.49 (m, 2H), 0.16 (m, 2H) | ++ |
| 116 | 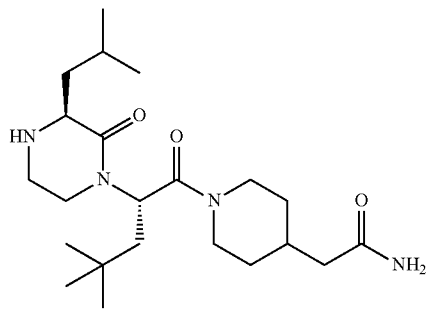 [SMILES: CC(C)C[C@@H]1NCCN([C@@H](CC(C)(C)C)C(=O)N2CCC(CC(N)=O)CC2)C1=O] | (1-{(S)-2-[(S)-3-Isobutyl-2-oxo-1-piperazinyl]-4,4-dimethylvaleryl}-4-piperidyl)acetamide | (4-Piperidyl)acetamide (Enamine BB) | CD$_3$OD: δ 5.68 (m, 1H), 4.51 (t, 1H), 2.08 (m, 2H), 1.82 (m, 4H), 0.97 (m, 15H) | +* |
| 117 | 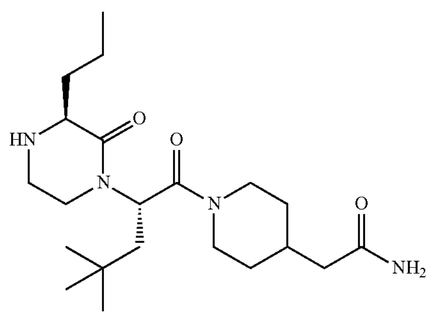 [SMILES: CCC[C@@H]1NCCN([C@@H](CC(C)(C)C)C(=O)N2CCC(CC(N)=O)CC2)C1=O] | (1-{(S)-2-((S)-2-Oxo-3-propyl-1-piperazinyl]-4,4-dimethylvaleryl}-4-piperidyl)acetamide | (4-Piperidyl)acetamide (Enamine BB) | CD$_3$OD: δ 5.70 (m, 1H), 4.52 (t, 1H), 1.85 (m, 3H), 1.69 (m, 1H), 0.98 (m, 12H) | +* |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 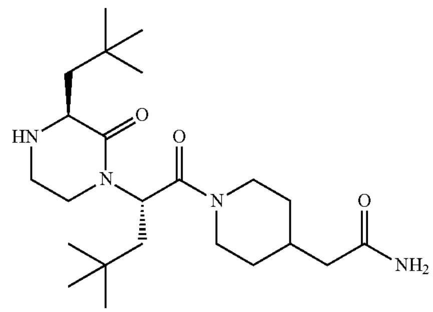 [SMILES: CC(C)(C)C[C@@H]1NCCN([C@@H](CC(C)(C)C)C(=O)N2CCC(CC(N)=O)CC2)C1=O] | 118 | (1-{(S)-2-[(S)-3-Neopentyl-2-oxo-1-piperazinyl]-4,4-dimethylvaleryl}-4-piperidyl)acetamide | (4-Piperidyl)acetamide (Enamine BB) | $CD_3OD$: δ 5.68 (m, 1H), 4.50 (t, 1H), 2.18 (d, 2H), 2.05 (m, 3H), 1.81 (m, 2H), 1.02 (s, 9H), 0.96 (d, 9H) | +* |
| 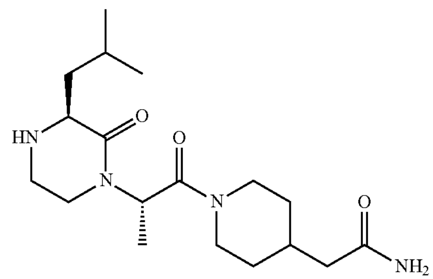 [SMILES: CC(C)C[C@@H]1NCCN([C@@H](C)C(=O)N2CCC(CC(N)=O)CC2)C1=O] | 119 | (1-{(S)-2-[(S)-3-Isobutyl-2-oxo-1-piperazinyl]propionyl}-4-piperidyl)acetamide | (4-Piperidyl)acetamide (Enamine BB) | $CD_3OD$: δ 5.51 (m, 1H), 4.52 (t, 1H), 2.20 (d, 2H), 1.34 (d, 3H), 0.99 (t, 6H) | +* |
| 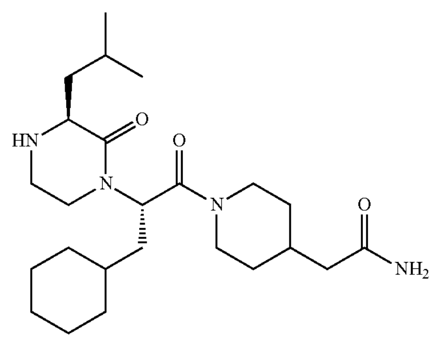 [SMILES: CC(C)C[C@@H]1NCCN([C@@H](CC2CCCCC2)C(=O)N2CCC(CC(N)=O)CC2)C1=O] | 120 | (1-{(S)-2-[(S)-3-Isobutyl-2-oxo-1-piperazinyl]-3-cyclohexylpropionyl}-4-piperidyl)acetamide | (4-Piperidyl)acetamide (Enamine BB) | $CD_3OD$: δ 5.64 (m, 1H), 4.52 (t, 1H), 3.48 (dd, 1H), 2.19 (d, 2H), 1.80 (m, 10H), 1.00 (s, 6H) | ++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 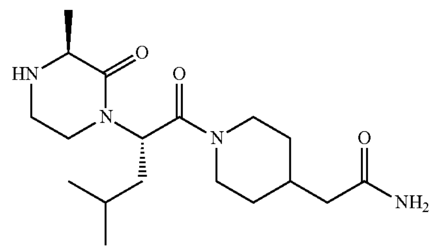 [SMILES: CC(C)C[C@@H](C(=O)N1CCC(CC(N)=O)CC1)N1CCN[C@@H](C)C1=O] | 121 | (1-{(S)-2-[(S)-3-Methyl-2-oxo-1-piperazinyl]-4-methylvaleryl}-4-piperidyl)acetamide | (4-Piperidyl)acetamide (Enamine BB) | CD$_3$OD: δ 5.63 (m, 1H), 4.53 (t, 1H), 3.56 (q, 1H), 2.21 (d, 2H), 1.42 (d, 3H), 1.02 (m, 6H) | +* |
| 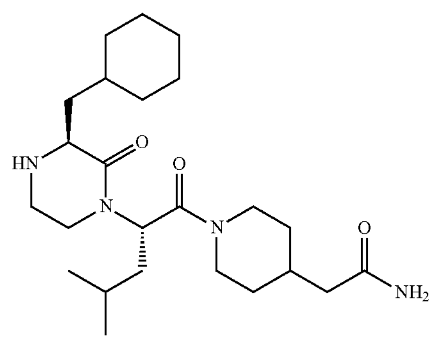 [SMILES: CC(C)C[C@@H](C(=O)N1CCC(CC(N)=O)CC1)N1CCN[C@@H](CC2CCCCC2)C1=O] | 122 | (1-{(S)-2-[(S)-3-(Cyclohexylmethyl)-2-oxo-1-piperazinyl]-4-methylvaleryl}-4-piperidyl)acetamide | (4-Piperidyl)acetamide (Enamine BB) | CD$_3$OD: δ 5.59 (m, 1H), 4.50 (t, 1H), 3.50 (dd, 1H), 2.18 (d, 2H), 1.77 (m, 10H), 0.99 (m, 6H) | ++ |
| 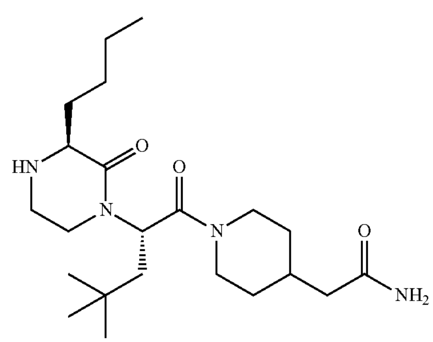 [SMILES: CCCC[C@@H]1NCCN([C@@H](CC(C)(C)C)C(=O)N2CCC(CC(N)=O)CC2)C1=O] | 123 | (1-{(S)-2-[(S)-3-Butyl-2-oxo-1-piperazinyl]-4,4-dimethylvaleryl}-4-piperidyl)acetamide | (4-Piperidyl)acetamide (Enamine BB) | CD$_3$OD: δ 5.65 (m, 1H), 4.47 (t, 1H), 2.69 (q, 1H), 1.22-1.00 (br m, 2H), 0.93 (m, 12H) | +* |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 124 | 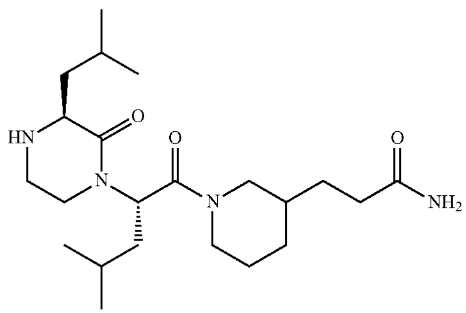 [SMILES: CC(C)C[C@@H]1NCCN([C@@H](CC(C)C)C(=O)N2CCCC(CCC(N)=O)C2)C1=O] | 3-(1-{(S)-2-[(S)-3-Isobutyl-2-oxo-1-piperazinyl]-4-methylvaleryl}-3-piperidyl)propionamide | 3-(3-Piperidyl)propionamide (Enamine BB) | CD$_3$OD: δ 5.56 (m, 1H), 4.43-4.04 (br m, 1H), 2.34-2.16 (br m, 2H), 0.95 (m, 12H) | +* |
| 125 | 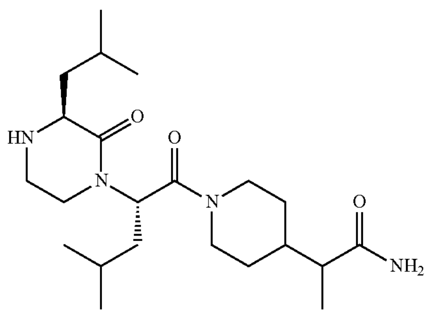 [SMILES: CC(C)C[C@@H]1NCCN([C@@H](CC(C)C)C(=O)N2CCC(C(C)C(N)=O)CC2)C1=O] | 2-(1-{(S)-2-[(S)-3-Isobutyl-2-oxo-1-piperazinyl]-4-methylvaleryl}-4-piperidyl)propionamide | 2-(1-tert-Butoxycarbonyl-4-piperidyl)propionic acid (AstaTech); amide coupling with NH$_4$OH, BOC removal | CD$_3$OD: δ 5.55 (m, 1H), 4.52 (m, 1H), 2.13 (m, 1H), 1.12 (d, 3H), 0.95 (m, 12H) | +* |
| 126 | 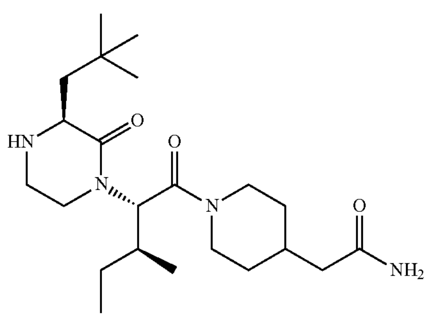 [SMILES: CC[C@H](C)[C@@H](C(=O)N1CCC(CC(N)=O)CC1)N1CCN[C@@H](CC(C)(C)C)C1=O] | (1-{(2S,3S)-2-[(S)-3-Isobutyl-2-oxo-1-piperazinyl]-3-methylvaleryl}-4-piperidyl)acetamide | (4-Piperidyl)acetamide (Enamine BB) | CD$_3$OD: δ 5.25 (dd, 1H), 4.56 (t, 1H), 2.19 (d, 2H), 1.84 (m, 4H), 0.97 (m, 12H) | +* |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 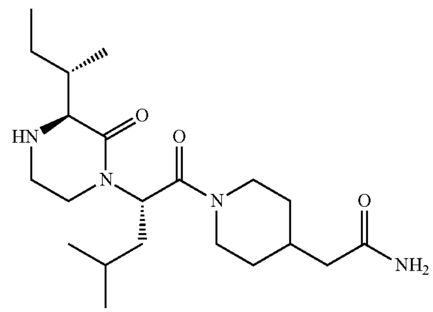 [SMILES: CC[C@H](C)[C@@H]1NCCN([C@@H](CC(C)C)C(=O)N2CCC(CC(N)=O)CC2)C1=O] | 127 | {1-[(S)-2-{(S)-3-[(S)-1-Methylpropyl]-2-oxo-3,4,5,6-tetrahydro-1H-pyrazin-1-yl]-4-methylvaleryl}-4-piperidyl}-acetamide | (4-Piperidyl) acetamide (Enamine BB) | CD₃OD: δ 5.57 (m, 1H), 4.47 (t, 1H), 2.14 (d, 2H), 1.78 (m, 3H), 1.51 (m, 2H), 0.96 (m, 12H) | +* |
| 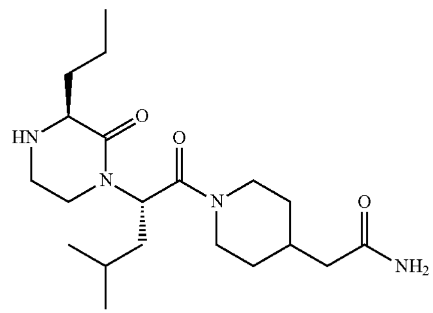 [SMILES: CCC[C@@H]1NCCN([C@@H](CC(C)C)C(=O)N2CCC(CC(N)=O)CC2)C1=O] | 128 | (1-{(S)-2-[(S)-2-Oxo-3-propyl-1-piperazinyl]-4-methylvaleryl}-4-piperidyl)acetamide | (4-Piperidyl) acetamide (Enamine BB) | CD₃OD: δ 5.60 (m, 1H), 4.50 (t, 1H), 3.14 (m, 2H), 2.17 (d, 2H), 0.99 (m, 9H) | +* |
| 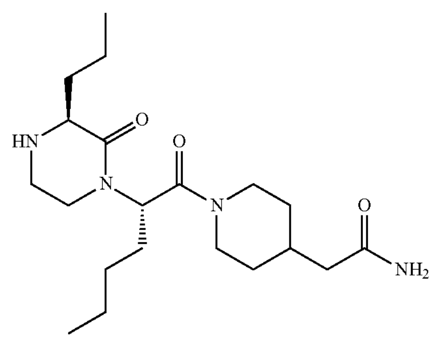 [SMILES: CCCC[C@@H](C(=O)N1CCC(CC(N)=O)CC1)N1CCN[C@@H](CCC)C1=O] | 129 | (1-{(S)-2-[(S)-2-Oxo-3-propyl-1-piperazinyl]hexanoyl}-4-piperidyl)acetamide | (4-Piperidyl) acetamide (Enamine BB) | CD₃OD: δ 5.48 (m, 1H), 4.50 (t, 1H), 3.44 (dd, 2H), 2.17 (d, 2H), 1.45 (m, 4H), 0.97 (m, 9H) | +* |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 130 | 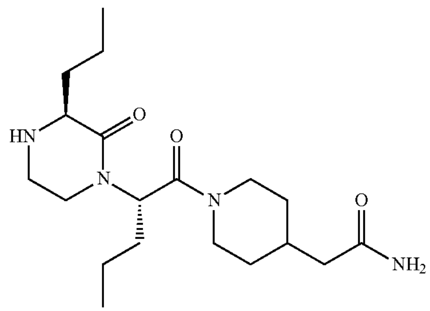 [SMILES: CCC[C@@H]1NCCN([C@@H](CCC)C(=O)N2CCC(CC(N)=O)CC2)C1=O] | (1-{(S)-2-[(S)-2-Oxo-3-propyl-1-piperazinyl]valeryl}-4-piperidyl)acetamide | (4-Piperidyl)acetamide (Enamine BB) | CD$_3$OD: δ 5.50 (m, 1H), 4.51 (t, 1H), 3.12 (m, 2H), 2.18 (d, 2H), 1.78 (m, 6H), 1.48 (m, 2H), 0.99 (t, 6H) | +* |
| 131 | 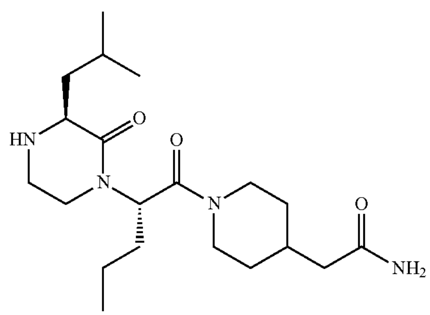 [SMILES: CCC[C@@H](C(=O)N1CCC(CC(N)=O)CC1)N1CCN[C@@H](CC(C)C)C1=O] | (1-{(S)-2-[(S)-3-Isobutyl-2-oxo-1-piperazinyl]valeryl}-4-piperidyl)acetamide | (4-Piperidyl)acetamide (Enamine BB) | CD$_3$OD: δ 5.49 (m, 1H), 4.51 (t, 1H), 3.13 (m, 2H), 2.18 (d, 2H), 1.79 (m, 6H), 0.98 (m, 9H) | +* |
| 132 | 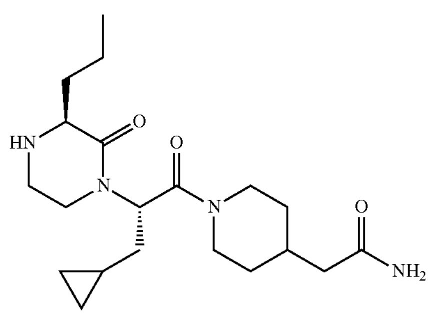 [SMILES: CCC[C@@H]1NCCN([C@@H](CC2CC2)C(=O)N2CCC(CC(N)=O)CC2)C1=O] | (1-{(S)-2-((S)-2-Oxo-3-propyl-1-piperazinyl]-3-cyclopropyl-propionyl}-4-piperidyl)acetamide | (4-Piperidyl)acetamide (Enamine BB) | CD$_3$OD: δ 5.59 (m, 1H), 4.54 (t, 1H), 2.19 (d, 2H), 0.99 (t, 3H), 0.69 (m, 1H), 0.49 (m, 2H), 0.16 (m, 2H) | +* |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 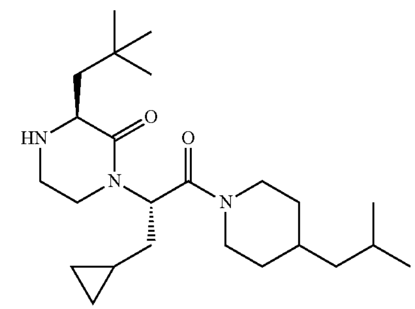 [SMILES: CC(C)CC1CCN(C(=O)[C@H](CC2CC2)N2CCN[C@@H](CC(C)(C)C)C2=O)CC1] | 133 | (S)-1-[(S)-1-(Cyclopropylmethyl)-2-(4-isobutyl-1-piperidyl)-2-oxoethyl]-3-neopentyl-2-piperazinone | 4-Isobutylpiperidine (Enamine BB) | CD₃OD: δ 5.58 (q, 1H), 4.54 (t, 1H), 0.96 (m, 9H), 0.85 (d, 6H), 0.63 (m, 1H), 0.42 (m, 2H), 0.08 (m, 2H) | +++ |
| 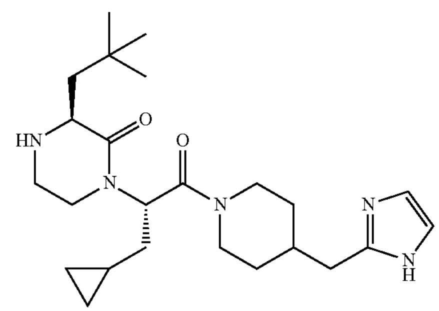 [SMILES: CC(C)(C)C[C@@H]1NCCN([C@@H](CC2CC2)C(=O)N2CCC(Cc3ncc[nH]3)CC2)C1=O] | 134 | (S)-1-[(S)-1-(Cyclopropylmethyl)-2-{4-[(1H-imidazol-2-yl)methyl]-1-piperidyl}-2-oxoethyl]-3-neopentyl-2-piperazinone | 2-[(4-Piperidyl)methyl]-1H-imidazole (Enamine BB) | CD₃OD: δ 6.91 (s, 2H), 5.51 (m, 1H), 4.45 (t, 1H), 0.96 (m, 9H), 0.62 (m, 1H), 0.41 (m, 2H), 0.08 (m, 2H) | +* |
| 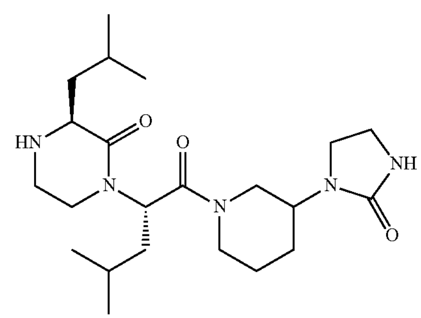 [SMILES: CC(C)C[C@@H]1NCCN([C@@H](CC(C)C)C(=O)N2CCCC(N3CCNC3=O)C2)C1=O] | 135 | 1-(1-{(S)-2-[(S)-3-Isobutyl-2-oxo-1-piperazinyl]-4-methylvaleryl}-3-piperidyl)-2-imidazolidinone | 1-(3-Piperidyl)-2-imidazolidinone (Enamine BB) | CD₃OD: δ 5.59 (m, 1H), 4.53 (t, 1H), 2.99 (m, 1H), 1.71 (m, 10H), 0.99 (m, 12H) | +* |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 232 | 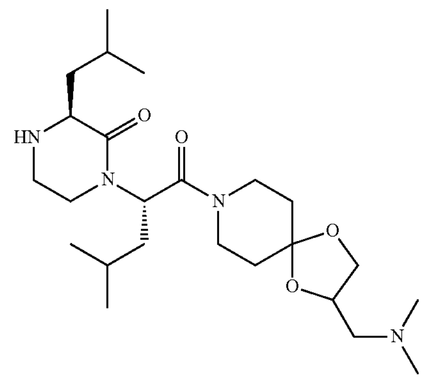 [SMILES: CC(C)C[C@@H]1NCCN([C@@H](CC(C)C)C(=O)N2CCC3(CC2)OCC(CN(C)C)O3)C1=O] | (S)-1-[(S)-1-{2-[(Dimethylamino)methyl]-1,4-dioxa-8-aza-8-spiro[4.5]decyl}carbonyl)-3-methylbutyl]-2-piperazinone | Benzyl 4-oxo-1-piperidine-carboxylate, ketalization with Glycerol, mesylation of alcohol, substitution of mesylate using Dimethylamine, Cbz removal | CD$_3$OD: δ 5.59, (dd, 1H), 4.37 (m, 1H), 2.39 (s, 6H), 0.97 (m, 12H) | ++++ |
| 233 | 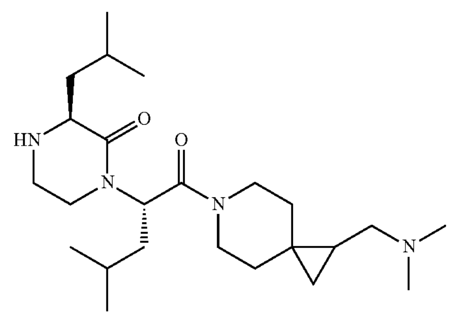 [SMILES: CC(C)C[C@@H]1NCCN([C@@H](CC(C)C)C(=O)N2CCC3(CC2)CC3CN(C)C)C1=O] | (S)-1-[(S)-1-{1-[(Dimethylamino)methyl]-6-aza-6-spiro[2.5]octyl}carbonyl)-3-methylbutyl]-2-pipprazinone | tert-Butyl 1-(hydroxymethyl)-6-aza-6-spiro[2.5]octane carboxylate (Enamine BB), mesylation of alcohol, substitution of mesylate using Dimethylamine, BOC removal | CD$_3$OD: δ 5.63-5.55, (m, 1H), 2.30 (s, 6H), 1.00-0.93 (m, 12H), 0.28 (m, 1H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 234 | 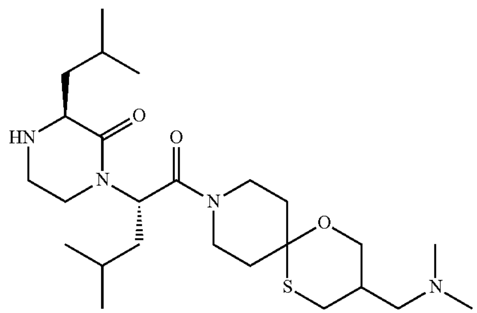 | (S)-1-[(S)-1-({3-[(Dimethylamino)methyl]-1-oxa-5-thia-9-aza-5-spiro[5.5]undecyl}carbonyl)-3-methylbutyl]-3-isobutyl-2-piperazinone | (2,2-Dimethyl-1,3-dioxan-5-yl)methanol (Combi-Blocks), mesylation of alcohol, substitution with potassium thioacetate, reduction of thioacetate to thiol, ketalization with Benzyl 4-oxo-1-piperidine-carboxylate, mesylation of alcohol, substitution of mesylate using Dimethylamine, Cbz removal | CD$_3$OD: δ 5.58 (dd, 1H), 2.82-2.72 (m, 1H), 2.53-2.43 (m, 1H), 0.97 (m, 12H) | ++++ |
| 235 | 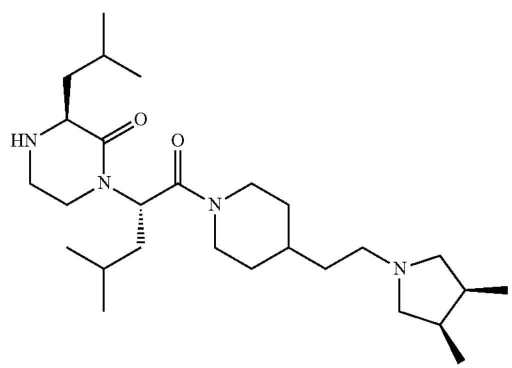 [SMILES: CC(C)C[C@@H]1NCCN([C@@H](CC(C)C)C(=O)N2CCC(CCN3C[C@@H](C)[C@@H](C)C3)CC2)C1=O] | (S)-1-[(S)-1-[(4-{2-[(3R,4S)-3,4-Dimethyl-1-pyrrolidinyl]ethyl}-1-piperidyl)carbonyl]-3-methylbutyl]-3-isobutyl-2-piperazinone | tert-Butyl 4-(formylmethyl)-1-piperidine-carboxylate, reductive amination with (3R,4S)-3,4-Dimethyl-pyrrolidine (ChemBridge BB), BOC removal | CD$_3$OD: δ 5.55 (m, 1H), 4.50 (m, 1H), 2.75 (2s, 6H), 0.96 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 236 | 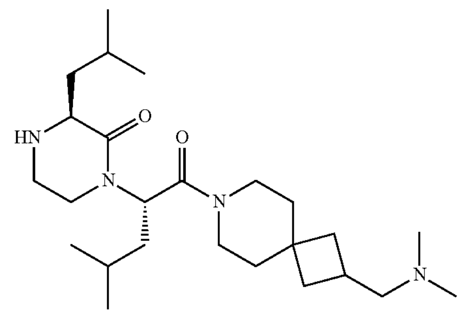 [SMILES: CC(C)C[C@@H]1NCCN([C@@H](CC(C)C)C(=O)N2CCC3(CC2)CC(CN(C)C)C3)C1=O] | (S)-1-[(S)-1-({2-[(Dimethylamino)methyl]-7-aza-7-spiro[3.5]nonyl} carbonyl)-3-methylbutyl]-3-isobutyl-2-piperazinone | tert-Butyl 2-oxo-7-aza-7-spiro[3.5]nonane carboxylate (AstaTech), Wittig reaction with Methyltriphenyl phosphonium bromide, hydroboration, oxidation to aldehyde, reductive amination with Dimethylamine, BOC removal | CD$_3$OD: δ 5.56 (m, 1H), 2.96 (m, 1H), 2.24 (s, 6H), 0.95 (m, 12H) | *+ |
| 237 | 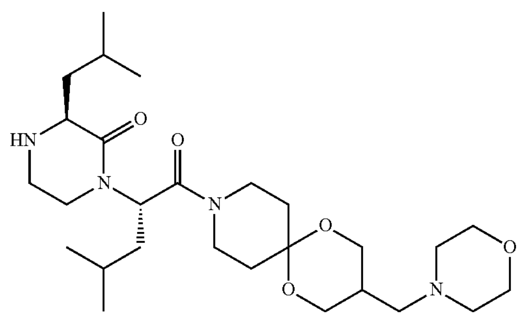 [SMILES: CC(C)C[C@@H]1NCCN([C@@H](CC(C)C)C(=O)N2CCC3(CC2)OCC(CN2CCOCC2)CO3)C1=O] | (S)-1-[(S)-3-Methyl-1-({3-(morpholinomethyl)-1,5-dioxa-9-aza-9-spiro[5.5]undecyl} carbonyl)butyl]-3-isobutyl-2-piperazinone | Benzyl 4-oxo-1-piperidine-carboxylate, ketalization with (2,2-Dimethyl-1,3-dioxan-5-yl)methanol (Combi-Blocks), tosylation of alcohol, substitution of tosylate using Morpholine, Cbz removal | CDCl$_3$: δ 5.56 (t, 1H), 2.34 (br s, 4H), 2.26 (t, 2H), 0.90 (m, 12H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 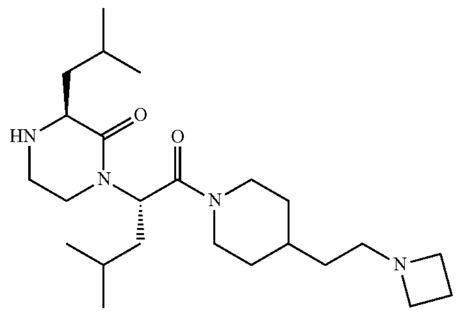 [SMILES: CC(C)C[C@@H]1NCCN([C@@H](CC(C)C)C(=O)N2CCC(CCN3CCC3)CC2)C1=O] | 238 | (S)-1-[(S)-1-({4-[2-(1-Azetidinyl)ethyl]-1-piperidyl}carbonyl)-3-methylbutyl]-3-isobutyl-2-piperazinone | tert-Butyl 4-(formylmethyl)-1-piperidine-carboxylate, reductive amination with Azetidine, BOC removal | CD₃OD: δ 5.56 (m, 1H), 4.47 (m, 1H), 4.08 (m, 1H), 2.63 (m, 3H), 2.16 (m, 2H), 1.66 (m, 10H), 1.32 (m, 2H), 1.03 (m, 15H) | ++++ |
| 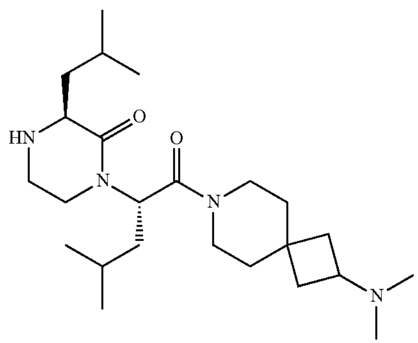 [SMILES: CC(C)C[C@@H]1NCCN([C@@H](CC(C)C)C(=O)N2CCC3(CC2)CC(N(C)C)C3)C1=O] | 239 | (S)-1-[(S)-1-({2-(Dimethylamino)-7-aza-7-spiro[3.5]nonane}carbonyl)-3-methylbutyl]-3-isobutyl-2-piperazinone | tert-Butyl 2-oxo-7-aza-7-spiro[3.5]nonane carboxylate (AstaTech), reductive amination with Dimethylamine, BOC removal | CD₃OD: δ 5.56 (m, 1H), 2.91 (m, 1H), 2.72 (m, 1H), 2.12 (m, 1H), 1.65 (m, 8H), 1.65 (m, 13H), 0.96 (m, 12H) | *+ |
| 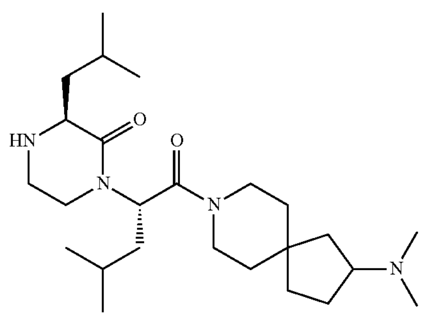 [SMILES: CC(C)C[C@@H]1NCCN([C@@H](CC(C)C)C(=O)N2CCC3(CCC(N(C)C)C3)CC2)C1=O] | 240 | (S)-1-[(S)-1-({2-(Dimethylamino)-8-aza-8-azaspiro[4.5]decane}carbonyl)-3-methylbutyl]-3-isobutyl-2-piperazinone | tert-Butyl 2-oxo-8-azaspiro[4.5]decane-8-carboxylate (AstaTech), reductive amination with Dimethylamine, BOC removal | CD₃OD: δ 5.56 (m, 1H), 3.67 (m, 2H), 2.91 (m, 1H), 2.71 (m, 1H), 2.31 (s, 6H), 1.63 (m, 17H), 0.97 (m, 12H) | +++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 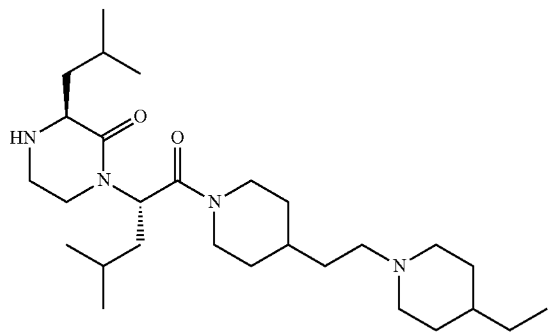 [SMILES: CCC1CCN(CCC2CCN(C(=O)[C@H](CC(C)C)N3CCN[C@@H](CC(C)C)C3=O)CC2)CC1] | 241 | (S)-1-[(S)-1-({4-[2-(4-Ethyl-1-piperidyl)ethyl]-1-piperidyl}-carbonyl)-3-methylbutyl]-2-isobutyl-piperazinone | tert-Butyl 4-(formylmethyl)-1-piperidine-carboxylate, reductive amination with 4-Ethylpiperidine (AstaTech), BOC removal | CD$_3$OD: δ 5.55 (m, 1H), 4.47 (m, 1H), 4.06 (m, 1H), 2.92 (m, 7H), 1.98 (m, 2H), 1.65 (m, 14H), 1.12 (m, 24H) | ++++ |
| 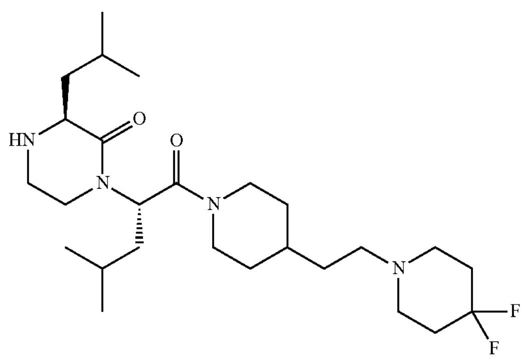 [SMILES: CC(C)C[C@@H]1NCCN([C@@H](CC(C)C)C(=O)N2CCC(CCN3CCC(F)(F)CC3)CC2)C1=O] | 242 | (S)-1-[(S)-1-({4-[2-(4,4-Difluoro-1-piperidyl)ethyl]-1-piperidyl}-carbonyl)-3-methylbutyl]-2-isobutyl-piperazinone | tert-Butyl 4-(formylmethyl)-1-piperidine-carboxylate, reductive amination with 4,4-Difluoropiperidine (AstaTech), BOC removal | CD$_3$OD: δ 5.56 (m, 1H), 4.47 (m, 1H), 4.08 (m, 2H), 2.57 (m, 6H), 1.75 (m, 15H), 1.05 (m, 15H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 243 | 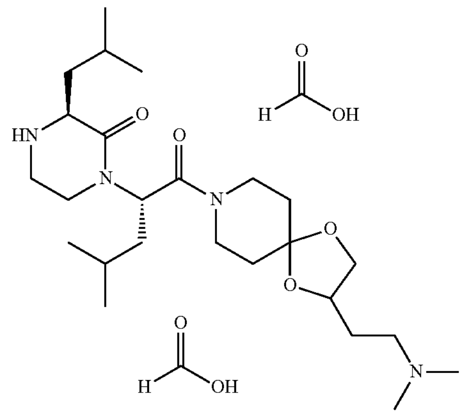 [SMILES: CC(C)C[C@@H]1NCCN([C@@H](CC(C)C)C(=O)N2CCC3(CC2)OCC(CCN(C)C)O3)C1=O ; O=CO ; O=CO] | (S)-1-[(S)-1-({2-[2-(Dimethylamino)ethyl]-1,4-dioxa-8-aza-8-spiro[4.5]decyl}carbonyl)-3-methylbutyl]-3-isobutyl-2-piperazinone, bis formic acid salt | Benzyl 4-oxo-1-piperidine-carboxylate, ketalization with 1,2,4-Butanetriol (Combi-Blocks), tosylation of alcohol, substitution of tosylate using Dimethylamine, Cbz removal, Formic acid treatment | CD$_3$OD: δ 5.56 (m, 1H), 2.89 (s, 6H), 2.12-1.35 (br m, 12H), 1.07-0.85 (br m, 12H) | ++++ |
| 244 | 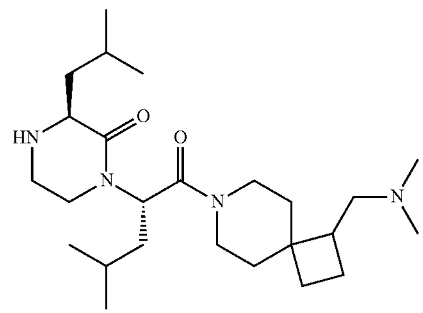 [SMILES: CC(C)C[C@@H]1NCCN([C@@H](CC(C)C)C(=O)N2CCC3(CCC3CN(C)C)CC2)C1=O] | (S)-1-[(S)-1-({1-[(Dimethylamino)methyl]-7-aza-7-spiro[3.5]nonyl}carbonyl)-3-methylbutyl]-3-isobutyl-2-piperazinone | tert-Butyl 1-oxo-7-aza-7-spiro[3.5]nonane carboxylate (AstaTech), Wittig reaction with Methyltriphenyl phosphonium bromide, hydroboration, oxidation to aldehyde, reductive amination with Dimethylamine, BOC removal | CD$_3$OD: δ 5.57 (m, 1H), 3.14 (m, 2H), 3.02-2.64 (br m, 2H), 2.48 (m, 1H), 0.96 (m, 12H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 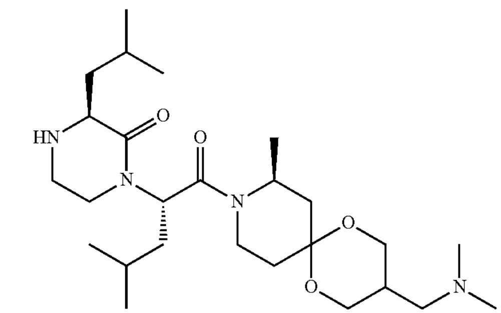 [SMILES: CC(C)C[C@@H]1NCCN([C@@H](CC(C)C)C(=O)N2CCC3(C[C@@H]2C)OCC(CN(C)C)CO3)C1=O] | 245 | (S)-1-[(S)-1-{[(S)-3-[(Dimethylamino)methyl]-8-methyl-1,5-dioxa-9-aza-9-spiro[5.5]undecyl]-carbonyl}-3-methylbutyl]-3-isobutyl-2-piperazinone | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, substitution of tosylate with Dimethylamine, catalytic hydrogenation | CD₃OD: δ 5.54 (m, 1H), 3.68 (m, 2H), 3.11 (m, 1H), 2.52-2.16 (br m, 9H), 0.95 (m, 12H) | ++++ |
| 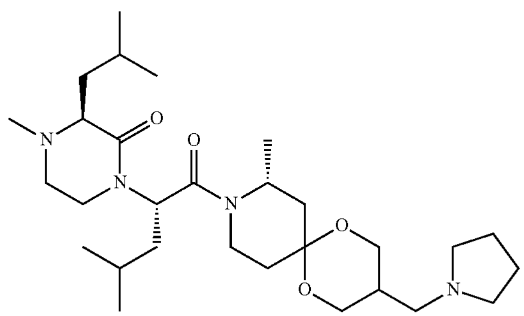 [SMILES: CC(C)C[C@H]1C(=O)N([C@@H](CC(C)C)C(=O)N2CCC3(C[C@H]2C)OCC(CN2CCCC2)CO3)CCN1C] | 246 | (S)-1-[(S)-1-{[(R)-8-Methyl-3-[(1-pyrrolidinyl)methyl]-1,5-dioxa-9-aza-9-spiro[5.5]undecyl]-carbonyl}-3-methylbutyl]-3-isobutyl-4-methyl-2-piperazinone | (R)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, substitution of tosylate with Pyrrolidine, catalytic hydrogenation | CDCl₃: δ 5.56 (m, 1H), 3.07-2.76 (br m, 2H), 2.33 (s, 3H), 1.09-0.76 (br m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 247 | 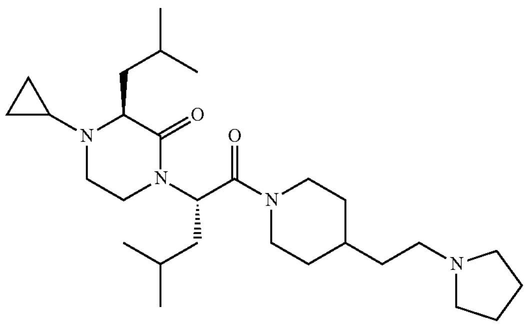 [SMILES: CC(C)C[C@@H](C(=O)N1CCC(CCN2CCCC2)CC1)N1CCN(C2CC2)[C@@H](CC(C)C)C1=O] | (S)-1-[(S)-3-Methyl-1-({4-[2-(1-pyrrolidinyl)-ethyl]-1-piperidyl}carbonyl)butyl]-4-cyclopropyl-3-isobutyl-2-piperazinone | tert-Butyl 4-(formylmethyl)-1-piperidine-carboxylate, reductive amination with Pyrrolidine, BOC removal | CD₃OD: δ 5.58 (m, 1H), 4.47 (m, 1H), 3.58 (m, 1H), 0.94 (m, 12H), 0.62-0.38 (br m, 4H) | ++++ |
| 248 | 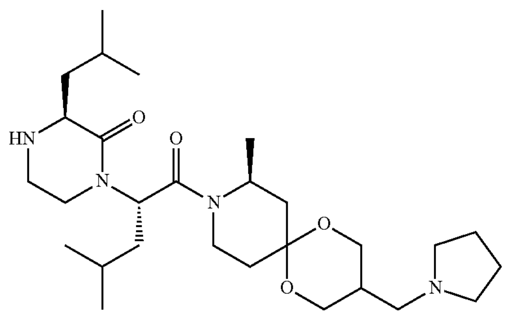 | (S)-1-[(S)-1-({(S)-8-Methyl-3-[(1-pyrrolidinyl)methyl]-1,5-dioxa-9-aza-spiro[5.5]undecyl}carbonyl)-3-methylbutyl]-3-isobutyl-2-piperazinone | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, substitution of tosylate with Pyrrolidine, catalytic hydrogenation | CD₃OD: δ 5.54 (m, 1H), 4.13-3.90 (m, 2H), 3.78-3.61 (m, 2H), 2.74-2.55 (m, 5H), 0.95 (m, 12H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 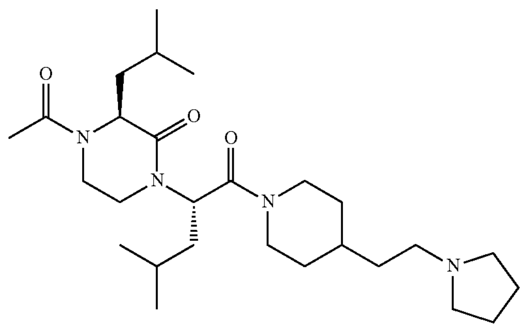 [SMILES: CC(=O)N1CCN([C@@H](CC(C)C)C(=O)N2CCC(CCN3CCCC3)CC2)C(=O)[C@@H]1CC(C)C] | 249 | (S)-1-[(S)-3-Methyl-1-({4-[2-(1-pyrrolidinyl)ethyl]-1-piperidyl}carbonyl)butyl]-4-acetyl-3-isobutyl-2-piperazinone | tert-Butyl 4-(formylmethyl)-1-piperidine-carboxylate, reductive amination with Pyrrolidine, BOC removal | CD$_3$OD: δ 5.51 (m, 1H), 1.52 (m, 4H), 2.28 (s, 3H), 0.88 (m, 12H) | ++++ |
| 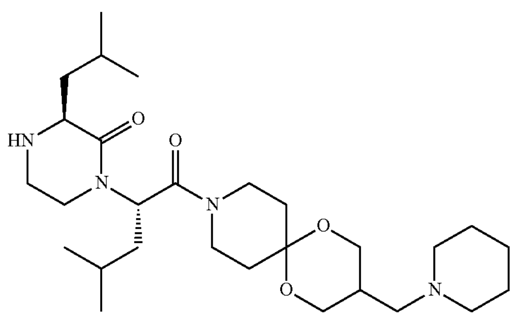 [SMILES: CC(C)C[C@@H]1NCCN([C@@H](CC(C)C)C(=O)N2CCC3(CC2)OCC(CN2CCCCC2)CO3)C1=O] | 250 | (S)-1-[(S)-3-Methyl-1-({3-(piperidinemethyl)-1,5-dioxa-9-aza-9-spiro[5.5]undecyl}carbonyl)butyl]-3-isobutyl-2-piperazinone | Benzyl 4-oxo-1-piperidine-carboxylate, ketalization with (2,2-Dimethyl-1,3-dioxan-5-yl)methanol (Combi-Blocks), tosylation of alcohol, substitution of tosylate using Piperidine, Cbz removal | CD$_3$OD: δ 5.61 (t, 1H), 3.16 (m, 1H), 2.23 (t, 2H), 1.59-1.35 (m, 10H), 0.97 (m, 12H) | ++++ |
| 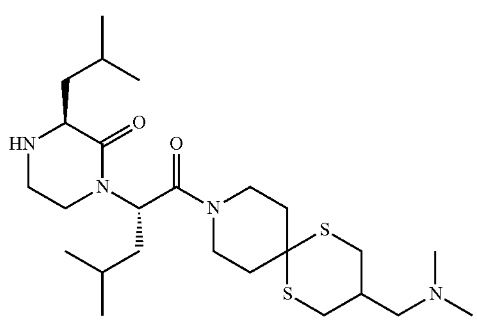 | 251 | (S)-1-[(S)-1-({3-[(Dimethylamino)methyl]-1,5-dithia-9-aza-9-spiro[5.5]undecyl}carbonyl)-3-methylbutyl]-3-isobutyl-2-piperazinone | 3-Bromo-2-(bromomethyl) propionic acid (AstaTech), substitution with potassium thioacetate, esterification of carboxylic acid, reduction with LAH, thio-ketalization with Benzyl 4-oxo-1-piperidine- | CD$_3$OD: δ 5.58 (t, 1H), 2.62 (m, 2H), 2.21 (s, 6H) 1.72-1.36 (m, 6H) 0.97 (m, 12H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| | | | carboxylate, mesylation of alcohol, substitution of mesylate using Dimethylamine, Cbz removal | | |
| 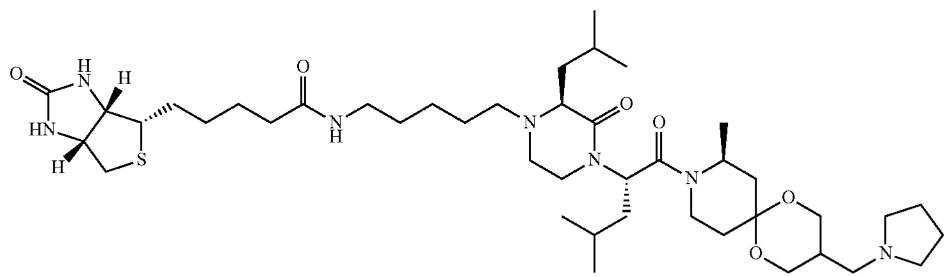 [SMILES: CC(C)C[C@H]1C(=O)N([C@@H](CC(C)C)C(=O)N2CCC3(C[C@@H]2C)OCC(CN2CCCC2)CO3)CCN1CCCCCNC(=O)CCCC[C@@H]1SC[C@@H]2NC(=O)N[C@@H]21] | 252 | (1R,5S,6S)-6-(5-{5-[(S)-4-[(S)-1-((S)-8-Methyl-3-[(1-pyrrolidinyl)methyl]-1,5-dioxa-9-aza-9-spiro[5.5]undecyl}carbonyl)-3-methylbutyl]-2-isobutyl-3-oxo-1-piperazinyl]pentyl-amino}-5-oxopentyl)-7-thia-2,4-diazabicyclo[3.3.0]octan-3-one | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, substitution of tosylate with Pyrrolidine, catalytic hydrogenation | CD₃OD: δ 5.54 (m, 1H), 4.51 (m, 1H), 4.32 (m, 1H), 4.12-3.36 (br m, 4H), 1.89-1.15 (br m, 25H), 0.97 (m, 12 H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 253 | 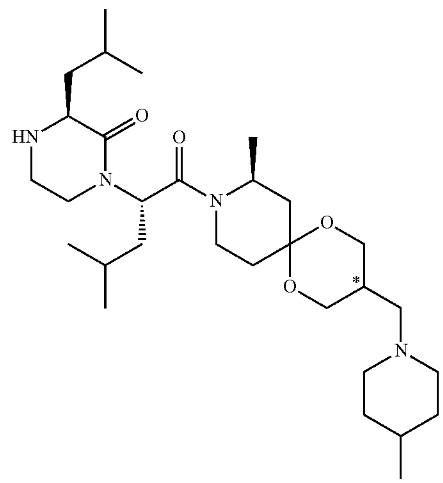 [SMILES: CC(C)C[C@@H]1NCCN([C@@H](CC(C)C)C(=O)N2CCC3(C[C@@H]2C)OCC(CN2CCC(C)CC2)CO3)C1=O] | (3S)-1-[(2S)-4-methyl-1-oxo-1-[(3s,6s,8S)-8-methyl-3-[(4-methylpiperidin-1-yl)methyl]-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation off and Z isomer, substitution of tosylate with 4-Methylpiperidine, catalytic hydrogenation | CD₃OD: δ 5.54 (m, 1H), 3.92 (m, 2H), 3.69 (m, 2H), 2.27 (d, 2H), 0.97 (m, 15H) | ++++ |
| 254 | 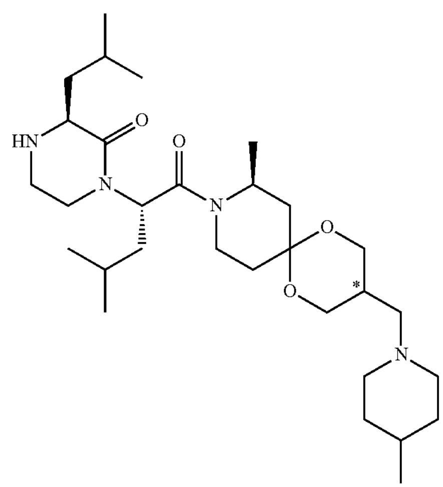 [SMILES: CC(C)C[C@@H]1NCCN([C@@H](CC(C)C)C(=O)N2CCC3(C[C@@H]2C)OCC(CN2CCC(C)CC2)CO3)C1=O] | (3S)-1-[(2S)-4-methyl-1-oxo-1-[(3r,6r,8S)-8-methyl-3-[(4-methylpiperidin-1-yl)methyl]-1,5-dioxa-9-azaspiro[5.5]undecan-9-yl]pentan-2-yl]-3-(2-methylpropyl)piperazin-2-one (*), isomer E | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation off and Z isomer, substitution of tosylate with 4-Methylpiperidine, catalytic hydrogenation | CD₃OD: δ 5.54 (m, 1H), 3.99 (m, 2H), 3.69 (m, 2H), 2.35 (d, 2H), 0.97 (m, 15H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 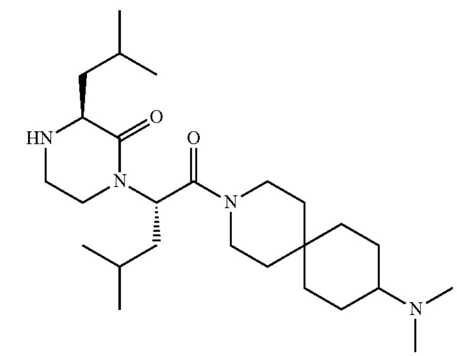 [SMILES: CC(C)C[C@@H]1NCCN([C@@H](CC(C)C)C(=O)N2CCC3(CCC(N(C)C)CC3)CC2)C1=O] | 255 | (S)-1-[(S)-1-({9-(Dimethylamino)-3-aza-3-spiro[5.5]undecyl}carbonyl)-3-methylbutyl]-2-piperazinone | tert-Butyl 9-oxo-3-aza-3-spiro[5.5]undecane-carboxylate (AstaTech), reductive amination with Dimethylamine, BOC removal | CD$_3$OD: δ 5.55 (m, 1H), 2.30 (s, 6H), 2.22 (m, 1H), 0.96 (m, 12H) | +++ |
| 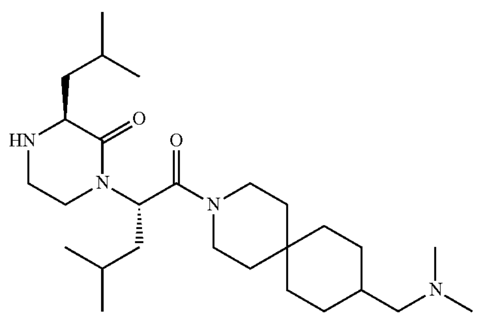 [SMILES: CC(C)C[C@@H]1NCCN([C@@H](CC(C)C)C(=O)N2CCC3(CCC(CN(C)C)CC3)CC2)C1=O] | 256 | (S)-1-[(S)-1-({9-[(Dimethylamino)methyl]-3-aza-3-spiro[5.5]undecyl}carbonyl)-3-methylbutyl]-2-piperazinone | tert-Butyl 9-oxo-3-aza-3-spiro[5.5]undecane-carboxylate (AstaTech), Wittig reaction with Methyltriphenyl phosphonium bromide, hydroboration, oxidation to aldehyde, reductive amination with Dimethylamine, BOC removal | CD$_3$OD: δ 5.58 (m, 1H), 3.15 (td, 1H), 2.92 (td, 1H), 2.25 (s, 6H), 0.98 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 257 | 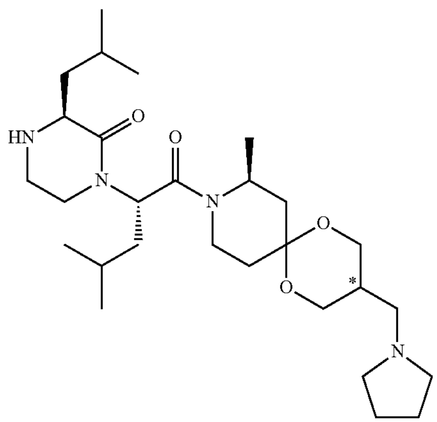 [SMILES: CC(C)C[C@@H]1NCCN([C@@H](CC(C)C)C(=O)N2CCC3(C[C@@H]2C)OCC(CN2CCCC2)CO3)C1=O] | (3S)-1-[(2S)-4-methyl-1-oxo-1-[(3r,6r,8S)-8-methyl-3-(pyrrolidin-1-ylmethyl)-1,5-dioxa-9-azaspiro[5.5]undecan-9-yl]pentan-2-yl]-3-(2-methylpropyl)piperazin-2-one (*), isomer E | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with Pyrrolidine, catalytic hydrogenation | CD₃OD: δ 5.53 (m, 1H), 4.45 (m, 1H), 4.10 (m, 2H), 3.75 (m, 2H), 2.33 (m, 1H), 1.92 (m, 4H), 0.96 (m, 12H) | ++++ |
| 258 | 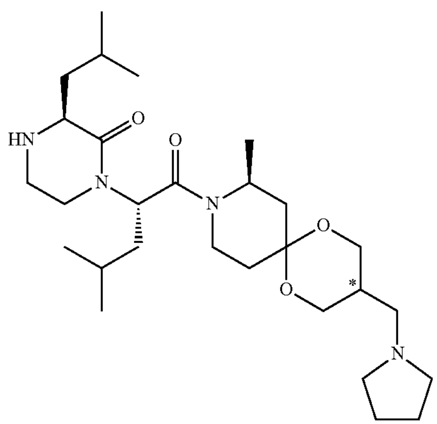 [SMILES: CC(C)C[C@@H]1NCCN([C@@H](CC(C)C)C(=O)N2CCC3(C[C@@H]2C)OCC(CN2CCCC2)CO3)C1=O] | (3S)-1-[(2S)-4-methyl-1-oxo-1-[(3s,6s,8S)-8-methyl-3-(pyrrolidin-1-ylmethyl)-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with Pyrrolidine, catalytic hydrogenation | CD₃OD: δ 5.57 (m, 1H), 4.49 (m, 1H), 4.02 (m, 2H), 3.76 (m, 2H), 2.70 (m, 4H), 2.45 (m, 1H), 1.89 (m, 4H), 1.00 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 259 | 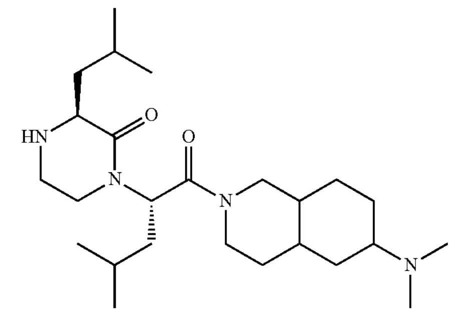 [SMILES: CC(C)C[C@@H]1NCCN([C@@H](CC(C)C)C(=O)N2CCC3CC(N(C)C)CCC3C2)C1=O] | (S)-1-[(S)-1-{[(4aS,8aR)-6-(Dimethylamino)perhydroisoquinol-2-yl]carbonyl}-3-methylbutyl]-isobutyl-2-piperazinone | tert-Butyl 6-hydroxy-decahydroisoquinoline-2-carboxylate (Enamine BB), oxidation to ketone, reductive amination with Dimethylamine, BOC removal | CDCl$_3$: δ 5.40 (m, 1H), 2.78 (m, 2H), 2.28 and 2.11 (s, 6H), 0.75 (m, 12H) | *+ |
| 260 | 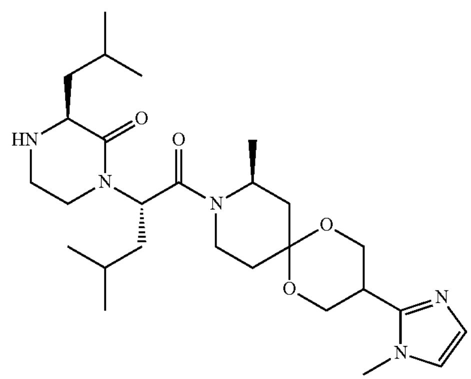 [SMILES: CC(C)C[C@@H]1NCCN([C@@H](CC(C)C)C(=O)N2CCC3(C[C@@H]2C)OCC(c2nccn2C)CO3)C1=O] | (S)-1-[(S)-1-(((S)-8-Methyl-3-(1-methyl-1H-imidazol-2-yl)-1,5-dioxa-9-aza-9-spiro[5.5]undecyl}carbonyl)-3-methylbutyl]-isobutyl-2-piperazinone | (S)-1-[(S)-1-Phenylethyl]-2-methyl-4-piperidinone (AstaTech), ketalization with (2,2-Dimethyl-1,3-dioxan-5-yl)methanol (Combi-Blocks), oxidation of alcohol to aldehyde, imidazole formation (with Glyoxal, methylamine and ammonium acetate), catalytic hydrogenation | CD$_3$OD: δ 7.02 (d, 1H), 6.91 (d, 1H), 5.55 (m, 1H), 3.71 (s, 3H), 1.08-0.86 (br m, 12H) | ND |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 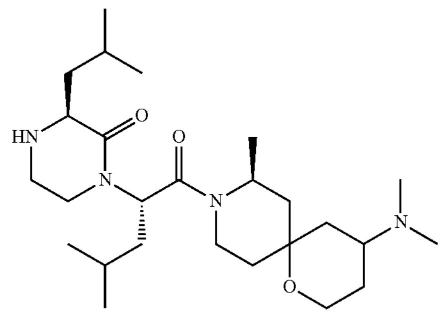 [SMILES: CC(C)C[C@@H]1NCCN([C@@H](CC(C)C)C(=O)N2CCC3(CC(N(C)C)CCO3)C[C@@H]2C)C1=O] | 261 | (S)-1-[(S)-1-({4-(Dimethylamino)-1-oxa-9-aza-9-spiro[5.5]undecyl}carbonyl)-3-methylbutyl]-3-isobutyl-2-piperazinone | tert-Butyl 4-oxo-1-oxa-9-aza-9-spiro[5.5]undecane-carboxylate (Enamine BB), reductive amination with Dimethylamine, BOC removal | CD$_3$OD: δ 5.60-5.52 (m, 1H), 4.29-4.10 (m, 1H), 2.68 (s, 6H), 0.97 (m, 12H) | +++ |
| 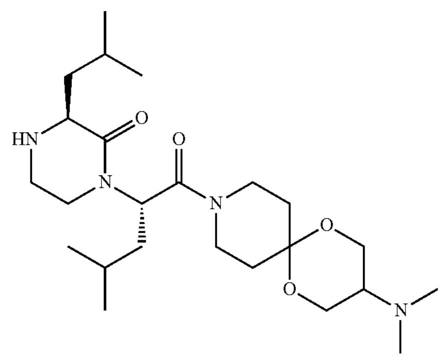 [SMILES: CC(C)C[C@@H]1NCCN([C@@H](CC(C)C)C(=O)N2CCC3(CC2)OCC(N(C)C)CO3)C1=O] | 262 | (S)-1-[(S)-1-({3-(Dimethylamino)-1,5-dioxa-9-aza-9-spiro[5.5]undecyl}carbonyl)-3-methylbutyl]-3-isobutyl-2-piperazinone | 2-Amino-1,3-propanediol, Fmoc protection of amine, ketalization with Benzyl 4-oxo-1-piperidine-carboxylate, Fmoc removal, reductive amination with formaldehyde, Cbz removal | CD$_3$OD: δ 5.58 (dd, 1H), 2.48 (m, 1H), 2.34 (s, 6H), 0.96 (m, 12H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 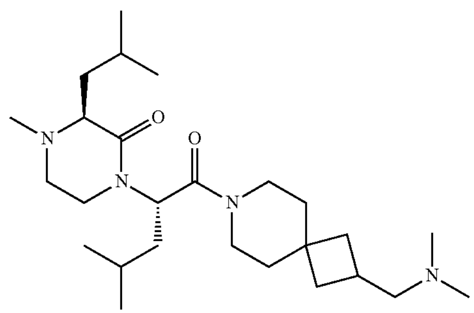 | 263 | (S)-1-[(S)-1-{[2-[(Dimethylamino)methyl]-7-aza-7-spiro[3.5]nonyl}carbonyl)-3-methylbutyl]-4-methyl-2-piperazinone | tert-Butyl 2-oxo-7-aza-7-spiro[3.5]nonane carboxylate (AstaTech), Wittig reaction with Methyltriphenyl phosphonium bromide, hydroboration, oxidation to aldehyde, reductive amination with Dimethylamine, BOC removal | CDCl₃: δ 5.52 (m, 1H), 2.32 (s, 3H), 2.19 (s, 6H), 0.93 (m, 15H) | ++++ |
| 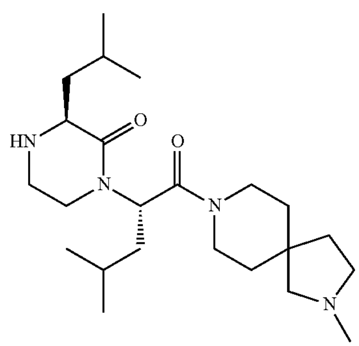 [SMILES: CC(C)C[C@@H]1NCCN([C@@H](CC(C)C)C(=O)N2CCC3(CCN(C)C3)CC2)C1=O] | 264 | (S)-1-[(S)-3-Methyl-1-{(2-methyl-2,8-diaza-8-spiro[4.5]decyl)carbonyl}butyl]-3-isobutyl-2-piperazinone | 2-Methyl-2,8-diazaspiro[4.5]decane (citrate salt, Combi-Blocks) | CD₃OD: δ 5.56 (m, 1H), 3.13 (m, 1H), 2.91 (m, 1H), 2.78 (m, 2H), 2.45 (s, 3H), 1.66 (m, 13H), 0.96 (m, 12H) | +++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 265 | 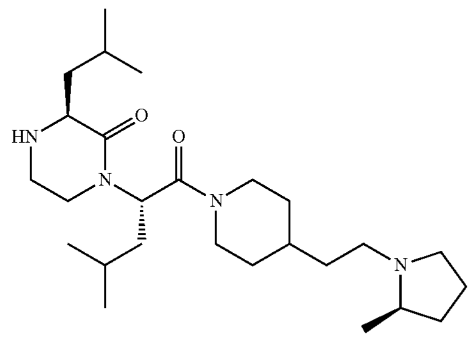 [SMILES: CC(C)C[C@@H]1NCCN([C@@H](CC(C)C)C(=O)N2CCC(CCN3CCC[C@H]3C)CC2)C1=O] | (S)-1-[(S)-1-[(4-{2-[(R)-2-Methyl-1-pyrrolidinyl]ethyl}-1-piperidyl)carbonyl]-3-methylbutyl]-3-isobutyl-2-piperazinone | tert-Butyl 4-(formylmethyl)-1-piperidine-carboxylate, reductive amination with (R)-2-Methylpyrrolidine, BOC removal | CD$_3$OD: δ 5.56 (m, 1H), 4.08 (m, 1H), 2.66 (m, 1H), 2.47 (m, 1H), 2.22 (m, 2H), 2.02 (m, 1H), 1.67 (m, 14H), 1.13 (m, 5H), 0.96 (m, 12H) | ++++ |
| 266 | 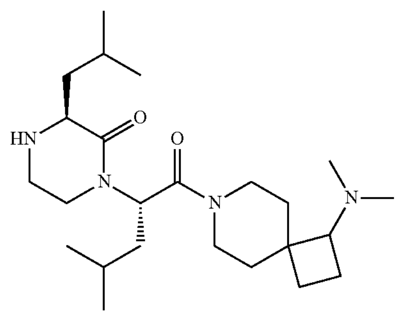 [SMILES: CC(C)C[C@@H]1NCCN([C@@H](CC(C)C)C(=O)N2CCC3(CCC3N(C)C)CC2)C1=O] | (S)-1-{(S)-1-{[1-(Dimethylamino)-7-aza-7-spiro[3.5]nonyl]carbonyl}-3-methylbutyl]-3-isobutyl-2-piperazinone | tert-Butyl 1-oxo-7-aza-7-spiro[3.5]nonane carboxylate (AstaTech), reductive amination with Dimethylamine, BOC removal | CD$_3$OD: δ 5.56 (m, 1H), 3.13 (m, 1H), 2.91 (m, 1H), 2.78 (m, 2H), 2.45 (s, 3H), 1.66 (m, 13H), 0.96 (m, 12H) | *+ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 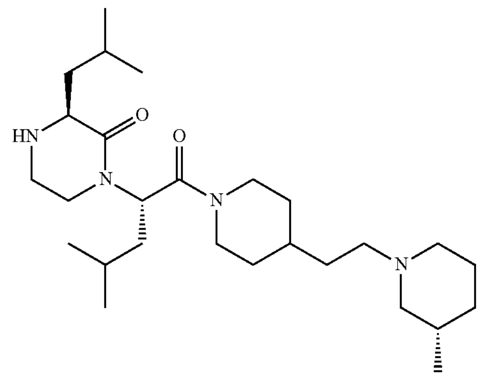 [SMILES: CC(C)C[C@@H]1NCCN([C@@H](CC(C)C)C(=O)N2CCC(CCN3CCC[C@H](C)C3)CC2)C1=O] | 267 | (S)-1-[(S)-1-[(4-{2-[(S)-3-Methyl-1-piperidyl]ethyl}-1-piperidyl)carbonyl]-3-methylbutyl]-3-isobutyl-2-piperazinone | tert-Butyl 4-(formylmethyl)-1-piperidine-carboxylate, reductive amination with (S)-3-Methylpiperidine (AstaTech), BOC removal | CD₃OD: δ 5.56 (m, 1H), 4.47 (m, 1H), 4.08 (m, 1H), 2.67 (m, 1H), 2.39 (m, 2H), 1.68 (m, 18H), 1.02 (m, 19H) | ++++ |
| 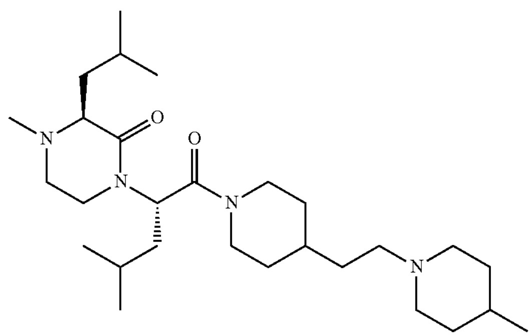 | 268 | (S)-1-[(S)-3-Methyl-1-({4-[2-(4-methyl-1-piperidyl)ethyl]-1-piperidyl}carbonyl)butyl]-3-isobutyl-4-methyl-2-piperazinone | tert-Butyl 4-(formylmethyl)-1-piperidine-carboxylate, reductive amination with 4-Methylpiperidine, BOC removal | CD₃OD: δ 5.53 (m, 1H), 4.46 (m, 1H), 4.08 (m, 1H), 2.62 (m, 1H), 2.39 (m, 2H), (s, 5H), 1.61 (m, 23H), 0.93 (m, 15H) | ++++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 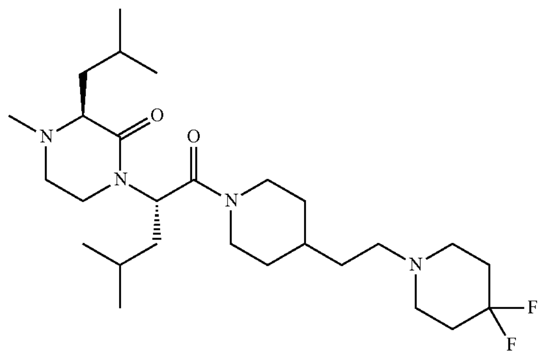 [SMILES: CC(C)C[C@H]1C(=O)N([C@@H](CC(C)C)C(=O)N2CCC(CCN3CCC(F)(F)CC3)CC2)CCN1C] | 269 | (S)-1-[(S)-1-({4-[2-(4,4-Difluoro-1-piperidyl)ethyl]-1-piperidyl}carbonyl)-3-methylbutyl]-4-methyl-2-piperazinone | tert-Butyl 4-(formylmethyl)-1-piperidine-carboxylate, reductive amination with 4,4-Difluoropiperidine (AstaTech), BOC removal | CD$_3$OD: δ 5.53 (m, 1H), 4.47 (m, 1H), 4.09 (m, 1H), 3.05 (m, 2H), 2.37 (s, 3H), 1.75 (m, 15H), 1.00 (m, 15H) | *+ |
| 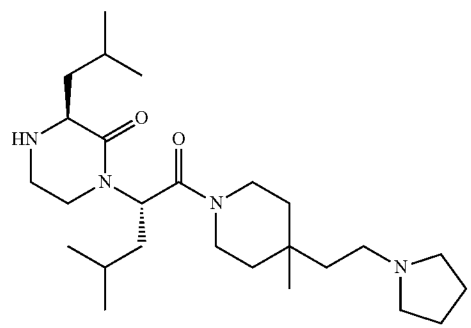 [SMILES: CC(C)C[C@@H]1NCCN([C@@H](CC(C)C)C(=O)N2CCC(C)(CCN3CCCC3)CC2)C1=O] | 270 | (S)-1-[(S)-3-Methyl-1-({4-methyl-4-[2-(1-pyrrolidinyl)ethyl]-1-piperidyl}carbonyl)butyl]-3-isobutyl-2-piperazinone | tert-Butyl 4-(2-hydroxyethyl)-4-methyl-1-piperidine-carboxylate (Combi-Blocks), oxidation to aldehyde, reductive amination with Pyrrolidine, BOC removal | CD$_3$OD: δ 5.55 (m, 1H), 3.19-3.06 (br m, 1H), 2.00-1.26 (br m, 16H), 1.04 (d, 3H), 0.95 (m, 12H) | +++ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 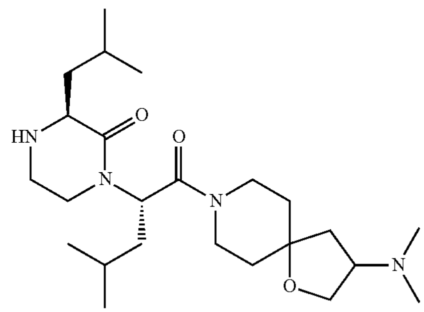 [SMILES: CC(C)C[C@@H]1NCCN([C@@H](CC(C)C)C(=O)N2CCC3(CC2)CC(N(C)C)CO3)C1=O] | 271 | (S)-1-[(S)-1-({3-(Dimethylamino)-1-oxa-8-aza-8-spiro[4.5]decyl}carbonyl)-3-methylbutyl]-3-isobutyl-2-piperazinone | tert-Butyl 3-oxo-1-oxa-8-azaspiro[4.5]decane-8-carboxylate (AstaTech), reductive amination with Dimethylamine, BOC removal | CD$_3$OD: δ 5.55 (m, 1H), 2.24 (s, 6H), 2.18-1.98 (br m, 1H), 1.92-1.40 (br m, 11H), 0.95 (m, 12H) | ++++ |
| 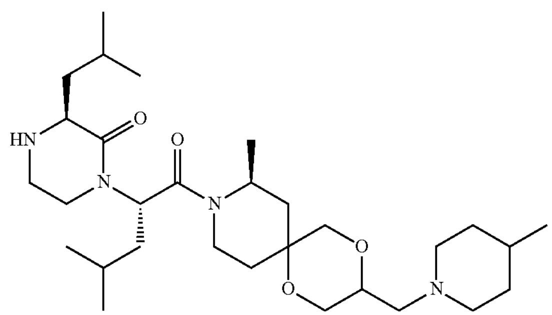 [SMILES: CC(C)C[C@@H]1NCCN([C@@H](CC(C)C)C(=O)N2CCC3(COC(CN4CCC(C)CC4)CO3)C[C@@H]2C)C1=O] | 272 | (S)-1-[(S)-1-({(S)-8-Methyl-3-[(4-methyl-1-piperidyl)methyl]-1,5-dioxa-9-aza-9-spiro[5.5]undecyl}carbonyl)-3-methylbutyl]-3-isobutyl-2-piperazinone | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, substitution of tosylate with 4-Methylpiperidine, catalytic hydrogenation | CD$_3$OD: δ 5.54 (m, 1H), 3.68 (m, 2H), 3.11 (m, 1H), 2.55-1.90 (br m, 7H), 0.95 (m, 15H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 273 | 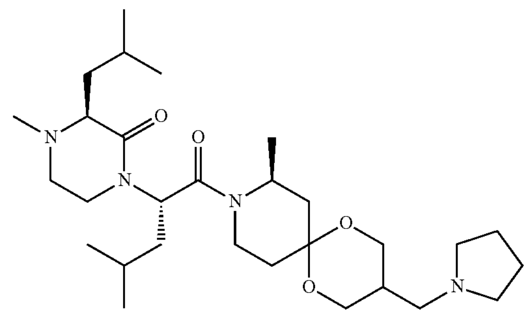 [SMILES: CC(C)C[C@H]1C(=O)N([C@@H](CC(C)C)C(=O)N2CCC3(C[C@@H]2C)OCC(CN2CCCC2)CO3)CCN1C] | (S)-1-[(S)-1-{[(S)-8-Methyl-3-[(1-pyrrolidinyl)methyl]-1,5-dioxa-9-aza-9-spiro[5.5]undecyl}carbonyl)-3-methylbutyl]-3-isobutyl-4-methyl-2-piperazinone | (S)-1-[(S)-1-Phenylethyl]-2-methyl-4-methyl-piperidinone (AstaTech), ketalization with (2,2-Dimethyl-1,3-dioxan-5-yl)methanol (Combi-Blocks), tosylation of alcohol, substitution of tosylate with Pyrrolidine, catalytic hydrogenation | CDCl₃: δ 5.50 (t, 1H), 3.00-2.35 (br m, 10H), 2.31 (s, 3H), 1.00-0.80 (br m, 12H) | ++++ |
| 274 | 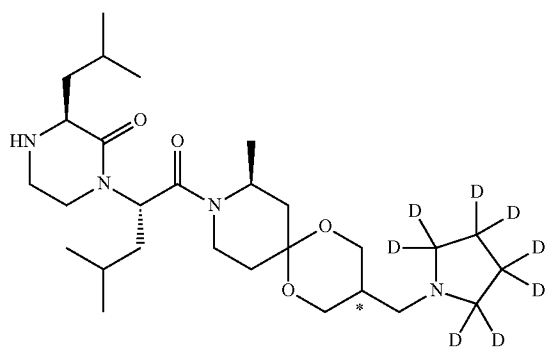 [SMILES: [2H]C1([2H])N(CC2COC3(CCN(C(=O)[C@H](CC(C)C)N4CCN[C@@H](CC(C)C)C4=O)[C@@H](C)C3)OC2)C([2H])([2H])C([2H])([2H])C1([2H])[2H]] | (3S)-1-[(2S)-4-methyl-1-oxo-1-[(3s,6s,8S)-8-methyl-3-[(²H₈)pyrrolidin-1-ylmethyl]-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-methyl-piperidinone (AstaTech), ketalization with (2,2-Dimethyl-1,3-dioxan-5-yl)methanol (Combi-Blocks), separation of E, and Z isomer, tosylation of alcohol, substitution of tosylate with Pyrrolidine-d₈, catalytic hydrogenation | CD₃OD: δ 5.54 (m, 1H), 2.46 (m, 3H), 2.07 (m, 2H), 0.96 (m, 12H) | ++++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 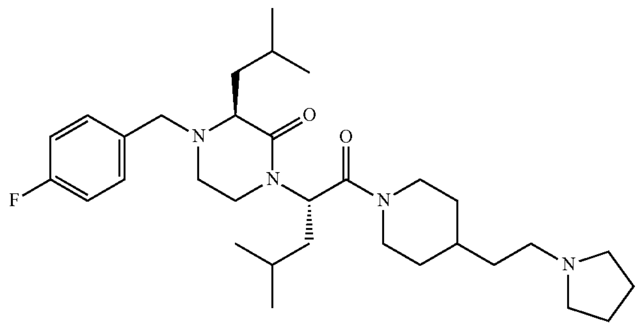 [SMILES: CC(C)C[C@H]1C(=O)N([C@@H](CC(C)C)C(=O)N2CCC(CCN3CCCC3)CC2)CCN1Cc1ccc(F)cc1] | 275 | (S)-1-[(S)-3-Methyl-1-({4-[2-(1-pyrrolidinyl)ethyl]-1-piperidyl}carbonyl)butyl]-4-[p-fluorophenyl)methyl]-3-isobutyl-2-piperazinone | tert-Butyl 4-(formylmethyl)-1-piperidine-carboxylate, reductive amination with Pyrrolidine, BOC removal | CD$_3$OD: δ 7.24 (m, 2H), 6.97 (m, 2H), 5.56 (m, 1H), 4.14 (t, 1H), 0.89 (m, 12H) | ++++ |
| 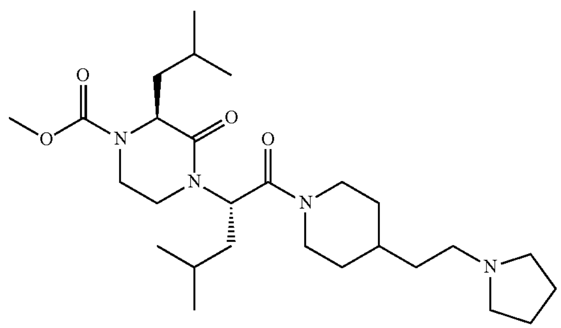 [SMILES: COC(=O)N1CCN([C@@H](CC(C)C)C(=O)N2CCC(CCN3CCCC3)CC2)C(=O)[C@@H]1CC(C)C] | 276 | Methyl (S)-4-[(S)-3-methyl-1-({4-[2-(1-pyrrolidinyl)ethyl]-1-piperidyl}carbonyl)butyl]-2-isobutyl-3-oxo-1-piperazine-carboxylate | tert-Butyl 4-(formylmethyl)-1-piperidine-carboxylate, reductive amination with Pyrrolidine, BOC removal | CD$_3$OD: δ 5.55 (m, 1H), 3.74 (d, 3H), 3.05 (m, 1H), 1.46 (m, 4H), 0.97 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 277 | 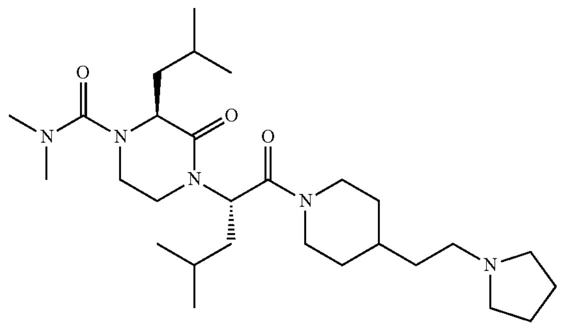 [SMILES: CC(C)C[C@@H](C(=O)N1CCC(CCN2CCCC2)CC1)N1CCN(C(=O)N(C)C)[C@@H](CC(C)C)C1=O] | (S)-1-[(S)-3-Methyl-1-({4-[2-(1-pyrrolidinyl)ethyl]-1-piperidyl)carbonyl}butyl]-4-(dimethylamino)carbonyl-3-isobutyl-2-piperazinone | tert-Butyl 4-(formylmethyl)-1-piperidine-carboxylate, reductive amination with Pyrrolidine, BOC removal | CD$_3$OD: δ 5.55 (m, 1H), 4.48 (d, 2H), 4.00 (m, 1H), 2.81 (d, 6H), 0.97 (m, 12H) | *+ |
| 278 | 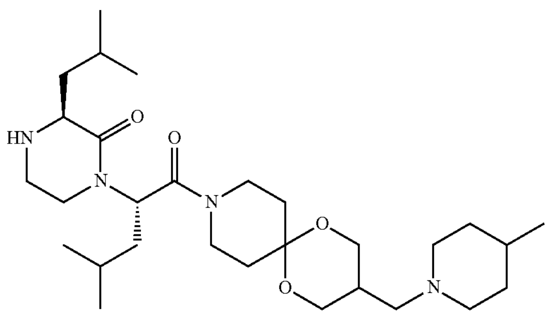 [SMILES: CC(C)C[C@@H]1NCCN([C@@H](CC(C)C)C(=O)N2CCC3(CC2)OCC(CN2CCC(C)CC2)CO3)C1=O] | (S)-1-[(S)-3-Methyl-1-({3-[(4-methyl)methyl]piperidyl)methyl]-1,5-dioxa-9-aza-9-spiro[5.5]undecyl}carbonyl]butyl]-3-isobutyl-2-piperazinone | Benzyl 4-oxo-1-piperidine-carboxylate, ketalization with (2,2-Dimethyl-1,3-dioxan-5-yl)methanol (Combi-Blocks), tosylation of alcohol, substitution of tosylate using 4-Methylpiperidine, Cbz removal | CD$_3$OD: δ 5.59 (t, 1H), 3.91 (br m, 1H), 2.23 (t, 2H), 1.69-1.41 (m, 8H), 1.39-1.25 (m, 1H) 0.97 (m, 15H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 279 | 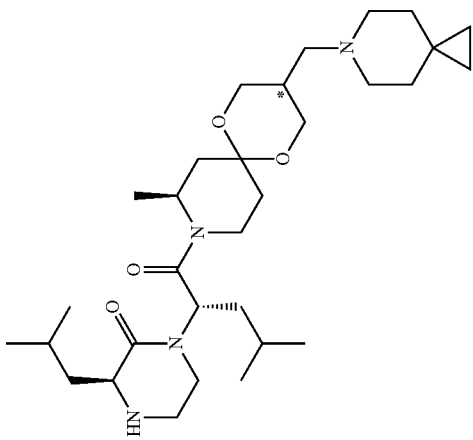 | (3S)-1-[(2S)-4-methyl-1-oxo-1-[(3s,6s,8S)-3-{(6-azaspiro[2.5]octan-6-yl)methyl}-8-methyl-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with 6-Azaspiro[2.5]octane (AstaTech), catalytic hydrogenation | CDCl₃: δ 5.45 (t, 1H), 4.63 (m, 1H), 1.89 (m, 1H), 0.83 (m, 12H), 0.16 (s, 4H) | ++++ |
| 280 | 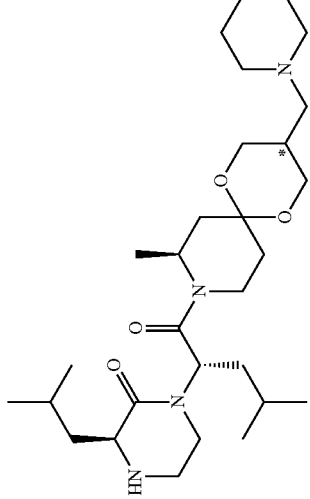 | (3S)-1-[(2S)-4-methyl-1-oxo-1-[(3r,6r,8S)-3-{(6-azaspiro[2.5]octan-6-yl)methyl}-8-methyl-1,5-dioxa-9-azaspiro[5.5]undecan-9-yl]pentan-2-yl]-3-(2-methylpropyl)piperazin-2-one (*), isomer E | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with 6-Azaspiro[2.5]octane (AstaTech), catalytic hydrogenation | CD₃OD: δ 5.54 (m, 1H), 4.01 (m, 2H), 3.71 (m, 2H), 0.97 (m, 12 H), 0.30 (s, 4 H) | +++ |

TABLE 2-continued

Compounds made through Method A

| Ex. Cmpd # | Structure | name | Precursor II synthesis | Characteristic $^1$H NMR signals (300 MHz) | Activity |
|---|---|---|---|---|---|
| 281 | 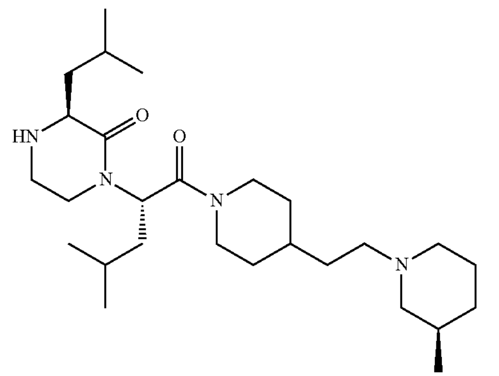 [SMILES: CC(C)C[C@@H]1NCCN([C@@H](CC(C)C)C(=O)N2CCC(CCN3CCC[C@@H](C)C3)CC2)C1=O] | (S)-1-[(S)-1-[(4-{2-[(R)-3-Methyl-1-piperidyl]ethyl}-1-piperidyl)carbonyl]-3-methylbutyl]-2-piperazinone | tert-Butyl 4-(formylmethyl)-1-piperidine-carboxylate, reductive amination with (R)-3-Methylpiperidine (AstaTech), BOC removal | CD$_3$OD: δ 5.59 (m, 1H), 4.51 (t, 1H), 2.04 (m, 1H), 0.99 (m, 12H), 0.94 (d, 3H) | ++++ |
| 282 | 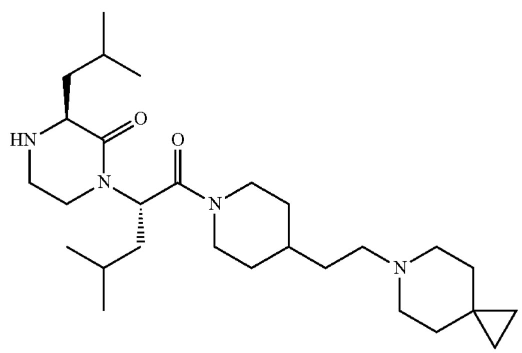 [SMILES: CC(C)C[C@@H]1NCCN([C@@H](CC(C)C)C(=O)N2CCC(CCN3CCC4(CC3)CC4)CC2)C1=O] | (S)-1-[(S)-1-[(4-{2-(6-Aza-6-spiro[2.5]octyl)ethyl}-1-piperidyl)carbonyl]-3-methylbutyl]-2-piperazinone | tert-Butyl 4-(formylmethyl)-1-piperidine-carboxylate, reductive amination with 6-Azaspiro[2.5]octane (AstaTech), BOC removal | CD$_3$OD: δ 5.58 (m, 1H), 4.48 (t, 1H), 3.35 (m, 2H), 3.11 (m, 2H), 0.97 (m, 12H), 0.36 (s, 4H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 283 | 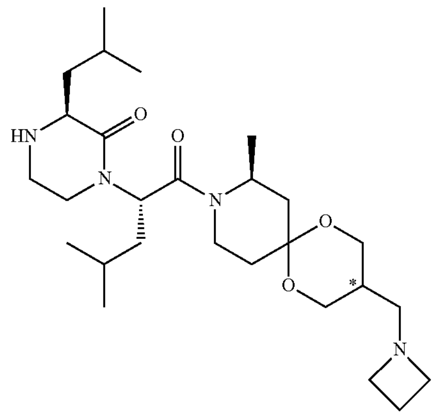 [SMILES: CC(C)C[C@@H]1NCCN([C@@H](CC(C)C)C(=O)N2CCC3(C[C@@H]2C)OCC(CN2CCC2)CO3)C1=O] | (3S)-1-[(2S)-4-methyl-1-oxo-1-[(3r,6r,8S)-3-(azetidin-1-ylmethyl)-8-methyl-1,5-dioxa-9-azaspiro[5.5]undecan-9-yl]pentan-2-yl]-3-(2-methylpropyl)piperazin-2-one (*), isomer E | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with Azetidine, catalytic hydrogenation | CD₃OD: δ 5.54 (m, 1H), 3.96 (m, 2H), 3.67 (m, 2H), 2.51 (d, 2H), 1.89-1.42 (m, 5H), 0.97 (m, 12H) | ++++ |
| 284 | 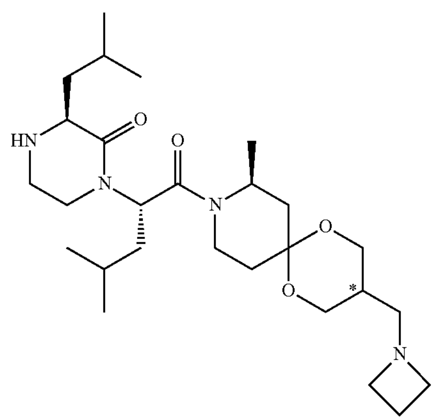 [SMILES: CC(C)C[C@@H]1NCCN([C@@H](CC(C)C)C(=O)N2CCC3(C[C@@H]2C)OCC(CN2CCC2)CO3)C1=O] | (3S)-1-[(2S)-4-methyl-1-oxo-1-[(3s,6s,8S)-3-(azetidin-1-ylmethyl)-8-methyl-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with Azetidine, catalytic hydrogenation | CD₃OD: δ 5.54 (m, 1H), 3.91 (m, 2H), 3.69 (m, 2H), 2.52 (d, 2H), 1.7-1.44 (m, 5H), 0.97 (m, 12H) | ++++ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 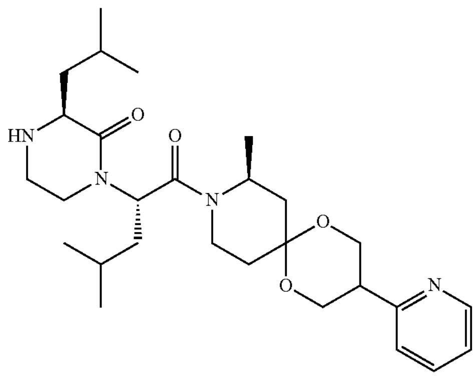 [SMILES: CC(C)C[C@@H]1NCCN([C@@H](CC(C)C)C(=O)N2CCC3(C[C@@H]2C)OCC(c2ccccn2)CO3)C1=O] | 285 | (S)-1-[(S)-1-({(S)-8-Methyl-3-(2-pyridyl)-1,5-dioxa-9-aza-9-spiro[5.5]undecyl}carbonyl)-3-methylbutyl]-2-piperazinone | 2-(2-Pyridyl)-1,3-propanediol (Combi-Blocks), ketalization with (S)-1-[(S)-1-Phenylethyl]-2-methyl-4-piperidinone (AstaTech), catalytic hydrogenation | CD$_3$OD: δ 8.51 (s, 1H), 7.80 (t, 1H), 7.51 (dd, 1H), 7.31 (t, 1H), 5.56 (m, 1H), 0.97 (m, 12H) | ND |
| 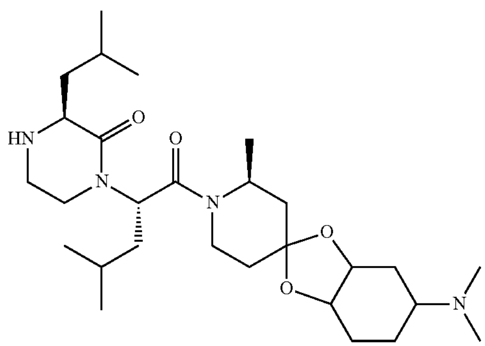 [SMILES: CC(C)C[C@@H]1NCCN([C@@H](CC(C)C)C(=O)N2CCC3(C[C@@H]2C)OC2CCC(N(C)C)CC2O3)C1=O] | 286 | (S)-1-[(S)-1-({(2'S)-5-(Dimethylamino)-2'-methyl-3a,4,5,6,7,7a-hexahydrospiro[indene-2,4'-piperidin]-1'-yl}carbonyl)-3-methylbutyl]-2-piperazinone | 4-Amino-1,2-cyclohexanediol (Enamine BB), reductive amination with formaldehyde, ketalization with (S)-1-[(S)-1-Phenylethyl]-2-methyl-4-piperidinone (AstaTech), catalytic hydrogenation | CD$_3$OD: δ 5.55 (m, 1H), 3.12 (m, 1H), 2.91 (m, 1H), 2.28 (br, 3, 6H), 1.94-1.44 (m, 13H), 0.96 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 287 | 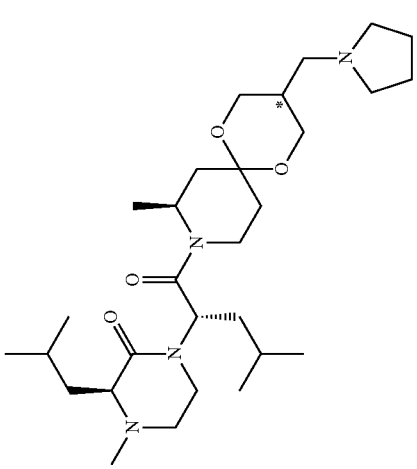 | (3S)-4-methyl-1-[(2S)-4-methyl-1-oxo-1-[(3s,6s,8S)-8-methyl-3-(pyrrolidin-1-ylmethyl)-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and Z isomer, substitution of tosylate with Pyrrolidine, catalytic hydrogenation | CDCl₃: δ 5.43 (t, 1H), 4.66 (m, 1H), 3.57 (m, 2H), 2.23 (m, 2H), 2.03 (s, 3H), 2.03 (m, 1H), 0.83 (m, 12H) | ++++ |
| 288 | 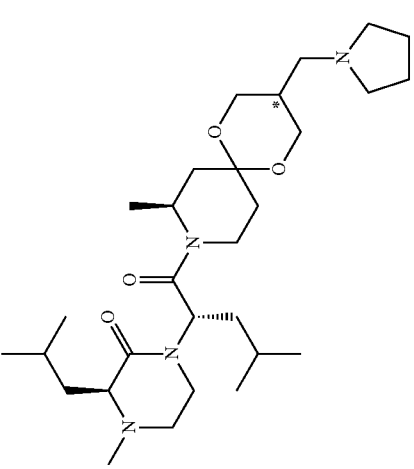 | (3S)-4-methyl-1-[(2S)-4-methyl-1-oxo-1-[(3r,6r,8S)-8-methyl-3-(pyrrolidin-1-ylmethyl)-1,5-dioxa-9-azaspiro[5.5]undecan-9-yl]pentan-2-yl]-3-(2-methylpropyl)piperazin-2-one (*), isomer E | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation of E and 2 isomer, substitution of tosylate with Pyrrolidine, catalytic hydrogenation | CDCl₃: δ 5.45 (t, 1H), 4.67 (m, 1H), 5.92 (m, 2H), 3.63 (m, 2H), 2.26 (s, 3H), 1.92 (m, 1H), 0.86 (m, 12H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 289 | 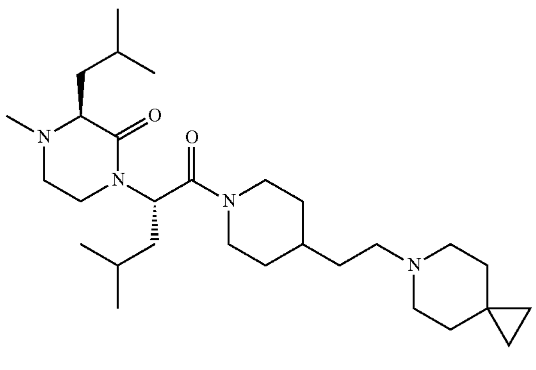 [SMILES: CC(C)C[C@H]1C(=O)N([C@@H](CC(C)C)C(=O)N2CCC(CCN3CCC4(CC3)CC4)CC2)CCN1C] | (S)-1-[(S)-1-(4-{2-(6-Aza-6-spiro[2.5]octyl) ethyl}-1-piperidyl)carbonyl]-3-methylbutyl]-3-isobutyl-4-methyl-2-piperazinone | tert-Butyl 4-(formylmethyl)-1-piperidine-carboxylate, reductive amination with 6-Azaspiro[2.5]octane (AstaTech), BOC removal | CD$_3$OD: δ 5.55 (m, 1H), 4.48 (t, 1H), 2.38 (s, 3H), 0.33 (s, 4H) | ++++ |
| 290 | 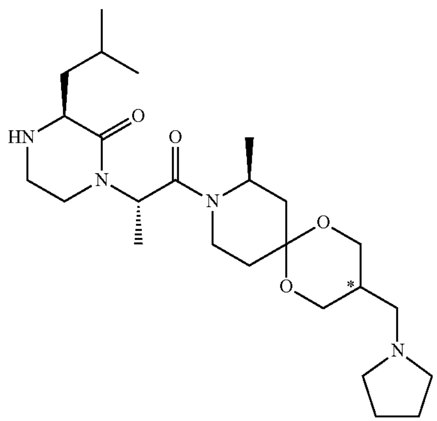 [SMILES: CC(C)C[C@@H]1NCCN([C@@H](C)C(=O)N2CCC3(C[C@@H]2C)OCC(CN2CCCC2)CO3)C1=O] | (3S)-3-(2-methylpropyl)-1-[(2S)-1-[(3s,6s,8S)-8-methyl-3-(pyrrolidin-1-yl)methyl]-1,5-dioxa-9-azaspiro[5.5] undecan-9-yl]propan-2-yl]piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), separation off and Z isomer, tosylation of alcohol, substitution of tosylate with Pyrrolidine, catalytic hydrogenation | CDCl$_3$: δ 5.45 (t, 1H), 4.63 (m, 1H), 1.89 (m, 1H), 0.83 (m, 12H), 0.16 (s, 4H) | ++++ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 291 | 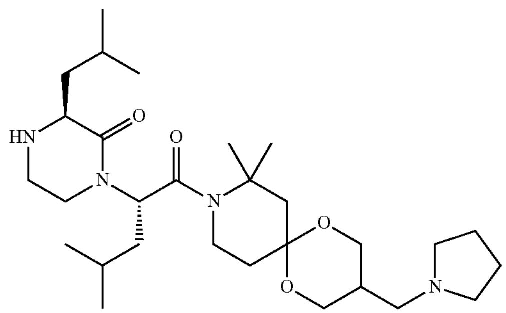 [SMILES: CC(C)C[C@@H]1NCCN([C@@H](CC(C)C)C(=O)N2CCC3(CC2(C)C)OCC(CN2CCCC2)CO3)C1=O] | (S)-1-[(S)-1-({8,8-Dimethyl-3-[(1-pyrrolidinyl)methyl]-1,5-dioxa-9-aza-9-spiro[5.5]undecyl}carbonyl)-3-methylbutyl]-3-isobutyl-2-piperazinone | 1-Benzyl-2,2-dimethyl-4-piperidinone (AstaTech), ketalization with (2,2-Dimethyl-1,3-dioxan-5-yl)methanol (Combi-Blocks), tosylation of alcohol, substitution of tosylate with Pyrrolidine, catalytic hydrogenation | CDCl$_3$: δ 5.41 (m, 1H), 3.85 (m, 2H), 3.55 (m, 2H), 1.38 (s, 6H 0.84 (m, 12H) | *+ |
| 292 | 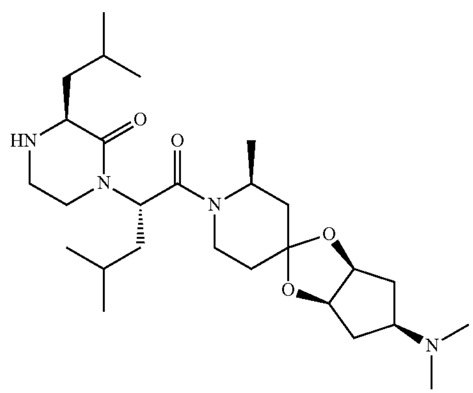 | (S)-1-[(S)-1-({(1R,5S,2S)-7-(Dimethylamino)-2'-methylspiro[2.4-dioxabicyclo[3.3.0]octane-3,4'-piperidin]-1'-yl}carbonyl)-3-methylbutyl]-3-isobutyl-2-piperazinone | (1R,2S,4R)-4-Amino-1,2-cyclopentanediol (HCl salt, Enamine BB), reductive amination with Formaldehyde, ketalization with (S)-1-[(S)-1-Phenylethyl]-2-methyl-4-piperidinone (AstaTech), catalytic hydrogenation | CD$_3$OD: δ 5.53 (m, 1H), 2.63 (m, 1H), 2.40-2.17 (br m, 8H), 0.96 (m, 12H) | ND |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 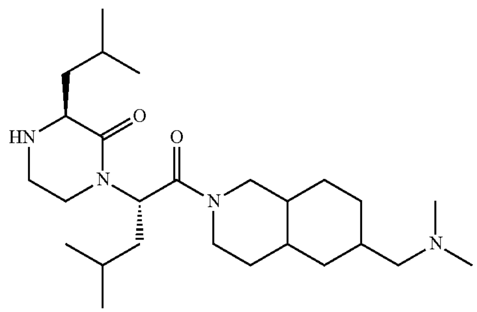 [SMILES: CC(C)C[C@@H]1NCCN([C@@H](CC(C)C)C(=O)N2CCC3CC(CN(C)C)CCC3C2)C1=O] | 293 | (S)-1-[(S)-1-({6-[(Dimethylamino)methyl]perhydroisoquinol-2-yl}carbonyl)-3-methylbutyl]-3-isobutyl-2-piperazinone | tert-Butyl 6-hydroxy-decahydro-isoquinoline-2-carboxylate (Enamine BB), oxidation to ketone, Wittig reaction with Methyltriphenyl phosphonium bromide, hydroboration, oxidation to aldehyde, reductive amination with Dimethylamine, BOC removal | CDCl$_3$: δ 5.48 (t, 1H), 3.05 (m, 2H), 2.86 (m, 2H), 2.22 (s, 6H), 0.84 (m, 12H) | *+ |
| 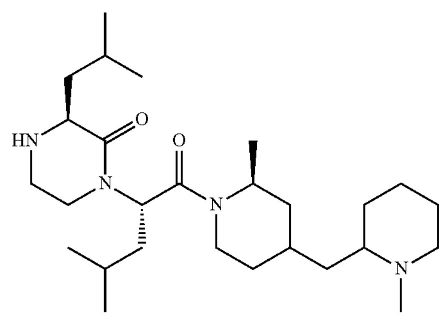 [SMILES: CC(C)C[C@@H]1NCCN([C@@H](CC(C)C)C(=O)N2CCC(CC3CCCCN3C)C[C@@H]2C)C1=O] | 294 | (S)-1-[(S)-1-(((2S)-2-Methyl-4-[(1-methyl-2-piperidyl)methyl]-1-piperidyl}carbonyl)-3-methylbutyl]-3-isobutyl-2-piperazinone | tert-Butyl 2-(hydroxymethyl)-1-piperidine-carboxylate (Combi-Blocks), Mitsunobu reaction with 1,3-Benzothiazole-2-thiol (Combi-Blocks), oxidation to sulfone, Julia-Kocienski olefination with with (S)-1-[(S)-1-Phenylethyl]-2-methyl-4-piperidinone (AstaTech), BOC removal, reductive amination with | CDCl$_3$: δ 5.37 (t, 1H), 4.21 (m, 1H), 3.84 (m, 1H), 2.41 (s, 3H), 0.84 (m, 12H) | *+ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 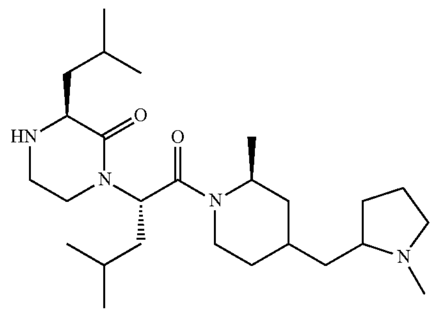 [SMILES: CC(C)C[C@@H]1NCCN([C@@H](CC(C)C)C(=O)N2CCC(CC3CCCN3C)C[C@@H]2C)C1=O] | 295 | (S)-1-[(S)-1-({(2S)-2-Methyl-4-[(1-methyl-2-pyrrolidinyl)methyl]-1-piperidyl}carbonyl)-3-methylbutyl]-2-piperazinone | Formaldehyde, catalytic hydrogenation tert-Butyl 2-(hydroxymethyl)-1-pyrrolidine-carboxylate (TCI America), Mitsunobu reaction with 1,3-Benzothiazole-2-thiol (Combi-Blocks), oxidation to sulfone, Julia-Kocienski olefination with with (S)-1-[(S)-1-Phenylethyl]-2-methyl-4-piperidinone (AstaTech), BOC removal, reductive amination with Formaldehyde, catalytic hydrogenation | CDCl$_3$: δ 5.37 (t, 1H), 4.16 (m, 1H), 2.78 (m, 2H), 2.24 (s, 3H), 0.80 (m, 12H) | *+ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 296 | 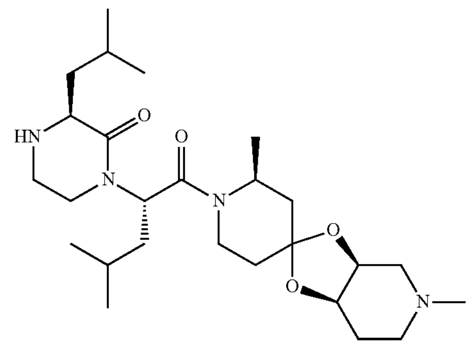 | (S)-1-[(S)-1-({(3aS,7aR,2'S)-5-Methyl-2'-methyl-3a,4,5,6,7,7a-hexahydrospiro[indene-2,4'-piperidin]-1'-yl}carbonyl)-3-methylbutyl]-3-isobutyl-2-piperazinone | (3S,4R)-3,4-Piperidinediol (HCL salt, AstaTech), reductive amination with Formaldehyde, ketalization with (S)-1-[(S)-1-Phenylethyl]-2-methyl-4-piperidinone (AstaTech), catalytic hydrogenation | CDCl$_3$: δ 5.54 (m, 1H), 4.14 (m, 5H), 2.25 (s, 3H), 0.92 (m, 15H) | ND |
| 297 | 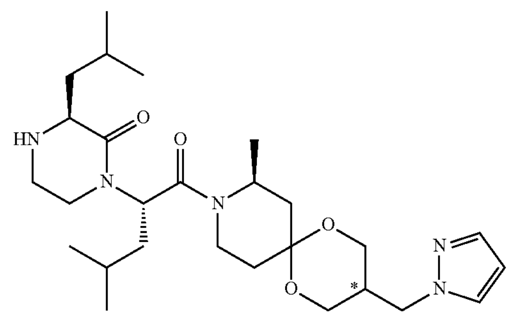 [SMILES: CC(C)C[C@@H]1NCCN([C@@H](CC(C)C)C(=O)N2CCC3(C[C@@H]2C)OCC(Cn2cccn2)CO3)C1=O] | (3S)-1-[(2S)-4-Methyl-1-oxo-1-[(3s,6s,8S)-8-methyl-3-(1H-pyrazol-1-ylmethyl)-1,5-dioxa-9-azaspiro[5.5]undecan-9-yl]pentan-2-yl]-3-(2-methylpropyl)piperazin-2-one (*), isomer Z | (S)-1-[(S)-1-Phenylethyl]-2-methyl-4-piperidinone (AstaTech), ketalization with (2,2-Dimethyl-1,3-dioxan-5-yl)methanol (Combi-Blocks), tosylation of alcohol, separation off and Z isomer, substitution of tosylate with 1H-Pyrazole, catalytic hydrogenation | CDCl$_3$: δ 7.46 (s, 1H), 7.36 (s, 1H), 6.20 (s, 1H), 5.50 (t, 1H), 0.92 (m, 15H) | *+ |

TABLE 2-continued

Compounds made through Method A

| Ex. Cmpd # | Structure | name | Precursor II synthesis | Characteristic ¹H NMR signals (300 MHz) | Activity |
|---|---|---|---|---|---|
| 298 | 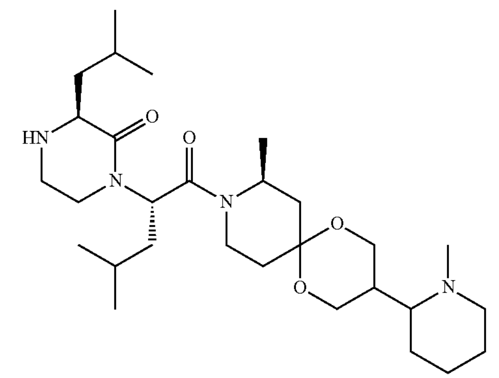 [SMILES: CC(C)C[C@@H]1NCCN([C@@H](CC(C)C)C(=O)N2CCC3(C[C@@H]2C)OCC(C2CCCCN2C)CO3)C1=O] | (S)-1-[(S)-1-{[(S)-8-Methyl-3-(1-methyl-2-piperidyl)-1,5-dioxa-9-aza-9-spiro[5.5]undecyl}-carbonyl)-3-methylbutyl]]-3-isobutyl-2-piperazinone | 2-(1-Methylpiperidin-2-yl)propane-1,3-diol (Oakwood Chemical), ketalization with (S)-1-[(S)-1-Phenylethyl]-2-methyl-4-piperidinone (AstaTech), catalytic hydrogenation | CD₃OD: δ 5.58-5.49 (m, 1H), 3.17-3.07 (m, 1H), 2.38 (s, 3H), 1.00-0.92 (m, 12H) | ++++ |
| 299 | 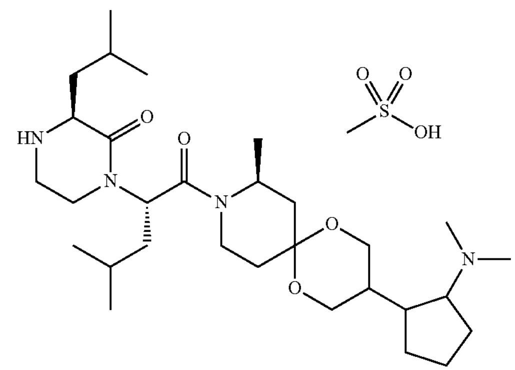 | (S)-1-[(S)-1-{[(10S)-1-(Dimethylamino)-10-methyl-7,14-dioxa-11-aza-11-dispiro[4.2.5.2]pentadecyl]-carbonyl)-3-methylbutyl]-3-isobutyl-2-piperazinone, methanesulfonic acid salt | Methyl 2-oxocyclopentane carboxylate, alkylation with Benzyloxymethyl chloride, reduction with LAH, catalytic hydrogenation, ketalization with (S)-1-[(S)-1-Phenylethyl]-2-methyl-4-piperidinone (AstaTech), mesylation of alcohol, substitution of mesylate with Dimethylamine, catalytic hydrogenation | CD₃OD: δ 5.60-5.48 (m, 1H), 4.16-4.05 (m, 2H), 3.01-2.88 (m, 6H), 1.06-0.94 (m, 12H) | *+ |

TABLE 2-continued

Compounds made through Method A

| Structure | Ex. Cmpd # | name | Precursor II synthesis | Characteristic ¹H NMR signals (300 MHz) | Activity |
|---|---|---|---|---|---|
| 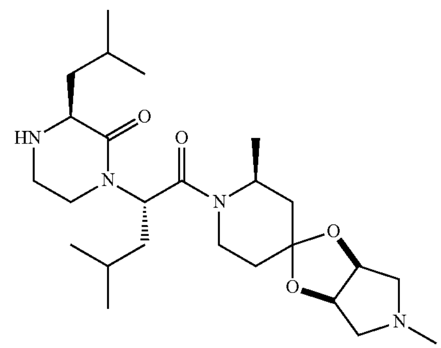 | 300 | (S)-1-[(S)-1-({(2'S)-7-Methyl-2'-methylspiro[2,4-dioxa-7-azabicyclo[3.3.0]octane-3,4'-piperidin]-1'-yl}carbonyl)-3-methylbutyl]-3-isobutyl-2-piperazinone | cis-Pyrrolidine-3,4-diol (HCl salt, Combi-Blocks), reductive amination with Formaldehyde, ketalization with (S)-1-[(S)-1-Phenylethyl]-2-methyl-4-piperidinone (AstaTech), catalytic hydrogenation | CD₃OD: δ 5.56 (m, 1H), 4.76 (m, 1H), 4.68 (m, 1H), 2.37 (s, 3H), 0.96 (m, 12H) | ND |
| 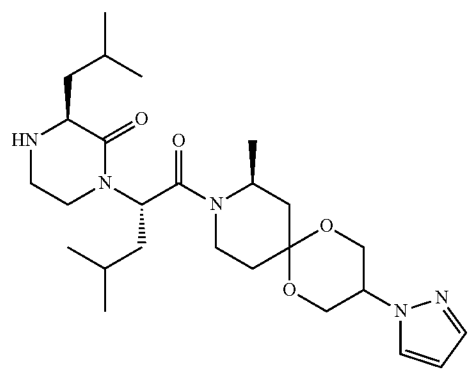 [SMILES: CC(C)C[C@@H]1NCCN([C@@H](CC(C)C)C(=O)N2CCC3(C[C@@H]2C)OCC(n2cccn2)CO3)C1=O] | 301 | (S)-1-[(S)-1-({(S)-8-Methyl-3-(1H-pyrazol-1-yl)-1,5-dioxa-9-aza-9-spiro[5.5]undecyl}carbonyl)-3-methylbutyl]-3-isobutyl-2-piperazinone | Glycerol, protection of primary alcohols with tert-Butyldimethylsilyl chloride, mesylation of secondary alcohol, substitution of mesylate with 1H-Pyrazole, TBDMS ether removal, ketalization with (S)-1-[(S)-1-Phenylethyl]-2-methyl-4-piperidinone (AstaTech), catalytic hydrogenation | CDCl₃: δ 7.52 (b s, 1H), 745 (b s, 1H), 6.26 (b s, 1H), 5.55 (m, 1H), 0.92 (m, 15H) | *+ |

TABLE 2-continued

Compounds made through Method A

| Structure | Ex. Cmpd # | name | Precursor II synthesis | Characteristic $^1$H NMR signals (300 MHz) | Activity |
|---|---|---|---|---|---|
| 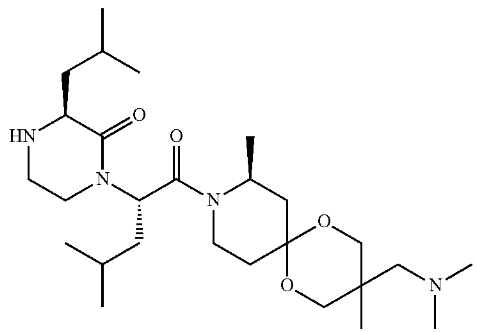 [SMILES: CC(C)C[C@@H]1NCCN([C@@H](CC(C)C)C(=O)N2CCC3(C[C@@H]2C)OCC(C)(CN(C)C)CO3)C1=O] | 302 | (S)-1-[(S)-3-{[(S)-3-[(Dimethylamino)methyl]-3,8-dimethyl-1,5-dioxa-9-aza-9-spiro[5.5]undecyl}carbonyl)-3-methylbutyl]-2-isobutyl-2-piperazinone | 2-(Hydroxymethyl)-2-methyl-1,3-propanediol (Combi-Blocks), ketalization with (S)-1-[(S)-1-Phenylethyl]-2-methyl-4-piperidinone (AstaTech), oxidation of alcohol to aldehyde, reductive amination with Dimethylamine, catalytic hydrogenation | CD$_3$OD: δ 5.54 (m, 1H), 4.58 (m, 2H), 2.34 (m, 6H), 1.52 (m, 10H), 0.95 (m, 15H) | ++++ |

TABLE 3

Compounds made through Method B1 and B2

| Structure | Ex. Cmpd # | name | Precursor III synthesis | Characterisitic $^1$H NMR signals (300 MHz) | Activity |
|---|---|---|---|---|---|
| 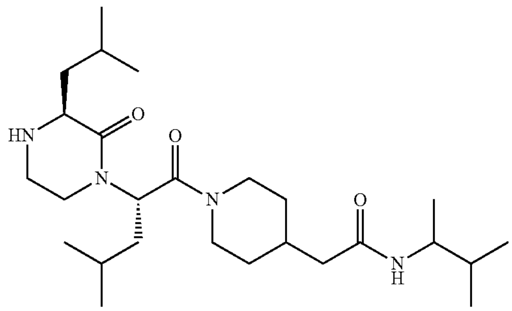 [SMILES: CC(C)C[C@@H]1NCCN([C@@H](CC(C)C)C(=O)N2CCC(CC(=O)NC(C)C(C)C)CC2)C1=O] | 136 | (S)-1-[(S)-1-({4-[2-(1,2-Dimethylpropylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 4.48 (t, 1H), 4.09 (m, 1H), 0.96 (m, 18H) | ++ |
| 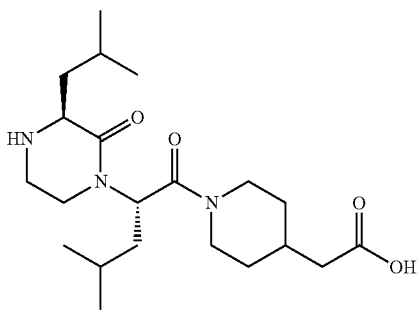 [SMILES: CC(C)C[C@@H]1NCCN([C@@H](CC(C)C)C(=O)N2CCC(CC(=O)O)CC2)C1=O] | 137 | (1-{(S)-2-[(S)-3-Isobutyl-2-oxo-1-piperazinyl]-4-methylvaleryl}-4-piperidyl)acetic acid | (B1) IIIb-Z = CHCH$_2$C(O)OCH$_2$CH$_3$ (Combi-Blocks), (B2) hydrolysis | CD$_3$OD: δ 5.48 (m, 1H), 4.39 (t, 1H), 2.61 (m, 2H), 1.62 (m, 11H), 0.88 (m, 12H) | +* |
| 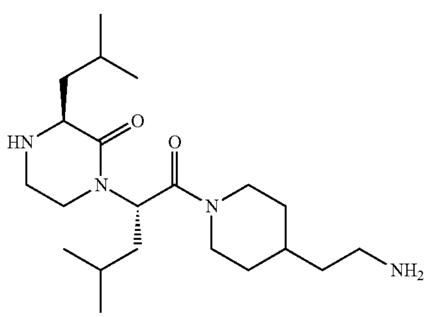 [SMILES: CC(C)C[C@@H]1NCCN([C@@H](CC(C)C)C(=O)N2CCC(CCN)CC2)C1=O] | 138 | (S)-1-[(S)-1-{[4-(2-Aminoethyl)-1-piperidyl]carbonyl}-3-methylbutyl]-3-isobutyl-2-piperazinone | (B1) IIIb-Z = CHCH$_2$CH$_2$NHBOC (Combi-Blocks), (B2) BOC deprotection | CD$_3$OD: δ 5.53 (m, 1H), 4.46 (t, 1H), 2.99 (m, 2H), 1.68 (m, 10H), 0.97 (m, 12H) | +++ |
| 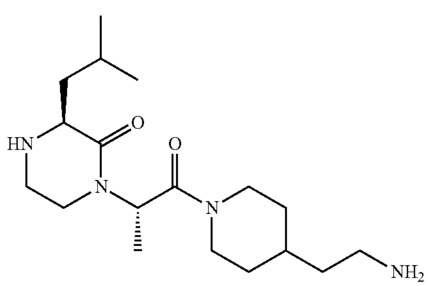 [SMILES: CC(C)C[C@@H]1NCCN([C@@H](C)C(=O)N2CCC(CCN)CC2)C1=O] | 139 | (S)-1-{(S)-2-[4-(2-Aminoethyl)-1-piperidyl]-1-methyl-2-oxoethyl}-3-isobutyl-2-piperazinone | (B1) IIIb-Z = CHCH$_2$CH$_2$NHBOC (Combi-Blocks), (B2) BOC deprotection | CD$_3$OD: δ 4.80 (m, 1H), 3.84 (d, 1H), 2.36 (m, 2H), 0.75 (d, 3H), 0.36 (m, 6H) | +* |
| 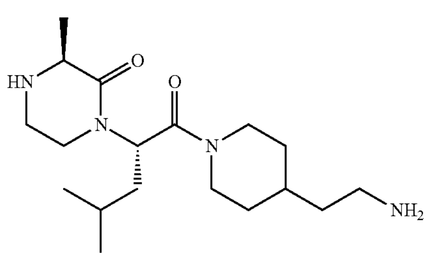 [SMILES: CC(C)C[C@@H](C(=O)N1CCC(CCN)CC1)N1CCN[C@@H](C)C1=O] | 140 | (S)-1-[(S)-1-{[4-(2-Aminoethyl)-1-piperidyl]carbonyl}-3-methylbutyl]-3-methyl-2-piperazinone | (B1) IIIb-Z = CHCH$_2$CH$_2$NHBOC (Combi-Blocks), (B2) BOC deprotection | CD$_3$OD: δ 4.77 (m, 1H), 3.76 (d, 1H), 2.27 (m, 2H), 0.88 (m, 3H), 0.24 (m, 6H) | +* |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 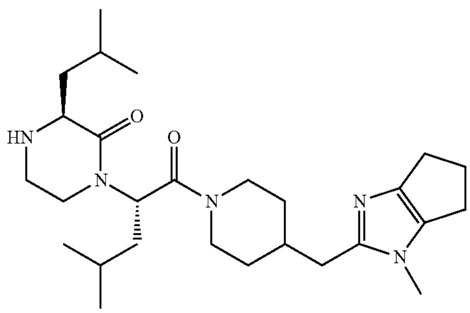 [SMILES: CC(C)C[C@@H]1NCCN([C@@H](CC(C)C)C(=O)N2CCC(Cc3nc4c(n3C)CCC4)CC2)C1=O] | 141 | (S)-1-[(S)-3-Methyl-1-{[4-({4-methyl-2,4-diazabicyclo[3.3.0]octa-1(5),2-dien-3-yl}methyl)-1-piperidyl]carbonyl}butyl]-3-isobutyl-2-piperazinone | Z = CHCH$_2$COOH (Combi-Blocks), amide coupling with 2-aminocyclo-pentanol, DMP oxidation to ketone, imine formation with methylamine using Ti(OiPr)$_4$, cyclization to imidazole by treatment with PCl$_5$ | CD$_3$OD: δ 5.55 (m, 1H), 4.47 (t, 1H), 3.55 (s, 3H), 2.65 (m, 6H), 2.49 (m, 2H), 0.95 (m, 12H) | +++ |
| 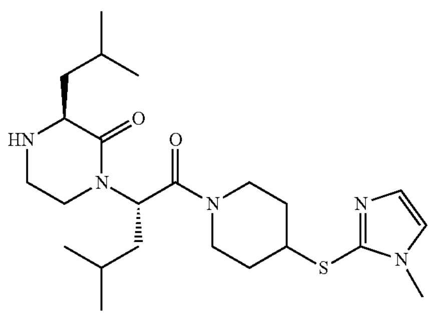 [SMILES: CC(C)C[C@@H]1NCCN([C@@H](CC(C)C)C(=O)N2CCC(Sc3nccn3C)CC2)C1=O] | 142 | (S)-1-[(S)-3-Methyl-1-{[4-(1-methyl-1H-imidazol-2-ylthio)-1-piperidyl]carbonyl}butyl]-3-isobutyl-2-piperazinone | Z = CHOH, Mitsunobu reaction with 1-methyl-1H-imidazole-2-thiol | CD$_3$OD: δ 7.25 (s, 1H), 7.06 (s, 1H), 5.53 (m, 1H), 3.75 (s, 3H), 0.95 (m, 12H) | ++ |
| 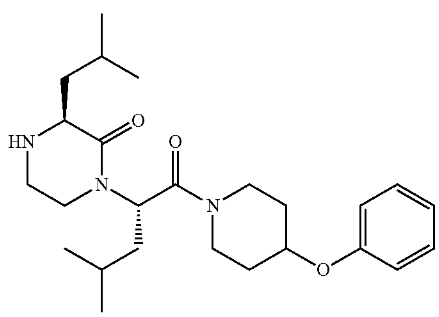 [SMILES: CC(C)C[C@@H]1NCCN([C@@H](CC(C)C)C(=O)N2CCC(Oc3ccccc3)CC2)C1=O] | 143 | (S)-1-{(S)-3-Methyl-1-[(4-phenoxy-1-piperidyl)carbonyl]butyl}-3-isobutyl-2-piperazinone | Z = CHOH, Mitsunobu reaction with phenol | CD$_3$OD: δ 7.27 (t, 2H), 7.01-6.88 (br m, 3H), 5.59 (m, 1H), 4.63 (m, 1H), 2.93 (m, 1H), 0.95 (m, 12H) | ++ |
| 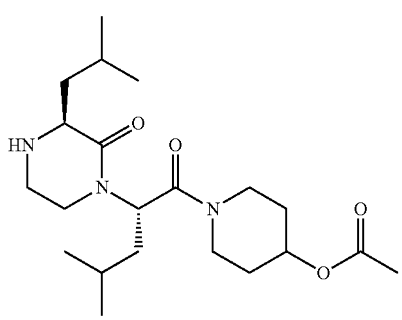 [SMILES: CC(=O)OC1CCN(C(=O)[C@H](CC(C)C)N2CCN[C@@H](CC(C)C)C2=O)CC1] | 144 | 1-{(S)-2-[(S)-3-Isobutyl-2-oxo-1-piperazinyl]-4-methylvaleryl}-4-piperidyl acetate | Z = CHOH, acylation with acyl chloride | CD$_3$OD: δ 5.57 (m, 1H), 4.99 (m, 1H), 2.91 (m, 1H), 2.05 (d, 3H), 0.95 (m, 12H) | +* |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 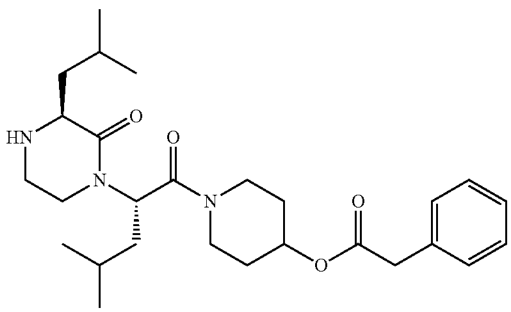 [SMILES: CC(C)C[C@@H]1NCCN([C@@H](CC(C)C)C(=O)N2CCC(OC(=O)Cc3ccccc3)CC2)C1=O] | 145 | 1-{(S)-2-[(S)-3-Isobutyl-2-oxo-1-piperazinyl]-4-methylvaleryl}-4-piperidyl phenylacetate | Z = CHOH, acylation with phenylacetyl chloride | CD$_3$OD: δ 7.40-7.21 (br m, 5H), 5.55 (m, 1H), 5.00 (m, 1H), 3.65 (d, 2H), 2.90 (m, 1H), 0.95 (m, 12H) | +* |
| 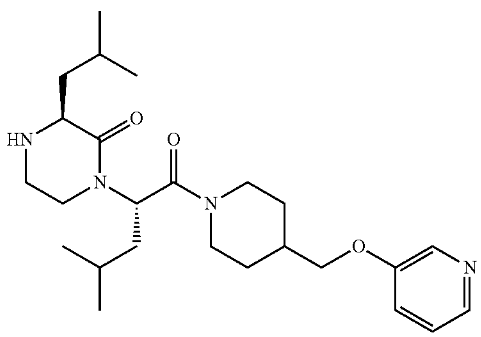 [SMILES: CC(C)C[C@@H]1NCCN([C@@H](CC(C)C)C(=O)N2CCC(COc3cccnc3)CC2)C1=O] | 146 | (S)-1-[(S)-3-Methyl-1-({4-[(3-pyridyloxy)methyl]-1-piperidyl}carbonyl)butyl]-3-isobutyl-2-piperazinone | Z = CHCH$_2$OH, Mitsunobu reaction with 3-Pyridinol | CD$_3$OD: δ 8.23 (d, 1H), 8.12 (dd, 1H), 7.43 (d, 1H), 7.35 (dd, 1H), 5.59 (m, 1H), 3.95 (d, 2H), 0.95 (m, 12H) | +* |
| 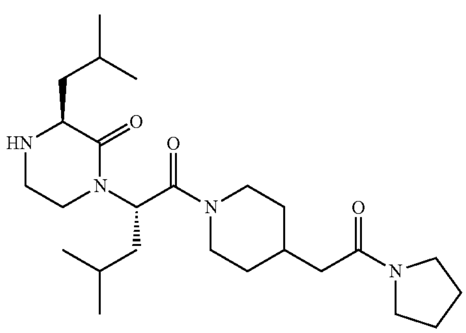 [SMILES: CC(C)C[C@@H]1NCCN([C@@H](CC(C)C)C(=O)N2CCC(CC(=O)N3CCCC3)CC2)C1=O] | 147 | (S)-1-[(S)-3-Methyl-1-({4-[2-oxo-2-(1-pyrrolidinyl)ethyl]-1-piperidyl}carbonyl)butyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.51 (t, 2H), 2.31 (m, 2H), 0.97 (m, 12H) | ++ |
| 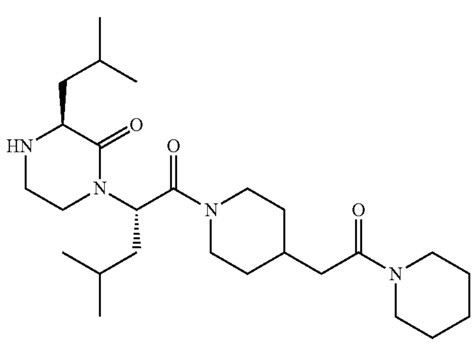 [SMILES: CC(C)C[C@@H]1NCCN([C@@H](CC(C)C)C(=O)N2CCC(CC(=O)N3CCCCC3)CC2)C1=O] | 148 | (S)-1-[(S)-3-Methyl-1-{[4-(2-oxo-2-piperidinoethyl)-1-piperidyl]carbonyl}butyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.54 (m, 4H), 2.36 (m, 2H), 0.97 (m, 12H) | ND |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 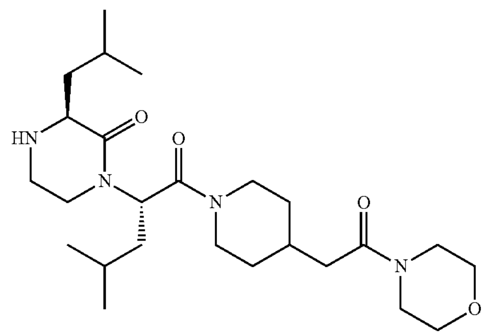 [SMILES: CC(C)C[C@@H]1NCCN([C@@H](CC(C)C)C(=O)N2CCC(CC(=O)N3CCOCC3)CC2)C1=O] | 149 | (S)-1-[(S)-3-Methyl-1-{[4-(2-morpholino-2-oxoethyl)-1-piperidyl]carbonyl}butyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.66 (m, 4H), 2.37 (m, 2H), 0.97 (m, 12H) | +* |
| 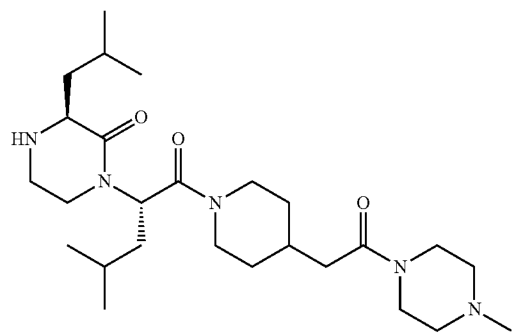 [SMILES: CC(C)C[C@@H]1NCCN([C@@H](CC(C)C)C(=O)N2CCC(CC(=O)N3CCN(C)CC3)CC2)C1=O] | 150 | (S)-1-[(S)-3-Methyl-1-({4-[2-(4-methyl-1-piperazinyl)-2-oxoethyl]-1-piperidyl}carbonyl)butyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.61 (m, 4H), 2.33 (s, 3H), 0.97 (m, 12H) | ++ |
| 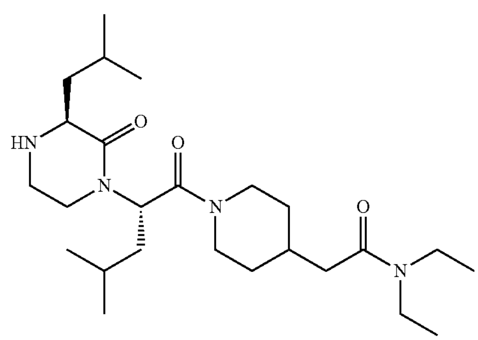 [SMILES: CCN(CC)C(=O)CC1CCN(C(=O)[C@H](CC(C)C)N2CCN[C@@H](CC(C)C)C2=O)CC1] | 151 | (S)-1-[(S)-1-({4-[2-(Diethylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.41 (m, 6H), 2.33 (m, 2H), 0.97 (m, 12H) | +* |
| 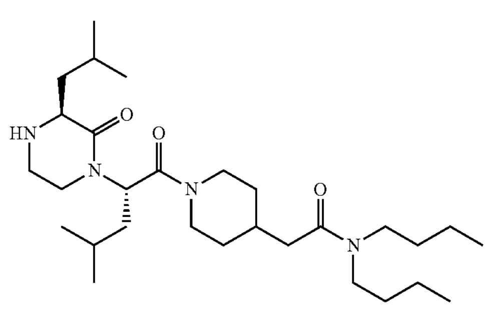 [SMILES: CCCCN(CCCC)C(=O)CC1CCN(C(=O)[C@H](CC(C)C)N2CCN[C@@H](CC(C)C)C2=O)CC1] | 152 | (S)-1-[(S)-1-({4-[2-(Dibutylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 2.33 (m, 2H), 1.36 (m, 6H), 0.98 (m, 12H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 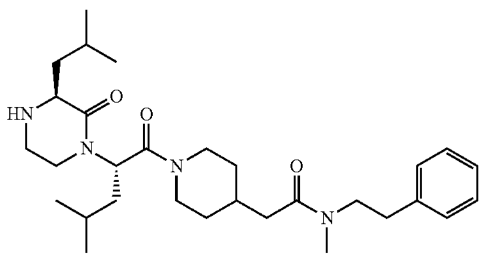 [SMILES: CC(C)C[C@@H]1NCCN([C@@H](CC(C)C)C(=O)N2CCC(CC(=O)N(C)CCc3ccccc3)CC2)C1=O] | 153 | (S)-1-[(S)-1-[(4-{2-[N-Methyl(phenethyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 7.34-7.18 (m, 5H), 5.55 (m, 1H), 3.63 (m, 2H), 0.97 (m, 12H) | ++ |
| 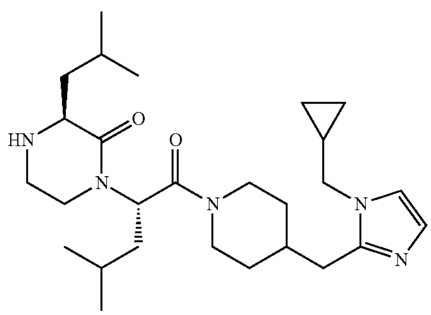 [SMILES: CC(C)C[C@@H]1NCCN([C@@H](CC(C)C)C(=O)N2CCC(Cc3nccn3CC3CC3)CC2)C1=O] | 154 | (S)-1-[(S)-1-[(4-{[1-(Cyclopropylmethyl)-1H-imidazol-2-yl]methyl}-1-piperidyl)carbonyl]-3-methylbutyl]-3-isobutyl-2-piperazinone | B1) IIIb-Z = CHCH$_2$(1H-imidazole) (Enamine BB) (B2) N-alkylation | CD$_3$OD: δ, 6.77 (d, 2H), 5.56 (q, 1H), 4.57 (t, 1H), 0.9 (m, 12H), 0.67 (m 2H), 0.33 (m, 2H). | ++ |
| 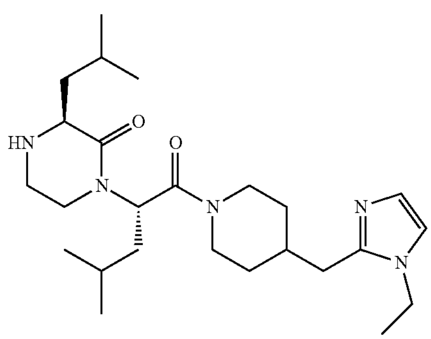 [SMILES: CCn1ccnc1CC1CCN(C(=O)[C@H](CC(C)C)N2CCN[C@@H](CC(C)C)C2=O)CC1] | 155 | (S)-1-[(S)-1-({4-[(1-Ethyl-1H-imidazol-2-yl)methyl]-1-piperidyl}carbonyl)-3-methylbutyl]-3-isobutyl-2-piperazinone | B1) IIIb-Z = CHCH$_2$(1H-imidazole) (Enamine BB) (B2) N-alkylation | CD$_3$OD: δ, 6.95 (S, 1H), 6.85 (s, 1H), 5.56 (q, 1H), 4.50 (t, 1H), 0.95, (m, 15H). | +++ |
| 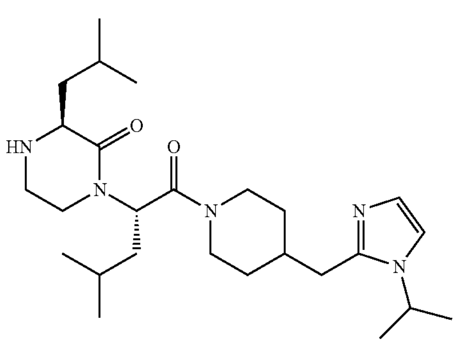 [SMILES: CC(C)C[C@@H]1NCCN([C@@H](CC(C)C)C(=O)N2CCC(Cc3nccn3C(C)C)CC2)C1=O] | 156 | (S)-1-[(S)-1-({4-[(1-Isopropyl-1H-imidazol-2-yl)methyl]-1-piperidyl}carbonyl)-3-methylbutyl]-3-isobutyl-2-piperazinone | B1) IIIb Z = CHCH$_2$(1H-imidazole) (Enamine BB) (B2) N-alkylation | CD$_3$OD: δ, 7.70 (s, 1H), 7.50 (s, 1H), 5.56 (q, 1H), 4.50 (t, 1H), 1.5 (d, 6 H), 0.95 (m, 12H). | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 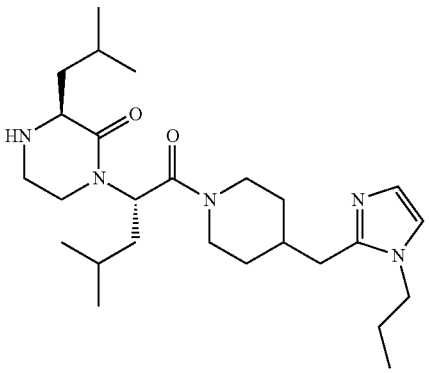 [SMILES: CCCn1ccnc1CC1CCN(C(=O)[C@H](CC(C)C)N2CCN[C@@H](CC(C)C)C2=O)CC1] | 157 | (S)-1-[(S)-3-Methyl-1-({4-[(1-propyl-1H-imidazol-2-yl)methyl]-1-piperidyl}carbonyl)butyl]-3-isobutyl-2-piperazinone | B1) IIIb-Z = CHCH$_2$(1H-imidazole) (Enamine BB) (B2) N-alkylation | CD$_3$OD: δ 6.96 (S, 1H), 6.86 (s, 1H), 5.55 (q, 1H)), 4.52 (t, 1H), 0.95, (m, 15H). | +++ |
| 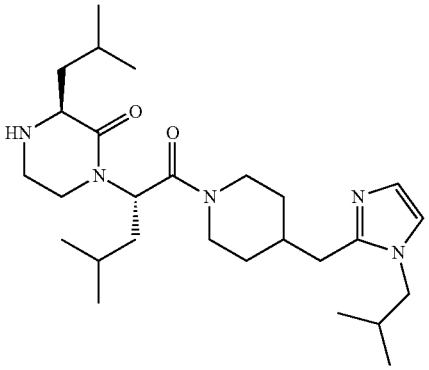 [SMILES: CC(C)C[C@@H]1NCCN([C@@H](CC(C)C)C(=O)N2CCC(Cc3nccn3CC(C)C)CC2)C1=O] | 158 | (S)-1-[(S)-1-({4-[(1-Isobutyl-1H-imidazol-2-yl)methyl]-1-piperidyl}carbonyl)-3-methylbutyl]-3-isobutyl-2-piperazinone | B1) IIIb-Z = CHCH$_2$(1H-imidazole) (Enamine BB) (B2) N-alkylation | CD$_3$OD: δ, 7.08 (S, 1H), 6.86 (s, 1H), 5.60 (q, 1H), 4.50 (t, 1H), 0.90, (m, 18H). | +++ |
| 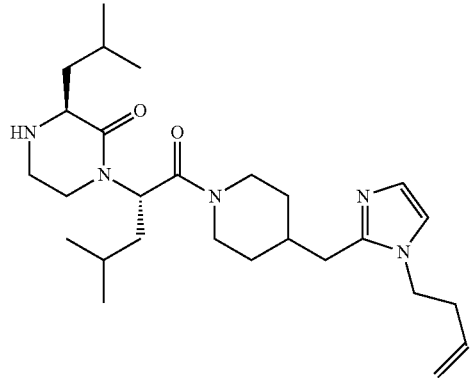 [SMILES: C=CCCn1ccnc1CC1CCN(C(=O)[C@H](CC(C)C)N2CCN[C@@H](CC(C)C)C2=O)CC1] | 159 | (S)-1-[(S)-1-[(4-{[1-(3-Butenyl)-1H-imidazol-2-yl]methyl}-1-piperidyl)carbonyl]-3-methylbutyl]-3-isobutyl-2-piperazinone | B1) IIIb-Z = CHCH$_2$(1H-imidazole) (Enamine BB) (B2) N-alkylation | CD$_3$OD: δ, 6.80 (m (1H), 6.75 (s, 1H), 5.56 (q, 1H) 4.45 (t, 1H), 0.94, (m, 12H). | +++ |
| 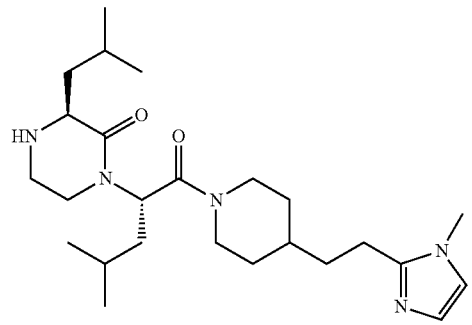 [SMILES: CC(C)C[C@@H]1NCCN([C@@H](CC(C)C)C(=O)N2CCC(CCc3nccn3C)CC2)C1=O] | 160 | (S)-1-[(S)-3-Methyl-1-({4-[2-(1-methyl-1H-imidazol-2-yl)ethyl]-1-piperidyl}carbonyl)butyl]-3-isobutyl-2-piperazinone | B1) IIIb-Z = CHCH$_2$CH$_2$OH, (B2) oxidation to aldehyde, N-methyl imidazole construction (with ammonia, methylamine and glyoxal), tBOC removal | CDCl3: δ, 6.90 (S, 1H), 6.78 (s, 1H), 5.60 (q, 1H), 4.50 (t, 1H), 3.55 (s, 3H), 0.95, (m, 13H). | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 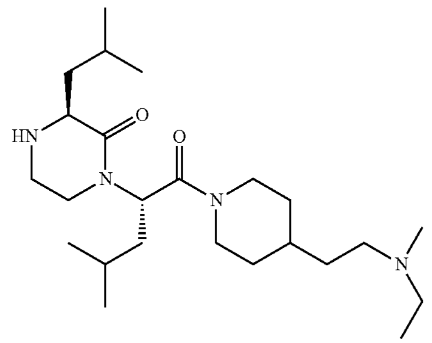 [SMILES: CCN(C)CCC1CCN(C(=O)[C@H](CC(C)C)N2CCN[C@@H](CC(C)C)C2=O)CC1] | 161 | (S)-1-[(S)-1-({4-[2-(N-Methyl-N-ethylamino)ethyl]-1-piperidyl}carbonyl)-3-methylbutyl]-3-isobutyl-2-piperazinone | Z = CHCH$_2$CH$_2$OH, oxidation to aldehyde, reductive amination | $^1$H NMR (CD$_3$OD) δ 0.98 (m, 12H), 1.23 (m, 5H), 1.71 (m, 10H), 2.86 (m, 4H), 4.48 (m, 1H), 5.55 (m, 1H) | ++++ |
| 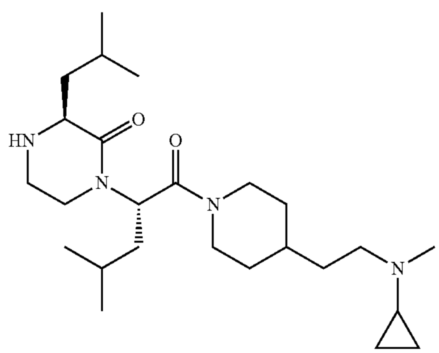 [SMILES: CC(C)C[C@@H]1NCCN([C@@H](CC(C)C)C(=O)N2CCC(CCN(C)C3CC3)CC2)C1=O] | 162 | (S)-1-[(S)-1-({4-[2-(N-Methyl-N-cyclopropylamino)ethyl]-1-piperidyl}carbonyl)-3-methylbutyl]-3-isobutyl-2-piperazinone | Z = CHCH$_2$CH$_2$OH, oxidation to aldehyde, reductive amination | $^1$H NMR (CD$_3$OD) δ 0.48 (m, 2H), 0.97 (m, 12H), 1.09 (m, 2H), 1.64 (m, 12H), 2.36 (s, 3H), 2.62 (m, 3H), 5.57 (m, 1H) | ++++ |
| 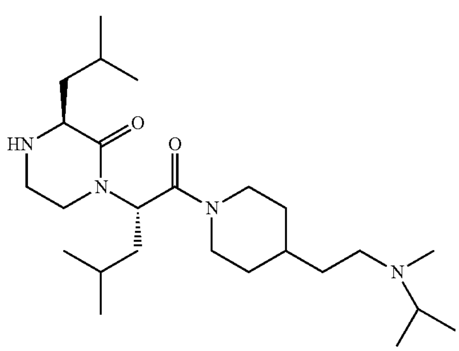 [SMILES: CC(C)C[C@@H]1NCCN([C@@H](CC(C)C)C(=O)N2CCC(CCN(C)C(C)C)CC2)C1=O] | 163 | (S)-1-[(S)-1-[(4-{2-[N-Methyl(isopropyl)amino]ethyl}-1-piperidyl)carbonyl]-3-methylbutyl]-3-isobutyl-2-piperazinone | Z = CHCH$_2$CH$_2$OH, oxidation to aldehyde, reductive amination | $^1$H NMR (CD$_3$OD) δ 0.96 (m, 12H), 1.15 (m, 5H), 2.34 (m, 2H), 4.08 (m, 1H), 4.49 (m, 1H), 5.56 (m, 1H) | ++ |
| 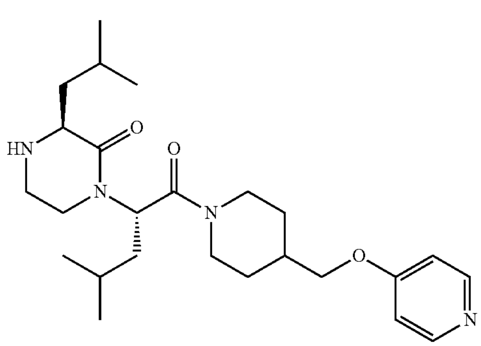 [SMILES: CC(C)C[C@@H]1NCCN([C@@H](CC(C)C)C(=O)N2CCC(COc3ccncc3)CC2)C1=O] | 164 | (S)-1-[(S)-3-Methyl-1-({4-[(4-pyridyloxy)methyl]-1-piperidyl}carbonyl)butyl]-3-isobutyl-2-piperazinone | Z = CHCH$_2$OH, Mitsunobu reaction with 4-Pyridinol | CD$_3$OD: δ 8.33 (d, 2H), 6.99 (d, 2H), 5.58 (m, 1H), 3.98 (d, 2H), 0.95 (m, 12H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 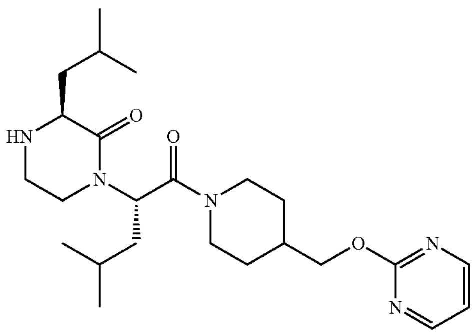 [SMILES: CC(C)C[C@@H]1NCCN([C@@H](CC(C)C)C(=O)N2CCC(COc3ncccn3)CC2)C1=O] | 165 | (S)-1-[(S)-3-Methyl-1-({4-[(2-pyrimidinyloxy)methyl]-1-piperidyl}carbonyl)butyl]-3-isobutyl-2-piperazinone | Z = CHCH$_2$OH, Mitsunobu reaction with methyl 2-hydroxypyrimidine | CD$_3$OD: δ 8.55 (d, 2H), 7.09 (t, 1H), 5.58 (m, 1H), 4.28 (d, 2H), 0.95 (m, 12H) | +* |
| 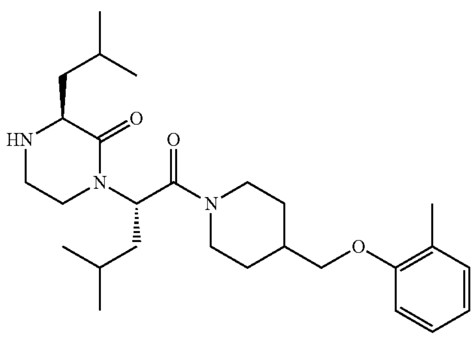 [SMILES: Cc1ccccc1OCC1CCN(C(=O)[C@H](CC(C)C)N2CCN[C@@H](CC(C)C)C2=O)CC1] | 166 | (S)-1-[(S)-3-Methyl-1-({4-[(o-tolyloxy)methyl]-1-piperidyl}carbonyl)butyl]-3-isobutyl-2-piperazinone | Z = CHCH$_2$OH, Mitsunobu reaction with o-cresol | CD$_3$OD: δ 7.17-7.03 (br m, 2H), 6.90-6.74 (br m, 2H), 5.59 (m, 1H), 3.85 (d, 2H), 2.18 (s, 3H), 0.95 (m, 12H) | +++ |
| 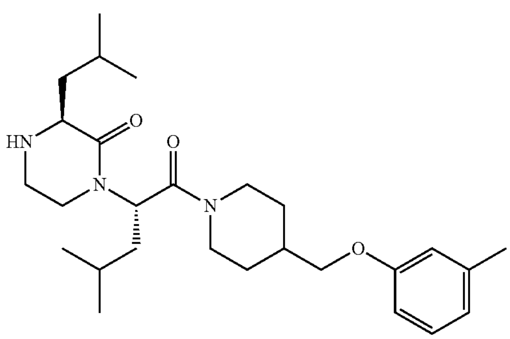 [SMILES: Cc1cccc(OCC2CCN(C(=O)[C@H](CC(C)C)N3CCN[C@@H](CC(C)C)C3=O)CC2)c1] | 167 | (S)-1-[(S)-3-Methyl-1-({4-[(m-tolyloxy)methyl]-1-piperidyl}carbonyl)butyl]-3-isobutyl-2-piperazinone | Z = CHCH$_2$OH, Mitsunobu reaction with m-cresol | CD$_3$OD: δ 7.11 (t, 1H), 6.77-6.60 (br m, 3H), 5.58 (m, 1H), 3.82 (d, 2H), 2.29 (s, 3H), 0.95 (m, 12H) | +++ |
| 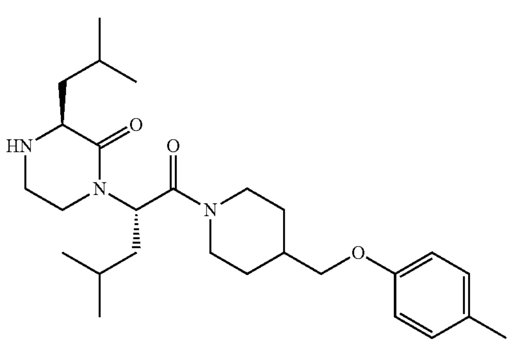 [SMILES: Cc1ccc(OCC2CCN(C(=O)[C@H](CC(C)C)N3CCN[C@@H](CC(C)C)C3=O)CC2)cc1] | 168 | (S)-1-[(S)-3-Methyl-1-({4-[(p-tolyloxy)methyl]-1-piperidyl}carbonyl)butyl]-3-isobutyl-2-piperazinone | Z = CHCH$_2$OH, Mitsunobu reaction with p-cresol | CD$_3$OD: δ 7.05 (d, 2H), 6.78 (d, 2H), 5.58 (m, 1H), 3.80 (d, 2H), 2.24 (s, 3H), 0.95 (m, 12H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 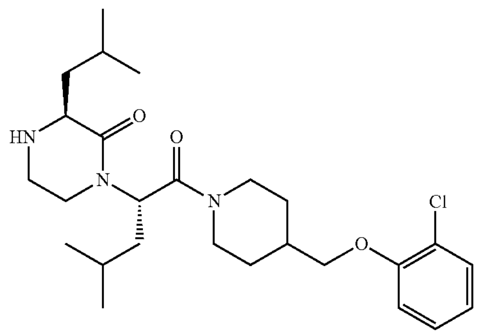 | 169 | (S)-1-[(S)-1-({4-[(o-Chlorophenoxy)methyl]-1-piperidyl}carbonyl)-3-methylbutyl]-3-isobutyl-2-piperazinone | Z = CHCH$_2$OH, Mitsunobu reaction with o-chlorophenol | CD$_3$OD: δ 7.34 (d, 1H), 7.24 (t, 1H), 7.04 (d, 1H), 6.90 (t, 1H), 5.60 (m, 1H), 4.00-3.87 (m, 2H), 0.96 (m, 12H) | +++ |
| 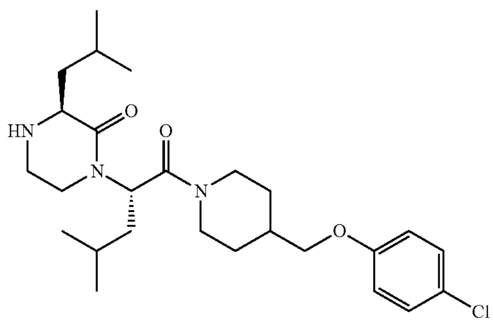 [SMILES: CC(C)C[C@@H]1NCCN([C@@H](CC(C)C)C(=O)N2CCC(COc3ccc(Cl)cc3)CC2)C1=O] | 170 | (S)-1-[(S)-1-({4-[(p-Chlorophenoxy)methyl]-1-piperidyl}carbonyl)-3-methylbutyl]-3-isobutyl-2-piperazinone | Z = CHCH$_2$OH, Mitsunobu reaction with p-chlorophenol | CD$_3$OD: δ 7.23 (d, 2H), 6.89 (d, 2H), 5.59 (m, 1H), 3.84 (d, 2H), 0.95 (m, 12H) | +++ |
| 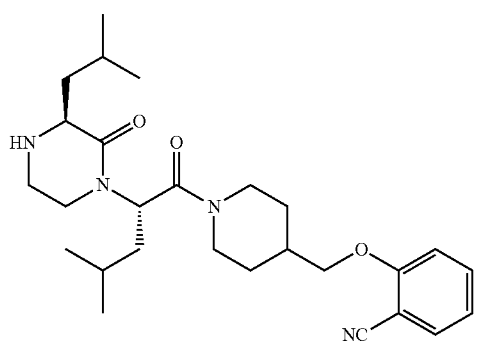 [SMILES: CC(C)C[C@@H]1NCCN([C@@H](CC(C)C)C(=O)N2CCC(COc3ccccc3C#N)CC2)C1=O] | 171 | o-[(1-{(S)-2-[(S)-3-Isobutyl-2-oxo-1-piperazinyl]-4-methylvaleryl}-4-piperidyl)methoxy]benzonitrile | Z = CHCH$_2$OH, Mitsunobu reaction with salicylonitrile | CD$_3$OD: δ 7.66-7.50 (br m, 2H), 7.15 (d, 1H), 7.05 (t, 1H), 5.59 (m, 1H), 4.02 (d, 2H), 0.94 (m, 12H) | +++ |
| 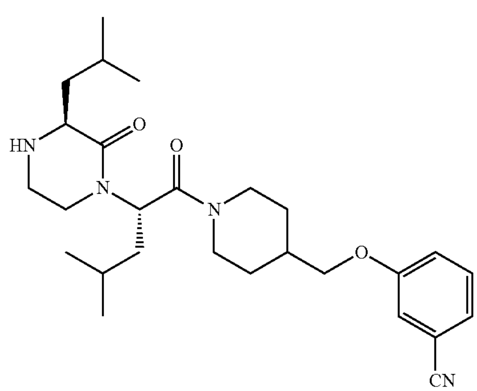 [SMILES: CC(C)C[C@@H]1NCCN([C@@H](CC(C)C)C(=O)N2CCC(COc3cccc(C#N)c3)CC2)C1=O] | 172 | m-[(1-{(S)-2-[(S)-3-Isobutyl-2-oxo-1-piperazinyl]-4-methylvaleryl}-4-piperidyl)methoxy]benzonitrile | Z = CHCH$_2$OH, Mitsunobu reaction with m-hydroxybenzonitrile | CD$_3$OD: δ 7.44 (t, 1H), 7.33-7.19 (br m, 3H), 5.59 (m, 1H), 3.91 (d, 2H), 0.95 (m, 12H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 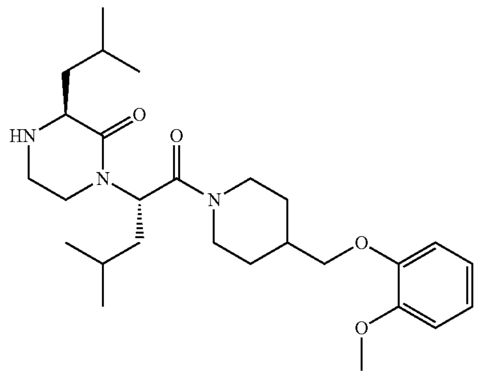 [SMILES: COc1ccccc1OCC1CCN(C(=O)[C@H](CC(C)C)N2CCN[C@@H](CC(C)C)C2=O)CC1] | 173 | (S)-1-[(S)-1-({4-[(o-Methoxyphenoxy)methyl]-1-piperidyl}carbonyl)-3-methylbutyl]-3-isobutyl-2-piperazinone | Z = CHCH$_2$OH, Mitsunobu reaction with guaiacol | CD$_3$OD: δ 6.98-6.78 (br m, 4H), 5.58 (m, 1H), 3.94-3.83 (br m, 2H), 3.81 (s, 3H), 0.95 (m, 12H) | ++ |
| 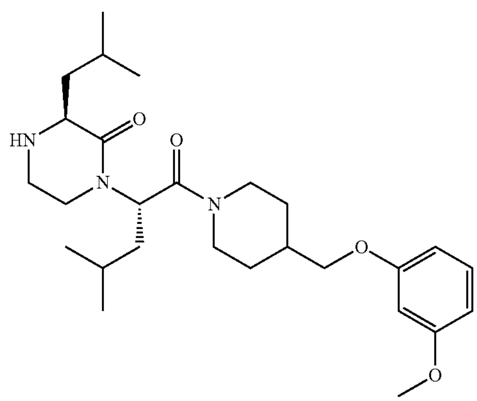 [SMILES: COc1cccc(OCC2CCN(C(=O)[C@H](CC(C)C)N3CCN[C@@H](CC(C)C)C3=O)CC2)c1] | 174 | (S)-1-[(S)-1-({4-[(m-Methoxyphenoxy)methyl]-1-piperidyl}carbonyl)-3-methylbutyl]-3-isobutyl-2-piperazinone | Z = CHCH$_2$OH, Mitsunobu reaction with m-methoxyphenol | CD$_3$OD: δ 7.14 (t, 1H), 6.54-6.42 (br m, 3H), 5.59 (m, 1H), 3.82 (d, 2H), 3.75 (s, 3H), 0.95 (m, 12H) | +++ |
| 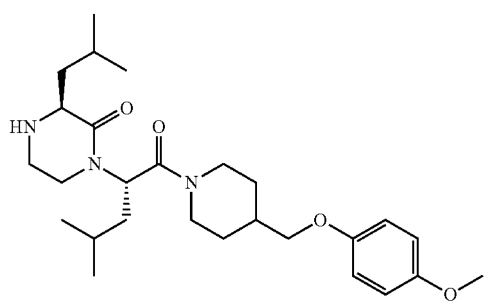 [SMILES: COc1ccc(OCC2CCN(C(=O)[C@H](CC(C)C)N3CCN[C@@H](CC(C)C)C3=O)CC2)cc1] | 175 | (S)-1-[(S)-1-({4-[(p-Methoxyphenoxy)methyl]-1-piperidyl}carbonyl)-3-methylbutyl]-3-isobutyl-2-piperazinone | Z = CHCH$_2$OH, Mitsunobu reaction with p-methoxyphenol | CD$_3$OD: δ 6.91-6.77 (br m, 4H), 5.58 (m, 1H), 3.78 (d, 2H), 3.73 (s, 3H), 0.95 (m, 12H) | +++ |
| 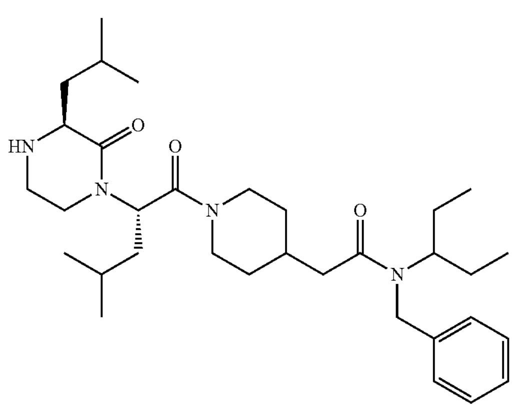 [SMILES: CCC(CC)N(Cc1ccccc1)C(=O)CC1CCN(C(=O)[C@H](CC(C)C)N2CCN[C@@H](CC(C)C)C2=O)CC1] | 176 | (S)-1-[(S)-1-[(4-{2-[(Benzyl)(1-ethylpropyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 7.41-7.18 (m, 5H), 5.57 (m, 1H), 0.97 (m, 12H), 0.90-0.78 (m, 6H) | +++ |

TABLE 3-continued

Compounds made through Method B1 and B2

| Structure | Ex. Cmpd # | name | Precursor III synthesis | Characterisitic ¹H NMR signals (300 MHz) | Activity |
|---|---|---|---|---|---|
| 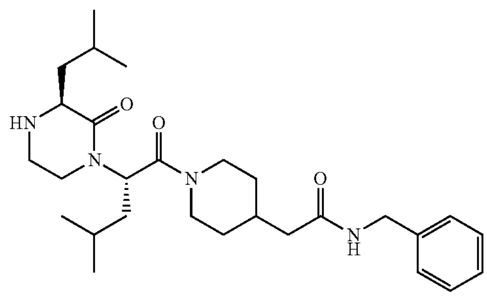 [SMILES: CC(C)C[C@@H]1NCCN([C@@H](CC(C)C)C(=O)N2CCC(CC(=O)NCc3ccccc3)CC2)C1=O] | 177 | (S)-1-[(S)-1-{[4-(2-Benzylamino-2-oxoethyl)-1-piperidyl]carbonyl}-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 4.38 (s, 2H), 2.20 (m, 2H), 0.96 (m, 12H) | ++ |
| 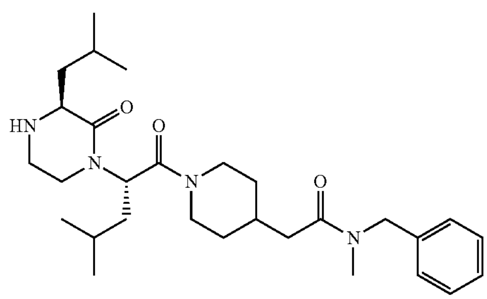 [SMILES: CC(C)C[C@@H]1NCCN([C@@H](CC(C)C)C(=O)N2CCC(CC(=O)N(C)Cc3ccccc3)CC2)C1=O] | 178 | (S)-1-[(S)-1-[(4-{2-[N-Methyl(benzyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 4.64 (m, 2H), 2.42 (m, 2H), 0.96 (m, 12H) | +++ |
| 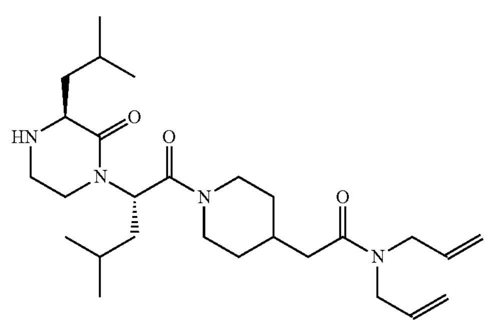 [SMILES: C=CCN(CC=C)C(=O)CC1CCN(C(=O)[C@H](CC(C)C)N2CCN[C@@H](CC(C)C)C2=O)CC1] | 179 | (S)-1-[(S)-1-({4-[2-(Diallylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.93-5.72 (m, 2H), 5.57 (m, 1H), 2.35 (m, 2H), 0.97 (m, 12H) | ++ |
| 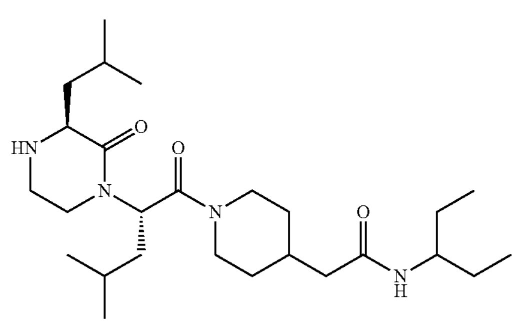 [SMILES: CCC(CC)NC(=O)CC1CCN(C(=O)[C@H](CC(C)C)N2CCN[C@@H](CC(C)C)C2=O)CC1] | 180 | (S)-1-[(S)-1-({4-[2-(1-Ethylpropylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.58 (m, 1H), 3.67 (m, 1H), 2.17 (m, 2H), 1.01-0.87 (m, 18H) | ++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 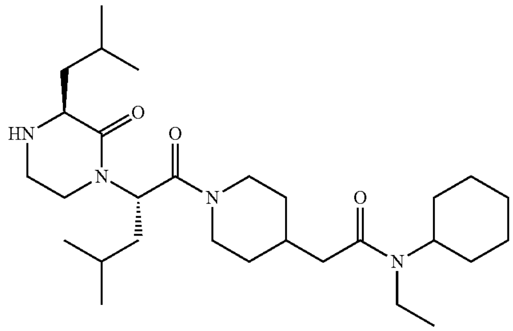 [SMILES: CCN(C(=O)CC1CCN(C(=O)[C@H](CC(C)C)N2CCN[C@@H](CC(C)C)C2=O)CC1)C1CCCCC1] | 181 | (S)-1-[(S)-1-({4-[2-(N-Ethyl-N-cyclohexylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.56 (m, 1H), 2.35 (m, 2H), 1.23-1.10 (m, 5H), 0.96 (m, 12H) | ++ |
| 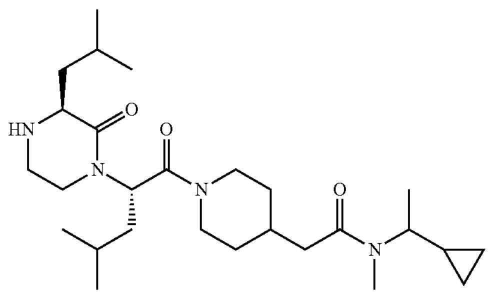 [SMILES: CC(C)C[C@@H]1NCCN([C@@H](CC(C)C)C(=O)N2CCC(CC(=O)N(C)C(C)C3CC3)CC2)C1=O] | 182 | (S)-1-[(S)-1-[(4-{2-[N-Methyl(1-cyclopropylethyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 2.39-2.26 (m, 2H), 0.96 (m, 12H), 0.24-0.12 (m, 1H) | +* |
| 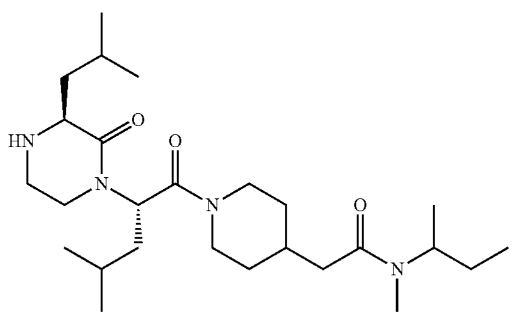 [SMILES: CCC(C)N(C)C(=O)CC1CCN(C(=O)[C@H](CC(C)C)N2CCN[C@@H](CC(C)C)C2=O)CC1] | 183 | (S)-1-[(S)-1-[(4-{2-[N-Methyl(sec-butyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 2.36 (m, 2H), 0.97 (m, 12H), 0.92-0.81 (m, 3H) | +* |
| 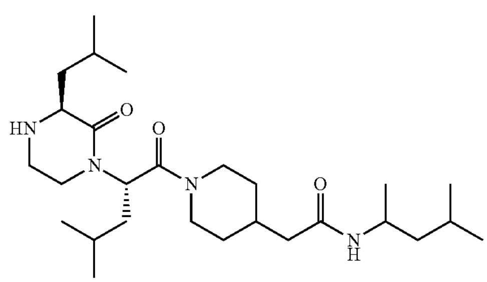 [SMILES: CC(C)CC(C)NC(=O)CC1CCN(C(=O)[C@H](CC(C)C)N2CCN[C@@H](CC(C)C)C2=O)CC1] | 184 | (S)-1-[(S)-1-({4-[2-(1,3-Dimethylbutylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.56 (m, 1H), 4.01 (m, 1H), 2.11 (m, 2H), 0.95 (m, 18H) | ++ |
| 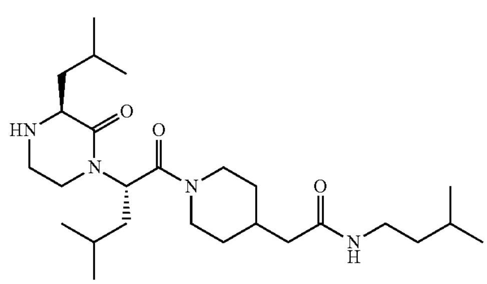 [SMILES: CC(C)CCNC(=O)CC1CCN(C(=O)[C@H](CC(C)C)N2CCN[C@@H](CC(C)C)C2=O)CC1] | 185 | (S)-1-[(S)-1-({4-[2-(Isopentylamino)-2-oxoethyl]-1-piperidyl}carbonyl)-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 3.21 (t, 2H), 2.13 (m, 2H), 0.96 (m, 18H) | ++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 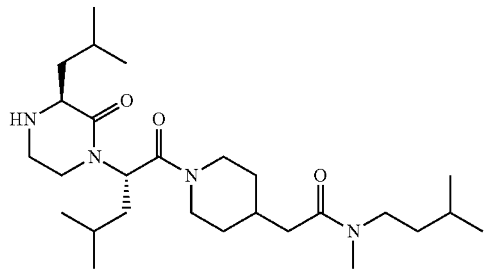 [SMILES: CC(C)CCN(C)C(=O)CC1CCN(C(=O)[C@H](CC(C)C)N2CCN[C@@H](CC(C)C)C2=O)CC1] | 186 | (S)-1-[(S)-1-[(4-{2-[N-Methyl(isopentyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.58 (m, 1H), 3.40 (m, 4H), 2.34 (m, 2H), 0.97 (m, 18H) | ++ |
| 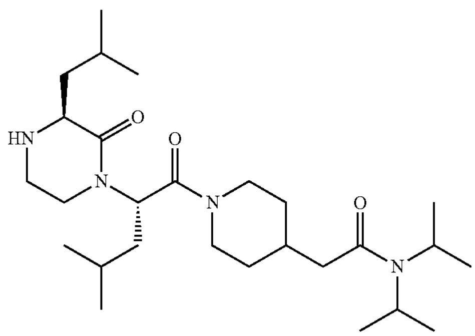 [SMILES: CC(C)C[C@@H]1NCCN([C@@H](CC(C)C)C(=O)N2CCC(CC(=O)N(C(C)C)C(C)C)CC2)C1=O] | 187 | (S)-1-[(S)-1-[(4-{2-[Bis(isopropyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 2.31 (m, 2H), 1.39 (d, 6H), 0.96 (m, 12H) | ++ |
| 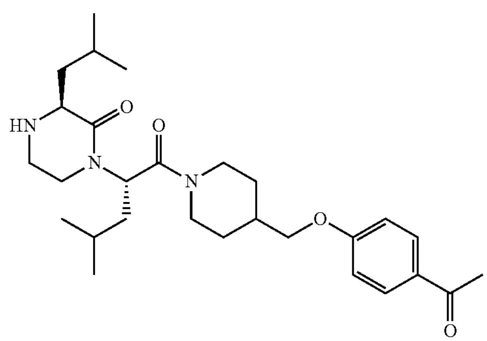 [SMILES: CC(=O)c1ccc(OCC2CCN(C(=O)[C@H](CC(C)C)N3CCN[C@@H](CC(C)C)C3=O)CC2)cc1] | 188 | (S)-1-[(S)-1-({4-[(p-Acetylphenoxy)methyl]-1-piperidyl}carbonyl)-3-methylbutyl]-3-isobutyl-2-piperazinone | Z = CHCH$_2$OH, Mitsunobu reaction with 4'-hydroxyacetophenone | CD$_3$OD: δ 7.96 (d, 2H), 7.00 (d, 2H), 5.59 (m, 1H), 3.95 (d, 2H), 2.54 (s, 3H), 0.95 (m, 12H) | +++ |
| 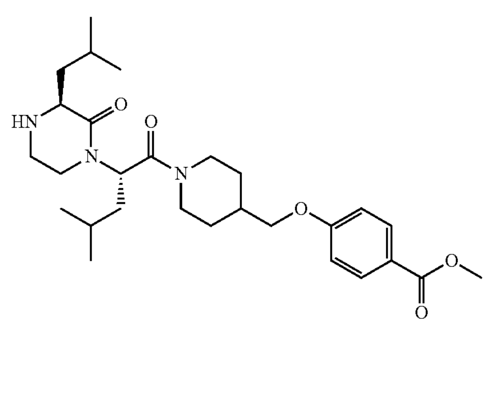 [SMILES: COC(=O)c1ccc(OCC2CCN(C(=O)[C@H](CC(C)C)N3CCN[C@@H](CC(C)C)C3=O)CC2)cc1] | 189 | Methyl p-[(1-{(S)-2-[(S)-3-isobutyl-2-oxo-1-piperazinyl]-4-methylvaleryl}-4-piperidyl)methoxy]benzoate | Z = CHCH$_2$OH, Mitsunobu reaction with methyl p-hydroxybenzoate | CD$_3$OD: δ 7.95 (d, 2H), 6.98 (d, 2H), 5.59 (m, 1H), 3.94 (d, 2H), 3.86 (s, 3H), 0.95 (m, 12H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 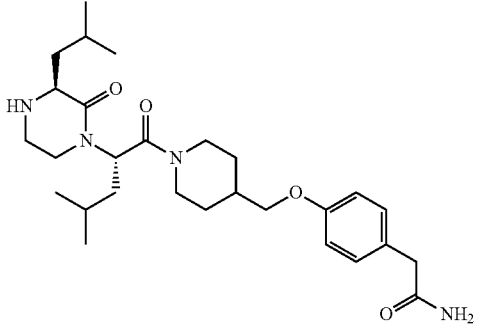 [SMILES: CC(C)C[C@@H]1NCCN([C@@H](CC(C)C)C(=O)N2CCC(COc3ccc(CC(N)=O)cc3)CC2)C1=O] | 190 | {p-[(1-{(S)-2-[(S)-3-Isobutyl-2-oxo-1-piperazinyl]-4-methylvaleryl}-4-piperidyl)methoxy]phenyl}acetamide | Z = CHCH$_2$OH, Mitsunobu reaction with 4-hydroxyphenyl-acetamide | CD$_3$OD: δ 7.20 (d, 2H), 6.86 (d, 2H), 5.58 (m, 1H), 3.84 (d, 2H), 3.43 (s, 2H), 0.95 (m, 12H) | ++ |
| 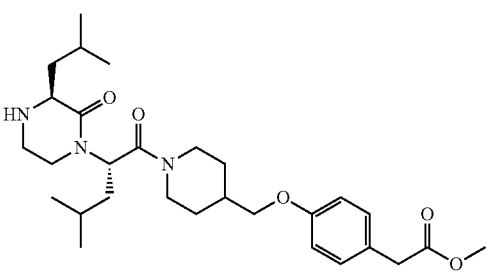 [SMILES: COC(=O)Cc1ccc(OCC2CCN(C(=O)[C@H](CC(C)C)N3CCN[C@@H](CC(C)C)C3=O)CC2)cc1] | 191 | Methyl {p-[(1-{(S)-2-[(S)-3-isobutyl-2-oxo-1-piperazinyl]-4-methylvaleryl}-4-piperidyl)methoxy]phenyl}acetate | Z = CHCH$_2$OH, Mitsunobu reaction with methyl 4-hydroxyphenyl-acetate | CD$_3$OD: δ 7.15 (d, 2H), 6.84 (d, 2H), 5.58 (m, 1H), 3.81 (d, 2H), 3.64 (s, 3H), 3.54 (s, 2H), 0.94 (m, 12H) | +++ |
| 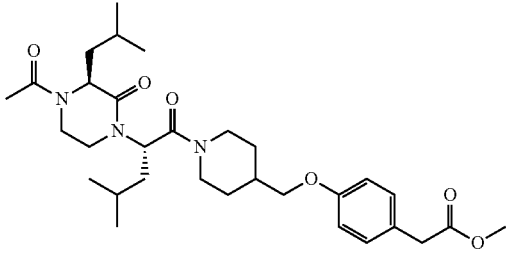 [SMILES: COC(=O)Cc1ccc(OCC2CCN(C(=O)[C@H](CC(C)C)N3CCN(C(C)=O)[C@@H](CC(C)C)C3=O)CC2)cc1] | 192 | Methyl {p-[(1-{(S)-2-[(S)-4-acetyl-3-isobutyl-2-oxo-1-piperazinyl]-4-methylvaleryl}-4-piperidyl)methoxy]phenyl}acetate | Z = CHCH$_2$OH, Mitsunobu reaction with methyl 4-hydroxyphenyl-acetate | CDCl$_3$: δ 7.18 (d, 2H), 6.83 (d, 2H), 3.80 (d, 2H), 3.68 (s, 3H), 3.56 (s, 3H), 0.97 (m, 12H) | +++ |
| 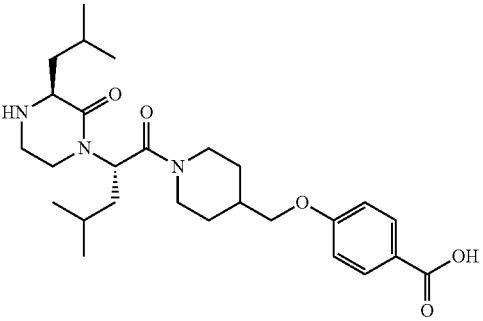 [SMILES: CC(C)C[C@@H]1NCCN([C@@H](CC(C)C)C(=O)N2CCC(COc3ccc(C(=O)O)cc3)CC2)C1=O] | 193 | p-[(1-{(S)-2-[(S)-3-Isobutyl-2-oxo-1-piperazinyl]-4-methylvaleryl}-4-piperidyl)methoxy]benzoic acid | Z = CHCH$_2$OH, Mitsunobu reaction with methyl p-hydroxybenzoate, ester hydrolysis | CD$_3$OD: δ 7.89 (d, 2H), 6.86 (d, 2H), 5.59 (m, 1H), 3.90 (d, 2H), 0.95 (m, 12H) | +* |

TABLE 3-continued

Compounds made through Method B1 and B2

| Structure | Ex. Cmpd # | name | Precursor III synthesis | Characterisitic ¹H NMR signals (300 MHz) | Activity |
|---|---|---|---|---|---|
| 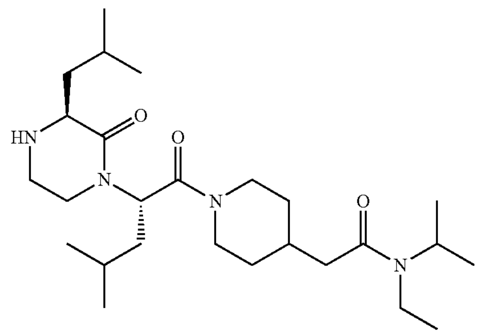 [SMILES: CCN(C(=O)CC1CCN(C(=O)[C@H](CC(C)C)N2CCN[C@@H](CC(C)C)C2=O)CC1)C(C)C] | 194 | (S)-1-[(S)-1-[(4-{2-[N-Ethyl(isopropyl)amino]-2-oxoethyl}-1-piperidyl)carbonyl]-3-methylbutyl]-3-isobutyl-2-piperazinone | (B1) IIIb-Z = CHCH$_2$C(O)OCH$_3$ (Combi-Blocks), (B2) hydrolysis, amide coupling | CD$_3$OD: δ 5.57 (m, 1H), 2.35 (m, 2H), 1.26-1.11 (m, 11H), 0.97 (m, 12H) | ++ |
| 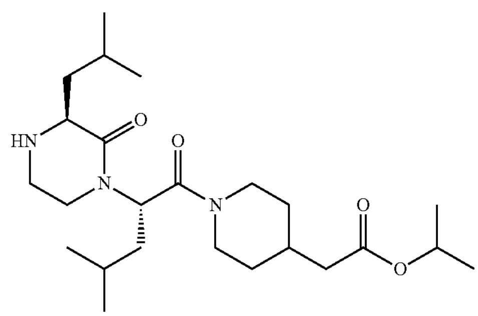 [SMILES: CC(C)C[C@@H]1NCCN([C@@H](CC(C)C)C(=O)N2CCC(CC(=O)OC(C)C)CC2)C1=O] | 195 | Isopropyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.57 (m, 1H), 2.27 (m, 2H), 1.24 (d, 6H), 0.96 (m, 12H) | ++ |
| 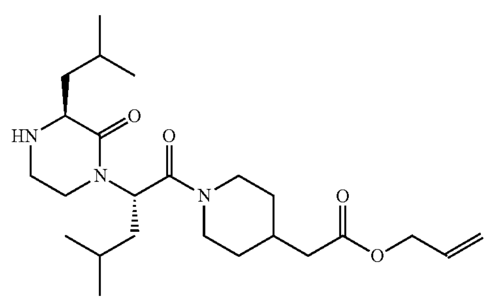 [SMILES: C=CCOC(=O)CC1CCN(C(=O)[C@H](CC(C)C)N2CCN[C@@H](CC(C)C)C2=O)CC1] | 196 | Allyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 6.03-5.88 (m, 1H), 5.57 (m, 1H), 2.35 (m, 2H), 0.96 (m, 12H) | +* |
| 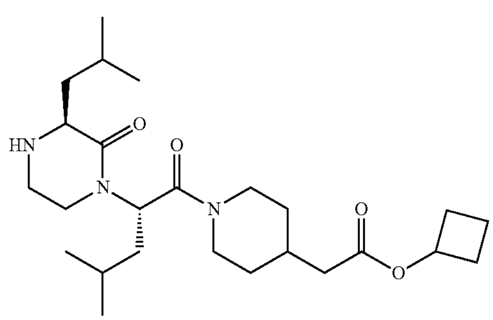 [SMILES: CC(C)C[C@@H]1NCCN([C@@H](CC(C)C)C(=O)N2CCC(CC(=O)OC3CCC3)CC2)C1=O] | 197 | Cyclobutyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.57 (m, 1H), 4.98 (m, 1H), 4.48 (t, 1H), 0.96 (m, 12H) | ++ |

TABLE 3-continued

Compounds made through Method B1 and B2

| Structure | Ex. Cmpd # | name | Precursor III synthesis | Characterisitic ¹H NMR signals (300 MHz) | Activity |
|---|---|---|---|---|---|
| 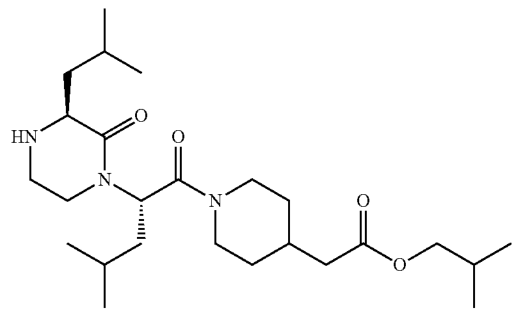 [SMILES: CC(C)COC(=O)CC1CCN(C(=O)[C@H](CC(C)C)N2CCN[C@@H](CC(C)C)C2=O)CC1] | 198 | Isobutyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.57 (m, 1H), 3.88 (d, 2H), 2.32 (m, 2H), 0.97 (m, 18H) | ++ |
| 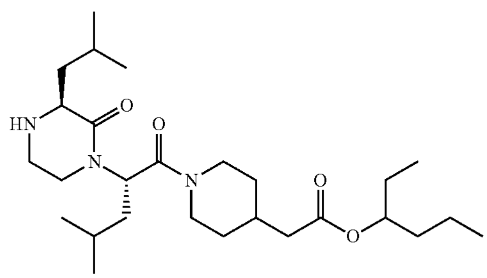 [SMILES: CCCC(CC)OC(=O)CC1CCN(C(=O)[C@H](CC(C)C)N2CCN[C@@H](CC(C)C)C2=O)CC1] | 199 | 1-Ethylbutyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.57 (m, 1H), 4.48 (t, 1H), 2.31 (m, 2H, 1.01-0.87 (m, 18H) | +++ |
| 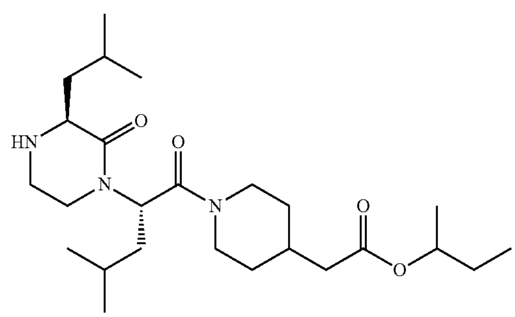 [SMILES: CCC(C)OC(=O)CC1CCN(C(=O)[C@H](CC(C)C)N2CCN[C@@H](CC(C)C)C2=O)CC1] | 200 | sec-Butyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 2.29 (m, 2H), 1.22 (d, 3H), 1.00-0.89 (m, 15H) | +++ |
| 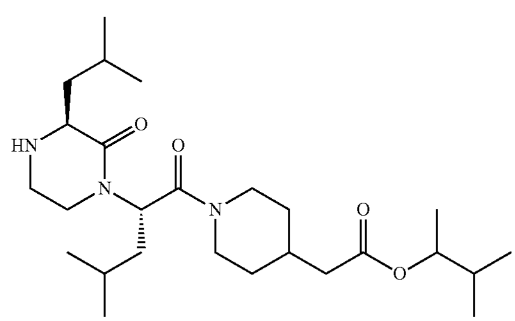 [SMILES: CC(C)C[C@@H]1NCCN([C@@H](CC(C)C)C(=O)N2CCC(CC(=O)OC(C)C(C)C)CC2)C1=O] | 201 | 1,2-Dimethylpropyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 4.74 (m, 1H), 2.30 (m, 2H), 0.96 (m, 18H) | +++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 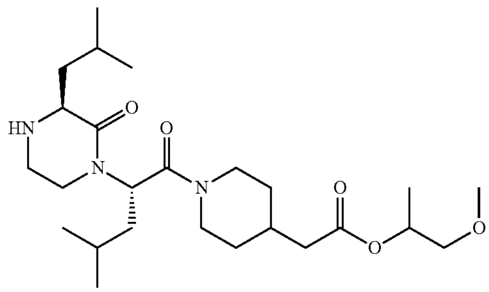 [SMILES: COCC(C)OC(=O)CC1CCN(C(=O)[C@H](CC(C)C)N2CCN[C@@H](CC(C)C)C2=O)CC1] | 202 | 2-Methoxy-1-methylethyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 5.09 (m, 1H), 3.36 (s, 3H), 0.97 (m, 12H) | +* |
| 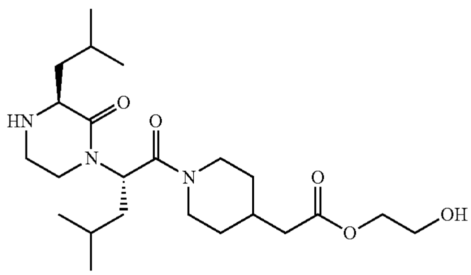 [SMILES: CC(C)C[C@@H]1NCCN([C@@H](CC(C)C)C(=O)N2CCC(CC(=O)OCCO)CC2)C1=O] | 203 | 2-Hydroxyethyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 4.35 (t, 2H), 2.37 (m, 2H), 0.97 (m, 12H) | ++ |
| 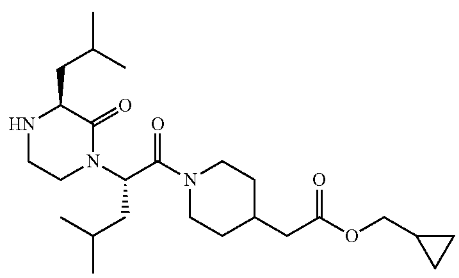 [SMILES: CC(C)C[C@@H]1NCCN([C@@H](CC(C)C)C(=O)N2CCC(CC(=O)OCC3CC3)CC2)C1=O] | 204 | Cyclopropylmethyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 3.93 (d, 2H), 0.97 (m, 12H), 0.29 (m, 2H) | ++ |
| 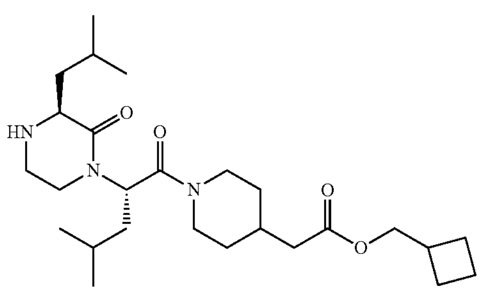 [SMILES: CC(C)C[C@@H]1NCCN([C@@H](CC(C)C)C(=O)N2CCC(CC(=O)OCC3CCC3)CC2)C1=O] | 205 | Cyclobutylmethyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 4.07 (d, 2H), 2.31 (m, 2H), 0.97 (m, 12H) | ++ |
| 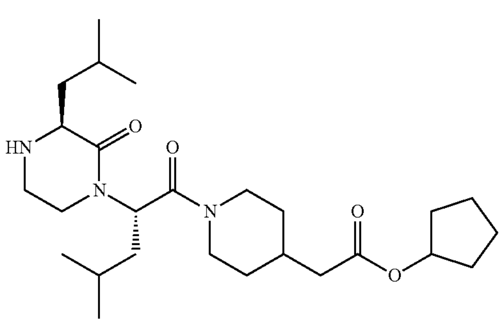 [SMILES: CC(C)C[C@@H]1NCCN([C@@H](CC(C)C)C(=O)N2CCC(CC(=O)OC3CCCC3)CC2)C1=O] | 206 | Cyclopentyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 5.16 (m, 1H), 2.27 (m, 2H), 0.97 (m, 12H) | ++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 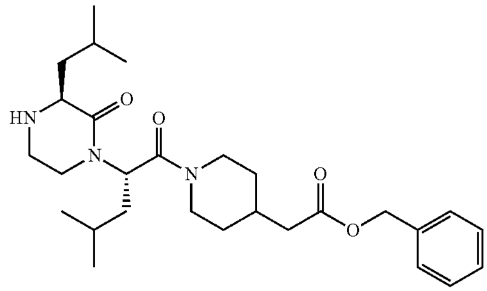 [SMILES: CC(C)C[C@@H]1NCCN([C@@H](CC(C)C)C(=O)N2CCC(CC(=O)OCc3ccccc3)CC2)C1=O] | 207 | Benzyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.57 (m, 1H), 5.13 (s, 2H), 2.36 (m, 2H), 0.96 (m, 12H) | ++ |
| 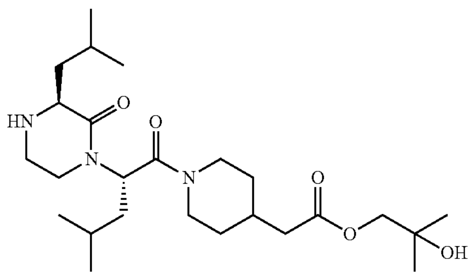 [SMILES: CC(C)C[C@@H]1NCCN([C@@H](CC(C)C)C(=O)N2CCC(CC(=O)OCC(C)(C)O)CC2)C1=O] | 208 | 2-Hydroxy-2-methylpropyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 3.94 (s, 2H), 2.37 (m, 2H), 0.96 (m, 12H) | +* |
| 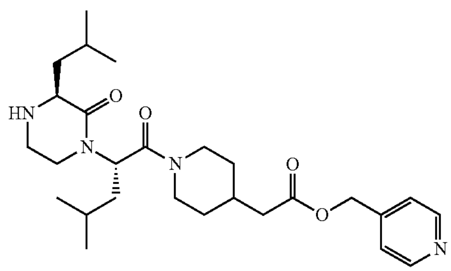 [SMILES: CC(C)C[C@@H]1NCCN([C@@H](CC(C)C)C(=O)N2CCC(CC(=O)OCc3ccncc3)CC2)C1=O] | 209 | (4-Pyridyl)methyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 8.55-8.47 (m, 2H), 7.43 (m, 2H), 5.56 (m, 1H), 0.96 (m, 12H) | ++ |
| 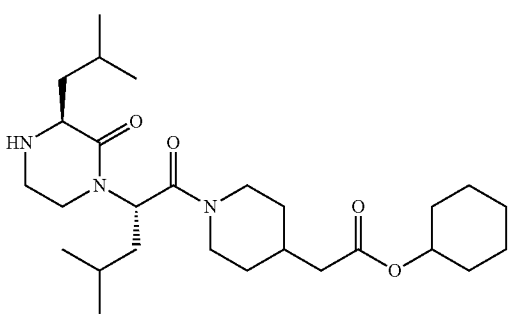 [SMILES: CC(C)C[C@@H]1NCCN([C@@H](CC(C)C)C(=O)N2CCC(CC(=O)OC3CCCCC3)CC2)C1=O] | 210 | Cyclohexyl (1-{(S)-2-[(S)-3-isobutyl-2-oxo-1-piperazinyl]-4-methylvaleryl}-4-piperidyl)acetate | (B1) IIIb-Z = CHCH$_2$C(O)OCH$_3$ (Combi-Blocks), (B2) hydrolysis, ester coupling | CD$_3$OD: δ 5.58 (m, 1H), 4.77 (m, 1H), 2.29 (m, 2H), 0.97 (m, 12H) | +++ |
| 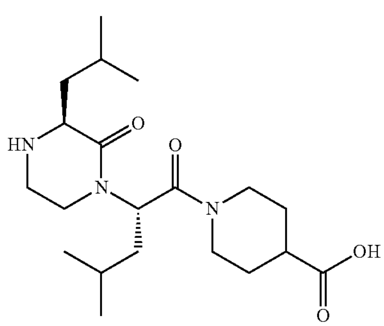 [SMILES: CC(C)C[C@@H]1NCCN([C@@H](CC(C)C)C(=O)N2CCC(C(=O)O)CC2)C1=O] | 211 | 1-{(S)-2-[(S)-3-Isobutyl-2-oxo-1-piperazinyl]-4-methylvaleryl}-4-piperidinecarboxylic acid | (B1) IIIb-Z = CHC(O)OCH$_3$, (B2) hydrolysis | CD$_3$OD: δ 5.53 (m, 1H), 4.46-4.22 (br m, 1H), 2.31 (m, 1H), 0.89 (m, 12H) | +* |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 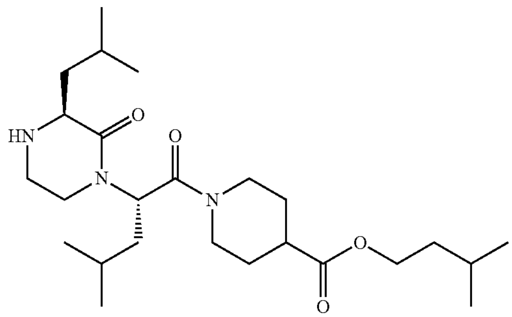 [SMILES: CC(C)CCOC(=O)C1CCN(C(=O)[C@H](CC(C)C)N2CCN[C@@H](CC(C)C)C2=O)CC1] | 212 | Isopentyl 1-{(S)-2-[(S)-3-isobutyl-2-oxo-1-piperazinyl]-4-methylvaleryl}-4-piperidinecarboxylate | (B1) IIIb-Z = CHC(O)OCH$_3$, (B2) hydrolysis, ester coupling | CD$_3$OD: δ 5.59 (m, 1H), 4.16 (m, 2H), 2.68 (m, 1H), 0.97 (m, 18H) | ++ |
| 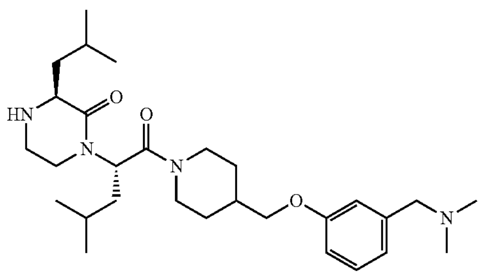 [SMILES: CC(C)C[C@@H]1NCCN([C@@H](CC(C)C)C(=O)N2CCC(COc3cccc(CN(C)C)c3)CC2)C1=O] | 213 | (S)-1-[(S)-1-{[4-({m-[(Dimethylamino)methyl]phenoxy}methyl)-1-piperidyl]carbonyl}-3-methylbutyl]-3-isobutyl-2-piperazinone | Z = CHCH$_2$OH, Mitsunobu reaction with m-hydroxybenzaldehyde, reductive amination with dimethylamine | CD$_3$OD: δ 7.27 (t, 1H), 7.00-6.86 (br m, 3H), 5.58 (m, 1H), 3.88 (d, 2H), 3.68 (s, 2H), 2.41 (s, 6H), 0.95 (m, 12H) | +++ |
| 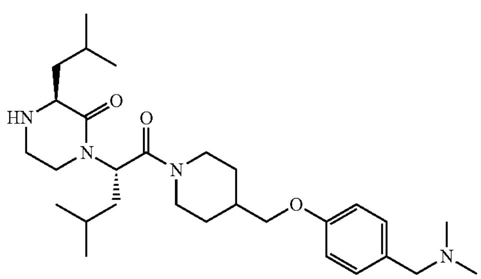 [SMILES: CC(C)C[C@@H]1NCCN([C@@H](CC(C)C)C(=O)N2CCC(COc3ccc(CN(C)C)cc3)CC2)C1=O] | 214 | (S)-1-[(S)-1-{[4-({p-[(Dimethylamino)methyl]phenoxy}methyl)-1-piperidyl]carbonyl}-3-methylbutyl]-3-isobutyl-2-piperazinone | Z = CHCH$_2$OH, Mitsunobu reaction with p-hydroxybenzaldehyde, reductive amination with dimethylamine | CD$_3$OD: δ 7.21 (d, 2H), 6.88 (d, 2H), 5.59 (m, 1H), 3.85 (d, 2H), 3.40 (s, 2H), 2.21 (s, 6H), 0.95 (m, 12H) | +++ |
| 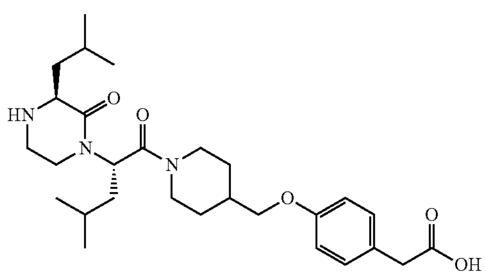 [SMILES: CC(C)C[C@@H]1NCCN([C@@H](CC(C)C)C(=O)N2CCC(COc3ccc(CC(=O)O)cc3)CC2)C1=O] | 215 | {p-[(1-{(S)-2-[(S)-3-Isobutyl-2-oxo-1-piperazinyl]-4-methylvaleryl}-4-piperidyl)methoxy]phenyl}acetic acid | Z = CHCH$_2$OH, Mitsunobu reaction with methyl 4-hydroxyphenylacetate, ester hydrolysis | CD$_3$OD: δ 7.20 (d, 2H), 6.81 (d, 2H), 5.58 (m, 1H), 3.83 (d, 2H), 3.39 (s, 2H), 0.95 (m, 12H) | +* |
| 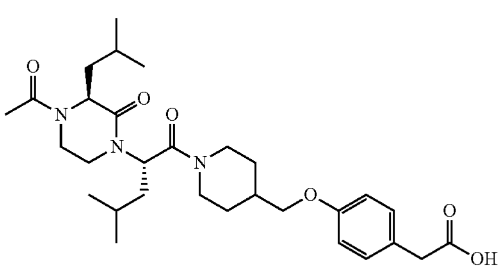 [SMILES: CC(=O)N1CCN([C@@H](CC(C)C)C(=O)N2CCC(COc3ccc(CC(=O)O)cc3)CC2)C(=O)[C@@H]1CC(C)C] | 216 | {p-[(1-{(S)-2-[(S)-4-Acetyl-3-isobutyl-2-oxo-1-piperazinyl]-4-methylvaleryl}-4-piperidyl)methoxy]phenyl}acetic acid | Z = CHCH$_2$OH, Mitsunobu reaction with methyl 4-hydroxyphenylacetate, ester hydrolysis | CD$_3$OD: δ 7.20 (d, 2H), 6.81 (d, 2H), 5.58 (m, 1H), 5.04 (m, 1H), 3.39 (s, 2H), 2.13 (s, 3H), 0.97 (m, 12H) | +* |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 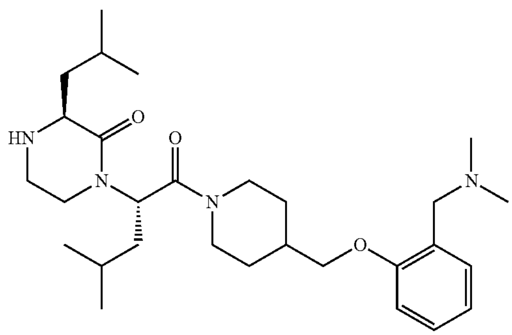 [SMILES: CC(C)C[C@@H]1NCCN([C@@H](CC(C)C)C(=O)N2CCC(COc3ccccc3CN(C)C)CC2)C1=O] | 217 | (S)-1-[(S)-1-{[4-({o-[(Dimethylamino)methyl]phenoxy}methyl)-1-piperidyl]carbonyl}-3-methylbutyl]-3-isobutyl-2-piperazinone | Z = CHCH$_2$OH, tosylation with tosyl choride, substitution reaction with salicylaldehyde, reductive amination with dimethylamine | CD$_3$OD: δ 7.42-7.30 (br m, 2H), 7.06 (d, 1H), 6.99 (t, 1H); 5.58 (m, 1H), 3.95 (m, 4H), 2.60 (s, 6H), 0.95 (m, 12H) | +++ |
| 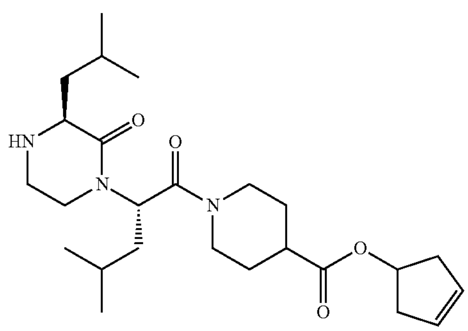 [SMILES: CC(C)C[C@@H]1NCCN([C@@H](CC(C)C)C(=O)N2CCC(C(=O)OC3CC=CC3)CC2)C1=O] | 218 | 3-Cyclopenten-1-yl 1-{(S)-2-[(S)-3-isobutyl-2-oxo-1-piperazinyl]-4-methylvaleryl}-4-piperidinecarboxylate | (B1) IIIb-Z = CHC(O)OCH$_3$, (B2) hydrolysis, ester coupling | CD$_3$OD: δ 5.74 (s, 2H), 5.58 (m, 1H), 2.64 (m, 1H), 0.98 (m, 12H) | ++ |
| 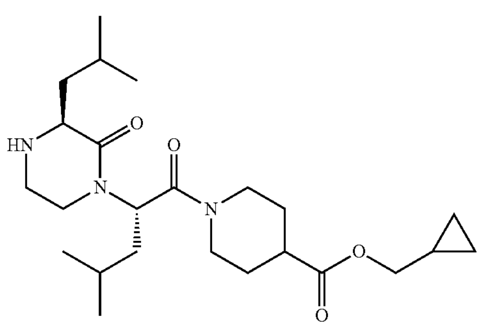 [SMILES: CC(C)C[C@@H]1NCCN([C@@H](CC(C)C)C(=O)N2CCC(C(=O)OCC3CC3)CC2)C1=O] | 219 | Cyclopropylmethyl 1-{(S)-2-[(S)-3-isobutyl-2-oxo-1-piperazinyl]-4-methylvaleryl}-4-piperidinecarboxylate | (B1) IIIb-Z = CHC(O)OCH$_3$, (B2) hydrolysis, ester coupling | CD$_3$OD: δ 5.60 (m, 1H), 2.70 (m, 1H), 0.98 (m, 12H), 0.31 (m, 2H) | +* |
| 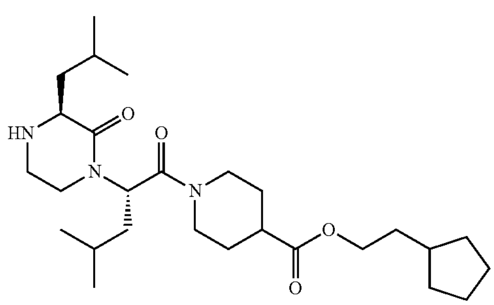 [SMILES: CC(C)C[C@@H]1NCCN([C@@H](CC(C)C)C(=O)N2CCC(C(=O)OCCC3CCCC3)CC2)C1=O] | 220 | 2-Cyclopentylethyl 1-{(S)-2-[(S)-3-isobutyl-2-oxo-1-piperazinyl]-4-methylvaleryl}-4-piperidinecarboxylate | (B1) IIIb-Z = CHC(O)OCH$_3$, (B2) hydrolysis, ester coupling | CD$_3$OD: δ 5.58 (m, 1H), 4.13 (m, 2H), 2.67 (m, 1H), 0.97 (m, 12H) | +* |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 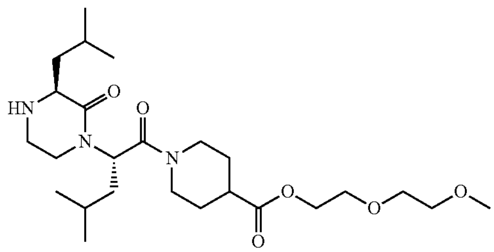 [SMILES: COCCOCCOC(=O)C1CCN(C(=O)[C@H](CC(C)C)N2CCN[C@@H](CC(C)C)C2=O)CC1] | 221 | 2-(2-Methoxyethoxy)ethyl 1-{(S)-2-[(S)-3-isobutyl-2-oxo-1-piperazinyl]-4-methylvaleryl}-4-piperidinecarboxylate | (B1) IIIb-Z = CHC(O)OCH$_3$, (B2) hydrolysis, ester coupling | CD$_3$OD: δ 5.58 (m, 1H), 3.37 (s, 3H), 2.71 (m, 1H), 0.97 (m, 12H) | ND |
| 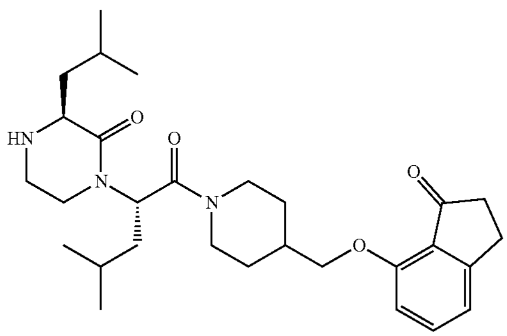 [SMILES: CC(C)C[C@@H]1NCCN([C@@H](CC(C)C)C(=O)N2CCC(COc3cccc4c3C(=O)CC4)CC2)C1=O] | 222 | (S)-1-[(S)-3-Methyl-1-({4-[(3-oxo-4-indanyloxy)methyl]-1-piperidyl}carbonyl)butyl]-3-isobutyl-2-piperazinone | (B1) IIIb-Z = CHCH$_2$OH, (B2) Mitsunobu reaction | CD$_3$OD: 5.60 (m, 1H), 3.87 (d, 2H), 2.63 (d, 2H), 0.97 (m, 12H) | ++ |
| 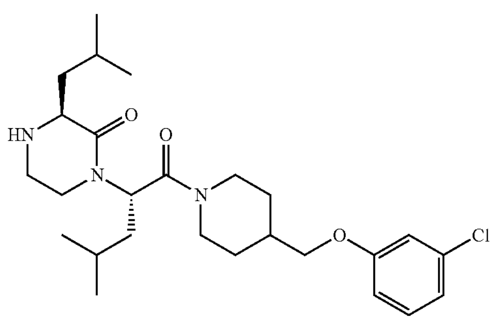 [SMILES: CC(C)C[C@@H]1NCCN([C@@H](CC(C)C)C(=O)N2CCC(COc3cccc(Cl)c3)CC2)C1=O] | 223 | (S)-1-[(S)-1-({4-[(m-Chlorophenoxy)methyl]-1-piperidyl}carbonyl)-3-methylbutyl]-3-isobutyl-2-piperazinone | (B1) IIIb-Z = CHCH$_2$OH, (B2) Mitsunobu reaction | CD$_3$OD: δ 6.95 (s, 1H), 5.60 (m, 1H), 3.87 (d, 2H), 0.97 (m, 12H) | +++ |
| 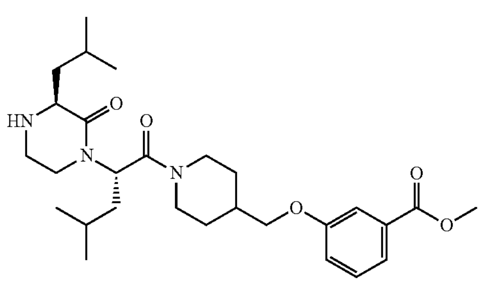 [SMILES: COC(=O)c1cccc(OCC2CCN(C(=O)[C@H](CC(C)C)N3CCN[C@@H](CC(C)C)C3=O)CC2)c1] | 224 | Methyl m-[(1-{(S)-2-[(S)-3-isobutyl-2-oxo-1-piperazinyl]-4-methylvaleryl}-4-piperidyl)methoxy]benzoate | (B1) IIIb-Z = CHCH$_2$OH, (B2) Mitsunobu reaction | CD$_3$OD: δ 7.54 (s, 1H), 5.60 (m, 1H), 3.92 (m, 5H), 0.97 (m, 12H) | +++ |
| 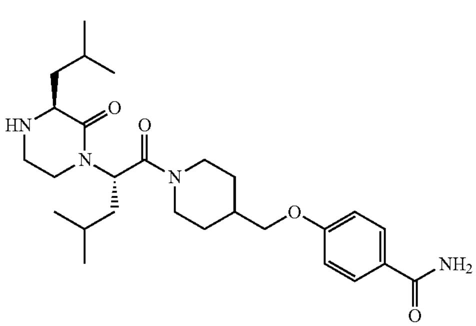 [SMILES: CC(C)C[C@@H]1NCCN([C@@H](CC(C)C)C(=O)N2CCC(COc3ccc(C(N)=O)cc3)CC2)C1=O] | 225 | p-[(1-{(S)-2-[(S)-3-Isobutyl-2-oxo-1-piperazinyl]-4-methylvaleryl}-4-piperidyl)methoxy]benzamide | (B1) IIIb-Z = CHCH$_2$OH, (B2) Mitsunobu reaction | CD$_3$OD: δ 7.85 (d, 2H), 5.60 (m, 1H), 3.94 (d, 2H), 0.97 (m, 12H) | ++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 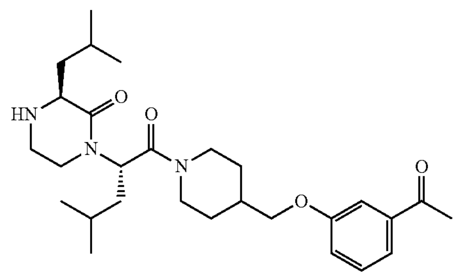 [SMILES: CC(=O)c1cccc(OCC2CCN(C(=O)[C@H](CC(C)C)N3CCN[C@@H](CC(C)C)C3=O)CC2)c1] | 226 | (S)-1-[(S)-1-({4-[(m-Acetylphenoxy)methyl]-1-piperidyl}carbonyl)-3-methylbutyl]-3-isobutyl-2-piperazinone | (B1) IIIb-Z = CHCH$_2$OH, (B2) Mitsunobu reaction | CD$_3$OD: δ 5.60 (m, 1H), 3.94 (d, 2H), 2.60 (s, 3H), 0.97 (m, 12H) | +++ |
| 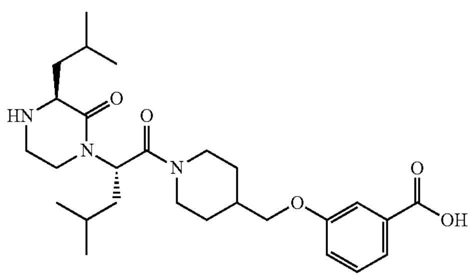 [SMILES: CC(C)C[C@@H]1NCCN([C@@H](CC(C)C)C(=O)N2CCC(COc3cccc(C(=O)O)c3)CC2)C1=O] | 227 | m-[(1-{(S)-2-[(S)-3-Isobutyl-2-oxo-1-piperazinyl]-4-methylvaleryl}-4-piperidyl)methoxy] benzoic acid | (B1) IIIb-Z = CHCH$_2$OH, (B2) Mitsunobu reaction | CD$_3$OD: δ 7.53 (m, 2H), 5.60 (m, 1H), 3.91 (d, 2H), 0.96 (m, 12H) | +* |
| 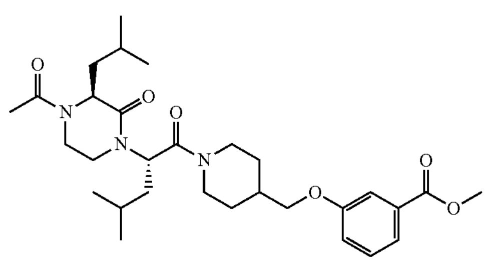 [SMILES: COC(=O)c1cccc(OCC2CCN(C(=O)[C@H](CC(C)C)N3CCN(C(C)=O)[C@@H](CC(C)C)C3=O)CC2)c1] | 228 | Methyl m-[(1-{(S)-2-[(S)-4-acetyl-3-isobutyl-2-oxo-1-piperazinyl]-4-methylvaleryl}-4-piperidyl)methoxy] benzoate | (B1) IIIb-Z = CHCH$_2$OH, (B2) Mitsunobu reaction | CDCl$_3$: δ 5.71-5.51 (m, 1H), 3.92 (s, 3H), 2.11 (m, 3H), 0.98 (m, 12H) | +++ |
| 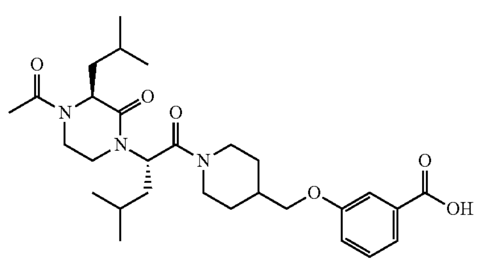 [SMILES: CC(=O)N1CCN([C@@H](CC(C)C)C(=O)N2CCC(COc3cccc(C(=O)O)c3)CC2)C(=O)[C@@H]1CC(C)C] | 229 | m-[(1-{(S)-2-[(S)-4-Acetyl-3-isobutyl-2-oxo-1-piperazinyl]-4-methylvaleryl}-4-piperidyl)methoxy] benzoic acid | (B1) IIIb-Z = CHCH$_2$OH, (B2) Mitsunobu reaction | CD$_3$OD: δ 7.53 (m, 2H), 5.59 (m, 1H), 2.14 (m, 3H), 0.98 (m, 12H) | ND |
| 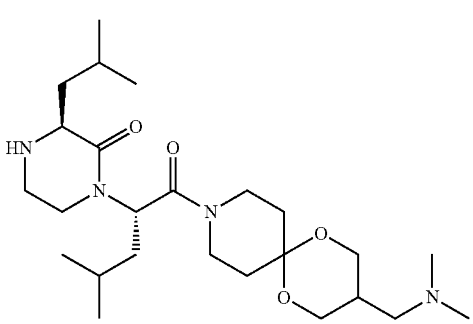 | 230 | (S)-1-[(S)-1-({3-[(Dimethylamino)methyl]-1,5-dioxa-9-aza-9-spiro[5.5]undecyl}carbonyl)-3-methylbutyl]-3-isobutyl-2-piperazinone | (B1) IIIb-Z = C═O, (B2) ketalization using (2,2-dimethyl-1,3-dioxan-5-yl)methanol (Combi-Blocks), tosylation of alcohol, substitution of tosylate using HNMe$_2$ | CD$_3$OD: δ 5.57 (m, 1H), 3.98 (d, 2H), 2.88 (m, 1H), 2.36 (d, 2H), 2.26 (s, 6H), 0.95 (m, 12H) | ++++ |

TABLE 3-continued

Compounds made through Method B1 and B2

| Structure | Ex. Cmpd # | name | Precursor III synthesis | Characterisitic ¹H NMR signals (300 MHz) | Activity |
|---|---|---|---|---|---|
| 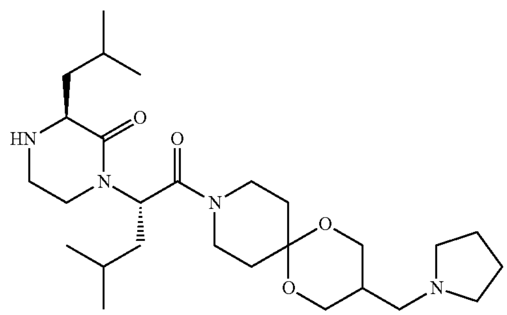 [SMILES: CC(C)C[C@@H]1NCCN([C@@H](CC(C)C)C(=O)N2CCC3(CC2)OCC(CN2CCCC2)CO3)C1=O] | 231 | (S)-1-[(S)-3-methyl-1-({3-[(1-pyrrolidinyl)methyl]-1,5-dioxa-9-aza-9-spiro[5.5]undecyl}carbonyl)butyl]-3-isobutyl-2-piperazinone | (B1) IIIb-Z = C=O, (B2) ketalization using (2,2-dimethyl-1,3-dioxan-5-yl)methanol (Combi-Blocks), tosylation of alcohol, substitution of tosylate using pyrrolidine | CD$_3$OD: δ 5.57 (m, 1H), 3.42 (d, 2H), 1.65 (m, 4H), 1.00 (m, 12H) | ++++ |
| 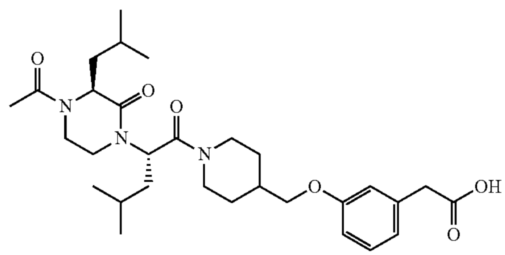 [SMILES: CC(=O)N1CCN([C@@H](CC(C)C)C(=O)N2CCC(COc3cccc(CC(=O)O)c3)CC2)C(=O)[C@@H]1CC(C)C] | 303 | {m-[(1-{(S)-2-[(S)-4-Acetyl-3-isobutyl-2-oxo-1-piperazinyl]-4-methylvaleryl}-4-piperidyl)methoxy]phenyl}acetic acid | (B1) IIIb-Z = CHCH$_2$OH (B2) Mitsunobu reaction with Methyl (m-hydroxyphenyl)acetate, ester hydrolysis | CD$_3$OD: δ 7.14 (t, 1H), 5.58 (m, 1H), 2.13 (m, 3H), 0.98 (m, 12H) | +* |
| 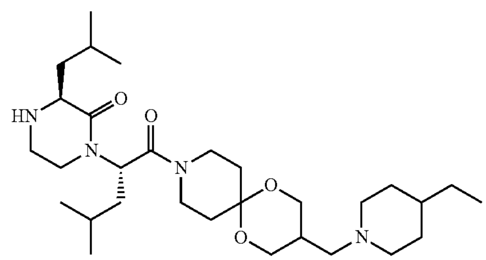 [SMILES: CCC1CCN(CC2COC3(CCN(C(=O)[C@H](CC(C)C)N4CCN[C@@H](CC(C)C)C4=O)CC3)OC2)CC1] | 304 | (S)-1-[(S)-1-({3-[(4-Ethyl-1-piperidyl)methyl]-1,5-dioxa-9-aza-9-spiro[5.5]undecyl}carbonyl)-3-methylbutyl]-3-isobutyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 4-Ethylpiperidine (AstaTech) | CD$_3$OD: δ 5.59 (dd, 1H), 3.98 (br d, 2H), 2.33 (d, 2H), 1.01-0.89 (m, 15H) | ++++ |
| 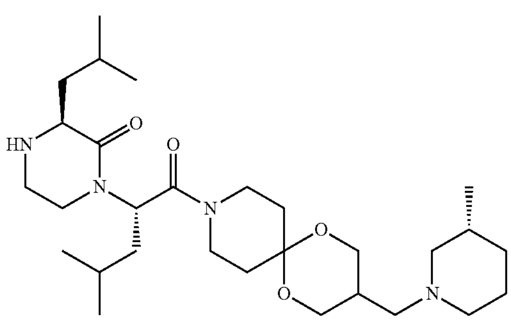 [SMILES: CC(C)C[C@@H]1NCCN([C@@H](CC(C)C)C(=O)N2CCC3(CC2)OCC(CN2CCC[C@@H](C)C2)CO3)C1=O] | 305 | (S)-1-[(S)-1-[(3-{[(R)-3-Methyl-1-piperidyl]methyl}-1,5-dioxa-9-aza-9-spiro[5.5]undecyl)carbonyl]-3-methylbutyl]-3-isobutyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using (R)-3-Methylpiperidine (AstaTech) | CD$_3$OD: δ 5.59 (m, 1H), 4.03-3.93 (m, 2H), 2.95-2.80 9m, 3H), 2.40-2.33 (m, 2H) | ++++ |
| 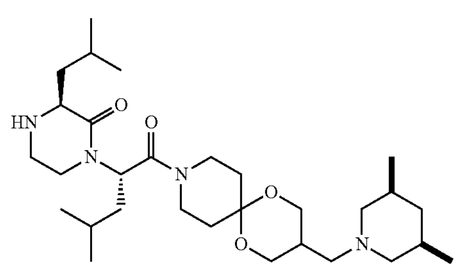 [SMILES: CC(C)C[C@@H]1NCCN([C@@H](CC(C)C)C(=O)N2CCC3(CC2)OCC(CN2C[C@H](C)C[C@H](C)C2)CO3)C1=O] | 306 | (S)-1-[(S)-1-({3-[(3,5-Dimethyl-1-piperidyl)methyl]-1,5-dioxa-9-aza-9-spiro[5.5]undecyl}carbonyl)-3-methylbutyl]-3-isobutyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 3,5-cis-Dimethylpiperidine (AstaTech) | CD$_3$OD: δ 5.58 (dd, 1H), 2.34 (d, 2H), 0.97 (m, 12H), 0.89 (d, 6H) | ++++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 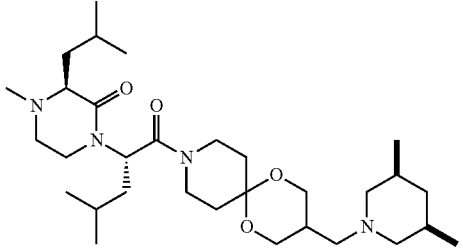 | 307 | (S)-1-[(S)-1-({3-[(3,5-Dimethyl-1-piperidyl)methyl]-1,5-dioxa-9-aza-9-spiro[5.5]undecyl}carbonyl)-3-isobutylbutyl]-3-isobutyl-4-methyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using cis-3,5-Dimethylpiperidine (AstaTech) | CDCl$_3$: δ 5.57 (m, 1H), 2.49 (m, 1H), 2.33 (s, 3H), 0.97-0.79 (m, 18H) | ++++ |
| 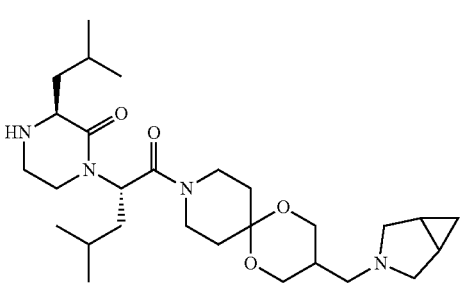 [SMILES: CC(C)C[C@@H]1NCCN([C@@H](CC(C)C)C(=O)N2CCC3(CC2)OCC(CN2CC4CC4C2)CO3)C1=O] | 308 | (S)-1-[(S)-1-[(3-{(3-Azabicyclo[3.1.0]hex-3-yl)methyl}-1,5-dioxa-9-aza-9-spiro[5.5]undecyl)carbonyl]-3-methylbutyl]-3-isobutyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 3-Azabicyclo[3.1.0]hexane (AstaTech) | CD$_3$OD: δ 5.61-5.55 (m, 1H), 2.66 (m, 1H), 0.97 (m, 12H), 0.40-0.31 (m, 1H) | ++++ |
| 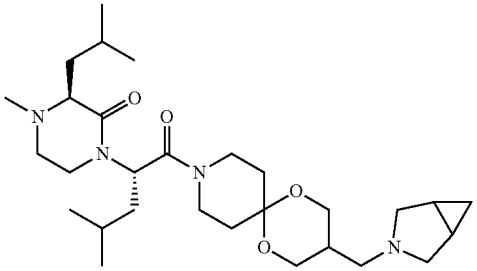 [SMILES: CC(C)C[C@H]1C(=O)N([C@@H](CC(C)C)C(=O)N2CCC3(CC2)OCC(CN2CC4CC4C2)CO3)CCN1C] | 309 | (S)-1-[(S)-1-[(3-{(3-Azabicyclo[3.1.0]hex-3-yl)methyl}-1,5-dioxa-9-aza-9-spiro[5.5]undecyl)carbonyl]-3-methylbutyl]-3-isobutyl-4-methyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 3-Azabicyclo[3.1.0]hexane (AstaTech) | CDCl$_3$: δ 5.62-5.54 (m, 1H), 2.34 (s, 3H), 0.98-0.87 (m, 12H), 0.38-0.26 (m, 1H) | ++++ |
| 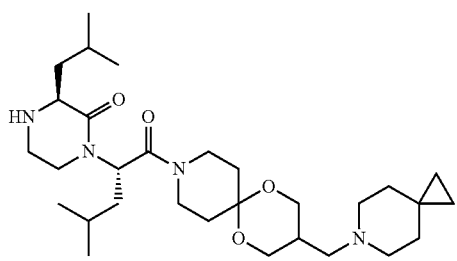 [SMILES: CC(C)C[C@@H]1NCCN([C@@H](CC(C)C)C(=O)N2CCC3(CC2)OCC(CN2CCC4(CC2)CC4)CO3)C1=O] | 310 | (S)-1-[(S)-1-[(3-{(6-Aza-6-spiro[2.5]octyl)methyl}-1,5-dioxa-9-aza-9-spiro[5.5]undecyl)carbonyl]-3-methylbutyl]-3-isobutyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 6-Azaspiro[2.5]octane (AstaTech) | CD$_3$OD: δ 5.62-5.56 (m, 1H), 2.43-2.37 (m, 2H), 0.97 (m, 12H), 0.31 (s, 4H) | ++++ |
| 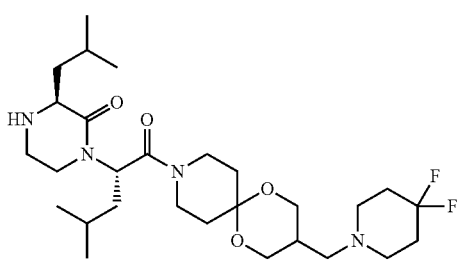 [SMILES: CC(C)C[C@@H]1NCCN([C@@H](CC(C)C)C(=O)N2CCC3(CC2)OCC(CN2CCC(F)(F)CC2)CO3)C1=O] | 311 | (S)-1-[(S)-1-({3-[(4,4-Difluoro-1-piperidyl)methyl]-1,5-dioxa-9-aza-9-spiro[5.5]undecyl}carbonyl)-3-methylbutyl]-3-isobutyl-2-piperazinone | (B1) IIIb-Z = C=O (Combi-Blocks) (B2) ketalization with (2,2-Dimethyl 1,3-dioxan-5-yl)methanol (Combi-Blocks), mesylation of alcohol, substitution of mesylate using 4,4 Difluoropiperidine (AstaTech) | CD$_3$OD: δ 5.62-5.55 (m, 1H), 2.96-2.76 (m, 3H), 2.43 (d, 2H), 0.97 (m, 12H) | *+ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 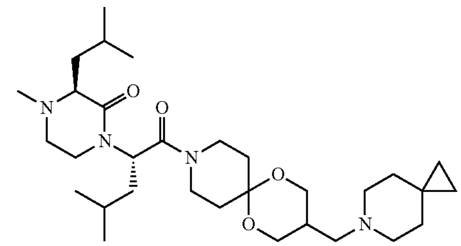 [SMILES: CC(C)C[C@H]1C(=O)N([C@@H](CC(C)C)C(=O)N2CCC3(CC2)OCC(CN2CCC4(CC2)CC4)CO3)CCN1C] | 312 | (S)-1-[(S)-1-[(3-{(6-Aza-6-spiro[2.5]octyl)methyl}-1,5-dioxa-9-aza-9-spiro[5.5]undecyl) carbonyl]-3-methylbutyl]-3-isobutyl-4-methyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 6-Azaspiro[2.5]octane (AstaTech) | CDCl$_3$: δ 5.62-5.55 (m, 1H), 2.34 (s, 3H), 0.98-0.87 (m, 12H), 0.26 (s, 4H) | ++++ |
| 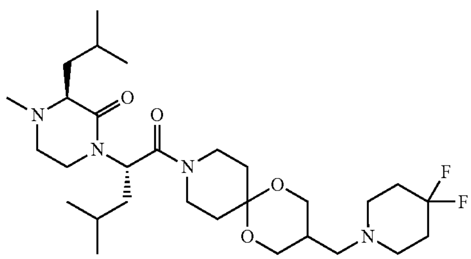 [SMILES: CC(C)C[C@H]1C(=O)N([C@@H](CC(C)C)C(=O)N2CCC3(CC2)OCC(CN2CCC(F)(F)CC2)CO3)CCN1C] | 313 | (S)-1-[(S)-1-({3-[(4,4-Difluoro-1-piperidyl)methyl]-1,5-dioxa-9-aza-9-spiro[5.5]undecyl} carbonyl)-3-methylbutyl]-3-isobutyl-4-methyl-2-piperazinone | (B1) IIIb-Z = C=O (Combi-Blocks) (B2) ketalization with (2,2-Dimethyl-1,3-dioxan-5-yl)methanol (Combi-Blocks), mesylation of alcohol, substitution of mesylate using 4,4-Difluoropiperidine (AstaTech) | CDCl$_3$: δ 5.62-5.55 (m, 1H), 2.86-2.80 (m, 1H), 2.35 (s, 3H), 0.98-0.87 (m, 12H) | ND |
| 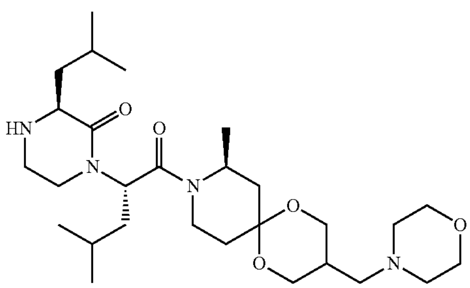 [SMILES: CC(C)C[C@@H]1NCCN([C@@H](CC(C)C)C(=O)N2CCC3(C[C@@H]2C)OCC(CN2CCOCC2)CO3)C1=O] | 314 | (S)-1-[(S)-1-({(S)-8-Methyl-3-(morpholinomethyl)-1,5-dioxa-9-aza-9-spiro[5.5]undecyl} carbonyl)-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using Morpholine | CD$_3$OD: δ 5.54 (m, 1H), 3.68 (m, 6H), 2.55-1.87 (br m, 9H), 0.95 (m, 12H) | ++++ |
| 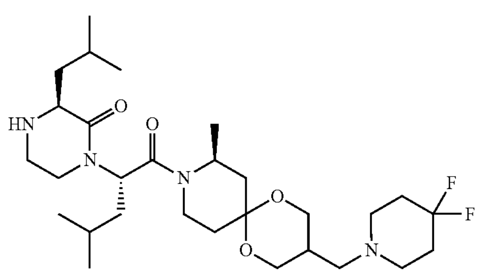 [SMILES: CC(C)C[C@@H]1NCCN([C@@H](CC(C)C)C(=O)N2CCC3(C[C@@H]2C)OCC(CN2CCC(F)(F)CC2)CO3)C1=O] | 315 | (S)-1-[(S)-1-({(S)-3-[(4,4-Difluoro-1-piperidyl)methyl]-8-methyl-1,5-dioxa-9-aza-9-spiro[5.5]undecyl} carbonyl)-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using 4,4-Difluoropiperidine (AstaTech) | CD$_3$OD: δ 5.54 (m, 1H), 4.11-3.59 (br m, 5H), 3.05-2.79 (br m, 2H), 0.95 (m, 12H) | ++++ |
| 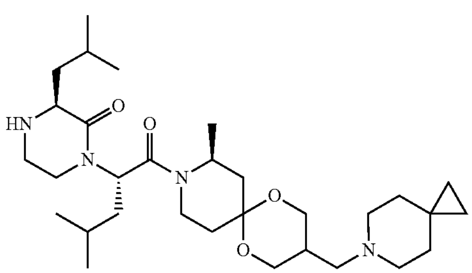 [SMILES: CC(C)C[C@@H]1NCCN([C@@H](CC(C)C)C(=O)N2CCC3(C[C@@H]2C)OCC(CN2CCC4(CC2)CC4)CO3)C1=O] | 316 | (S)-1-[(S)-1-{[(S)-3-{(6-Aza-6-spiro[2.5]octyl)methyl}-8-methyl-1,5-dioxa-9-aza-9-spiro[5.5]undecyl] carbonyl}-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using 6-Azaspiro[2.5]octane (AstaTech) | CD$_3$OD: δ 5.55 (m, 1H), 4.09-3.83 (br m, 2H), 2.61-1.88 (br m, 9 H), 0.95 (m, 12H), 0.29 (s, 4H) | ++++ |

TABLE 3-continued

Compounds made through Method B1 and B2

| Structure | Ex. Cmpd # | name | Precursor III synthesis | Characterisitic $^1$H NMR signals (300 MHz) | Activity |
|---|---|---|---|---|---|
| 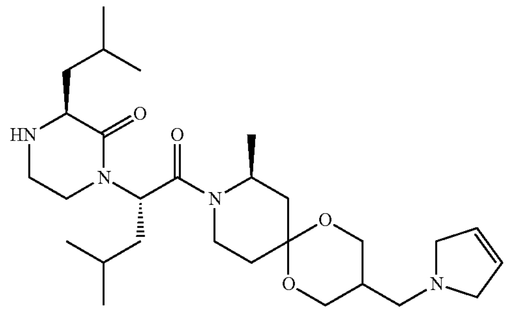 [SMILES: CC(C)C[C@@H]1NCCN([C@@H](CC(C)C)C(=O)N2CCC3(C[C@@H]2C)OCC(CN2CC=CC2)CO3)C1=O] | 317 | (S)-1-[(S)-1-({(S)-3-[(2,5-Dihydro-1H-pyrrol-1-yl)methyl]-8-methyl-1,5-dioxa-9-aza-9-spiro[5.5]undecyl}carbonyl)-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using 2,5-Dihydro-1H-pyrrole (AstaTech) | CD$_3$OD: δ 5.81 (s, 2H), 5.52 (m, 1H), 4.12-3.89 (br m, 2H), 0.95 (m, 12H) | ++++ |
| 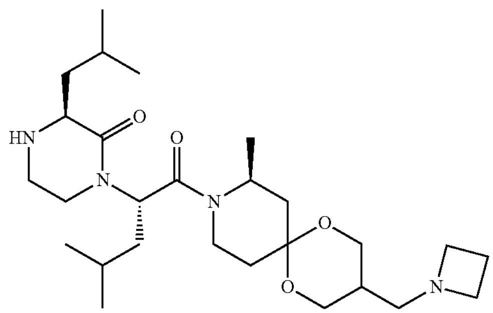 [SMILES: CC(C)C[C@@H]1NCCN([C@@H](CC(C)C)C(=O)N2CCC3(C[C@@H]2C)OCC(CN2CCC2)CO3)C1=O] | 318 | (S)-1-[(S)-1-({(S)-3-[(1-Azetidinyl)methyl]-8-methyl-1,5-dioxa-9-aza-9-spiro[5.5]undecyl}carbonyl)-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using Azetidine | CD$_3$OD: δ 5.52 (m, 1H), 2.59-1.97 (br m, 6H), 1.91-1.42 (br m, 9H); 0.95 (m, 12H) | ++++ |
| 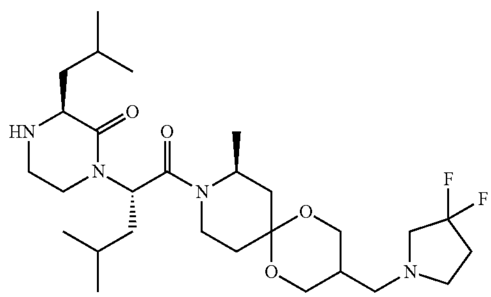 [SMILES: CC(C)C[C@@H]1NCCN([C@@H](CC(C)C)C(=O)N2CCC3(C[C@@H]2C)OCC(CN2CCC(F)(F)C2)CO3)C1=O] | 319 | (S)-1-[(S)-1-({(S)-3-[(3,3-Difluoro-1-pyrrolidinyl)methyl]-8-methyl-1,5-dioxa-9-aza-9-spiro[5.5]undecyl}carbonyl)-3-methylbutyl]-3-isobutyl-2-piperazinone | (B1) IIIb-Z = C=O (HCl salt, AstaTech) (B2) ketalization with (2,2-Dimethyl-1,3-dioxan-5-yl)methanol (Combi-Blocks), mesylation of alcohol, substitution of mesylate using 3,3-Difluoropyrrolidine (AstaTech) | CD$_3$OD: δ 5.53 (m, 1H), 4.10-3.88 (br m, 2H), 3.87-3.60 (br m, 5H); 0.95 (m, 12H) | ++++ |

All starting materials for precursor II and III have been obtained from Sigma-Aldrich unless otherwise noted in Table 2 and 3 above.

The biological properties of compounds were investigated by way of the experimental protocols described below:

Colony Formation Assay (CFA)

Cell Culture:

CaSki cells were obtained from CLS GmbH, Eppelheim, Germany (cat. 300145) and subcultured in ready-to-use RPMI1640 Media (CLS GmbH cat. 820700) after addition of "Antibiotic Antimycotic Solution" (Sigma-Aldrich, St Louis, USA, cat. A5955) at 1:100 dilution. CaSki cells were expanded and aliquots kept frozen in liquid nitrogen according to manufacturer's instructions. Once thawed, aliquots were passaged every second or third day at a seed density of 20'000 cells/cm$^2$; and used for a maximum of twenty passages.

Preparation of the Cells for CFA:

Cell culture flasks were rinsed twice with Ca++/Mg++-free Phosphate-Buffered Saline (DPBS, CLS GmbH cat. 860015) and incubated with Accutase (CLS GmbH cat. 830100) for 15 min at 37° C. Cells were resuspended in a four-fold volume of ready-to use RPMI, centrifuged at 300 g for 10 minutes, the supernatant discarded and the cells resuspended in ready-to-use RPMI1640 by pipetting up and down ten times with a serological pipette. Cell density was determined with a Via-1 Cassette (Chemometec, Allerod, Denmark) on a Nucleocounter NC 3000 (Chemometec). The required amount of cells was first diluted 1:10 in ready-to-use RPMI; cells pipetted five times up-down with a serological pipette; and the 1:10 solution added to the final volume needed for the whole assay setup. Cells were mixed again by pipetting up and down twenty times with a serological pipette. The final cell density was 70 cells/ml.

Seeding:

Cells were seeded column-wise in 6-well plates, while triplicates were treated row-wise. Three ml cell suspension solution (210 cells) were added per well.

Treatment:

Compound stock solutions were prepared at a concentration of 30 mM in 50% DMSO/50% water; and diluted in the same solution so that the volume added to the wells was of 511 and the final DMSO well concentration 0.08%. Untreated cells (negative controls) were incubated in a) medium only; and b) 0.08% DMSO. Test performance was monitored by a standard treatment with a fixed concentration of a reference compound (10 M Compound 57) that resulted in ~80-90% inhibition of colony formation. Tests showing less than 75% or more than 95% inhibition were repeated. The plates were swirled gently after addition of the compounds and the cells incubated for 14 days at 37° C. Culture incubation solutions were replaced after one week.

Staining:

Colonies were washed twice with ice-cold DPBS and fixed on ice with 1 ml ice-cold 10% methanol solution for 30 min. The methanol solution was removed and colonies incubated with 0.1% Crystal Violet/DBPS for 20 min at room temperature. The wells were rinsed with water at room temperature, let dry and colonies were counted. Compounds e.g., compounds of Table 2 and 3 were classified as follows:

++++ more than 90% inhibition of colony formation at a concentration of 6 µM
+++ more than 90% inhibition of colony formation at a concentration of 50 µM
++ more than 50% inhibition of colony formation at a concentration of 50 µM
+* greater than 0% but less than or equal to 50% inhibition of colony formation at a concentration of 50 µM
*+ greater than 0% but less than or equal to 50% inhibition of colony formation at a concentration of 0.7 µM
ND activity not detectable at 0.7 µM in this assay Tumor Growth Inhibition in a Patient-Derived Xenograft Model of Head and Neck Cancer NMRI nude mice bearing HN11873 subcutaneous tumors (Experimental Pharmacology and Oncology Berlin Buch GmbH, Berlin, Germany) were treated p.o. BID with either vehicle (control) or 30 mg/kg test compound (S)-1-[(S)-1-({4-[(1H-Imidazol-2-yl)methyl]-1-piperidyl)}carbonyl)-3-methylbutyl]-3-isobutyl-2-piperazinone. The test compound was dissolved in 0.5% methylcellulose with tween 80. Treatment started at a mean tumor volume of 100 mm³ at study day 17. The experiment was finished at day 58 of the study because of large tumors in group A and unchanged outcome. Tumor diameters were determined twice weekly. Statistical analysis was performed with the software Graph Pad Prism, Vers. 5.02 by using 2-Way-ANOVA with Bonferroni posttest. FIG. 1 shows tumor growth inhibition for the vehicle and the test compound.

Example 320: Colony Formation Assay (CFA) with a Cervical Cancer Cell Line

Cell Culture.

CaSki cells (cervical cancer) were obtained from CLS GmbH, Eppelheim, Germany (cat #300145) and subcultured in ready-to-use RPMI1640 Media (CLS #820700) after addition of "Antibiotic Antimycotic Solution" (Sigma-Aldrich, St Louis, USA) at 1:100 dilution. The cells were expanded, and aliquots kept frozen in liquid nitrogen according to manufacturer's instructions; tested for *mycoplasma* contamination and genotyped (Microsynth AG, Balgach, Switzerland). Once thawed, aliquots were passaged every second or third day at a seed density of 20'000 cells/cm²; and used for a maximum of twenty passages. For passaging, cell culture flasks were rinsed twice with Ca++/Mg++-free Phosphate-Buffered Saline (DPBS, CLS #860015) and incubated with Accutase (CLS #830100) for 15 min at 37° C. Cells were resuspended in a four-fold volume of ready-to-use RPMI, centrifuged at 300 g for ten minutes, the supernatant discarded and the cells resuspended in ready-to-use RPMI1640 by pipetting up and down five times with a serological pipette. Cell density was determined with a Via-1 Cassette (Chemometec, Allerod, Denmark) on a Nucleocounter NC 3000 (Chemometec). Where not stated, consumables and chemicals were purchased from well-known suppliers.

Preparation of the Cells for CFA.

Cell culture flasks were rinsed twice with DPBS and incubated with Accutase for 15 min at 37° C. Cells were resuspended in a four-fold volume of ready-to use RPMI, centrifuged at 300 g for ten minutes, the supernatant discarded and the cells resuspended in ready-to-use RPMI1640 by pipetting up and down ten times with a serological pipette. Cell density was determined with a Via-1 Cassette on a Nucleocounter NC 3000. The required amount of cells was first diluted 1:10 in ready-to-use RPMI; cells pipetted five times up-down with a serological pipette; and the 1:10 solution added to the final volume needed for the whole assay setup. Cells were mixed again by pipetting up and down twenty times with a serological pipette. The cell density used for the experiment was of 140 cells/ml.

Seeding.

Cells were seeded row-wise in 12-well plates, while triplicates were treated column-wise (i.e. all the first rows were seeded first, then the second rows, and finally the third rows). One and a half ml cell suspension solution (a total of 210 cells) were added per well.

Treatment.

Compound stock solutions were prepared at a concentration of 30 mM in 50% DMSO/50% water; and diluted in the same solution so that the volume added to the wells was of 2.5 µl and the final DMSO well concentration of 0.08%. Untreated cells (negative controls) were incubated in a) medium only; and b) 0.08% DMSO. Test performance was monitored by a standard treatment with a fixed concentration of a reference compound that resulted in ~80-90% inhibition of colony formation. The plates were swirled gently after addition of the compounds and the cells incubated for nine days at 37° C. Culture incubation solutions were replaced after five days.

Staining.

Colonies were washed twice with ice-cold DPBS and fixed on ice with 1 ml ice-cold 10% methanol solution for 30 min. The methanol solution was removed and colonies incubated with 0.1% Crystal Violet/DBPS for 20 min at room temperature. The wells were rinsed consecutively with 1.5, 1, and 0.5 ml water at room temperature and let dry.

Destaining and Data Evaluation.

Colony-bound crystal violet was solubilized in 500 µl 10% Acetic Acid. Plates were shaked for 30 sec and the acetic acid solution was transferred to a 2 ml well in a 96-deep-well plate. Five-hundred microliter 10% acetic acid were added again to each well of the 12-well plates, the plates shaken for 30 sec and the acetic acid transferred to the same well of the 96-deep-well plate, mixed well and 100 µl transferred to a clear-bottom 96-Well plate. Absorbance was measured at 600 nm with a SpectraMax M2e reader (Molecular Devices, Sunnyvale, Calif., USA). Percentage of colony formation was calculated from the average of the well triplicates compared to the untreated DMSO controls after subtraction of blank values. Blanks were obtained from wells incubated for nine days with ready-to-use RPMI1640 only and processed the same way as colony-containing wells. A typical result is shown in TABLE 4 for four cell lines and four different compounds.

TABLE 4

Shows the GI50 (50% growth inhibition) concentrations (nM = nmol/lt) for Compound 258; Compound 287; Compound 279; Compound 253; and Compound 284, in a 9-day colony survival assay of cancer cell lines derived from prostate (PC3); lung (A549); cervix (CaSki); and colon (HCT116).

| Compound     | PC3 | A549 | CaSki | HCT116 |
|--------------|-----|------|-------|--------|
| Compound 258 | 3   | 5    | 2     | 1.5    |
| Compound 287 | 7   | 20   | 13    | 1.5    |
| Compound 279 | 1.5 | 5    | 4     | 1      |
| Compound 253 | 4   | 7    | 4.5   | 2      |
| Compound 284 | 3   | 10   | 6     | 1.5    |

Example 321: Cell Proliferation Screening with a Sixty-Seven Cancer Cell Line Panel For screening using a proliferation assay, the cells used were cultured at 37° C. with 5% CO2, except for those being cultured with L-15 medium (37° C. and 100% air, TABLE 7). Compound stock solutions (10 mM) were made in sterile water, aliquoted and stored at room temperature. Cisplatin was used as reference Control. Plastic consumables, culture media and supplements were purchased from well-known suppliers (TABLE 8).

Cell Seeding (Day −1).

When necessary, cells were trypsinized using standard methods (see e.g. example 01). Cells were collected and resuspended in 5-6 mL of appropriate culture medium, counted and diluted to the needed density. Fifty-four µl (microliter) cells were seeded per well in a 384-well plate. Extra four wells per cell line were seeded on an additional plate for Day 0 reading (baseline cell density). Cells were incubated at 37° C. overnight.

Compound Treatment and Day 0 Reading (Day 0).

Tenfold final concentration of test compounds and Cisplatin were prepared in cell culture media (work dilutions). Six µl of work dilution solutions were dispensed into the corresponding wells in 384-well plates to bring the total volume up to 60 µl. Conditions were tested in triplicate. The plates were then incubated at 37° C. for five days. For the day 0 reading, 30 µl of CTG and 6 µl cell culture medium were added to the day 0 plates, contents mixed for 2 min on a plate shaker, and the plates incubated for 10 min at room temperature in the dark. Luminescence was recorded on an EnVision Multi Label Reader (2104-0010A, PerkinElmer, USA).

Endpoint CTG Reading (Day 5).

The amounts of cells in the plates was determined by endpoint CTG-test. Thirty µl of CTG were added to the 60 µl of cell culture per well, contents mixed for 2 min on a plate shaker, and the plates incubated for 10 min at room temperature in the dark. Luminescence was recorded on an EnVision Multi Label Reader.

Data Analysis.

Fifty percent growth inhibition concentrations (GI50) were calculated based on percentage of control data (untreated cells) from each cell line (TABLE 5 (this example) and TABLE 6). Curves were fitted using a nonlinear regression model with a sigmoidal dose response. Examples of obtained curves are depicted in FIG. 2A-2F.

TABLE 5

Compound 258 GI50 for sixty-seven tested cell lines. Shows the GI50 (50% growth inhibition) concentration (nM = nmol/lt) for Compound 258 in a 5-day cell proliferation assay of 67 cancer cell lines derived from 15 different tissues/organs. Cells with a value ">10'000" mean that GI50 is higher than the highest tested concentration (10 µM).

| Tumor Type | Cell Line | GI50 (nM) |
|---|---|---|
| Lymphoma | Granta-519 | 38 |
|  | KARPAS-422 | 48 |
|  | KARPAS-299 | 5 |
|  | Ramos | 27 |
|  | Daudi | 80 |
|  | Raji | 28 |
| Leukemia | MOLM-13 | 4 |
|  | HL-60 | 5 |
|  | Kasumi-1 | 19 |
|  | Jurkat | 18 |
|  | MOLT-4 | 9 |
|  | K562 | 17 |
|  | U937 | 22 |
|  | HS-5 | 5 |
| Brain/Nerves | H4 | 11 |
|  | SF268 | 30 |
| Breast | MCF7 | 55 |
|  | BT-20 | 15 |
|  | BT474 | 72 |
|  | SK-BR-3 | 12 |
|  | AU565 | 3 |
| Cervix | CaSki | 35 |
|  | SiHa | 52 |
|  | MS751 | 51 |
|  | DoTc2 4510 | 14 |
|  | HT-3 | 330 |
| Ovary | OVCAR-3 | 44 |
|  | OVCAR-4 | 12 |
| Colorectal | Caco-2 | 10 |
|  | HCT116 | 5 |
|  | HT-29 | 4 |
|  | SW480 | 22 |
|  | SW48 | 9 |
|  | SW948 | 10 |
|  | SW620 | 4 |
| Stomach/Gastric | MKN-45 | 4 |
|  | IM95m | 4 |
|  | MKN-1 | 2 |
|  | HS 746.T | 8 |
|  | SNU-16 | 13 |
|  | SNU-5 | 4 |
| Kidney | 786-O | 28 |
|  | Caki 2 | 14 |
| Liver | HEP-3B | 23 |
|  | Hep G2 | 6 |
|  | HUH-7 | 10 |
| Lung | A549 | 10 |
|  | HCC4006 | 8 |
|  | H460 | 11 |
|  | HCC2935 | >10'000 |
|  | MRC-5 | 12 |
| Oesophagus | KYSE-150 | 11 |
|  | KYSE-270 | 44 |
| Pancreas | MIA PaCa-2 | 11 |
|  | PANC-1 | 22 |
| Prostate | LNCaP-FGC | 2 |
|  | DU145 | 7 |
|  | 22RV1 | 9 |
|  | PC-3 | 13 |
|  | RPWE-1 | 4 |
|  | VCAP | 128 |
| Skin | WM-266-4 | 41 |
|  | SK-MEL28 | 50 |
|  | SK-MEL5 | 51 |
|  | A375 | 6 |
|  | Malme-3M | >10'000 |
|  | HDFA (fibroblast) | >10'000 |

TABLE 6

Cell proliferation GI50 (nM) of Compound 279, Compound 258 and Compound 284, Shows the GI50 (50% growth inhibition) concentration (nM = nmol/lt) for Compound 258; Compound 279; and Compound 284 in a 5-day cell proliferation assay of twelve cancer cell lines derived from six different tissues/organs. Cells with a value ">10'000" mean that GI50 is higher than the highest tested concentration (10 μM).

| Tissue/Organ | Cell line | Compound 279 | Compound 258 | Compound 284 |
|---|---|---|---|---|
| Skin (fibroblast) | HDFA | >10'000 | >10'000 | >10'000 |
| Colorectal | HCT 116 | 3 | 5 | 9 |
|  | HS 746.T | 5 | 8 | 14 |
|  | HT-29 | 4 | 4 | 7 |
|  | SW48 | 6 | 9 | 14 |
|  | SW620 | 2 | 4 | 7 |
|  | SW948 | 3 | 10 | 12 |
| Leukemia | HS-5 | 3 | 5 | 10 |
| Lung | MRC-5 | 10 | 12 | 24 |
| Prostate | RWPE-1 | 3 | 4 | 10 |
| Stomach | SNU-16 | 10 | 13 | 22 |
|  | SNU-5 | 3 | 4 | 6 |

TABLE 7

Example cell culture media for human cancer cell lines used in the proliferation assay.

| Cell Line | Tissue Origin/ Growth property | Culture medium |
|---|---|---|
| HL-60 | Blood/Suspension | RPMI-1640 + 10% FBS |
| Kasumi-1 | Blood/Suspension | RPMI-1640 + 20% FBS |
| Granta-519 | Blood/Suspension | DMEM + 10% FBS |
| H4 | Brain&Nerves/Adherent | RPMI1640 + 10% FBS + Glutamax |
| BT-20 | Breast/Adherent | MEM + 0.01 mM NEAA + 10% FBS |
| MCF7 | Breast/Adherent | MEM + 0.01 mM NEAA + 10% FBS + 10 μg/mL Insulin |
| SK-BR-3 | Breast/Adherent | McCoy's 5a + 10% FBS |
| Caco-2 | Colorectum/Adherent | MEM + 0.01 mM NEAA + 10% FBS |
| SW480 | Colorectum/Adherent | L-15 + 10% FBS |
| KYSE-270 | Esophagus/Adherent | RPMI-1640/F12 + 2% FBS |
| Caki2 | Kidney/Adherent | McCoy's 5a + 10% FBS |
| A549 | Lung/Adherent | Ham's F12K + 10% FBS |
| OVCAR3 | Ovary/Adherent | RPMI1640 + 20% FBS + 10 μg/ml Insulin |
| MIA PaCa-2 | Pancreas/Adherent | DMEM + 10% FBS + 2.5% HS |

TABLE 8

Reagent suppliers.

| Reagent | Supplier | Cat# |
|---|---|---|
| F-12K | GIBCO | 21127022 |
| RPMI1640 | GIBCO | C22400500BT |
| DMEM | Hyclone | SH30243.01 |
| McCoy's 5A | GIBCO | 12330-031 |
| MEM | Hyclone | SH30024.01 |
| IMDM | GIBCO | 31980-030 |
| FBS | ExCell | FND500 |
| L-15 | GIBCO | 11415-064 |
| NEAA | GIBCO | 11140-050 |
| L-Glutamine 200 mM | GIBCO | 25030-081 |
| Trypsin (0.25%) | Hyclone | SH30042.02 |
| Insulin | Sigma | 11070-73-8 |
| GlutaMAX | GIBCO | 35050-061 |
| DMSO | Amresco | 0231 |
| 384 well cell culture plate | Corning | 3765 |
| CellTiter-Glo Luminescent Cell Viability kit (CTG) | Promega | G7573 |

Example 322: Castration Resistant Prostate Cancer Patient-Derived Xenograft

Figure 3:
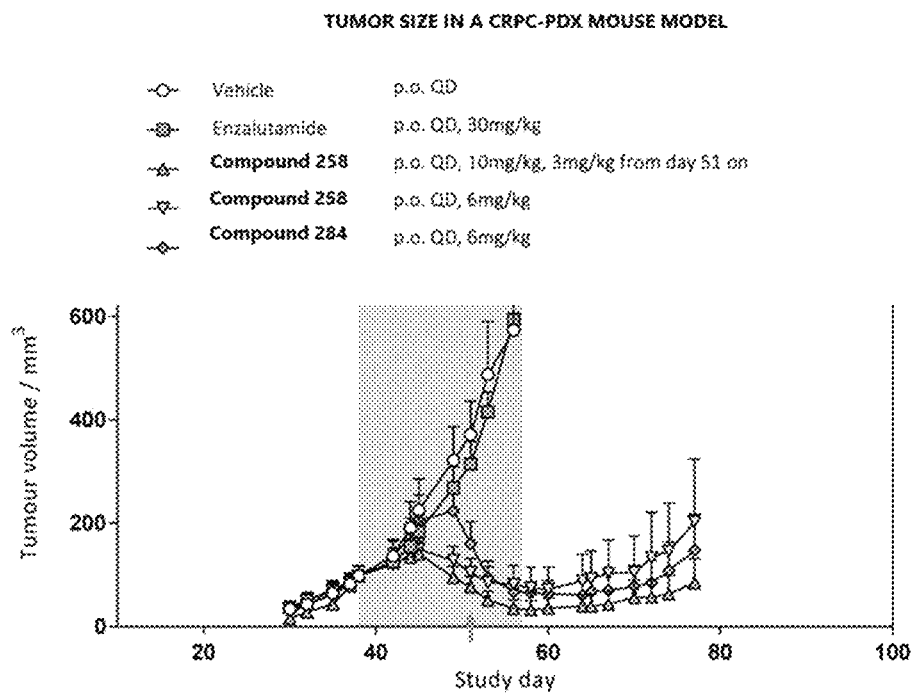
FIG. 3 is a graph showing the tumor size development in a castration-resistant patient-derived xenograft mouse model of prostate cancer at various concentrations of Compound 258 and Compound 284, compared to standard-of-care treatment (Enzalutamide). The arrow indicates a concentration switch from Compound 258 10 mg/kg to 3 mg/kg at day 51.
Figure 4:
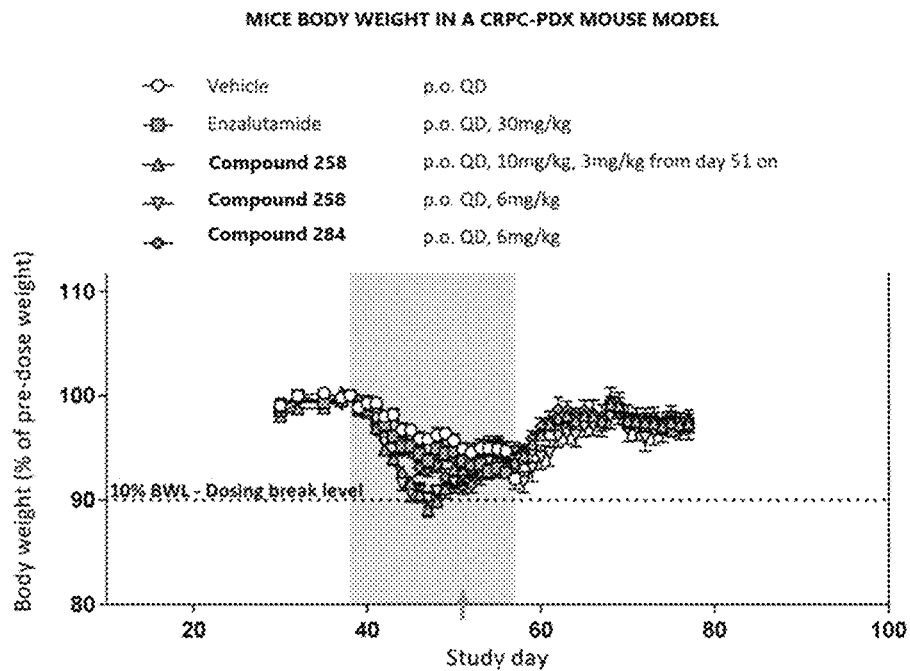
FIG. 4 is a graph showing mice body weight development in a castration-resistant patient-derived xenograft mouse model of prostate cancer at various concentration of Compound 258 and Compound 284, compared to standard-of-care treatment (Enzalutamide). The arrow indicates a concentration switch from Compound 258 10 mg/kg to 3 mg/kg at day 51.

NSG NOD.Cg-PrkdcscidIj2rgtmIWjl/SzJ mice (6-8 weeks of age) were injected with patient-derived castration-resistant prostate tumor cells (model # PR6511, Crown Bioscience UK Ltd Hillcrest, Osgathorpe Leicestershire, UK). The cells were inoculated subcutaneously into the left flank of 40 male NSG mice. When tumors reached a mean volume of approximately 100 mm$^3$ (i.e. 100 mm$^3$+/−54 mm$^3$, FIG. 3), mice were randomly assigned to five treatment groups of each eight mice (TABLE 9). Body weights were measured three times weekly prior to the initiation of dosing and daily thereafter. Tumor burden was assessed by caliper measurement three times weekly. Dosing breaks were applied when tolerability issues arose (body weight loss >10%). Upon completion of the scheduled dosing phase at day 57, tumor outgrowth was monitored for groups 3, 4 and 5 up to study day 77. Groups 1 and 2 were terminated on study day 57. Results of the experiment are shown in TABLES 10 and 11; and FIGS. 3 and 4. The experiment was performed in the Crown Bioscience Ltd. testing facility (Crown Bioscience UK Ltd Hillcrest, Dodgeford Lane, Osgathorpe Leicestershire LE12 9TE, UK).

TABLE 9

CRPC PDX mice treatment group assignment.

| Group | Compound | Formulation | Treatment schedule |
|---|---|---|---|
| 1 | Vehicle | 0.5% Methylcellulose + 0.1% Tween-80 | p.o. QD |
| 2 | Enzalutamide | 1% w/v Carboxymethyl Cellulose (CMC; low viscosity); 0.1% v/v Tween-80; 5% v/v DMSO | p.o. QD, 30 mg/kg |
| 3 | Compound 258 | 0.5% Methylcellulose + 0.1% Tween-80 | p.o. QD, 10 mg/kg, 3 mg/kg from day 51 on |
| 4 | Compound 258 | 0.5% Methylcellulose + 0.1% Tween-80 | p.o. QD, 6 mg/kg |
| 5 | Compound 284 | 0.5% Methylcellulose + 0.1% Tween-80 | p.o. QD, 6 mg/kg | p.o. = oral administration (oral gavage).
QD = once a day.
v/v = volume/volume

TABLE 10

CRPC PDX RESPONSE SUMMARY.

| Treatment (group) | PR | CR | TFS |
|---|---|---|---|
| Vehicle (1) | 0 | 0 | 0 |
| Enzalutamide (2) | 0 | 0 | 0 |
| Compound 258 10 mg/kg (3) | 2 | 4 | 3 |
| Compound 258 6 mg/kg (4) | 2 | 3 | 3 |
| Compound 284 6 mg/kg (5) | 2 | 3 | 3 |

PR (partial regression) = number of mice presenting a tumor size ≤50% lower than initial tumor size during at least 3 consecutive measurements and ≥13.5 mm³ for one or more of these three measurements;
CR (complete regression) = number of mice presenting ≤13.5 mm³ tumor size during at least 3 consecutive measurements;
TFS (Tumor Free Survival) = number of complete regressions recorded up to Group Day End. Animals were scored only once during the study for a PR or CR event and only as CR if both PR and CR criteria were satisfied.

TABLE 11

CRPC PDX TWO-WAY ANOVA (tumor size at the end of the study).

| vs. | Enzalutamide | Compound 258 10 mg/kg | Compound 258 6 mg/kg | Compound 284 6 mg/kg |
|---|---|---|---|---|
| Vehicle | n.s. | p < 0.0001 | p < 0.0001 | p < 0.0001 |
| Enzalutamide | — | p < 0.0001 | p < 0.0001 | p < 0.0001 |
| Compound 258 10 mg/kg | — | — | n.s. | n.s. |
| Compound 258 6 mg/kg | — | — | — | n.s. |
| Compound 284 6 mg/kg | — | — | — | — | n.s. = not significant.

Example 323: Cell-Derived Xenograft Mouse Model for Prostate Cancer

Figure 5:
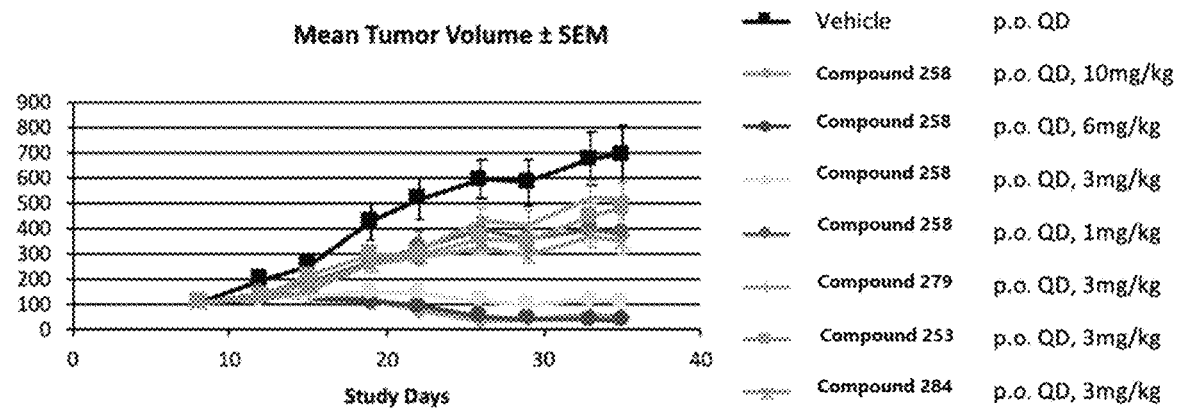
FIG. 5 is a graph showing tumor size development in a hormone-resistant cell-derived xenograft mouse model of prostate cancer (DU-145 cells) at various concentrations of Compound 258, Compound 279, Compound 253 and Compound 284.
Figure 6:
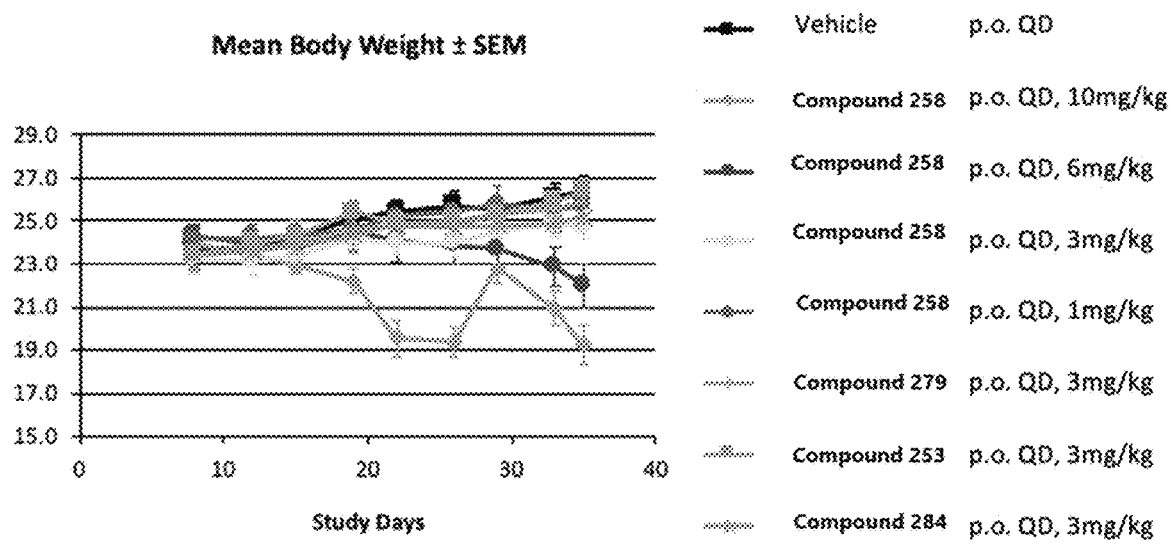
FIG. 6 is a graph showing mice body weight development in a hormone-resistant cell-derived xenograft mouse model of prostate cancer (DU-145 cells) at various concentrations of Compound 258, Compound 279, Compound 253 and Compound 284.

Male BALB/c nude mice (7-9 weeks of age) were injected with hormone-refractory DU-145 human prostate cancer cells. The cells were inoculated subcutaneously into the left flank of 48 mice. When tumors reached a mean volume of approximately 105 mm³, mice were randomly assigned to eight treatment groups of each six mice (TABLE 12). Body weights were measured three times weekly prior to the initiation of dosing and daily thereafter. Tumor burden was assessed by caliper measurement three times weekly. Dosing breaks were applied when tolerability issues arose (body weight loss >10%). The study was terminated 4 weeks post first dosing. Results of the experiment are shown in TABLE 13, FIG. 5 and FIG. 6. The experiment was performed in the Crown Bioscience Ltd. (Bejing) testing facility (Ground Floor, Light Muller Building, Changping Sector of Zhongguancun Scientific Park, No. 21 Huoju Road, Changping District, Bejing, CHN).

TABLE 12

DU-145 CDX mice treatment group assignment.

| Group | Compound | Formulation | Treatment schedule |
|---|---|---|---|
| 1 | Vehicle | 0.5% Methylcellulose + 0.1% Tween-80 | p.o. QD |
| 2 | Compound 258 | 0.5% Methylcellulose + 0.1% Tween-80 | p.o. QD, 10 mg/kg |
| 3 | Compound 258 | 0.5% Methylcellulose + 0.1% Tween-80 | p.o. QD, 6 mg/kg |
| 4 | Compound 258 | 0.5% Methylcellulose + 0.1% Tween-80 | p.o. QD, 3 mg/kg |
| 5 | Compound 258 | 0.5% Methylcellulose + 0.1% Tween-80 | p.o. QD, 1 mg/kg |
| 6 | Compound 279 | 0.5% Methylcellulose + 0.1% Tween-80 | p.o. QD, 3 mg/kg |
| 7 | Compound 253 | 0.5% Methylcellulose + 0.1% Tween-80 | p.o. QD, 3 mg/kg |
| 8 | Compound 284 | 0.5% Methylcellulose + 0.1% Tween-80 | p.o. QD, 3 mg/kg | p.o. = oral administration (oral gavage).
QD = once a day.

TABLE 13

Test compound antitumoral activity on subcutaneous DU-145 prostate cancer CDX model in Male BALB/c Nude Mice.

| Group | Treatment Description | Tumor Size (mm³)[a] day 35 | T/C (%) | P value[b] |
|---|---|---|---|---|
| 1 | Vehicle | 693 ± 116 | — | — |
| 2 | Compound 258, 10 mg/kg, QD × 4 weeks | 47 ± 4 | 6.8 | 0.003 |
| 3 | Compound 258, 6 mg/kg, QD × 4 weeks | 32 ± 2 | 4.6 | 0.002 |
| 4 | Compound 258, 3 mg/kg, QD × 4 weeks | 105 ± 25 | 15.2 | 0.003 |
| 5 | Compound 258, 1 mg/kg, QD × 4 weeks | 378 ± 27 | 54.5 | 0.4 |
| 6 | Compound 279, 3 mg/kg, QD × 4 weeks | 516 ± 59 | 74.5 | 0.204 |
| 7 | Compound 253, 3 mg/kg, QD × 4 weeks | 480 ± 49 | 69.3 | 0.120 |
| 8 | Compound 284, 3 mg/kg, QD × 4 weeks | 347 ± 48 | 50.1 | 0.02 |

[a]Mean ± SEM;
[b]vs. vehicle control (T-test);
T/C = tumor-to-control ratio (volume/volume)

Example 324: Cell-Derived Xenograft Mouse Model for Colorectal Cancer

Figure 7:
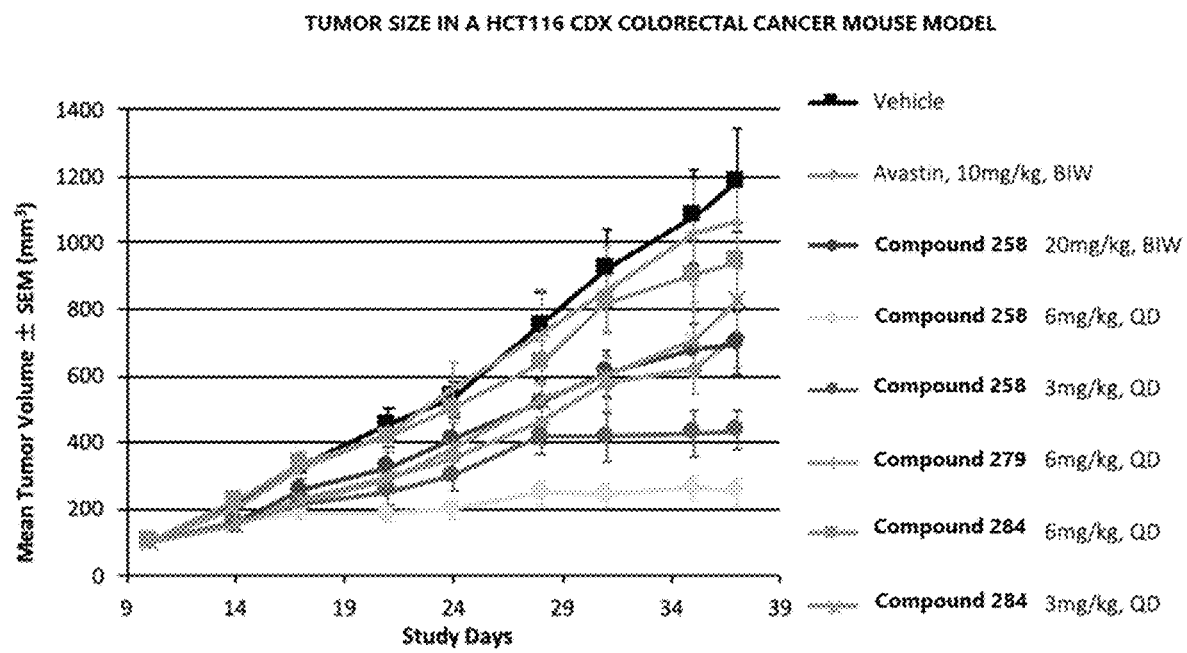
FIG. 7 is a graph showing tumor size development in a colorectal cancer cell-derived xenograft mouse model (HCT116 cells) at various concentrations of Compound 258, Compound 279 and Compound 284, compared to standard-of-care treatment (Avastin, also called bevacizumab).
Figure 8:
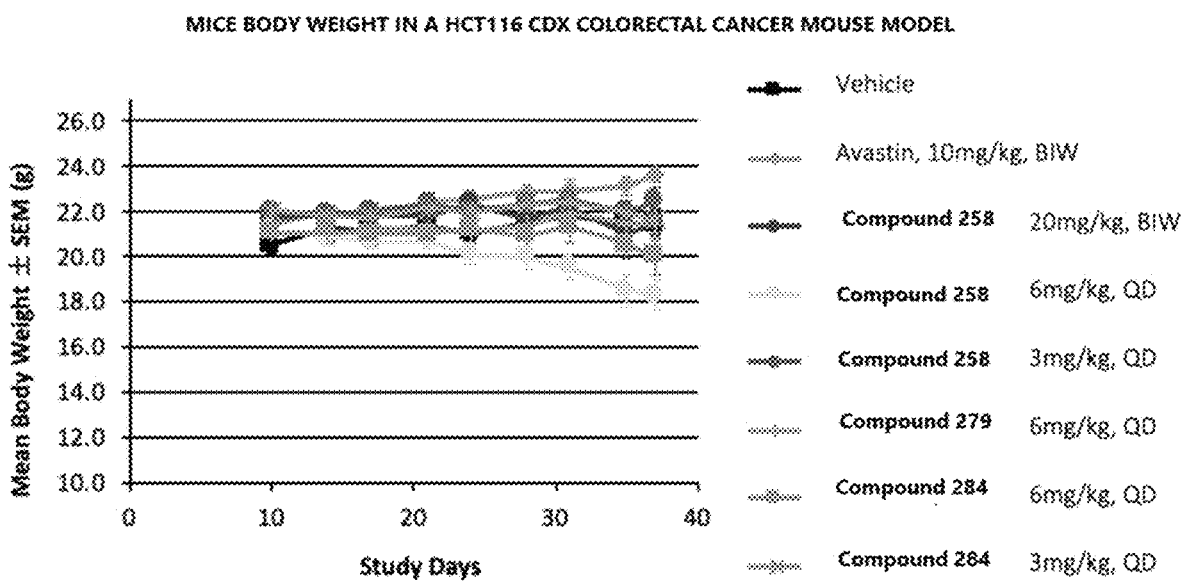
FIG. 8 is a graph showing mice body weight development in a colorectal cancer cell-derived xenograft mouse model (HCT116 cells) at various concentrations of Compound 258, Compound 279 and Compound 284, compared to standard-of-care treatment (Avastin).

Female BALB/c nude mice (8-9 weeks of age) were injected with HCT116 human colon cancer cells. The cells were inoculated subcutaneously into the left flank of 48 mice. When tumors reached a mean volume of approximately 100 mm³, mice were randomly assigned to eight treatment groups of each six mice (TABLE 14). Body weights were measured three times weekly prior to the initiation of dosing and daily thereafter. Tumor burden was assessed by caliper measurement twice weekly. Dosing breaks were applied when tolerability issues arose (body weight loss >10%). The study was terminated four weeks post first dosing. Results of the experiment are shown in TABLE 15, FIG. 7 and FIG. 8. The experiment was performed in the Crown Bioscience Ltd. (Bejing) testing facility (Ground Floor, Light Muller Building, Changping Sector of Zhongguancun Scientific Park, No. 21 Huoju Road, Changping District, Bejing, CHN).

TABLE 14

HCT116 CDX mice treatment group assignment.

| Group | Compound | Formulation | Treatment schedule |
|---|---|---|---|
| 1 | Vehicle | 0.5% Methylcellulose + 0.1% Tween-80 | p.o. QD |
| 2 | Avastin | PBS | i.v. BIW, 10 mg/kg |
| 3 | Compound 258 | 0.5% Methylcellulose + 0.1% Tween-80 | p.o. BIW, 20 mg/kg |
| 4 | Compound 258 | 0.5% Methylcellulose + 0.1% Tween-80 | p.o. QD, 6 mg/kg |
| 5 | Compound 258 | 0.5% Methylcellulose + 0.1% Tween-80 | p.o. QD, 3 mg/kg |
| 6 | Compound 279 | 0.5% Methylcellulose + 0.1% Tween-80 | p.o. QD, 6 mg/kg |
| 7 | Compound 284 | 0.5% Methylcellulose + 0.1% Tween-80 | p.o. QD, 6 mg/kg |
| 8 | Compound 284 | 0.5% Methylcellulose + 0.1% Tween-80 | p.o. QD, 3 mg/kg | p.o. = oral administration (oral gavage).
i.v. = intravenous administration.
QD = once a day.
BIW = twice a week.

TABLE 15

Test compound antitumoral activity on subcutaneous HCT116 colorectal cancer CDX model in female BALB/c nude mice.

| Group | Treatment Description | Tumor Size (mm³)$^a$ day 37 | T/C (%) | P value$^b$ |
|---|---|---|---|---|
| 1 | Vehicle | 1187.9 ± 154.3 | — | — |
| 2 | Avastin, 10 mg/kg, BIW | 719.9 ± 93.9 | 60.6 | 0.027 |
| 3 | Compound 258, 20 mg/kg, BIW | 696.8 ± 93.7 | 58.7 | 0.022 |
| 4 | Compound 258, 6 mg/kg, QD | 253.2 ± 39.2 | 21.3 | <0.001 |
| 5 | Compound 258, 3 mg/kg, QD | 436.2 ± 58.9 | 36.7 | 0.001 |
| 6 | Compound 279, 6 mg/kg, QD | 1064.0 ± 141.1 | 89.6 | 0.567 |
| 7 | Compound 284, 6 mg/kg, QD | 942.0 ± 114.9 | 79.3 | 0.230 |
| 8 | Compound 284, 3 mg/kg, QD | 827.4 ± 125.7 | 69.7 | 0.100 |

$^a$Mean ± SEM;
$^b$vs. vehicle control (T-test);
T/C = tumor-to-control ratio (volume/volume)
Group-2 vs. Group-3, p = 0.865;
Group-2 vs. Group-4, p = 0.001;
Group-2 vs. Group-5, p = 0.028;
Group-2 vs. Group-6, p = 0.070;
Group-2 vs. Group-7, p = 0.165;
Group-2 vs. Group-8, p = 0.509;

Example 325: Cell-Derived Xenograft Mouse Model for Gastric Cancer

Figure 9:
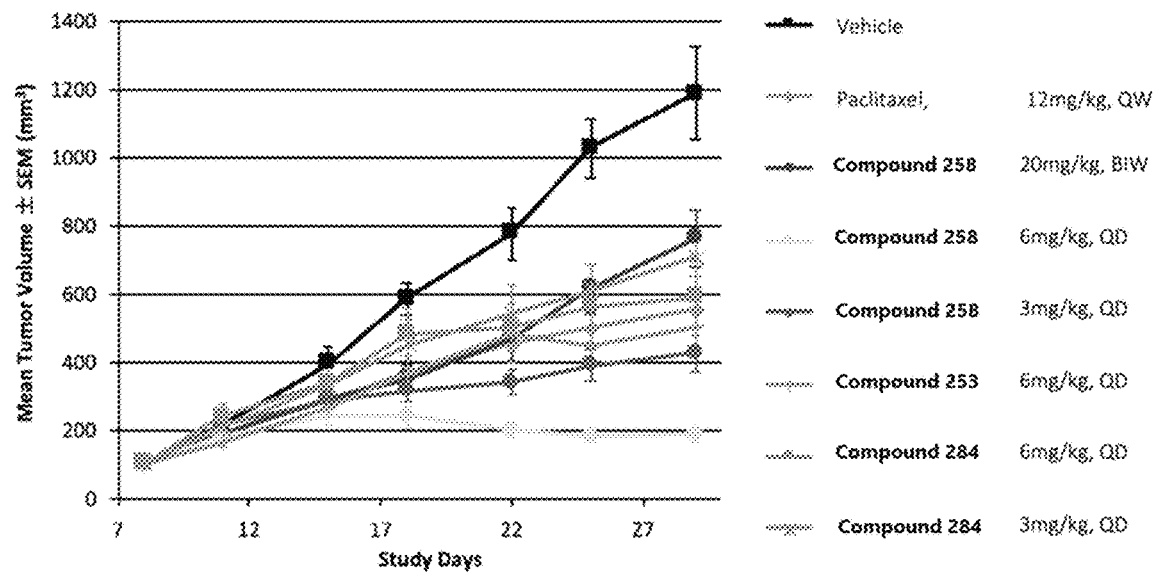
FIG. 9 is a graph showing the tumor size development in a gastric cancer cell-derived xenograft mouse model (MKN45 cells) at various concentrations of Compound 258, Compound 253 and Compound 284, compared to standard-of-care treatment (Paclitaxel).
Figure 10:
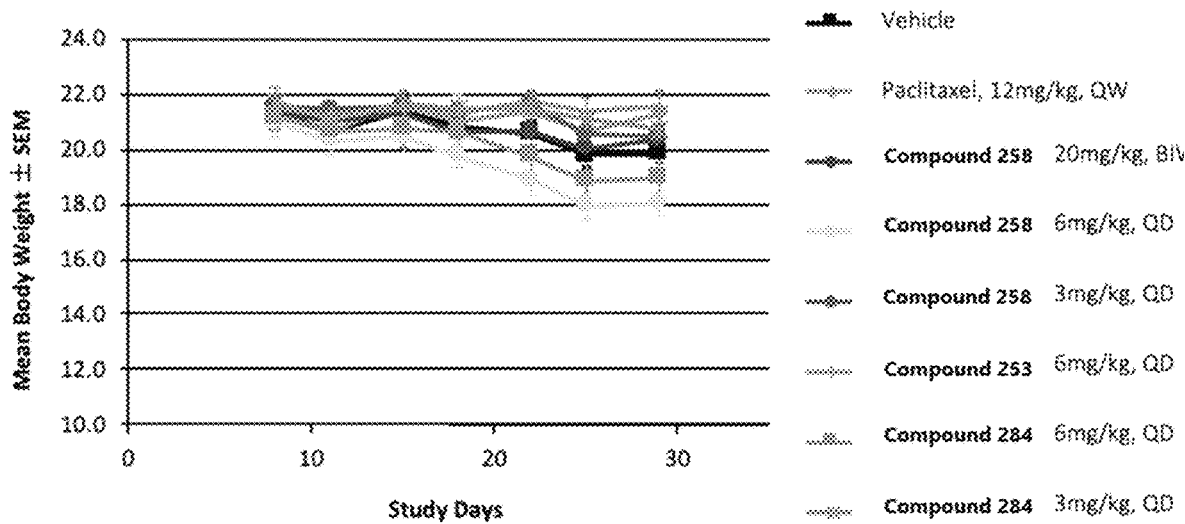
FIG. 10 is a graph showing mice body weight development in a gastric cancer cell-derived xenograft mouse model (MKN45 cells) at various concentrations of Compound 258, Compound 253 and Compound 284, compared to standard-of-care treatment (Paclitaxel).

Female BALB/c nude mice (8-9 weeks of age) were injected with MKN45 human gastric adenocarcinoma cells. The cells were inoculated subcutaneously into the left flank of 48 mice. When tumors reached a mean volume of approximately 103 mm³, mice were randomly assigned to eight treatment groups of each six mice (TABLE 16). Body weights were measured three times weekly prior to the initiation of dosing and daily thereafter. Tumor burden was assessed by caliper measurement twice weekly. Dosing breaks were applied when tolerability issues arose (body weight loss >10%). The study was terminated four weeks post first dosing. Results of the experiment are shown in TABLE 17, FIG. 9 and FIG. 10. The experiment was performed in the Crown Bioscience Ltd. (Bejing) testing facility (Ground Floor, Light Muller Building, Changping Sector of Zhongguancun Scientific Park, No. 21 Huoju Road, Changping District, Bejing, CHN).

TABLE 16

MKN45 CDX mice treatment group assignment.

| Group | Compound | Formulation | Treatment schedule |
|---|---|---|---|
| 1 | Vehicle | 0.5% Methylcellulose + 0.1% Tween-80 | p.o. QD |
| 2 | Paclitaxel | PBS | i.v. QW, 12 mg/kg |
| 3 | Compound 258 | 0.5% Methylcellulose + 0.1% Tween-80 | p.o. BIW, 20 mg/kg |
| 4 | Compound 258 | 0.5% Methylcellulose + 0.1% Tween-80 | p.o. QD, 6 mg/kg |
| 5 | Compound 258 | 0.5% Methylcellulose + 0.1% Tween-80 | p.o. QD, 3 mg/kg |
| 6 | Compound 253 | 0.5% Methylcellulose + 0.1% Tween-80 | p.o. QD, 6 mg/kg |
| 7 | Compound 284 | 0.5% Methylcellulose + 0.1% Tween-80 | p.o. QD, 6 mg/kg |
| 8 | Compound 284 | 0.5% Methylcellulose + 0.1% Tween-80 | p.o. QD, 3 mg/kg | p.o. = oral administration (oral gavage).
i.v. = intravenous administration.
QD = once a day.
QW = once a week.

TABLE 17

Test compound antitumoral activity on subcutaneous MKN45 gastric cancer CDX model in female BALB/c nude mice.

| Group | Treatment Description | Tumor Size (mm³)$^a$ day 29 | T/C (%) | P value$^b$ |
|---|---|---|---|---|
| 1 | Vehicle | 1189.6 ± 139.6 | — | — |
| 2 | Paclitaxel, 12 mg/kg, QW | 554.9 ± 52.8 | 46.6 | 0.002 |
| 3 | Compound 258, 20 mg/kg, BIW | 763.4 ± 84.5 | 64.2 | 0.026 |
| 4 | Compound 258, 6 mg/kg, QD | 186.9 ± 17.3 | 15.7 | <0.001 |
| 5 | Compound 258, 3 mg/kg, QD | 428.0 ± 52.5 | 36.0 | <0.001 |
| 6 | Compound 253, 6 mg/kg, QD | 506.5 ± 71.0 | 42.6 | 0.001 |
| 7 | Compound 284, 6 mg/kg, QD | 592.6 ± 109.7 | 49.8 | 0.007 |
| 8 | Compound 284, 3 mg/kg, QD | 709.0 ± 55.6 | 59.6 | 0.010 |

$^a$Mean ± SEM;
$^b$vs. vehicle control (T-test);
T/C = tumor-to-control ratio (volume/volume)
Group-2 vs. Group-3, p = 0.063;
Group-2 vs. Group-4, p < 0.001;
Group-2 vs. Group-5, p = 0.119;
Group-2 vs. Group-6, p = 0.596;
Group-2 vs. Group-7, p = 0.764;
Group-2 vs. Group-8, p = 0.072

Example 326: Cell-Derived Xenograft Mouse Model for Cervical Cancer

Figure 11:
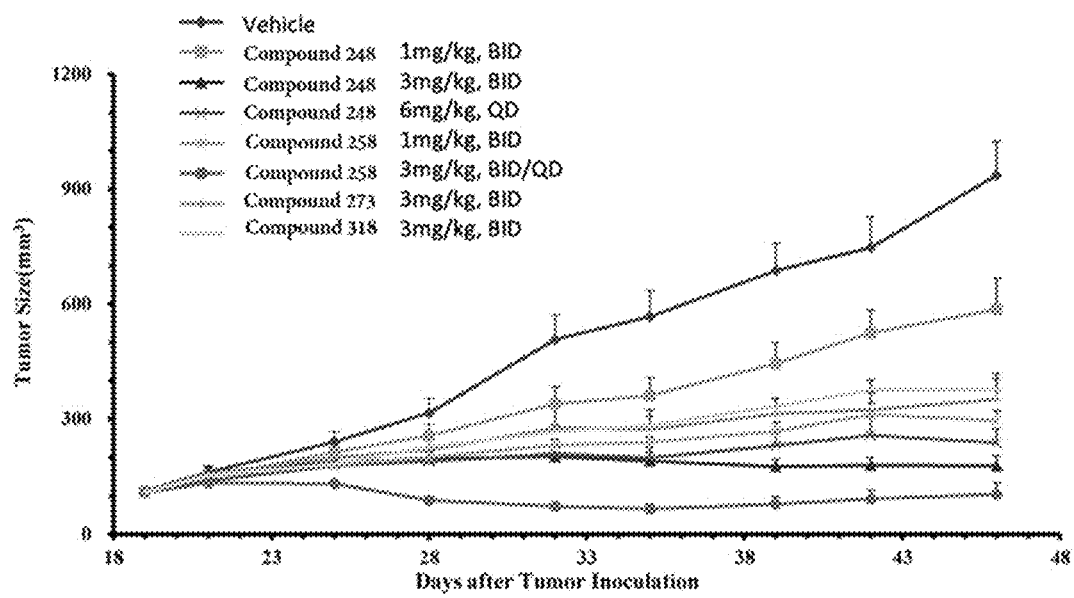
FIG. 11 is a graph showing tumor size development in an HPV-positive cervical cancer cell-derived xenograft mouse model (SiHa cells) at various concentrations of Compound 248, Compound 273, Compound 318 and Compound 258.
Figure 12:
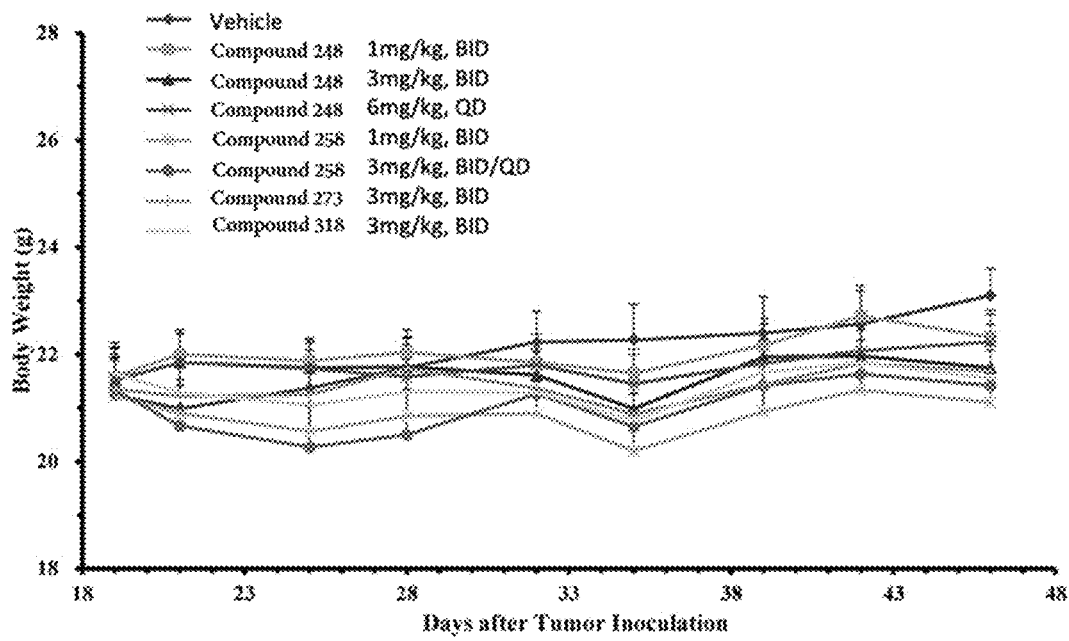
FIG. 12 is a graph showing mice body weight development in an HPV-positive cervical cancer cell-derived xenograft mouse model (SiHa cells) at various concentrations of Compound 248, Compound 273, Compound 318 and Compound 258.

Female BALB/c nude mice (7-9 weeks of age) were injected with SiHa human HPV16-positive (Human Papillomavirus type 16) cervical cancer cells. The cells were inoculated subcutaneously into the left flank of 48 mice. When tumors reached a mean volume of approximately 111 mm$^3$, mice were randomly assigned to eight treatment groups of each six mice (TABLE 18). Body weights were measured three times weekly prior to the initiation of dosing and daily thereafter. Tumor burden was assessed by caliper measurement twice weekly. Dosing breaks were applied when tolerability issues arose (body weight loss >10%). The study was terminated four weeks post first dosing. Results of the experiment are shown in TABLE 19, FIG. 11 and FIG. 12. The experiment was performed in the Crown Bioscience Ltd. (Bejing) testing facility (Ground Floor, Light Muller Building, Changping Sector of Zhongguancun Scientific Park, No. 21 Huoju Road, Changping District, Bejing, CHN).

TABLE 18

SiHa CDX mice treatment group assignment.

| Group | Compound | Formulation | Treatment schedule |
|---|---|---|---|
| 1 | Vehicle | 0.5% Methylcellulose + 0.1% Tween-80 | p.o. BID |
| 2 | Compound 248 | 0.5% Methylcellulose + 0.1% Tween-80 | p.o. BID, 1 mg/kg |
| 3 | Compound 248 | 0.5% Methylcellulose + 0.1% Tween-80 | p.o. BID, 3 mg/kg |
| 4 | Compound 248 | 0.5% Methylcellulose + 0.1% Tween-80 | p.o. QD, 6 mg/kg |
| 5 | Compound 258 | 0.5% Methylcellulose + 0.1% Tween-80 | p.o. BID, 1 mg/kg |
| 6 | Compound 258 | 0.5% Methylcellulose + 0.1% Tween-80 | p.o. BID, 3 mg/kg, p.o. QD from treatment day 7 on |
| 7 | Compound 273 | 0.5% Methylcellulose + 0.1% Tween-80 | p.o. BID, 3 mg/kg |
| 8 | Compound 318 | 0.5% Methylcellulose + 0.1% Tween-80 | p.o. BID, 3 mg/kg | p.o. = oral administration (oral gavage).
QD = once a day.
BID = twice a day.

TABLE 19

Test compound antitumoral activity on subcutaneous HPV16-positive SiHa cervical cancer CDX model in female BALB/c nude mice.

| Group | Treatment Description | Tumor Size (mm$^3$)[a] day 37 | T/C (%) | P value[b] |
|---|---|---|---|---|
| 1 | Vehicle | 936 ± 89 | — | — |
| 2 | Compound 248, 1 mg/kg, BID | 586 ± 82 | 62.6 | 0.016 |
| 3 | Compound 248, 3 mg/kg, BID | 178 ± 27 | 19 | <0.001 |
| 4 | Compound 248, 6 mg/kg, QD | 238 ± 37 | 25.4 | <0.001 |
| 5 | Compound 258, 1 mg/kg, BID | 296 ± 27 | 31.6 | <0.001 |
| 6 | Compound 258, 3 mg/kg, BID/QD | 104 ± 30 | 11.1 | <0.001 |
| 7 | Compound 273, 3 mg/kg, BID | 942.0 ± 114.9 | 79.3 | 0.230 |
| 8 | Compound 318, 3 mg/kg, BID | 351 ± 68 | 37.5 | <0.001 |

[a]Mean ± SEM;
[b]vs. vehicle control (T-test);
T/C = tumor-to-control ratio (volume/volume)

Example 327: Cell-Derived Xenograft Mouse Model for Acute Myeloid Leukemia Tumor Spread (Bone Marrow Engraftment)

Figure 13A:
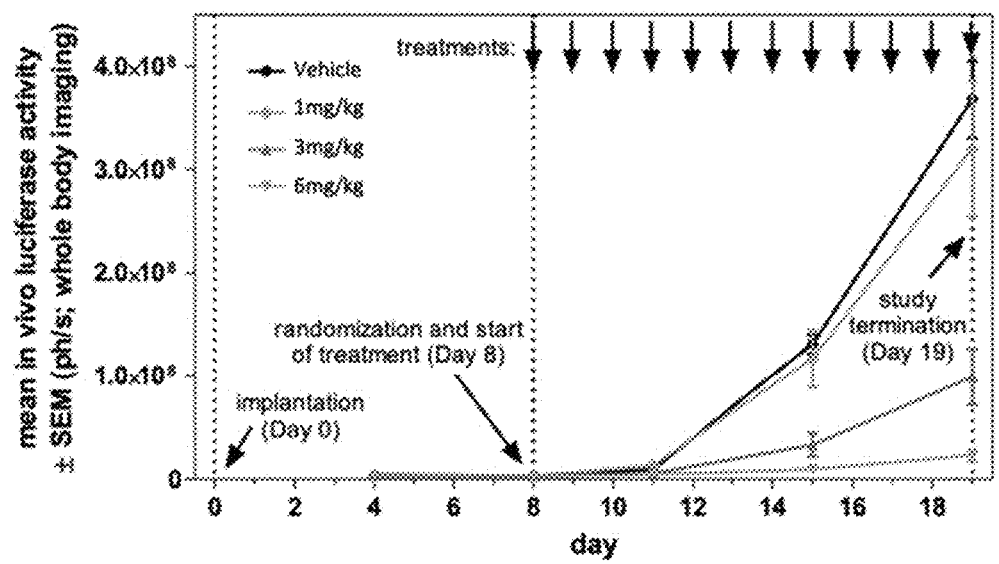
FIGS. 13A and 13B are graphs showing luciferase activity in a MOLM13-Luc mouse model for acute myeloid leukemia tumor spread. (A) Mean in vivo luciferase activity (photons/s) profile (whole body imaging): test compound is Compound 258, administered at 1, 3 and 6 mg/kg, displayed versus the corresponding vehicle control group. Data are displayed as mean values+/−SEM. (B) Luciferase activity (photons/s), measured in vivo on Day 19 (whole body imaging at necropsy): test compound is Compound 258, administered at 1, 3 and 6 mg/kg, displayed versus the corresponding vehicle control group. Data are displayed as individual data points together with their corresponding median values and interquartile ranges. P-values were calculated compared to the corresponding vehicle control group and between the 3 mg/kg and 6 mg/kg groups, using the Mann Whitney test and the unpaired t-test (in parentheses) as well as the one-way ANOVA with Dunnett's post test. *=p<0.05; =p<0.01; *=p<0.001.
Figure 13B:
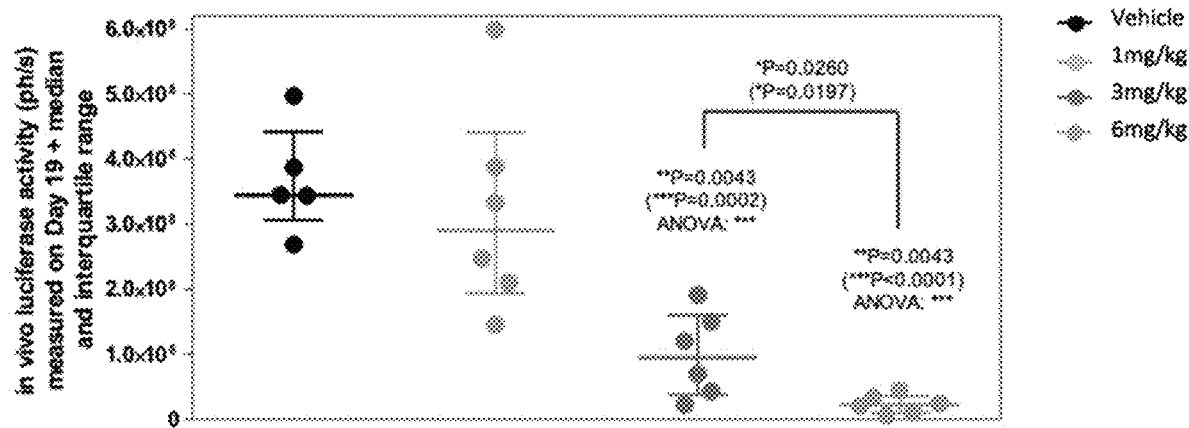
Figure 14:
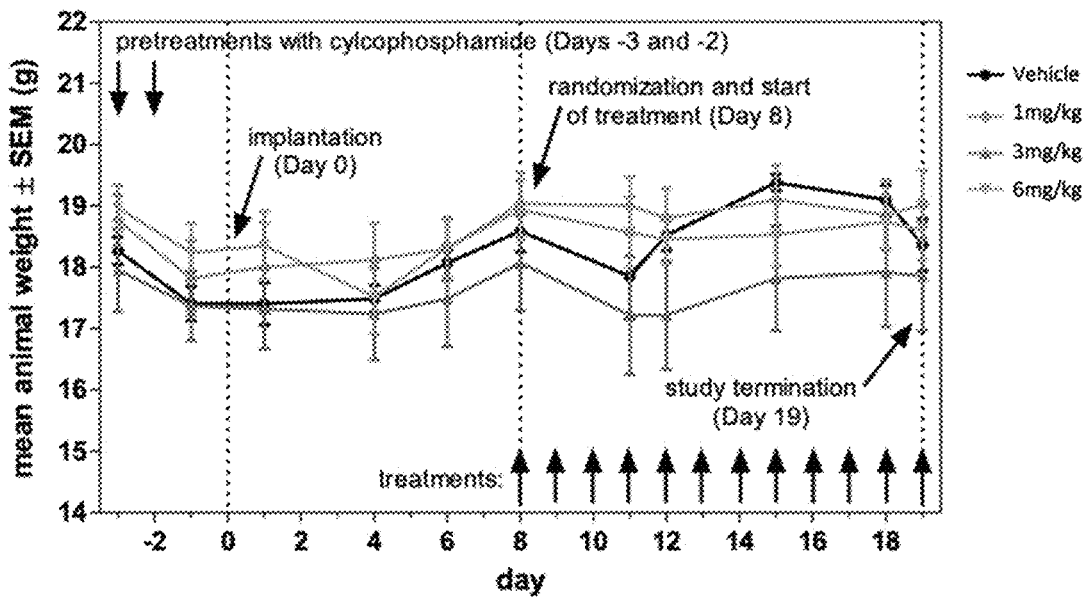
FIG. 14 is a graph showing the mean animal weight (g) profile in a MOLM13-Luc mouse model for acute myeloid leukemia tumor spread. The test compound is Compound 258, administered at 1, 3 and 6 mg/kg, displayed versus the corresponding vehicle control group. Data are displayed as mean values+/−SEM.
Figure 15:
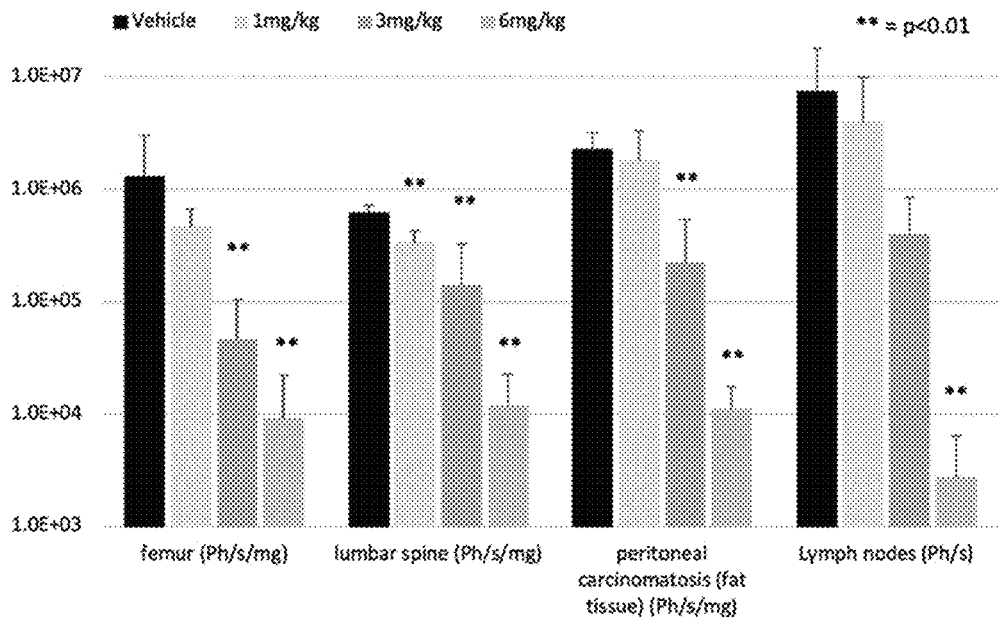
FIG. 15 is a graph showing the ex vivo, post-necropsy organ/tissue luciferase activity (Photons/s/mg weight or Photon/s for lymph nodes) in a MOLM13-Luc mouse model for acute myeloid leukemia tumor spread. Test compound is Compound 258, administered at 1, 3 and 6 mg/kg is displayed versus the corresponding Vehicle Control Group, for femur, lumbar spine, peritoneal carcinomatosis (fat tissue) and lymph nodes (both axillary and inguinal). Data are displayed as means+/−SD. P values were calculated compared to the corresponding Vehicle Control Group using the Mann Whitney test.

Twenty-four female NOD-SCID mice (NOD.CB17-Prkd-c$^{scid}$/J, 4-5 weeks of age) were pretreated for two days once daily i.p. with 100 mg/kg cyclophosphamide in order to reduce the endogenous bone marrow population and to facilitate bone marrow engraftment of MOLM13-Luc cells, an acute myeloid leukemia cell line transduced using a plasmid encoding a luciferase-neomycin fusion protein (cell line identifier #200, Proqinase GmbH, Freiburg, Germany). Forty-eight hours after the last cyclophosphamide treatment, one million MOLM13-Luc cells in 100 µl 0.9% NaCl were intravenously implanted into the animals. In the following study period, the growth of the MOLM13-Luc cells was monitored on days 4, 8, 11, 15 and 19 using in vivo bioluminescence imaging. On day 8, animals were randomly assigned to three treatment groups of six mice each (TABLE 20) and treatment was initiated for all groups on the same day. The study was terminated 19 days post first dosing. Animals were weighed and euthanized by cervical dislocation. Selected organs (femur, lumbar spine, lymph nodes (inguinal and axillary) and peritoneal carcinomatosis samples from fatty tissues) were collected, weighed, appropriately processed and the luciferase activity of the homogenates measured using an ex vivo luciferase assay (# E1501, Promega, Madison, Wis., USA) according to the instructions from the manufacturer. The luciferase activity was read with an Enspire Reader (Perkin Elmer, Waltham, Mass., USA). Except for lymph nodes, organ weights were determined during necropsy in order to normalize luciferase activities. Results of the experiment are shown in FIGS. 13-15. The experiment was performed in the Proqinase animal test facility (Proqinase GmbH, D-79106 Freiburg, Germany).

TABLE 20

MOLM13-Luc CDX mice treatment group assignment.

| Group | Compound | Formulation | Treatment schedule |
|---|---|---|---|
| 1 | Vehicle | 0.5% Methylcellulose + 0.1% Tween-80 | p.o. QD |
| 2 | Compound 258 | 0.5% Methylcellulose + 0.1% Tween-80 | p.o. QD, 1 mg/kg |
| 3 | Compound 258 | 0.5% Methylcellulose + 0.1% Tween-80 | p.o. QD, 3 mg/kg |
| 4 | Compound 258 | 0.5% Methylcellulose + 0.1% Tween-80 | p.o. QD, 6 mg/kg | p.o. = oral administration (oral gavage).
QD = once a day.

Figure 16:
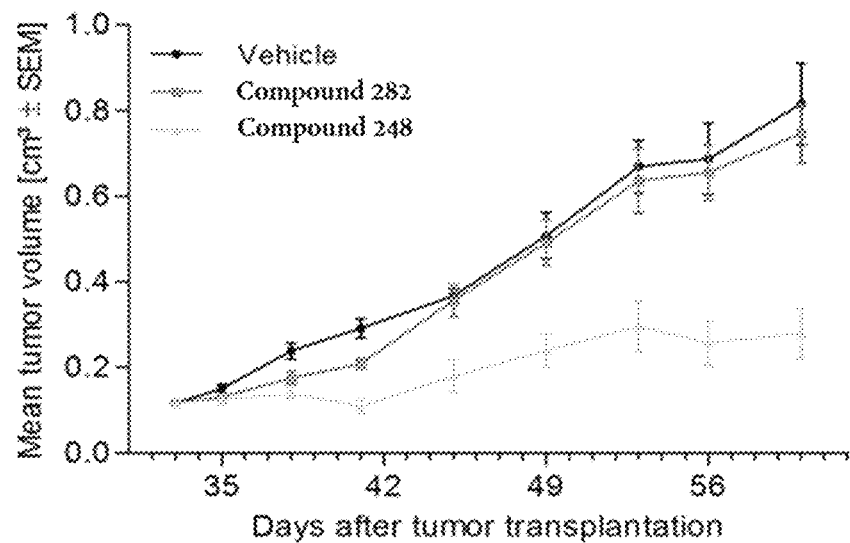
FIG. 16 is a graph showing the tumor volume development in a patient-derived HPV-positive human head-and-neck squamous cell carcinoma xenograft mouse model for Compound 248 and Compound 282 (both 30 mg/kg, twice a day, administered orally).
Figure 17:
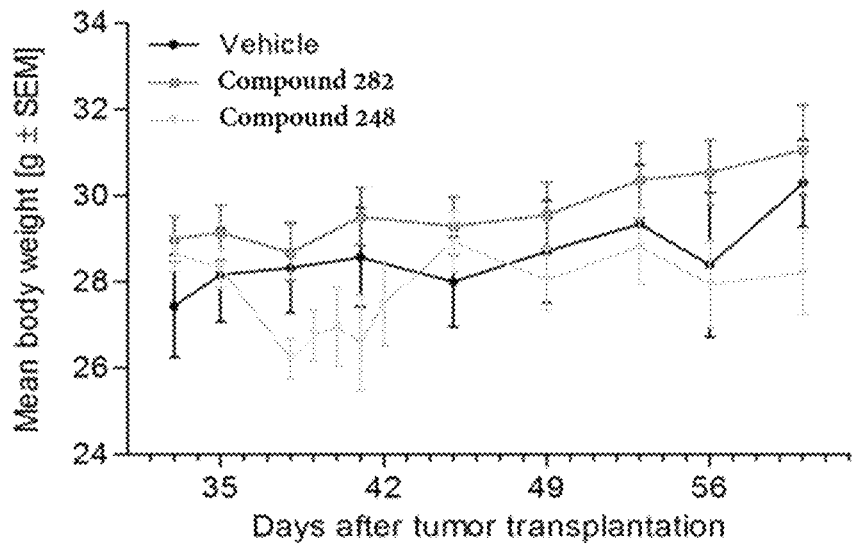
FIG. 17 is a graph showing mice body weight development in a patient-derived HPV-positive human head-and-neck squamous cell carcinoma xenograft mouse model for Compound 248 and Compound 282 (both 30 mg/kg, twice a day, administered orally).

Example 328: Patient-Derived Xenograft Mouse Model for Head-and-Neck Squamous Cell Carcinoma Female NMRI nu/nu mice were injected with cells derived from a human head-and-neck cancer (model # HN10309, an HPV-positive head-and-neck squamous cell carcinoma, EPO-GmbH, Berlin, Germany). The cells were inoculated subcutaneously into the left flank of 24 mice. Thirty-three days later tumors reached a mean volume of approximately 116 mm$^3$, and mice were randomly assigned to three treatment groups of each eight mice (TABLE 21). Body weights were measured twice weekly. Tumor burden was assessed by caliper measurement twice weekly. Dosing breaks were applied when tolerability issues arose (body weight loss >10%). The study was terminated four weeks post first dosing. Results of the experiment are shown in TABLE 22, FIG. 16 and FIG. 17. The experiment was performed in the EPO animal testing facility (Experimental Pharmacology and Oncology GmbH, 13125 Berlin-Buch, Germany).

TABLE 21

HNSCC PDX mice treatment group assignment.

| Group | Compound | Formulation | Treatment schedule |
|---|---|---|---|
| A | Vehicle | 0.5% Methylcellulose + 0.1% Tween-80 | p.o. BID |
| B | Compound 282 | 0.5% Methylcellulose + 0.1% Tween-80 | p.o. BID, 30 mg/kg |
| C | Compound 248 | 0.5% Methylcellulose + 0.1% Tween-80 | p.o. BID, 30 mg/kg | p.o. = oral administration (oral gavage).
BID = twice a day.

TABLE 22

Test compound antitumoral activity on subcutaneous HPV-positive HNSCC model in female NMRI nu/nu mice. Bonferroni posttests to vehicle group (mean TV values in $cm^3$).

| Day | Vehicle | Compound 282 | Significance | Compound 248 | Significance |
|---|---|---|---|---|---|
| 33 | 0.1156 | 0.1161 | ns | 0.1159 | ns |
| 35 | 0.1499 | 0.1308 | ns | 0.1248 | ns |
| 38 | 0.2386 | 0.1751 | ns | 0.1389 | ns |
| 41 | 0.2908 | 0.2086 | ns | 0.1093 | * |
| 45 | 0.3670 | 0.3560 | ns | 0.1794 | * |
| 49 | 0.5079 | 0.4920 | ns | 0.2398 | *** |
| 53 | 0.6693 | 0.6364 | ns | 0.2964 | *** |
| 56 | 0.6875 | 0.6558 | ns | 0.2569 | *** | ns not significant
* = $p < 0.05$,
** = $p < 0.01$;
*** = $p < 0.001$.

Figure 18:
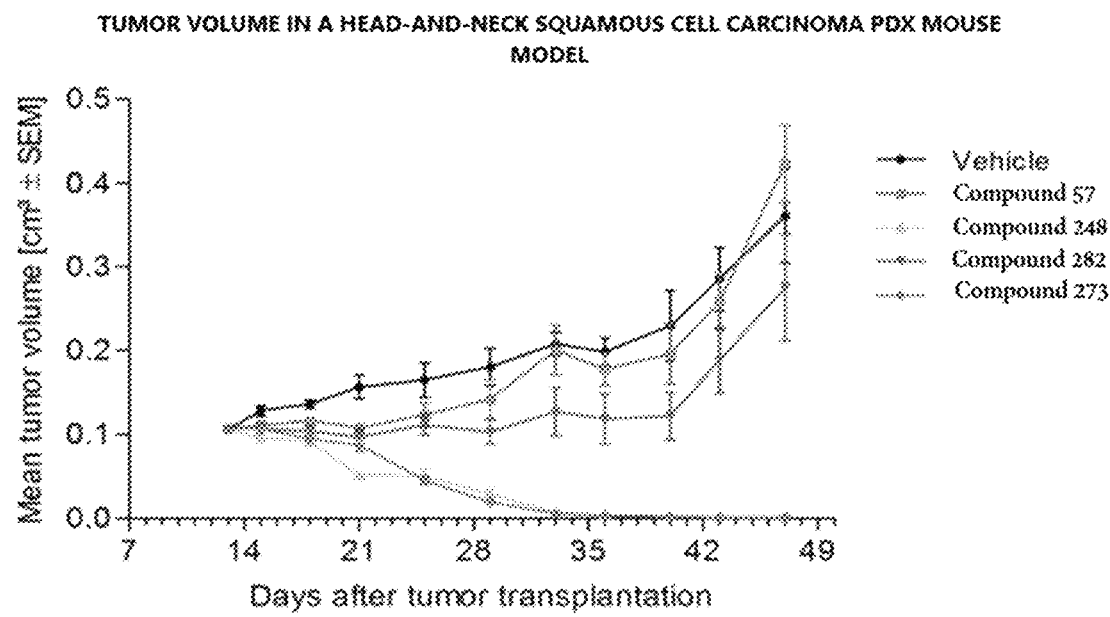
FIG. 18 is a graph showing the tumor volume development in a patient-derived HPV-positive human head-and-neck squamous cell carcinoma xenograft mouse model for Compound 57, Compound 248, Compound 282 and Compound 273, at variable dosages (TABLE 23). All sixteen mice treated with Compound 248 and Compound 273 were tumor-free at the end of the observation period.
Figure 19:
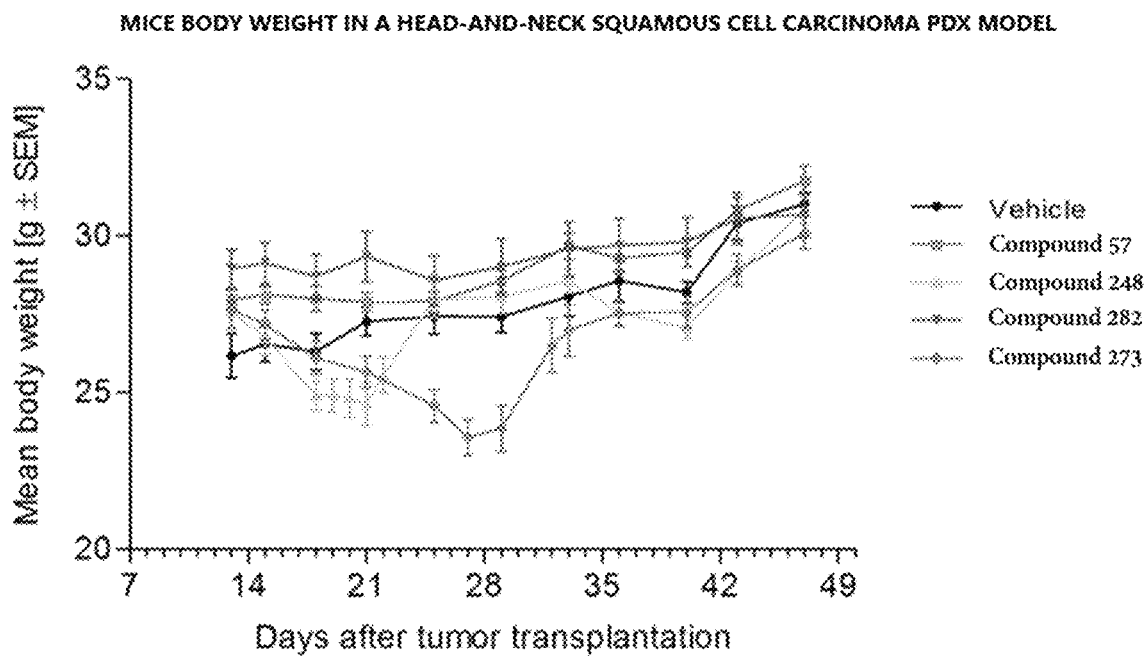
FIG. 19 is a graph showing mice body weight development in a patient-derived HPV-positive human head-and-neck squamous cell carcinoma xenograft mouse model for Compound 57, Compound 248, Compound 282 and Compound 273, at variable dosages (TABLE 23).

Example 329: Patient-Derived Xenograft Mouse Model for Head-and-Neck Squamous Cell Carcinoma Female NMRI nu/nu mice were injected with cells derived from a human head-and-neck cancer (model # HN11303, an HPV-positive head-and-neck squamous cell carcinoma, EPO-GmbH, Berlin, Germany). The cells were inoculated subcutaneously into the left flank of 40 mice. Thirteen days later tumors reached a mean volume of approximately 107 $mm^3$, and mice were randomly assigned to five treatment groups of each eight mice (TABLE 23). Body weights were measured twice weekly. Tumor burden was assessed by caliper measurement twice weekly. Dosing breaks were applied when tolerability issues arose (body weight loss >10%). The study was terminated five weeks post first dosing. Results of the experiment are shown in TABLE 24, FIG. 18 and FIG. 19. The experiment was performed in the EPO animal testing facility (Experimental Pharmacology and Oncology GmbH, 13125 Berlin-Buch, Germany).

TABLE 23

HNSCC PDX mice treatment group assignment.

| Group | Compound | Formulation | Treatment schedule |
|---|---|---|---|
| A | Vehicle | 0.5% Methylcellulose + 0.1% Tween-80 | i.p. BID |
| B | Compound 57 | 0.5% Methylcellulose + 0.1% Tween-80 | i.p. BID, 30 mg/kg |
| C | Compound 248 | 0.5% Methylcellulose + 0.1% Tween-80 | i.p. BID, 30 mg/kg day 13-17 dosing break day 18-19 i.p. QD, 10 mg/kg day 20 i.p. QD, 3 mg/kg day 21-31 i.p. QD, 10 mg/kg day 32-47 |
| D | Compound 282 | 0.5% Methylcellulose + 0.1% Tween-80 | i.p. BID, 30 mg/kg |
| E | Compound 273 | 0.5% Methylcellulose + 0.1% Tween-80 | i.p. BID, 30 mg/kg day 13-27 dosing break day 28-31 i.p. QD, 10 mg/kg day 32-47 | i.p. = intraperitoneal injection.
BID = twice a day.
QD = once a day.

TABLE 24

Test compound antitumoral activity on subcutaneous
HPV-positive HNSCC model in female NMRI nu/nu mice.

| Day | Vehicle | Compound 57 | Sign. | Compound 248 | Sign. | Compound 282 | Sign. | Compound 273 | Sign. |
|---|---|---|---|---|---|---|---|---|---|
| 13 | 0.1060 | 0.1073 | ns | 0.1064 | ns | 0.1073 | ns | 0.1063 | ns |
| 15 | 0.1286 | 0.1106 | ns | 0.0958 | ns | 0.1061 | ns | 0.1073 | ns |
| 18 | 0.1363 | 0.1166 | ns | 0.0916 | ns | 0.1040 | ns | 0.0948 | ns |
| 21 | 0.1566 | 0.1081 | ns | 0.0511 | *** | 0.0971 | * | 0.0875 | ** |
| 25 | 0.1650 | 0.1233 | ns | 0.0499 | *** | 0.1111 | ns | 0.0451 | *** |
| 29 | 0.1805 | 0.1421 | ns | 0.0288 | *** | 0.1030 | *** | 0.0194 | *** |
| 33 | 0.2081 | 0.2009 | ns | 0.0068 | *** | 0.1273 | *** | 0.0056 | *** |
| 36 | 0.1988 | 0.1776 | ns | 0.0041 | *** | 0.1185 | *** | 0.0031 | *** |

Bonferroni posttests to vehicle group (mean TV values in $cm^3$).
ns not significant;
* = $p < 0.05$;
** = $p < 0.01$;
*** = $p < 0.001$.
According to RECIST guidelines (Response Evaluation Criteria In Solid Tumors; Eisenhauer et al., Eur. J. Cancer 45 (2009) 228-247), treatment outcome of all mice in group C (Compound 248) and E (Compound 273) was classified as complete remission.

Figure 20:
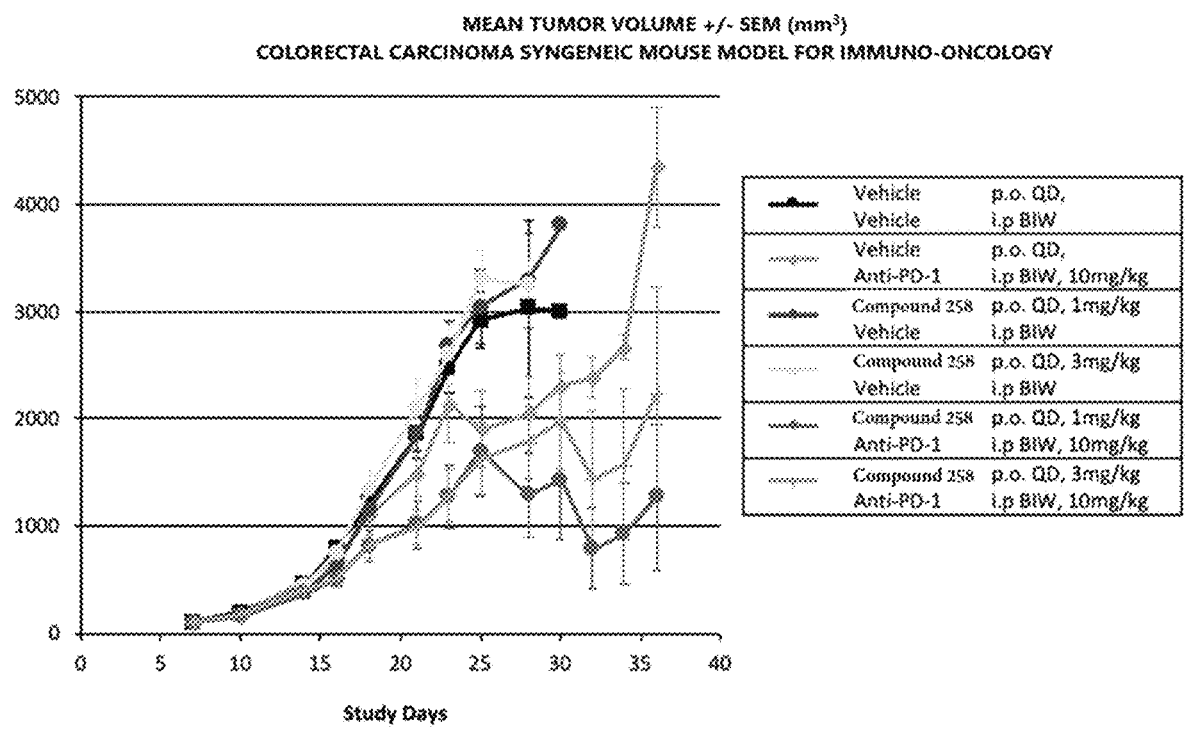
FIG. 20 is a graph showing the tumor volume development in a cell-derived syngeneic mouse model for colorectal carcinoma (CT-26 cells) combined with an immuno-oncology treatment (anti-PD1 antibodies). Compound 258 was administered as single agent and as a combination. Data after day 21 are mean+/−SEM of mice still in the experiment. Only the combination therapies and anti-PD1 have data after day 28 (TABLE 26). Two mice displayed complete regression in the combination groups, hence the huge SEM-values.
Figure 21:
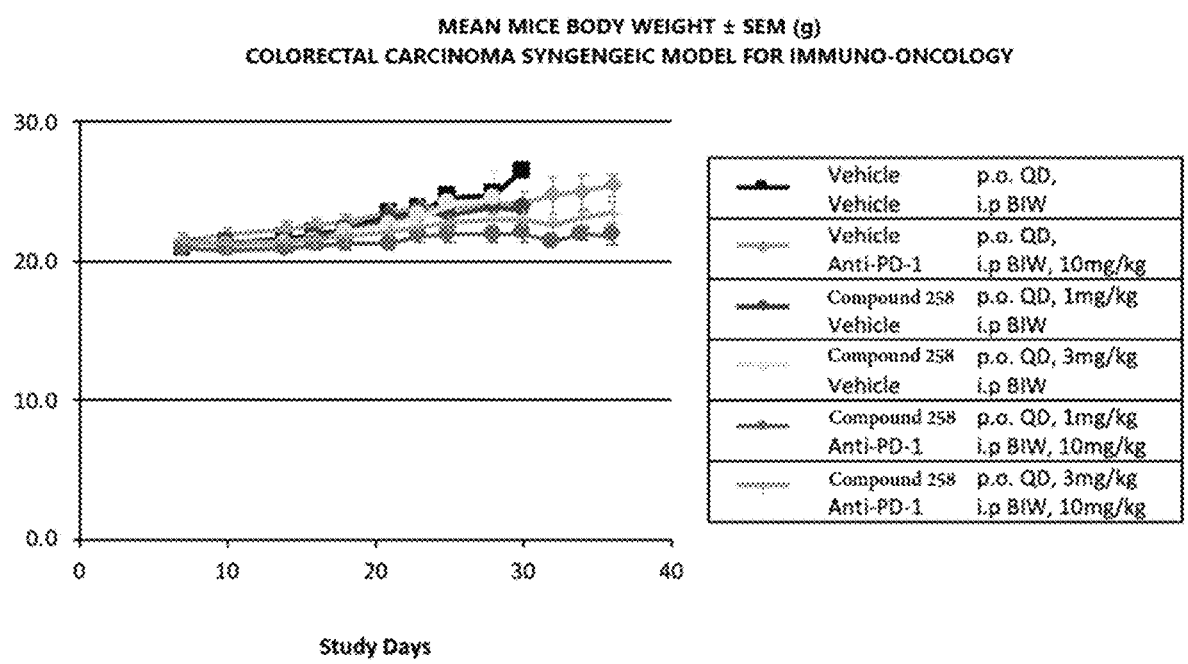
FIG. 21 is a graph showing mice body weight development in a cell-derived syngeneic mouse model for colorectal carcinoma (CT-26 cells) combined with an immuno-oncology treatment (anti-PD1 antibodies). Compound 258 was administered as single agent and as a combination. Data after day 21 are mean+/−SEM of mice still in the experiment. Only the combination therapies and anti-PD1 have data after day 28 (TABLE 26).

Example 330: Cell-Derived Syngeneic Mouse Model for Colorectal Carcinoma Combined with an Immuno-Oncology Treatment Female BALB/c mice (6-8 weeks of age) were injected with cells derived from a syngeneic chemically induced colon cancer (CT-26 cells). The cells were inoculated subcutaneously into the left flank of 60 mice. After seven days, tumors reached a mean volume of approximately 100 $mm^3$, and mice were randomly assigned to six treatment groups of each ten mice (TABLE 25). Body weights were measured daily until treatment start, then twice weekly. Tumor burden was assessed twice weekly by caliper measurement. The study was terminated four weeks post first dosing. Results of the experiment are shown in TABLE 26, FIG. 20 and FIG. 21. The experiment was performed in the Crown Bioscience Inc. (Beijing) animal testing facility (Ground Floor, Light Muller Building, Changping Sector of Zhongguancun Scientific Park, No. 21 Huoju Street, Changping District, Beijing, China, 102200).

TABLE 25

CT26 tumor model mice treatment group assignment.

| Group | Compound | Formulation | Treatment schedule |
|---|---|---|---|
| 1 | Vehicle Vehicle | 0.5% Methylcellulose + 0.1% Tween-80 | p.o. QD, i.p BIW |
| 2 | Vehicle Anti-PD-1* | 0.5% Methylcellulose + 0.1% Tween-80 | p.o. QD, i.p BIW, 10 mg/kg |
| 3 | Compound 258 Vehicle | 0.5% Methylcellulose + 0.1% Tween-80 | p.o. QD, 1 mg/kg i.p BIW |
| 4 | Compound 258 Vehicle | 0.5% Methylcellulose + 0.1% Tween-80 | p.o. QD, 3 mg/kg i.p BIW |
| 5 | Compound 258 Anti-PD-1* | 0.5% Methylcellulose + 0.1% Tween-80 | p.o. QD, 1 mg/kg i.p BIW, 10 mg/kg |
| 6 | Compound 258 Anti-PD-1* | 0.5% Methylcellulose + 0.1% Tween-80 | p.o. QD, 3 mg/kg i.p BIW, 10 mg/kg | p.o. = oral administration (oral gavage).
BIW = twice a week.
QD = once a day.
*= RMP1-14 antibody.

TABLE 26

Survival data for test compound antitumoral activity on subcutaneous syngeneic colon cancer model in female BALB/c mice in combination with anti-PD1 antibodies

| Day | Vehicle | Anti-PD1 | Compound 258 1 mg/kg | Compound 258 3 mg/kg | Compound 258 1 mg/kg + Anti-PD1 | Compound 258 3 mg/kg + Anti-PD1 |
|---|---|---|---|---|---|---|
| 21 | 10 | 10 | 10 | 10 | 10 | 10 |
| 23 | 9 | 10 | 10 | 8 | 10 | 10 |
| 25 | 7 | 7 | 5 | 6 | 10 | 10 |
| 28 | 2 | 5 | 2 | 2 | 7 | 9 |
| 30 | 1 | 5 | 1 | 0 | 6 | 8 |
| 32 | 0 | 3 | 0 | 0 | 4 | 4 |
| 34 | 0 | 3 | 0 | 0 | 4 | 4 |
| 36 | 0 | 3 | 0 | 0 | 4(*) | 4(*) |

(mice alive between day 21 and day 36 of the experiment).

(*)One mouse in group 5 (combination of Compound 258 1 mg/kg and anti-PD1 antibodies) and one mouse in group 6 (combination Compound 258 3 mg/kg and anti-PD1 antibodies) had a complete tumor regression (tumor volume not measurable).

Figure 22:
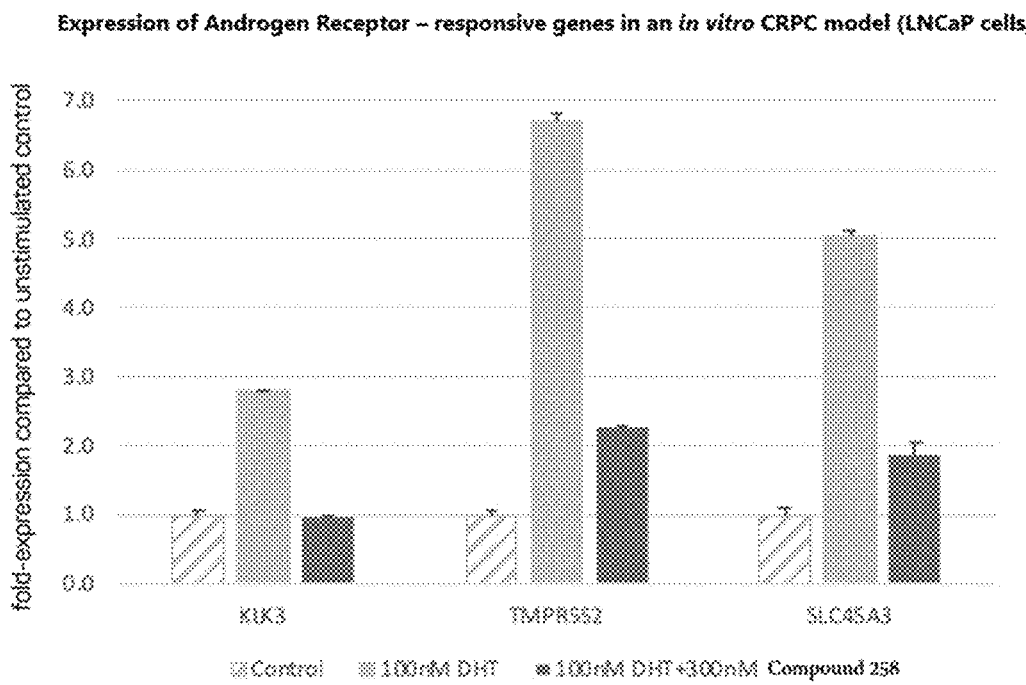
FIG. 22 is a graph showing gene expression inhibition of three well-characterized androgen receptor (AR)-targets through Compound 258-mediated disruption of p300-CH1/TAZ1-AR signaling in the castration-resistant prostate cancer cell line LNCaP. Prostate-specific antigen (PSA/KLK3); transmembrane serine protease 2 (TMPRSS2); and prostein (SLC45A3) gene expression was measured in 4-hour dihydrotestosterone-stimulated cells (DHT, 100 nM) and compared to untreated cells. 300 nM Compound 258 was added concomitantly to DHT. Treatment with Compound 258 resulted in complete repression of PSA stimulation, and 85%, respectively 80% repression of TMPRSS2 and SLC45A3 stimulation.
Figure 23:
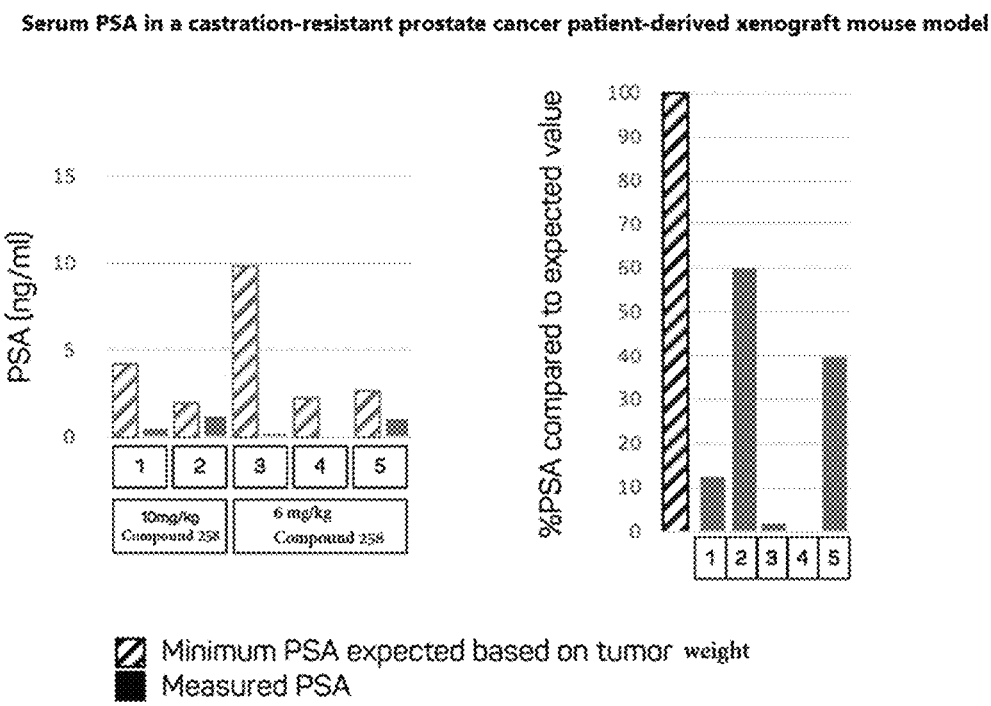
FIG. 23 is a graph showing serum prostate-specific antigen (PSA) levels in a castration resistant prostate cancer (CRPC) patient-derived xenograft mouse model. Serum levels were determined in five mice that still had detectable tumors at experiment termination (following a 19 day treatment period, blood samples taken 3 h after the last dose was applied, FIG. 3, numbering on the x-axis of FIG. 23). Two mice were treated daily with 10 and 3 mg/kg and three mice daily with 6 mg/kg Compound 258 (FIG. 3). Minimal relative expected PSA-levels were calculated based on minimal PSA/tumor size ratio of vehicle-treated mice. All five mice had a clear reduction of the expected serum PSA levels.

Example 331: P300/CBP—Androgen Receptor Target Gene Expression Regulation in Prostate Cancer Cells LNCaP prostate cancer cells (CLS GmbH) were seeded at a density of 15'000 cells/cm$^2$ in 48-well cell culture-treated plates and cultured for 72 hours in RPMI1640 medium (Sigma-Aldrich) supplemented with Glutamax I (Thermo-Fisher-Gibco), "Antibiotic and Antimycotic Solution" (Sigma-Aldrich) and 1% fetal calf serum (Sigma-Aldrich). AR-driven gene expression response was induced by addition of the androgen signaling agonist dihydrotestosterone (Selleck Chemicals, Houston, Tex., USA) to a concentration of 100 nanomol/Lt for 4 hours. Cells were treated with Compound 258 during dihydrotestosterone induction. Culture medium was carefully removed, cells were washed 1× with Phosphate-Buffered Saline (Sigma-Aldrich) and lysed using the SingleShot Cell Lysis Kit (Bio-Rad, Hercules, Calif., USA). Gene expression of well-known AR-responsive genes prostate-specific antigen (KLK3, ThermoFisher), transmembrane serine protease 2 (TMPRSS2, Thermo-Fisher) and prostein (SLC45A3, ThermoFisher) was assessed by quantitative PCR after reverse transcription of the LNCaP RNA with the Applied Biosystem High-Capacity cDNA Reverse Transcription Kit (ThermoFisher). Gene expression was normalized against four reference genes (RPLPO, GUSB, GAPDH and ACTB, all probe detection systems were from Bio-Rad). Results of the experiment are shown in FIG. 22.

Example 332: P300/CBP—Androgen Receptor-Dependent Protein Expression Regulation in a Castration-Resistant Prostate Cancer Patient-Derived Xenograft Mouse Model Mice from groups 1, 3 and 4 of the CPRC prostate patient-derived xenograft model (TABLE 9, EXAMPLE 322) were used to analyze serum PSA at the end of the experiment. In groups 3 and 4, only serum from mice that had a detectable tumor was analyzed. PSA was detected by ELISA (Human Kallikrein 3/PSA Quantikine ELISA Kit, R&D Systems, Minneapolis, Minn., USA) according to manufacturer's instructions. Minimal relative expected PSA-levels were calculated based on minimal PSA/tumor size ratio of vehicle-treated mice. Results of the analysis are presented in FIG. 22.

Figure 24:
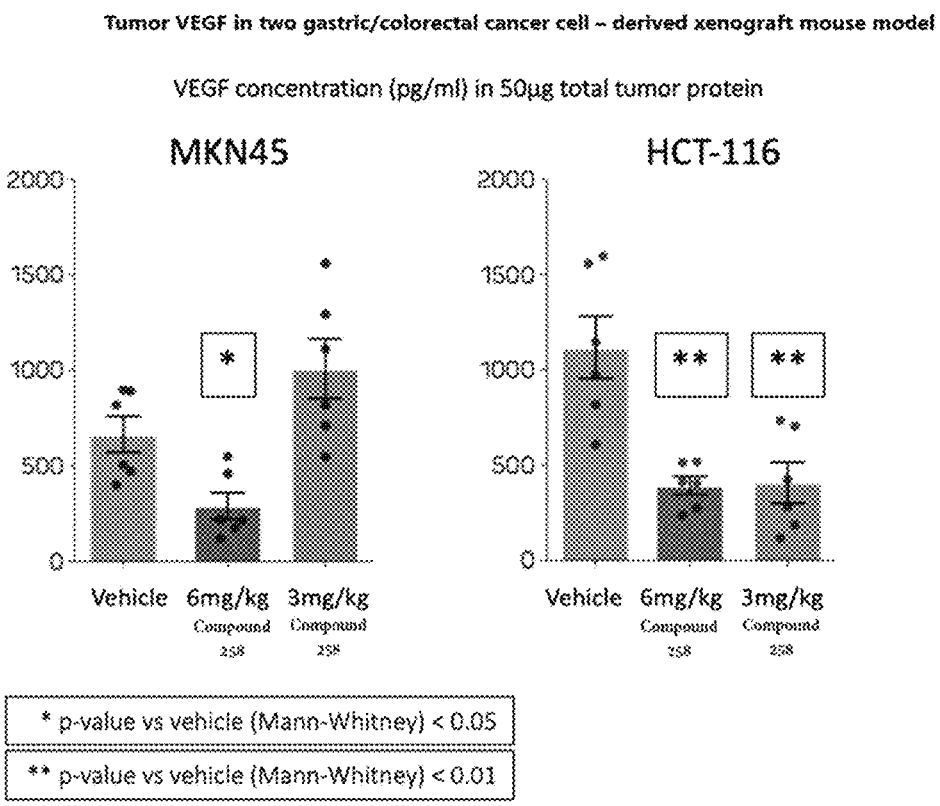
FIG. 24 is a graph showing tumor Vascular Endothelial Growth Factor A (VEGF) protein levels in HCT-116 and MKN45 colorectal/gastric cancer cell-derived xenograft mouse model after approximately 4 and 3 weeks, respectively, of treatment with 3 mg/kg or 6 mg/kg Compound 258 (FIGS. 7 and 9). In accordance with the proposed mode of action of Compound 258, the p300/CBP-HIF1alpha transcriptional complex was disturbed, resulting in VEGF protein levels which were significantly reduced upon Compound 258-treatment. The effect is more evident in the HCT-116 than in the MKN45 xenograft, reflecting the higher VEGF-dependence of HCT-116 xenograft vascularization (described in Dang et al. Cancer Res 2008; 68(6): 1872-80).

Example 333: P300/CBP—Hypoxia Inducible Factor Alpha-Dependent Protein Expression Regulation in Two Gastric/Colorectal Cancer Cell-Derived Xenograft Mouse Model Mice from groups 1, 2, 4 and 5 of the HCT-116 colorectal cancer model (TABLE 12, EXAMPLE 324) and MKN45 gastric cancer model (TABLE 14, EXAMPLE 325) were used to analyze tumor Vascular Endothelial Growth Factor A (VEGF) protein expression at the end of the experiment. Tumors homogenates were prepared using a 2× Lysis Buffer (RayBiotech Life, Norcross, Ga., USA) according to manufacturer's instructions. VEGF was quantified in 50 micrograms tumor by ELISA (Human VEGF Quantikine ELISA Kit, R&D Systems) according to manufacturer's instructions. Results of the analysis are presented in FIG. 24.

Figure 25:
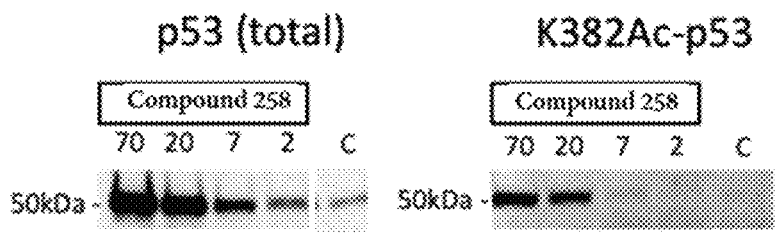
FIG. 25 is a pair of Western blots of Compound 258-treated HPV16-positive cervical cancer CaSki cells. The figure depicts a characteristic rescue of p53 protein expression and p53 lysine 382 acetylation (K382Ac-p53) after Compound 258-mediated inhibition of p300/CBP-HPVE6-p53 protein-protein-interactions. Cells were treated with the indicated concentrations (nM) for 72 h. Induction of p53 protein above baseline is evident at 7 nM already, acetylation of p53 lysine 382 is detectable at 20 nM. Equivalent amounts of protein were loaded on the blot and the loading quantity assessed by total protein detection of the same blot on a Bio-Rad ChemiDoc Touch imager.

Example 334: P53 Protein Reactivation in an HPV16-Positive Cervical Cancer Tumor Cell Line HPV16-positive cervical cancer cells CaSki were subcultured as described in EXAMPLE 1, seeded at a density of 20'000 cells/cm$^2$; and readily treated with Compound 258 for 72 hrs. For western blot analysis, cells were removed from the cell culture vessels by trypsinization, washed twice with PBS (Sigma-Aldrich), lysed with a RIPA-buffer/Protease inhibitor cocktail (Sigma-Aldrich) by shaking on ice for 30 minutes followed by sonication on ice, 20 minutes centrifugation at 16'000×g, 4° C. Lysates were mixed 1:1 with 4× Lämmli Buffer (Bio-Rad) prior to loading onto a Mini-PROTEAN TGX precast 4-20% PAGE gel (Bio-Rad). Gels were run for 1 hour at 110V. Gel were transferred to a Trans-Blot Turbo Mini PVDF membrane (Bio-Rad) using a Bio-Rad Trans-Blot Turbo System according to manufacturer's instructions. Equal amounts of cells were used, and the total transferred protein visualized on a Bio-Rad Chemi-Doc Touch Imager prior to incubation with the primary antibody. After blocking for 1 hr with 5% non-fat-dry-milk (for p53 detection) or 5% BSA (for detection of p53-acetyllysine-382) in 1×TBS with 0.1% Tween-20 (Bio-Rad), blots were incubated overnight at 4° C. with p53 or p53-acetyl-lysine-382-specific antibodies (mouse monoclonal antibodies (SC-47698 from Santa Cruz Biotechnologies, Dallas, Tex., USA), respectively rabbit polyclonal antibodies (#2525S from Cell Signaling Technologies, Boston, Mass., USA), both at 1:1'000 dilution) and subsequently with the corresponding secondary HRP-conjugated antibodies (Cell Signaling Technologies, both 1:1'000 dilution) according to manufacturer's instructions. Specific antibody binding was detected with the SuperSignal West Femto Maximum Sensitivity Substrate (ThermoFisher) and visualized using a Bio-Rad ChemiDoc Touch Imager. Results from the experiment are shown in FIG. 25.

EQUIVALENTS

Those skilled in the art will recognize, or be able to ascertain using no more than routine experimentation, many equivalents to the specific embodiments and methods described herein. Such equivalents are intended to be encompassed by the scope of the present application.

All patents, patent applications, and literature references cited herein are hereby expressly incorporated by reference.

The invention claimed is:

1. A compound of formula (Ia)

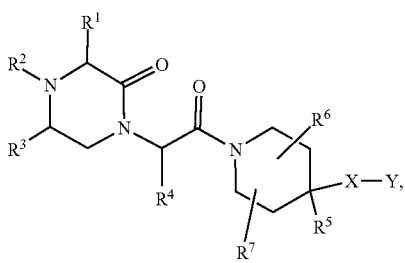

(Ia)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by cycloalkyl, aryl, or heteroaryl, wherein the cycloalkyl, aryl, or the heteroaryl is optionally substituted by halogen, $C_{1-4}$ alkyl, or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, and $C_{1-3}$ alkyl substituted by cycloalkyl, aryl, or heteroaryl, wherein the cycloalkyl, aryl, or the heteroaryl is optionally substituted by halogen, $C_{1-4}$ alkyl, or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, the ring is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, and $C_{4-7}$ cycloalkenyl, wherein the alkyl, alkenyl, alkynyl, cycloalkyl, or cycloalkenyl is optionally substituted by halogen, $OR^8$, or $NR^8R^{11}$; or $R^3$ and $R^7$ are each independently $C_{1-3}$ alkyl substituted by aryl or heteroaryl, wherein the aryl or the heteroaryl is optionally substituted by halogen, $C_{1-4}$ alkyl, or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by cycloalkyl, aryl, or heteroaryl, wherein the cycloalkyl, aryl, or the heteroaryl is optionally substituted by halogen, $C_{1-4}$ alkyl, or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, and $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, and $C_{4-7}$ cycloalkenyl, wherein the alkyl, alkenyl, alkynyl, cycloalkyl, or cycloalkenyl is optionally substituted by halogen, $OR^8$, or $NR^8R^{11}$; or $R^6$ is $C_{1-3}$ alkyl substituted by $C(O)NR^8R^{11}$; or $R^6$ is $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; and wherein $R^6$ can form a ring with any part of X; or $R^6$ is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, and $C_{4-7}$ cycloalkenyl;

X is selected from a bond, $C_{1-7}$ alkanediyl, $C_{2-7}$ alkenediyl, $C_{2-7}$ alkynediyl, $C_{3-9}$ cycloalkanediyl, $C_{4-6}$ cycloalkenediyl, —O—, $C_{1-3}$ alkanediyl-O—, —O—$C_{1-7}$ alkanediyl, —O—$C_{3-9}$ cycloalkanediyl, $C_{1-3}$ alkanediyl-O—$C_{1-7}$ alkanediyl, $C_{1-7}$ heteroalkanediyl, and —S—$C_{1-7}$ alkanediyl; and wherein X can form a ring or a polycyclic system with any part of $R^5$, $R^6$, or Y, wherein the ring optionally contains a carbonyl group;

Y is selected from H, $C(O)NR^{10}R^{12}$, $C(O)OR^{10}$, $R^{10}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N, wherein if the heteroatom is N it is optionally substituted by $R^8$, S-aryl, O-aryl, S-heteroaryl, and O-heteroaryl, wherein the S-aryl, O-aryl, S-heteroaryl, or O-heteroaryl is optionally substituted by one or more $R^9$ or $R^{14}$; or Y is aryl or heteroaryl, wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}R$, $OC(O)NR^8R^{11}$, $SO_2NR^8R^{11}$, $NR^8SO_2R^8$, $OR^8$, $NR^8R^{11}$, and $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, and $C_{1-3}$ alkyl-heteroaryl, wherein the alkyl, alkenyl, alkynyl, cycloalkyl, cycloalkenyl, alkanediyl, aryl, or heteroaryl is optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, and $C_{1-3}$ alkyl-$OR^8$.

2. The compound of claim 1, wherein the compound is of formula (I)

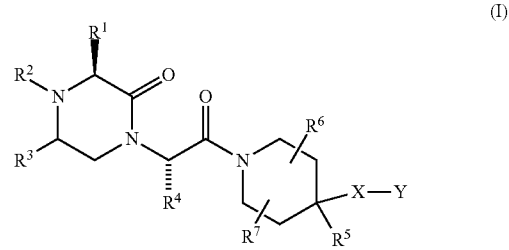

(I)

or a pharmaceutically acceptable salt, hydrate, solvate or stereoisomer thereof, wherein:

$R^1$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl;

$R^2$ is selected from H, $C(O)R^{14}$, $C(O)NR^{15}R^{15}$, $C(O)OR^{15}$, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-5}$ alkyl-$OR^8$, $C_{1-3}$ alkanediyl-O—$C_{1-3}$ alkanediyl-O—$C_{1-3}$ alkanediyl, $C_{1-5}$ alkyl-$NHCOR^{13}$, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; with the proviso that when $R^2$ is $C(O)NR^{15}R^{15}$, both $R^{15}$ can form a ring wherein the ring contains the N of $NR^{15}R^{15}$ and optionally one further heteroatom selected from O and N, wherein if the one further heteroatom is N, the ring is optionally substituted by $R^8$;

$R^3$ and $R^7$ are each independently selected from H, $C_{1-7}$ alkyl, $C_{2-7}$ alkenyl, $C_{2-7}$ alkynyl, $C_{3-7}$ cycloalkyl, and $C_{4-7}$ cycloalkenyl, wherein the alkyl, alkenyl, alkynyl, cycloalkyl, or cycloalkenyl is optionally substituted by halogen, $OR^8$, or $NR^8R^{11}$; or $R^3$ and $R^7$ are each independently $C_{1-3}$ alkyl substituted by aryl or heteroaryl, wherein the aryl or the heteroaryl is optionally substituted by halogen, $C_{1-4}$ alkyl, or $C_{3-5}$ cycloalkyl;

$R^4$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl;

$R^5$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, $C_{1-3}$ alkyl-$OR^8$, and $SR^8$; and wherein $R^5$ can form a ring with any part of X or Y, wherein the ring optionally contains a carbonyl group;

$R^6$ is selected from H, $C_{1-7}$ alkyl, $C_{2-7}$ alkenyl, $C_{2-7}$ alkynyl, $C_{3-7}$ cycloalkyl, and $C_{4-7}$ cycloalkenyl, wherein the alkyl, alkenyl, alkynyl, cycloalkyl, or cycloalkenyl is optionally substituted by halogen, $OR^8$, or $NR^8R^{11}$; or $R^6$ is $C_{1-3}$ alkyl substituted by $C(O)NR^8R^{11}$; or $R^6$ is $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; or $R^6$ is imidazolidinone;

$R^8$ and $R^{11}$ are each independently selected from H, $C_{1-7}$ alkyl, $C_{2-7}$ alkenyl, $C_{2-7}$ alkynyl, $C_{3-7}$ cycloalkyl, and $C_{4-7}$ cycloalkenyl;

X is selected from a bond, $C_{1-7}$ alkanediyl, $C_{2-7}$ alkenediyl, $C_{2-7}$ alkynediyl, $C_{3-6}$ cycloalkanediyl, $C_{4-6}$ cycloalkenediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, and —S—$C_{1-7}$ alkanediyl; and wherein X can form a ring with any part of $R^5$ or Y, wherein the ring optionally contains a carbonyl group;

Y is selected from H, $C(O)NR^{10}R^{12}$, $C(O)OR^{10}$, $R^{10}NC(O)NR^{10}R^{12}$, $OC(O)R^{10}$, $OC(O)NR^{10}R^{12}$, $S(O)_nR^8$ wherein n is 0, 1 or 2, $SO_2NR^{10}R^{12}$, $NR^{10}SO_2R^{10}$, $NR^{10}R^{12}$, $HNCOR^8$, CN, $C_{3-7}$-cycloalkyl optionally containing a heteroatom in the ring selected from O and N wherein if the heteroatom is N it is optionally substituted by $R^8$, S-aryl, O-aryl, S-heteroaryl, and O-heteroaryl, wherein the S-aryl, O-aryl, S-heteroaryl, or O-heteroaryl is optionally substituted by one or more $R^9$ or $R^{14}$; or Y is aryl or heteroaryl, wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$;

$R^9$ is selected from H, halogen, $C_{1-5}$ alkyl, $C_{2-5}$ alkenyl, $C_{2-5}$ alkynyl, $C_{3-5}$ cycloalkyl, $C_{1-5}$ alkyl-$OR^8$, $C_{1-5}$ alkyl-$SR^8$, $C_{1-5}$ alkyl-$NR^8R^{11}$, $C_{1-5}$ alkyl-$C(O)OR^8$, $C_{1-5}$ alkyl-$C(O)NR^8R^{11}$, $C_{1-5}$ alkyl-$C(O)R^{10}$, CN, $C(O)R^8$, $C(O)NR^8R^{11}$, $C(O)OR^8$, $NR^8C(O)NR^8R^{11}$, $OC(O)NR^8R^{11}$, $SO_2NR^8R^{11}$, $NR^8SO_2R^8$, $OR^8$, $NR^8R^{11}$, and $S(O)_nR^8$ wherein n is 0, 1 or 2;

$R^{10}$ and $R^{12}$ are each independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, and $C_{1-3}$ alkyl-heteroaryl, wherein the alkyl, alkenyl, alkynyl, cycloalkyl, cycloalkenyl, alkanediyl, aryl, or heteroaryl is optionally substituted by halogen, $OR^8$, or $NR^8R^{11}$;

$R^{13}$ is $C_{1-5}$ alkyl substituted by a bicyclic ring optionally containing at least one heteroatom and a carbonyl group;

$R^{14}$ is selected from H, $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; and each $R^{15}$ is independently selected from H, $C_{1-7}$ alkyl, $C_{2-7}$ alkenyl, $C_{2-7}$ alkynyl, $C_{3-7}$ cycloalkyl, $C_{4-7}$ cycloalkenyl, $OR^8$, and $C_{1-3}$ alkyl-$OR^8$.

3. The compound of claim 1, wherein (1) $R^1$ is selected from $C_{1-7}$ alkyl, $C_{2-7}$ alkenyl, $C_{2-7}$ alkynyl, $C_{3-7}$ cycloalkyl, $C_{4-7}$ cycloalkenyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; (2) $R^2$ is selected from H, $C(O)R^{14}$, $C(O)OR^{15}$, $C_{1-7}$ alkyl, $C_{3-7}$ cycloalkyl, $C_{1-3}$ alkanediyl-O—$C_{1-3}$ alkanediyl-O—$C_{1-3}$ alkanediyl, $C_{1-5}$ alkyl-$OR^8$, $C_{1-5}$ alkyl-$NHCOR^{13}$, and $C_{1-3}$ alkyl substituted by aryl, wherein the aryl is optionally substituted by halogen, $C_{1-4}$ alkyl, or $C_{3-5}$ cycloalkyl; (3) $R^3$ and $R^7$ are each independently selected from H, $C_{1-7}$ alkyl, $C_{2-7}$ alkenyl, $C_{2-7}$ alkynyl, $C_{3-7}$ cycloalkyl, and $C_{4-7}$ cycloalkenyl; and/or (4) $R^4$ is selected from $C_{1-7}$ alkyl, $C_{3-7}$ cycloalkyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl.

4. The compound of claim 1, wherein (1) $R^1$ is selected from $C_{3-7}$ alkyl, $C_{3-7}$ cycloalkyl, and $C_{1-3}$ alkyl substituted by aryl or heteroaryl; (2) $R^2$ is selected from H and $C(O)R^{14}$, wherein $R^{14}$ is $C_{1-7}$ alkyl; or $R^2$ is $C_{1-7}$ alkyl, $C_{3-7}$ cycloalkyl, $C_{1-5}$ alkyl-$OR^8$, or $C_{1-5}$ alkyl-$NHCOR^{13}$, wherein $R^{13}$ is pentylamino-5-oxopentyl-7-thia-2,4-diazabicyclo[3.3.0]octan-3-one; or $R^2$ is $C_{1-3}$ alkyl substituted by aryl, wherein the aryl is optionally substituted by halogen, $C_{1-4}$ alkyl, or $C_{3-5}$ cycloalkyl; (3) $R^3$ and $R^7$ are H; and/or (4) $R^4$ is selected from $C_{3-7}$ alkyl, $C_{3-7}$ cycloalkyl, and $C_{1-3}$ alkyl substituted by aryl or heteroaryl.

5. The compound of claim 1, wherein the compound is of any one of Formulae (IIa), (IIb), (IIc), (IIIa), (IIIb), (IIIc), (IIId), (IVa), (IVb), (IVc), or (IVd):

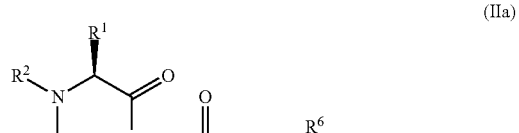

(IIa)

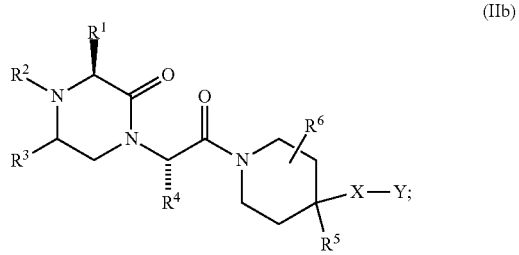

(IIb)

-continued (IIc)
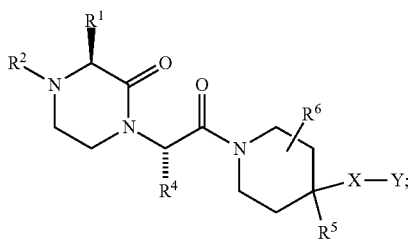

(IIIa)
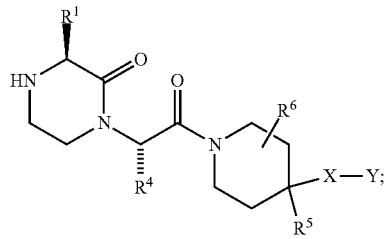

(IIIb)
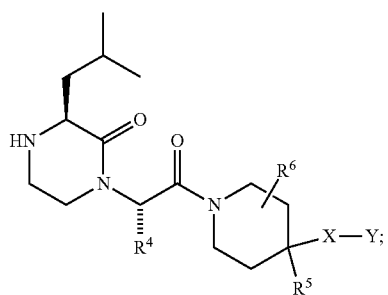

(IIIc)
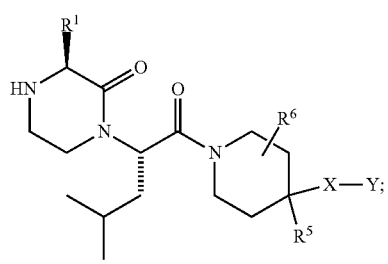

(IIId)
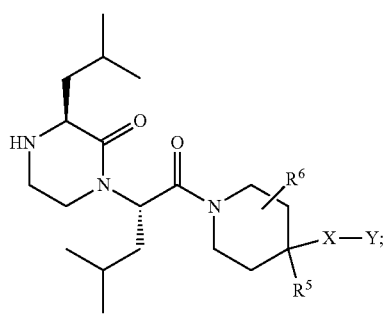

(IVa)
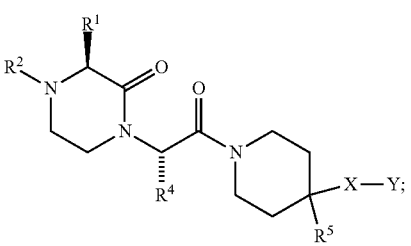

-continued (IVb)
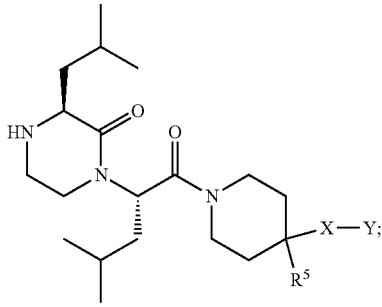

(IVc)
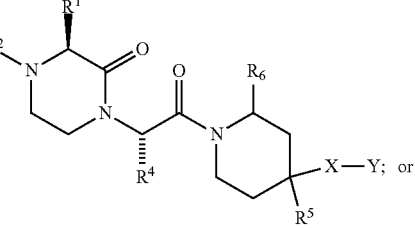

(IVd)
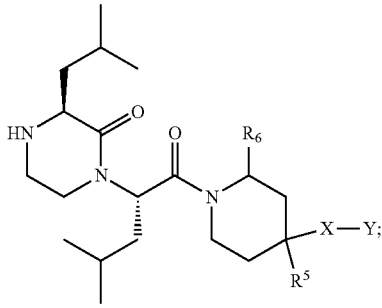

or a pharmaceutically acceptable salt, hydrate, solvate or stereoisomer thereof.

6. The compound of claim 1, wherein (1) $R^5$ is selected from H, $C_{1-7}$ alkyl, $OR^8$, and $SR^8$; and wherein $C_{1-7}$ alkyl, $OR^8$, or $SR^8$ of $R^5$ can form a ring with any part of X or Y, wherein the ring optionally contains a carbonyl group and/or (2) $R^6$ is selected from H, $C_{1-7}$ alkyl, $C_{2-7}$ alkenyl, $C_{2-7}$ alkynyl, $C_{3-7}$ cycloalkyl, and $C_{4-7}$ cycloalkenyl; or $R^6$ is imidazolidinone.

7. The compound of claim 1, wherein (1) $R^8$ and $R^{11}$ are each independently selected from H, $C_{1-7}$ alkyl, $C_{2-7}$ alkenyl, and $C_{3-7}$ cycloalkyl; (2) $R^9$ is selected from H, $C_{1-5}$ alkyl, halogen, $C_{1-5}$ alkyl-$NR^8R^{11}$, $C_{1-5}$ alkyl-$C(O)OR^8$, $C_{1-5}$ alkyl-$C(O)NR^8R^{11}$, CN, $C(O)R^8$, $C(O)NR^8R^{11}$, $C(O)OR^8$, and $OR^8$; (3) $R^{10}$ and $R^{12}$ are each independently selected from H, $C_{1-7}$ alkyl, $C_{2-7}$ alkenyl, $C_{3-7}$ cycloalkyl, $C_{4-7}$ cycloalkenyl, $C_{1-3}$ alkanediyl-O—$C_{1-3}$ alkanediyl-O—$C_{1-3}$ alkanediyl, $C_{1-3}$ alkyl-aryl, and $C_{1-3}$ alkyl-heteroaryl, wherein the alkyl, alkenyl, cycloalkyl, cycloalkenyl, alkanediyl, aryl, or heteroaryl is optionally substituted by halogen or $OR^8$; (4) $R^{14}$ is selected from $C_{1-7}$ alkyl, $C_{3-7}$ cycloalkyl, and $C_{1-3}$ alkyl substituted by aryl or heteroaryl, wherein the aryl or the heteroaryl is optionally substituted by halogen, $C_{1-4}$ alkyl, or $C_{3-5}$ cycloalkyl; and/or (5) each $R^{15}$ is independently selected from H, $C_{1-7}$ alkyl, and $C_{3-7}$ cycloalkyl.

8. The compound of claim 1, wherein (1) $R^{14}$ is $C_{1-7}$ alkyl and/or (2) each $R^{15}$ is independently selected from H and $C_{1-7}$ alkyl.

9. The compound of claim 1, wherein (1) X is selected from a bond, $C_{1-7}$ alkanediyl, —O—, $C_{1-3}$ alkanediyl-O—, —O—$C_{1-7}$ alkanediyl, $C_{1-3}$ alkanediyl-O—$C_{1-7}$ alkanediyl, $C_{1-7}$ heteroalkanediyl, and —S—$C_{1-7}$ alkanediyl; and wherein X can form a ring with any part of $R^5$ or Y, wherein the ring optionally contains a carbonyl group; (2) X is selected from a bond and $C_{1-7}$ alkanediyl, and wherein $C_{1-7}$ alkanediyl of X can form a ring with any part of Y; or (3) X is selected from a bond, —O—$C_{1-7}$ alkanediyl, —S—$C_{1-7}$ alkanediyl, and $C_{1-7}$ alkanediyl, wherein —O—$C_{1-7}$ alkanediyl, —S—$C_{1-7}$ alkanediyl, or $C_{1-7}$ alkanediyl of X can form a ring with any part of $R^5$, wherein the ring optionally contains a carbonyl group.

10. The compound of claim 1, wherein (1) Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N the ring is optionally substituted by $R^8$, S-aryl, O-aryl, S-heteroaryl, and O-heteroaryl wherein the S-aryl, O-aryl, S-heteroaryl, or O-heteroaryl is optionally substituted by one or more $R^9$ or $R^{14}$; or Y is aryl or heteroaryl, wherein the aryl or heteroaryl is optionally substituted by one or more of $R^8$; and wherein when Y is $C(O)NR^{10}R^{12}$ or $NR^{10}R^{12}$, Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$; (2) Y is selected from H, $C(O)NR^{10}R^{12}$, $C(O)OR^{10}$, $NR^{10}R^{12}$, CN, $C_{3-7}$-cycloalkyl optionally containing a heteroatom in the ring selected from O and N wherein if the heteroatom is N the ring is optionally substituted by $R^8$, S-aryl, O-aryl, S-heteroaryl, and O-heteroaryl wherein the S-aryl, O-aryl, S-heteroaryl, or O-heteroaryl is optionally substituted by one or more $R^9$ or $R^{14}$; or Y is aryl or heteroaryl wherein the aryl or heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$; (3) Y is selected from $C(O)NR^{10}R^{12}$, $NR^{10}R^{12}$, $C_{3-7}$-cycloalkyl optionally containing a heteroatom in the ring selected from O and N, wherein if the heteroatom is N it is optionally substituted by $R^8$, S-aryl, O-aryl, S-heteroaryl, and O-heteroaryl wherein the S-aryl, O-aryl, S-heteroaryl, or O-heteroaryl is optionally substituted by one or more $R^9$ or $R^{14}$; or Y is heteroaryl wherein the heteroaryl is optionally substituted by one or more of $R^8$; and wherein Y can form a ring with any part of X or $R^5$, wherein the ring optionally contains a carbonyl group; with the proviso that when Y is $C(O)NR^{10}R^{12}$ or $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$; or (4) Y is selected from $NR^{10}R^{12}$ and $C_{3-7}$-cycloalkyl optionally containing a heteroatom in the ring selected from O and N, wherein if the heteroatom is N the ring is optionally substituted by $R^8$; and wherein Y can form a ring with any part of X or $R^5$; with the proviso that when Y is $NR^{10}R^{12}$, $R^{10}$ and $R^{12}$ can form a ring wherein the ring contains the N of $NR^{10}R^{12}$ and optionally one further heteroatom selected from O and N, wherein if the one further heteroatom is N, the ring is optionally substituted by $R^8$.

11. The compound of claim 1, wherein the compound is of any one of Formulae (Va), (Vb), (Vc), (Vd), (VIa), (VIb), (VIc), (VId), (VIIa), (VIIb), (VIIc), (VIId), (VIIe), or (VIIf):

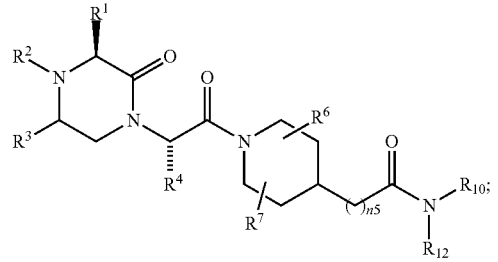

(Va)

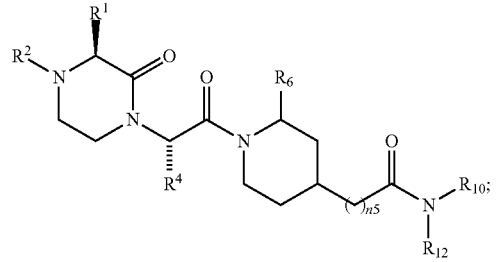

(Vb)

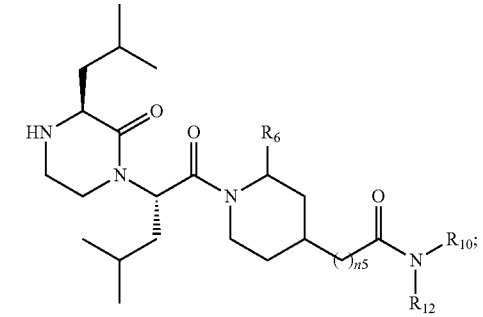

(Vc)

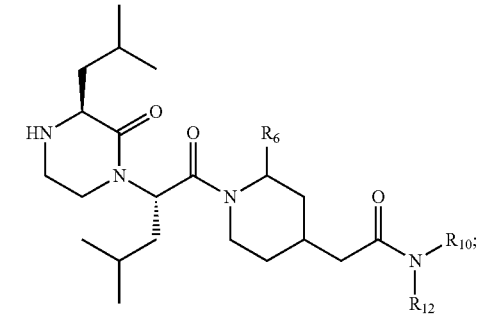

(Vd)

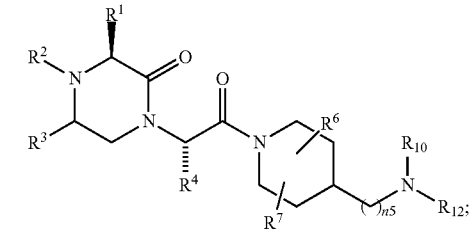

(VIa)

(VIb)
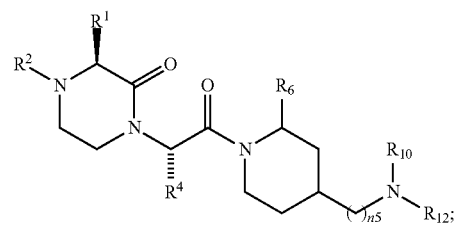

(VIc)
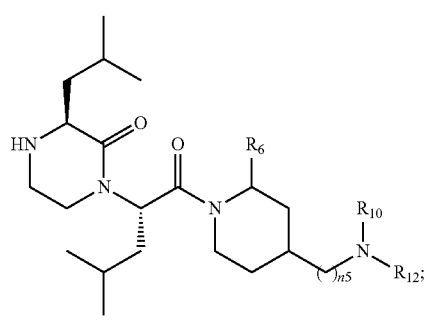

(VId)
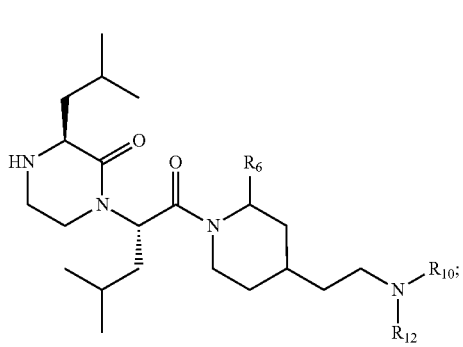

(VIIa)
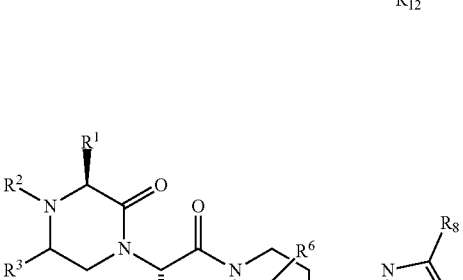

(VIIb)
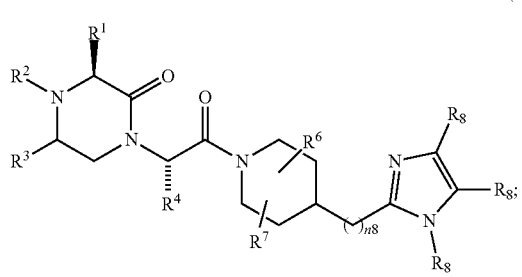

(VIIc)
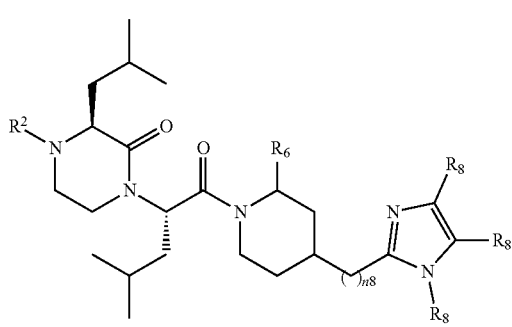

(VIId)
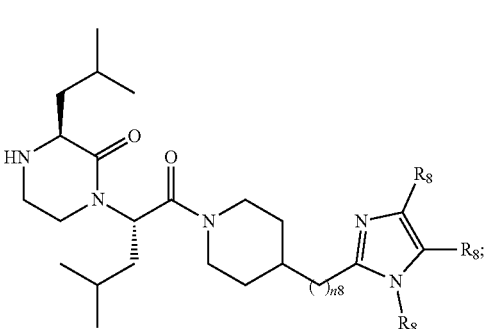

(VIIe)
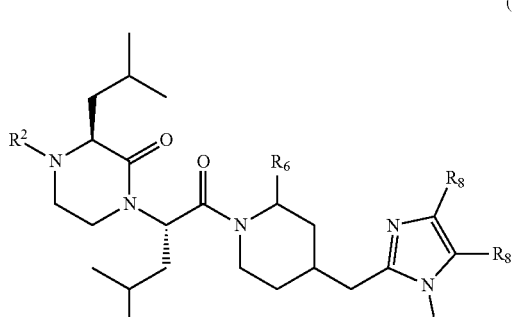

or (VIIf)
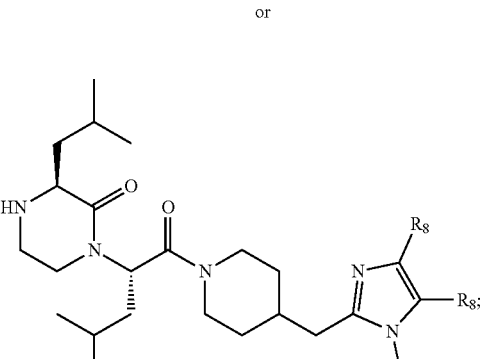

or a pharmaceutically acceptable salt, hydrate, solvate or stereoisomer thereof, wherein n5 is 0, 1, 2, 3, 4, 5, 6, or 7 and n8 is 0, 1, 2, 3, 4, 5, 6, or 7.

12. The compound of claim 1, wherein (1a) $R^5$ is selected from H and $C_{1-7}$ alkyl; wherein $C_{1-7}$ alkyl of $R^5$ can form a ring with any part of Y; (1b) $R^5$ is selected from $C_{1-7}$ alkyl, $OR^8$, and $SR^8$; wherein $C_{1-7}$ alkyl, $OR^8$, or $SR^8$ of $R^5$ can form a ring with any part of X; or (1c) $R^5$ is $OR^8$, wherein $R^8$ of $OR^8$ is $C_{1-7}$ alkyl, and wherein $OR^8$ of $R^5$ can form a ring with any part of X;

wherein (2a) X is selected from a bond and C$_{1-7}$ alkanediyl, wherein C$_{1-7}$ alkanediyl of X can form a ring with any part of Y; (2b) X is selected from —O—C$_{1-7}$ alkanediyl, —S—C$_{1-7}$ alkanediyl, and C$_{1-7}$ alkanediyl, and wherein —O—C$_{1-7}$ alkanediyl, —S—C$_{1-7}$ alkanediyl, or C$_{1-7}$ alkanediyl of X can form a ring with any part of R$^5$; or (2c) X is —O—C$_{1-7}$ alkanediyl, wherein —O—C$_{1-7}$ alkanediyl of X can form a ring with any part of R$^5$;

wherein (3a) Y is selected from NR$^{10}$R$^{12}$ and C$_{3-7}$-cycloalkyl optionally containing a heteroatom in the ring wherein the heteroatom is N and is optionally substituted by R$^8$, wherein R$^8$ is C$_{1-7}$ alkyl; and wherein Y can form a ring with any part of C$_{1-7}$ alkanediyl of X or with any part of C$_{1-7}$ alkyl of R$^5$; with the proviso that when Y is NR$^{10}$R$^{12}$, R$^{10}$ and R$^{12}$ can form a ring wherein the ring contains the N of NR$^{10}$R$^{12}$ and optionally one further heteroatom selected from O and N, wherein if the one further heteroatom is N, the ring is optionally substituted by R$^8$; (3b) Y is NR$^{10}$R$^{12}$ wherein R$^{10}$ and R$^{12}$ can form a ring wherein the ring contains the N of NR$^{10}$R$^{12}$ and optionally one further heteroatom selected from O and N, wherein if the one further heteroatom is N, the ring is optionally substituted by R$^8$; or (3c) Y is NR$^{10}$R$^{12}$ wherein R$^{10}$ and R$^{12}$ can form a ring wherein the ring contains the N of NR$^{10}$R$^{12}$ and four or five carbon atoms; and wherein R$^{10}$ and R$^{12}$ are each independently selected from H, C$_{1-7}$ alkyl, C$_{3-7}$ cycloalkyl, and C$_{1-3}$ alkyl-aryl, wherein the alkyl, cycloalkyl, or aryl is optionally substituted by halogen.

13. The compound of claim 1, wherein (1) Y is aryl or heteroaryl, wherein the aryl or heteroaryl is optionally substituted by one or more of R$^8$; or Y is S-heteroaryl, wherein the S-heteroaryl is optionally substituted by one or more R$^{14}$; (2) Y is C(O)NR$^{10}$R$^{12}$; wherein R$^{10}$ and R$^{12}$ can form a ring wherein the ring contains the N of NR$^{10}$R$^{12}$ and optionally one further heteroatom selected from O and N, wherein if the one further heteroatom is N, the ring is optionally substituted by R$^8$; (3) Y is selected from S-aryl, O-aryl, S-heteroaryl, and O-heteroaryl, wherein the S-aryl, O-aryl, S-heteroaryl, or O-heteroaryl is optionally substituted by one or more R$^9$ or R$^{14}$; (4) Y is C(O)OR$^{10}$; (5) Y is H; or (6) Y is CN.

14. The compound of claim 1,
wherein R$^5$ is selected from H and C$_{1-7}$ alkyl;
X is selected from a bond and C$_{1-7}$ alkanediyl;
Y is (1) heteroaryl, wherein the heteroaryl is optionally substituted by one or more of R$^8$; or Y is S-heteroaryl, wherein the S-heteroaryl is optionally substituted by one or more R$^{14}$; (2) C(O)NR$^{10}$R$^{12}$; wherein R$^{10}$ and R$^{12}$ can form a ring wherein the ring contains the N of NR$^{10}$R$^{12}$ and optionally one further heteroatom selected from O and N, wherein if the one further heteroatom is N, the ring is optionally substituted by R$^8$; wherein R$^{10}$ and R$^{12}$ are each independently selected from H, C$_{1-7}$ alkyl, C$_{2-7}$ alkenyl, C$_{3-7}$ cycloalkyl, and C$_{1-3}$ alkyl-aryl; (3) Y is selected from O-aryl and O-heteroaryl, wherein the O-aryl or O-heteroaryl is optionally substituted by one or more R$^9$; wherein R$^9$ is selected from H, C$_{1-5}$ alkyl, halogen, C$_{1-5}$ alkyl-NR$^8$R$^{11}$, C$_{1-5}$ alkyl-C(O)OR$^8$, C$_{1-5}$ alkyl-C(O)NR$^8$R$^{11}$, CN, C(O)R$^8$, C(O)NR$^8$R$^{11}$, C(O)OR$^8$, and OR$^8$; or (4) Y is C(O)OR$^{10}$; wherein R$^{10}$ is selected from H, C$_{1-7}$ alkyl, C$_{2-7}$ alkenyl, C$_{3-7}$ cycloalkyl, C$_{4-7}$ cycloalkenyl, C$_{1-3}$ alkanediyl-O—C$_{1-3}$ alkanediyl-O— C$_{1-3}$ alkanediyl, C$_{1-3}$ alkyl-aryl, and C$_{1-3}$ alkyl-heteroaryl, wherein the alkyl, alkenyl, cycloalkyl, cycloalkenyl, alkanediyl, aryl, or heteroaryl is optionally substituted by OR$^8$.

15. The compound of claim 1, wherein

R$^5$ is C$_{1-7}$ alkyl or H;

X is a bond or C$_{1-7}$ alkanediyl; and

Y is H or CN.

16. The compound of claim 1, wherein the compound is of any one of Formulae (VIIIa), (VIIIb), (VIIIc), (VIIId), (VIIIe), (VIIIf), (VIIIg), (VIIIh), (VIIIi), (VIIIj), (VIIIk), (VIII) (IXa), (IXb), (IXc), or (IXd):

(VIIIa)

(VIIIb)

(VIIIc)

(VIIId)

(VIIIe)

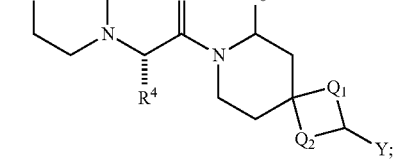

(VIIIf)
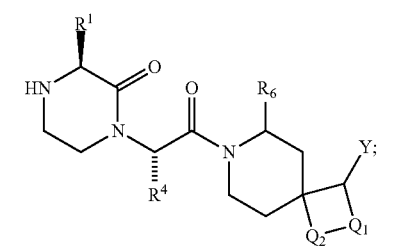
(VIIIg)
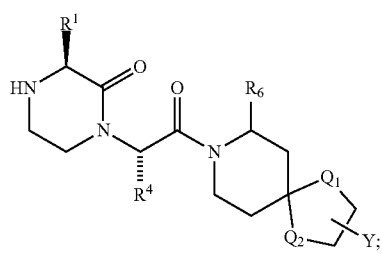
(VIIIh)
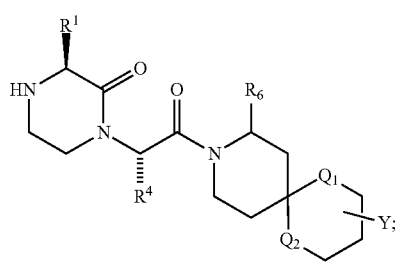
(VIIIi)
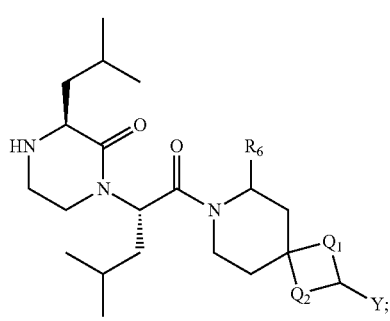
(VIIIj)
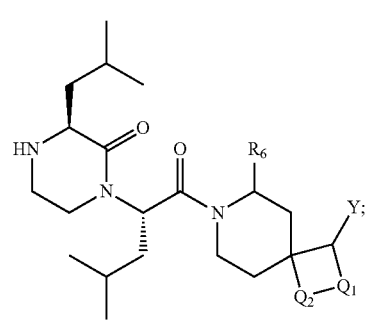
(VIIIk)
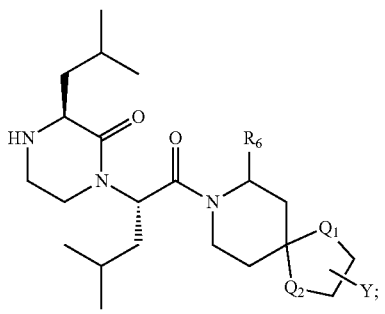
(VIIIl)
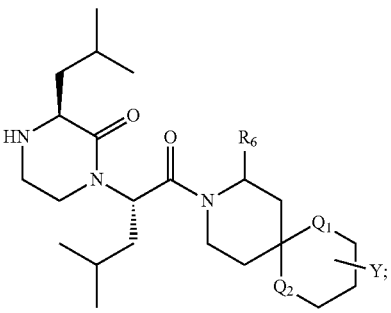
(IXa)
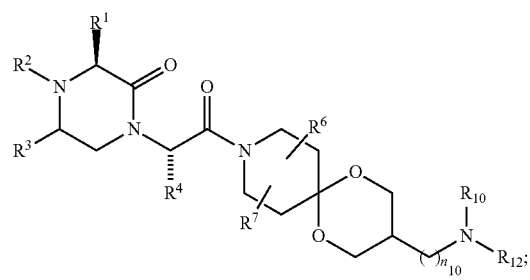
(IXb)
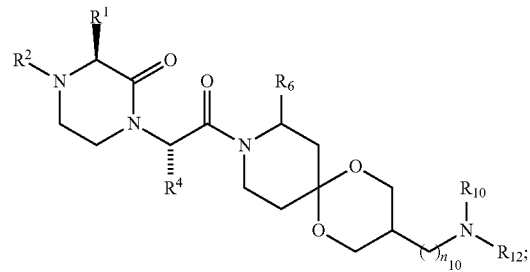
(IXc)
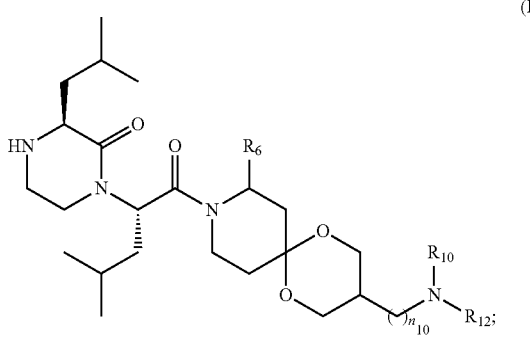
or

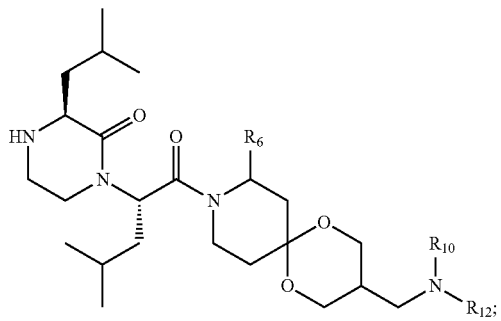
or a pharmaceutically acceptable salt, hydrate, solvate, or stereoisomer thereof, wherein $Q_1$ and $Q_2$ are each independently O, S, $NR^8$, or $CR^8$ and $n_{10}$ is 0, 1, 2, 3, 4, 5, 6, or 7.
17. A compound selected from the group consisting of:
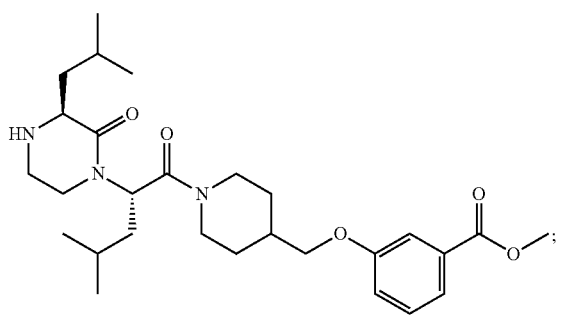
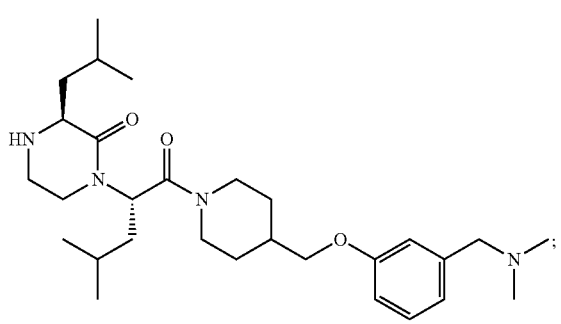
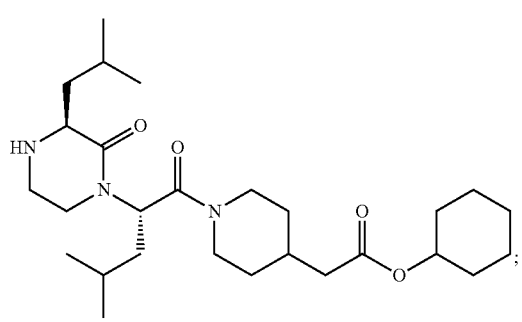
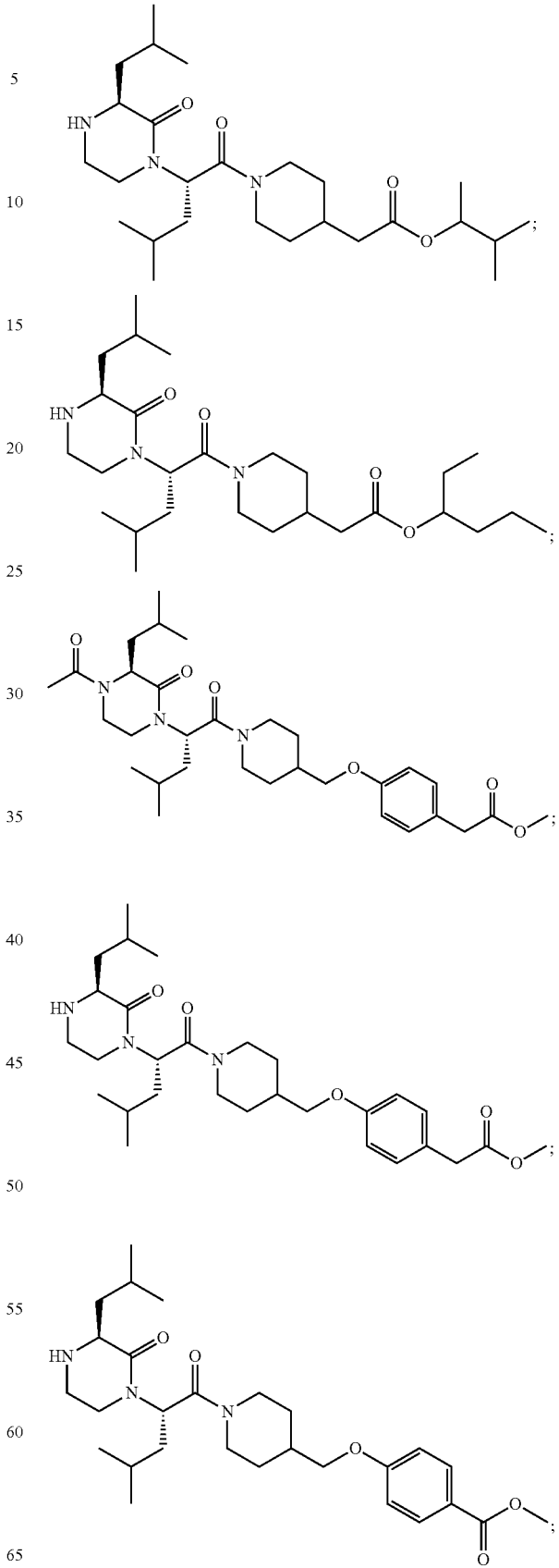

481
-continued

482
-continued

483
-continued
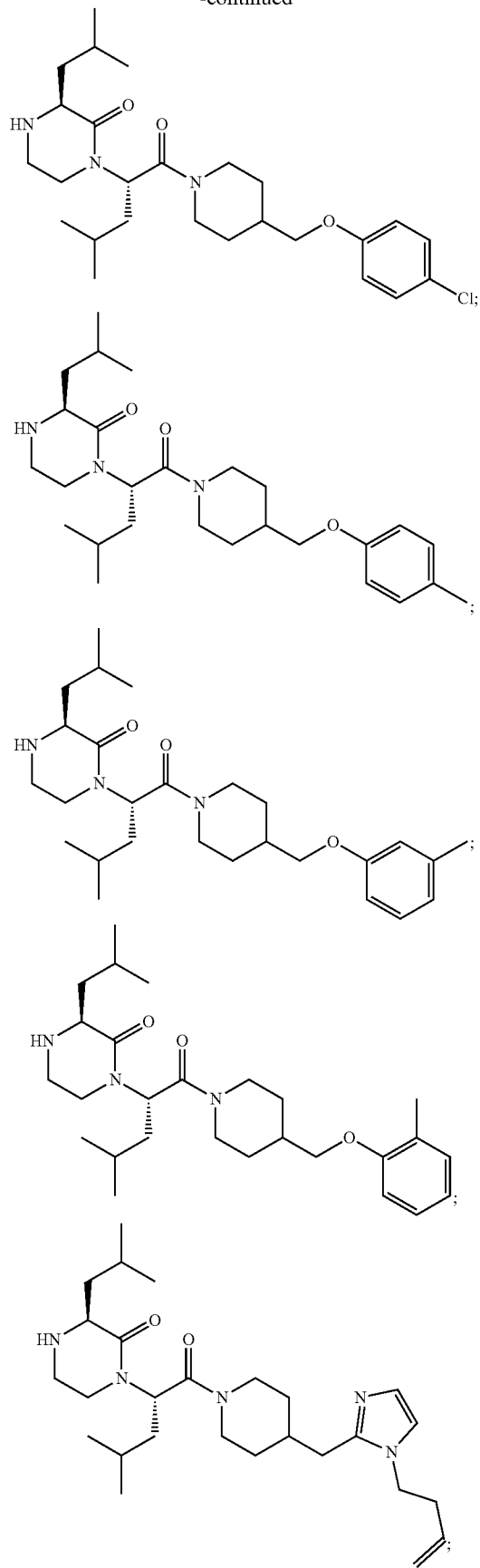
484
-continued
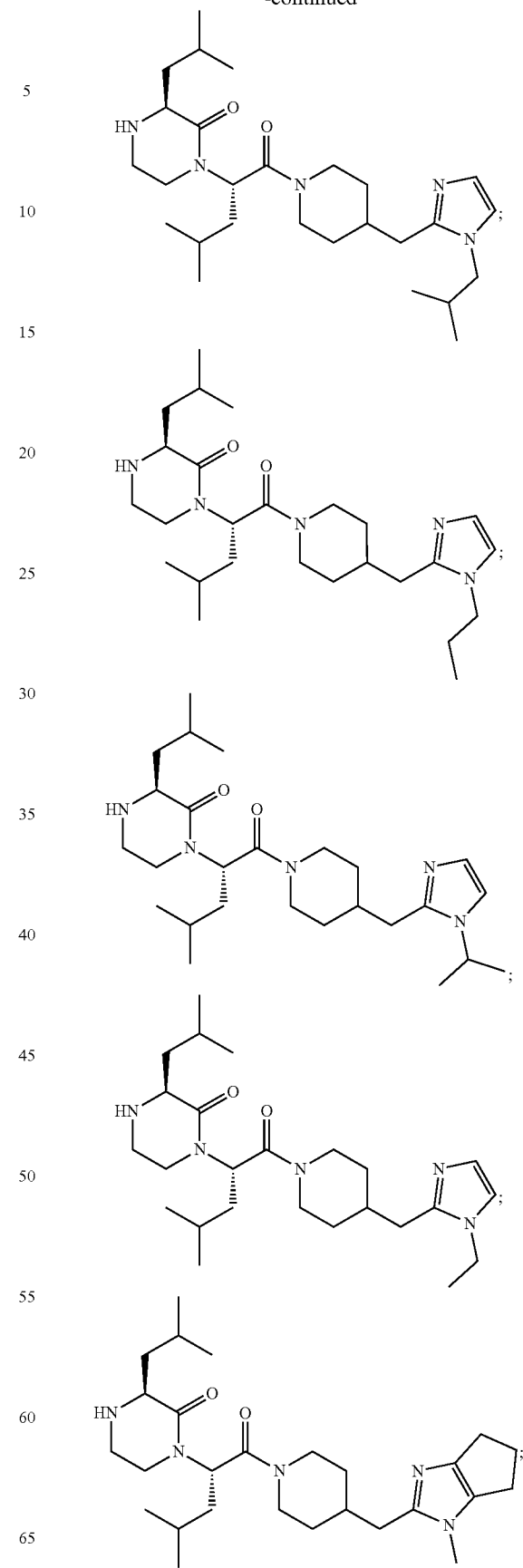

485
-continued
486
-continued
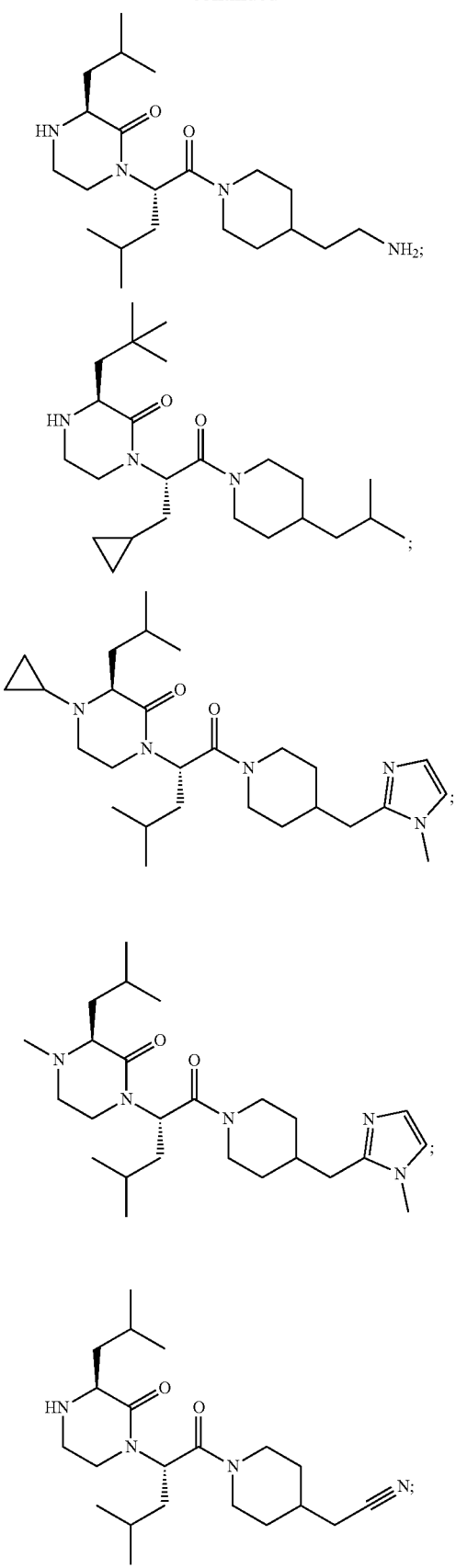
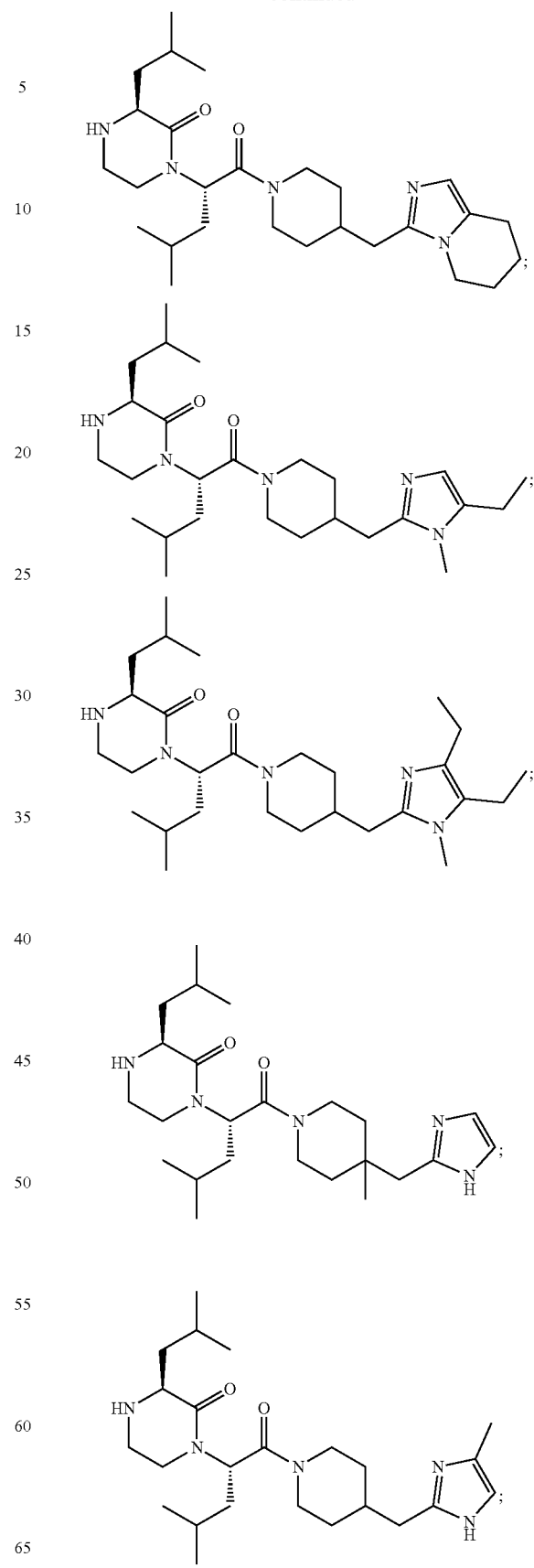

487
-continued
488
-continued
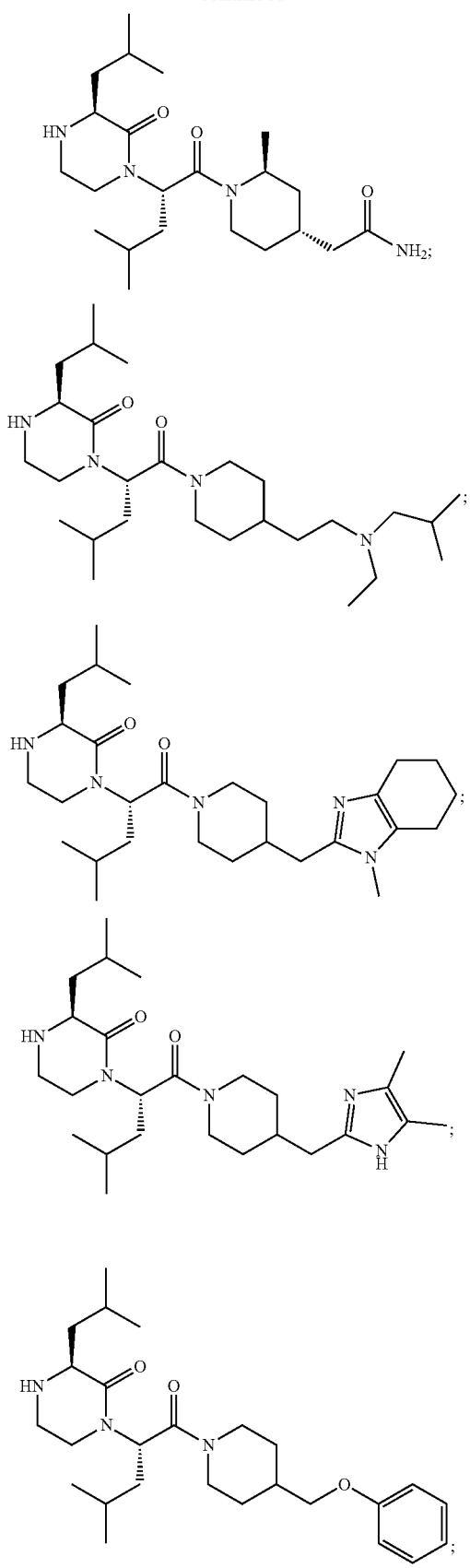
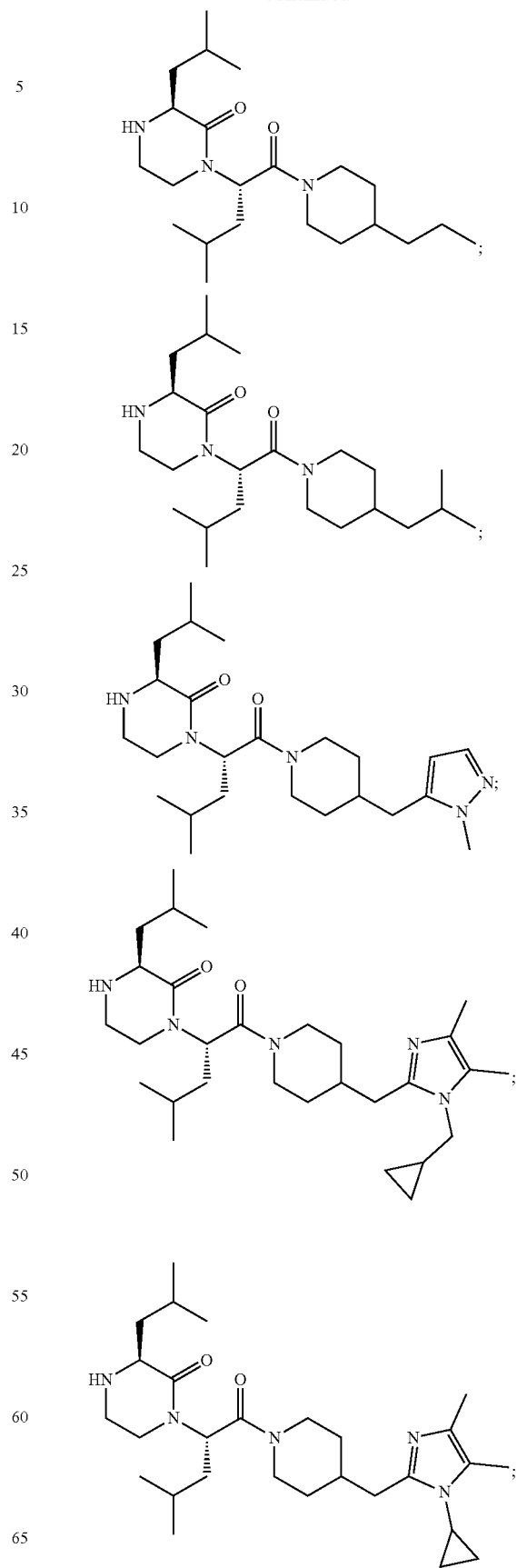

489
-continued
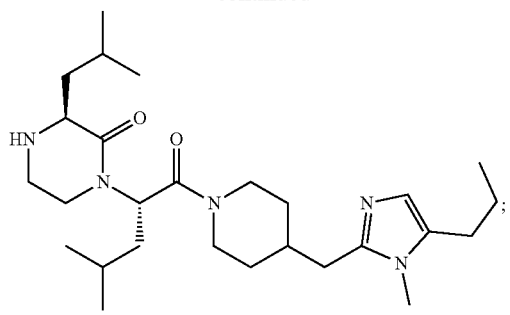
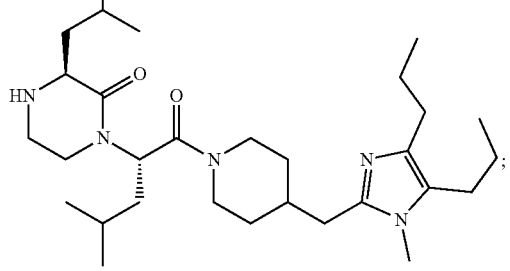
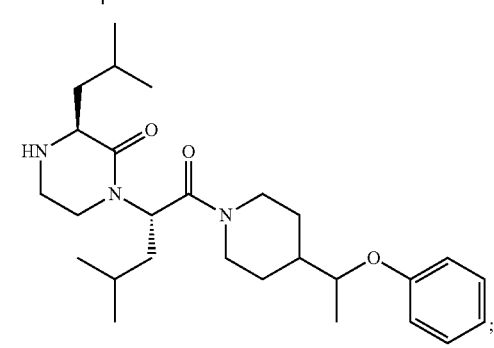
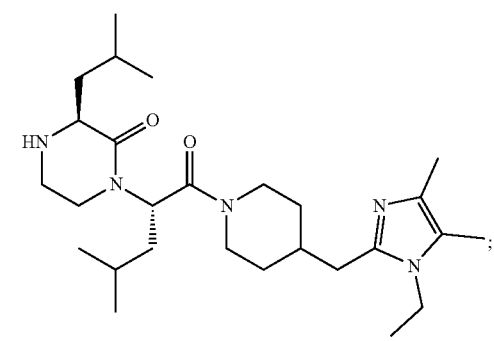
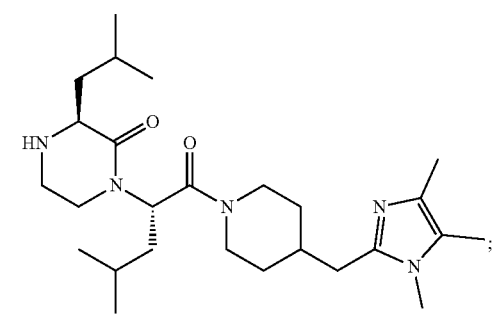
490
-continued
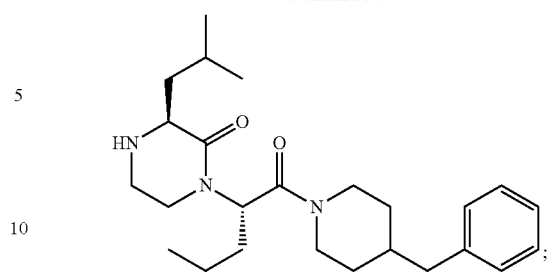
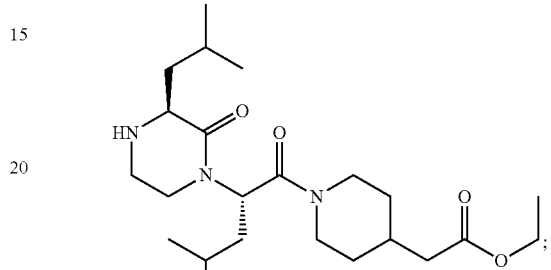
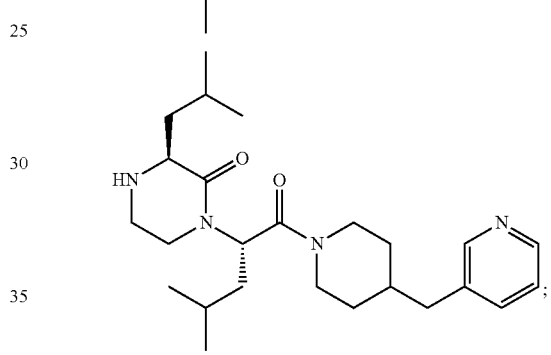
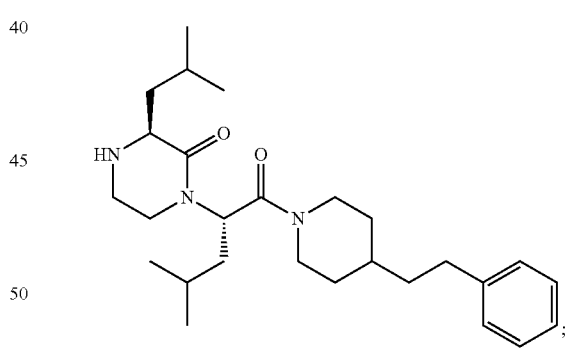
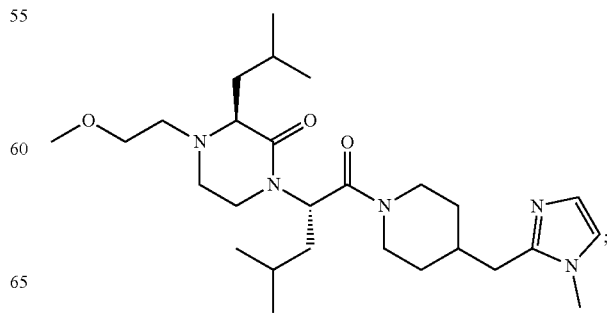

491
-continued
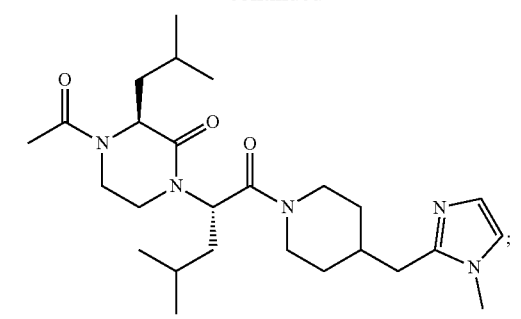
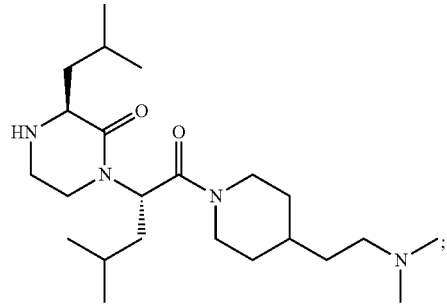
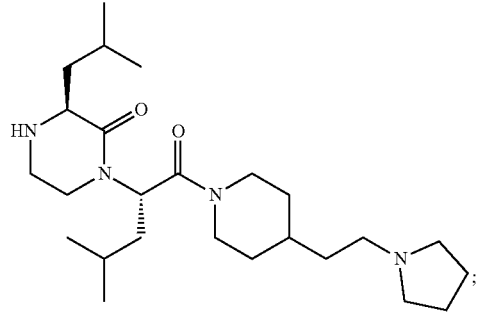
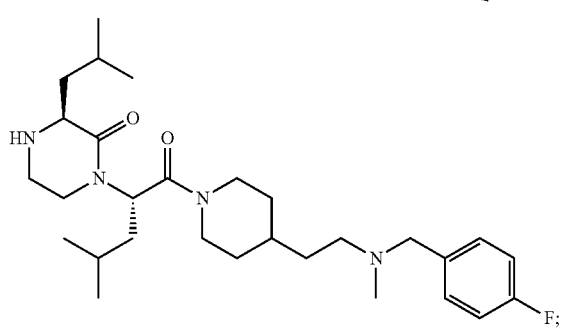
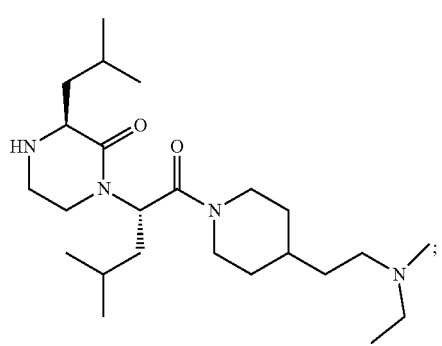
492
-continued
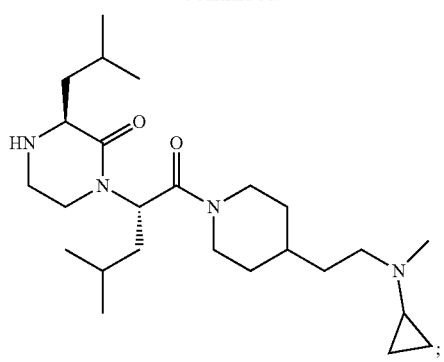
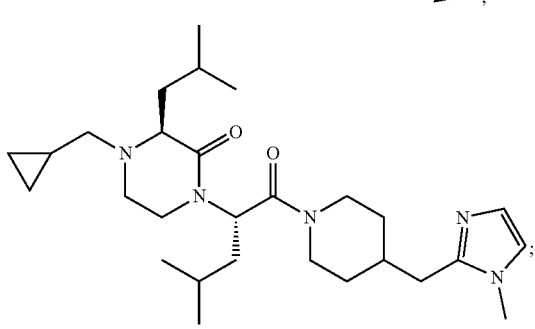
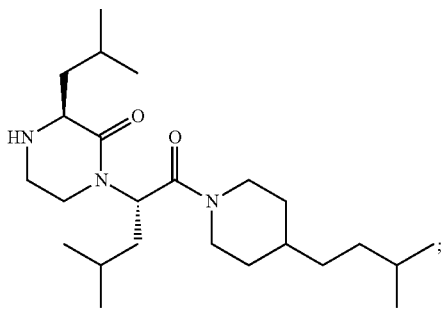
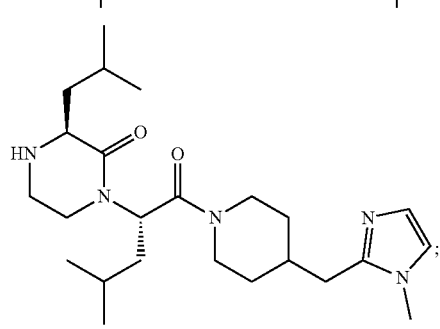
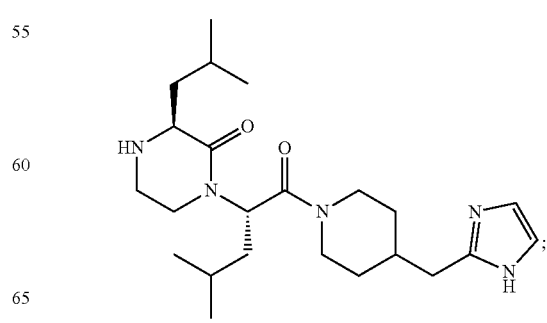

493
-continued
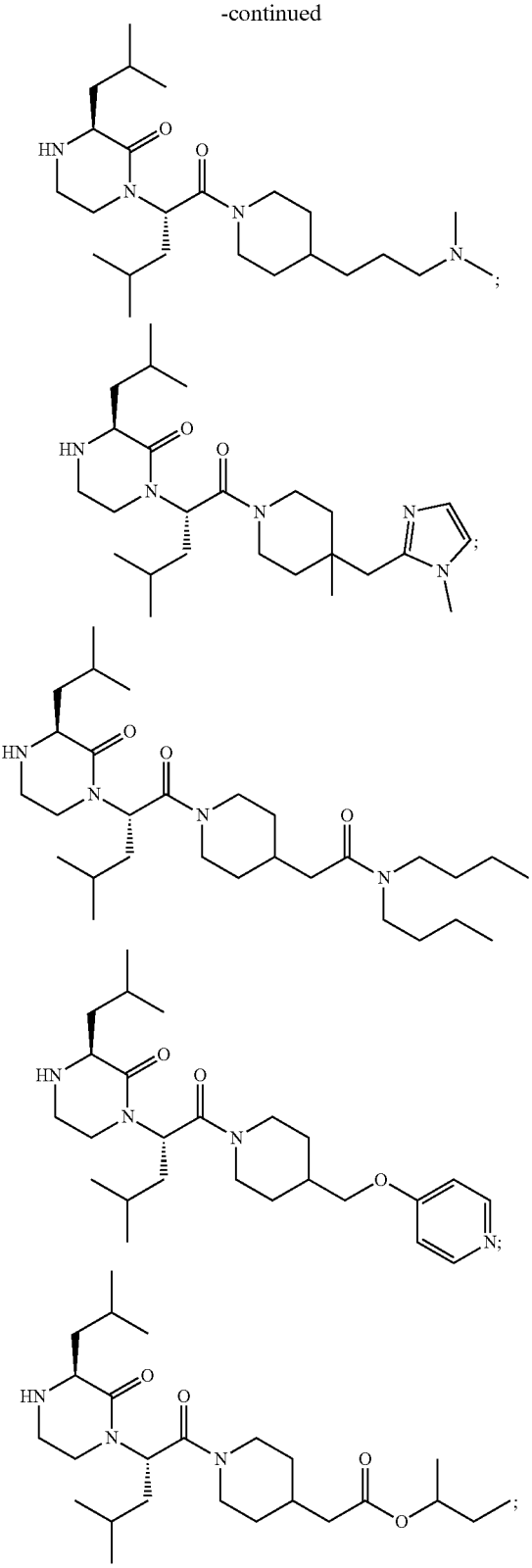
494
-continued
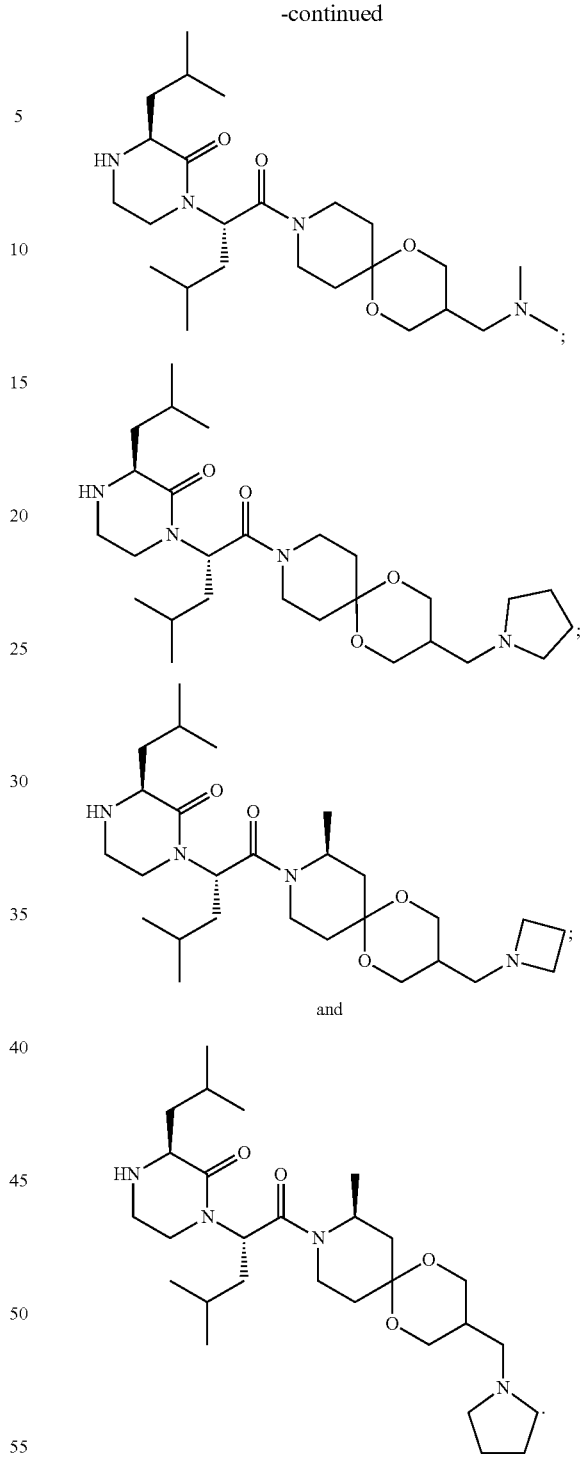
18. A pharmaceutical composition comprising a compound of claim 1 and a pharmaceutically acceptable diluent, excipient or carrier.
* * * * *

UNITED STATES PATENT AND TRADEMARK OFFICE
CERTIFICATE OF CORRECTION

PATENT NO.         : 10,710,975 B2
APPLICATION NO.    : 16/222479
DATED              : July 14, 2020
INVENTOR(S)        : Marc Labelle et al.

Page 1 of 2

It is certified that error appears in the above-identified patent and that said Letters Patent is hereby corrected as shown below:

On the Title Page

Item (74):
"(74) Attorney, Agent, or Firm – Cooley LLP, Heidei A. Erlacher, Timothy R. McFadden"

Should read:
-- (74) Attorney, Agent, or Firm – Cooley LLP, Heidi A. Erlacher, Timothy R. McFadden --

In the Claims

At Column 466, Claim number 1, Line number 5:
"$R^8$ C(O)NR$^8$R$^{11}$, C(O)OR$^8$, NR$^8$C(O)NR$^8$R$^{11}$R,"

Should read:
-- $R^8$ C(O)NR$^8$R$^{11}$, C(O)OR$^8$, NR$^8$C(O)NR$^8$R$^{11}$, --

At Column 467, Claim number 2, Line number 40:
"N wherein if the heteroatom is N it is optionally"

Should read:
-- N, wherein if the heteroatom is N it is optionally --

At Column 471, Claim number 10, Line number 18:
"selected from O and N wherein if the heteroatom is N the"

Should read:
-- selected from O and N, wherein if the heteroatom is N the --

At Column 471, Claim number 10, Line number 35:
"O and N wherein if the heteroatom is N the ring is optionally"

Signed and Sealed this
Eighth Day of September, 2020

Andrei Iancu
*Director of the United States Patent and Trademark Office*

CERTIFICATE OF CORRECTION (continued)
U.S. Pat. No. 10,710,975 B2

Should read:
-- O and N, wherein if the heteroatom is N the ring is optionally --

At Column 471, Claim number 10, Line number 37:
"eroaryl wherein the S-aryl, O-aryl, S-heteroaryl, or O-het-"

Should read:
-- eroaryl, wherein the S-aryl, O-aryl, S-heteroaryl, or O-het- --

At Column 471, Claim number 10, Line number 51:
"O-aryl, S-heteroaryl, and O-heteroaryl wherein the S-aryl,"

Should read:
-- O-aryl, S-heteroaryl, and O-heteroaryl, wherein the S-aryl, --

At Column 476, Claim number 16, Line number 13:
"(VIII) (IXa), (IXb ), (IXc ), or (IXd):"

Should read:
-- (VIIIl) (IXa), (IXb ), (IXc ), or (IXd): --